(12) United States Patent
Shelton, IV et al.

(10) Patent No.: US 11,369,443 B2
(45) Date of Patent: Jun. 28, 2022

(54) METHOD OF USING A SURGICAL MODULAR ROBOTIC ASSEMBLY

(71) Applicant: Cilag GmbH International, Zug (CH)

(72) Inventors: Frederick E. Shelton, IV, Hillsboro, OH (US); Jason L. Harris, Lebanon, OH (US); Nicholas M. Morgan, Loveland, OH (US); Joshua P. Morgan, Loveland, OH (US); Christopher J. Hess, Blue Ash, OH (US); Chad E. Eckert, Milford, OH (US); Daniel J. Mumaw, Liberty Township, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/454,702

(22) Filed: Jun. 27, 2019

(65) Prior Publication Data

US 2020/0405403 A1 Dec. 31, 2020

(51) Int. Cl.
*A61B 18/00* (2006.01)
*A61B 34/30* (2016.01)
(Continued)

(52) U.S. Cl.
CPC ............ *A61B 34/30* (2016.02); *A61B 18/00* (2013.01); *A61B 17/068* (2013.01); *A61B 90/361* (2016.02); *A61B 2017/00199* (2013.01); *A61B 2017/00221* (2013.01); *A61B 2017/00411* (2013.01); *A61B 2017/00477* (2013.01); *A61B 2018/00994* (2013.01); *A61B 2018/126* (2013.01); *A61B 2018/1253* (2013.01); *A61B 2034/2055* (2016.02); *A61B 2034/302* (2016.02); *A61B 2218/006* (2013.01); *A61B 2218/008* (2013.01); *A61B 2560/0443* (2013.01)

(58) Field of Classification Search
CPC .......... A61B 34/30; A61B 2017/00017; A61B 34/20; A61B 90/37; A61B 18/00; A61B 17/1626
See application file for complete search history.

(56) References Cited

U.S. PATENT DOCUMENTS 5,383,860 A 1/1995 Lau
5,662,615 A 9/1997 Blake, III
(Continued)

OTHER PUBLICATIONS

IEEE Std 802.3-2012 (Revision of IEEE Std 802.3-2008, published Dec. 28, 2012.
(Continued)

*Primary Examiner* — Thai T Dinh

(57) ABSTRACT

A method of using a surgical modular robotic assembly including an interchangeable motor pack, a hand-held surgical instrument, and a robotic surgical instrument is disclosed. The method includes releasably attaching an interface portion of the interchangeable motor pack to the hand-held surgical instrument, causing the interchangeable motor pack to drive a first surgical tool of the hand-held surgical instrument, stopping the interchangeable motor pack from driving the first surgical tool, disconnecting the interface portion from the hand-held surgical instrument, and releasably attaching the interface portion of the interchangeable motor pack to the robotic surgical instrument.

18 Claims, 238 Drawing Sheets

(51) Int. Cl.
  *A61B 17/00* (2006.01)
  *A61B 18/12* (2006.01)
  *A61B 17/068* (2006.01)
  *A61B 90/00* (2016.01)
  *A61B 34/20* (2016.01)

(56) References Cited

U.S. PATENT DOCUMENTS

| | | | |
|---|---|---|---|
| 5,980,493 A | 11/1999 | Smith et al. | |
| 6,537,290 B2 | 3/2003 | Adams et al. | |
| 7,134,587 B2 | 11/2006 | Schwemberger et al. | |
| 7,955,322 B2 | 6/2011 | Devengenzo et al. | |
| 7,982,776 B2 | 7/2011 | Dunki-Jacobs et al. | |
| 7,995,045 B2 | 8/2011 | Dunki-Jacobs | |
| 8,054,184 B2 | 11/2011 | Cline et al. | |
| 8,070,731 B2 | 12/2011 | Wenchell et al. | |
| 8,197,446 B2 | 6/2012 | Beardsley | |
| 8,348,126 B2 * | 1/2013 | Olson | A61B 17/07292 227/175.1 |
| 8,491,533 B2 | 7/2013 | Parihar et al. | |
| 8,613,727 B2 | 12/2013 | Hart et al. | |
| 8,616,431 B2 | 12/2013 | Timm et al. | |
| 8,628,529 B2 | 1/2014 | Aldridge et al. | |
| 8,828,023 B2 | 9/2014 | Neff et al. | |
| 8,912,746 B2 * | 12/2014 | Reid | A61B 34/30 318/560 |
| 9,060,775 B2 | 6/2015 | Wiener et al. | |
| 9,072,535 B2 | 7/2015 | Shelton, IV et al. | |
| 9,072,536 B2 | 7/2015 | Shelton, IV et al. | |
| 9,106,270 B2 | 8/2015 | Puterbaugh et al. | |
| 9,107,684 B2 | 8/2015 | Ma | |
| 9,204,879 B2 | 12/2015 | Shelton, IV | |
| 9,345,481 B2 | 5/2016 | Hall et al. | |
| 9,526,407 B2 | 12/2016 | Hoeg et al. | |
| 9,561,038 B2 | 2/2017 | Shelton, IV et al. | |
| 9,572,552 B1 | 2/2017 | Bodor et al. | |
| 9,597,104 B2 * | 3/2017 | Nicholas | A61B 17/068 |
| 9,649,110 B2 | 5/2017 | Parihar et al. | |
| 9,757,128 B2 | 9/2017 | Baber et al. | |
| 9,763,661 B2 * | 9/2017 | Zergiebel | A61B 17/07207 |
| 9,820,740 B2 * | 11/2017 | Zemlok | A61B 17/072 |
| 9,888,942 B1 | 2/2018 | Savage et al. | |
| 9,937,626 B2 | 4/2018 | Rockrohr | |
| 9,987,008 B2 * | 6/2018 | Scirica | A61B 17/07207 |
| 10,098,527 B2 | 10/2018 | Weisenburgh, II et al. | |
| 10,164,466 B2 | 12/2018 | Calderoni | |
| 10,166,080 B2 | 1/2019 | Balicki et al. | |
| 10,166,082 B1 | 1/2019 | Hariri et al. | |
| 10,172,687 B2 | 1/2019 | Garbus et al. | |
| 10,179,413 B2 | 1/2019 | Rockrohr | |
| 10,213,266 B2 | 2/2019 | Zemlok et al. | |
| 10,231,775 B2 | 3/2019 | Shelton, IV et al. | |
| 10,251,672 B2 | 4/2019 | Meglan | |
| 10,258,359 B2 | 4/2019 | Kapadia | |
| 10,321,964 B2 | 6/2019 | Grover et al. | |
| 10,376,338 B2 | 8/2019 | Taylor et al. | |
| 10,390,895 B2 | 8/2019 | Henderson et al. | |
| 10,398,517 B2 | 9/2019 | Eckert et al. | |
| 10,420,620 B2 | 9/2019 | Rockrohr | |
| 10,426,516 B2 | 10/2019 | Racenet et al. | |
| 10,507,068 B2 | 12/2019 | Kopp et al. | |
| 10,517,686 B2 | 12/2019 | Vokrot et al. | |
| 10,537,351 B2 | 1/2020 | Shelton, IV et al. | |
| 10,548,504 B2 | 2/2020 | Shelton, IV et al. | |
| 10,561,470 B2 * | 2/2020 | Hourtash | A61B 34/30 |
| 10,588,706 B2 | 3/2020 | Limon | |
| 10,624,691 B2 | 4/2020 | Wiener et al. | |
| 10,639,111 B2 | 5/2020 | Kopp | |
| 10,653,489 B2 | 5/2020 | Kopp | |
| 10,667,877 B2 | 6/2020 | Kapadia | |
| 10,675,104 B2 | 6/2020 | Kapadia | |
| 10,716,639 B2 | 7/2020 | Kapadia et al. | |
| 10,736,219 B2 | 8/2020 | Seow et al. | |
| 10,743,872 B2 | 8/2020 | Leimbach et al. | |
| 10,751,087 B2 | 8/2020 | Morgan et al. | |
| 10,772,688 B2 | 9/2020 | Peine et al. | |
| 10,779,849 B2 | 9/2020 | Shelton, IV et al. | |
| 10,779,897 B2 | 9/2020 | Rockrohr | |
| 10,779,900 B2 | 9/2020 | Pedros et al. | |
| 10,799,304 B2 | 10/2020 | Kapadia et al. | |
| 10,806,454 B2 | 10/2020 | Kopp | |
| 10,813,703 B2 | 10/2020 | Swayze et al. | |
| 10,849,700 B2 | 12/2020 | Kopp et al. | |
| 10,893,884 B2 | 1/2021 | Stoddard et al. | |
| 10,912,616 B2 | 2/2021 | Dachs, II et al. | |
| 10,959,788 B2 | 3/2021 | Grover et al. | |
| 10,980,610 B2 | 4/2021 | Rosenberg et al. | |
| 11,013,569 B2 | 5/2021 | Shelton, IV et al. | |
| 11,026,764 B2 | 6/2021 | Kopp | |
| 11,045,265 B2 | 6/2021 | Seow et al. | |
| 11,058,504 B2 | 7/2021 | Blanco et al. | |
| 11,090,125 B2 | 8/2021 | Peine et al. | |
| 11,160,623 B2 | 11/2021 | Hagn | |
| 2002/0072736 A1 | 6/2002 | Tierney et al. | |
| 2006/0069306 A1 | 3/2006 | Banik et al. | |
| 2006/0135978 A1 | 6/2006 | Franer | |
| 2007/0078395 A1 | 4/2007 | Valaie | |
| 2008/0064921 A1 | 3/2008 | Larkin et al. | |
| 2011/0230719 A1 | 9/2011 | Katakura et al. | |
| 2011/0306840 A1 | 12/2011 | Allen et al. | |
| 2012/0132018 A1 | 5/2012 | Tang et al. | |
| 2012/0238827 A1 | 9/2012 | Berry et al. | |
| 2013/0331730 A1 | 12/2013 | Fenech et al. | |
| 2014/0066944 A1 | 3/2014 | Taylor et al. | |
| 2014/0263552 A1 | 9/2014 | Hall et al. | |
| 2014/0343569 A1 | 11/2014 | Turner | |
| 2016/0015261 A1 | 1/2016 | Kishi et al. | |
| 2016/0175062 A1 * | 6/2016 | Limon | A61B 90/70 134/116 |
| 2016/0361127 A1 * | 12/2016 | Dachs, II | A61B 17/00234 |
| 2017/0188802 A1 | 7/2017 | Lawrence et al. | |
| 2017/0202591 A1 | 7/2017 | Shelton, IV et al. | |
| 2017/0207467 A1 * | 7/2017 | Shelton, IV | A61B 18/1445 |
| 2017/0224428 A1 | 8/2017 | Kopp | |
| 2017/0296213 A1 | 10/2017 | Swensgard et al. | |
| 2018/0263717 A1 | 9/2018 | Kopp | |
| 2018/0296286 A1 | 10/2018 | Peine et al. | |
| 2018/0360452 A1 | 12/2018 | Shelton, IV et al. | |
| 2019/0000446 A1 | 1/2019 | Shelton, IV et al. | |
| 2019/0000478 A1 | 1/2019 | Messerly et al. | |
| 2019/0053866 A1 | 2/2019 | Seow et al. | |
| 2019/0059986 A1 | 2/2019 | Shelton, IV et al. | |
| 2019/0104919 A1 | 4/2019 | Shelton, IV et al. | |
| 2019/0133703 A1 | 5/2019 | Seow et al. | |
| 2019/0183596 A1 | 6/2019 | Dachs, II | |
| 2019/0200844 A1 | 7/2019 | Shelton, IV et al. | |
| 2019/0200981 A1 | 7/2019 | Harris et al. | |
| 2019/0200998 A1 | 7/2019 | Shelton, IV et al. | |
| 2019/0201045 A1 | 7/2019 | Yates et al. | |
| 2019/0201046 A1 | 7/2019 | Shelton, IV et al. | |
| 2019/0201047 A1 | 7/2019 | Yates et al. | |
| 2019/0201120 A1 | 7/2019 | Shelton, IV et al. | |
| 2019/0201136 A1 | 7/2019 | Shelton, IV et al. | |
| 2019/0201137 A1 | 7/2019 | Shelton, IV et al. | |
| 2019/0201594 A1 | 7/2019 | Shelton, IV et al. | |
| 2019/0206562 A1 | 7/2019 | Shelton, IV et al. | |
| 2019/0206563 A1 | 7/2019 | Shelton, IV et al. | |
| 2019/0206564 A1 | 7/2019 | Shelton, IV et al. | |
| 2019/0206569 A1 | 7/2019 | Shelton, IV et al. | |
| 2019/0208641 A1 | 7/2019 | Yates et al. | |
| 2019/0254755 A1 * | 8/2019 | Bonutti | G06T 7/194 |
| 2019/0298471 A1 * | 10/2019 | Holop | A61B 34/00 |
| 2019/0321112 A1 | 10/2019 | Cecil | |
| 2020/0214776 A1 | 7/2020 | Hingwe et al. | |
| 2020/0315715 A1 | 10/2020 | Rockrohr et al. | |
| 2020/0405375 A1 | 12/2020 | Shelton, IV et al. | |
| 2020/0405401 A1 | 12/2020 | Shelton, IV et al. | |
| 2020/0405404 A1 | 12/2020 | Shelton, IV et al. | |
| 2020/0405405 A1 | 12/2020 | Shelton, IV et al. | |
| 2020/0405406 A1 | 12/2020 | Harris et al. | |
| 2020/0405407 A1 | 12/2020 | Shelton, IV et al. | |
| 2020/0405408 A1 | 12/2020 | Shelton, IV et al. | |
| 2020/0405414 A1 | 12/2020 | Shelton, IV et al. | |
| 2020/0405415 A1 | 12/2020 | Shelton, IV et al. | |

(56) References Cited

U.S. PATENT DOCUMENTS

2020/0405416 A1   12/2020  Shelton, IV et al.
2020/0405417 A1   12/2020  Shelton, IV et al.
2020/0405421 A1   12/2020  Luck
2020/0405422 A1   12/2020  Shelton, IV et al.
2021/0212777 A1    7/2021  Cheng

OTHER PUBLICATIONS

"ATM-MPLS Network Interworking Version 2.0, af-aic-0178.001" ATM Standard, The ATM Forum Technical Committee, published Aug. 2003.

\* cited by examiner

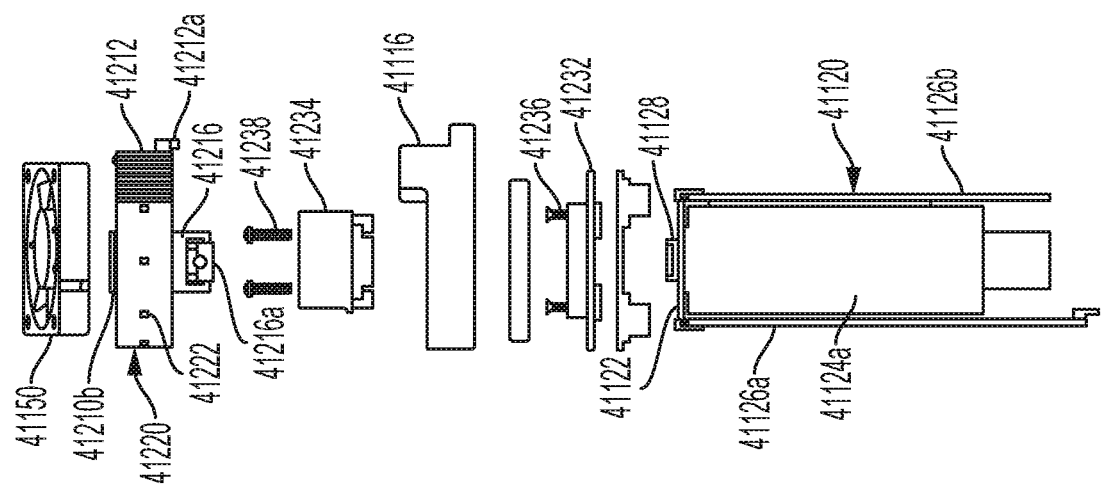

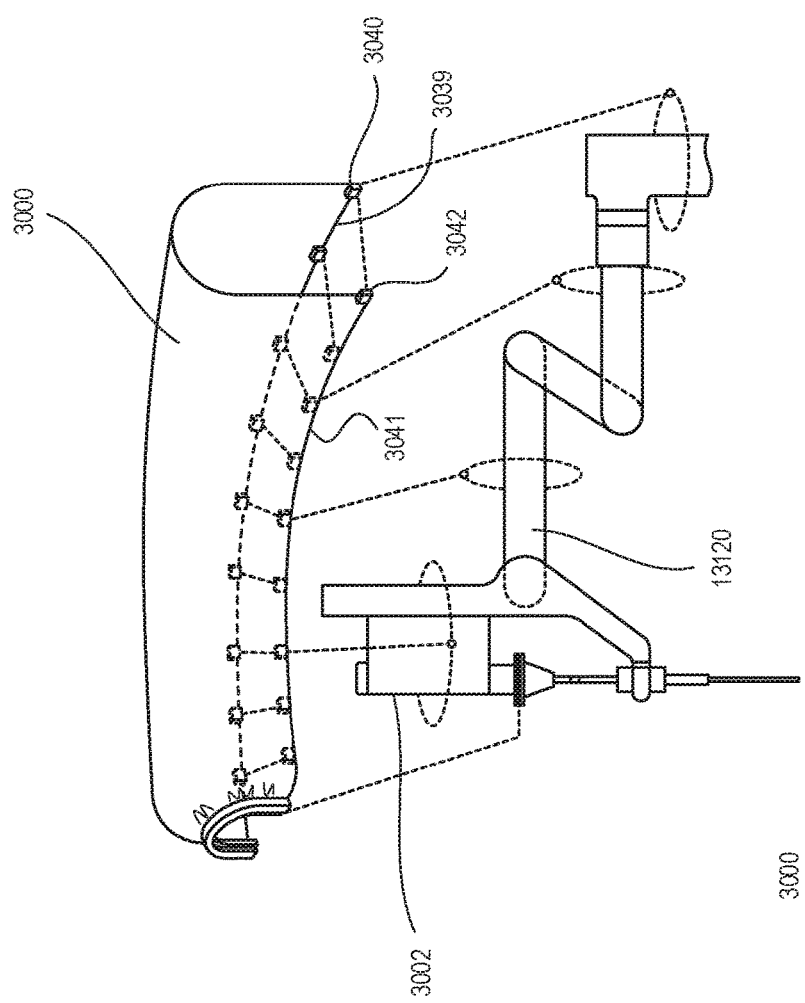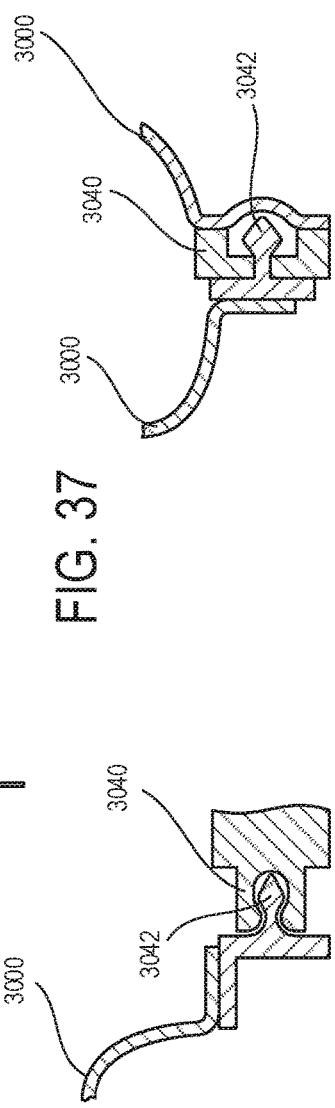

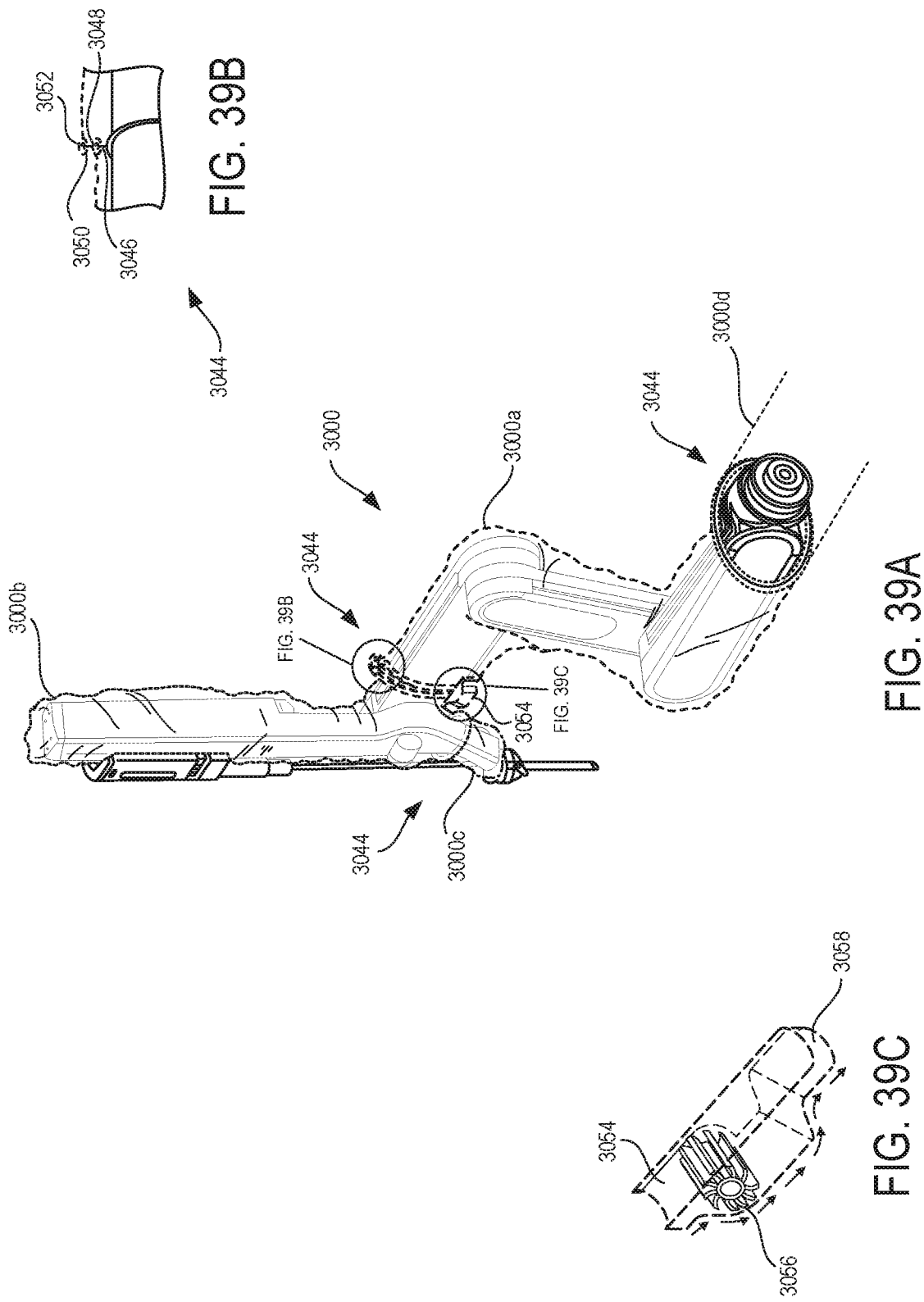

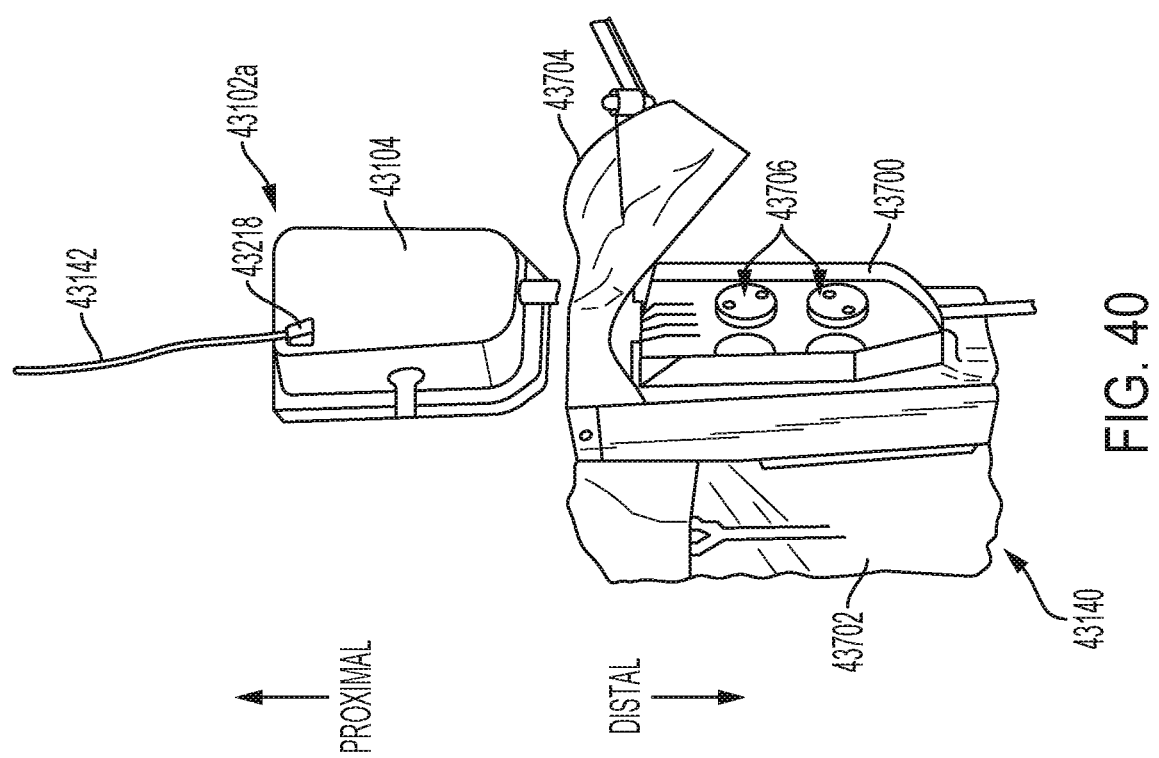

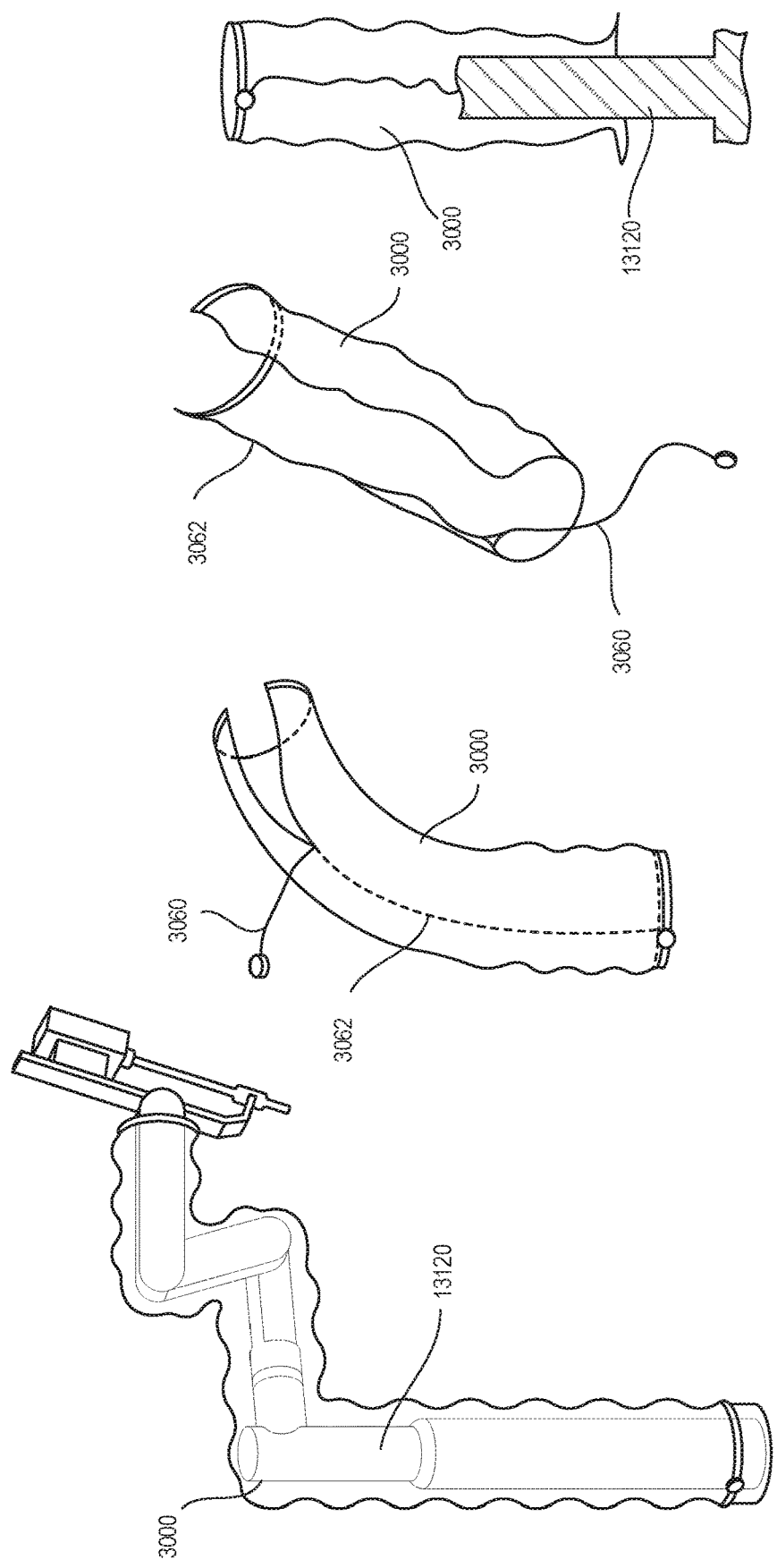

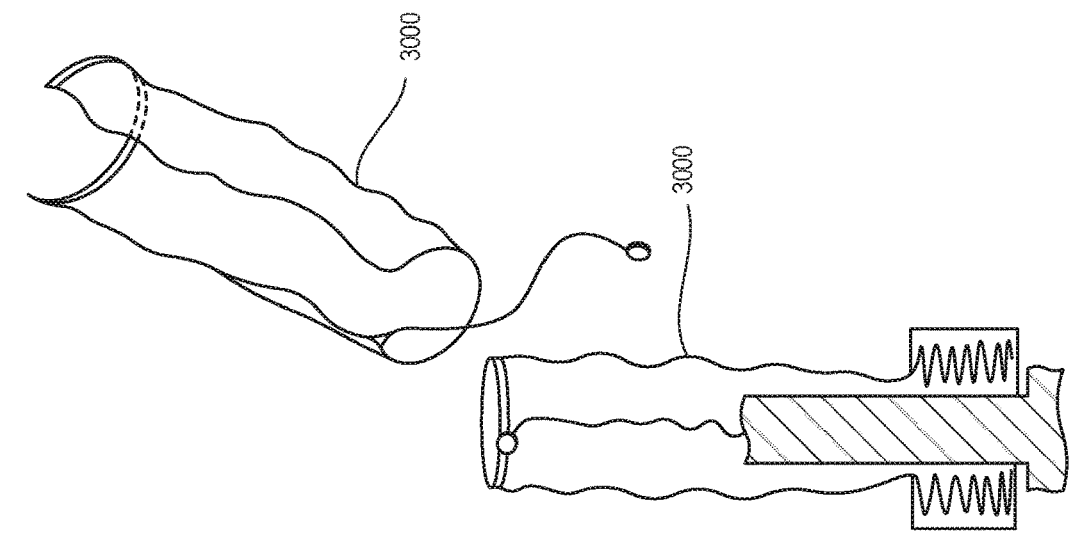
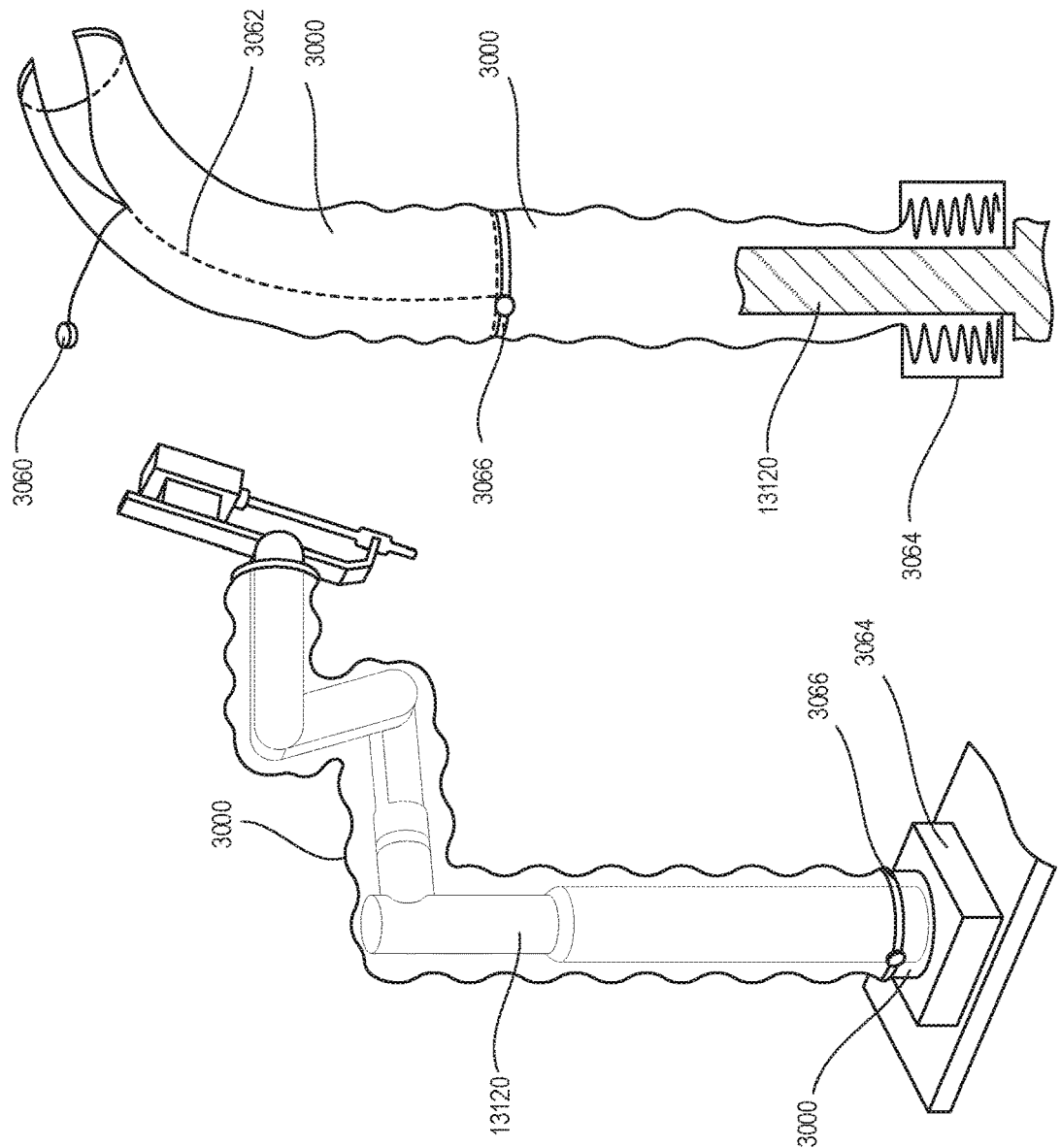

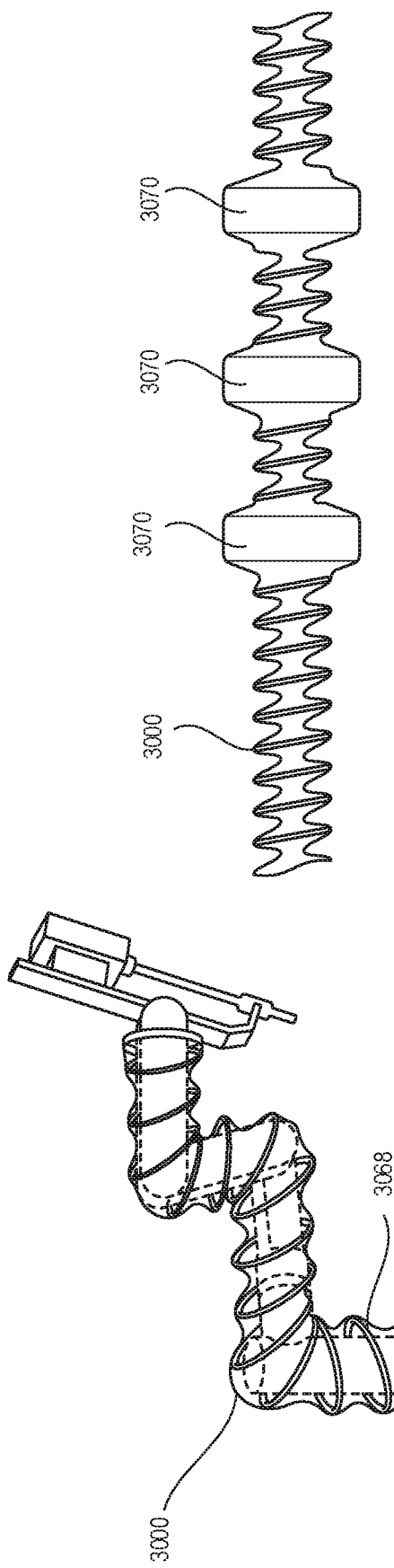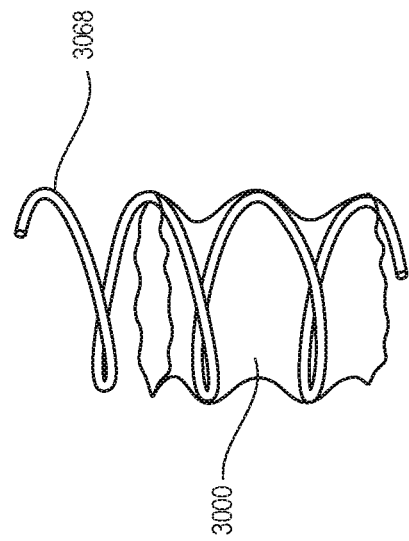

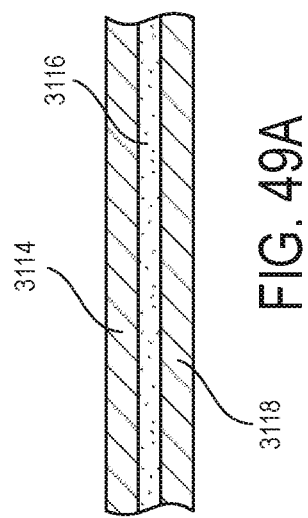
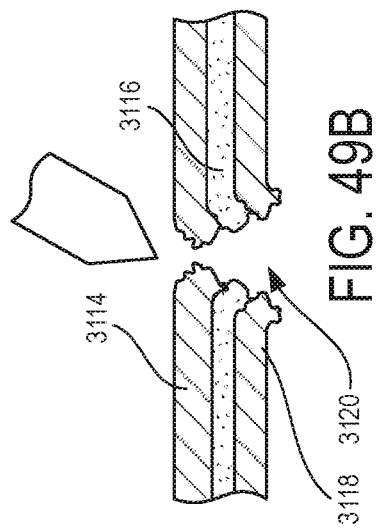
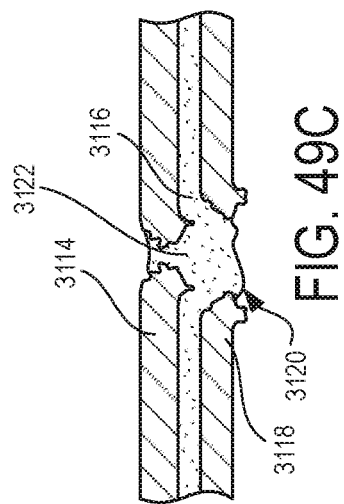

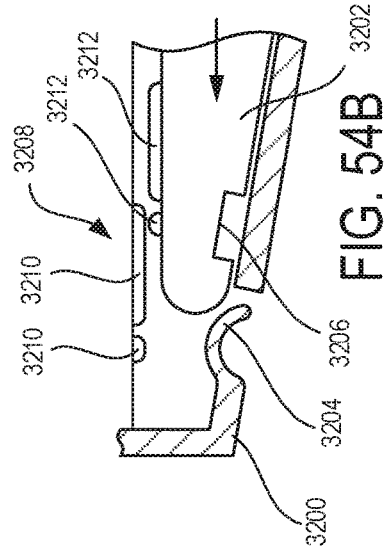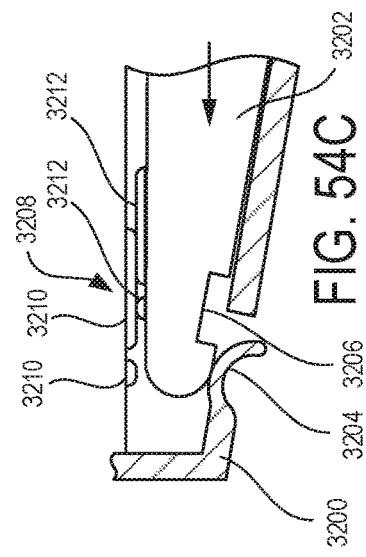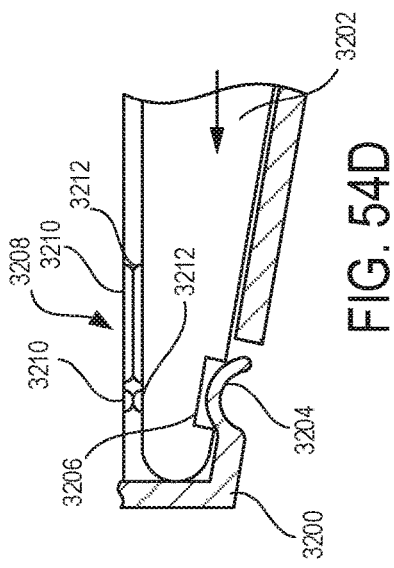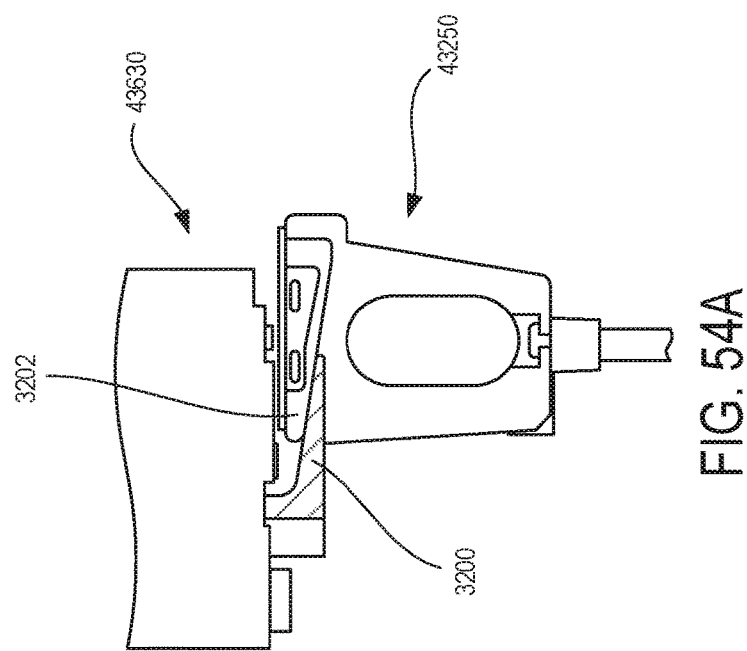

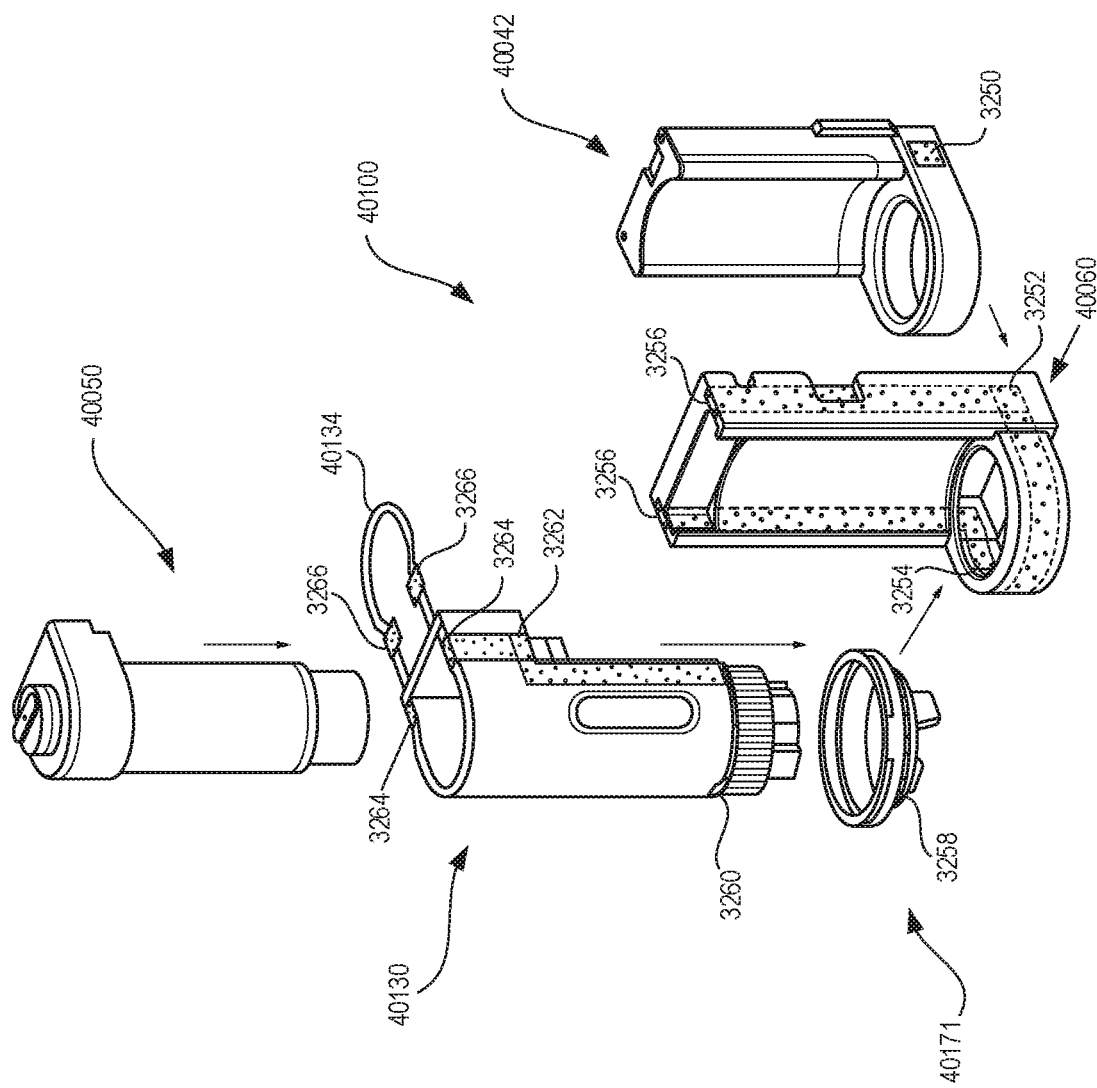

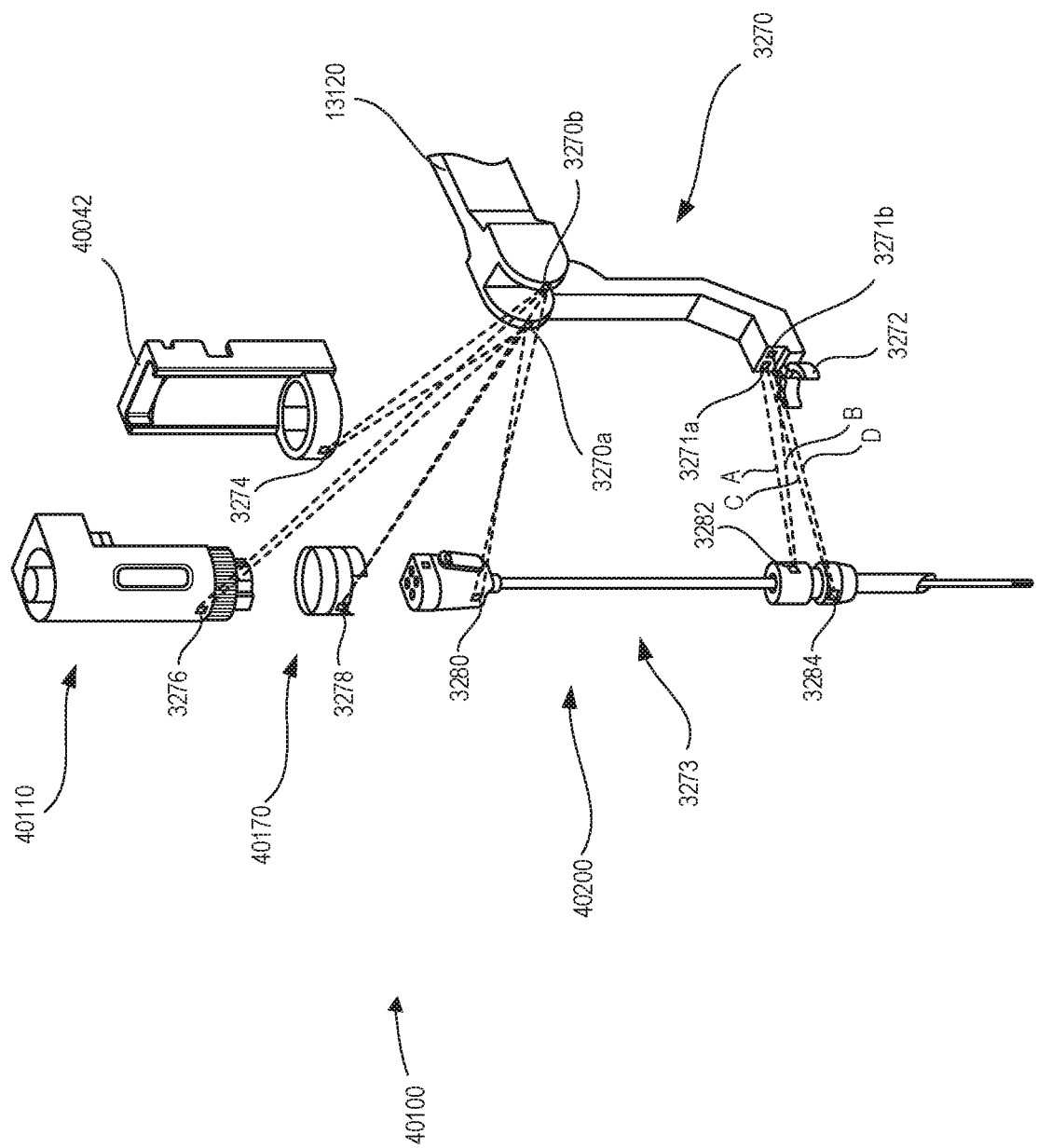

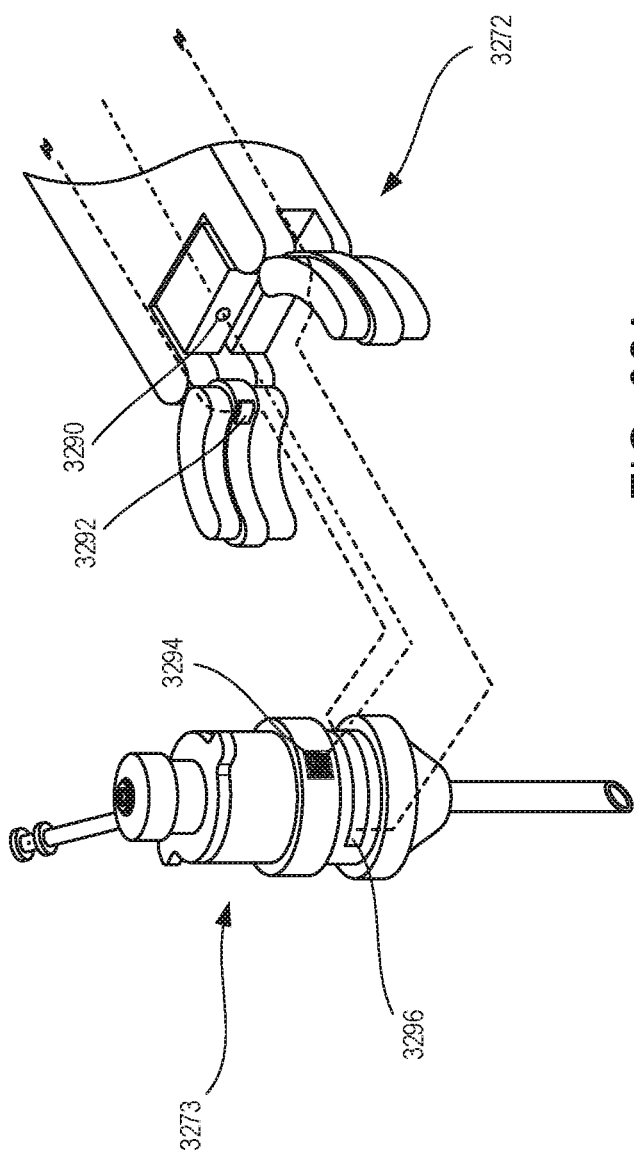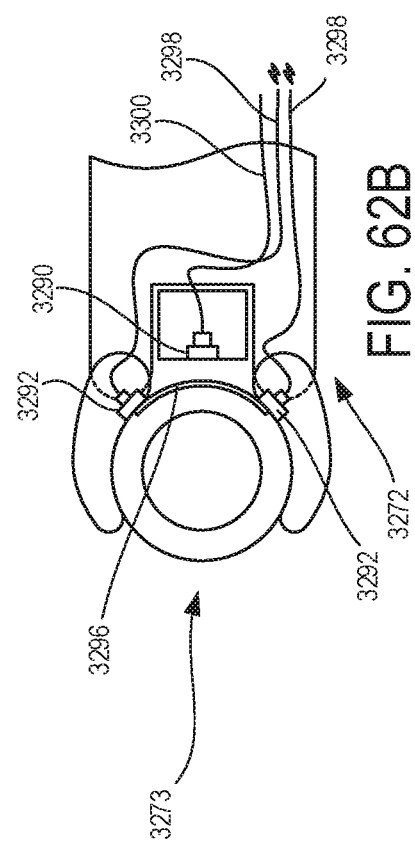
FIG. 62A
FIG. 62B

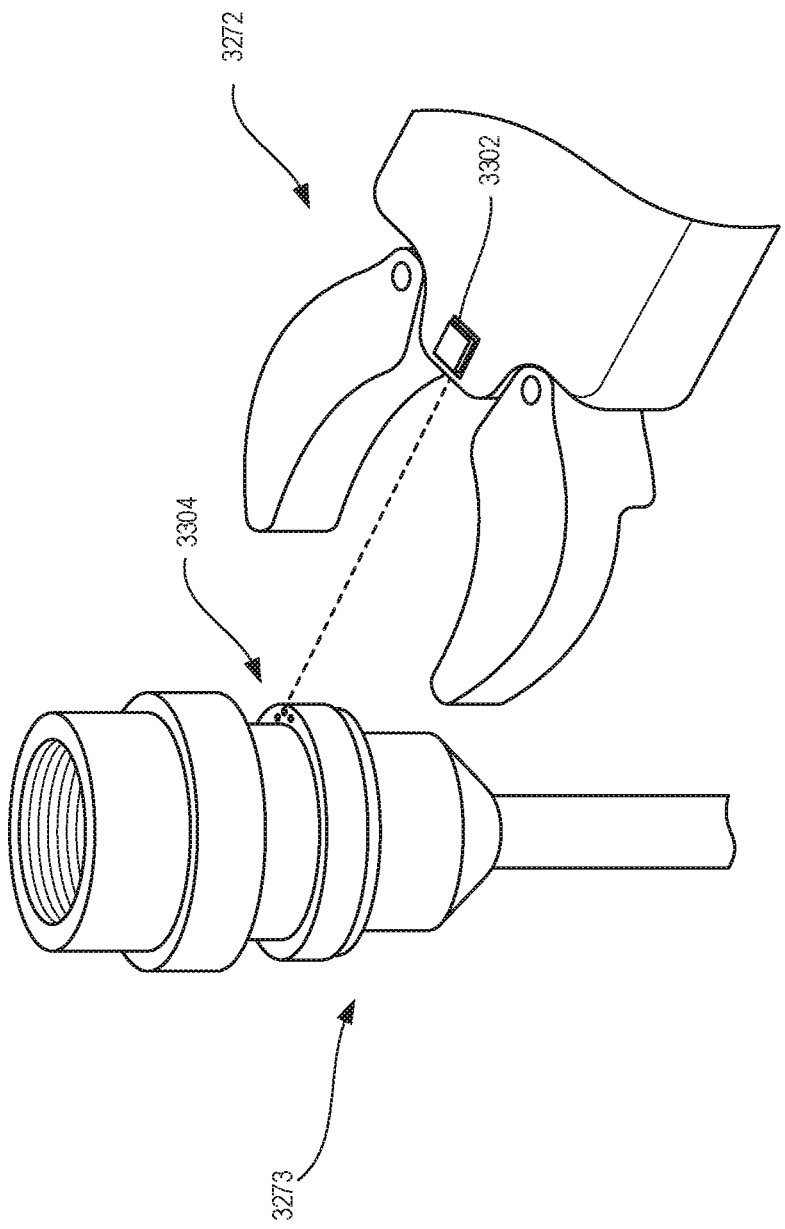
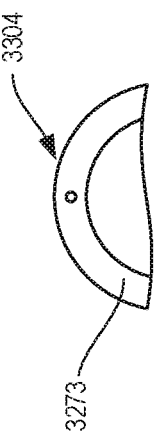
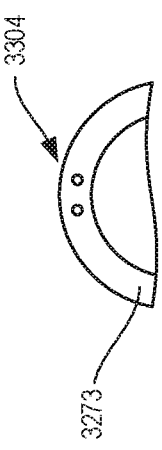
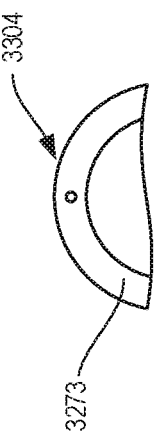

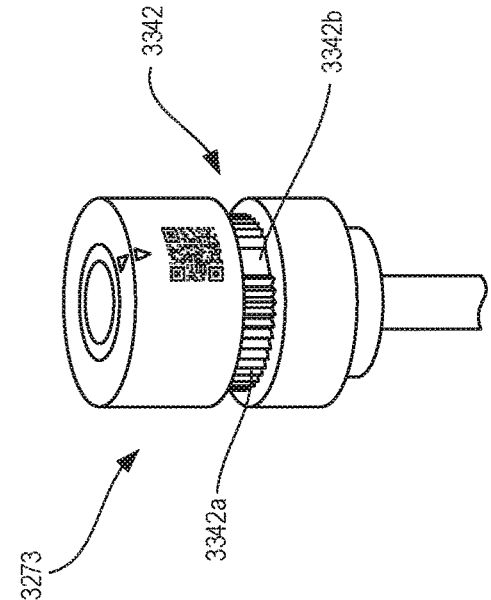
FIG. 66A
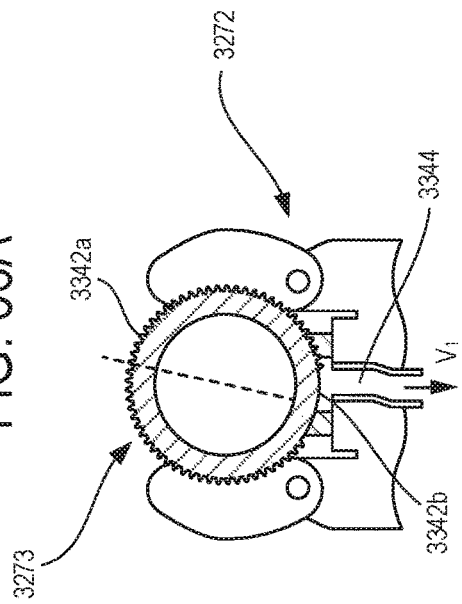
FIG. 66B
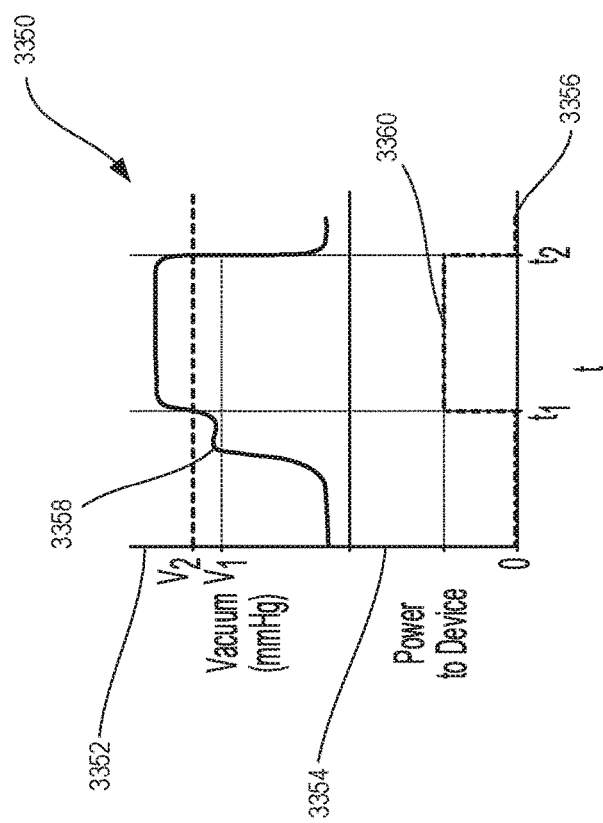
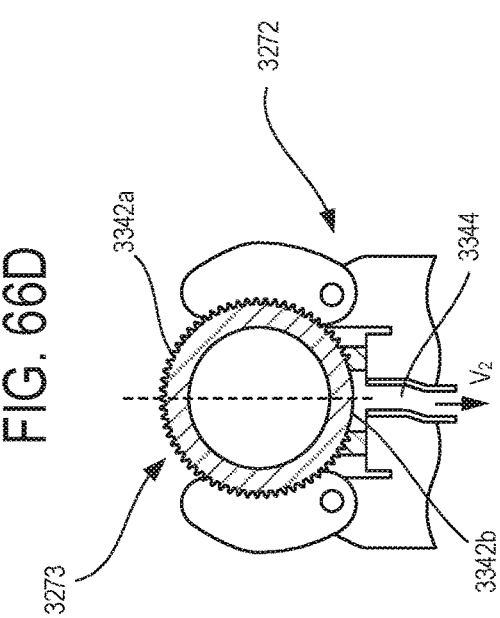
FIG. 66C
FIG. 66D

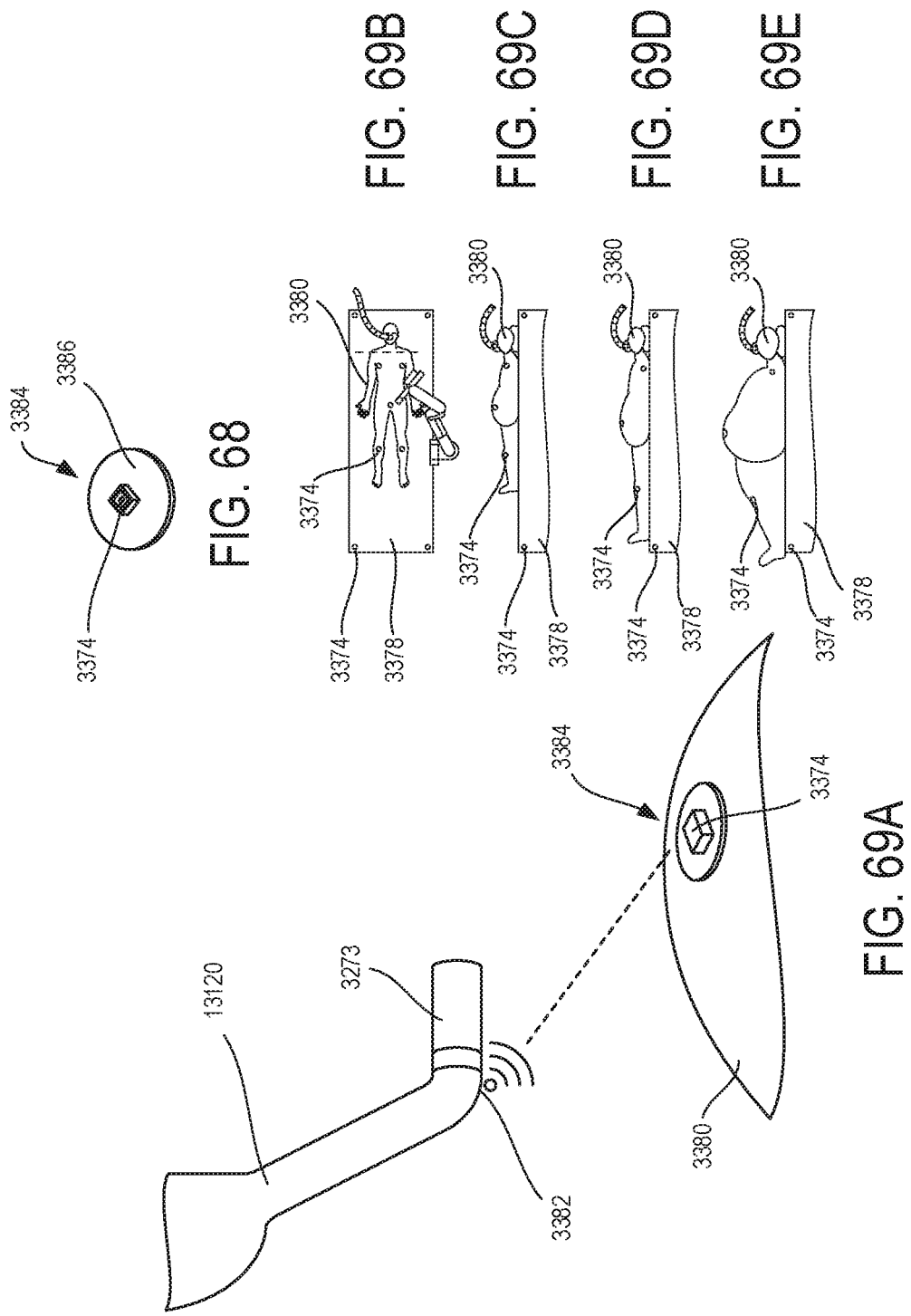

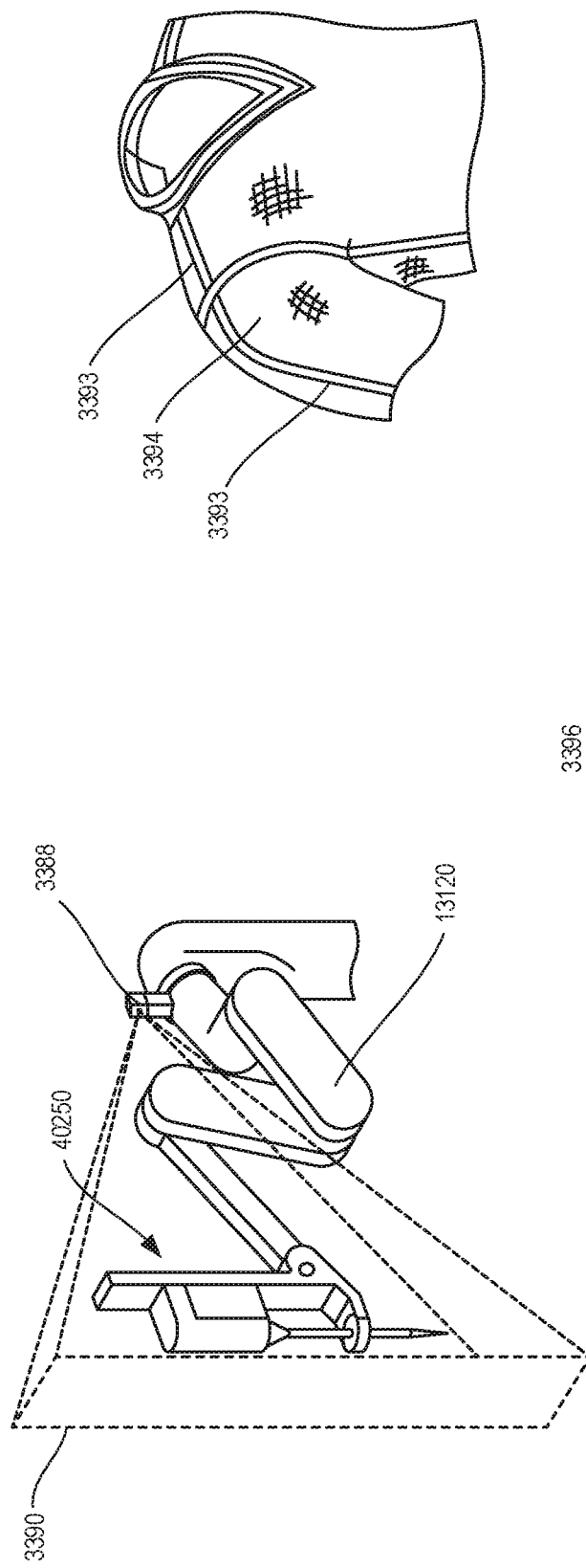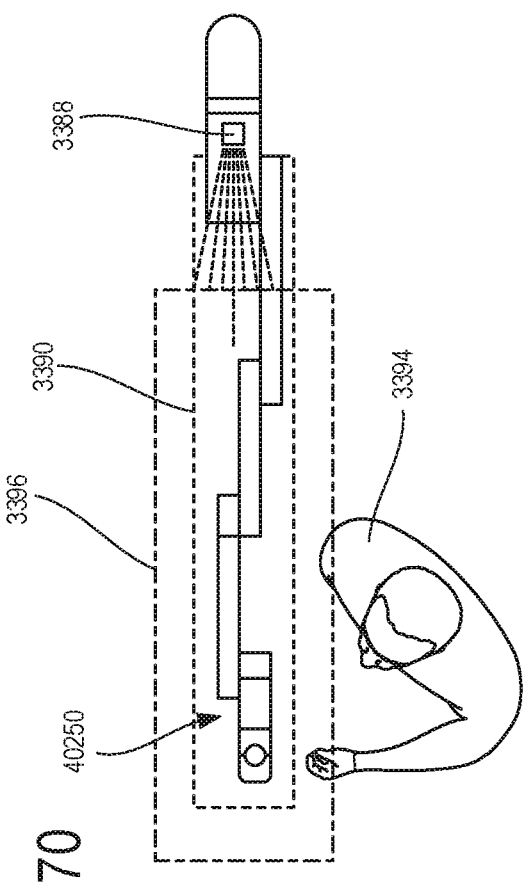
FIG. 70
FIG. 71
FIG. 72

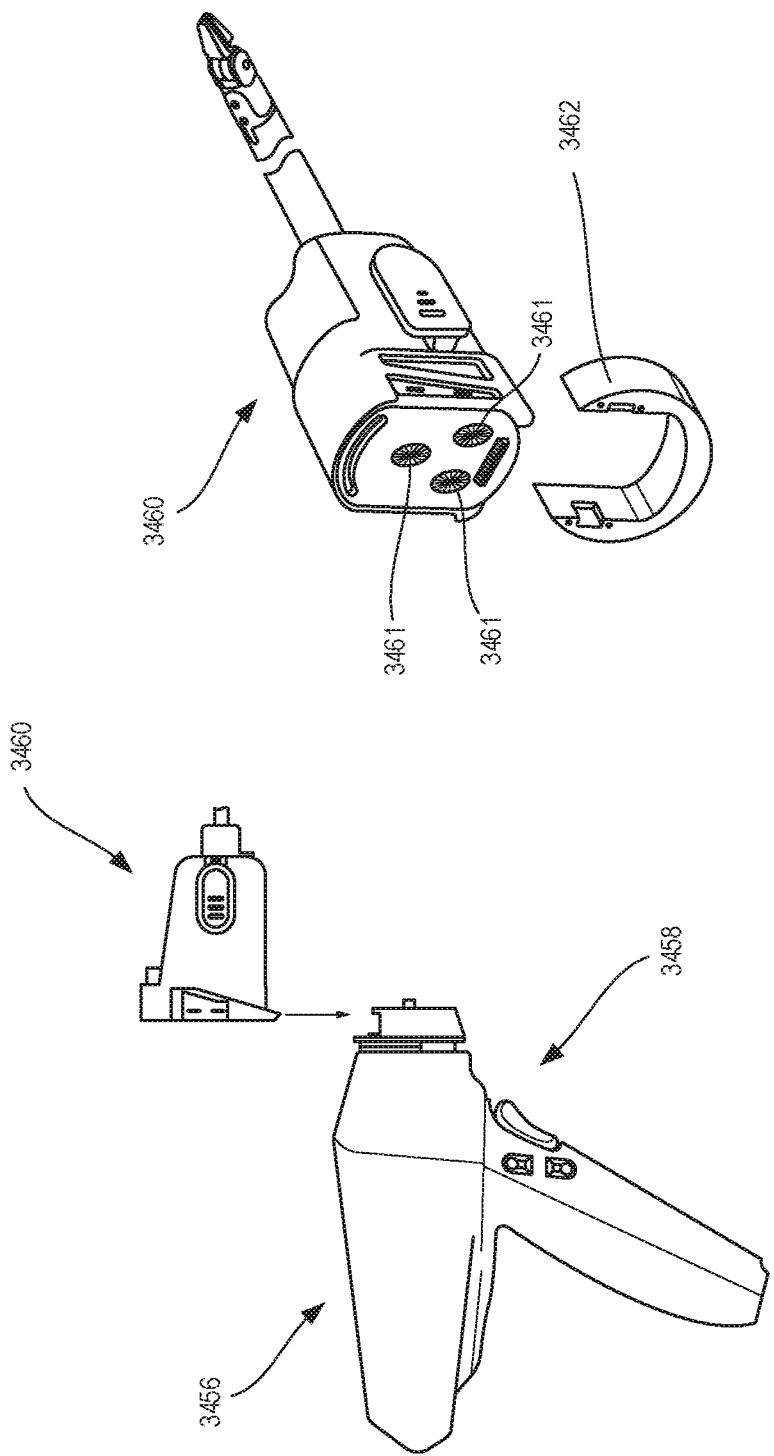

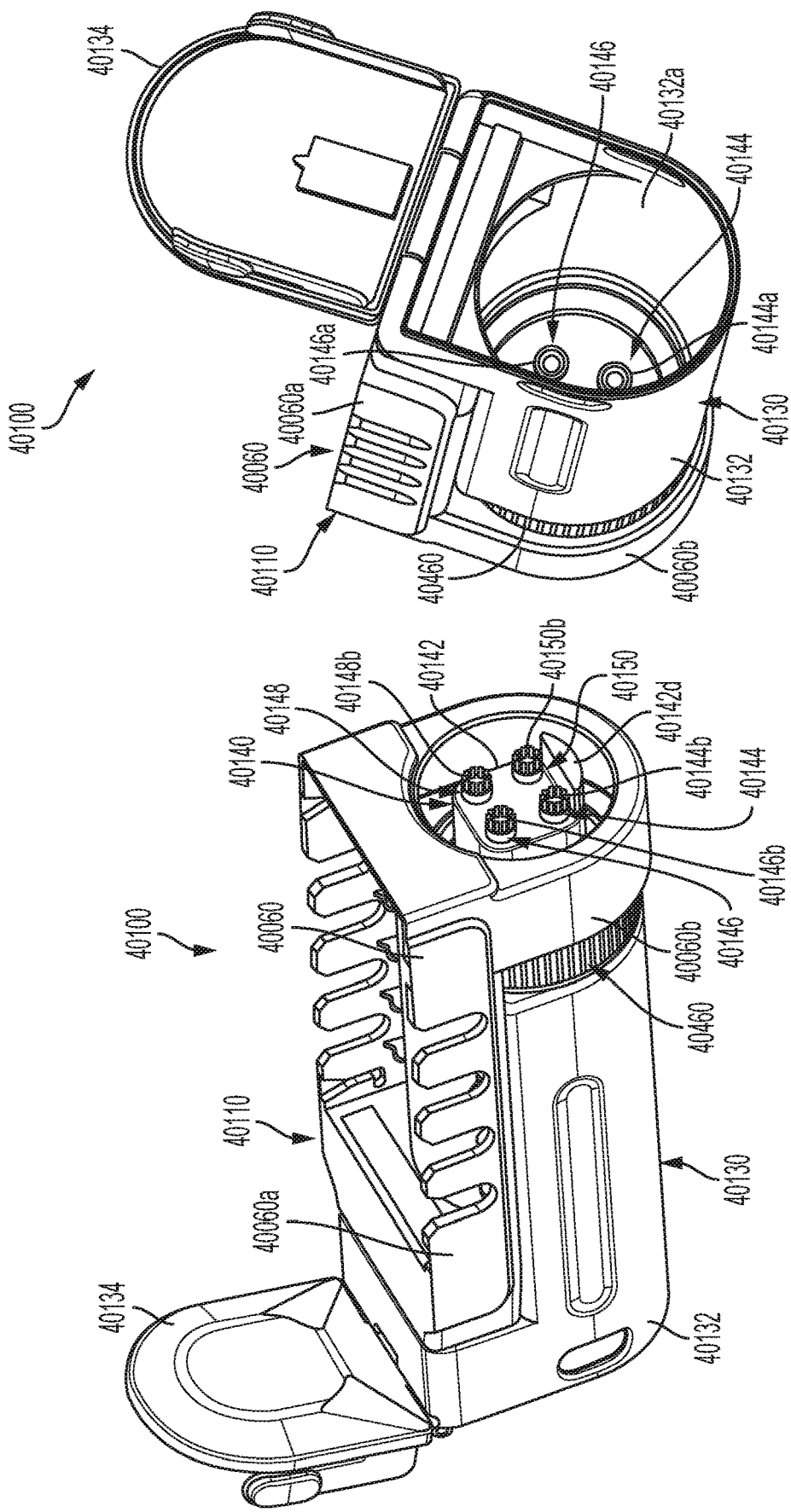

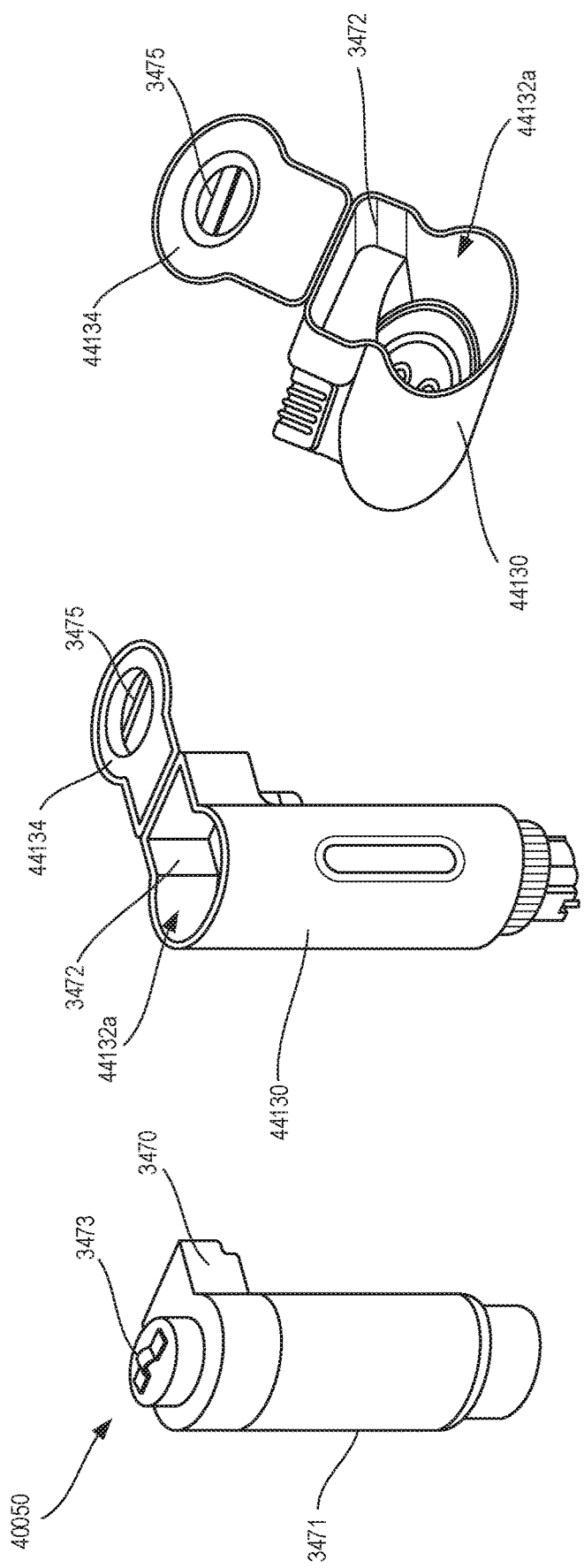

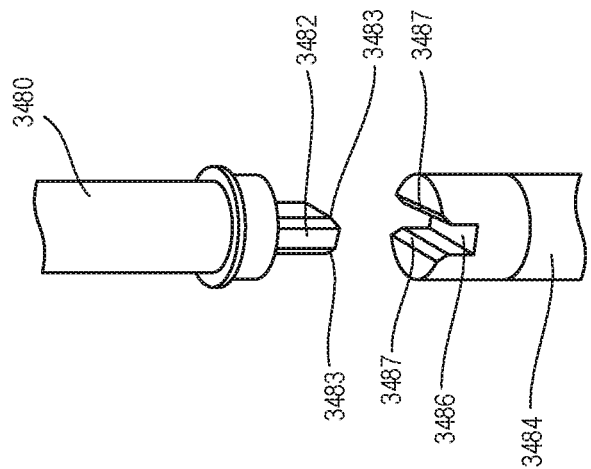
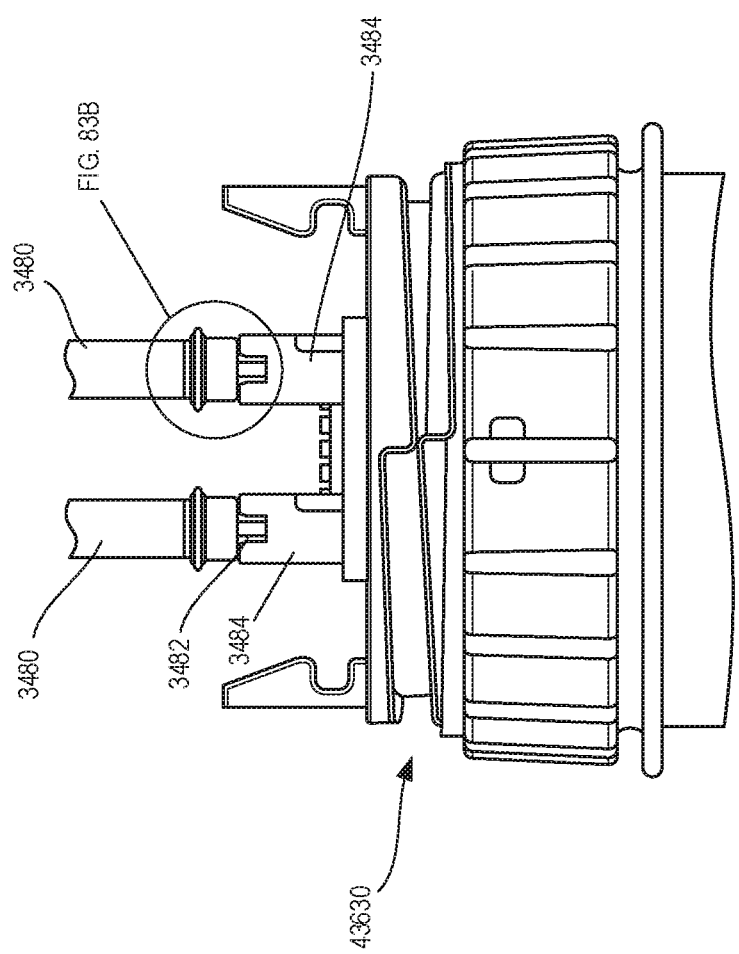

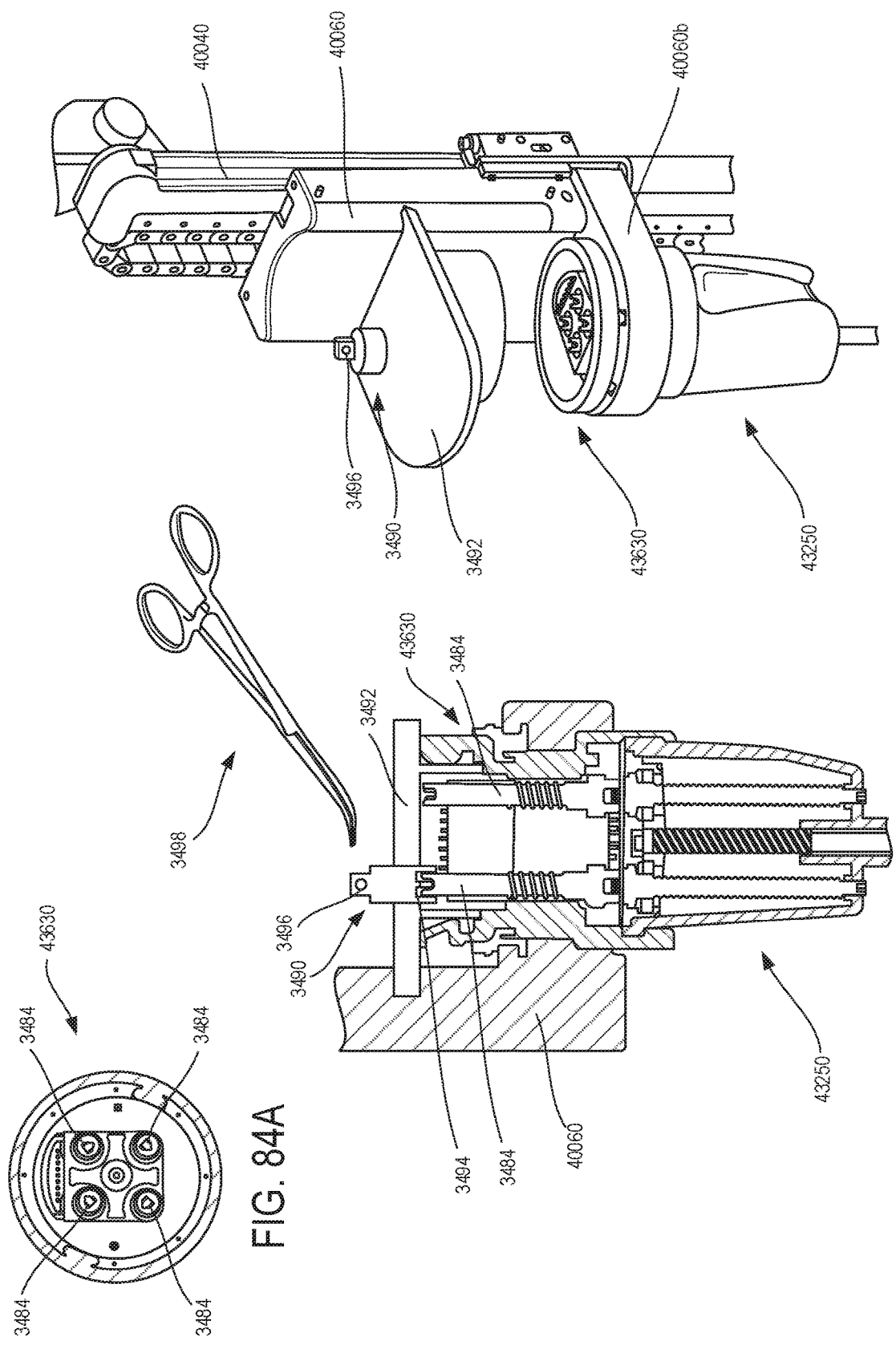

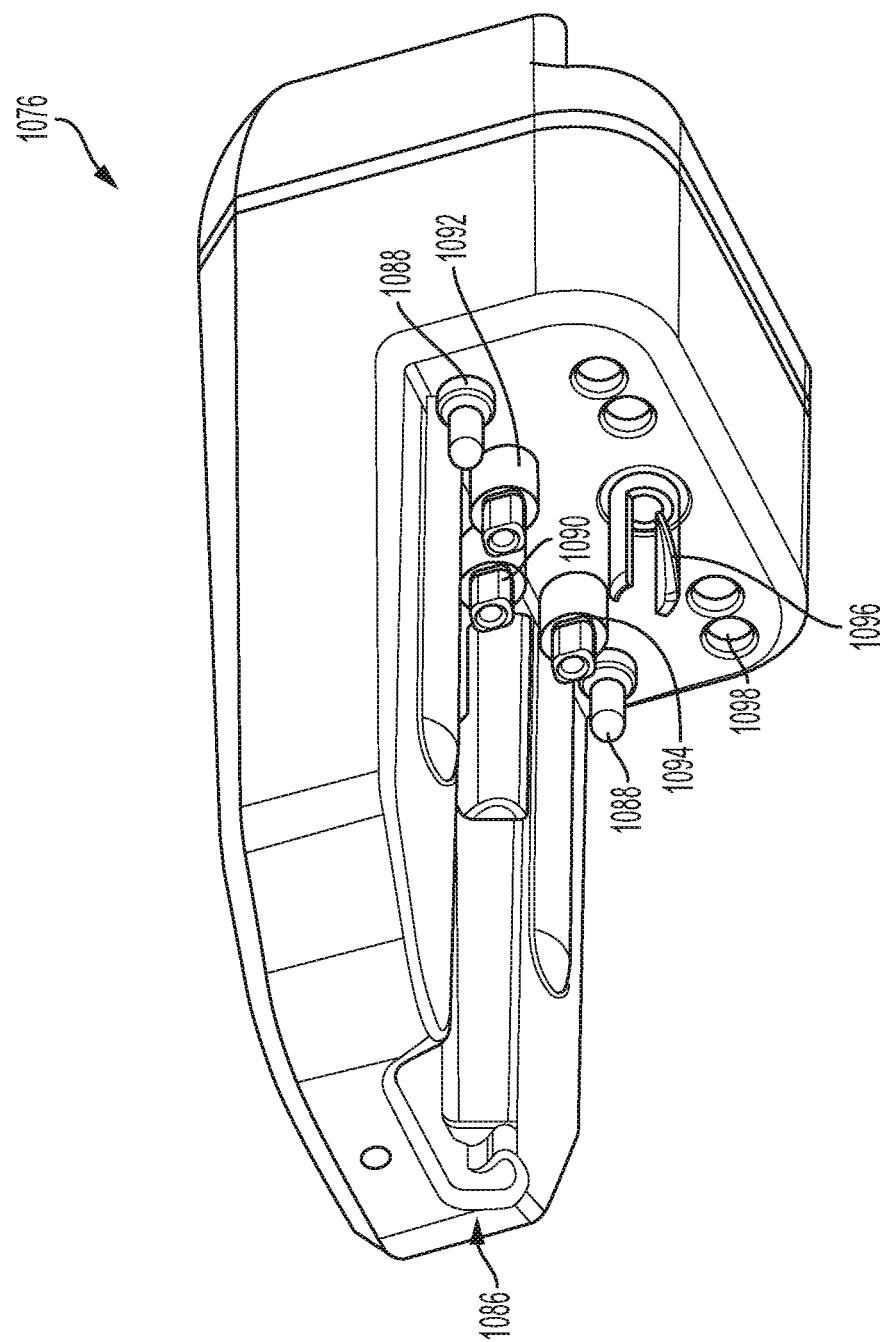

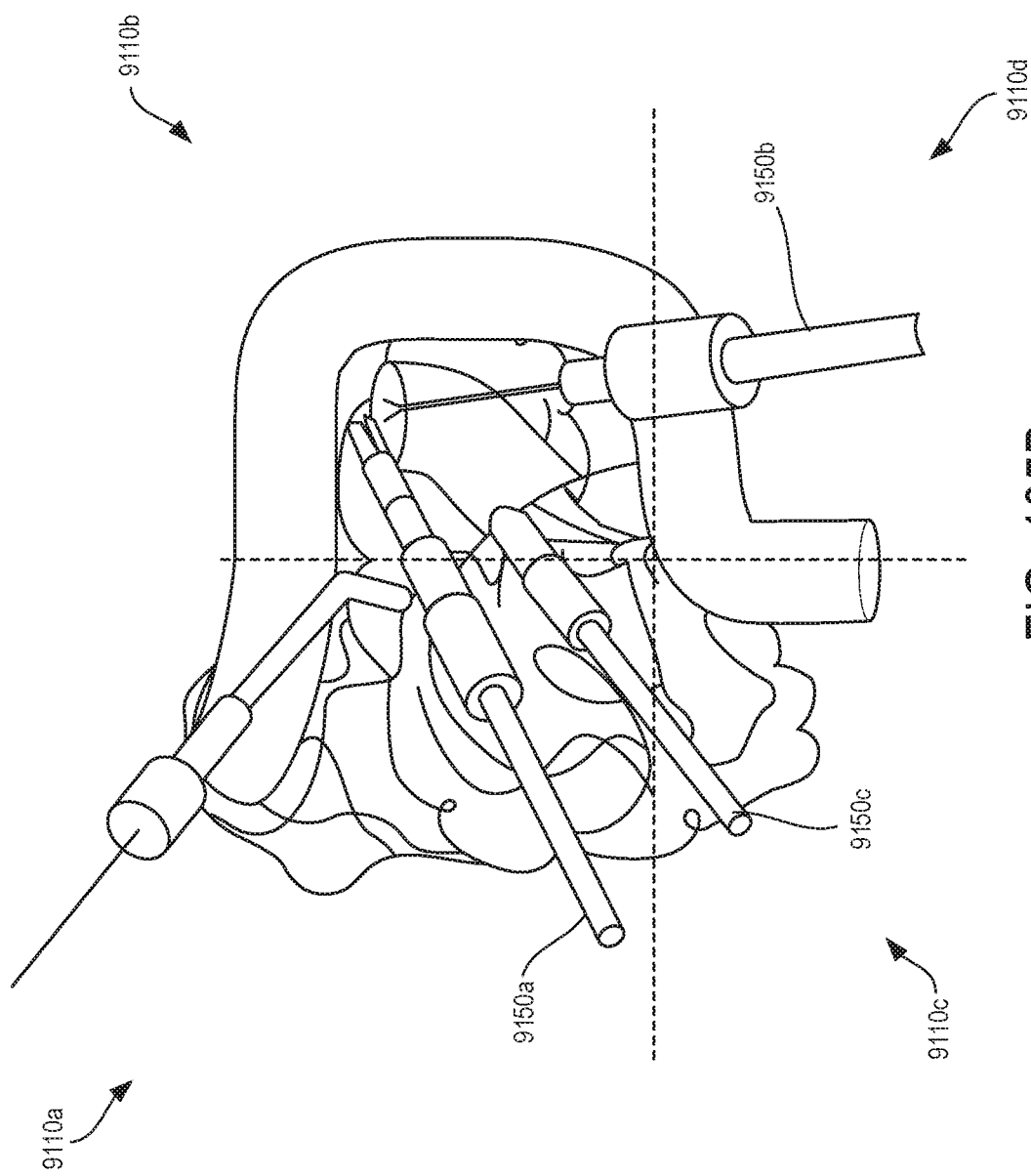

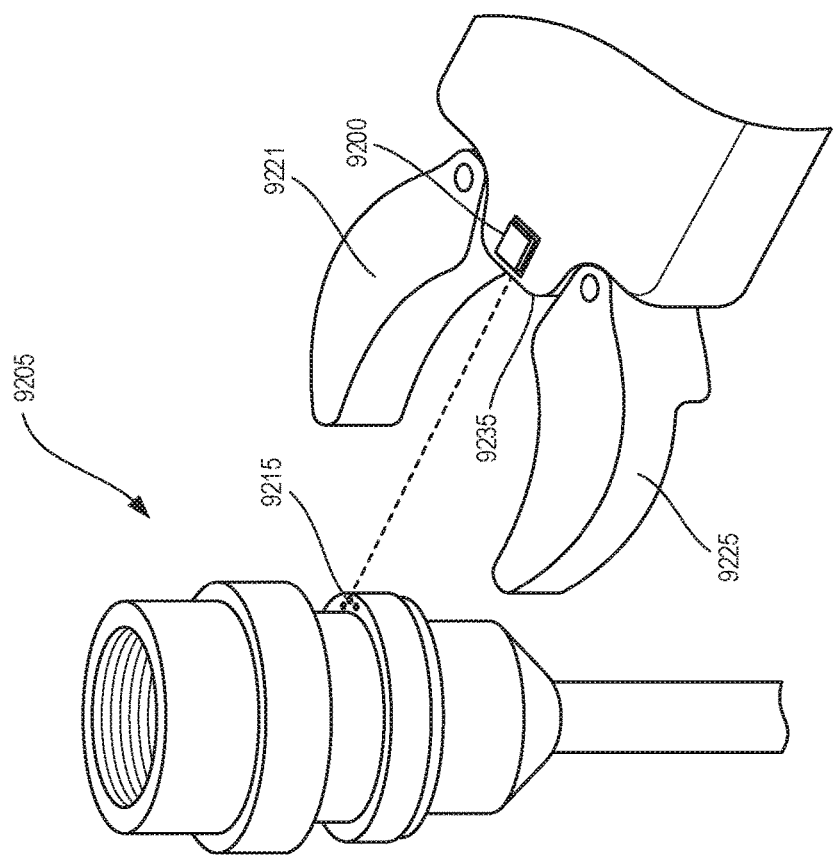
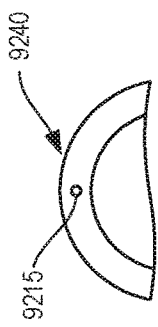
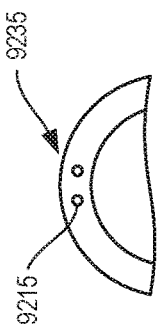
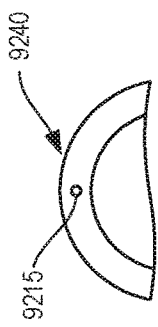

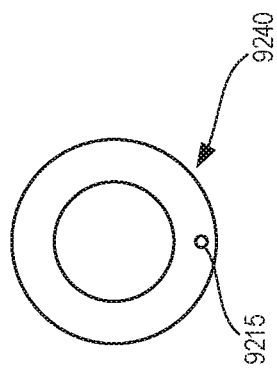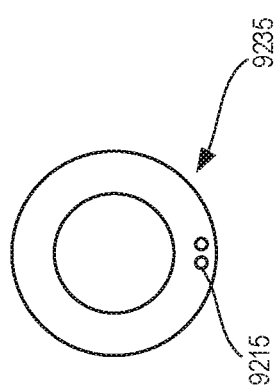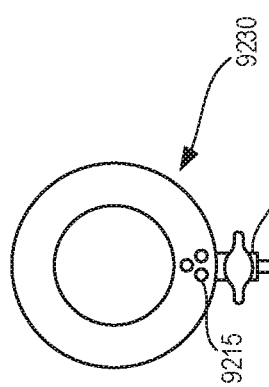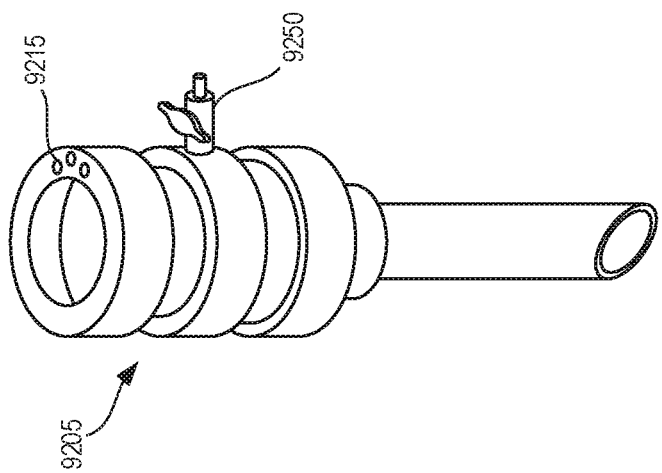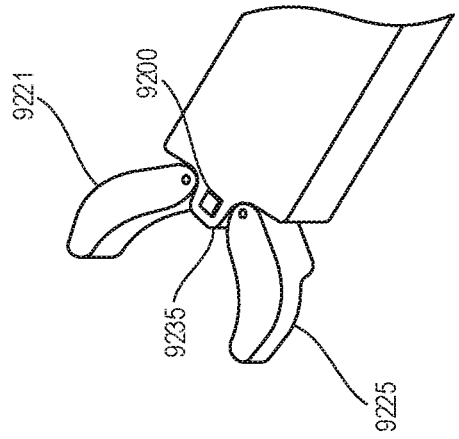

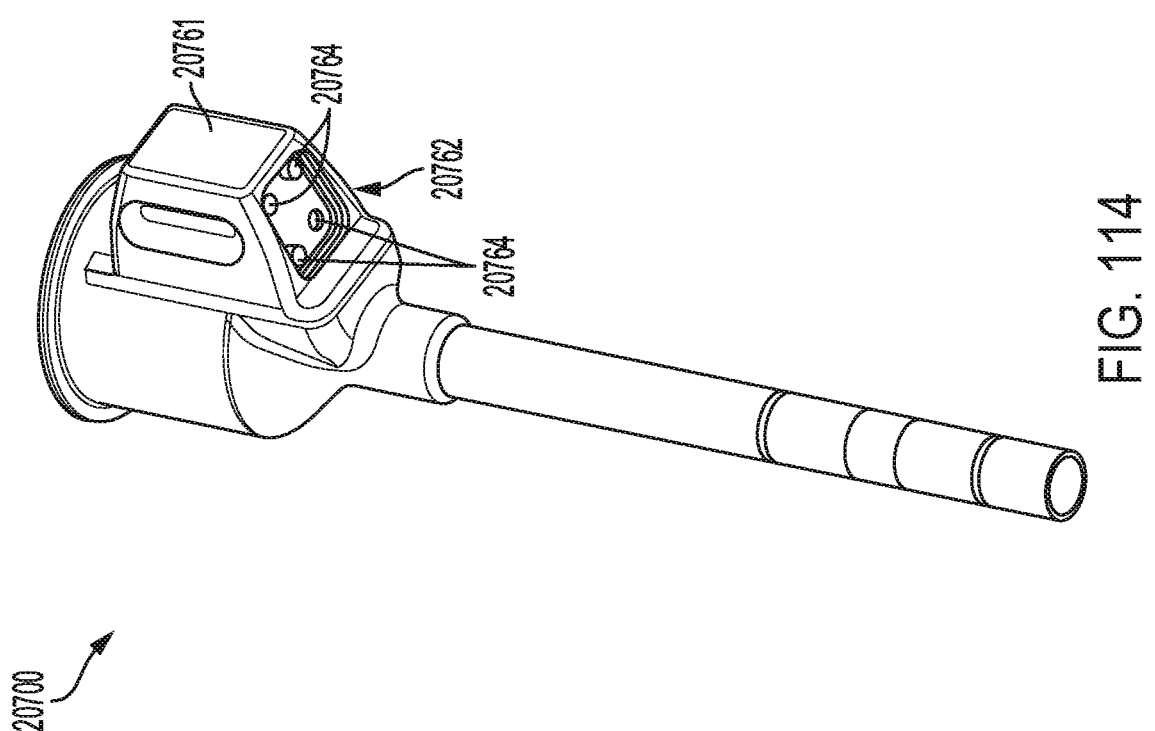

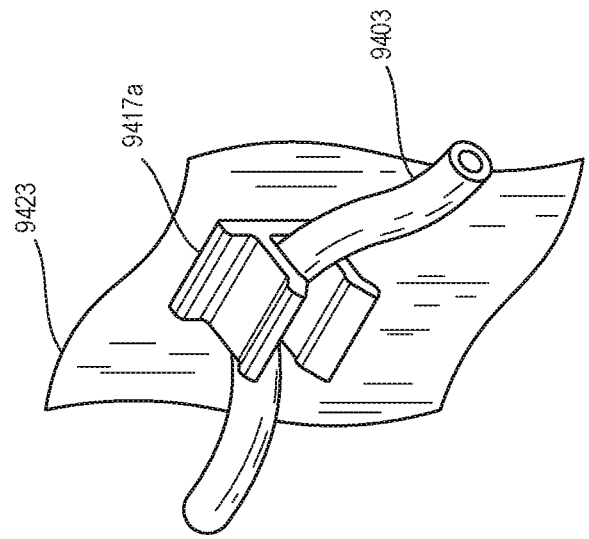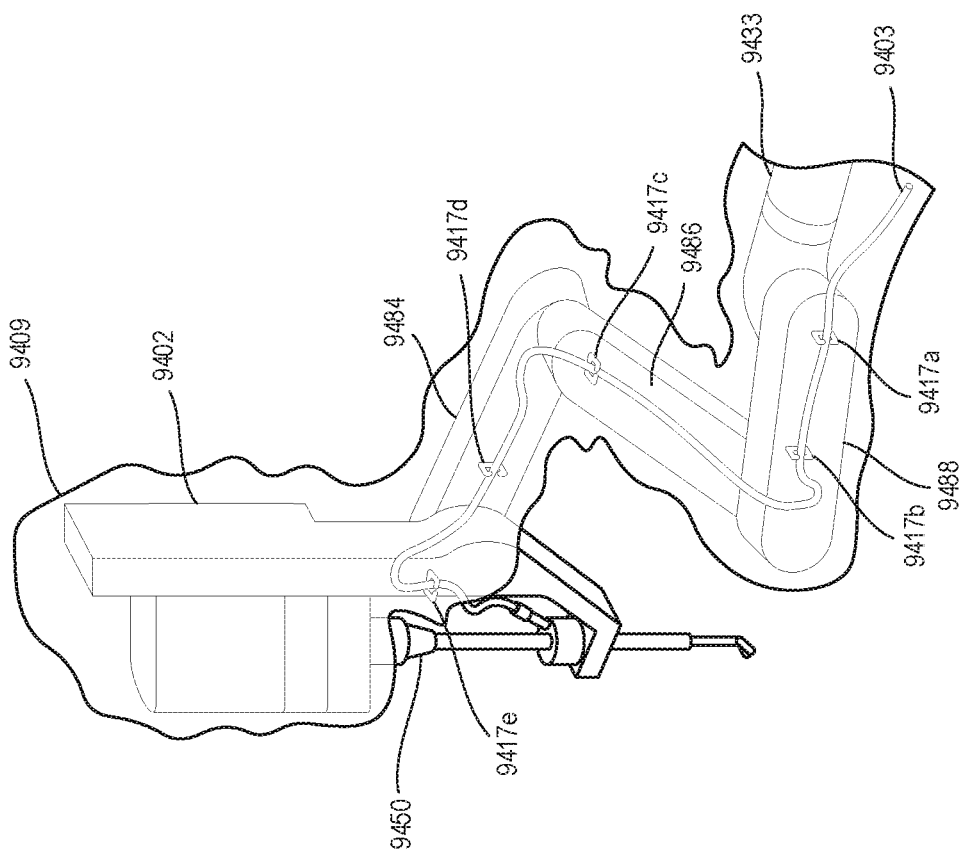

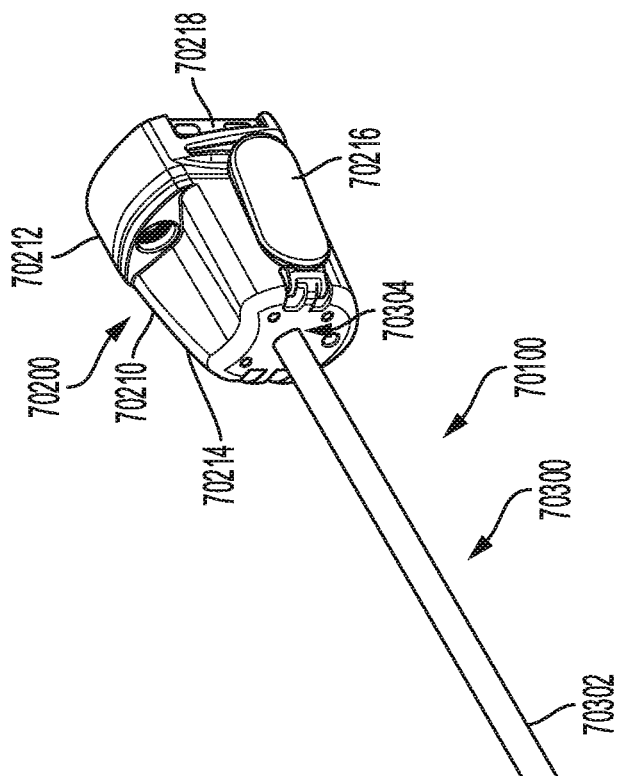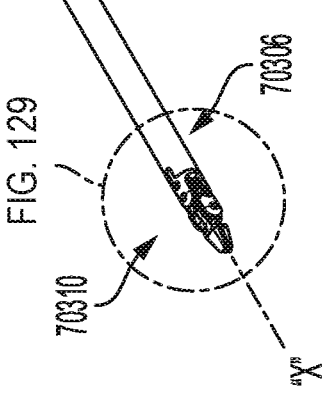
FIG. 121

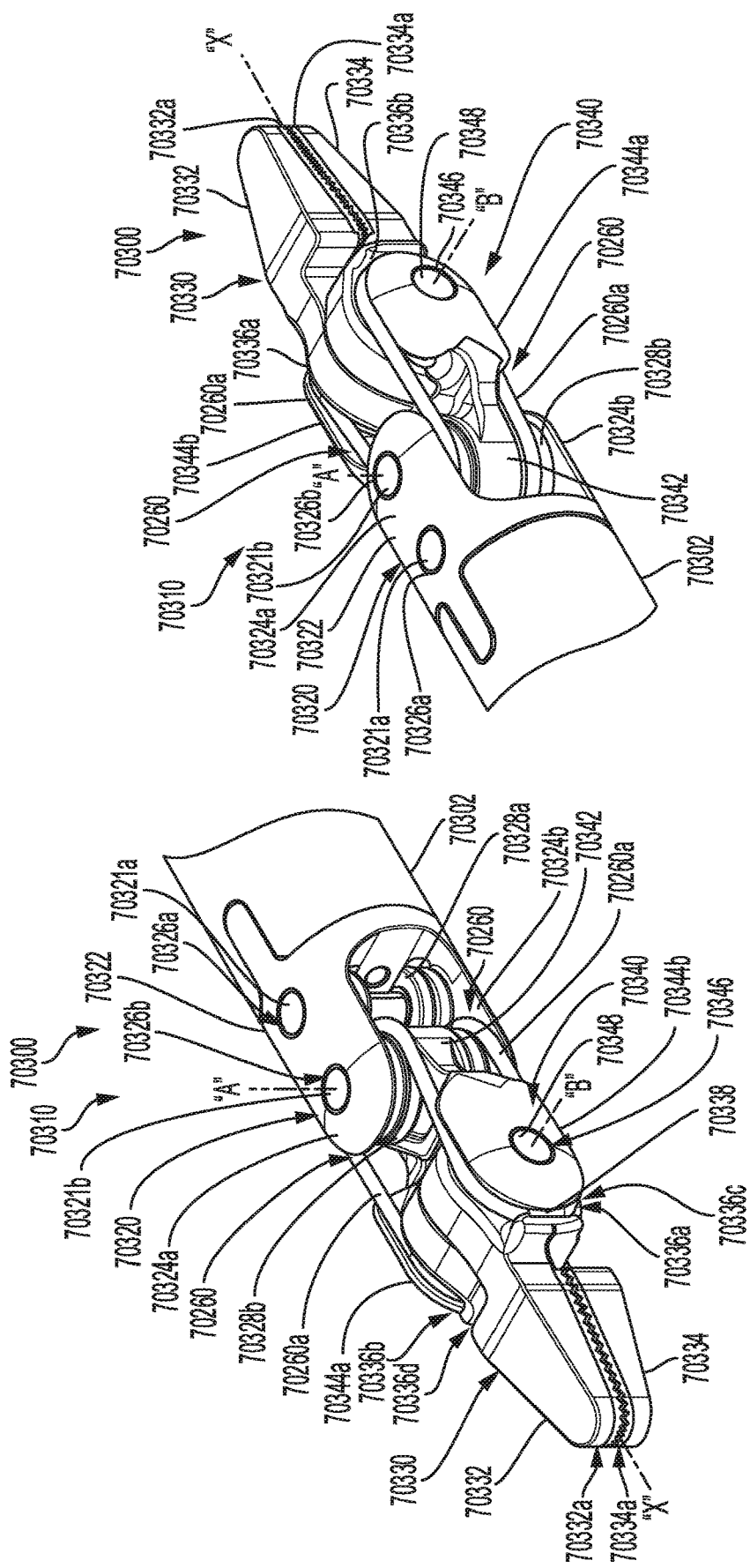

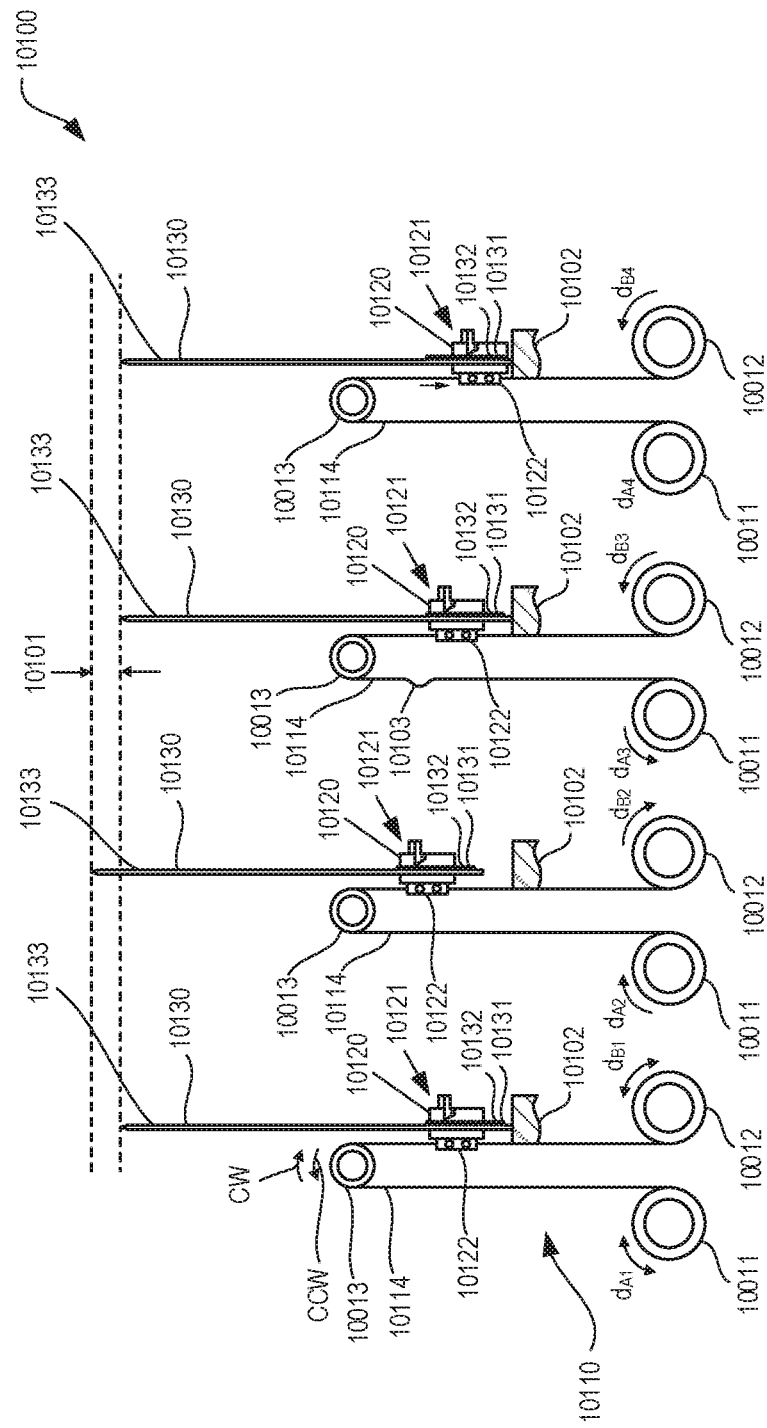

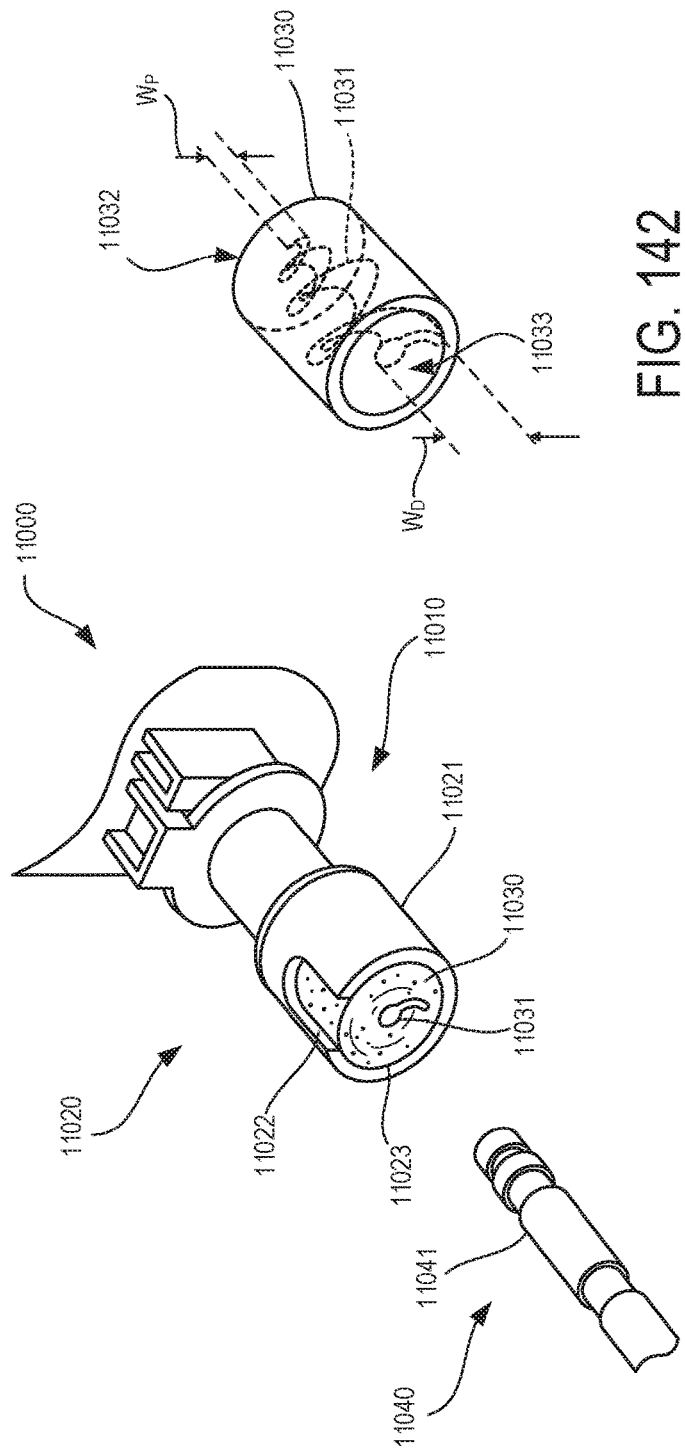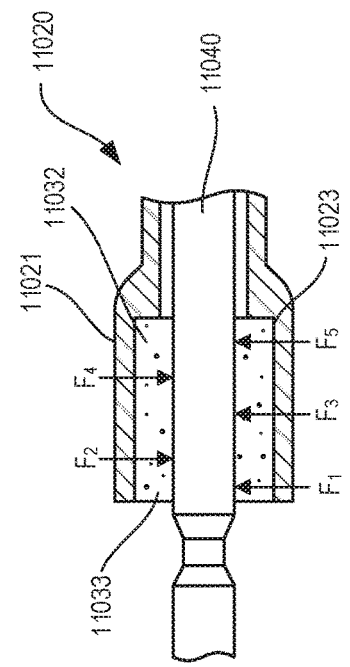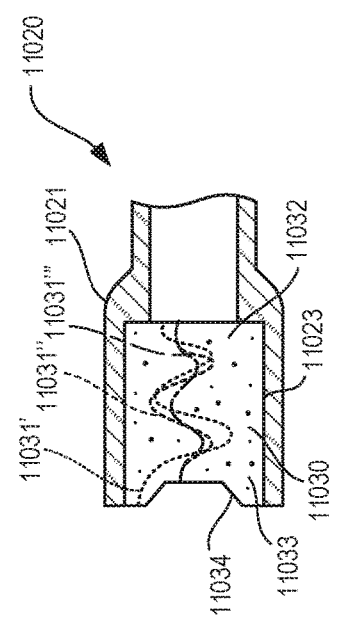
FIG. 141
FIG. 142
FIG. 143
FIG. 144

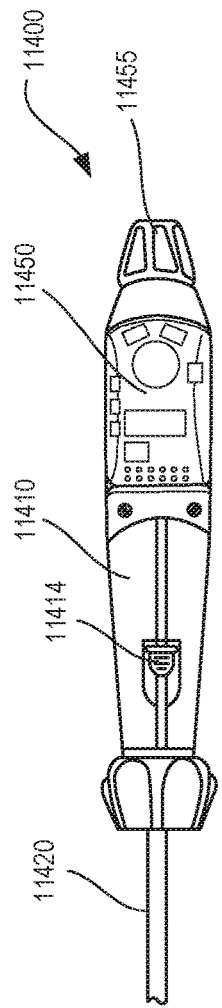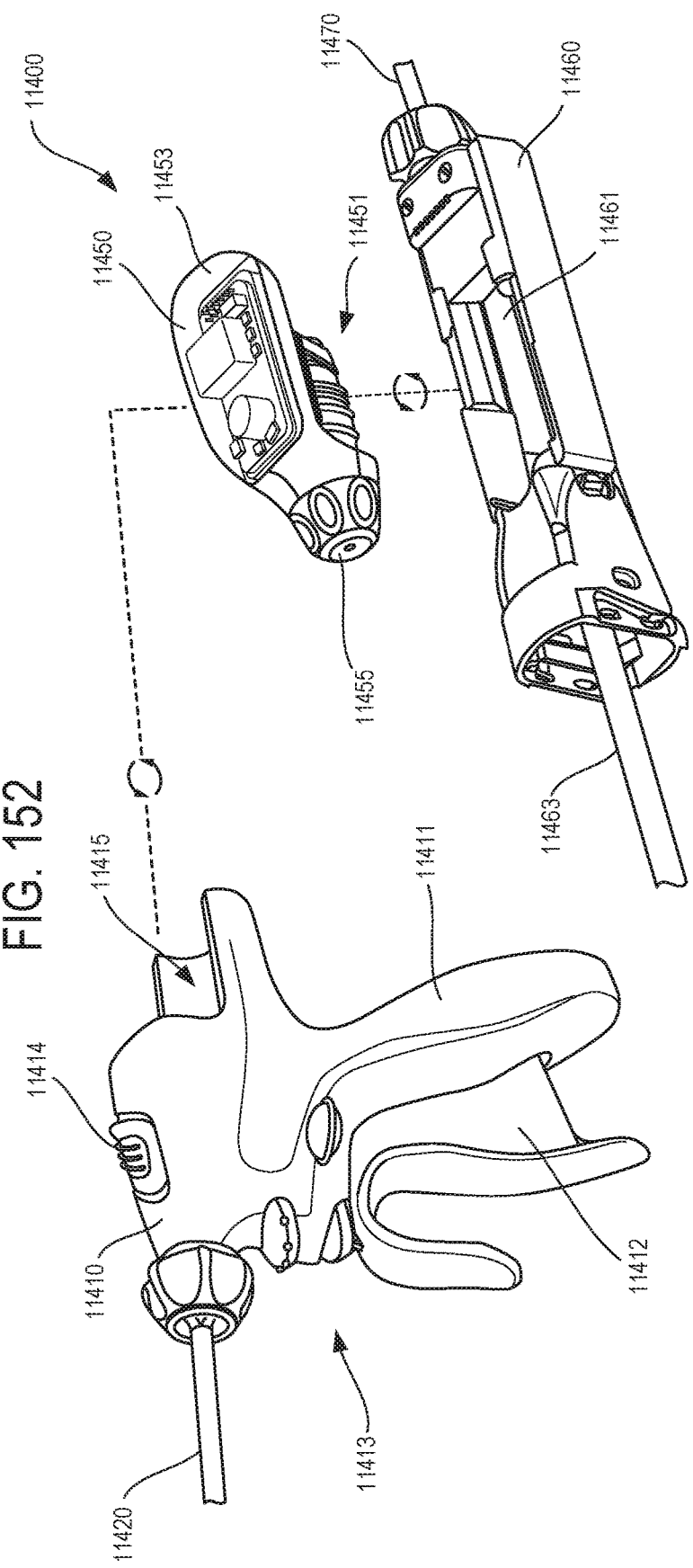

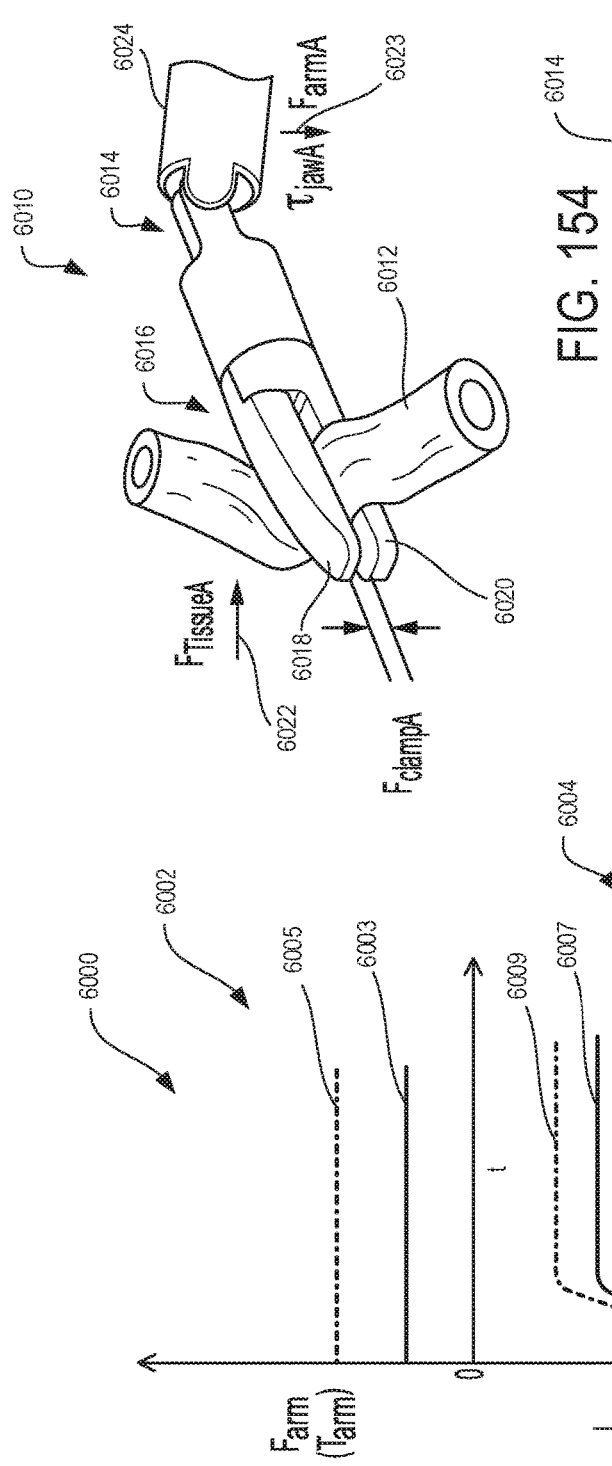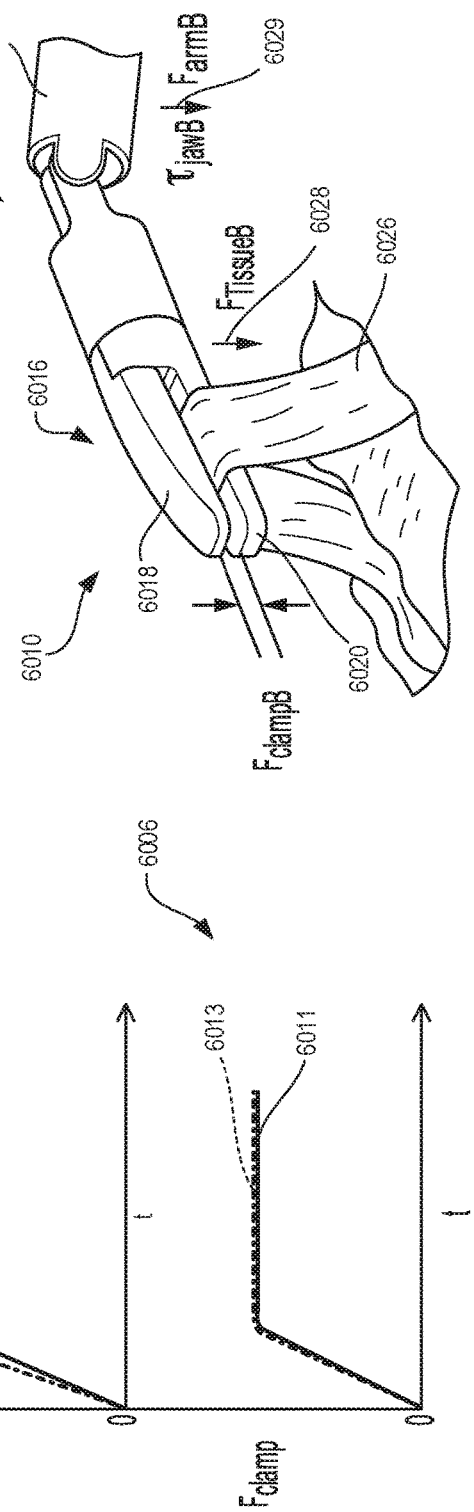
FIG. 153
FIG. 154
FIG. 155

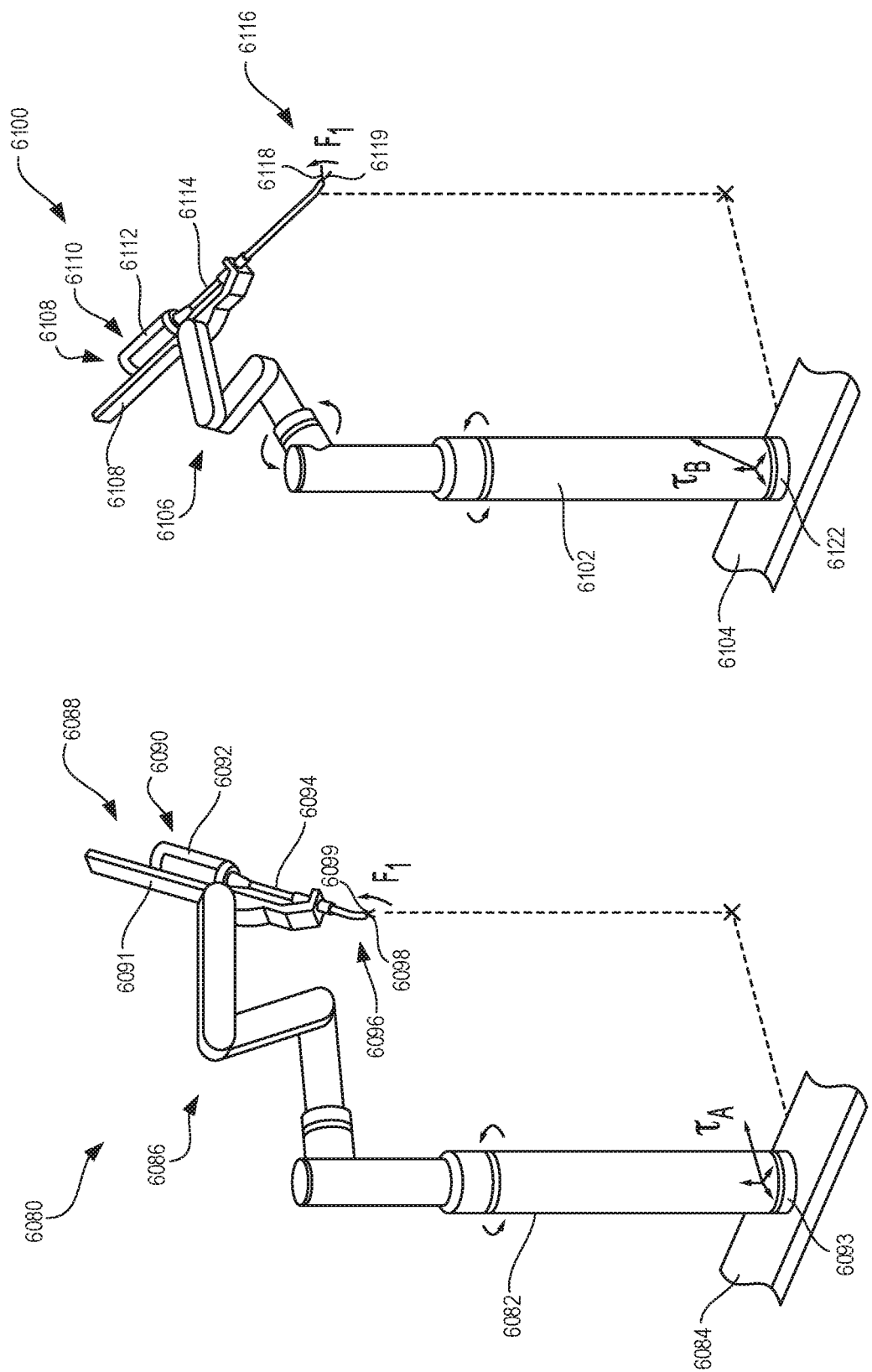

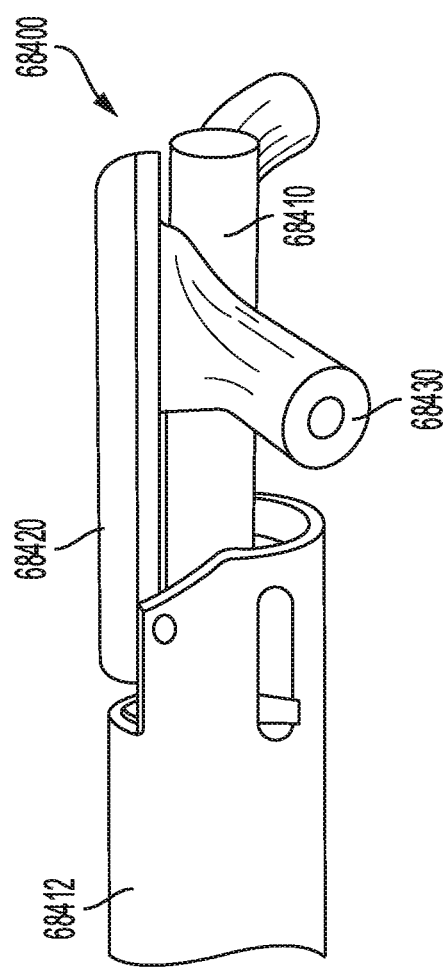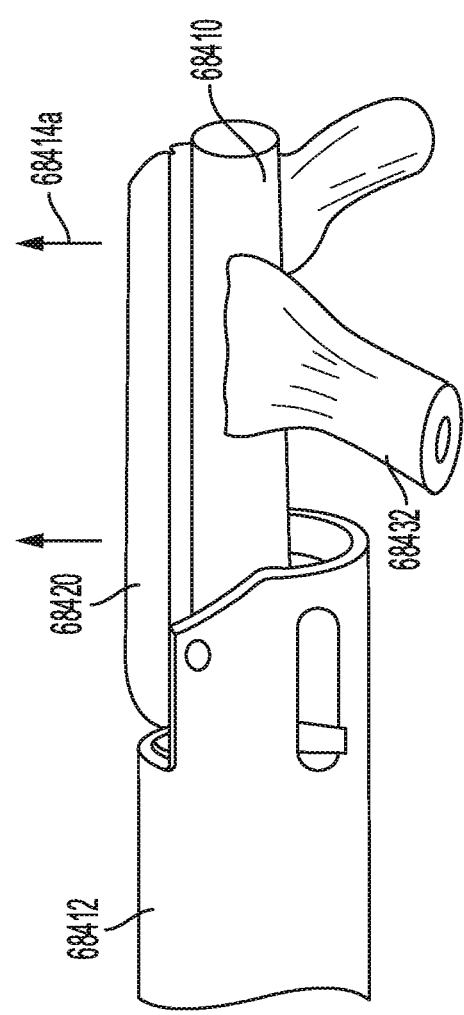

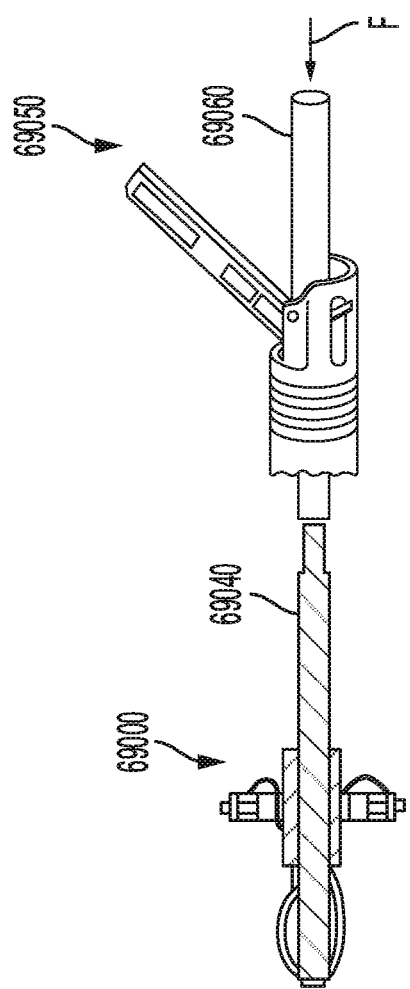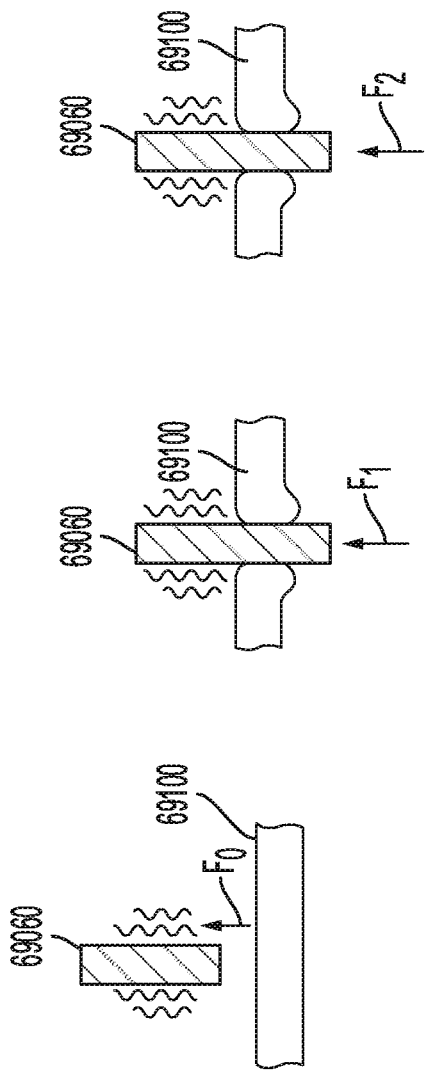

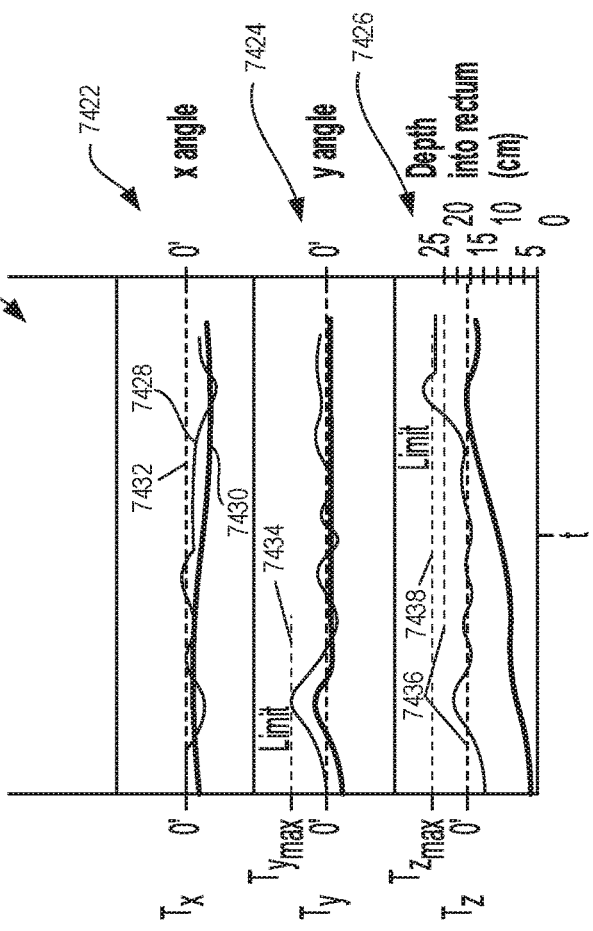
FIG. 195
FIG. 198
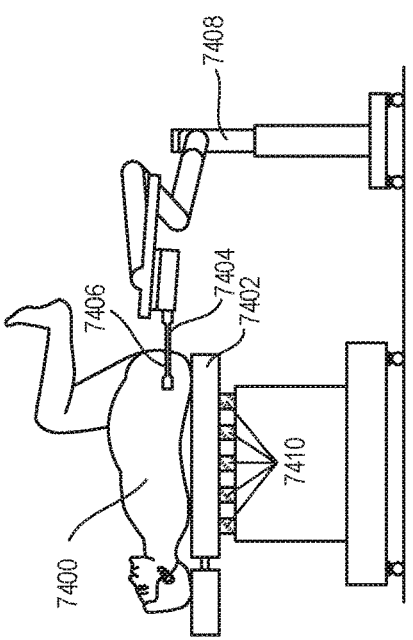
FIG. 194
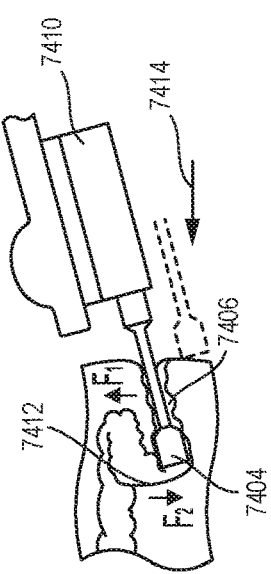
FIG. 196
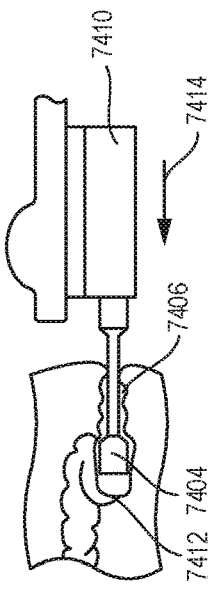
FIG. 197

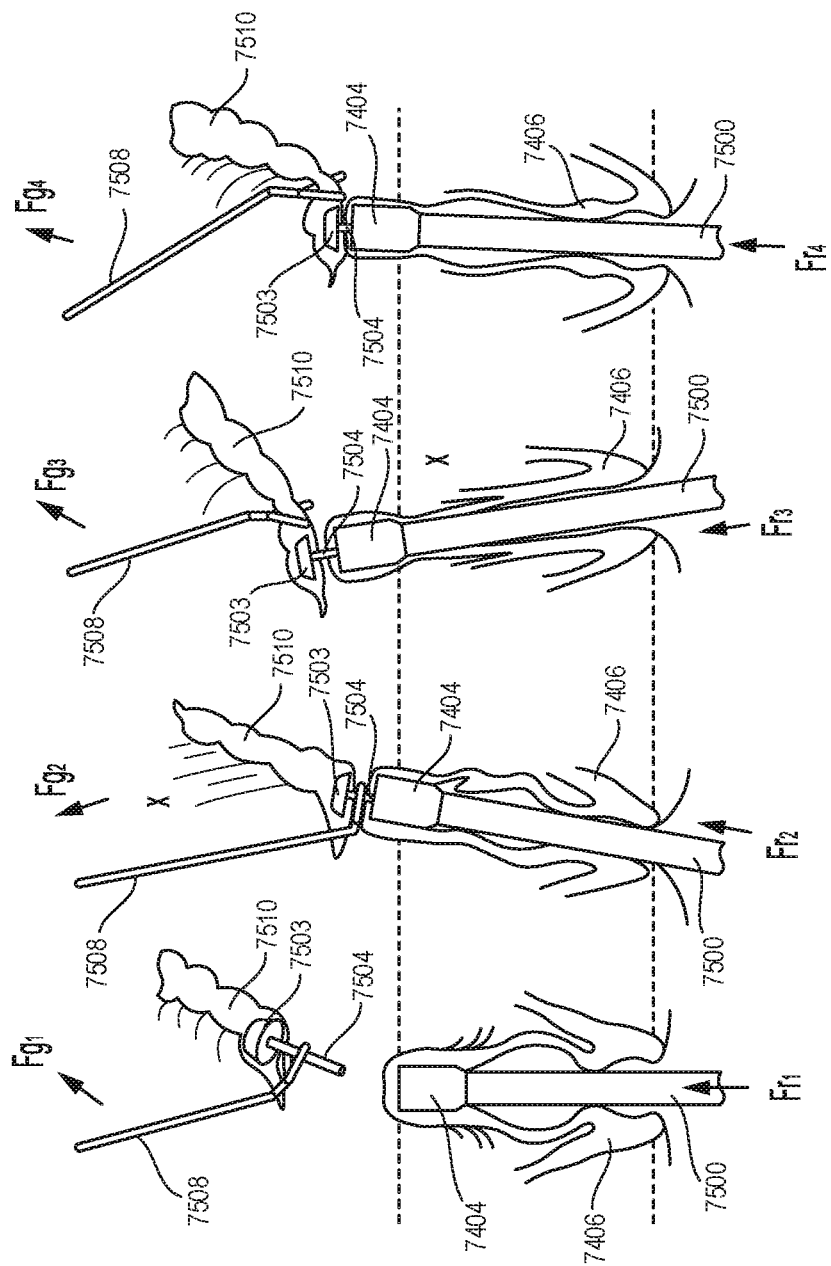

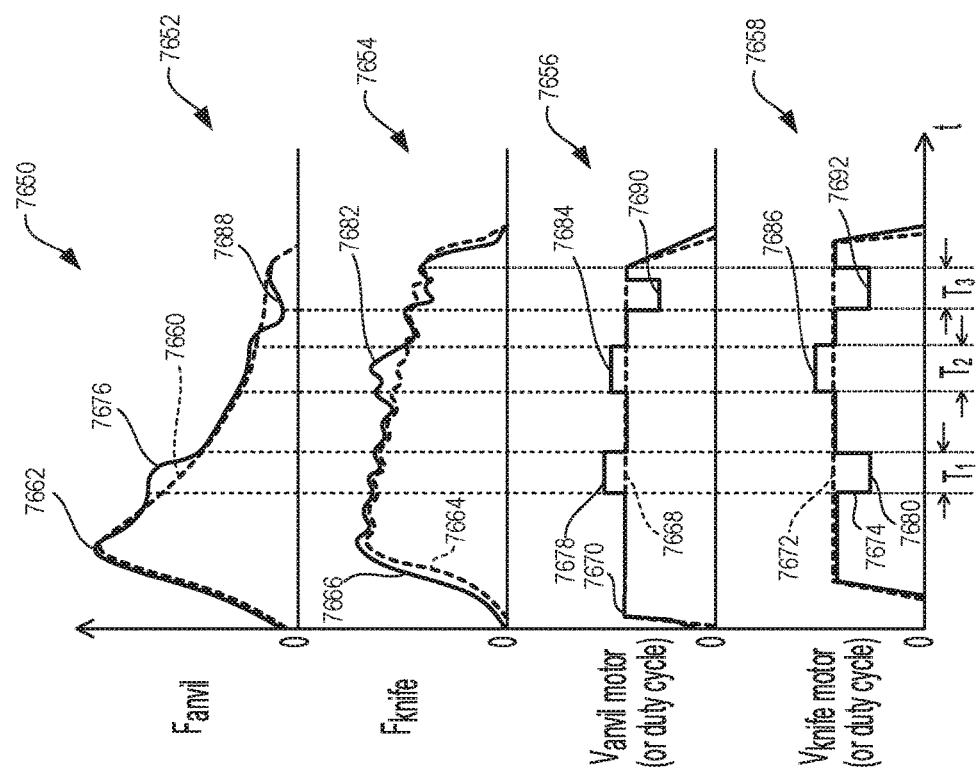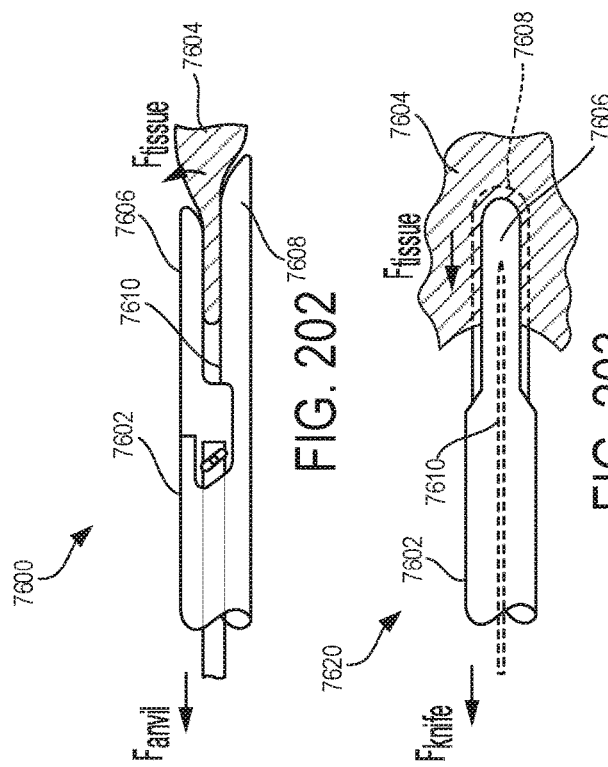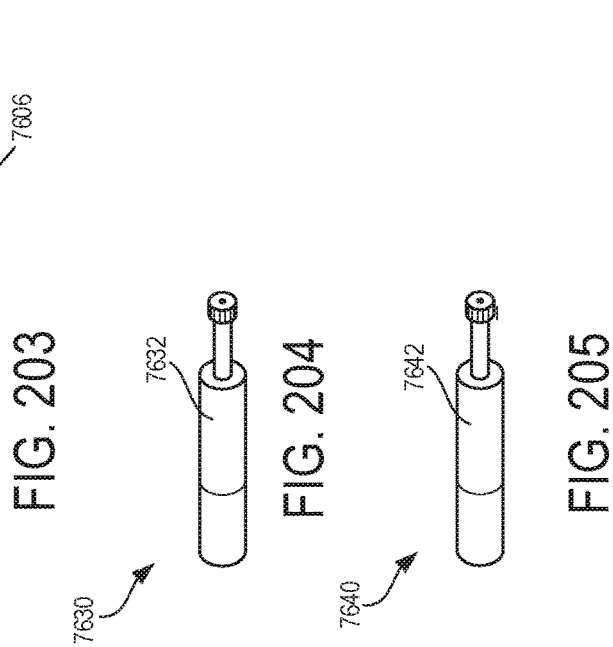

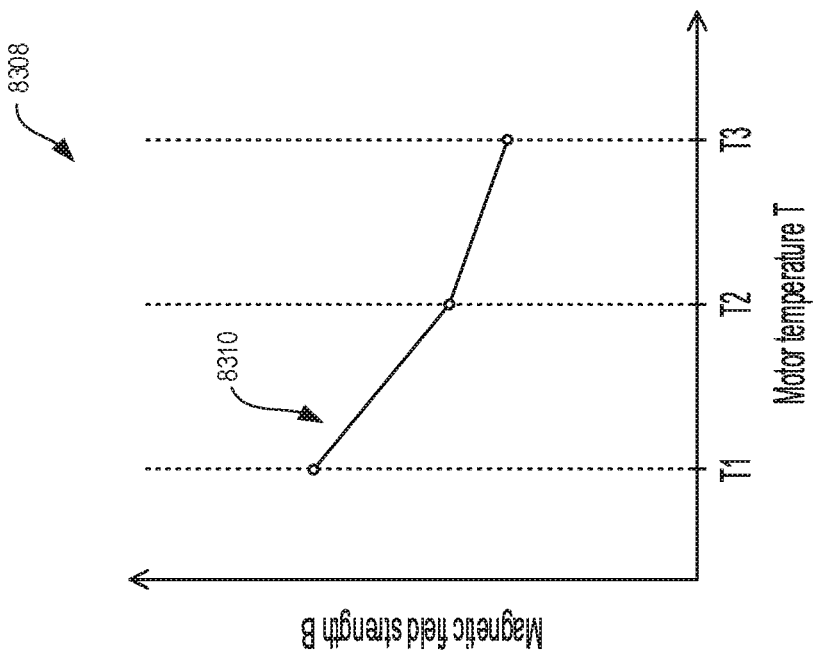
FIG. 220
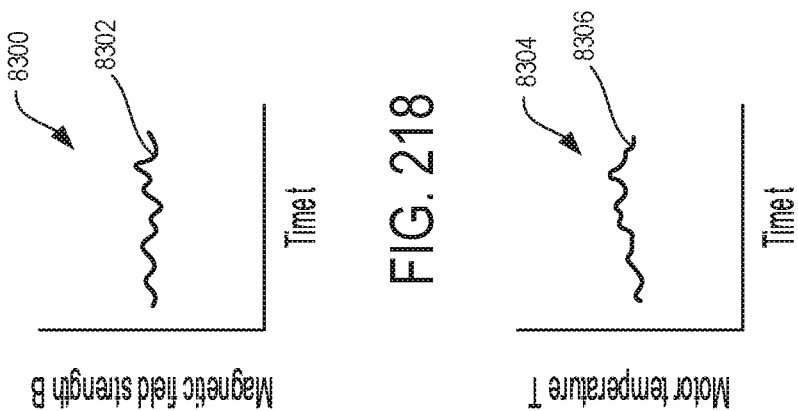
FIG. 218
FIG. 219

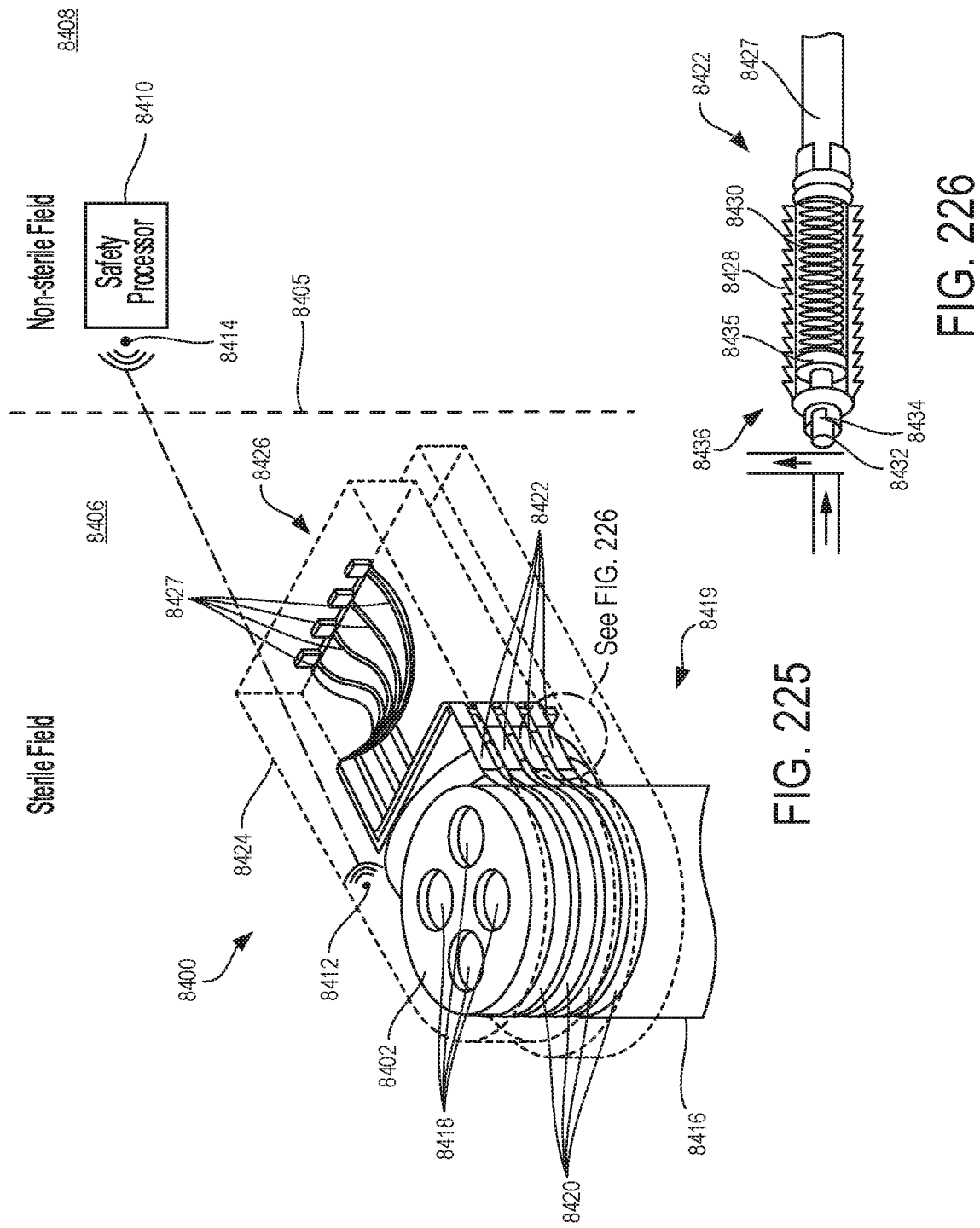

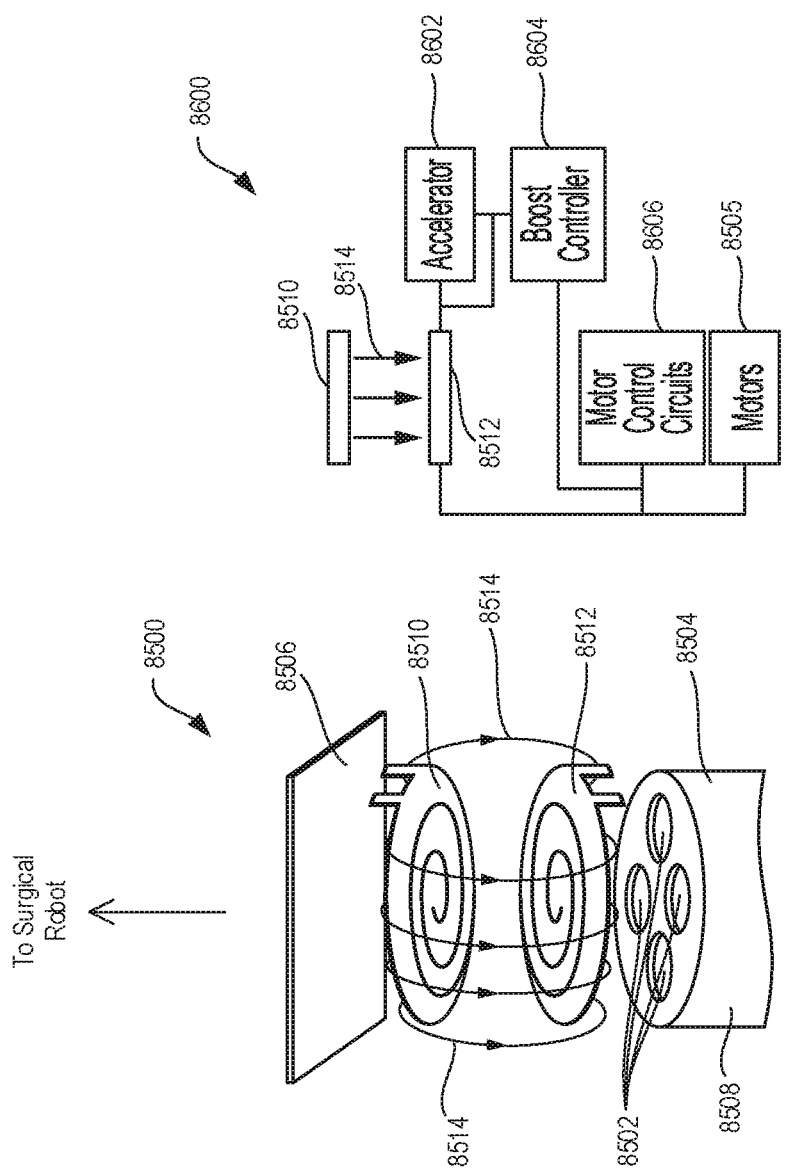

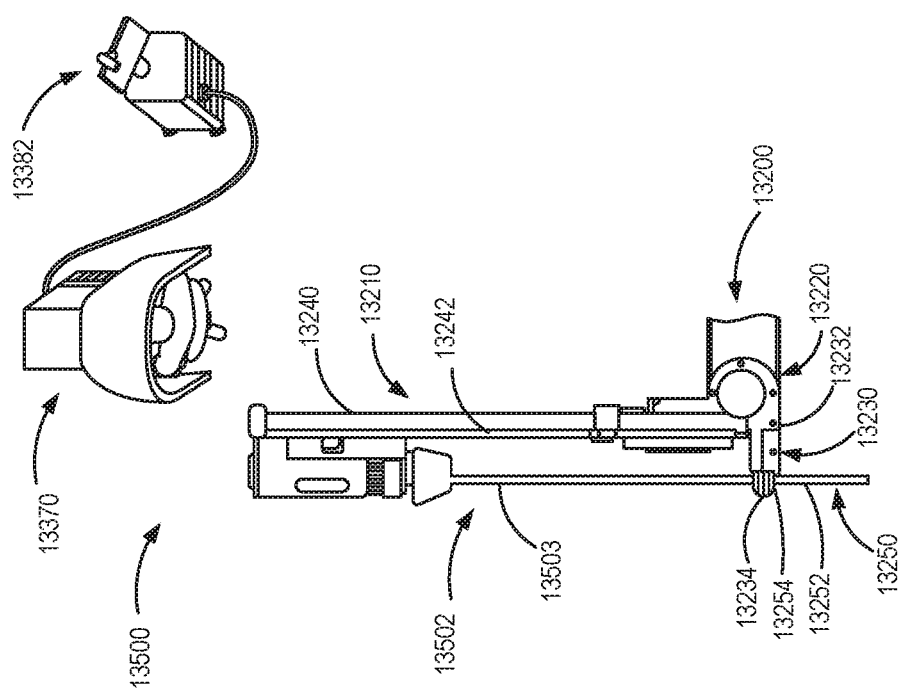
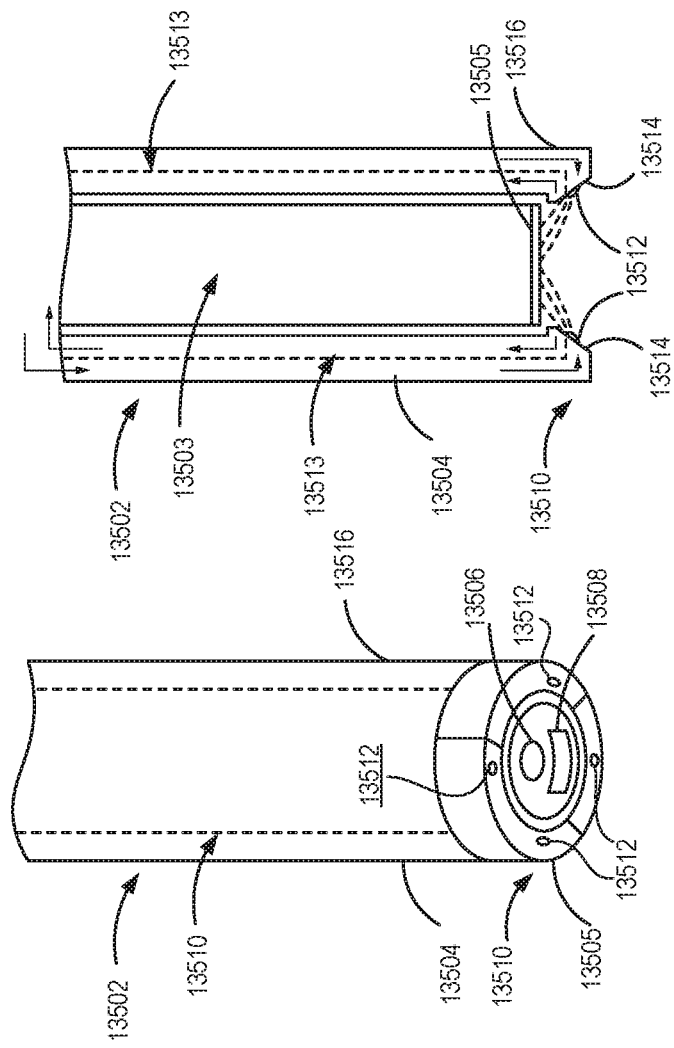
FIG. 241
FIG. 242
FIG. 243

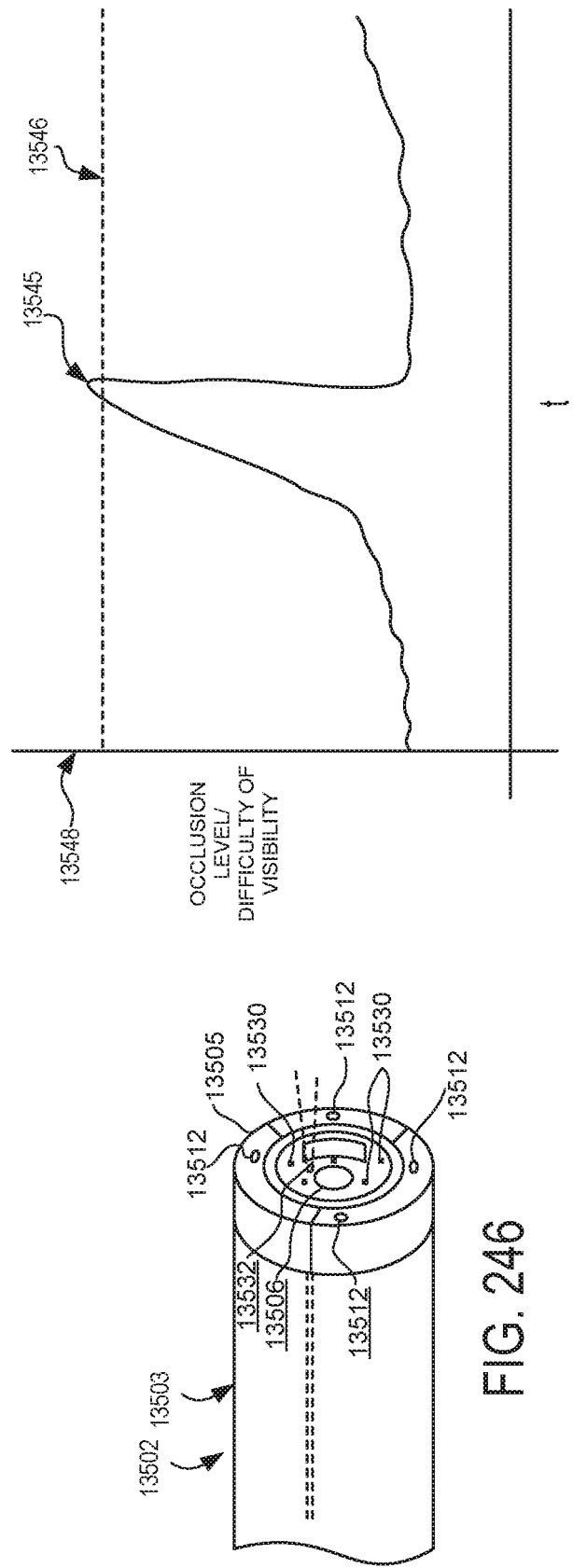

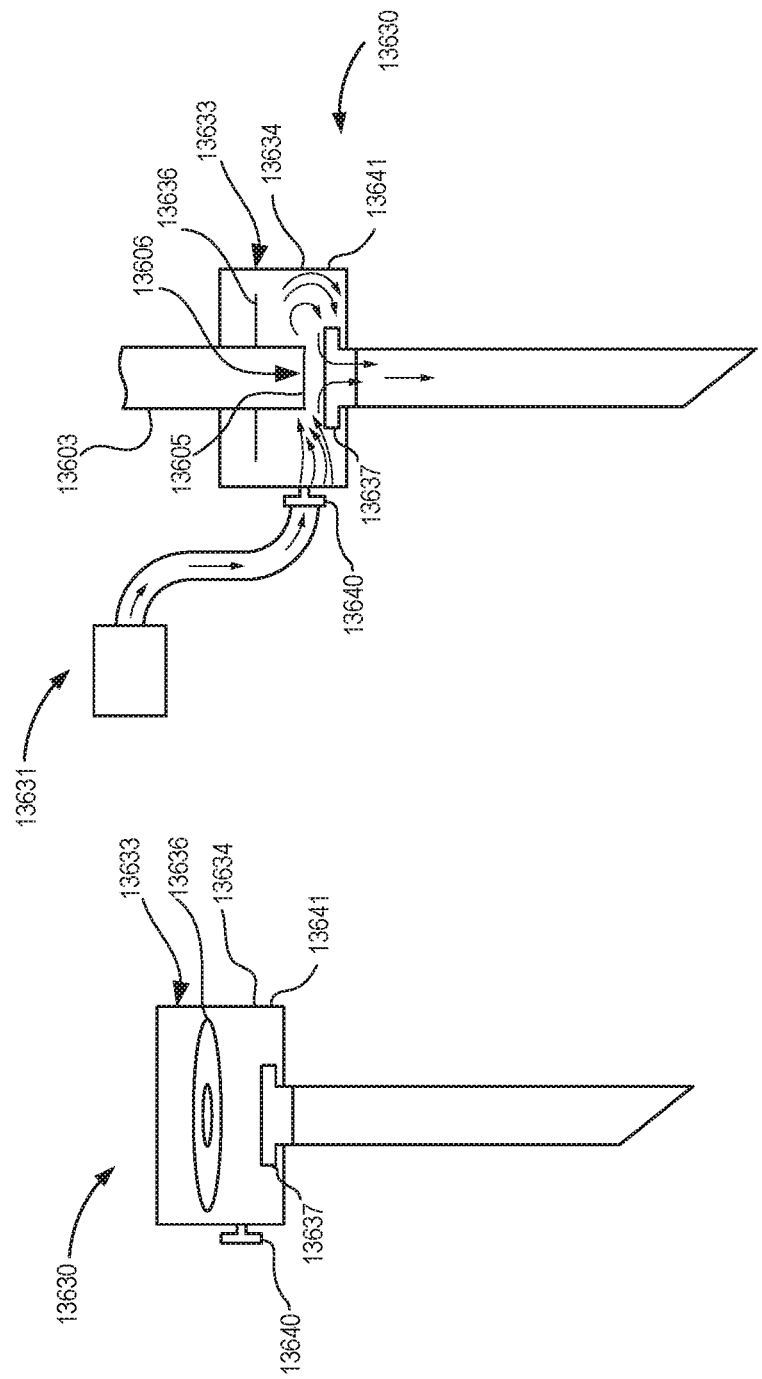

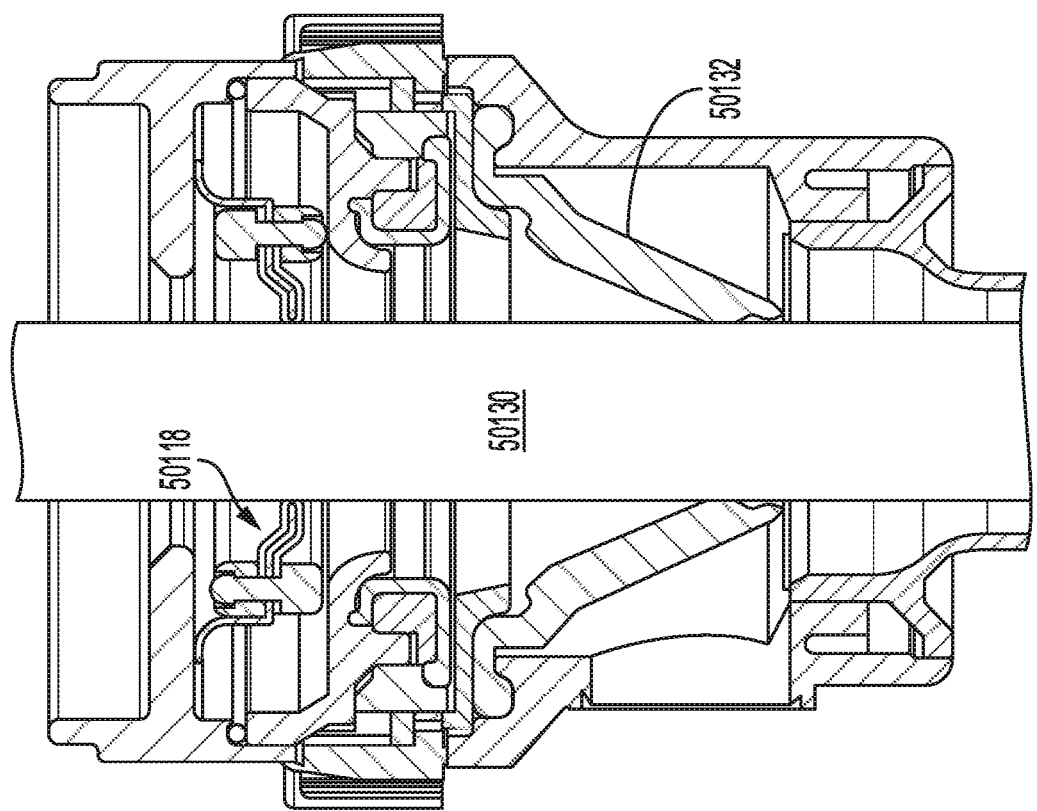

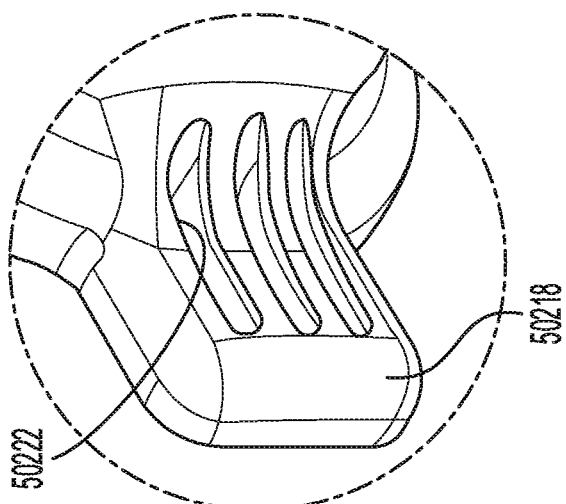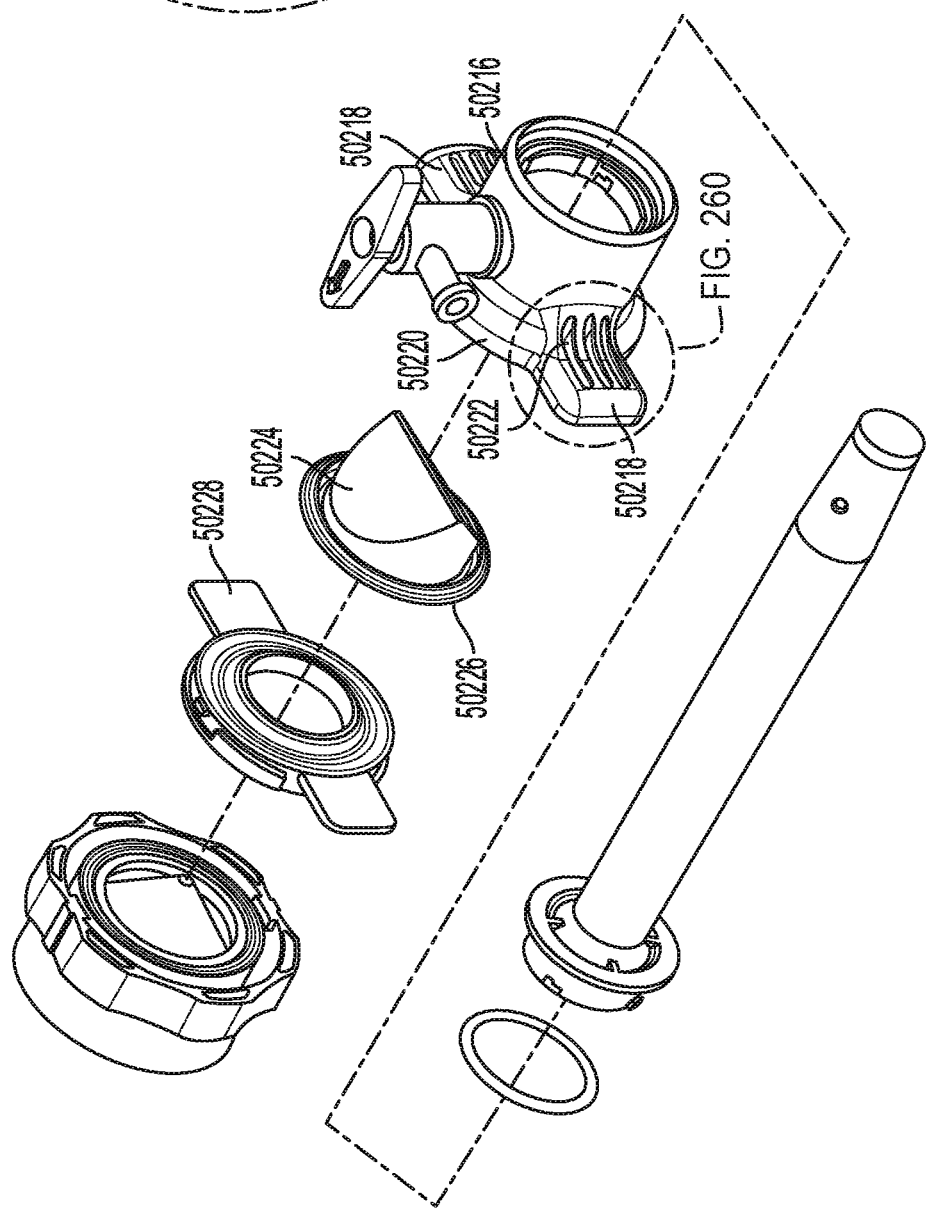

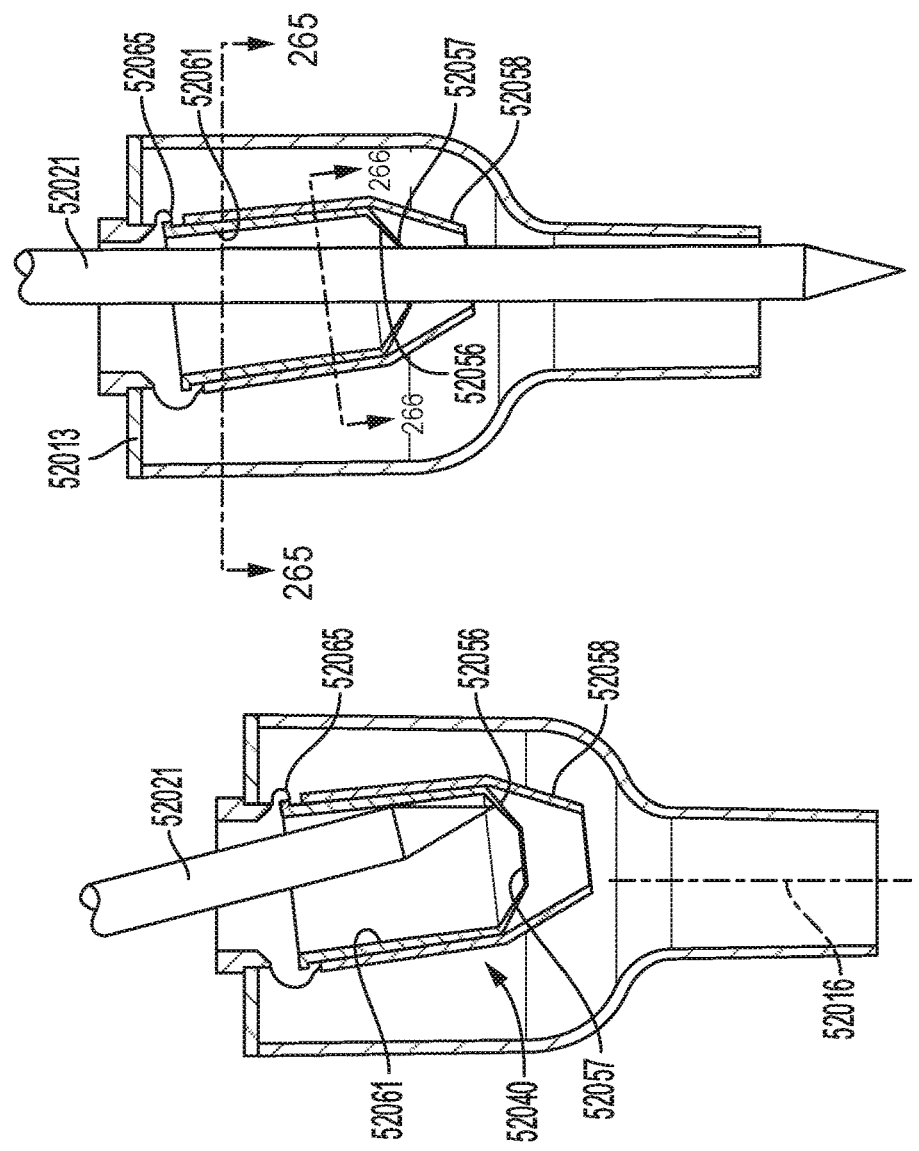

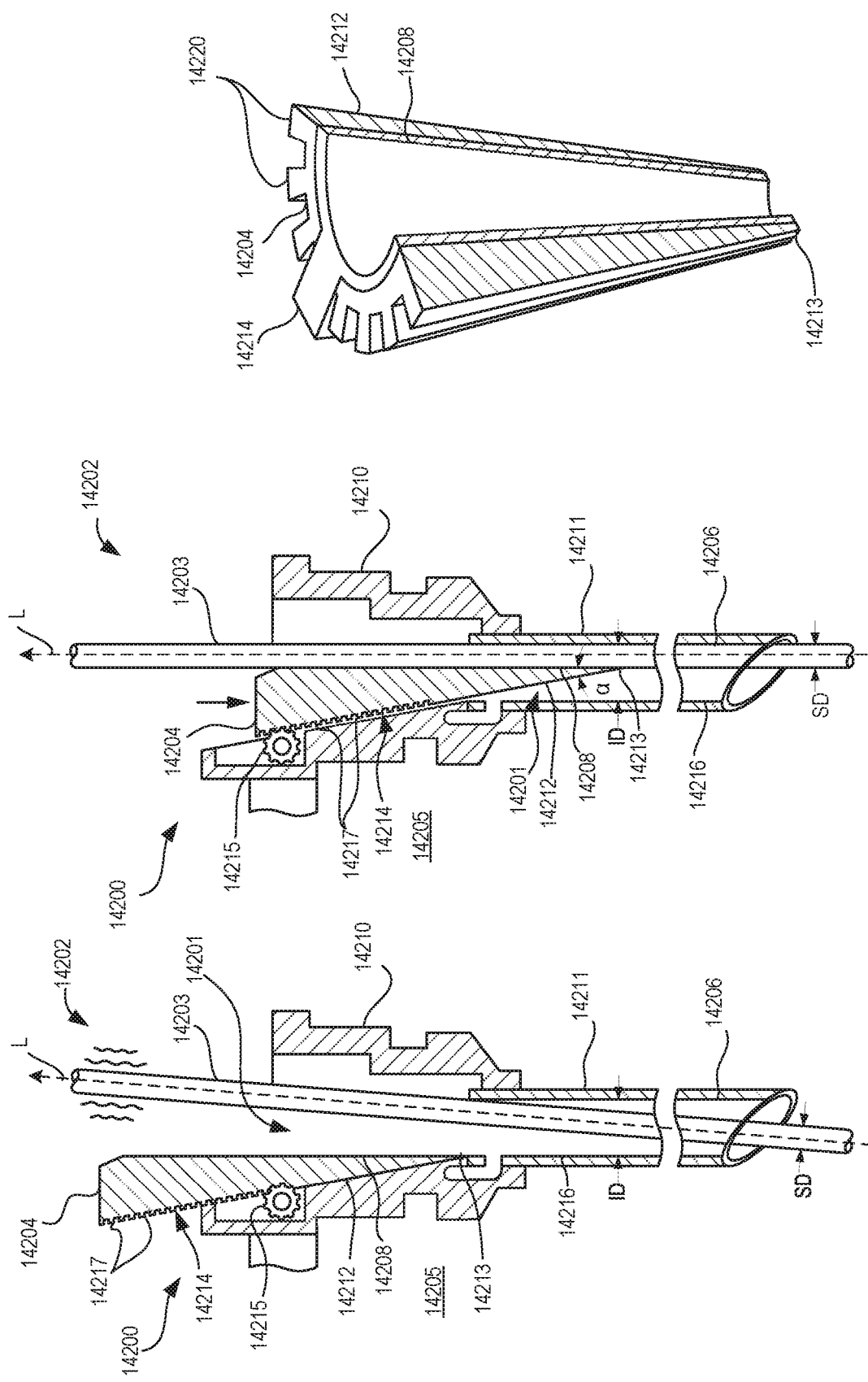

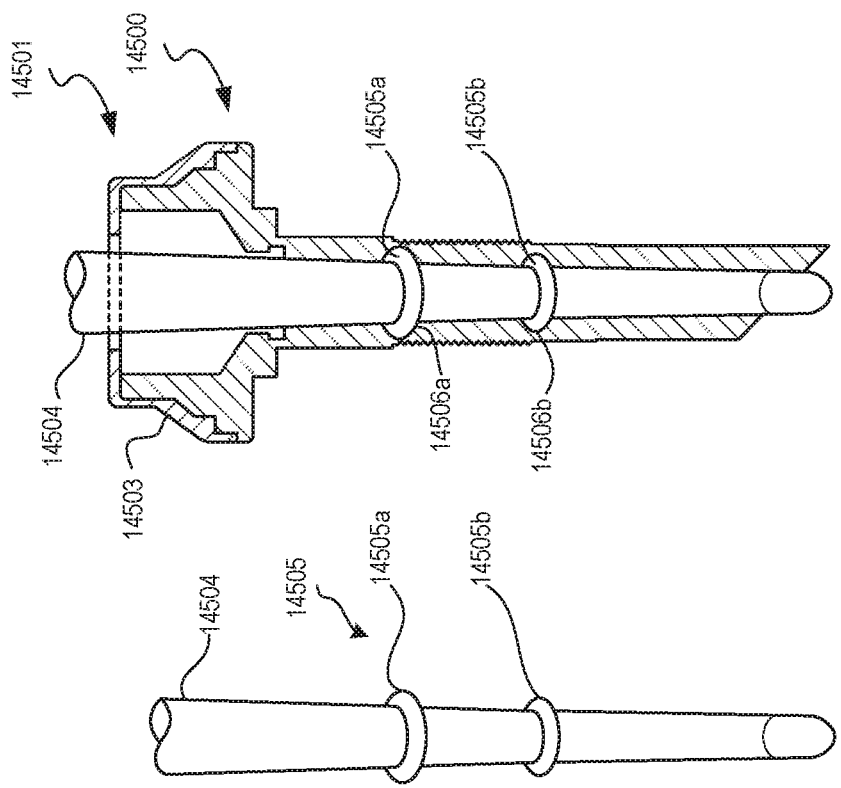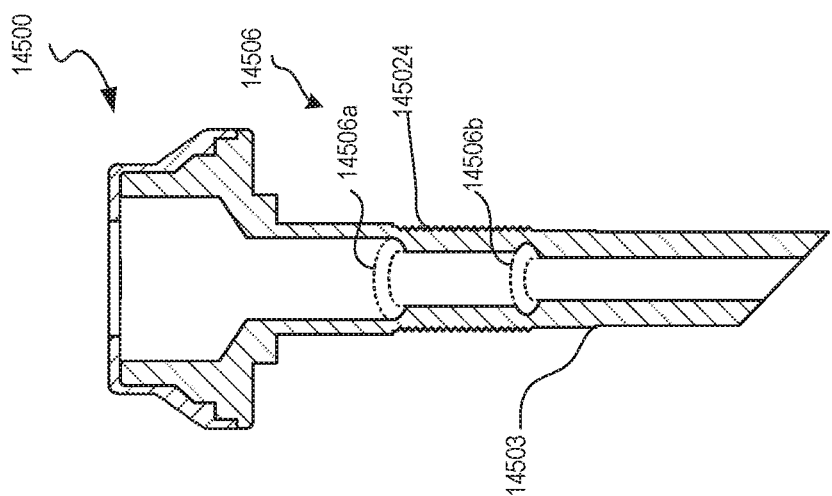

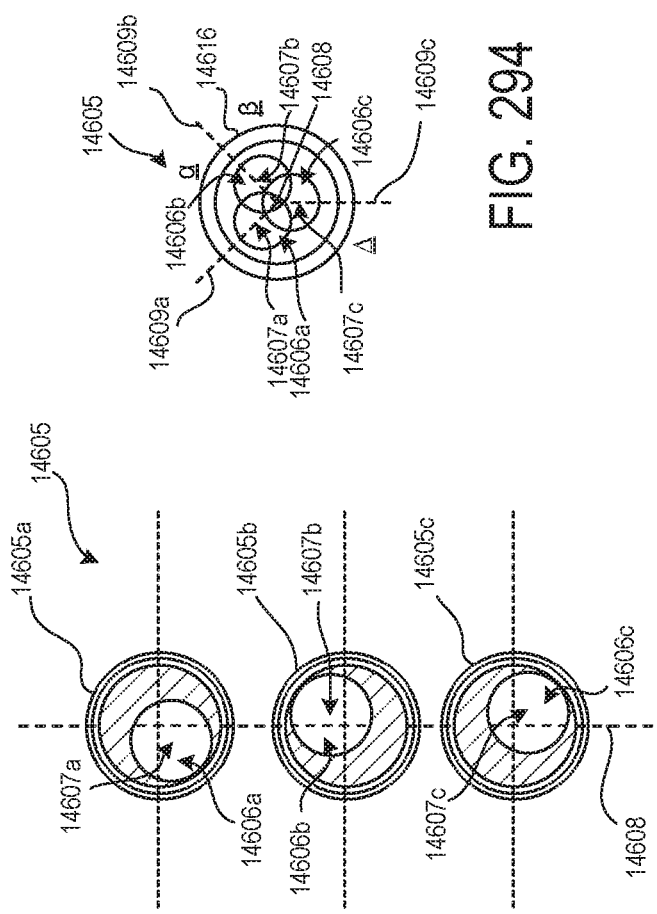
FIG. 294
FIG. 293
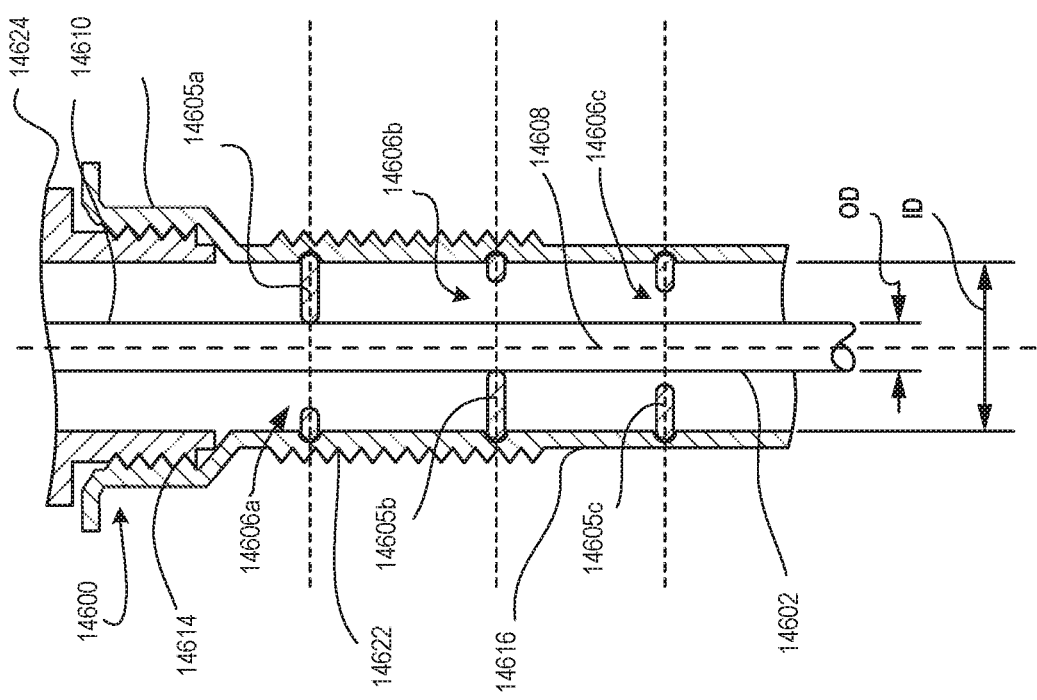
FIG. 292

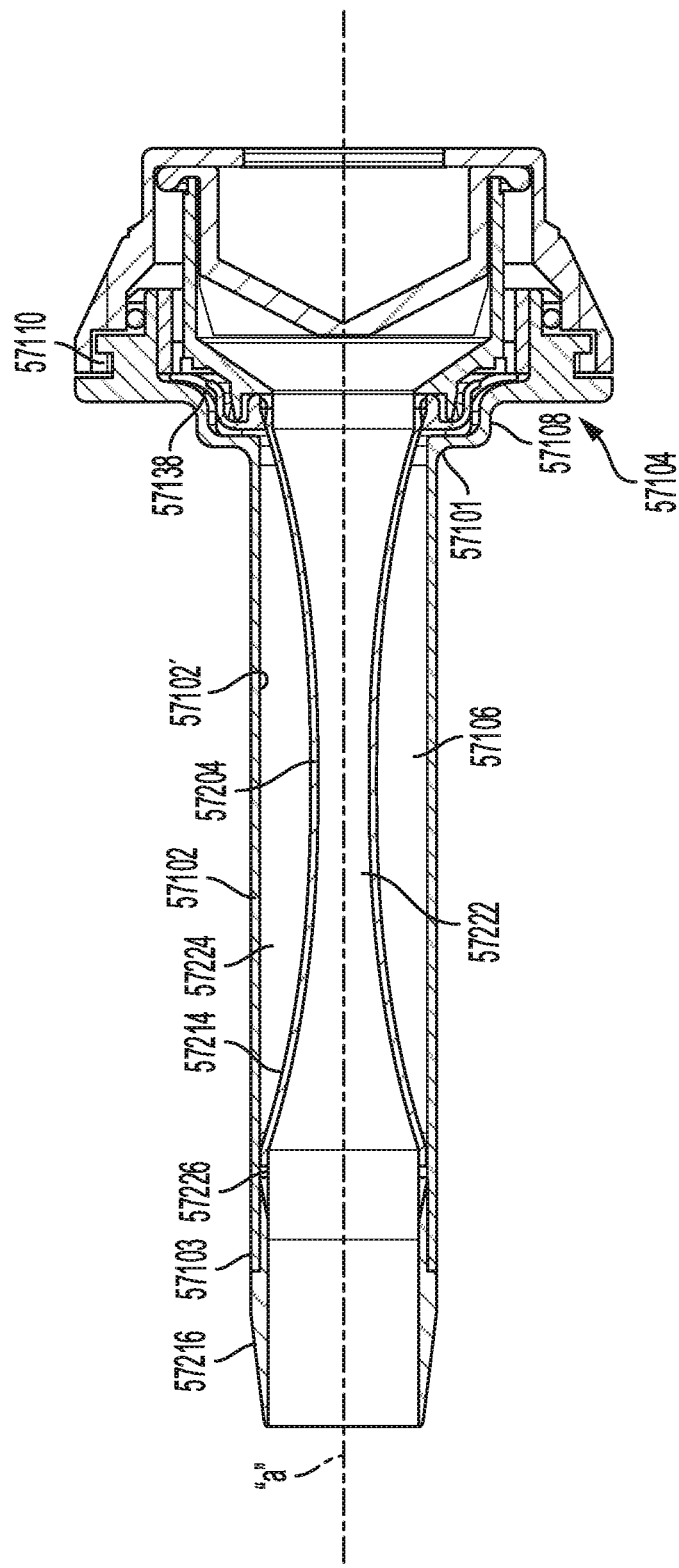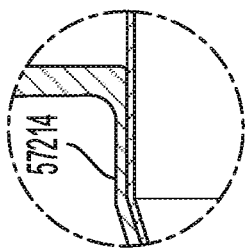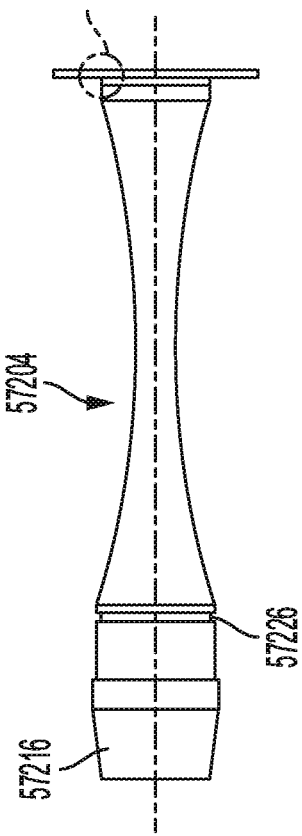

METHOD OF USING A SURGICAL MODULAR ROBOTIC ASSEMBLY

BACKGROUND

The present disclosure relates to robotic surgical systems. Robotic surgical systems can include a central control unit, a surgeon's command console, and a robot having one or more robotic arms. Robotic surgical tools can be releasably mounted to the robotic arm(s). The number and type of robotic surgical tools can depend on the type of surgical procedure. Robotic surgical systems can be used in connection with one or more displays and/or one or more handheld surgical instruments during a surgical procedure.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 29 is an exploded view of an instrument drive unit comprising a cooling unit, in accordance with at least one aspect of the present disclosure.

FIG. 37 is a perspective view of a sterile drape securable to a robotic arm, in accordance with at least one aspect of the present disclosure.

FIG. 38A is a detail view of a first attachment assembly for the sterile drape, in accordance with at least one aspect of the present disclosure.

FIG. 38B is a detail view of a second attachment assembly for the sterile drape, in accordance with at least one aspect of the present disclosure.

FIG. 39A is a perspective view of a segmented sterile drape positioned on a robotic arm, in accordance with at least one aspect of the present disclosure.

FIG. 39B is a detail view of a portion of FIG. 39A, in accordance with at least one aspect of the present disclosure.

FIG. 39C is a detail view of a portion of FIG. 39B, in accordance with at least one aspect of the present disclosure.

FIG. 40 is a perspective view of an adapter interface for a sterile drape, in accordance with at least one aspect of the present disclosure.

FIG. 41A is a perspective view of a sterile drape comprising a release cord positioned on a robotic arm, in accordance with at least one aspect of the present disclosure.

FIG. 41B is a perspective view of the sterile drape of FIG. 41A with the release cord being pulled proximally, in accordance with at least one aspect of the present disclosure.

FIG. 41C is a perspective view of the sterile drape of FIG. 41A released from the robotic arm, in accordance with at least one aspect of the present disclosure.

FIG. 41D is a perspective view of a replacement sterile drape being positioned over the robotic arm, in accordance with at least one aspect of the present disclosure.

FIG. 42A is a perspective view of a sterile drape comprising a release cord positioned on a robotic arm, in accordance with at least one aspect of the present disclosure.

FIG. 42B is a perspective view of the sterile drape of FIG. 42A being released from the robotic arm and a replacement sterile drape being deployed from the sterile drape holder, in accordance with at least one aspect of the present disclosure.

FIG. 42C is a perspective view of a replacement sterile drape being fully deployed from the sterile drape holder, in accordance with at least one aspect of the present disclosure.

FIG. 43A is a perspective view of a sterile drape comprising a support skeleton positioned on a robotic arm, in accordance with at least one aspect of the present disclosure.

FIG. 43B is a detail view of the sterile drape of FIG. 43A, in accordance with at least one aspect of the present disclosure.

FIG. 44 is a perspective view of a sterile drape comprising joint zones, in accordance with at least one aspect of the present disclosure.

FIG. 49A is a sectional view of a self-healing sterile drape, in accordance with at least one aspect of the present disclosure.

FIG. 49B is a sectional view of the sterile drape of FIG. 49A, where the sterile drape has been breached, in accordance with at least one aspect of the present disclosure.

FIG. 49C is a sectional view of the sterile drape of FIG. 49B, where the sterile drape has healed the breach, in accordance with at least one aspect of the present disclosure.

FIG. 54A is a side elevational view of a surgical instrument being coupled to a sterile interface module, in accordance with at least one aspect of the present disclosure.

FIG. 54B is a detail view of the surgical instrument in a first uncoupled position with the sterile interface module, in accordance with at least one aspect of the present disclosure.

FIG. 54C is a detail view of the surgical instrument in a second uncoupled position with the sterile interface module, in accordance with at least one aspect of the present disclosure.

FIG. 54D is a detail view of the surgical instrument in a coupled position with the sterile interface module, in accordance with at least one aspect of the present disclosure.

FIG. 59 is an exploded view of a robotic surgical assembly comprising continuity circuits, in accordance with at least one aspect of the present disclosure.

FIG. 60 is an exploded view of a robotic surgical assembly comprising proximity sensors, in accordance with at least one aspect of the present disclosure.

FIG. 62A is a perspective view of a robotic grasper comprising a surgical instrument identification sensor assembly, in accordance with at least one aspect of the present disclosure.

FIG. 62B is an overhead elevational view of the robotic grasper of FIG. 62A grasping a surgical instrument, in accordance with at least one aspect of the present disclosure.

FIG. 63A is a perspective view of a robotic grasper comprising a surgical instrument identification sensor, in accordance with at least one aspect of the present disclosure.

FIG. 63B is a detail view of a surgical instrument comprising a first identification element, in accordance with at least one aspect of the present disclosure.

FIG. 63C is a detail view of a surgical instrument comprising a second identification element, in accordance with at least one aspect of the present disclosure.

FIG. 63D is a detail view of a surgical instrument comprising a third identification element, in accordance with at least one aspect of the present disclosure.

FIG. 66A is a perspective view of a surgical instrument comprising an irregular gripping interface, in accordance with at least one aspect of the present disclosure.

FIG. 66B is an overhead elevational view of a robotic grasper comprising a vacuum source grasping the surgical instrument of FIG. 66A, where the surgical instrument is not properly aligned, in accordance with at least one aspect of the present disclosure.

FIG. 66C is an overhead elevational view of a robotic grasper comprising a vacuum source grasping the surgical instrument of FIG. 66A, where the surgical instrument is properly aligned, in accordance with at least one aspect of the present disclosure.

FIG. 66D is a graph of vacuum pressure and device power verse time for a robotic surgical system configured to control device power according to surgical instrument alignment, in accordance with at least one aspect of the present disclosure.

FIG. 68 is a perspective view of a sensor tag, in accordance with at least one aspect of the present disclosure.

FIG. 69A is a schematic view of a sensor tag positioned on a patient, in accordance with at least one aspect of the present disclosure.

FIG. 69B is a schematic view of a sensor of sensor tags positioned on a patient and an operating table, in accordance with at least one aspect of the present disclosure.

FIG. 69C is a schematic view of a sensor of sensor tags positioned on a first patient and an operating table, in accordance with at least one aspect of the present disclosure.

FIG. 69D is a schematic view of a sensor of sensor tags positioned on a second patient and an operating table, in accordance with at least one aspect of the present disclosure.

FIG. 69E is a schematic view of a sensor of sensor tags positioned on a third patient and an operating table, in accordance with at least one aspect of the present disclosure.

FIG. 70 is a schematic view of a robotic surgical system comprising an image sensor to sense a robotic arm positioned within a detection zone, in accordance with at least one aspect of the present disclosure.

FIG. 71 is a perspective view of a pair of scrubs comprising a reflective material, in accordance with at least one aspect of the present disclosure.

FIG. 72 is an overhead view of a surgical staff member wearing the scrubs of FIG. 71 violating a detection zone with respect to the robotic arm, in accordance with at least one aspect of the present disclosure.

FIG. 79 is an exploded view of the surgical instrument handle of FIG. 78 being coupled to an end effector assembly of FIG. 80, in accordance with at least one aspect of the present disclosure.

FIG. 80 is a perspective view of an end effector assembly drivable via a three motor system, in accordance with at least one aspect of the present disclosure.

FIG. 81A is perspective view of a motor pack sterile barrier, in accordance with at least one aspect of the present disclosure.

FIG. 81B is perspective view of a motor pack sterile barrier, in accordance with at least one aspect of the present disclosure.

FIG. 82A is a perspective view of a motor pack comprising an alignment tab, in accordance with at least one aspect of the present disclosure.

FIG. 82B is a perspective view of a motor pack sterile barrier configured to receive the motor pack of FIG. 82A, in accordance with at least one aspect of the present disclosure.

FIG. 82C is a perspective view of the motor pack sterile barrier of FIG. 82B, in accordance with at least one aspect of the present disclosure.

FIG. 83A is a side elevational view of a sterile interface module of a robotic surgical system, in accordance with at least one aspect of the present disclosure.

FIG. 83B is a detail view of portion C of FIG. 83A, in accordance with at least one aspect of the present disclosure.

FIG. 84A is an overhead elevational view of a sterile interface module, in accordance with at least one aspect of the present disclosure.

FIG. 84B is a sectional view of an instrument drive unit comprising an interface couplable to the drive couplers of a sterile interface module, in accordance with at least one aspect of the present disclosure.

FIG. 84C is a perspective view of the instrument drive unit of FIG. 84B, in accordance with at least one aspect of the present disclosure.

FIG. 87 is a perspective view of the detachable motor pack of FIG. 6A.

FIGS. 105A-105B illustrate operation in a lower quadrant for a lower anterior resection procedure, in accordance with at least one aspect of the present disclosure.

FIGS. 111A-111D depict various detections of magnetic signatures of correlated field magnets located on a trocar by a Hall effect sensor, in accordance with at least one aspect of the present disclosure.

FIGS. 112A-112E depict various detections of magnetic signatures of correlated field magnets located on a trocar by a Hall effect sensor, in accordance with at least one aspect of the present disclosure.

FIG. 114 is a bottom perspective view of a cannula including an array of plural magnet positions, in accordance with at least one aspect of the present disclosure.

FIGS. 115A and 115B depict the management of an insufflation tubing used in conjunction with a robotic arm within a sterile barrier, in accordance with at least one aspect of the present disclosure.

FIG. 121 is a perspective view of a surgical instrument of the surgical assembly of FIG. 118 including an instrument drive connector.

FIG. 129 is an enlarged view of the area of detail indicated in FIG. 121.

FIG. 130 is an enlarged view of the area of detail indicated in FIG. 122.

FIG. 136A is a plan view of a surgical instrument drive system comprising a cable-driven actuation member, wherein the actuation member is illustrated in a pre-actuated position.

FIG. 136B is a plan view of the surgical instrument drive system of FIG. 136A, wherein the actuation member is illustrated in a fully-actuated position.

FIG. 136C is a plan view of the surgical instrument drive system of FIG. 136A, wherein the actuation member is illustrated in a retracted position and a cable of the surgical instrument drive system has incurred slack.

FIG. 136D is a plan view of the surgical instrument drive system of FIG. 136A, wherein the actuation member is illustrated in the retracted position and the cable is tensioned to eliminate the slack introduced in FIG. 136C.

FIG. 141 is a perspective view of an attachment interface and a surgical tool configured to be attached to the attachment interface, wherein the attachment interface comprises a seal.

FIG. 142 is a perspective view of the seal of FIG. 141, wherein the seal comprises a spiral slit.

FIG. 143 is a cross-sectional view of the attachment interface and seal of FIG. 141.

FIG. 144 is a partial cross-sectional view of the attachment interface and surgical tool of FIG. 141, wherein the surgical tool is attached to the attachment interface.

FIG. 151 is a perspective view of a surgical system comprising an interchangeable transducer, a first attachment interface, and a second attachment interface, wherein the interchangeable transducer is configured to be attached to and use with both the first attachment interface and the second attachment interface.

FIG. 152 is a plan view of the interchangeable transducer and first attachment interface of FIG. 151.

FIG. 153 is a graphical illustration of an algorithm implemented in a robotic surgical system for controlling robotic surgical tools based on motor current (I) and externally sensed parameters according to at least one aspect of the present disclosure.

FIG. 154 illustrates a distal portion of a motor driven powered robotic surgical tool grasping tissue under low lateral tension according to at least one aspect of the present disclosure.

FIG. 155 illustrates a distal portion of the motor driven powered robotic surgical tool grasping tissue under high downward tension according to at least one aspect of the present disclosure.

FIG. 158 illustrates a first robotic arm in a first position A according to at least one aspect of the present disclosure.

FIG. 159 illustrates a second robotic arm in a second position B according to at least one aspect of the present disclosure.

FIG. 187A illustrates an end-effector with a lower jaw or ultrasonic blade, and an upper jaw or clamp member that are configured to clamp tissue therebetween according to at least one aspect of the present disclosure.

FIG. 187B illustrates that the end-effector and thus the blade is lifted, as schematically shown by arrows one of which is labeled as, and the tissue is cut, such that a portion of the tissue is disassociated from the end-effector according to at least one aspect of the present disclosure.

FIG. 190 illustrates a sensor assembly coupled adjacent to an embodiment of an end-effector that includes a cutting robotic surgical tool (e.g., tissue boring robotic surgical tool) according to at least one aspect of the present disclosure.

FIG. 191A illustrates a distal end of a cutting robotic surgical tool that is not in contact with tissue and therefore a force is not applied against the distal end of the cutting robotic surgical tool by the tissue according to at least one aspect of the present disclosure.

FIG. 191B illustrates a distal end of a cutting robotic surgical tool that is in contact with tissue and a force is applied against the distal end of the cutting robotic surgical tool by the tissue according to at least one aspect of the present disclosure.

FIG. 191C illustrates a distal end of a cutting robotic surgical tool that is extending through the tissue and is no longer in contact with the tissue according to at least one aspect of the present disclosure.

FIG. 194 illustrates a patient lying on an operating room table with a robot controlled circular stapler inserted in the rectal stump of the patient according to at least one aspect of the present disclosure.

FIG. 195 illustrates a limiting robotic surgical tool induced tissue loading relative to a hard anatomic reference according to at least one aspect of the present disclosure.

FIG. 196 illustrates a robotic surgical tool improperly inserted at an angle to the proper direction of insertion indicated by the arrow.

FIG. 197 illustrates a robotic surgical tool properly inserted in the direction indicated by the arrow.

FIG. 198 is a graphical illustration of measured torque T on the operating room table and robotic surgical tool positioning and orientation as a function of time t according to at least one aspect of the present disclosure.

FIG. 199A illustrates a grasper device holding an anvil shaft and applying a first tissue tension $F_{g1}$ on the colon according to at least one aspect of the present disclosure.

FIG. 199B illustrates the grasper device shown in FIG. 199A with the anvil shaft extended into the shaft of the circular stapler, which has been further extended into the colon and the rectal stump according to at least one aspect of the present disclosure.

FIG. 199C illustrates the grasper device shown in FIG. 199B with the anvil shaft released and the tissue tension $F_{g3}$ on the colon reduced according to at least one aspect of the present disclosure.

FIG. 199D illustrates the grasper device shown in FIG. 199C with the anvil shaft released and the tissue tension $F_{g4}$ on the colon within an acceptable range according to at least one aspect of the present disclosure.

FIG. 202 is a schematic diagram of an anvil clamping control system of a surgical stapler grasping tissue between an anvil and a staple cartridge and the force $F_{anvil}$ on the anvil according to at least one aspect of the present disclosure.

FIG. 203 is a schematic diagram of a tissue cutting member control system of the surgical stapler depicted in FIG. 202 grasping tissue between the anvil and the staple cartridge and the force $F_{knife}$ on the knife while cutting the tissue according to at least one aspect of the present disclosure.

FIG. 204 is a schematic diagram of an anvil motor according to at least one aspect of the present disclosure.

FIG. 205 is a schematic diagram of a knife motor according to at least one aspect of the present disclosure.

FIG. 206 is a graphical illustration of an algorithm for antagonistic or cooperative control of the anvil clamping control system and the tissue cutting member control system as illustrated in FIGS. 202-205 according to at least one aspect of the present disclosure.

Figure 208:
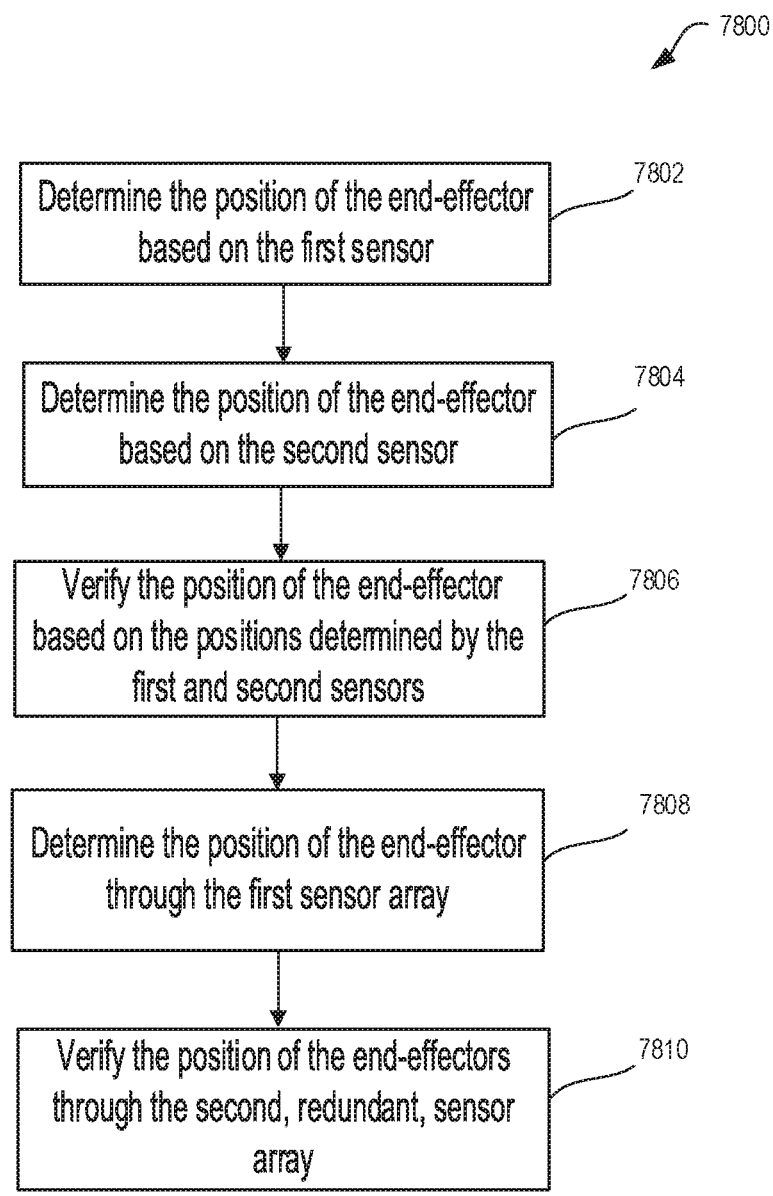

FIG. 208 is a flow diagram of a process depicting a control program or a logic configuration for verifying a position or velocity of an end-effector jaw of a first surgical tool coupled to a first robotic arm based on a redundant calculation of a resulting movement of the end-effector from a motor application of control parameters of a second robotic arm coupled to a second surgical tool according to at least one aspect of the present disclosure.

Figure 209:
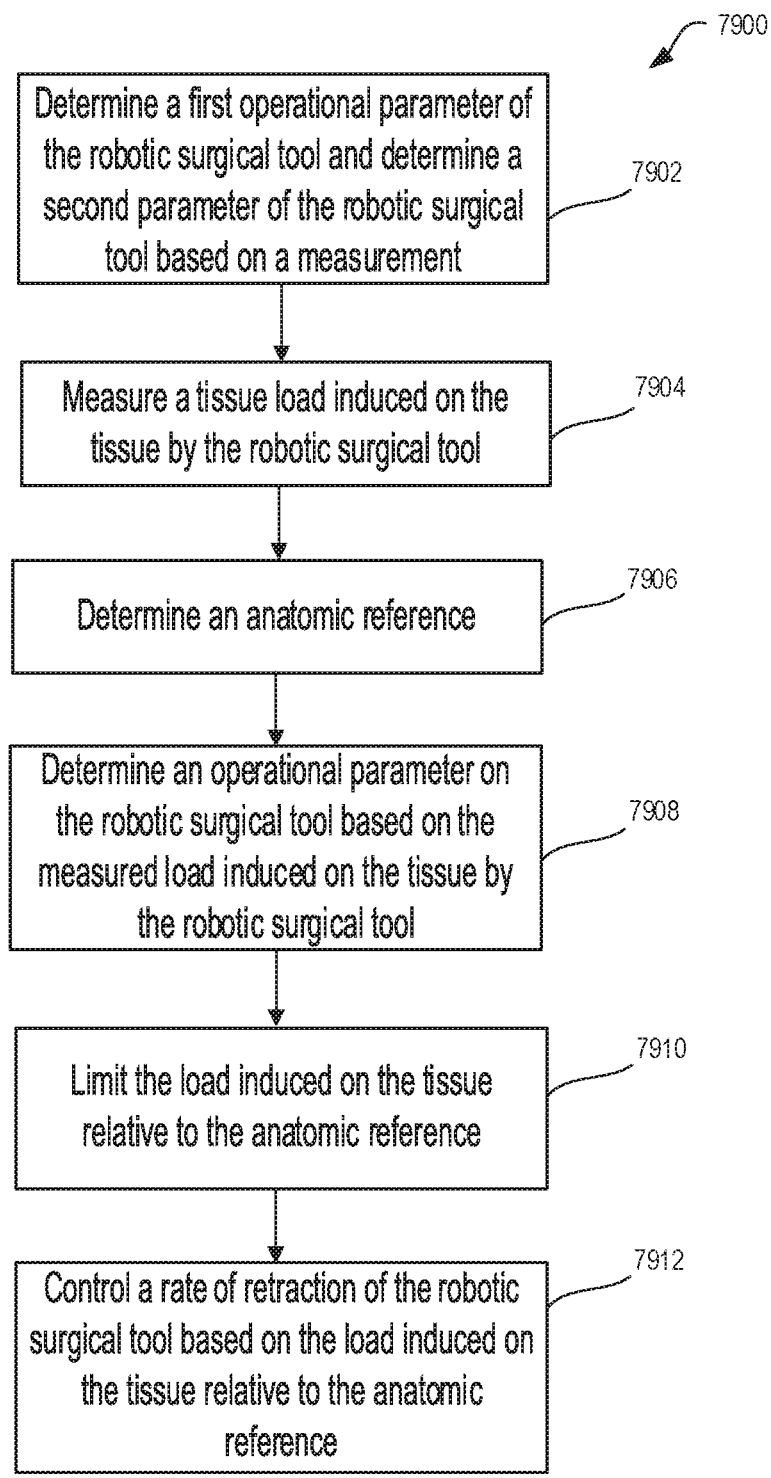

FIG. 209 is a flow diagram of a process depicting a control program or a logic configuration of controlling at least one operational parameter of a robotic surgical tool driver controlling a circular stapler robotic surgical tool based on another parameter measured within the robotic surgical tool driver controlling the circular stapler according to at least one aspect of the present disclosure.

Figure 210:
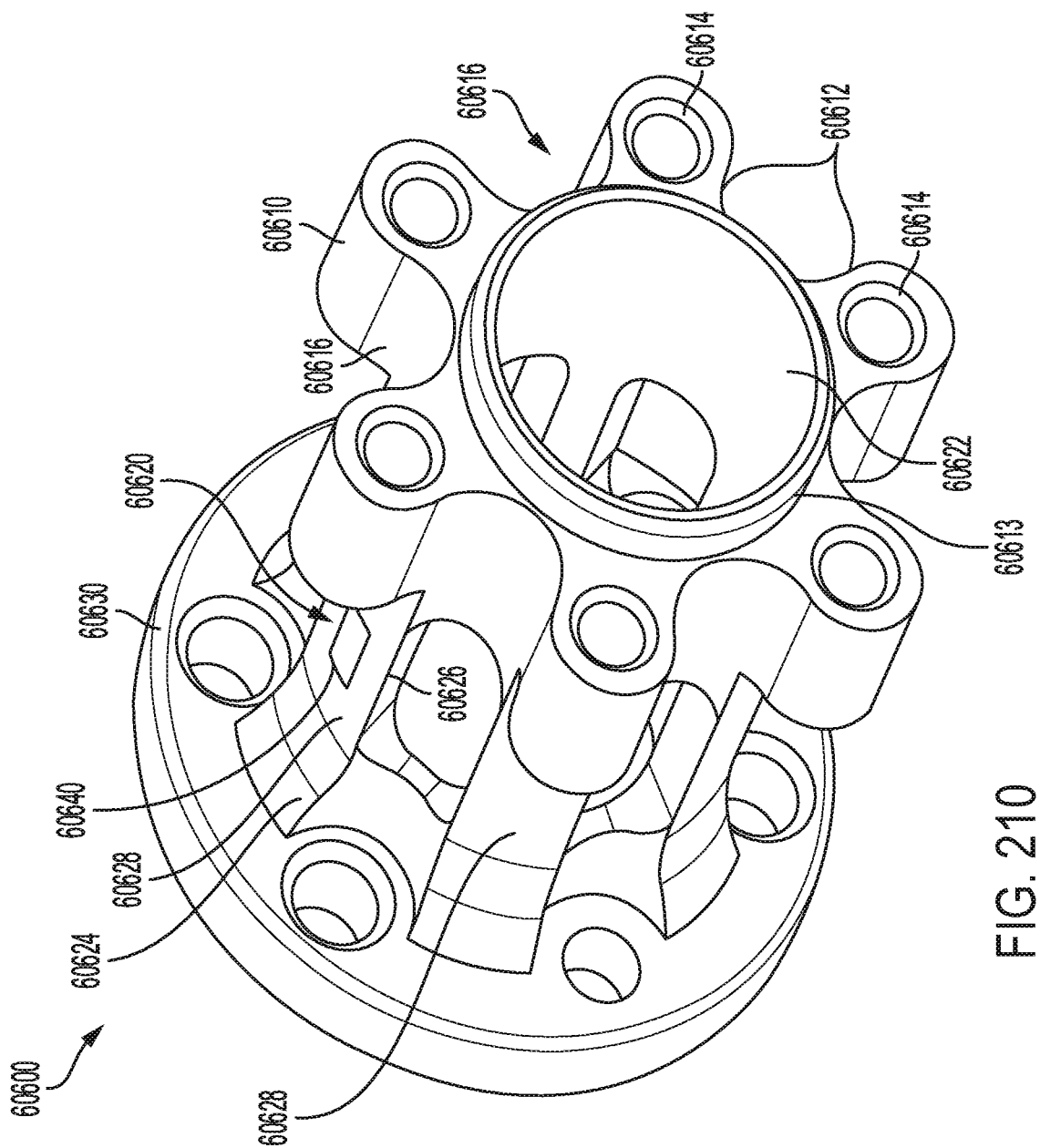

FIG. 210 is a torque transducer having a body connecting a mounting flange and a motor flange according to at least one aspect of the present disclosure.

Figure 211:
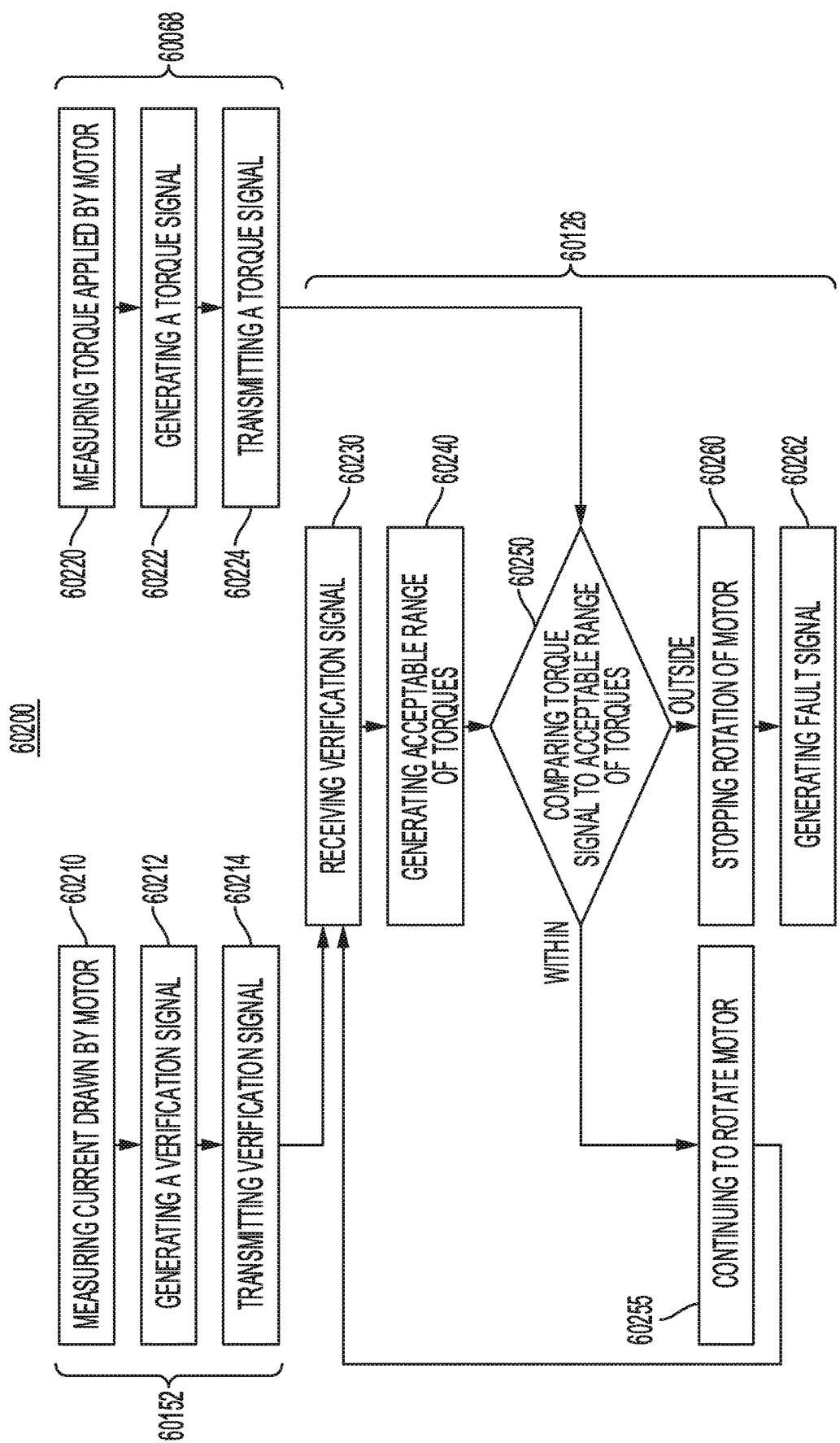

FIG. 211 is a flowchart illustrating a method of controlling an instrument drive unit according to at least one aspect of the present disclosure.

Figure 212:
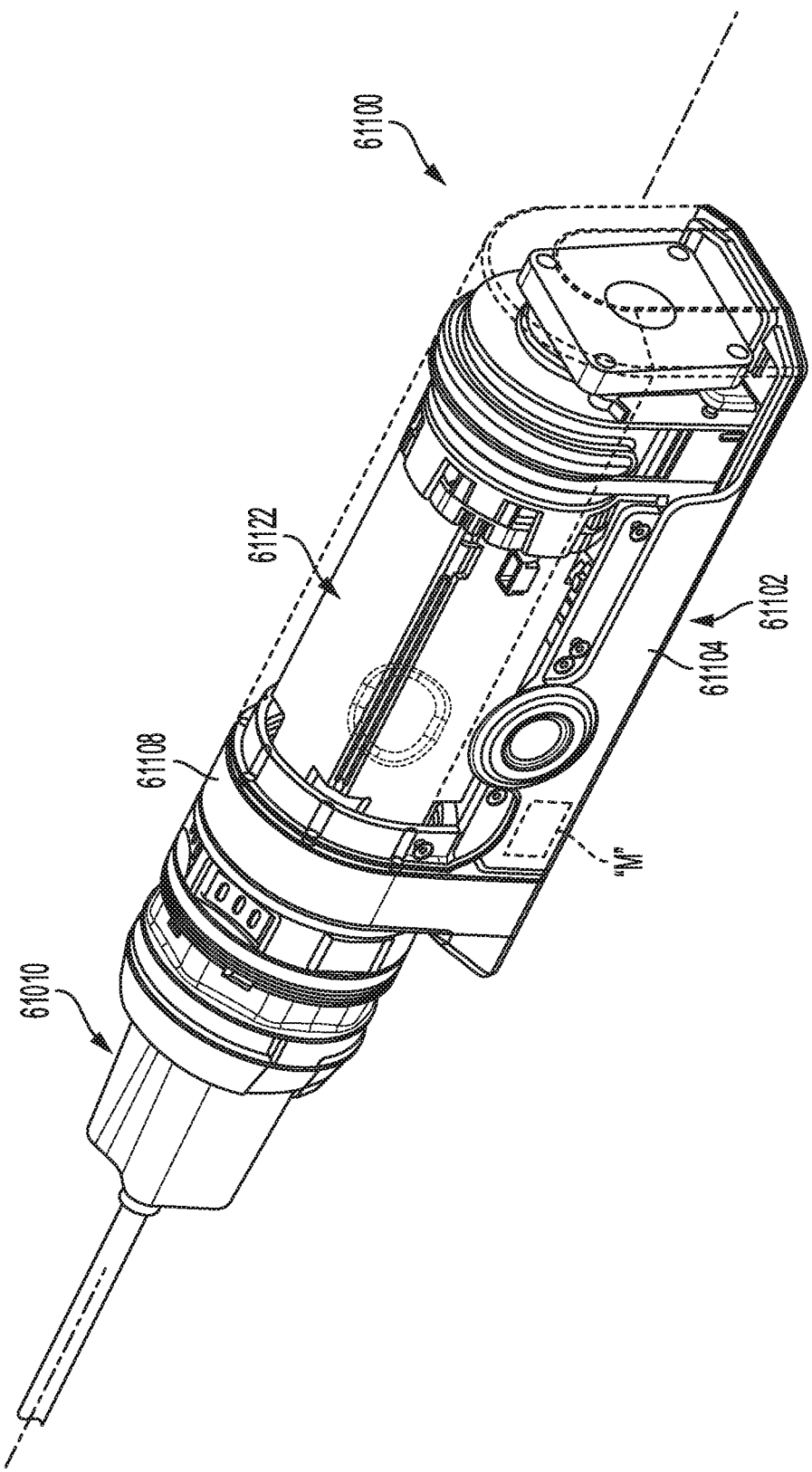

FIG. 212 is a front perspective view of an instrument drive unit holder of a robotic surgical assembly with an instrument drive unit and a surgical instrument coupled thereto according to at least one aspect of the present disclosure.

Figure 213A:
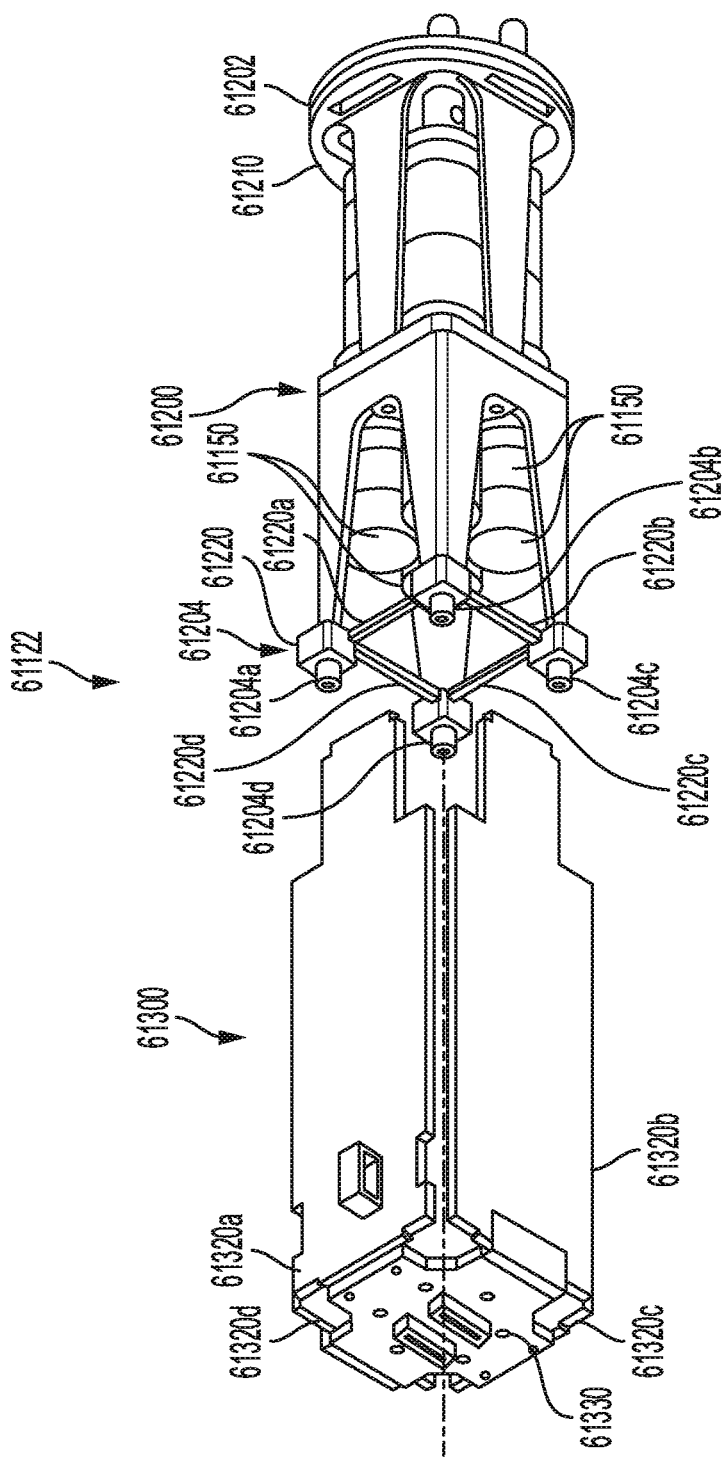

FIG. 213A is a side perspective view of a motor pack of the instrument drive unit of FIG. 212 with an integrated circuit in a second configuration and separated from the motor assembly according to at least one aspect of the present disclosure.

Figure 213B:
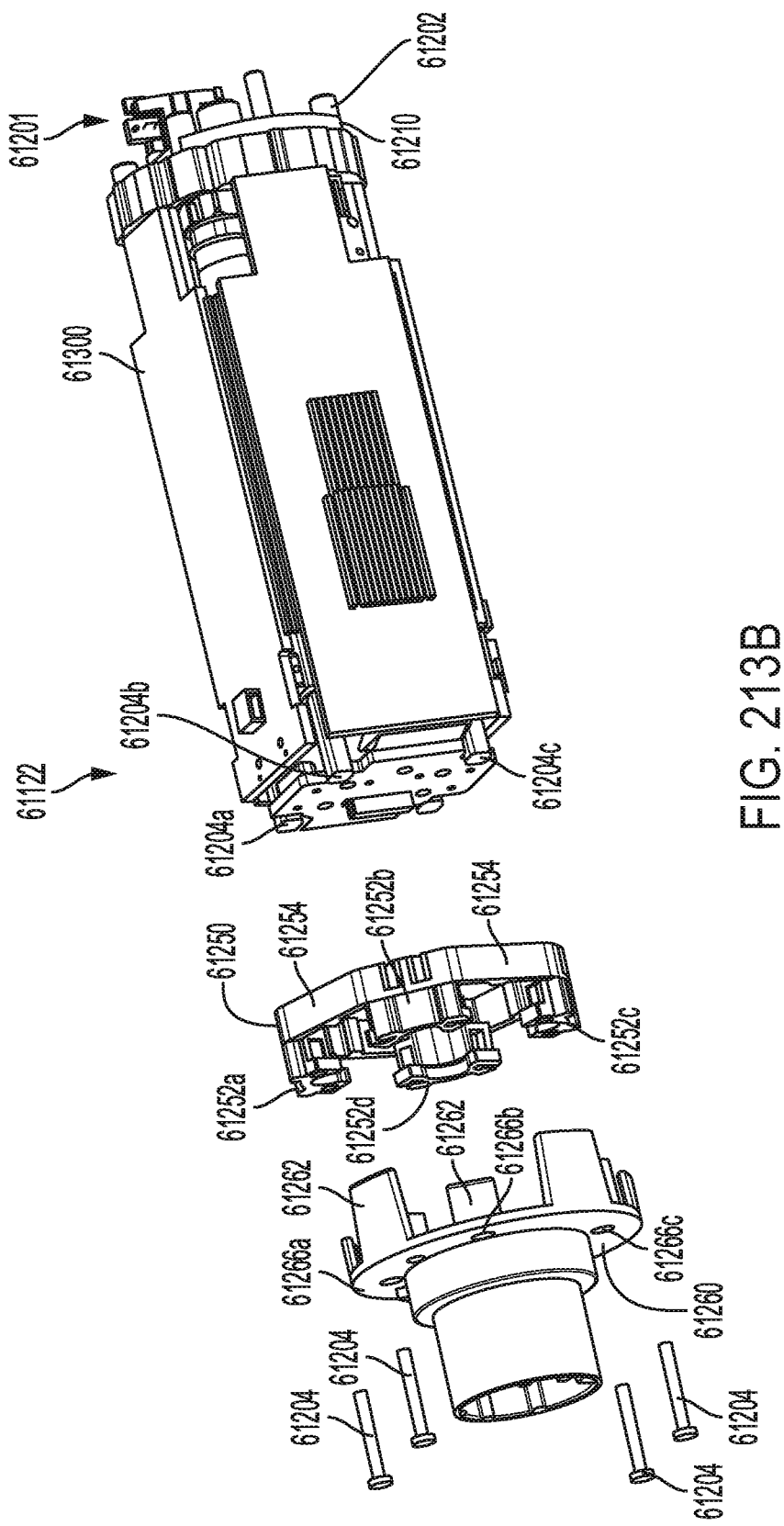

FIG. 213B is a side perspective view of the motor pack of the instrument drive unit of FIG. 212 with the integrated circuit in a second configuration and separated from the motor assembly according to at least one aspect of the present disclosure.

Figure 214:
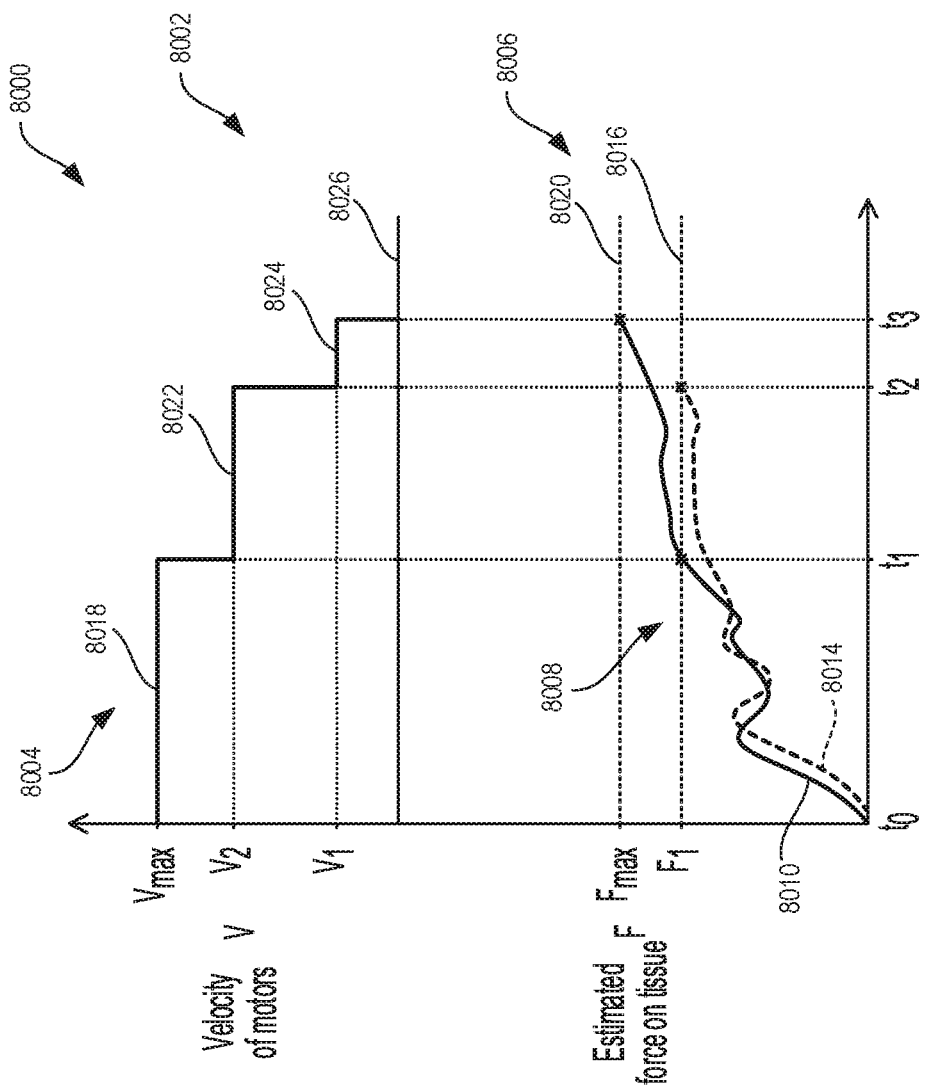

FIG. 214 is a graphical illustration of limiting combined functional loading on the patient by determining the torques within robotic surgical tool driver and robotic arm/system according to at least one aspect of the present disclosure.

Figure 215:
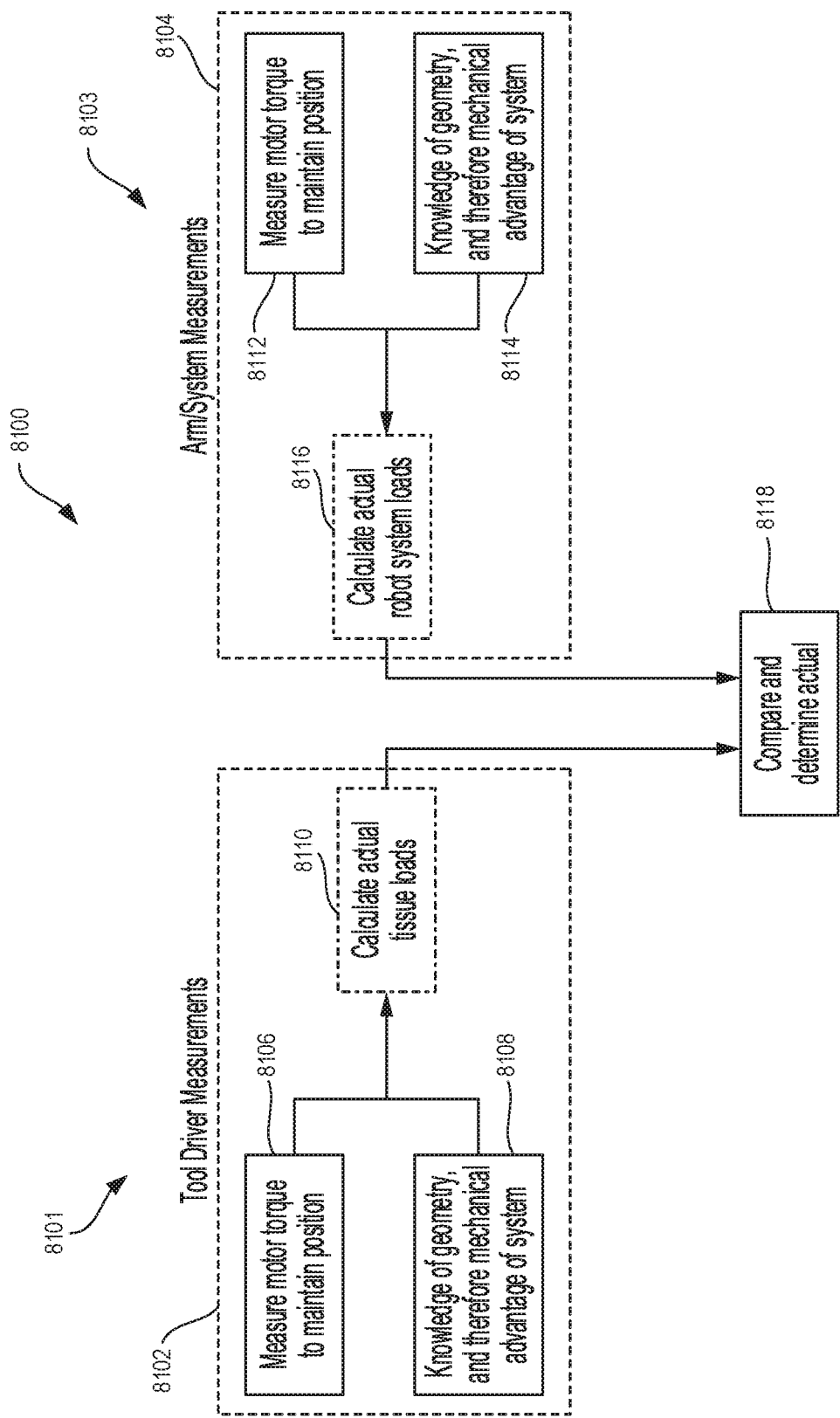

FIG. 215 is a flow diagram of a system and method of limiting combined functional loading on the patient by determining the torques within robotic surgical tool driver and robotic arm/system according to at least one aspect of the present disclosure.

Figure 216:
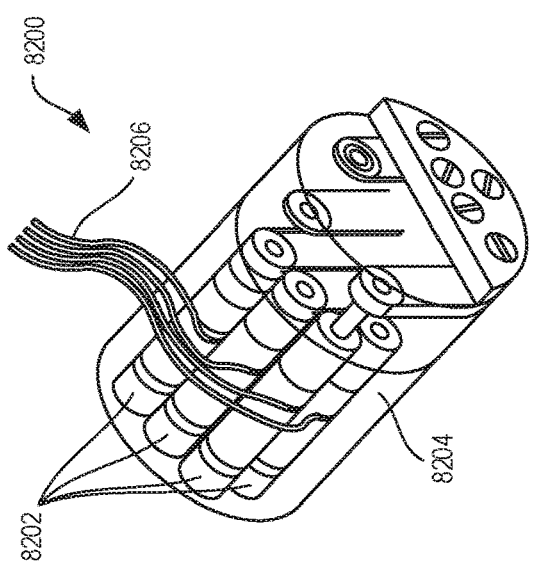

FIG. 216 illustrates a motor pack according to at least one aspect of the present disclosure.

Figure 217:
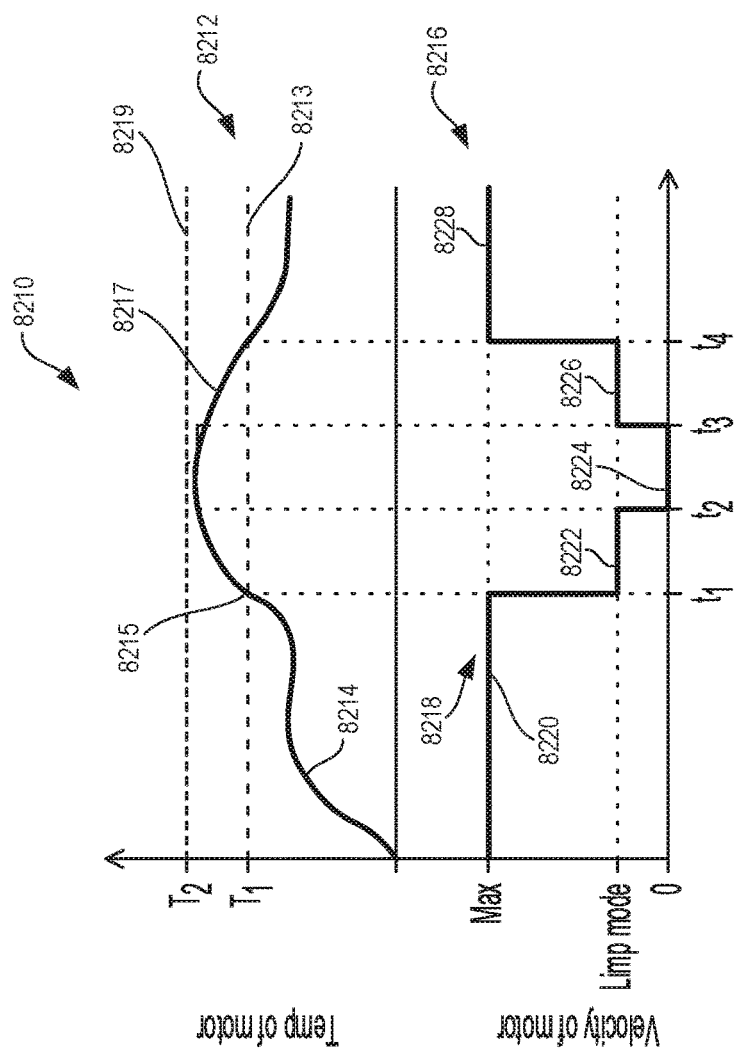

FIG. 217 is a graphical illustration of a temperature control algorithm for monitoring external parameters associated with the operation of a motor according to at least one aspect of the present disclosure.

FIG. 218 is a graphical illustration of magnetic field strength (B) of a motor as a function of time t according to at least one aspect of the present disclosure.

FIG. 219 is a graphical illustration of motor temperature as a function of time t according to at least one aspect of the present disclosure.

FIG. 220 is a graphical illustration of magnetic field strength (B) as a function motor temperature (T) according to at least one aspect of the present disclosure.

Figure 221:
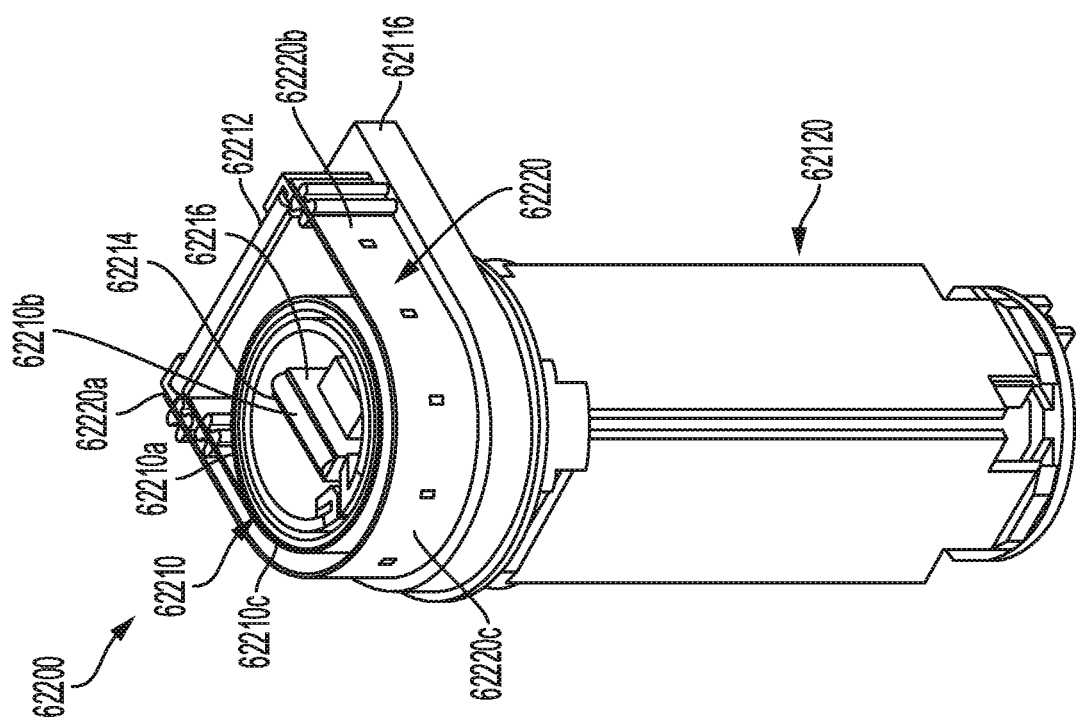

FIG. 221 illustrates a flex spool assembly that includes a first printed circuit board, a second printed circuit board, and a third printed circuit board according to at least one aspect of the present disclosure.

Figure 222:
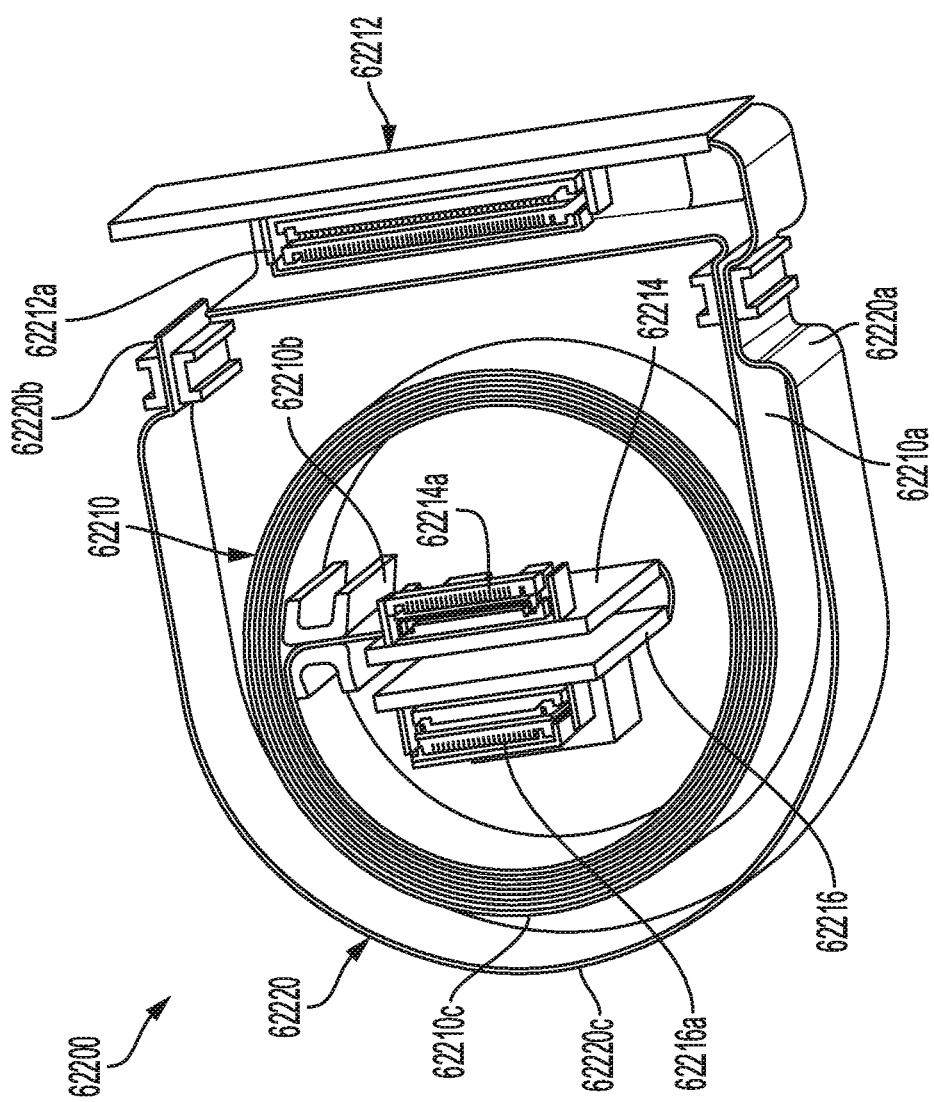

FIG. 222 is a detailed view of the flex spool assembly shown in FIG. 221 according to at least one aspect of the present disclosure.

Figure 223:
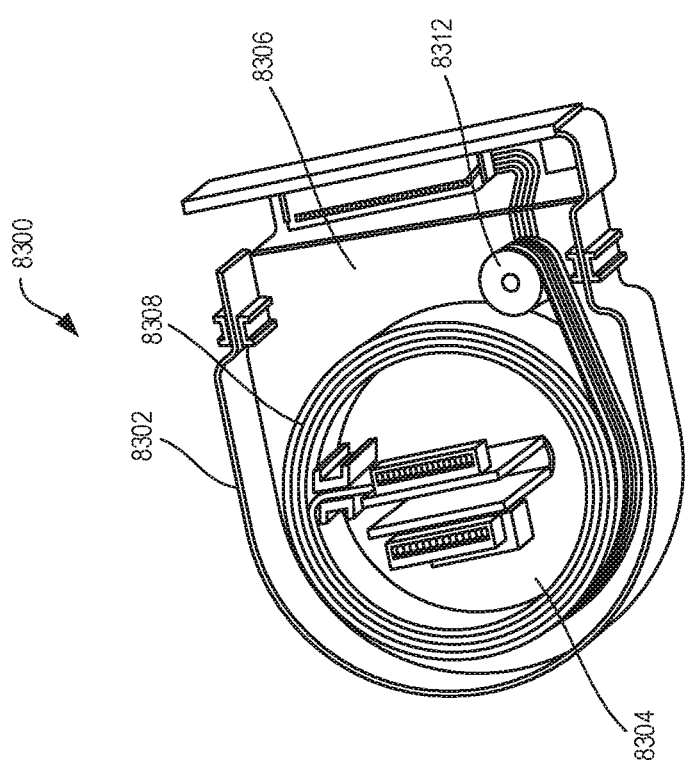

FIG. 223 illustrates an internal receiver with multiple cavities wire control features to maintain orientation and order of the wiring harness during rotation according to at least one aspect of the present disclosure.

Figure 224:
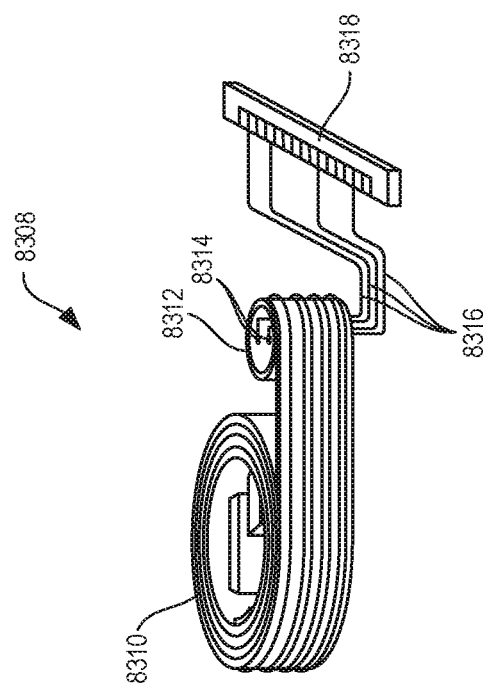

FIG. 224 illustrates a wiring harness according to at least one aspect of the present disclosure.

FIG. 225 illustrates a semiautonomous motor controller local to a motor pack according to at least aspect of the present disclosure.

FIG. 226 is a detailed view of the spring loaded plunger depicted in FIG. 225 according to at least one aspect of the present disclosure.

FIG. 227 illustrates a wireless power system for transmission of electrical power between a surgical robot and a motor pack comprising a plurality of motors according to at least one aspect of the present disclosure FIG. 228 is a diagram of the wireless power system for transmission of electrical power between a robot and a motor pack depicted in FIG. 227 according to at least one aspect of the present disclosure.

Figure 229:
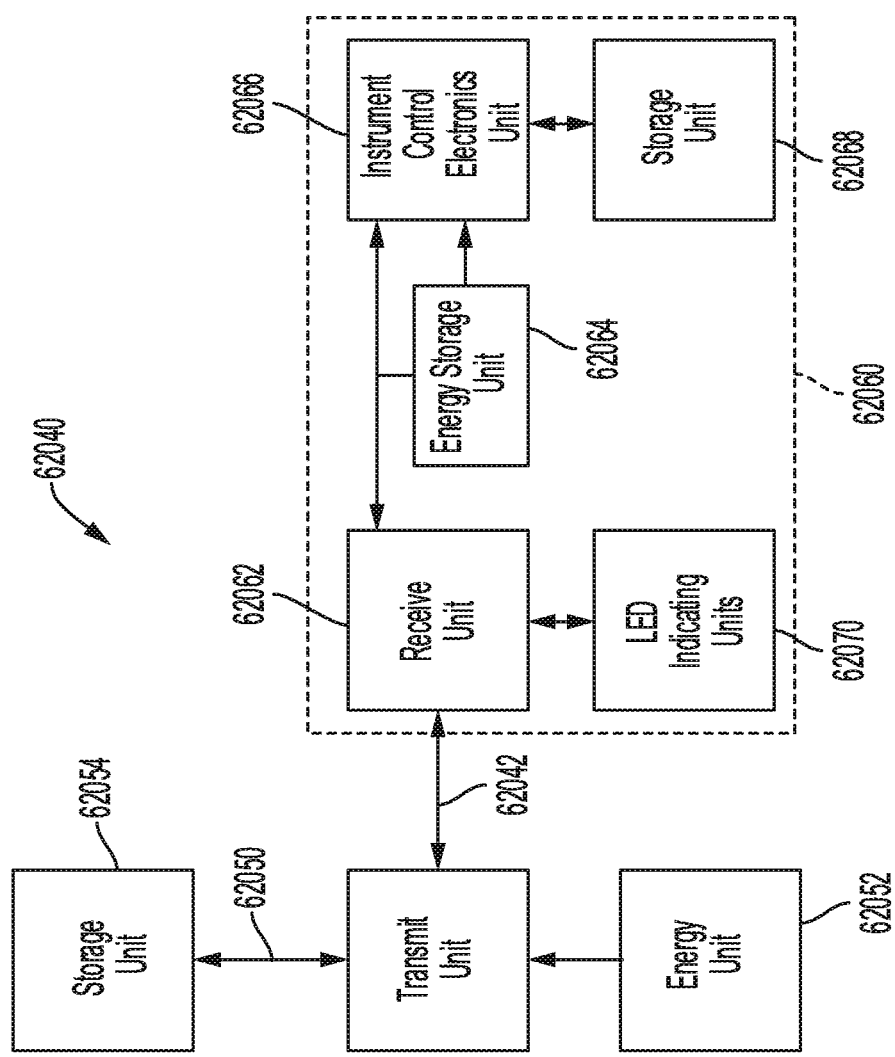

FIG. 229 is a block diagram of an information transfer system according to at least one aspect of the present disclosure.

Figure 230:
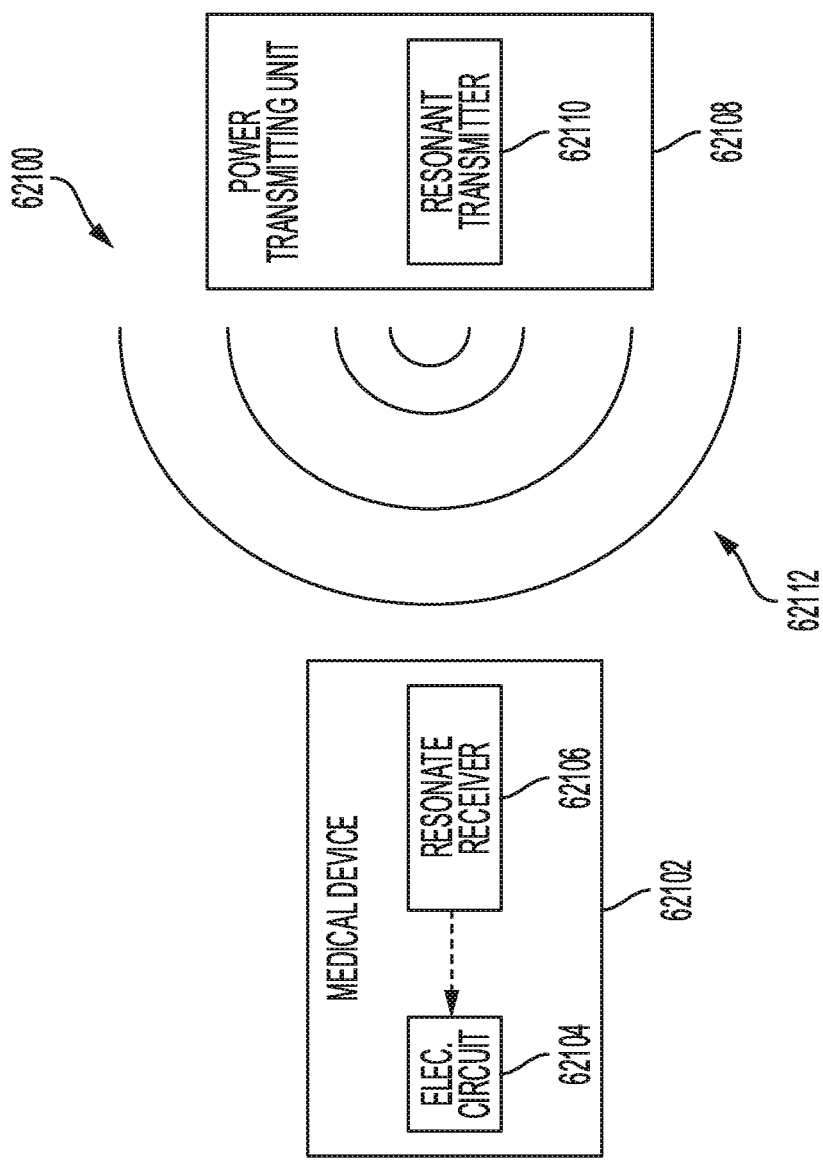

FIG. 230 generally depicts system for providing electrical power to a medical device according to at least one aspect of the present disclosure.

Figure 231:
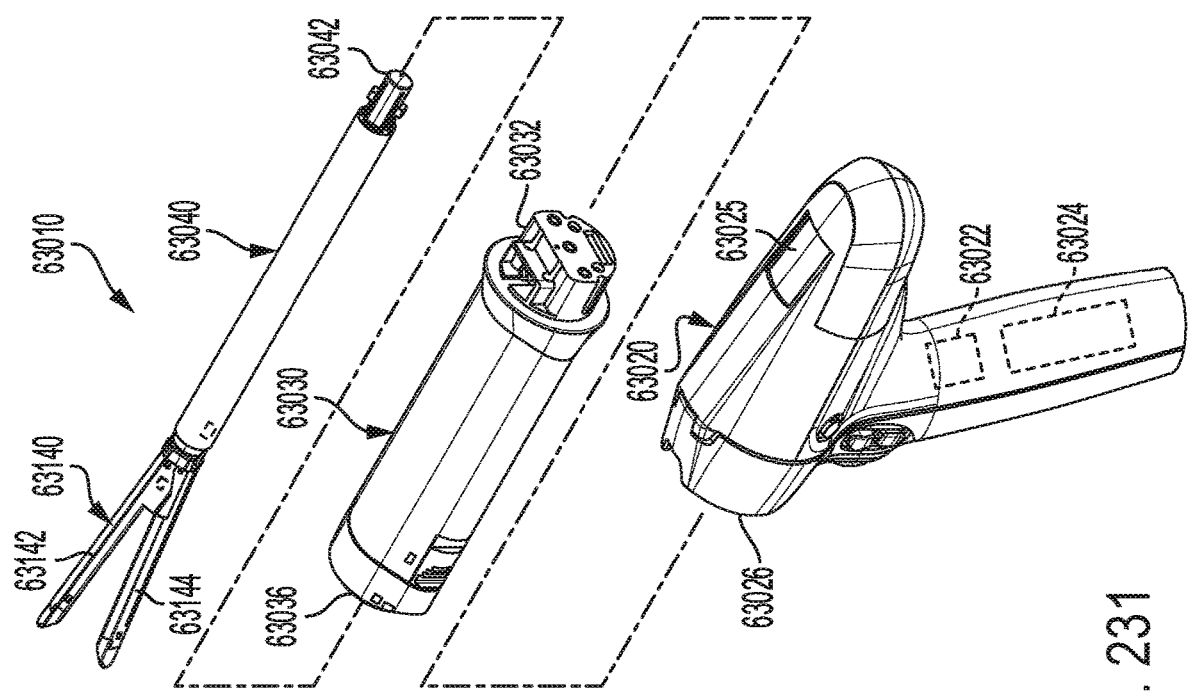

FIG. 231 illustrates a surgical instrument according to at least one aspect of the present disclosure.

Figure 232:
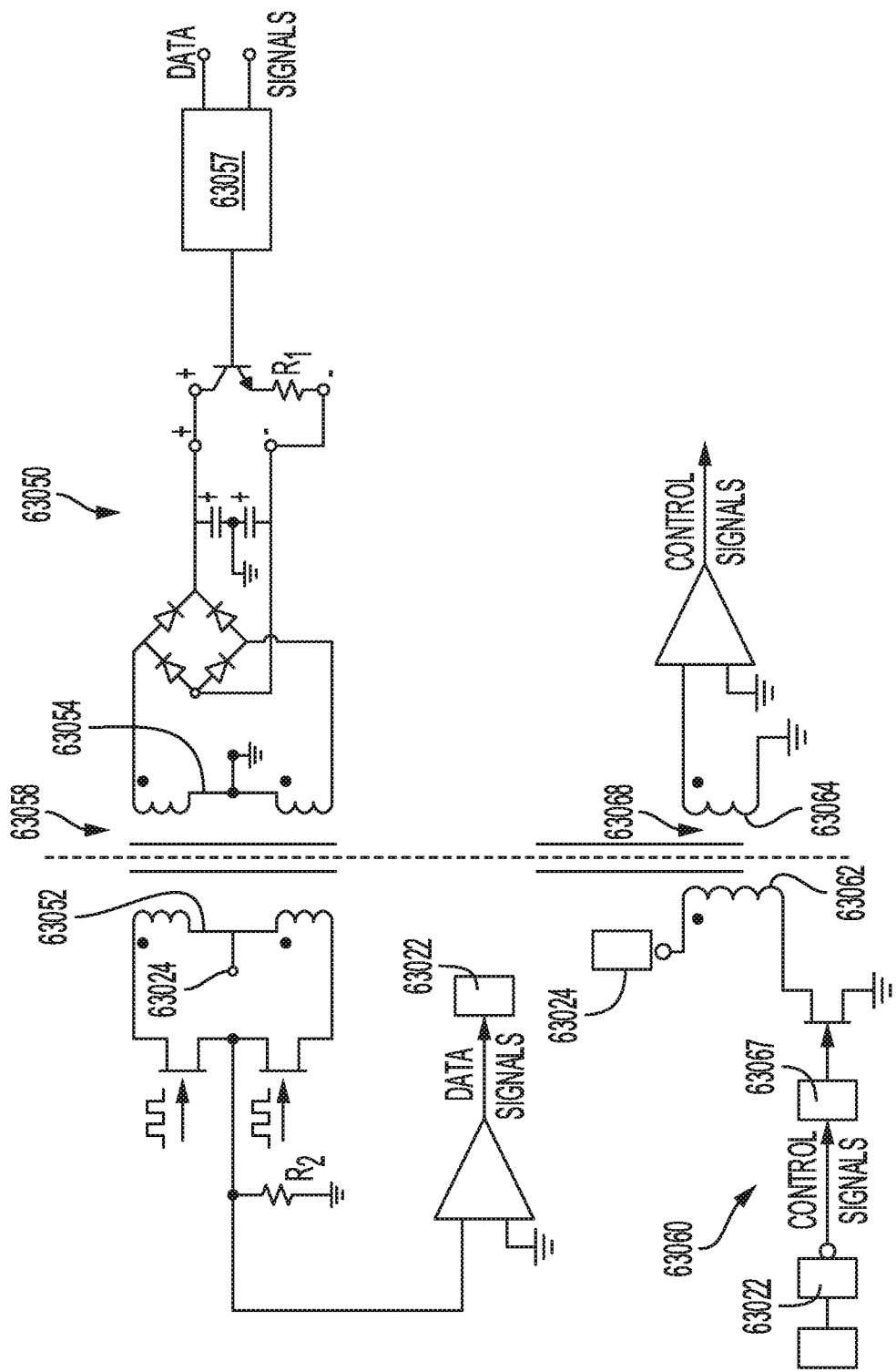

FIG. 232 illustrates an electrical interface including a control circuit for transmitting the control signals according to at least one aspect of the present disclosure.

Figure 233:
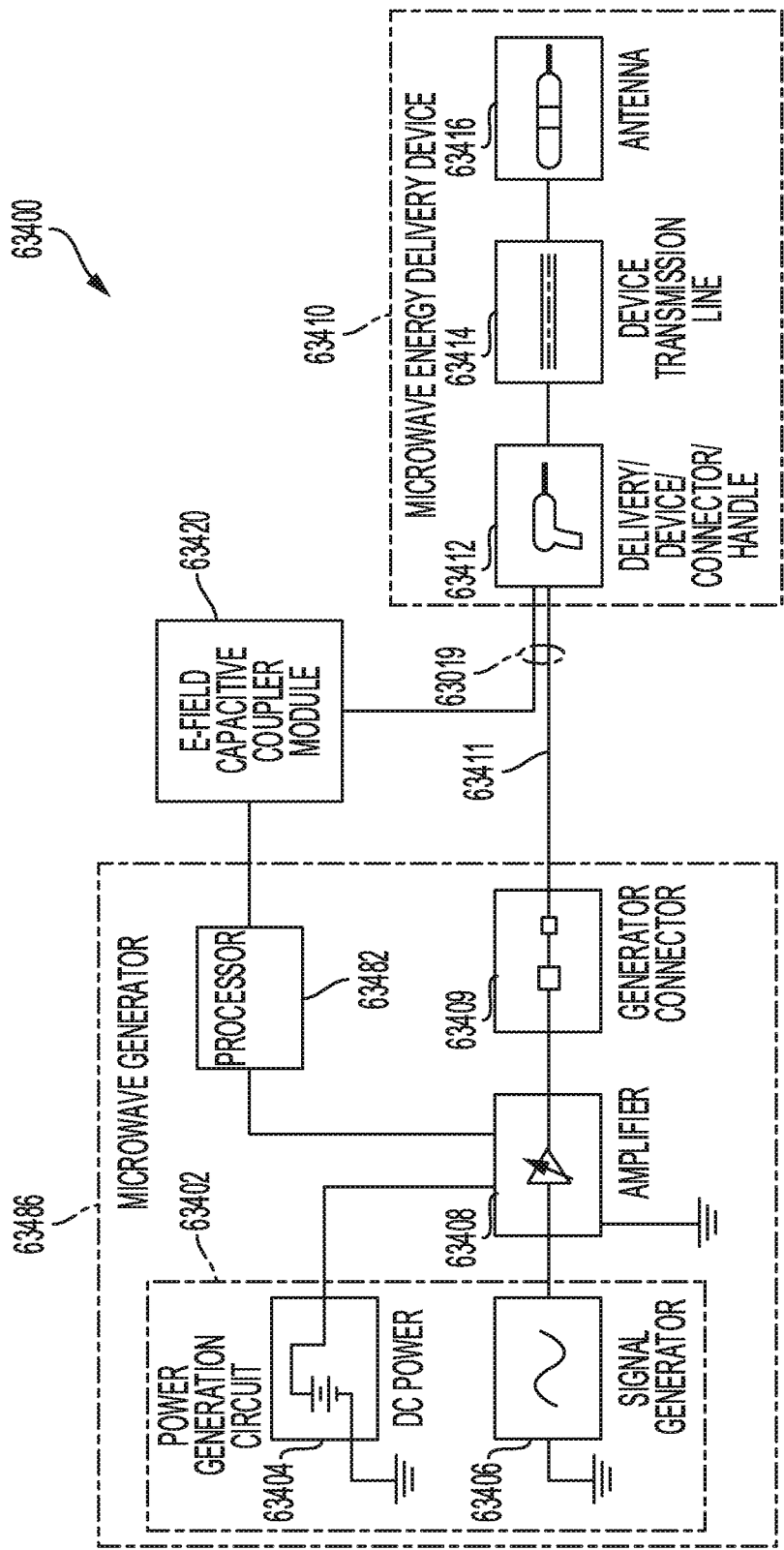

FIG. 233 schematically illustrates an electrosurgical system that includes an electric-field capacitive coupler module coupled between a microwave generator assembly and a microwave energy delivery device according to at least one aspect of the present disclosure.

Figure 234:
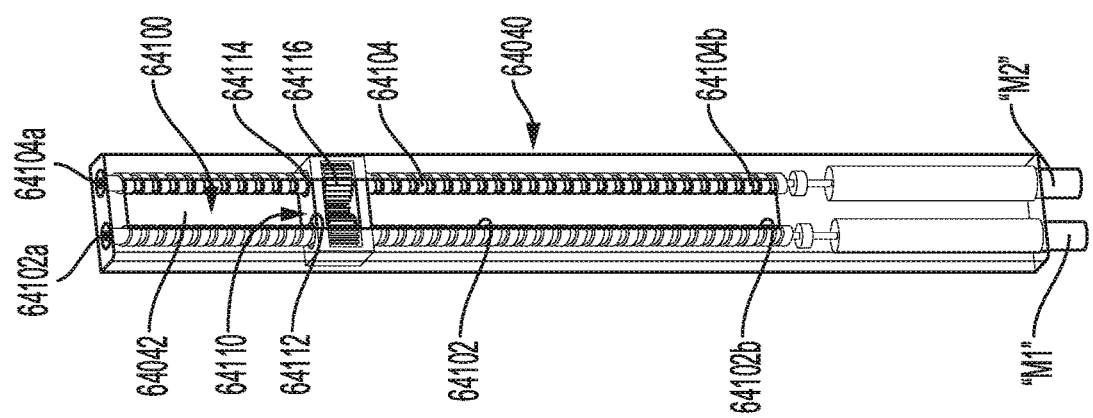

FIG. 234 illustrates an elongate link or slide rail that includes a multidirectional movement mechanism configured to axially move a surgical instrument along a longitudinal axis of an elongate link or slide rail and to rotate the surgical instrument about its longitudinal axis according to at least one aspect of the present disclosure.

Figure 235B:
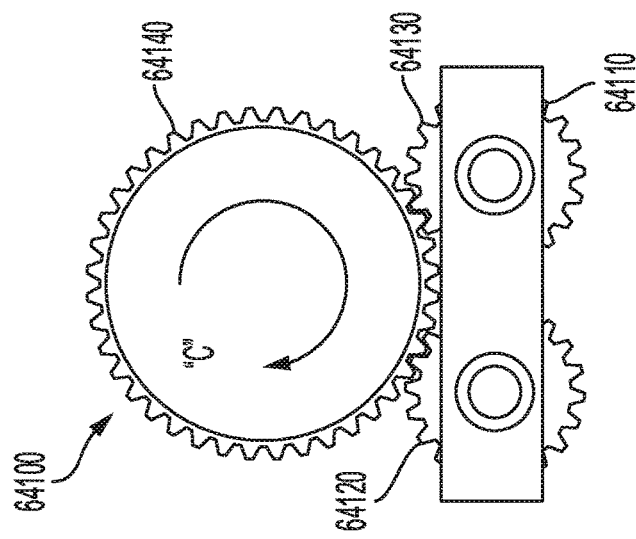
Figure 235A:
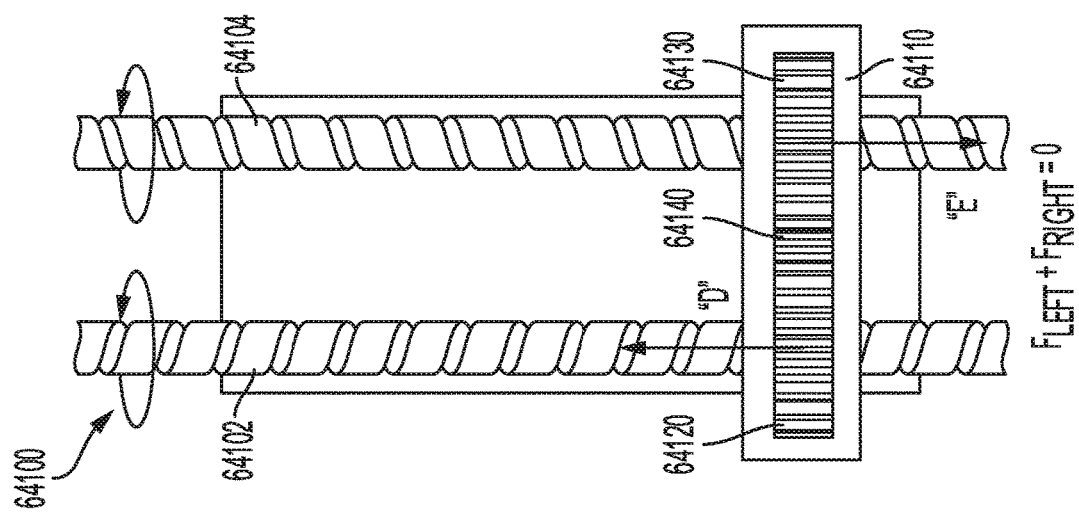

FIGS. 235A and 235B illustrate first and second motors "M1," "M2" of a multi-directional movement mechanism actuated to rotate both a left-handed lead screw and a right-handed lead screw in a counter-clockwise direction to cause a cogwheel, and the attached surgical instrument, to rotate in a clockwise direction as indicated by arrow "C" shown in FIG. 235B, according to at least one aspect of the present disclosure.

Figure 236:
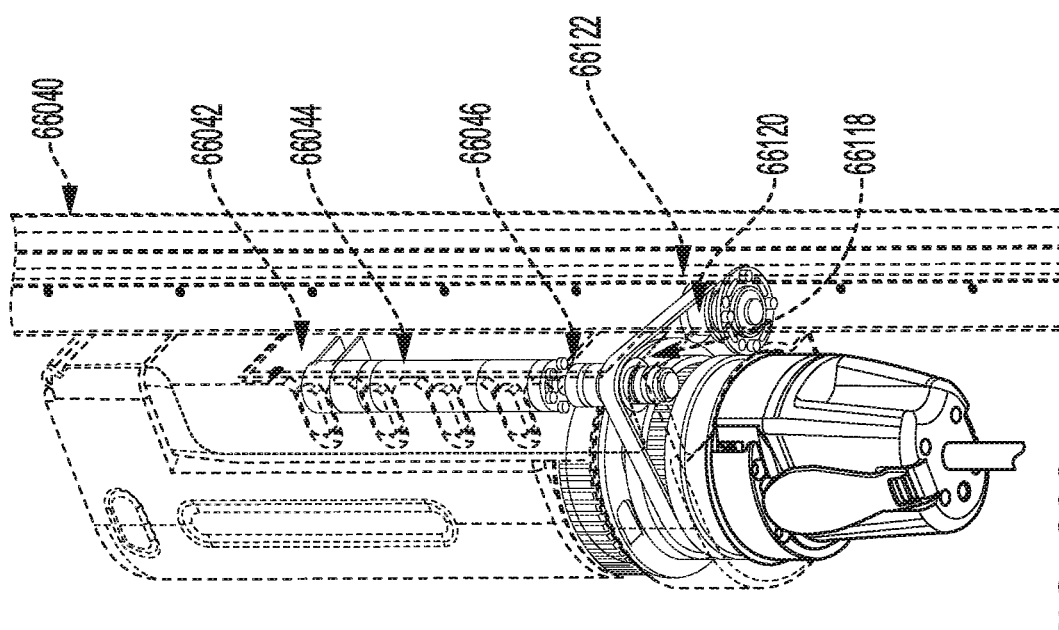

FIG. 236 illustrates a robotic surgical assembly that is connectable to an interface panel or carriage which is slidably mounted onto the rail according to at least one aspect of the present disclosure.

Figure 237:
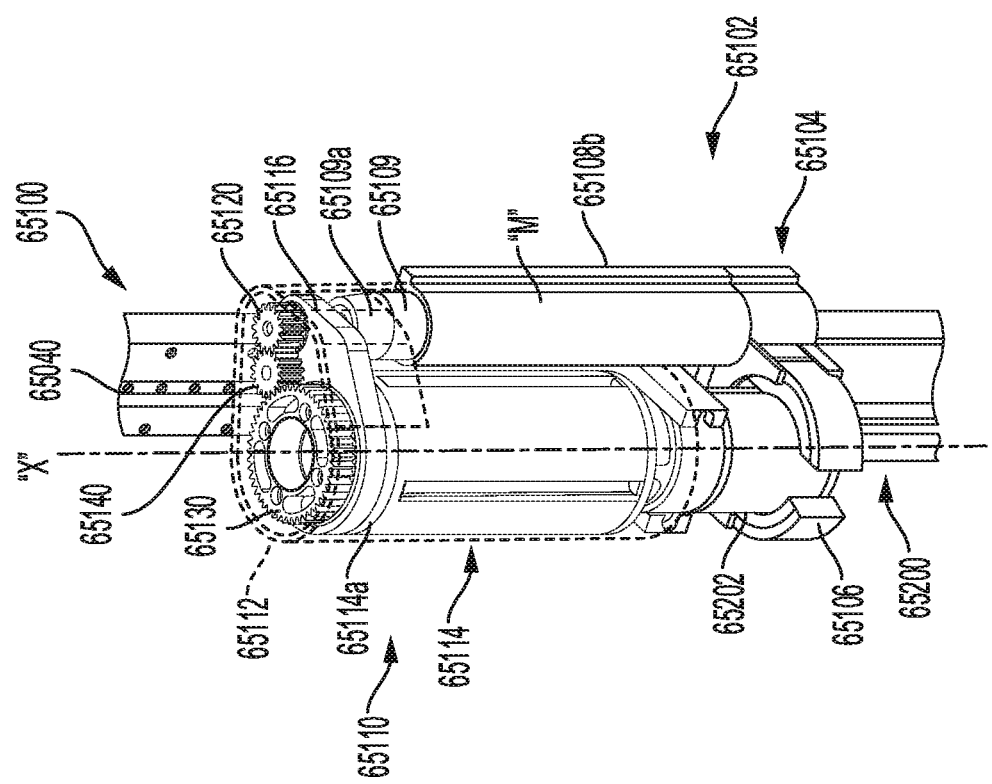

FIG. 237 illustrates a surgical instrument holder of a surgical assembly that functions both to actuate a rotation of a body of an instrument drive unit and to support a housing of a surgical instrument according to at least one aspect of the present disclosure.

Figure 238:
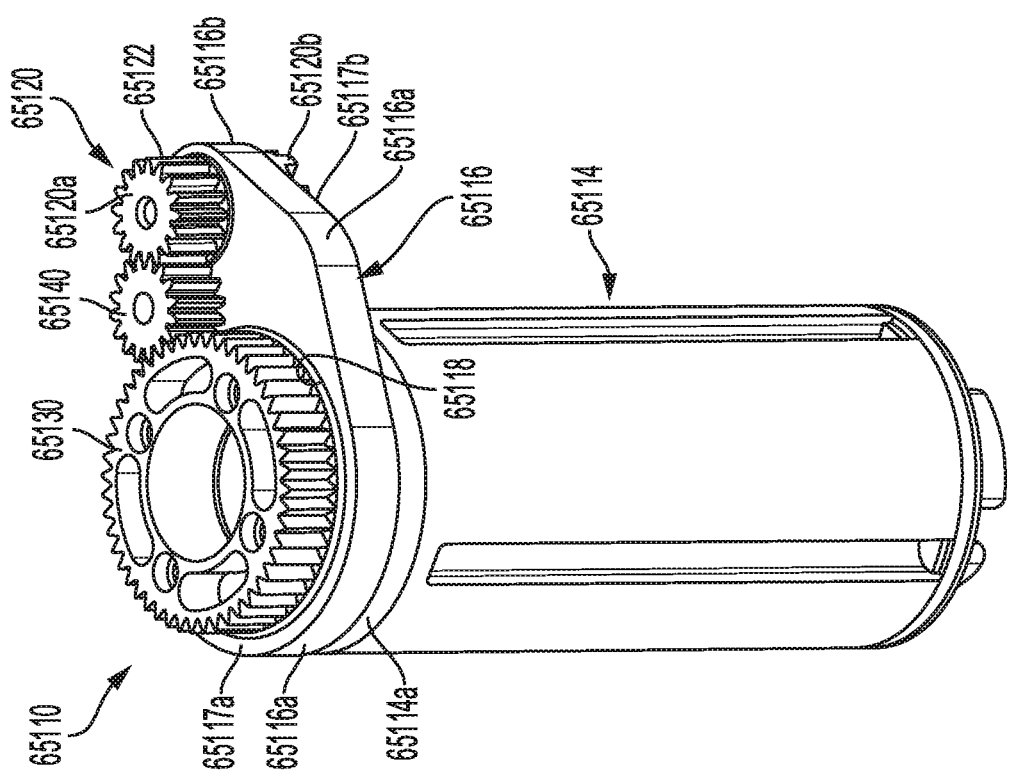

FIG. 238 illustrates the surgical instrument holder of a surgical assembly shown in FIG. 237 that functions both to actuate a rotation of a body of an instrument drive unit and to support a housing of a surgical instrument according to at least one aspect of the present disclosure.

Figure 239:
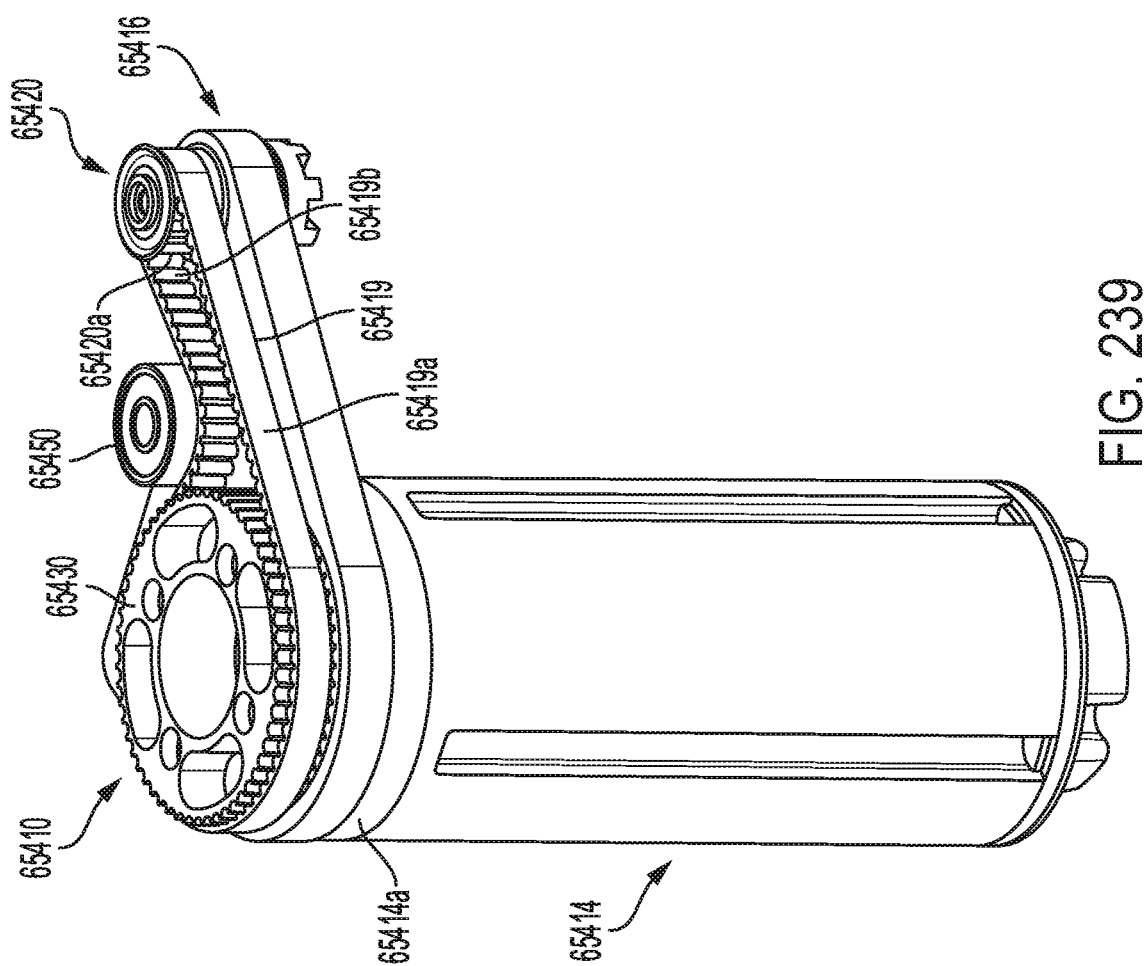

FIG. 239 illustrates an instrument drive unit according to at least one aspect of the present disclosure.

Figure 240:
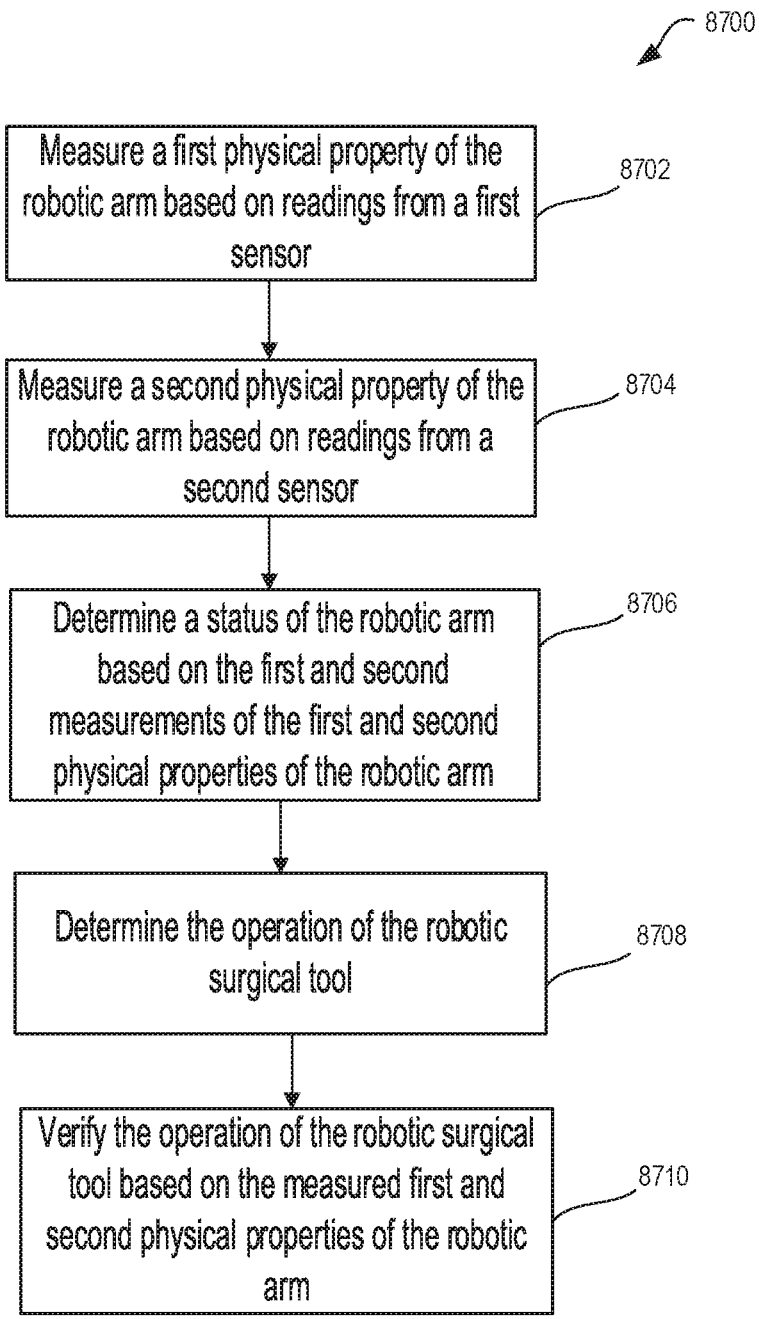

FIG. 240 is a flow diagram of a process depicting a control program or a logic configuration for controlling a robotic arm according to at least one aspect of the present disclosure.

FIG. 241 illustrates a surgical visualization system including a robotic arm coupled to a visualization assembly, in accordance with at least one aspect of the present disclosure.

FIG. 242 illustrates a perspective view of a distal portion of the visualization assembly of FIG. 241.

FIG. 243 illustrates a longitudinal cross-sectional view of the distal portion of the visualization assembly of FIG. 242.

Figure 244:
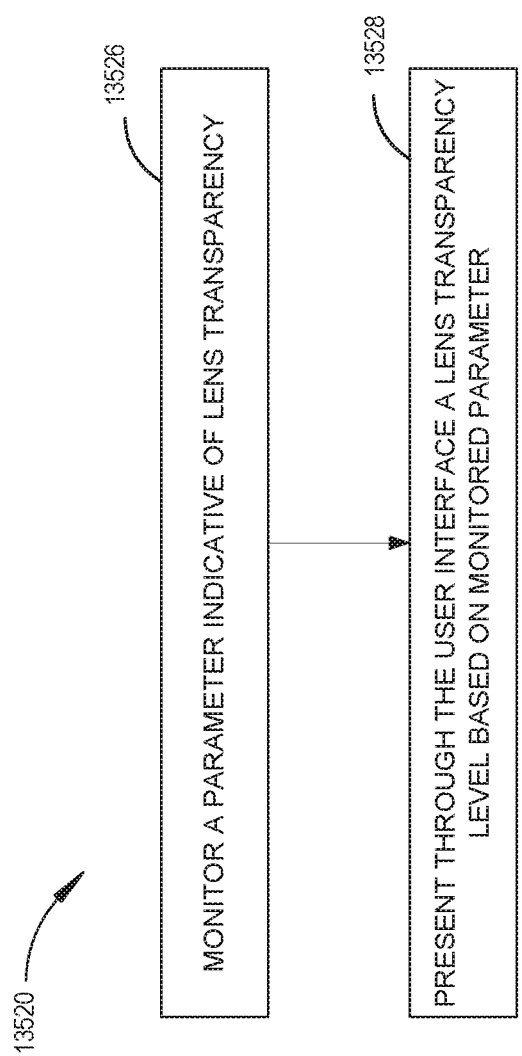

FIG. 244 is a logic flow diagram of a process depicting a control program or a logic configuration for detecting lens transparency of a surgical visualization system and reporting the same, in accordance with at least one aspect of the present disclosure.

Figure 244A:
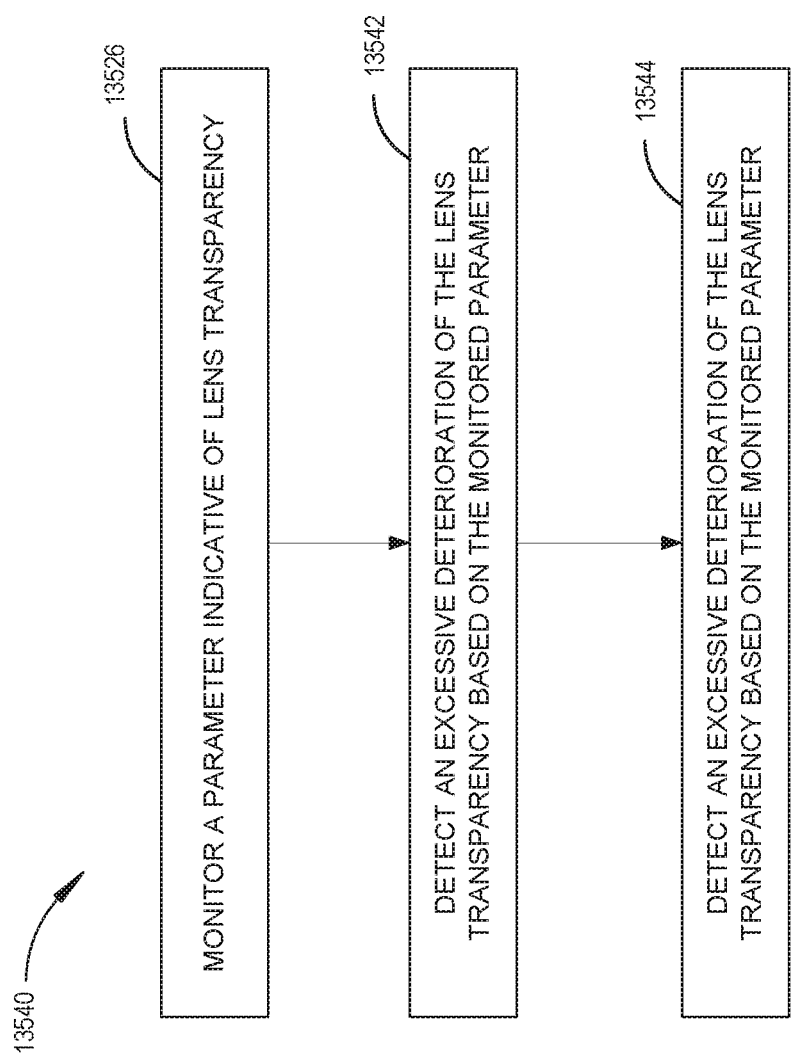

FIG. 244A is a is a logic flow diagram of a process depicting a control program or a logic configuration for determining whether a visualization lens of a surgical visualization system needs cleaning and triggering the cleaning, in accordance with at least one aspect of the present disclosure.

Figure 245:
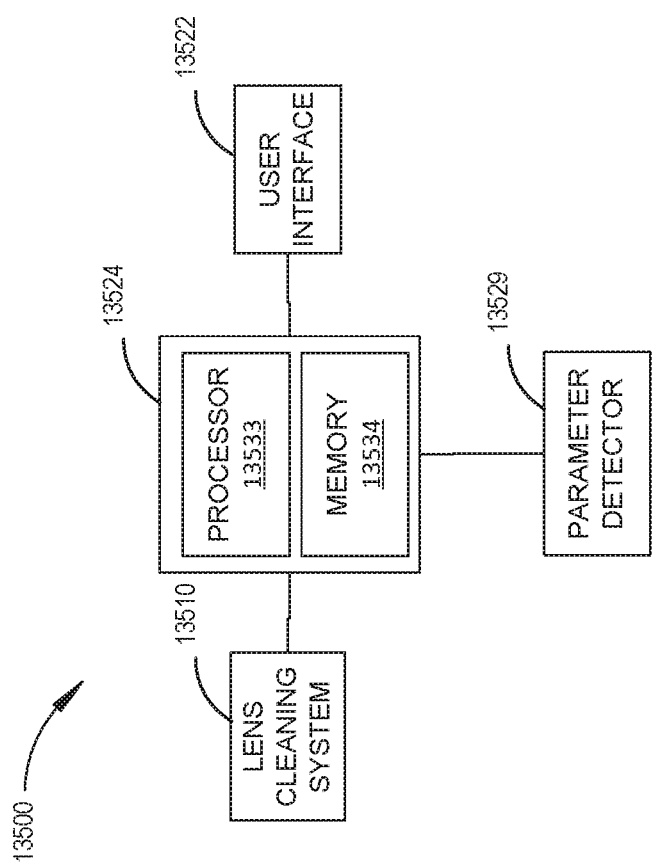

FIG. 245 is a schematic diagram of a surgical visualization system, in accordance with at least one aspect of the present disclosure.

FIG. 246 illustrates a perspective view of a distal portion of a visualization assembly of a surgical visualization system, in accordance with at least one aspect of the present disclosure.

FIG. 247 is a graph depicting time (t) on the x-axis and occlusion level through a visualization lens of a surgical visualization system on the y-axis, in accordance with at least one aspect of the present disclosure.

Figure 248:
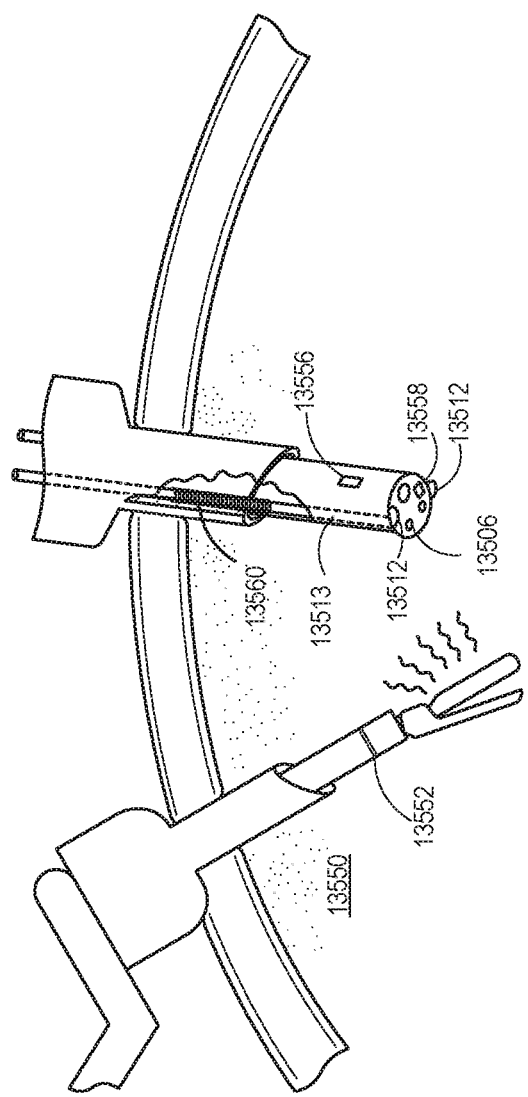

FIG. 248 illustrates two trocars inserted into a body cavity, the first trocar accommodating a visualization assembly, and the second trocar accommodating an electrosurgical instrument, in accordance with at least one aspect of the present disclosure.

Figure 249:
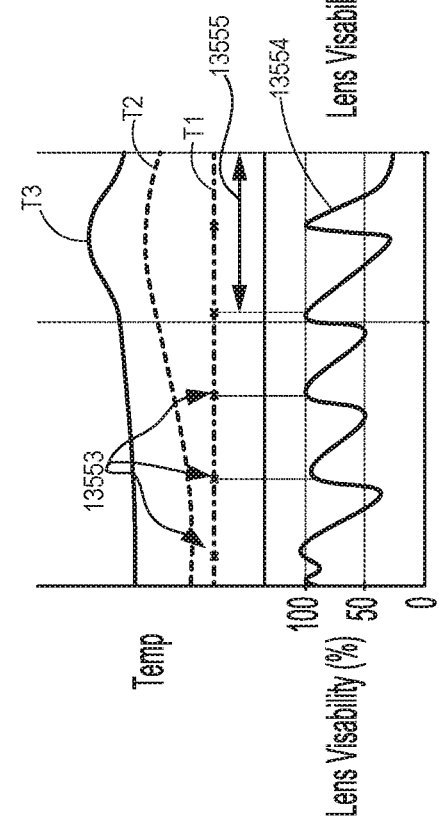

FIG. 249 is a graph including a top graph that represents temperature on the Y-axis vs time on the X-axis and a bottom graph that represents lens visibility percentage on the Y-axis vs time on the X-axis, in accordance with at least one aspect of the present disclosure.

Figure 250:
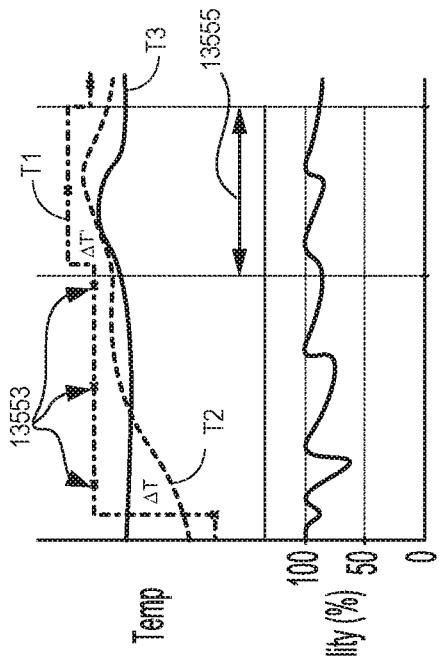

FIG. 250 is a graph including a top graph that represents temperature on the Y-axis vs time on the X-axis and a bottom graph that represents lens visibility percentage on the Y-axis vs time on the X-axis, in accordance with at least one aspect of the present disclosure.

Figure 251:
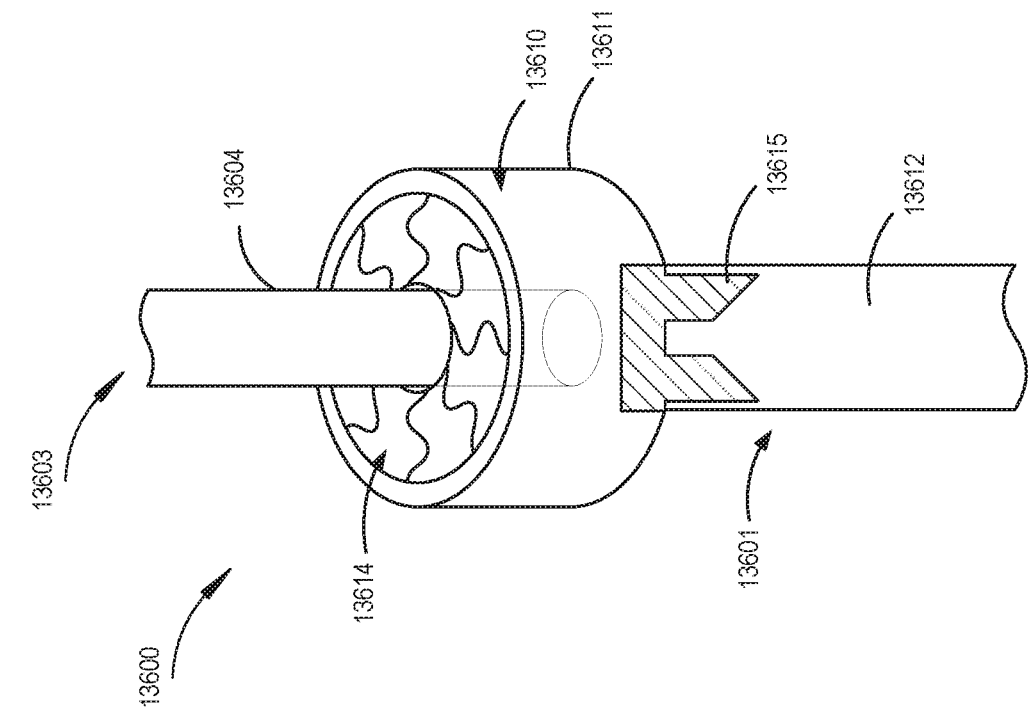

FIG. 251 illustrates an imaging device including a distal end a distance D1 from an iris seal of a seal assembly of a trocar, in accordance with at least one aspect of the present disclosure.

Figure 252:
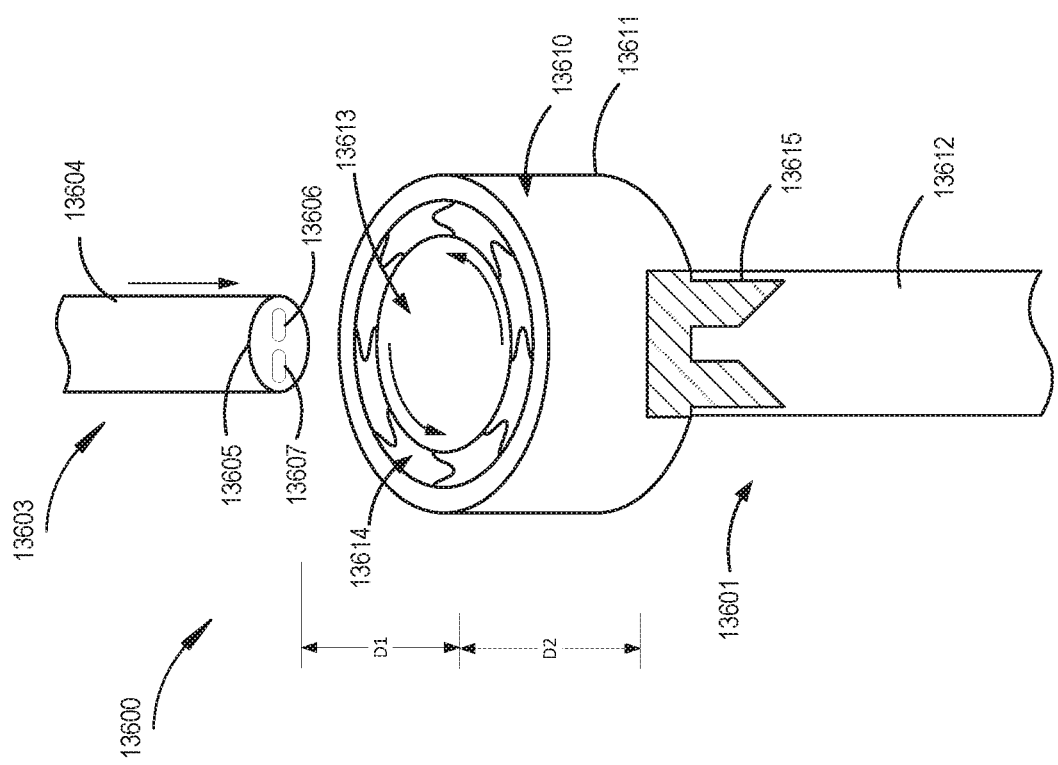

FIG. 252 illustrates the imaging device inserted into the iris seal of the seal assembly of the trocar of FIG. 251, in accordance with at least one aspect of the present disclosure.

FIG. 253 illustrates a trocar connected to a lens cleaning system, in accordance with at least one aspect of the present disclosure.

FIG. 254 illustrates the trocar of FIG. 253 with an imaging device being cleaned inside the trocar by a flushing fluid from the lens cleaning system, in accordance with at least one aspect of the present disclosure.

Figures 255, 256:
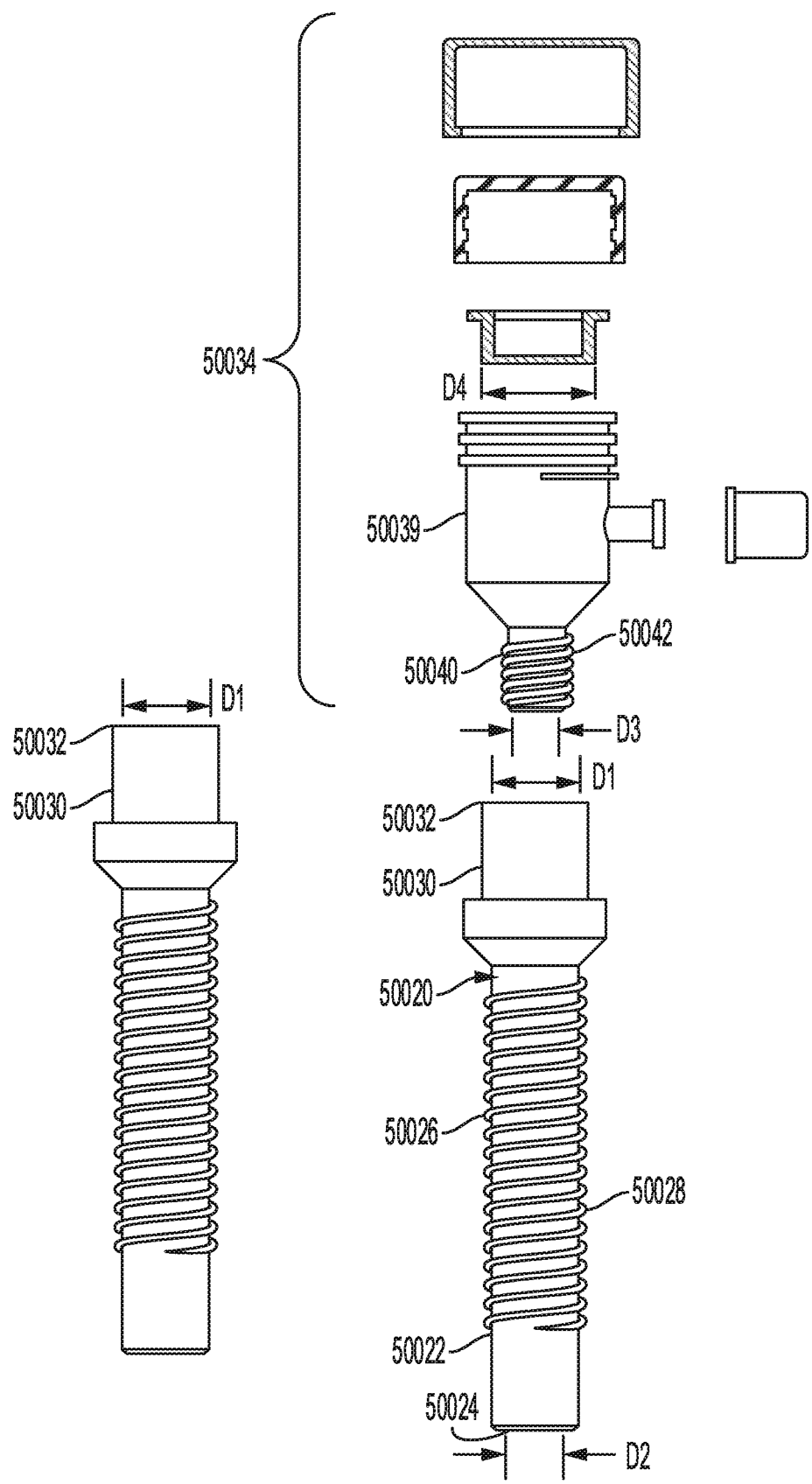

FIG. 255 is an exploded view of a device.

FIG. 256 is an alternative embodiment of a portion of the device shown in FIG. 255.

Figure 257:
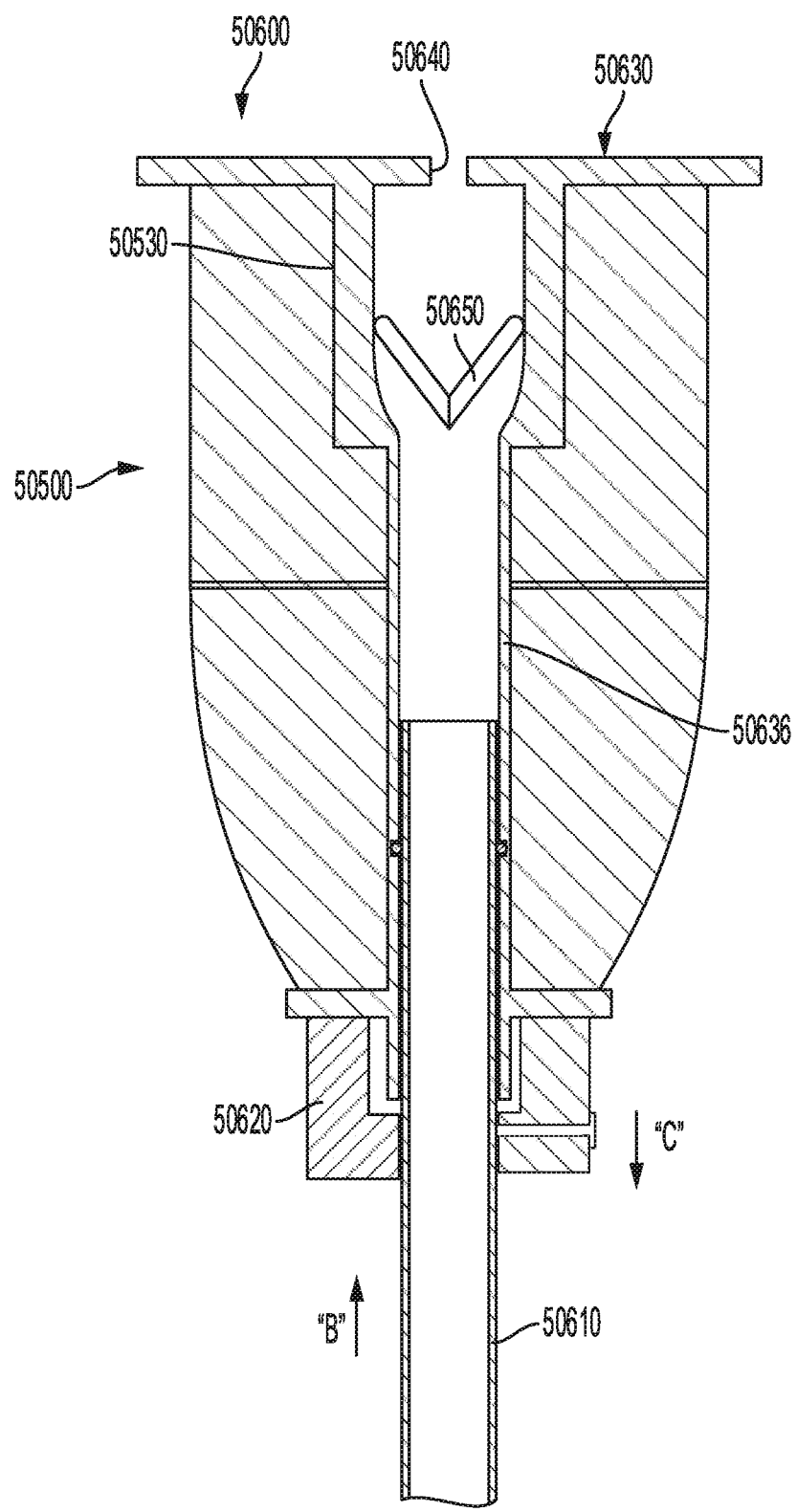

FIG. 257 is a cross-sectional view of a mounting structure and cannula assembly.

FIG. 258 is a partial cross-sectional view showing a seal body housing.

FIG. 259 is a perspective view with parts separated of a cannula assembly.

FIG. 260 is an enlarged view of the indicated area of detail of FIG. 259.

Figure 261:
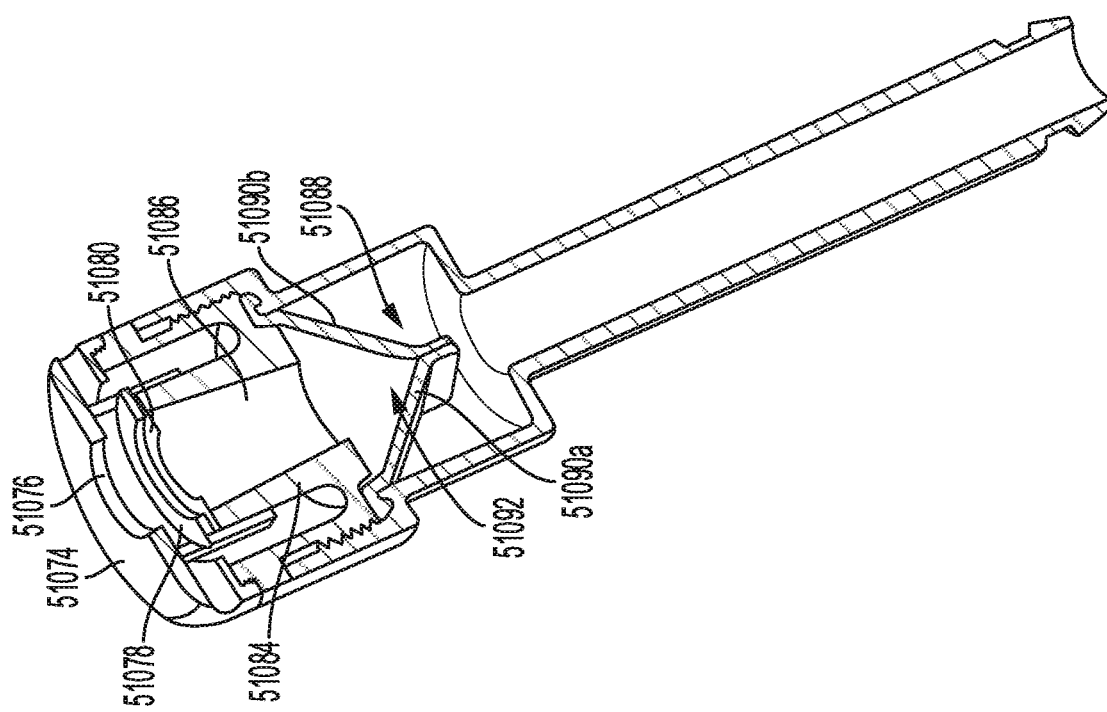

FIG. 261 is a cross sectional view of a sealing cannula.

Figure 262:
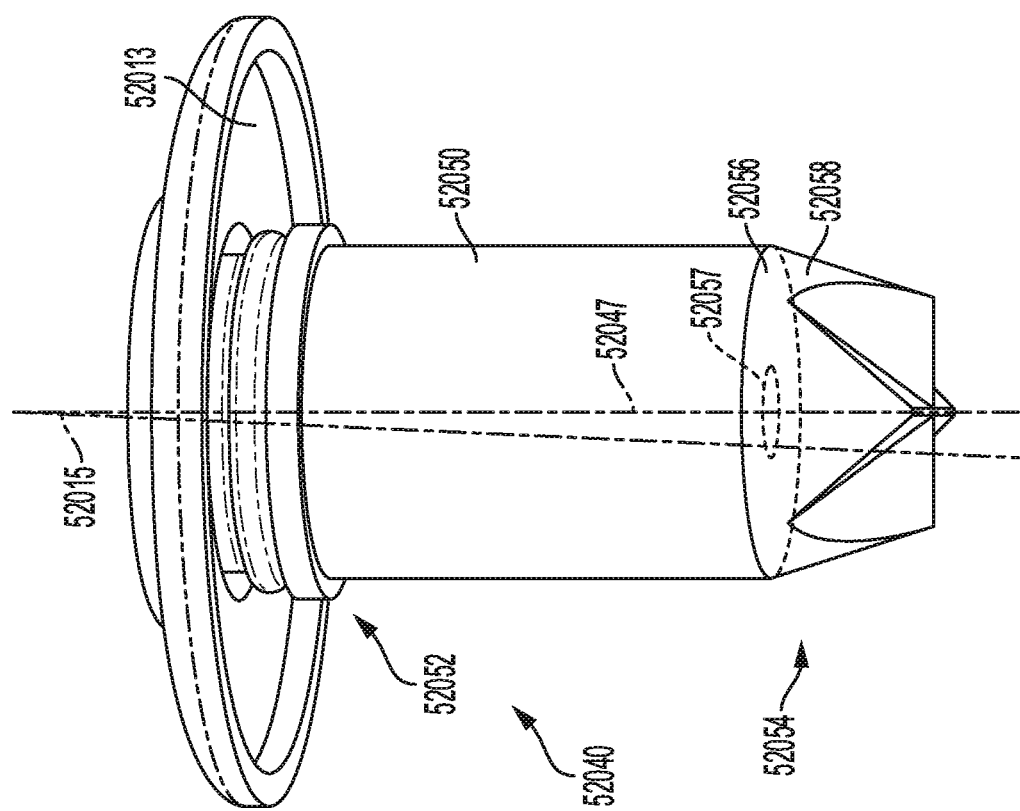

FIG. 262 is a perspective view of a pendent valve mounted to an end cap of a trocar.

FIG. 263 is an axial cross-section view illustrating operation of the pendent valve during off-axis insertion of an instrument.

FIG. 264 is an axial cross-section view showing an instrument fully inserted with effective seal formation notwithstanding an off-axis position of the instrument.

FIG. 265 is a cross-section view taken along lines 265-265 of FIG. 264.

FIG. 266 is a cross-section view taken along lines 266-266 of FIG. 264.

Figure 267:
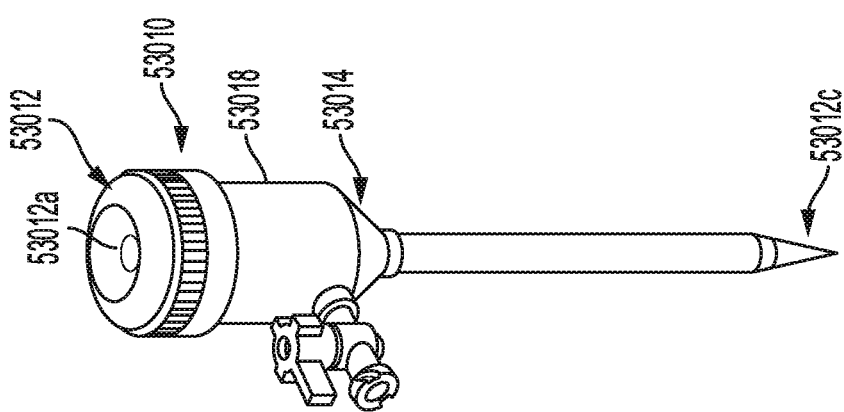

FIG. 267 is a perspective view of an assembled trocar.

Figure 268:
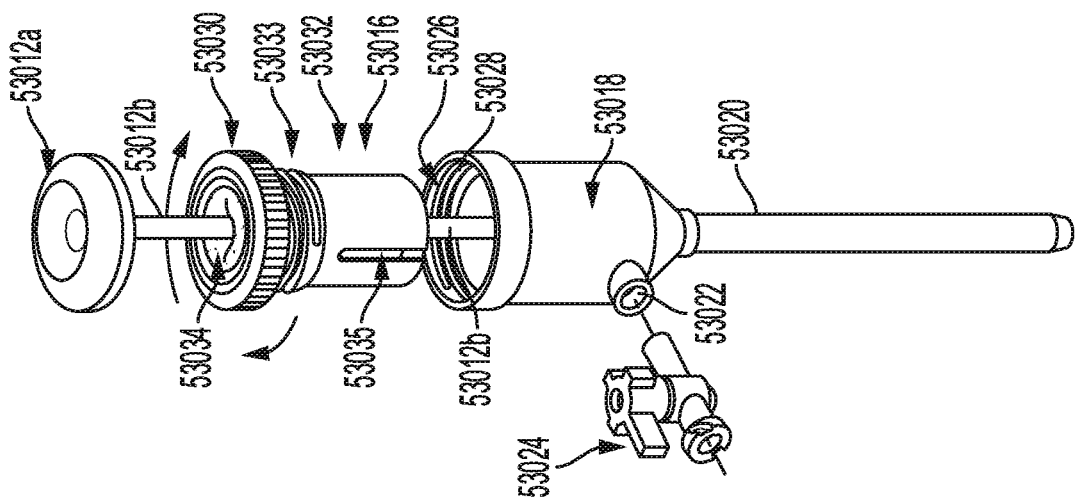

FIG. 268 is an exploded perspective view of the components of the trocar of FIG. 267.

Figure 269:
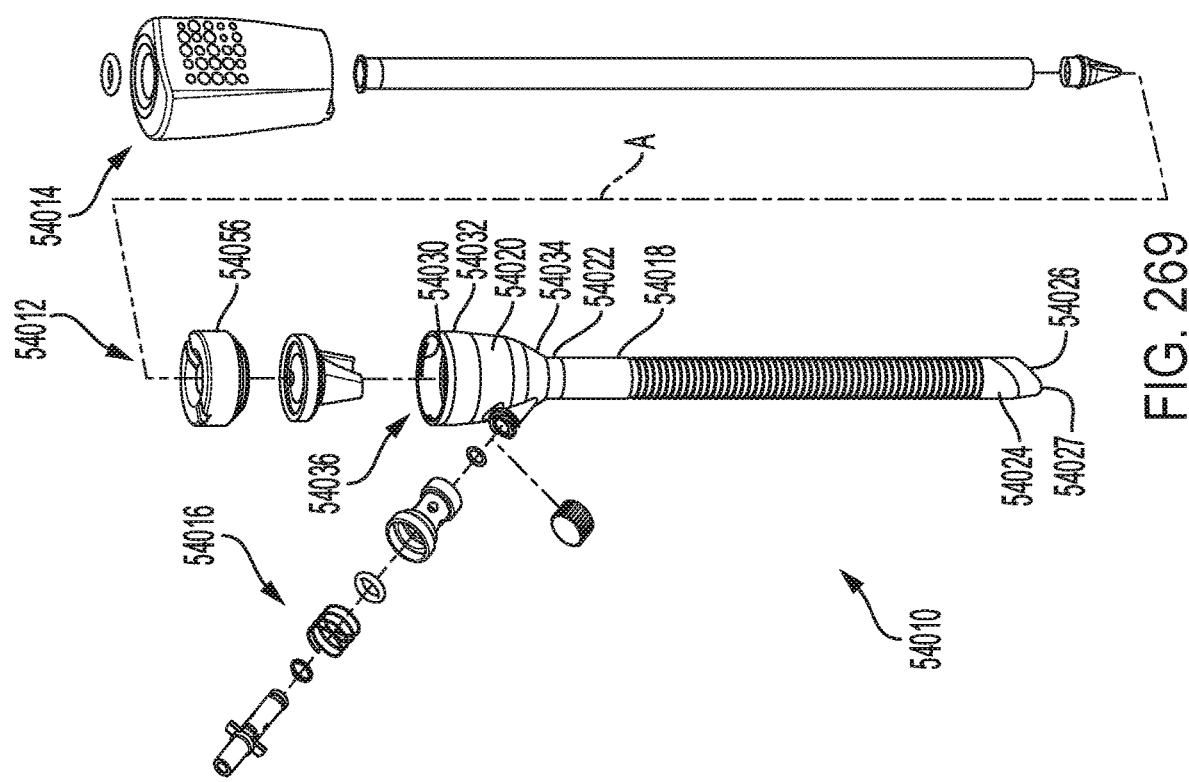

FIG. 269 is an exploded perspective view of a trocar assembly.

Figure 270:
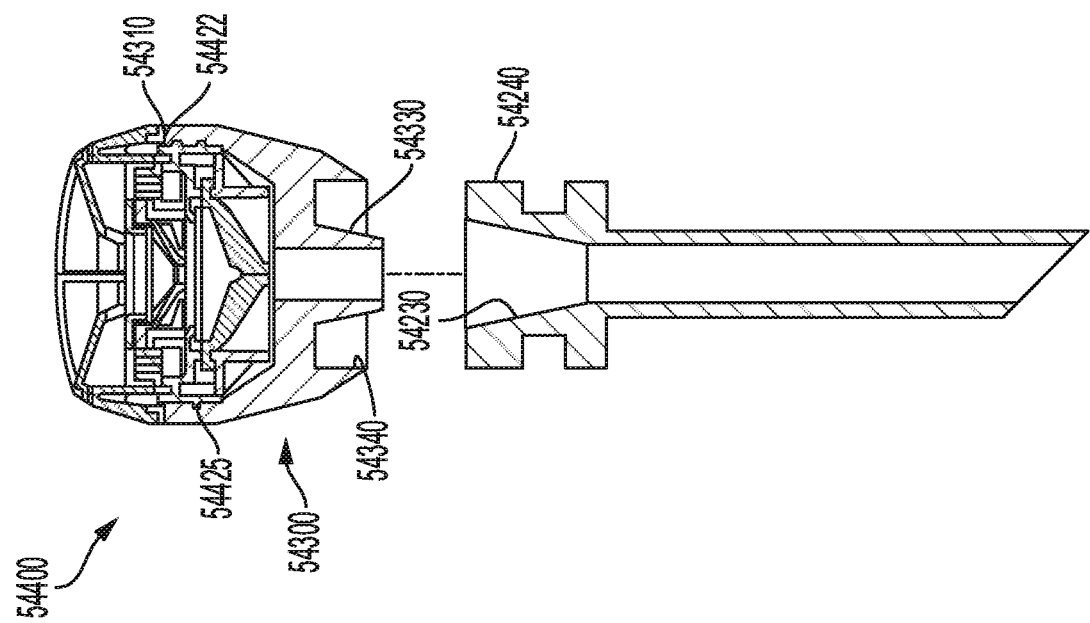

FIG. 270 is an exploded cross-sectional side view of an adaptor attached to a seal assembly positioned above a cannula.

Figure 271:
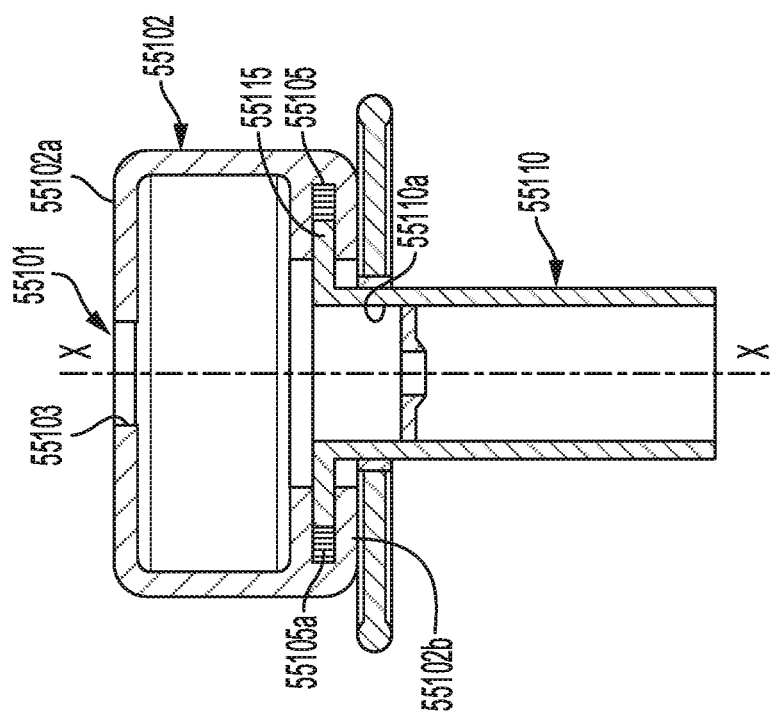

FIG. 271 is a side cross-sectional view of a trocar assembly.

Figure 272:
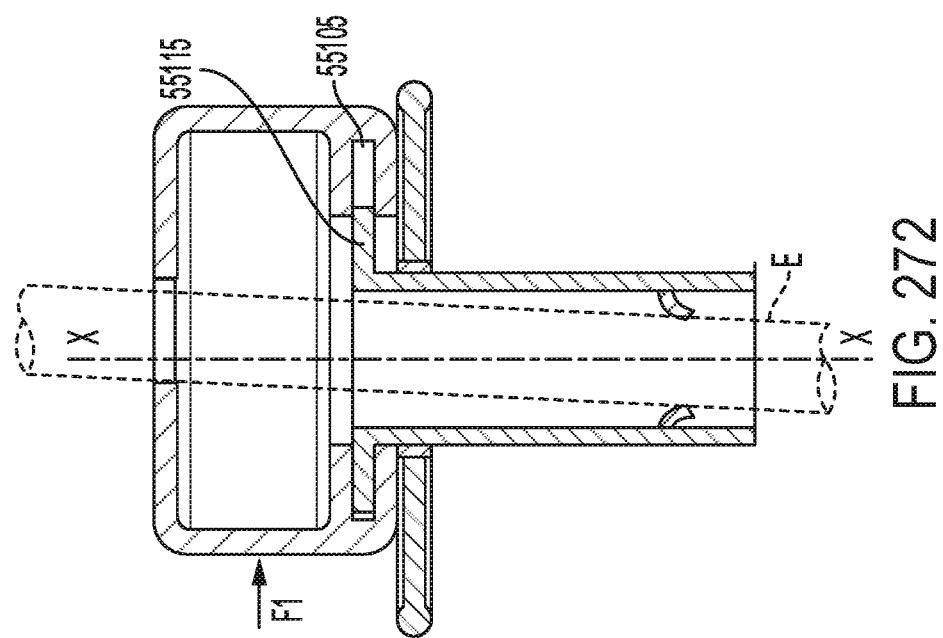

FIG. 272 is a cross-sectional side view of the trocar assembly of FIG. 271, in a first shifted condition.

Figure 273:
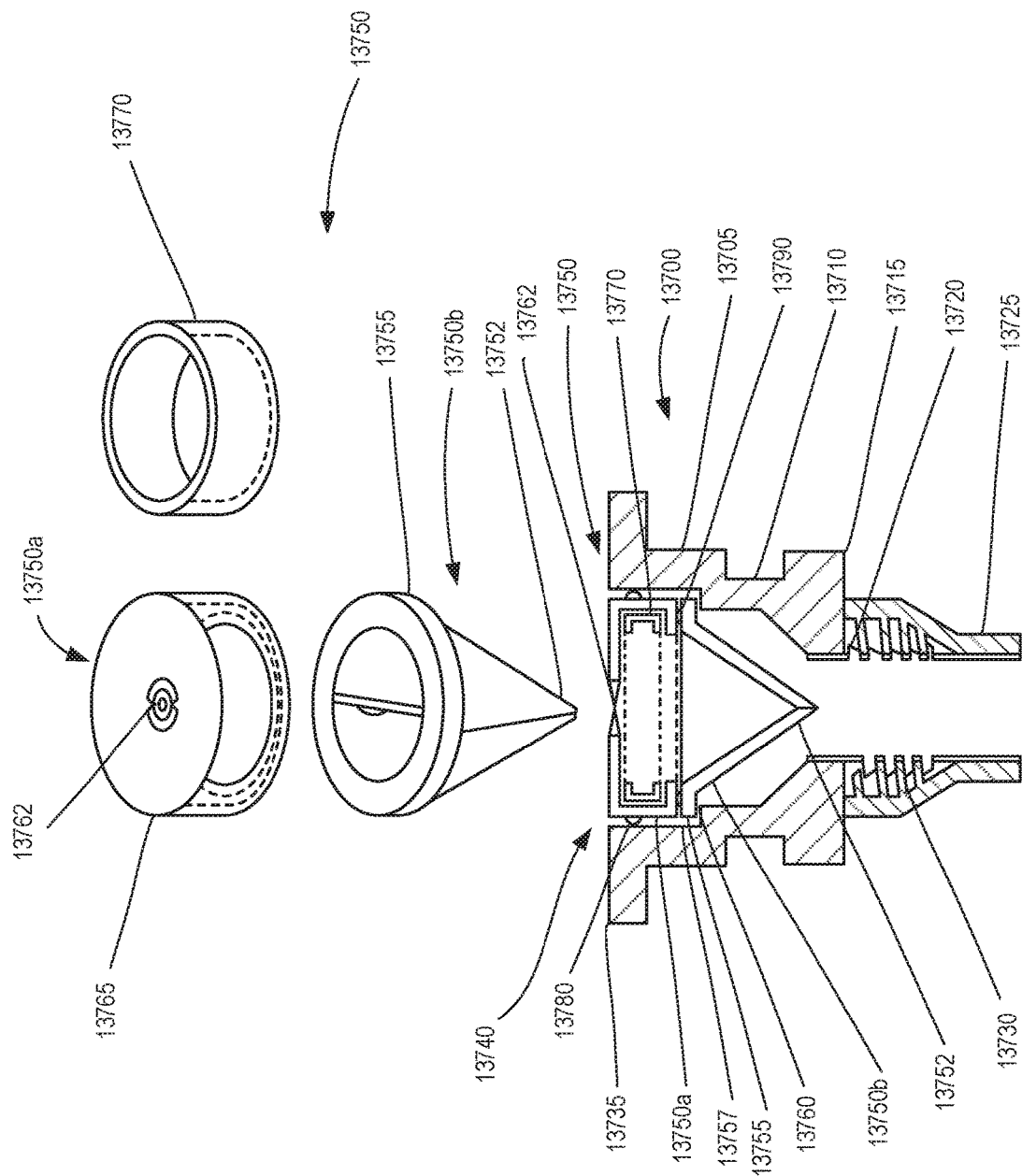

FIG. 273 is an exploded view of an insertable seal system and a cross sectional view of a trocar assembly including the insertable seal system positioned therein.

Figure 274:
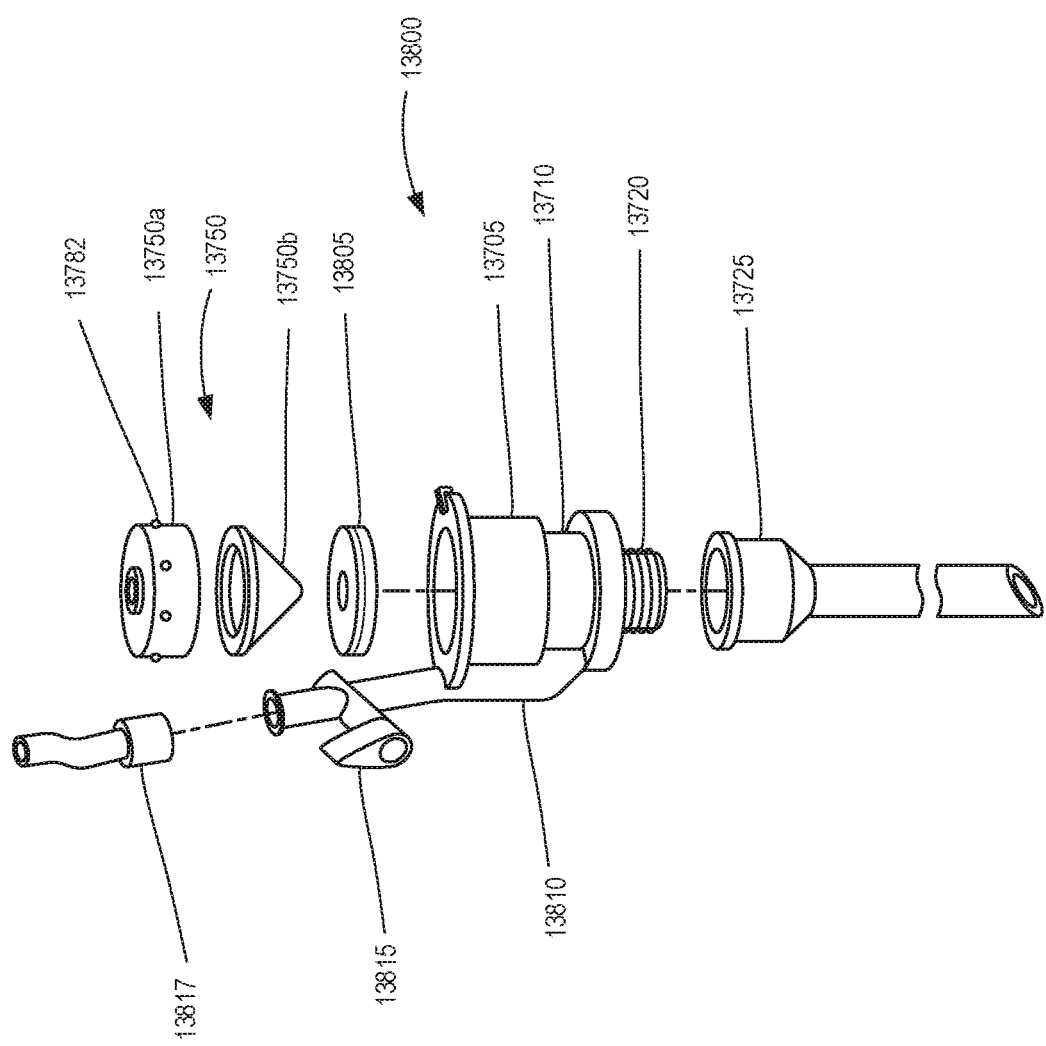

FIG. 274 is an exploded view of a trocar assembly including a third seal with an insertable seal system.

Figure 275:
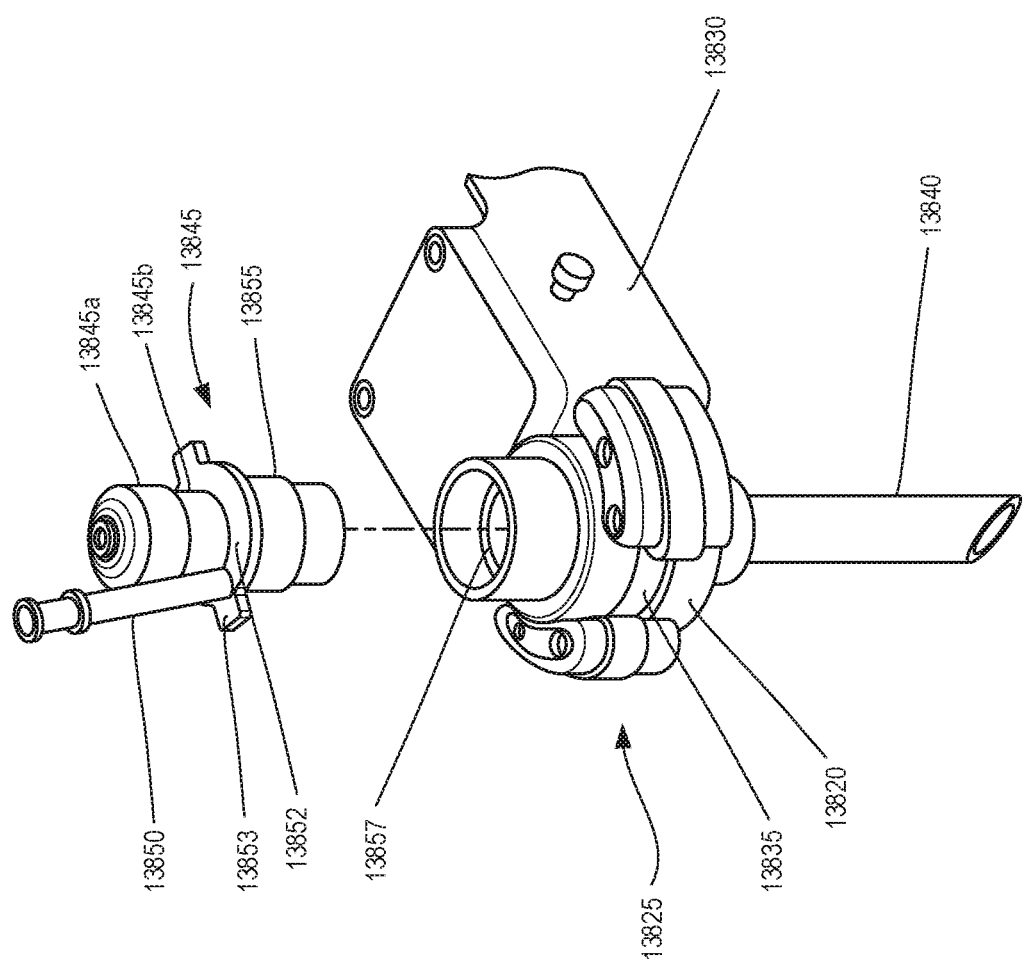
Figure 276:
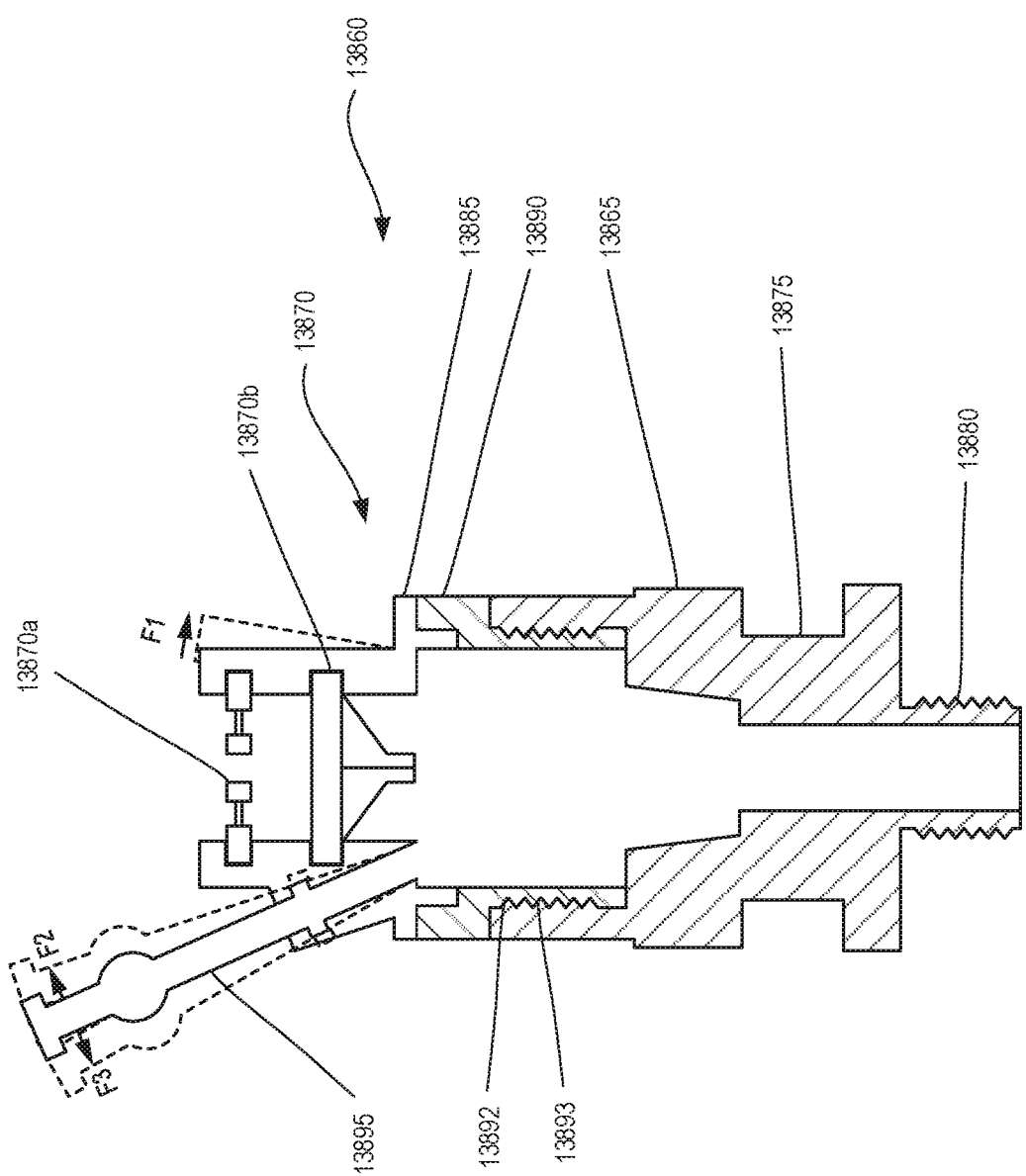

FIG. 275 is a seal assembly positioned above a trocar assembly that is held by a robot arm of a robotic surgical system FIG. 276 is a cross sectional view of a trocar assembly with a flexible seal housing.

Figure 277:
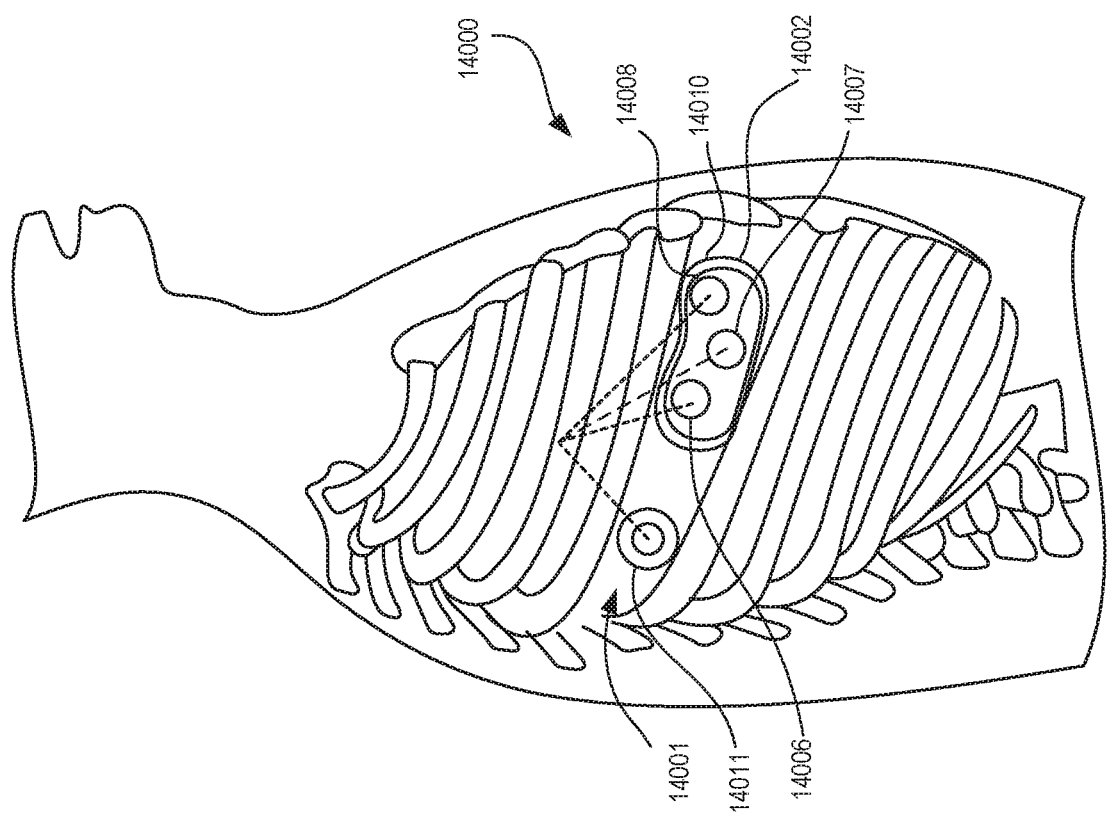

FIG. 277 illustrates a surgical access device positioned in an intercostal space of a patient, in accordance with at least one aspect of the present disclosure.

Figure 278:
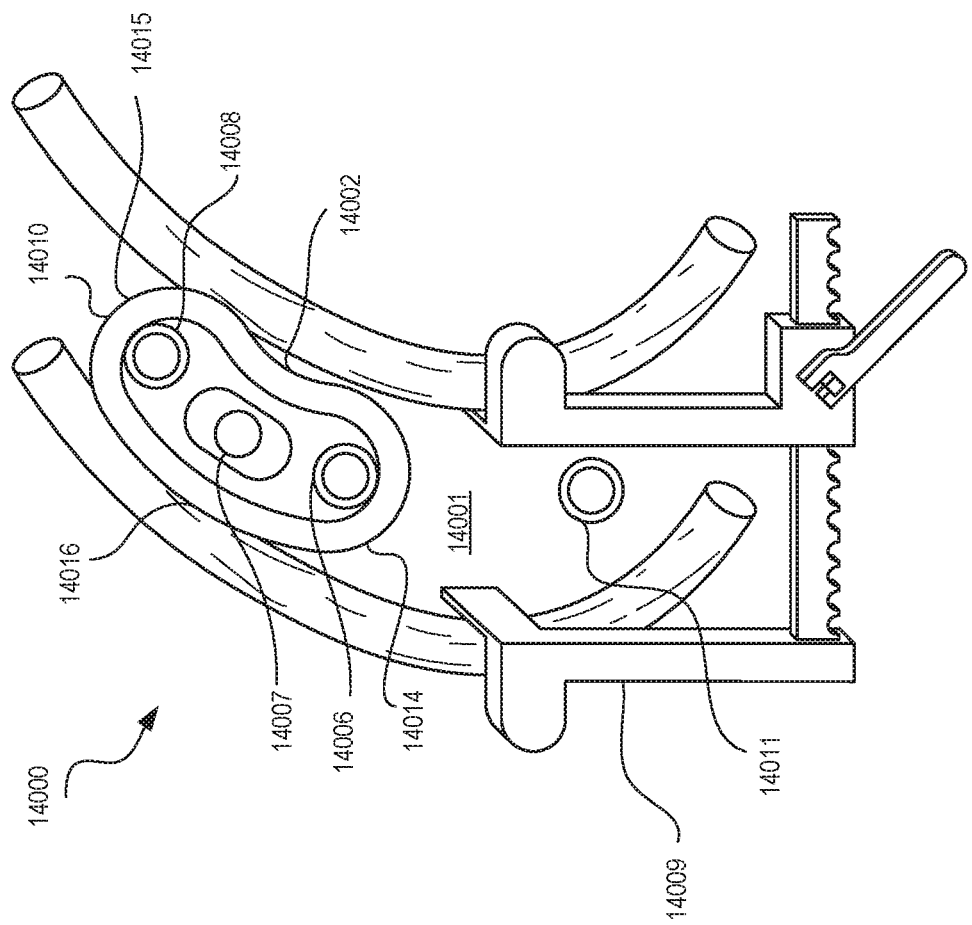

FIG. 278 illustrates two ribs spread apart via a surgical retractor, and a surgical access device position between the ribs, in accordance with at least one aspect of the present disclosure.

Figure 279:
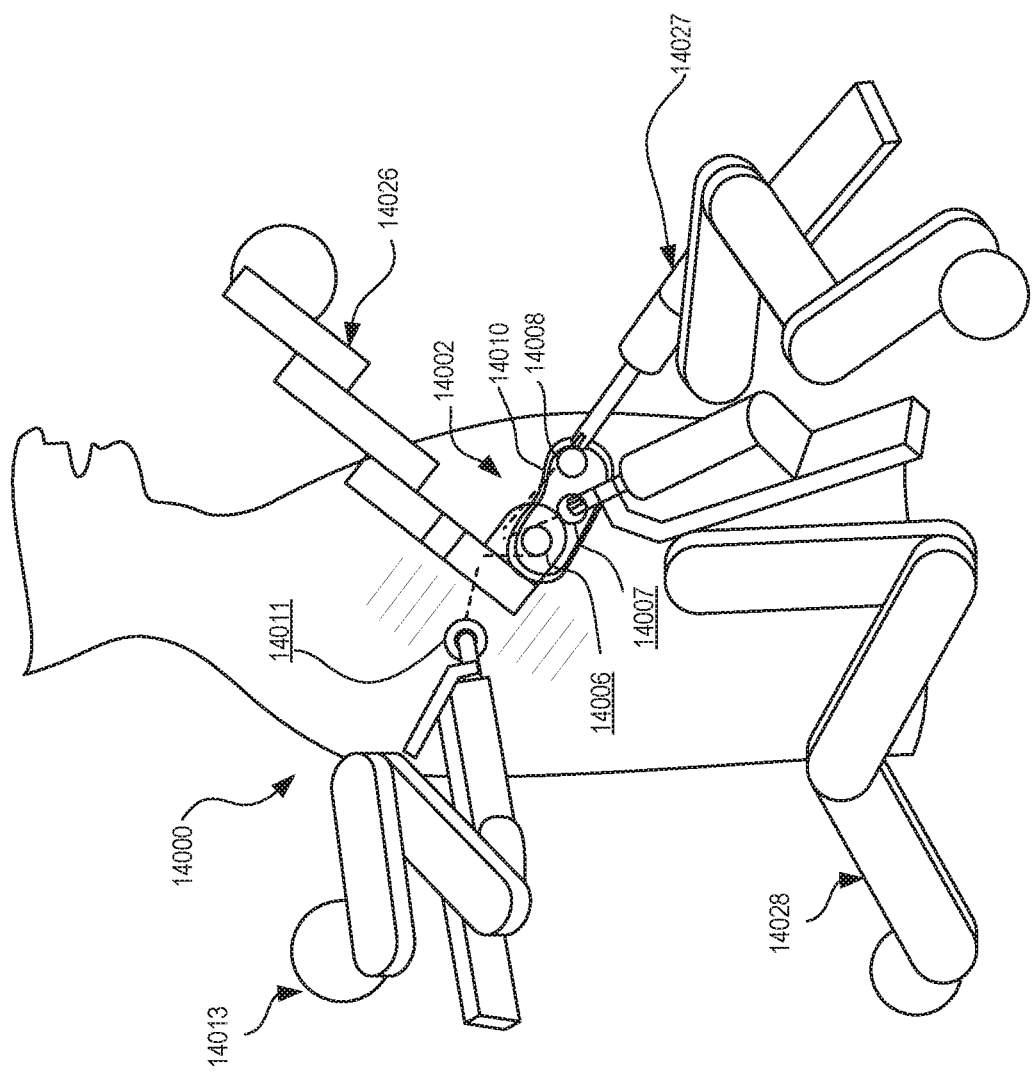

FIG. 279 illustrates a surgical access device with three access ports facilitating access of three surgical tools into a patient thoracic cavity, wherein the surgical tools are controlled by three robotic arms, in accordance with at least one aspect of the present disclosure.

Figure 280:
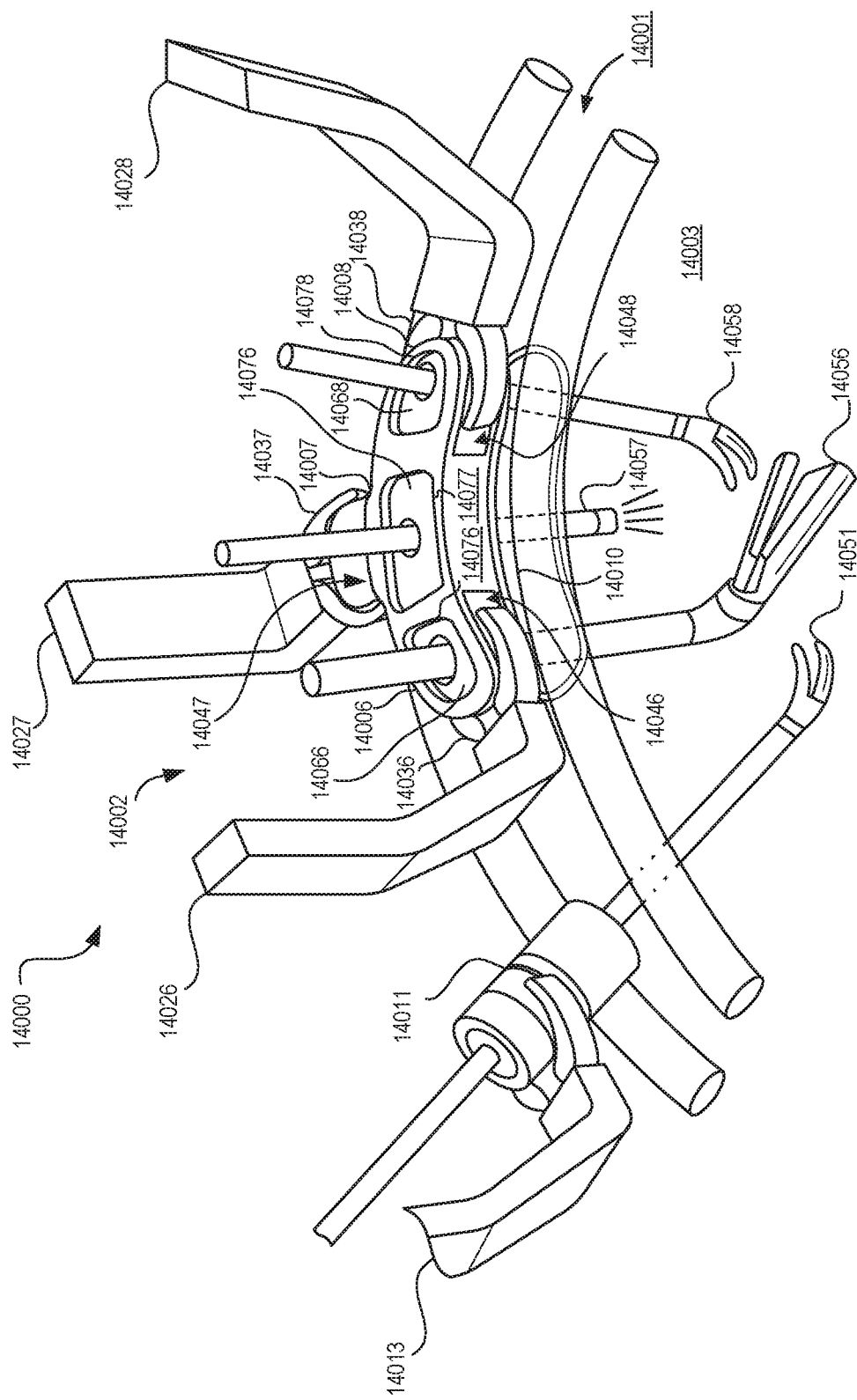

FIG. 280 illustrates a partial perspective view of the robotic arms and surgical tools of FIG. 279.

Figure 281:
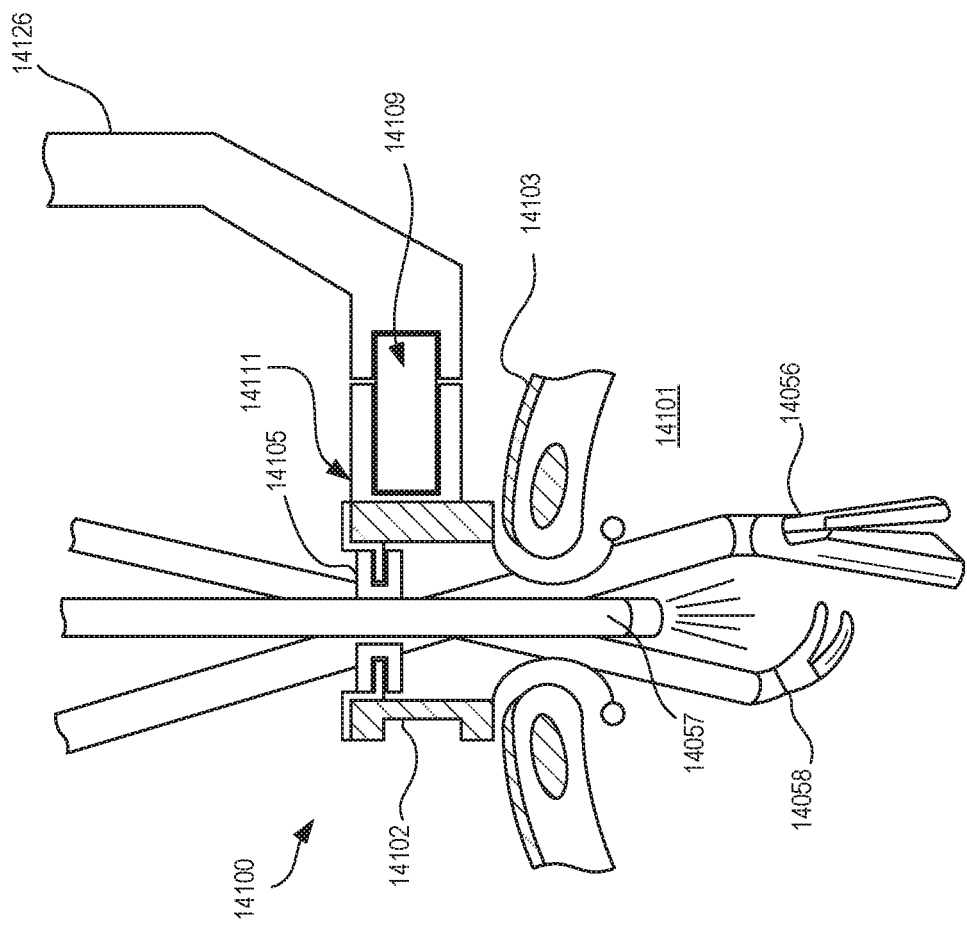

FIG. 281 illustrates a surgical access device with a single access port facilitating access of three surgical tools into a patient cavity, in accordance with at least one aspect of the present disclosure.

FIG. 282 is a surgical access device with a translatable member in a first position, in accordance with at least one aspect of the present disclosure.

FIG. 283 illustrates a surgical access device with a translatable member in a second position, in accordance with at least one aspect of the present disclosure.

FIG. 284 illustrates a translatable member of a surgical access device, in accordance with at least one aspect of the present disclosure.

Figure 285:
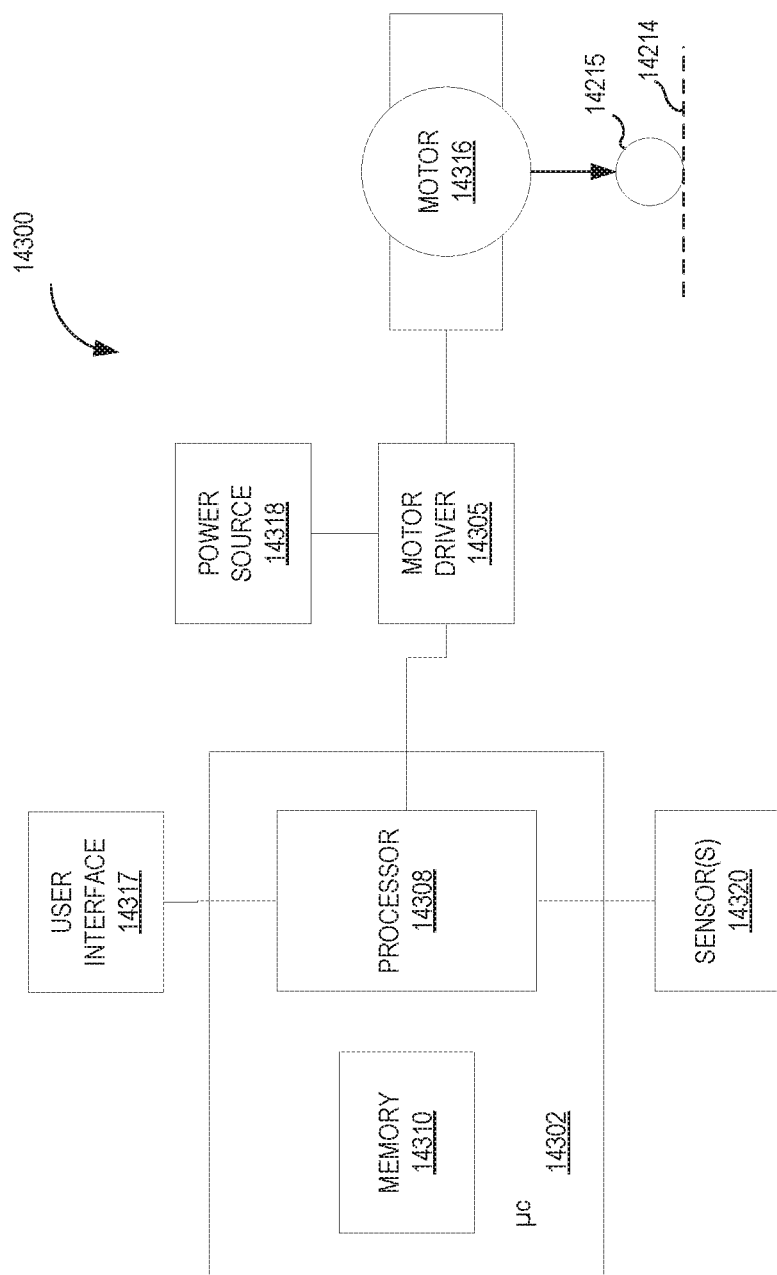

FIG. 285 is a block diagram illustrating a control circuit for moving a translatable member of a surgical access device, in accordance with at least one aspect of the present disclosure.

Figure 286:
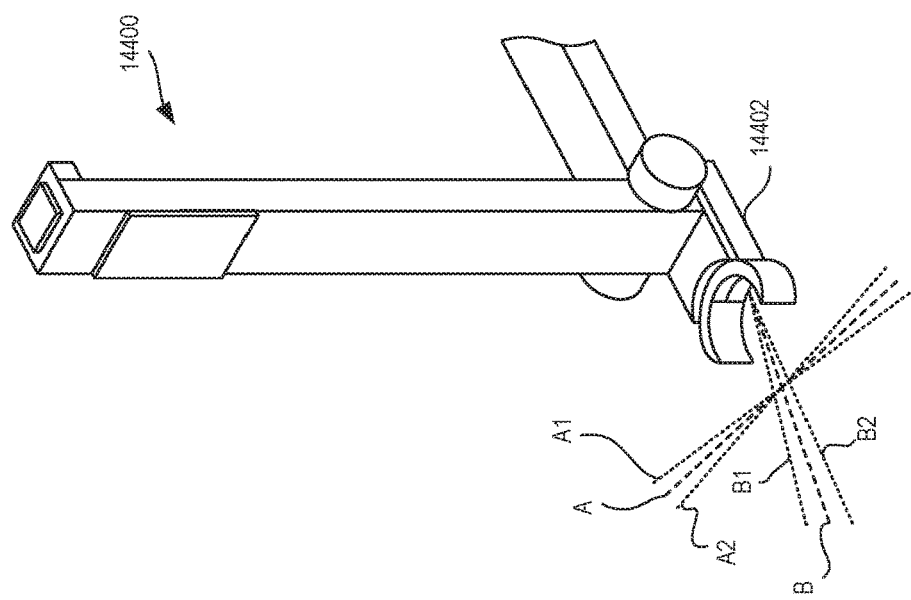

FIG. 286 illustrates a partial perspective view of a robotic arm before assembly with a surgical access device and a surgical instrument, in accordance with at least one aspect of the present disclosure.

Figure 287:
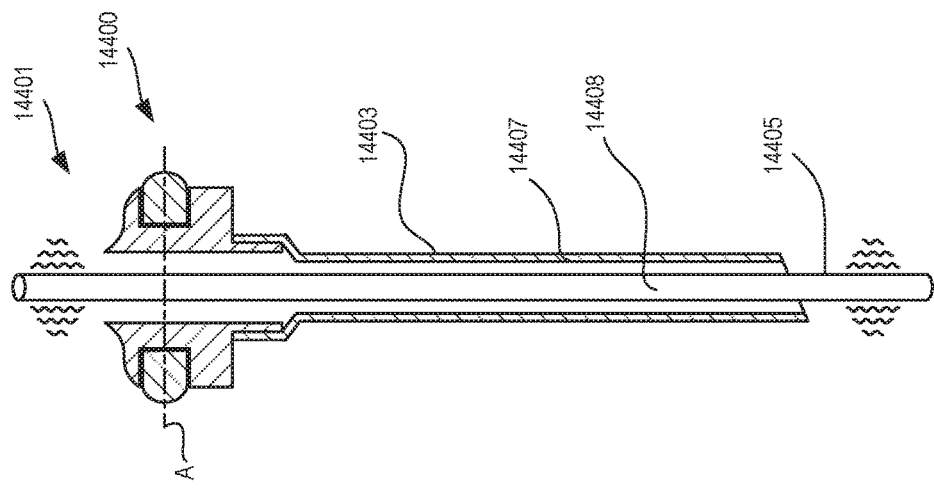

FIG. 287 illustrates a partial cross-sectional view of the robotic arm of FIG. 286 assembled with a surgical instrument and a surgical access device, in accordance with at least one aspect of the present disclosure.

Figure 288:
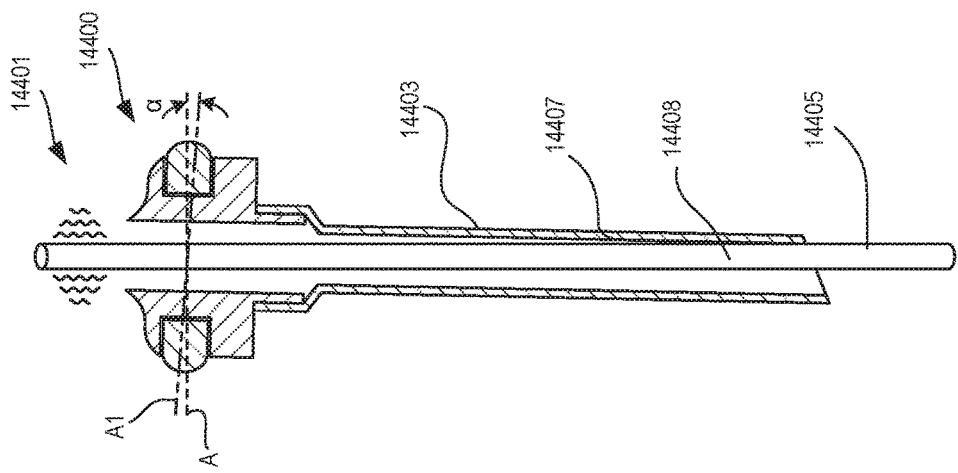

FIG. 288 illustrates a partial cross-sectional view of the robotic arm of FIG. 286 assembled with a surgical instrument and a surgical access device, in accordance with at least one aspect of the present disclosure.

FIG. 289 illustrates a partial cross-sectional view of a surgical access device including stabilizing compartments, in accordance with at least one aspect of the present disclosure.

FIG. 290 illustrates a partial elevational view of a surgical instrument including dampening features, in accordance with at least one aspect of the present disclosure.

FIG. 291 illustrates the surgical instrument of FIG. 290 assembled with the surgical access device of FIG. 289, in accordance with at least one aspect of the present disclosure.

FIG. 292 illustrates a surgical access device with non-concentric instrument support features, in accordance with at least one aspect of the present disclosure.

FIG. 293 illustrates three transverse cross-sectional views of the surgical access device of FIG. 292, in accordance with at least one aspect of the present disclosure.

FIG. 294 is a schematic diagram illustrating a top view of the surgical access device of FIG. 292, in accordance with at least one aspect of the present disclosure.

Figure 295:
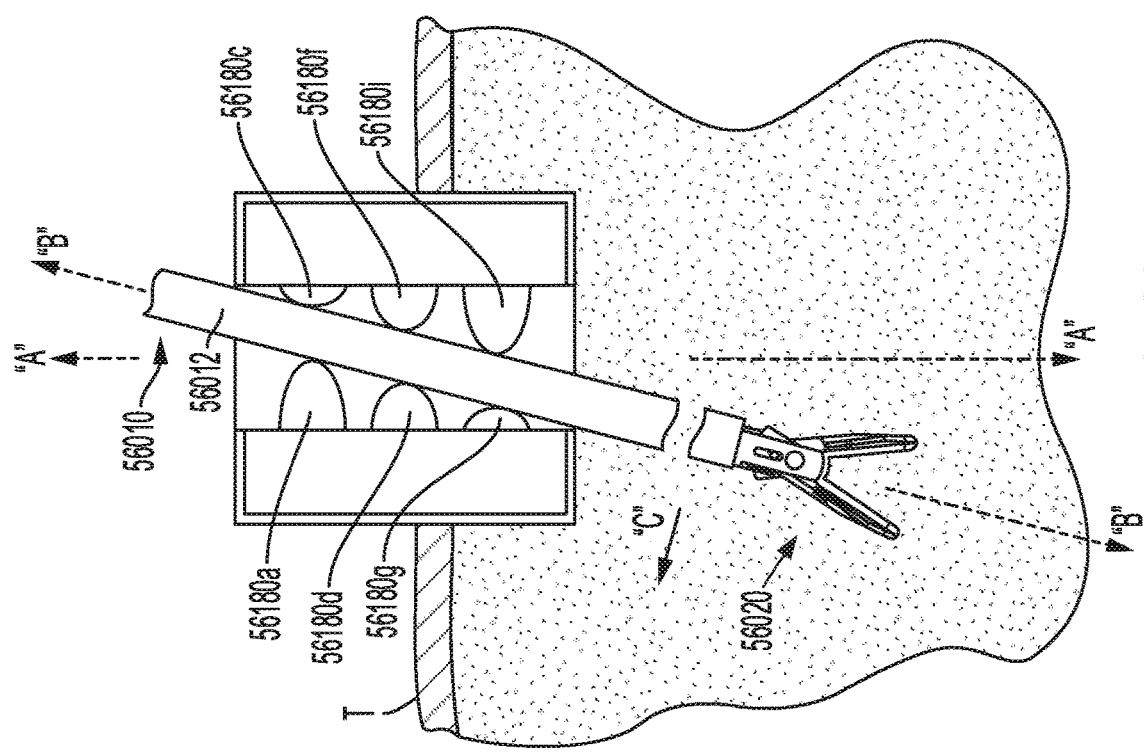

FIG. 295 is a cross-sectional view of a port assembly shown with a surgical instrument extending through the interior space of the port assembly at an angle.

FIG. 296 is a side cross-sectional view of an access apparatus.

FIG. 297 is a side plan view of the seal assembly of the access apparatus of FIG. 296.

FIG. 298 is an enlarged isolated view in cross-section of FIG. 297, detailing the components of the seal of the access apparatus.

Figure 299:
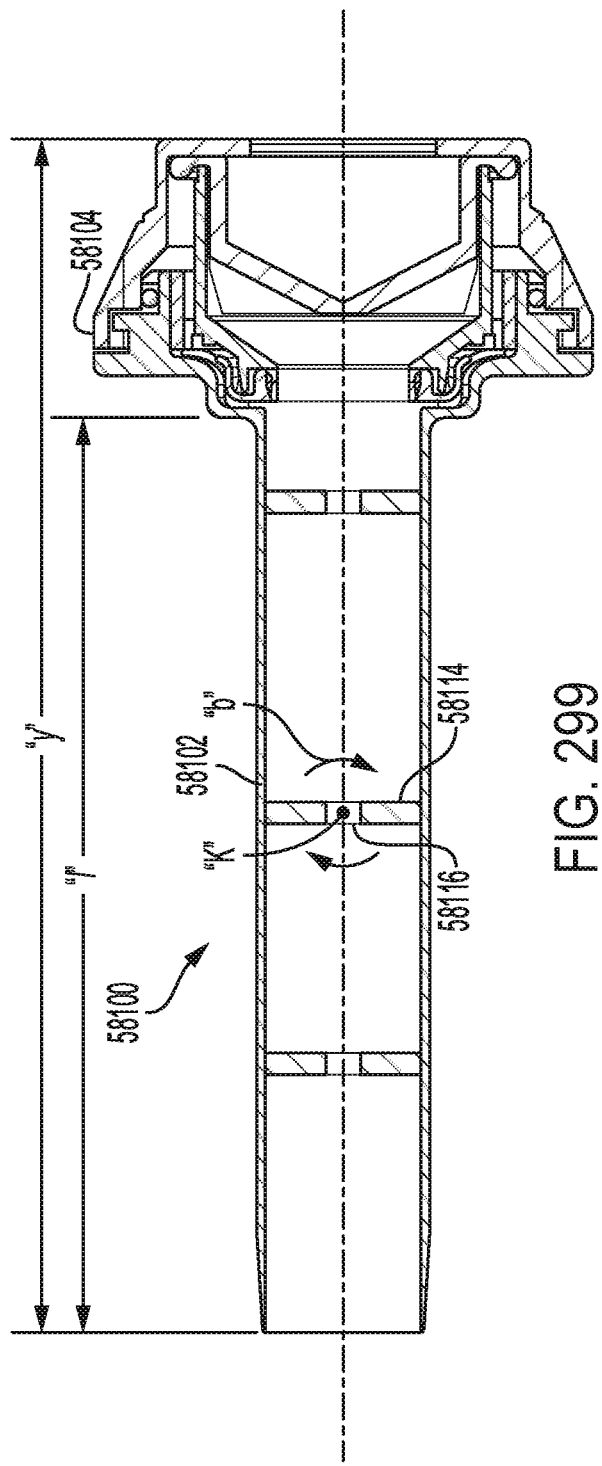

FIG. 299 is a side cross-sectional view of the access apparatus.

Figure 300:
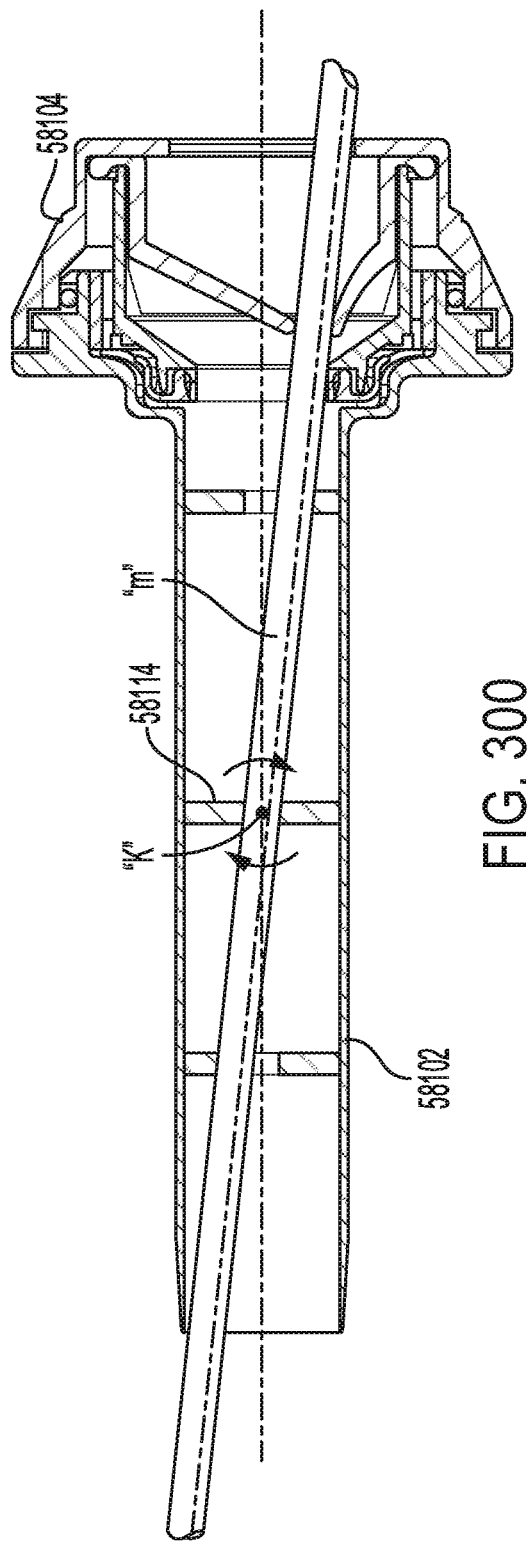

FIG. 300 is a view similar to the view of FIG. 299 illustrating insertion and manipulation of a surgical instrument within the access apparatus with the instrument rotating about a central axis of rotation defined by the access apparatus.

Figure 301:
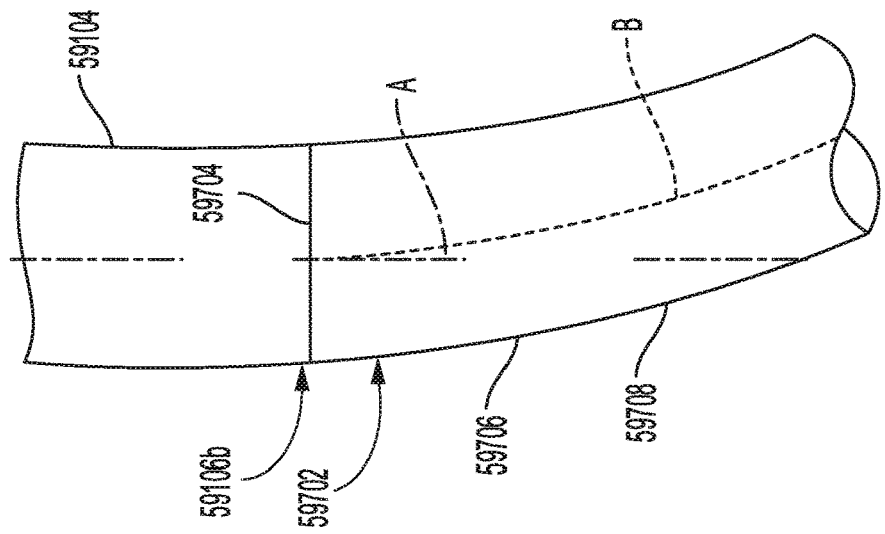

FIG. 301 is a side view of an example radial biasing device that may be used with a trocar assembly.

Figure 303:
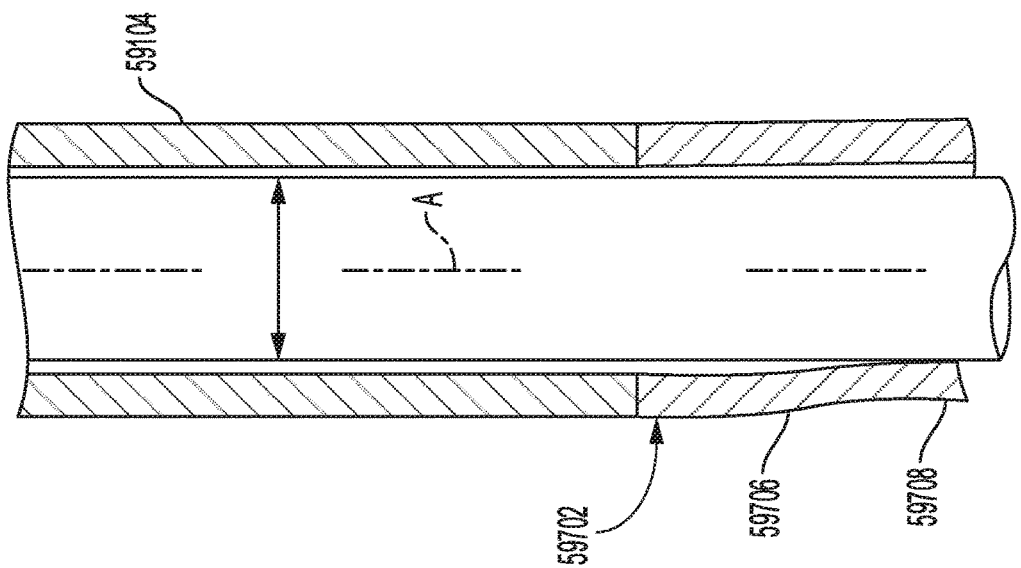
Figure 302:
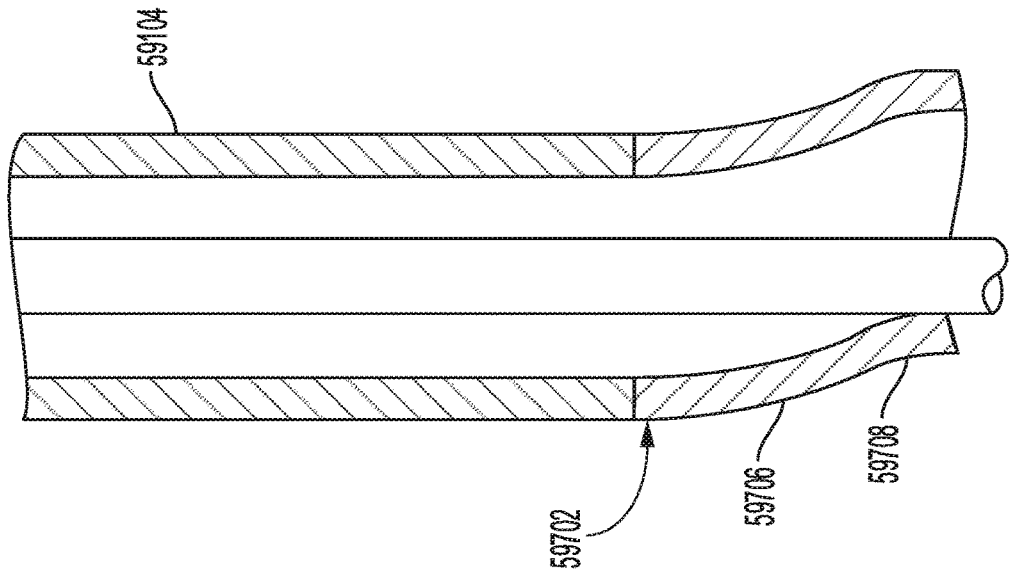

FIGS. 302 and 303 are cross-sectional side views of the radial biasing device of FIG. 301 depicting example operation.

Figure 304:
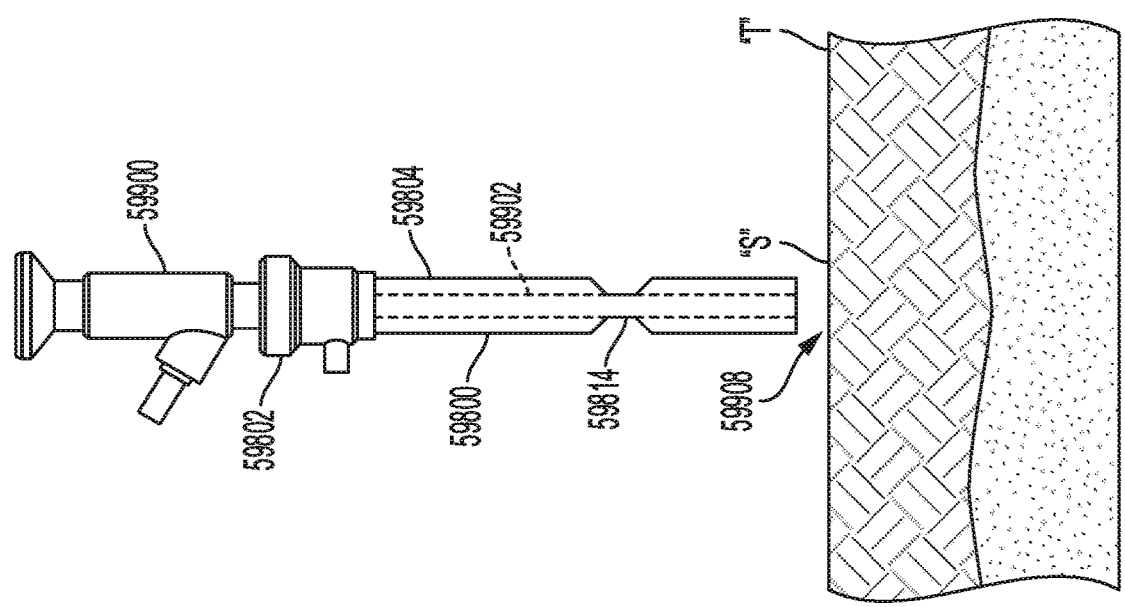

FIG. 304 is a perspective view illustrating the obturator assembly mounted to the cannula assembly to permit the penetration of tissue.

DESCRIPTION

Applicant of the present application owns the following U.S. patent applications, filed on Jun. 27, 2019, the disclosure of each of which is herein incorporated by reference in its entirety:

U.S. patent application Ser. No. 16/454,710, titled SURGICAL SYSTEMS WITH INTERCHANGEABLE MOTOR PACKS, now U.S. Pat. No. 11,013,569;

U.S. patent application Ser. No. 16/454,715, titled COOPERATIVE ROBOTIC SURGICAL SYSTEMS, now U.S. Patent Application Publication No. 2020/0405404;

U.S. patent application Ser. No. 16/454,740, titled HEAT EXCHANGE SYSTEMS FOR ROBOTIC SURGICAL SYSTEMS, now U.S. Patent Application Publication No. 2020/0405415;

U.S. patent application Ser. No. 16/454,757, titled DETERMINING ROBOTIC SURGICAL ASSEMBLY COUPLING STATUS, now U.S. Patent Application Publication No. 2020/0405406;

U.S. patent application Ser. No. 16/454,780, titled ROBOTIC SURGICAL ASSEMBLY COUPLING SAFETY MECHANISMS, now U.S. Patent Application Publication No. 2020/0405408;

U.S. patent application Ser. No. 16/454,707, titled ROBOTIC SURGICAL SYSTEM WITH SAFETY AND COOPERATIVE SENSING CONTROL, now U.S. Patent Application Publication No. 2020/0405375;

U.S. patent application Ser. No. 16/454,726, titled ROBOTIC SURGICAL SYSTEM FOR CONTROLLING CLOSE OPERATION OF END-EFFECTORS, now U.S. Patent Application Publication No. 2020/0405414;

U.S. patent application Ser. No. 16/454,737, titled ROBOTIC SURGICAL SYSTEM WITH LOCAL SENSING OF FUNCTIONAL PARAMETERS BASED ON MEASUREMENTS OF MULTIPLE PHYSICAL INPUTS, now U.S. Patent Application Publication No. 2020/0405405;

U.S. patent application Ser. No. 16/454,751, titled COOPERATIVE OPERATION OF ROBOTIC ARMS, now U.S. Patent Application Publication No. 2020/0405417;

U.S. patent application Ser. No. 16/454,760, titled SURGICAL INSTRUMENT DRIVE SYSTEMS, now U.S. Patent Application Publication No. 2020/0405407;

U.S. patent application Ser. No. 16/454,769, titled SURGICAL INSTRUMENT DRIVE SYSTEMS WITH CABLE-TIGHTENING SYSTEM, now U.S. Pat. No. 11,207,146;

U.S. patent application Ser. No. 16/454,727, titled VISUALIZATION SYSTEM WITH AUTOMATIC CONTAMINATION DETECTION AND CLEANING CONTROLS, now U.S. Patent Application Publication No. 2020/0405401; and U.S. patent application Ser. No. 16/454,741, titled MULTI-ACCESS PORT FOR SURGICAL ROBOTIC SYSTEMS, now U.S. Patent Application Publication No. 2020/0405416.

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY;

U.S. patent application Ser. No. 16/209,395, titled METHOD OF HUB COMMUNICATION;

U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Figure 1:
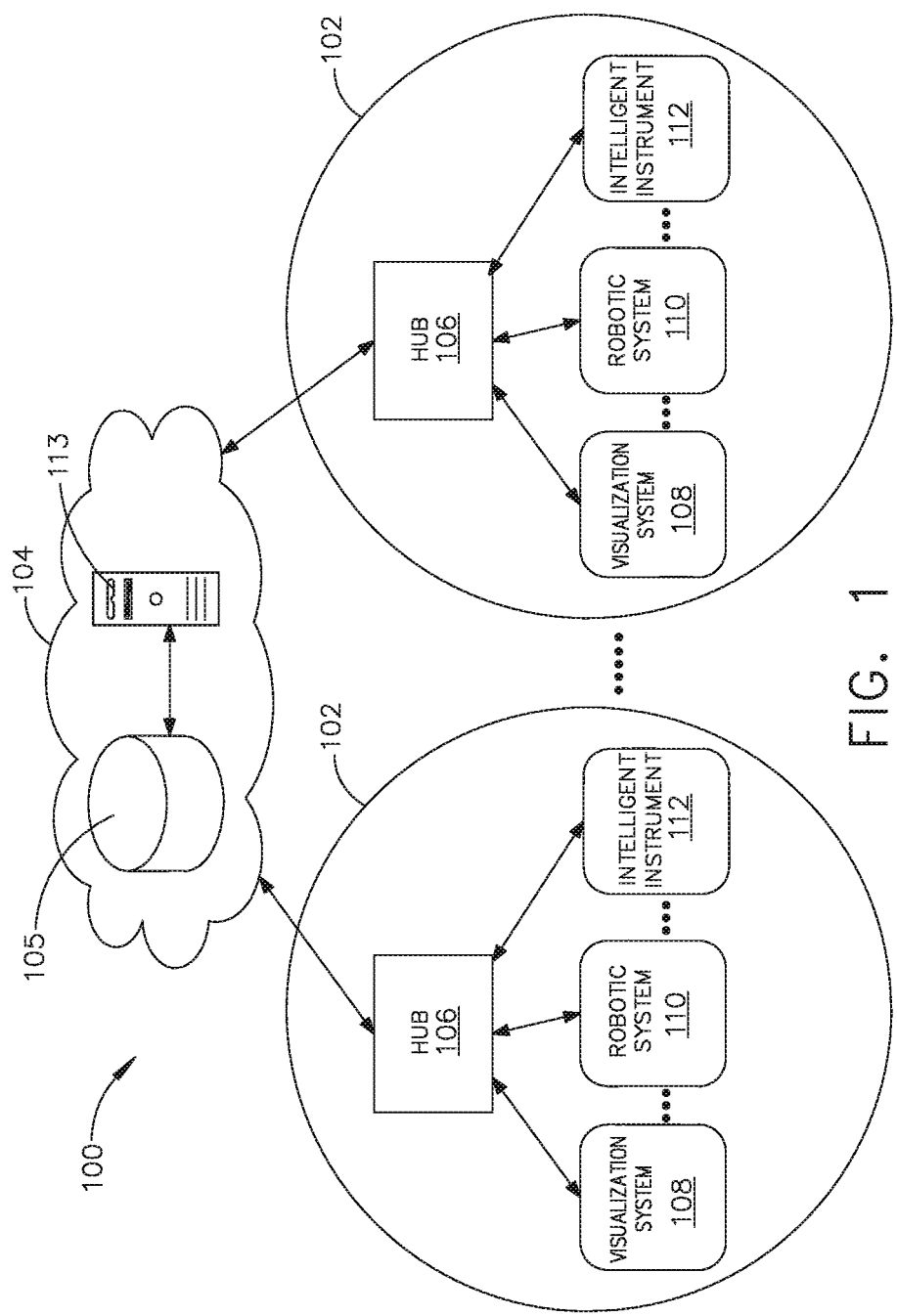
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
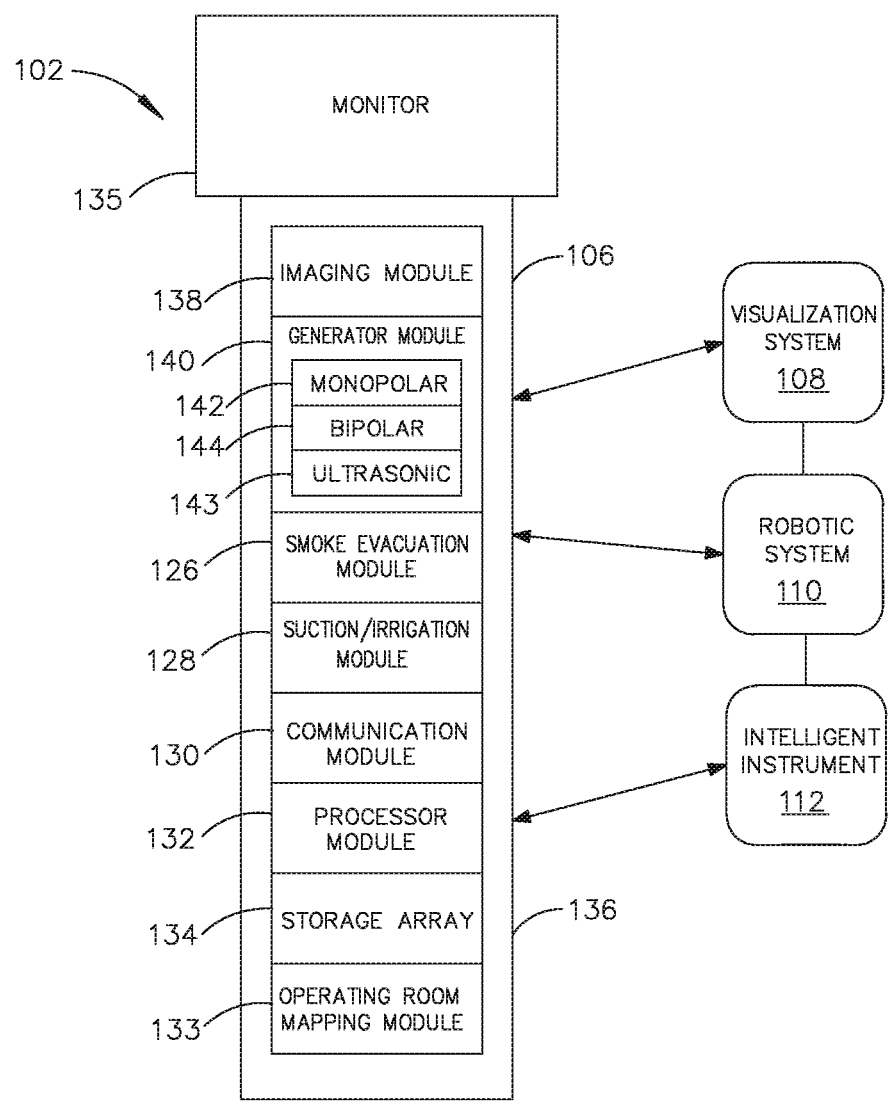
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
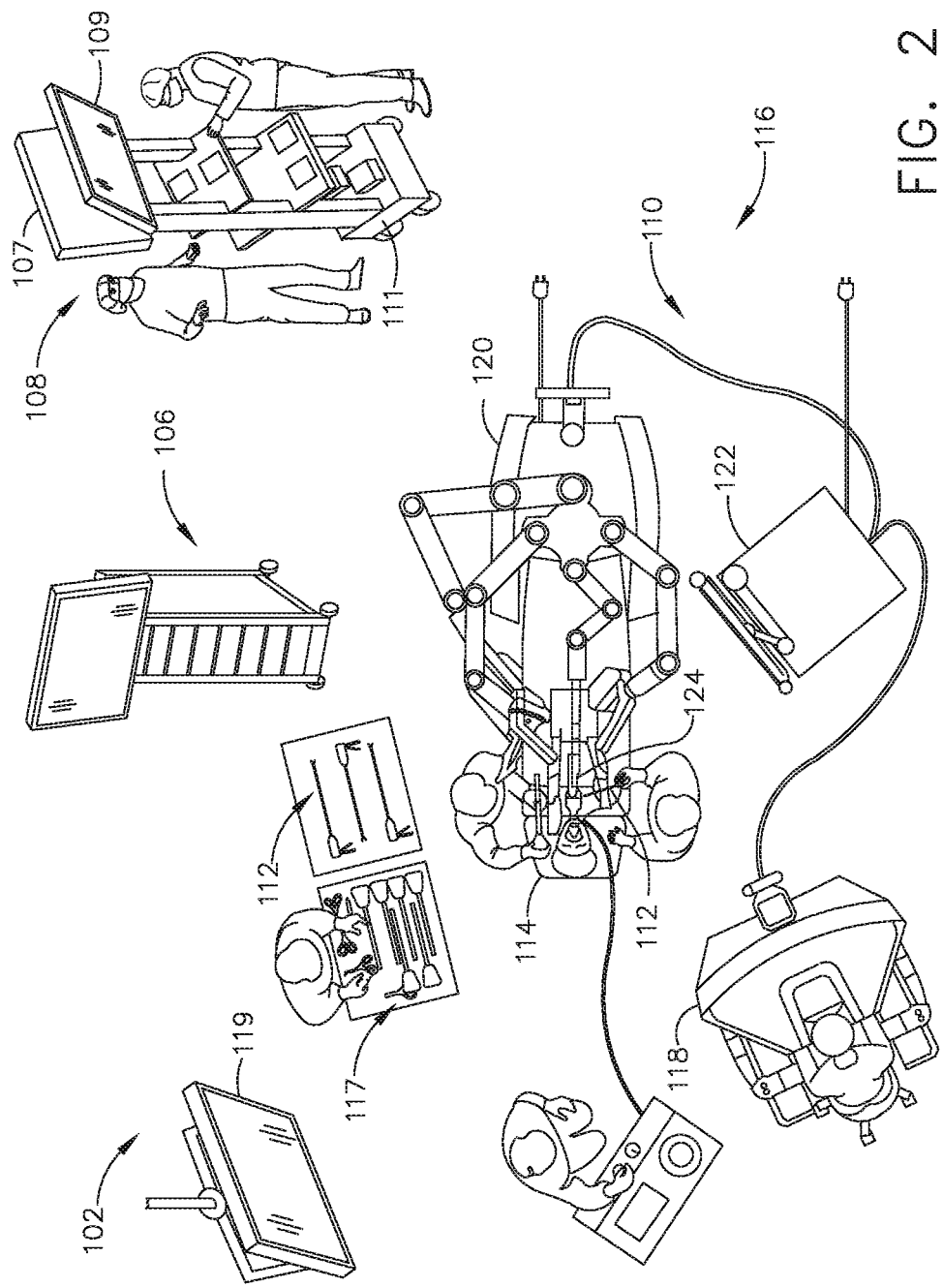
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts.

Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. In various aspects, the hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane with external and wireless communication headers to enable the removable attachment of the modules 140, 126, 128 and interactive communication therebetween.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Robotic Surgical System

Figure 4:
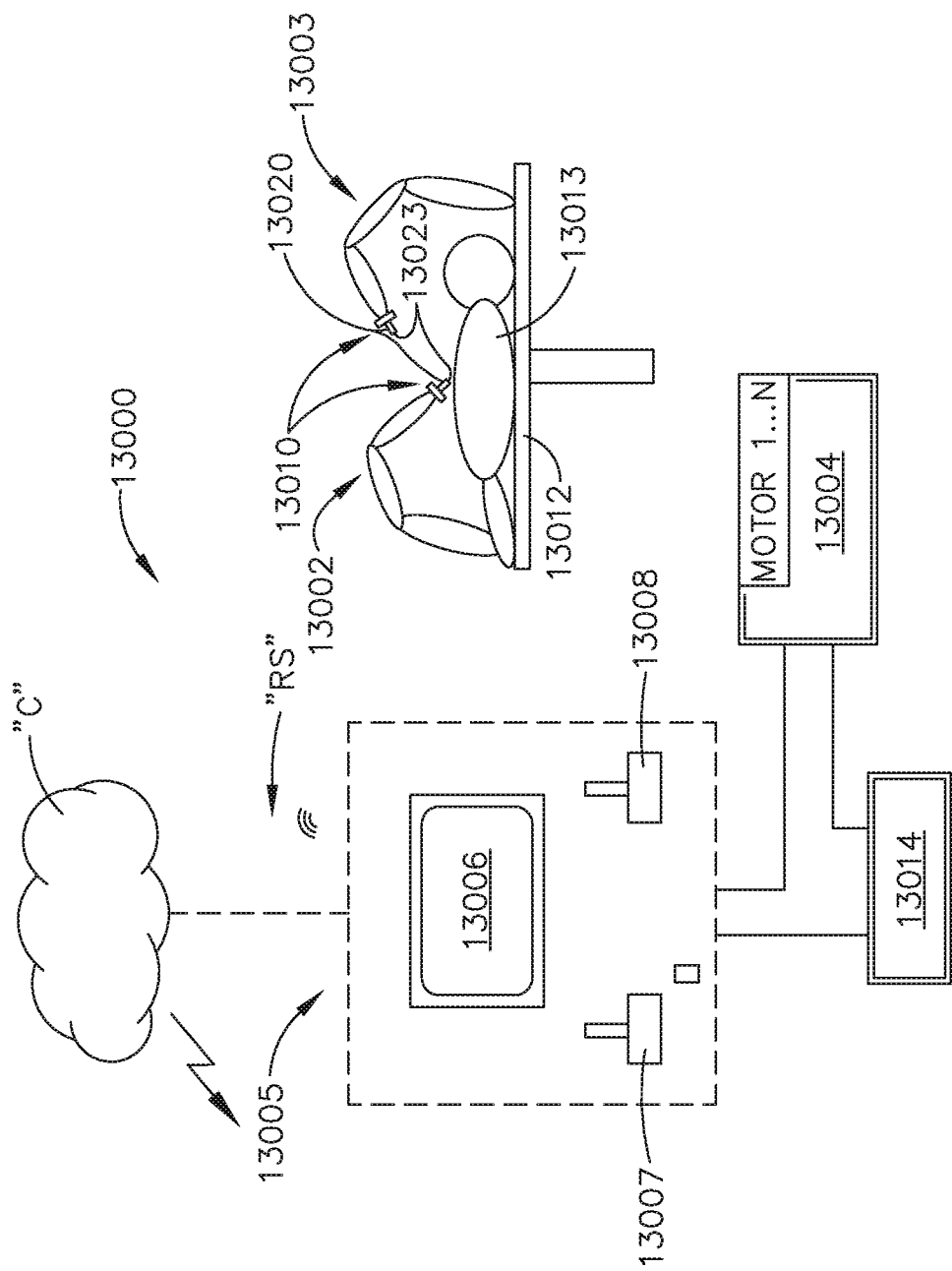
FIG. 4 is a schematic of a robotic surgical system, in accordance with at least one aspect of the present disclosure.
Figure 5:
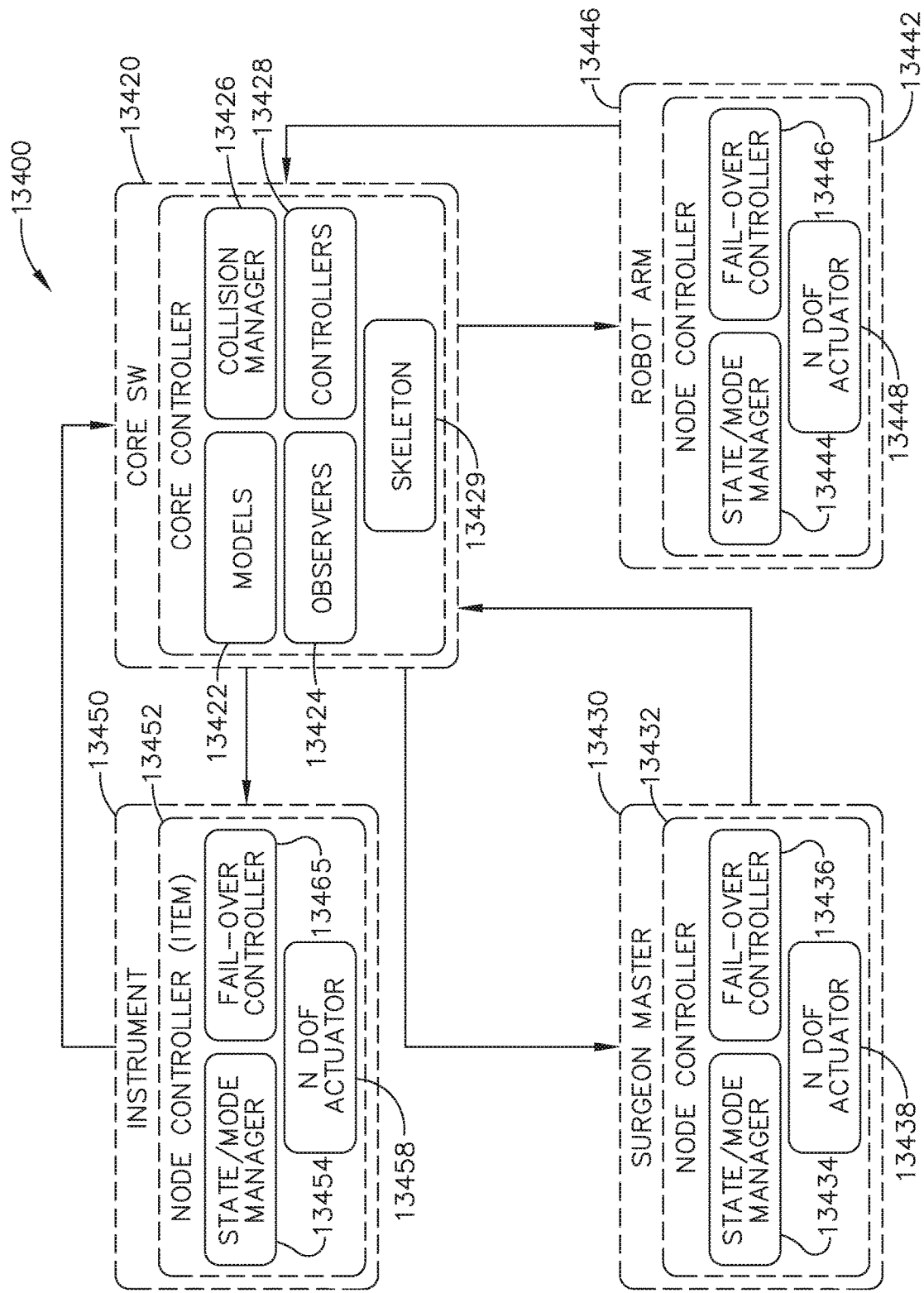
FIG. 5 is a block diagram of control components for the robotic surgical system of FIG. 4, in accordance with at least one aspect of the present disclosure.

An example robotic surgical system is depicted in FIGS. 4 and 5. With reference to FIG. 4, the robotic surgical system 13000 includes robotic arms 13002, 13003, a control device 13004, and a console 13005 coupled to the control device 13004. As illustrated in FIG. 4, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Controls for a surgeon's console, such as the console 13005, are further described in International Patent Publication No. WO2017/075121, filed Oct. 27, 2016, titled HAPTIC FEEDBACK FOR A ROBOTIC SURGICAL SYSTEM INTERFACE, which is herein incorporated by reference in its entirety.

Each of the robotic arms 13002, 13003 is made up of a plurality of members connected through joints and includes a surgical assembly 13010 connected to a distal end of a corresponding robotic arm 13002, 13003. Support of multiple arms is further described in U.S. Patent Application Publication No. 2017/0071693, filed Nov. 11, 2016, titled SURGICAL ROBOTIC ARM SUPPORT SYSTEMS AND METHODS OF USE, which is herein incorporated by reference in its entirety. Various robotic arm configurations are further described in International Patent Publication No. WO2017/044406, filed Sep. 6, 2016, titled ROBOTIC SURGICAL CONTROL SCHEME FOR MANIPULATING ROBOTIC END EFFECTORS, which is herein incorporated by reference in its entirety. In an exemplification, the surgical assembly 13010 includes a surgical instrument 13020 supporting an end effector 13023. Although two robotic arms 13002, 13003, are depicted, the surgical system 13000 may include a single robotic arm or more than two robotic arms 13002, 13003. Additional robotic arms are likewise connected to the control device 13004 and are telemanipulatable via the console 13005. Accordingly, one or more additional surgical assemblies 13010 and/or surgical instruments 13020 may also be attached to the additional robotic arm(s).

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor I . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023. For example, articulation of an end effector by a robotic assembly such as the surgical assembly 13010 is further described in U.S. Patent Application Publication No. 2016/0303743, filed Jun. 6, 2016, titled WRIST AND JAW ASSEMBLIES FOR ROBOTIC SURGICAL SYSTEMS and in International Patent Publication No. WO2016/144937, filed Mar. 8, 2016, titled MEASURING HEALTH OF A CONNECTOR MEMBER OF A ROBOTIC SURGICAL SYSTEM, each of which is herein incorporated by reference in its entirety. In an exemplification, each motor is configured to actuate a drive rod or a lever arm to affect operation and/or movement of end effectors 13023 in addition to, or instead of, one or more cables.

Driver configurations for surgical instruments, such as drive arrangements for a surgical end effector, are further described in International Patent Publication No. WO2016/183054, filed May 10, 2016, titled COUPLING INSTRUMENT DRIVE UNIT AND ROBOTIC SURGICAL INSTRUMENT, International Patent Publication No. WO2016/205266, filed Jun. 15, 2016, titled ROBOTIC SURGICAL SYSTEM TORQUE TRANSDUCTION SENSING, International Patent Publication No. WO2016/205452, filed Jun. 16, 2016, titled CONTROLLING ROBOTIC SURGICAL INSTRUMENTS WITH BIDIRECTIONAL COUPLING, and International Patent Publication No. WO2017/053507, filed Sep. 22, 2016, titled ELASTIC SURGICAL INTERFACE FOR ROBOTIC SURGICAL SYSTEMS, each of which is herein incorporated by reference in its entirety. The modular attachment of surgical instruments to a driver is further described in International Patent Publication No. WO2016/209769, filed Jun. 20, 2016, titled ROBOTIC SURGICAL ASSEMBLIES, which is herein incorporated by reference in its entirety. Housing configurations for a surgical instrument driver and interface are further described in International Patent Publication No. WO2016/144998, filed Mar. 9, 2016, titled ROBOTIC SURGICAL SYSTEMS, INSTRUMENT DRIVE UNITS, AND DRIVE ASSEMBLIES, which is herein incorporated by reference in its entirety. Various surgical instrument configurations for use with the robotic arms 13002, 13003 are further described in International Patent Publication No. WO2017/053358, filed Sep. 21, 2016, titled SURGICAL ROBOTIC ASSEMBLIES AND INSTRUMENT ADAPTERS THEREOF and International Patent Publication No. WO2017/053363, filed Sep. 21, 2016, titled ROBOTIC SURGICAL ASSEMBLIES AND INSTRUMENT DRIVE CONNECTORS THEREOF, each of which is herein incorporated by reference in its entirety. Bipolar instrument configurations for use with the robotic arms 13002, 13003 are further described in International Patent Publication No. WO2017/053698, filed Sep. 23, 2016, titled ROBOTIC SURGICAL ASSEMBLIES AND ELECTROMECHANICAL INSTRUMENTS THEREOF, which is herein incorporated by reference in its entirety. Shaft arrangements for use with the robotic arms 13002, 13003 are further described in International Patent Publication No. WO2017/116793, filed Dec. 19, 2016, titled ROBOTIC SURGICAL SYSTEMS AND INSTRUMENT DRIVE ASSEMBLIES, which is herein incorporated by reference in its entirety.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The remote system "RS" can include any suitable electronic service, database, platform, cloud "C" (see FIG. 4), or the like. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

In accordance with an exemplification, the distal end of each robotic arm 13002, 13003 is configured to releasably secure the end effector 13023 (or other surgical tool) therein and may be configured to receive any number of surgical tools or instruments, such as a trocar or retractor, for example.

A simplified functional block diagram of a system architecture 13400 of the robotic surgical system 13010 is depicted in FIG. 5. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. For example, the core module 13420 maps control devices to the arms 13002, 13003, determines current status, performs all kinematics and frame transformations, and relays resulting movement commands. In this regard, the core module 13420 receives and analyzes data from each of the other modules 13430, 13440, 13450 in order to provide instructions or commands to the other modules 13430, 13440, 13450 for execution within the robotic surgical system 13000. Although depicted as separate modules, one or more of the modules 13420, 13430, 13440, and 13450 are a single component in other exemplifications.

The core module 13420 includes models 13422, observers 13424, a collision manager 13426, controllers 13428, and a skeleton 13429. The models 13422 include units that provide abstracted representations (base classes) for controlled components, such as the motors (for example, Motor I . . . n) and/or the arms 13002, 13003. The observers 13424 create state estimates based on input and output signals received from the other modules 13430, 13440, 13450. The collision manager 13426 prevents collisions between components that have been registered within the system 13010. The skeleton 13429 tracks the system 13010 from a kinematic and dynamics point of view. For example, the kinematics item may be implemented either as forward or inverse kinematics, in an exemplification. The dynamics item may be implemented as algorithms used to model dynamics of the system's components.

The surgeon master module 13430 communicates with surgeon control devices at the console 13005 and relays inputs received from the console 13005 to the core module 13420. In accordance with an exemplification, the surgeon master module 13430 communicates button status and control device positions to the core module 13420 and includes a node controller 13432 that includes a state/mode manager 13434, a fail-over controller 13436, and a N-degree of freedom ("DOF") actuator 13438.

The robotic arm module 13440 coordinates operation of a robotic arm subsystem, an arm cart subsystem, a set up arm, and an instrument subsystem in order to control movement of a corresponding arm 13002, 13003. Although a single robotic arm module 13440 is included, it will be appreciated that the robotic arm module 13440 corresponds to and controls a single arm. As such, additional robotic arm modules 13440 are included in configurations in which the system 13010 includes multiple arms 13002, 13003. The robotic arm module 13440 includes a node controller 13442, a state/mode manager 13444, a fail-over controller 13446, and a N-degree of freedom ("DOF") actuator 13348.

The instrument module 13450 controls movement of an instrument and/or tool component attached to the arm 13002, 13003. The instrument module 13450 is configured to correspond to and control a single instrument. Thus, in configurations in which multiple instruments are included, additional instrument modules 13450 are likewise included. In an exemplification, the instrument module 13450 obtains and communicates data related to the position of the end effector or jaw assembly (which may include the pitch and yaw angle of the jaws), the width of or the angle between the jaws, and the position of an access port. The instrument module 13450 has a node controller 13452, a state/mode manager 13454, a fail-over controller 13456, and a N-degree of freedom ("DOF") actuator 13458.

The position data collected by the instrument module 13450 is used by the core module 13420 to determine when the instrument is within the surgical site, within a cannula, adjacent to an access port, or above an access port in free space. The core module 13420 can determine whether to provide instructions to open or close the jaws of the instrument based on the positioning thereof. For example, when the position of the instrument indicates that the instrument is within a cannula, instructions are provided to maintain a jaw assembly in a closed position. When the position of the instrument indicates that the instrument is outside of an access port, instructions are provided to open the jaw assembly.

Additional features and operations of a robotic surgical system, such as the surgical robot system depicted in FIGS. 4 and 5, are further described in the following references, each of which is herein incorporated by reference in its entirety:

U.S. Patent Application Publication No. 2016/0303743, filed Jun. 6, 2016, titled WRIST AND JAW ASSEMBLIES FOR ROBOTIC SURGICAL SYSTEMS;

U.S. Patent Application Publication No. 2017/0071693, filed Nov. 11, 2016, titled SURGICAL ROBOTIC ARM SUPPORT SYSTEMS AND METHODS OF USE;

International Patent Publication No. WO2016/144937, filed Mar. 8, 2016, titled MEASURING HEALTH OF A CONNECTOR MEMBER OF A ROBOTIC SURGICAL SYSTEM;

International Patent Publication No. WO2016/144998, filed Mar. 9, 2016, titled ROBOTIC SURGICAL SYSTEMS, INSTRUMENT DRIVE UNITS, AND DRIVE ASSEMBLIES;

International Patent Publication No. WO2016/183054, filed May 10, 2016, titled COUPLING INSTRUMENT DRIVE UNIT AND ROBOTIC SURGICAL INSTRUMENT;

International Patent Publication No. WO2016/205266, filed Jun. 15, 2016, titled ROBOTIC SURGICAL SYSTEM TORQUE TRANSDUCTION SENSING;

International Patent Publication No. WO2016/205452, filed Jun. 16, 2016, titled CONTROLLING ROBOTIC SURGICAL INSTRUMENTS WITH BIDIRECTIONAL COUPLING;

International Patent Publication No. WO2016/209769, filed Jun. 20, 2016, titled ROBOTIC SURGICAL ASSEMBLIES;

International Patent Publication No. WO2017/044406, filed Sep. 6, 2016, titled ROBOTIC SURGICAL CONTROL SCHEME FOR MANIPULATING ROBOTIC END EFFECTORS;

International Patent Publication No. WO2017/053358, filed Sep. 21, 2016, titled SURGICAL ROBOTIC ASSEMBLIES AND INSTRUMENT ADAPTERS THEREOF;

International Patent Publication No. WO2017/053363, filed Sep. 21, 2016, titled ROBOTIC SURGICAL ASSEMBLIES AND INSTRUMENT DRIVE CONNECTORS THEREOF;

International Patent Publication No. WO2017/053507, filed Sep. 22, 2016, titled ELASTIC SURGICAL INTERFACE FOR ROBOTIC SURGICAL SYSTEMS;

International Patent Publication No. WO2017/053698, filed Sep. 23, 2016, titled ROBOTIC SURGICAL ASSEMBLIES AND ELECTROMECHANICAL INSTRUMENTS THEREOF;

International Patent Publication No. WO2017/075121, filed Oct. 27, 2016, titled HAPTIC FEEDBACK CONTROLS FOR A ROBOTIC SURGICAL SYSTEM INTERFACE; and International Patent Publication No. WO2017/116793, filed Dec. 19, 2016, titled ROBOTIC SURGICAL SYSTEMS AND INSTRUMENT DRIVE ASSEMBLIES.

The robotic surgical systems and features disclosed herein can be employed with the robotic surgical system of FIGS. 4 and 5. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, and/or the robotic hub 222, for example.

In various instances, a robotic surgical system can include a robotic control tower, which can house the control unit of the system. For example, the control unit 13004 of the robotic surgical system 13000 (FIG. 4) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 13004, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

In certain instances, the activation of a surgical tool at certain times during a surgical procedure and/or for certain durations may cause tissue trauma and/or may prolong a surgical procedure. For example, a robotic surgical system can utilize an electrosurgical tool having an energy delivery surface that should only be energized when a threshold condition is met. In one example, the energy delivery surface should only be activated when the energy delivery surface is in contact with the appropriate, or targeted, tissue. As another example, a robotic surgical system can utilize a suction element that should only be activated when a threshold condition is met, such as when an appropriate volume of fluid is present. Due to visibility restrictions, evolving situations, and the multitude of moving parts during a robotic surgical procedure, it can be difficult for a clinician to determine and/or monitor certain conditions at the surgical site. For example, it can be difficult to determine if an energy delivery surface of an electrosurgical tool is in contact with tissue. It can also be difficult to determine if a particular suctioning pressure is sufficient for the volume of fluid in the proximity of the suctioning port.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. One or more of the surgical devices can include a sensor. For example, multiple sensors can be positioned around the surgical site and/or the operating room. A sensor system including the one or more sensors can be configured to detect one or more conditions at the surgical site. For example, data from the sensor system can determine if a surgical tool mounted to the surgical robot is being used and/or if a feature of the surgical tool should be activated. More specifically, a sensor system can detect if an electrosurgical device is positioned in abutting contact with tissue, for example. As another example, a sensor system can detect if a suctioning element of a surgical tool is applying a sufficient suctioning force to fluid at the surgical site.

When in an automatic activation mode, the robotic surgical system can automatically activate one or more features of one or more surgical tools based on data, images, and/or other information received from the sensor system. For example, an energy delivery surface of an electrosurgical tool can be activated upon detecting that the electrosurgical tool is in use (e.g. positioned in abutting contact with tissue). As another example, a suctioning element on a surgical tool can be activated when the suction port is moved into contact with a fluid. In certain instances, the surgical tool can be adjusted based on the sensed conditions.

A robotic surgical system incorporating an automatic activation mode can automatically provide a scenario-specific result based on detected condition(s) at the surgical site. The scenario-specific result can be outcome-based, for example, and can streamline the decision-making process of the clinician. In certain instances, such an automatic activation mode can improve the efficiency and/or effectiveness of the clinician. For example, the robotic surgical system can aggregate data to compile a more complete view of the surgical site and/or the surgical procedure in order to determine the best possible course of action. Additionally or alternatively, in instances in which the clinician makes fewer decisions, the clinician can be better focused on other tasks and/or can process other information more effectively.

Figure 6:
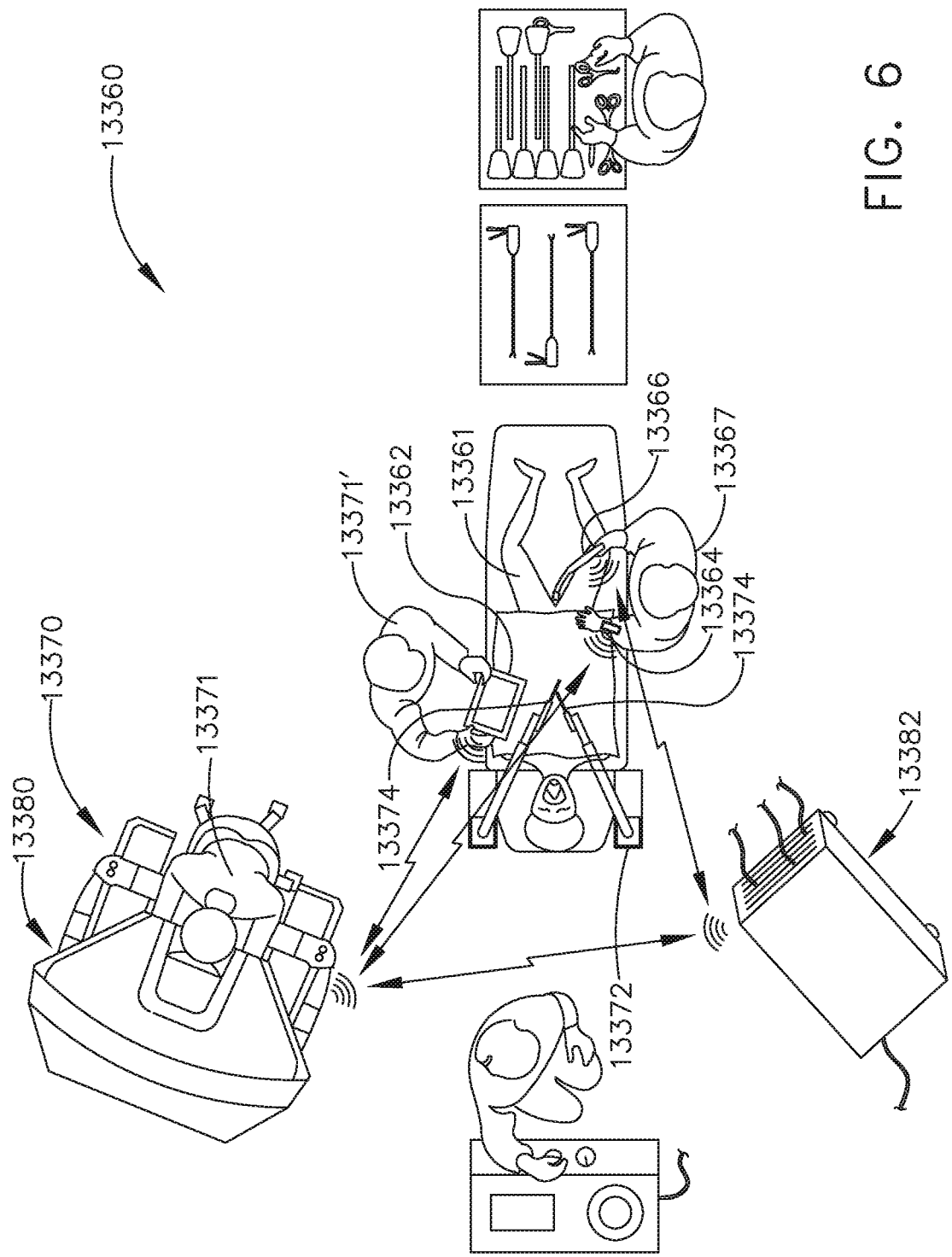
FIG. 6 is a schematic of a robotic surgical system during a surgical procedure including a plurality of hubs and interactive secondary displays, in accordance with at least one aspect of the present disclosure.
Figure 7:
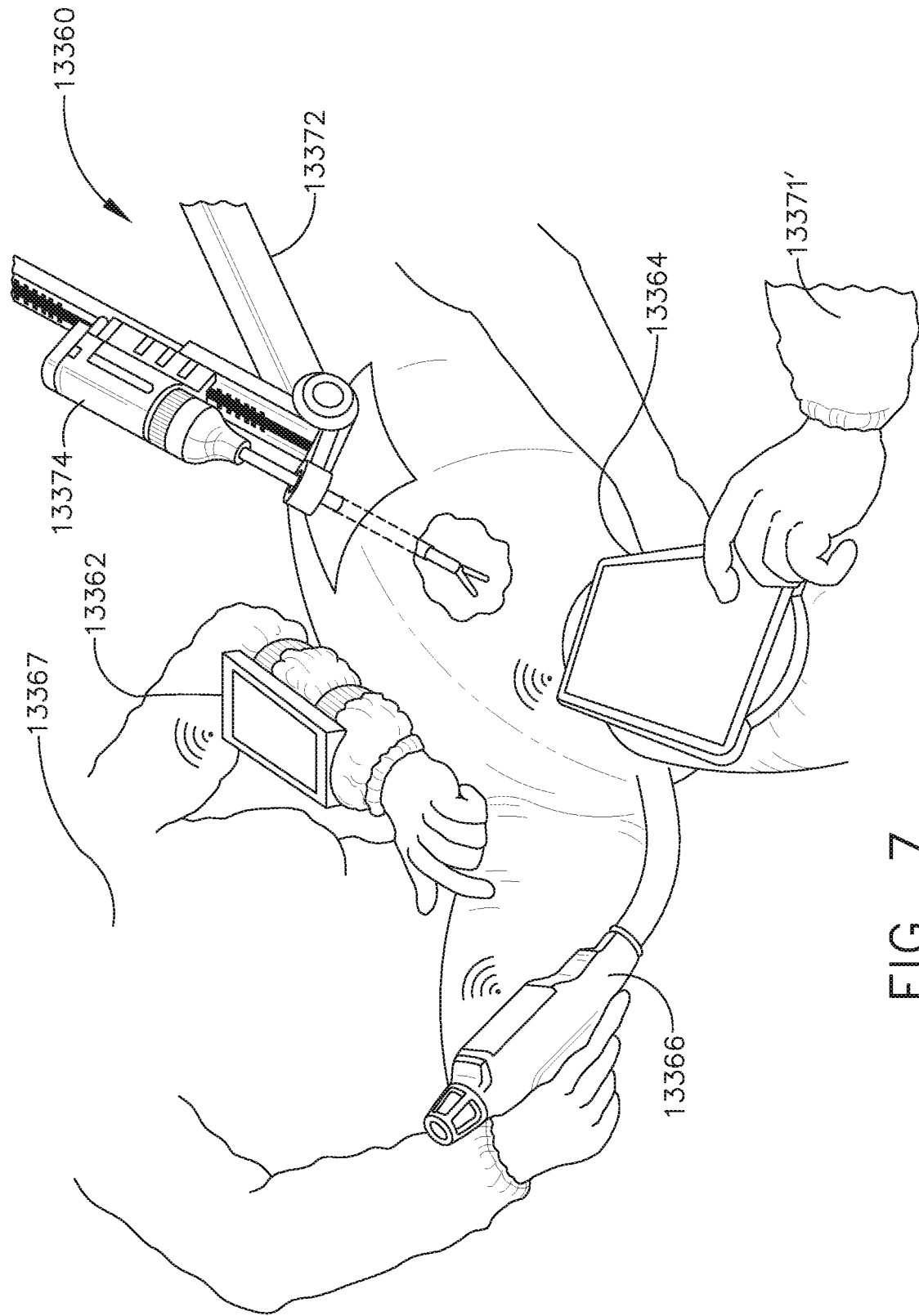
FIG. 7 is a detail view of the interactive secondary displays of FIG. 6, in accordance with at least one aspect of the present disclosure.

Referring primarily to FIGS. 6 and 7, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the displays 13362, 13364). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system, such as the robotic surgical systems 13000 (FIG. 4), 13400 (FIG. 5), 13360 (FIG. 6), and/or the surgical hub 13380, 13382, for example, is programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instances, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In one aspect, the robotic surgical system includes a processor and a memory communicatively coupled to the processor, as described herein. The memory stores instructions executable by the processor to receive a first user input from a console and to receive a second user input from a mobile wireless control module for controlling a function of a robotic surgical tool, as described herein.

In various aspects, the present disclosure provides a control circuit to receive a first user input from a console and to receive a second user input from a mobile wireless control module for controlling a function of a robotic surgical tool, as described herein. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

A robotic surgical system may include multiple robotic arms that are configured to assist the clinician during a surgical procedure. Each robotic arm may be operable independently of the others. A lack of communication may exist between each of the robotic arms as they are independently operated, which may increase the risk of tissue trauma. For example, in a scenario where one robotic arm is configured to apply a force that is stronger and in a different direction than a force configured to be applied by a second robotic arm, tissue trauma can result. For example, tissue trauma and/or tearing may occur when a first robotic arm applies a strong retracting force to the tissue while a second robotic arm is configured to rigidly hold the tissue in place.

In various instances, one or more sensors are attached to each robotic arm of a robotic surgical system. The one or more sensors are configured to sense a force applied to the surrounding tissue during the operation of the robotic arm. Such forces can include, for example, a holding force, a retracting force, and/or a dragging force. The sensor from each robotic arm is configured to communicate the magnitude and direction of the detected force to a control unit of the robotic surgical system. The control unit is configured to analyze the communicated forces and set limits for maximum loads to avoid causing trauma to the tissue in a surgical site. For example, the control unit may minimize the holding force applied by a first robotic arm if the retracting or dragging force applied by a second robotic arm increases.

Figure 4A:
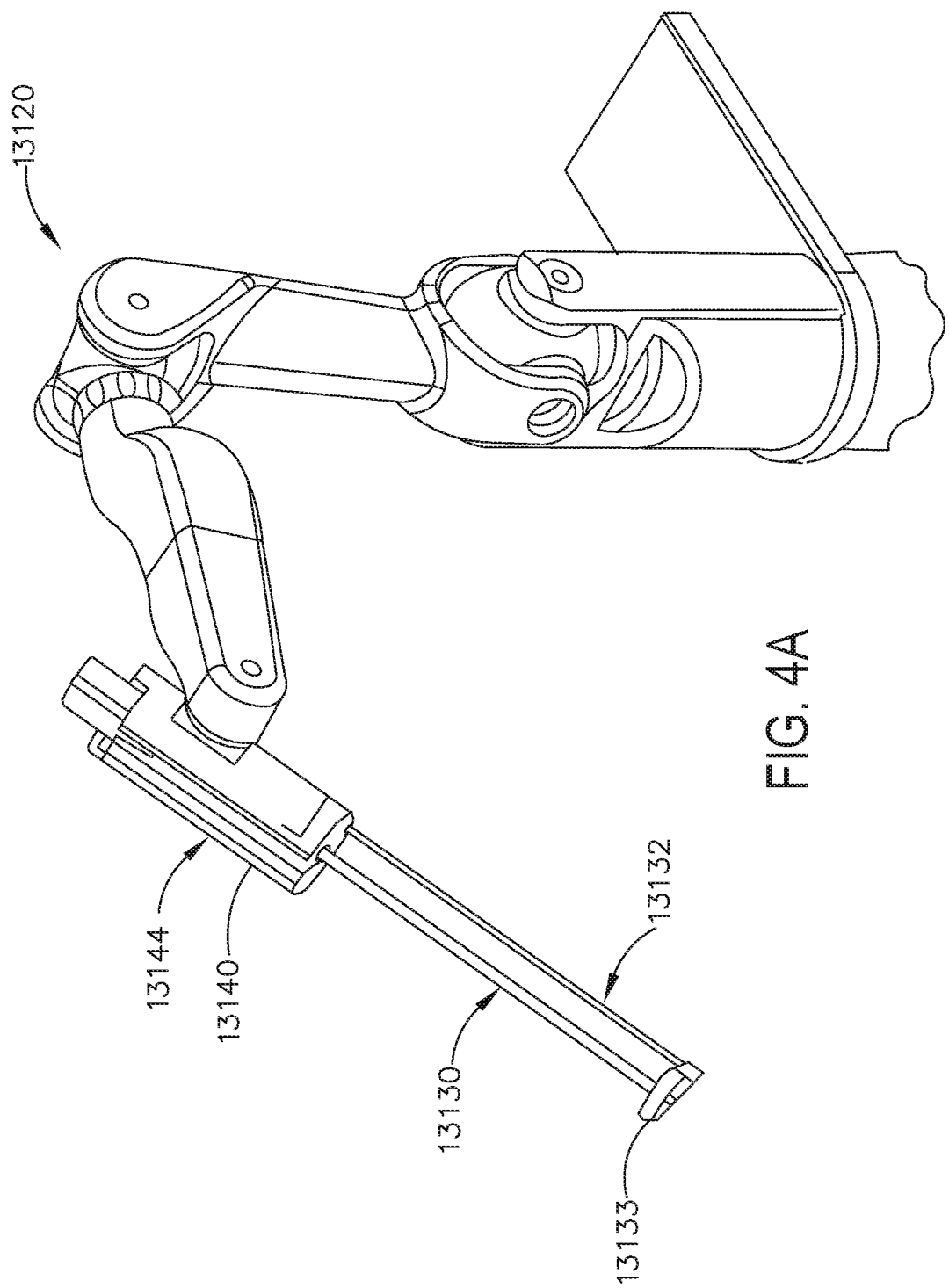
FIG. 4A illustrates another exemplification of a robotic arm and another exemplification of a tool assembly releasably coupled to the robotic arm, according to one aspect of the present disclosure.

FIG. 4A illustrates an exemplification of a robotic arm 13120 and a tool assembly 13130 releasably coupled to the robotic arm 13120. The robotic arm 13120 can support and move the associated tool assembly 13130 along one or more mechanical degrees of freedom (e.g., all six Cartesian degrees of freedom, five or fewer Cartesian degrees of freedom, etc.), The robotic arm 13120 can include a tool driver 13140 at a distal end of the robotic arm 13120, which can assist with controlling features associated with the tool assembly 13130, The robotic arm 13120 can also include a movable tool guide 13132 that can retract and extend relative to the tool driver 13140. A shaft of the tool assembly 13130 can extend parallel to a threaded shaft of the movable tool guide 13132 and can extend through a distal end feature 13133 (e.g., a ring) of the movable tool guide 13132 and into a patient, In order to provide a sterile operation area while using the surgical system, a barrier can be placed between the actuating portion of the surgical system (e.g., the robotic arm 13120) and the surgical Instruments (e.g., the tool assembly 13130) in the sterile surgical field. A sterile component, such as an instrument sterile adapter (ISA), can also be placed at the connecting interface between the tool assembly 13130 and the robotic arm 13120. The placement of an ISA between the tool assembly 13130 and the robotic arm 13120 can ensure a sterile coupling point for the tool assembly 13130 and the robotic arm 13120. This permits removal of tool assemblies 13130 from the robotic arm 13120 to exchange with other tool assemblies 13130 during the course of a surgery without compromising the sterile surgical field.

The tool assembly 13130 can be loaded from a top side of the tool driver 13140 with the shaft of the tool assembly 13130 being positioned in a shaft-receiving channel 13144 formed along the side of the tool driver 13140. The shaft-receiving channel 13144 allows the shaft, which extends along a central axis of the tool assembly 13130, to extend along a central axis of the tool driver 13140 when the tool assembly 13130 is coupled to the tool driver 13140. In other exemplifications, the shaft can extend through on opening in the tool driver 13140, or the two components can mate in various other configurations.

As discussed above, the robotic surgical system can include one or more robotic arms with each robotic arm having a tool assembly coupled thereto. Each tool assembly can include an end effector that has one or more of a variety of features, such as one or more tools for assisting with performing a surgical procedure. For example, the end effector can include a cutting or boring tool that can be used to perforate or cut through tissue (e.g., create an incision).

Furthermore, some end effectors include one or more sensors that can sense a variety of characteristics associated with either the end effector or the tissue. Each robotic arm and end effector can be controlled by a control system to assist with creating a desired cut or bore and prevent against undesired cutting of tissue. As an alternative to (or in addition to) controlling the robotic arm, it is understood that the control system can control either the tool itself or the tool assembly.

One or more aspects associated with the movement of the robotic arm can be controlled by the control system, such as either a direction or a velocity of movement. For example, when boring through tissue, the robotic arm can be controlled to perform jackhammer-like movements with the cutting tool. Such jackhammer movements can include the robotic arm moving up and down along an axis (e.g., an axis that is approximately perpendicular to the tissue being perforated) in a rapid motion while also advancing the cutting tool in a downward direction towards the tissue to eventually perforate the tissue with the cutting tool (e.g. an ultrasonic blade). While performing such movements in a robotic surgical procedure, not only can it be difficult to see the tissue being perforated to thereby determine a relative position of the cutting tool, but it can also be difficult to determine when the cutting tool has completed perforating the tissue. Such position of the cutting tool relative to the tissue can include the cutting tool approaching or not yet in contact with the tissue, the cutting tool drilling down or cutting into the tissue, and the cutting tool extending through or having perforated the tissue. These positions can be difficult for either a user controlling the robotic arm or the robotic surgical system to determine which can result in potential harm to the patient due to over or under-penetrating the tissue, as well as result in longer procedure times. As such, in order to reduce procedure time and surgical errors, the robotic surgical system includes a control system that communicates with at least one sensor assembly configured to sense a force applied at a distal end of the end effector or cutting tool. The control system can thereby determine and control, based on such sensed forces, one or more appropriate aspects associated with the movement of the robotic arm, such as when boring or cutting into tissue, as will be described in greater detail below.

Although a cutting tool for perforating tissue is described in detail herein, the sensor assembly of the present disclosure that is in communication with the control system can be implemented in any number of robotic surgical systems for detecting any number of a variety of tools and/or end effectors used for performing any number of a variety of procedures without departing from the scope of this disclosure. Furthermore, any number of movements can be performed by the robotic arm to perforate or cut tissue using the robotic surgical system including the sensor assembly and control system described herein and is not limited to the jackhammering or boring of tissue.

FIG. 4A and additional exemplifications are further described in U.S. patent application Ser. No. 15/237,753, entitled CONTROL OF ADVANCEMENT RATE AND APPLICATION FORCE BASED ON MEASURED FORCES, filed Aug. 16, 2016, the entire disclosure of which is incorporated by reference herein.

The entire disclosures of:

U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015;

U.S. Pat. No. 9,072,536, filed Jun. 28, 2012, entitled DIFFERENTIAL LOCKING ARRANGEMENTS FOR ROTARY POWERED SURGICAL INSTRUMENTS, which issued Jul. 7, 2015;

U.S. Pat. No. 9,204,879, filed Jun. 28, 2012, entitled FLEXIBLE DRIVE MEMBER, which issued on Dec. 8, 2015;

U.S. Pat. No. 9,561,038, filed Jun. 28, 2012, entitled INTERCHANGEABLE CLIP APPLIER, which issued on Feb. 7, 2017;

U.S. Pat. No. 9,757,128, filed Sep. 5, 2014, entitled MULTIPLE SENSORS WITH ONE SENSOR AFFECTING A SECOND SENSOR'S OUTPUT OR INTERPRETATION, which issued on Sep. 12, 2017;

U.S. patent application Ser. No. 14/640,935, entitled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071;

U.S. patent application Ser. No. 15/382,238, entitled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591; and U.S. patent application Ser. No. 15/237,753, entitled CONTROL OF ADVANCEMENT RATE AND APPLICATION FORCE BASED ON MEASURED FORCES, filed Aug. 16, 2016 are hereby incorporated by reference herein in their respective entireties.

The surgical devices, systems, and methods disclosed herein can be implemented with a variety of different robotic surgical systems and surgical devices. Surgical devices include robotic surgical tools and handheld surgical instruments. The reader will readily appreciate that certain devices, systems, and methods disclosed herein are not limited to applications within a robotic surgical system. For example, certain systems, devices, and methods for communicating, detecting, and/or control a surgical device can be implemented without a robotic surgical system.

Surgical Network

Figure 8:
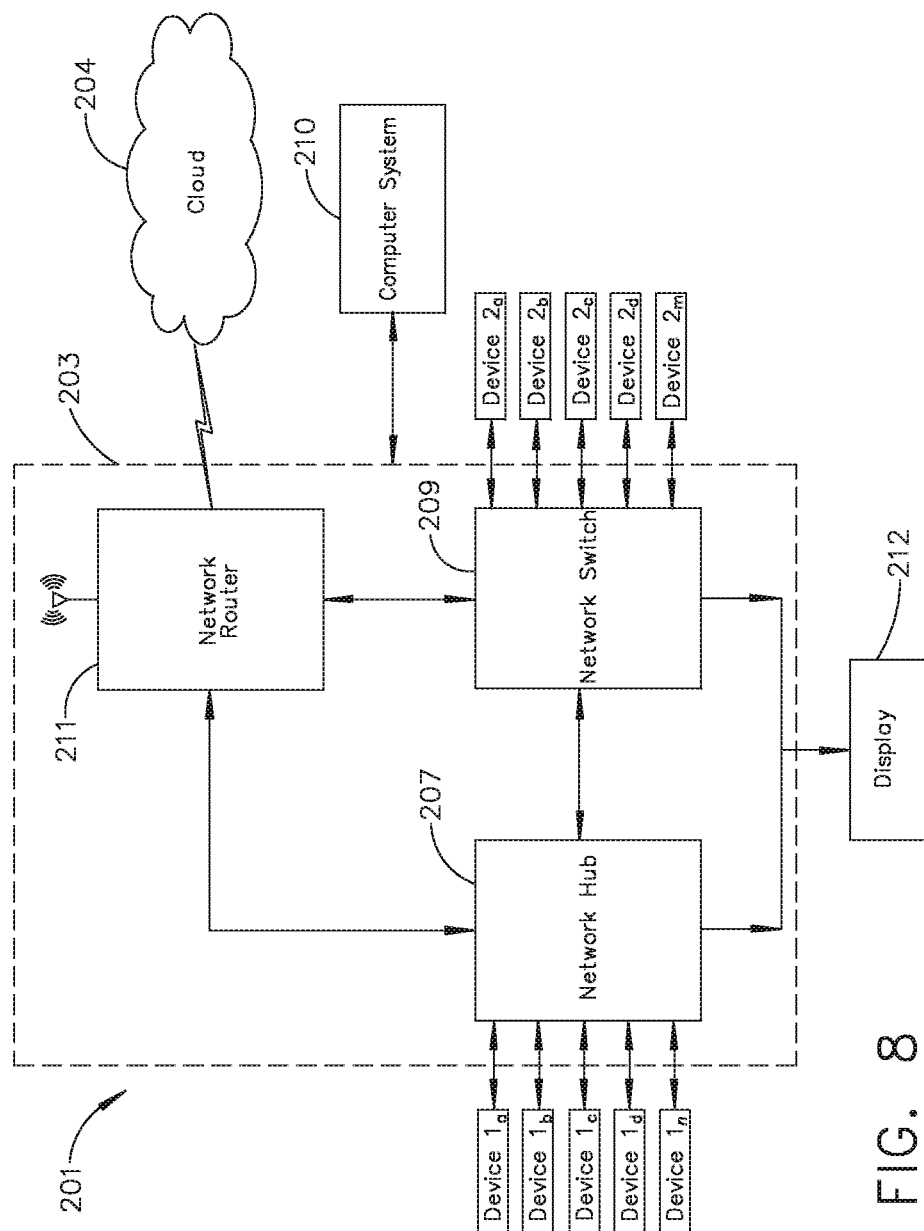
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
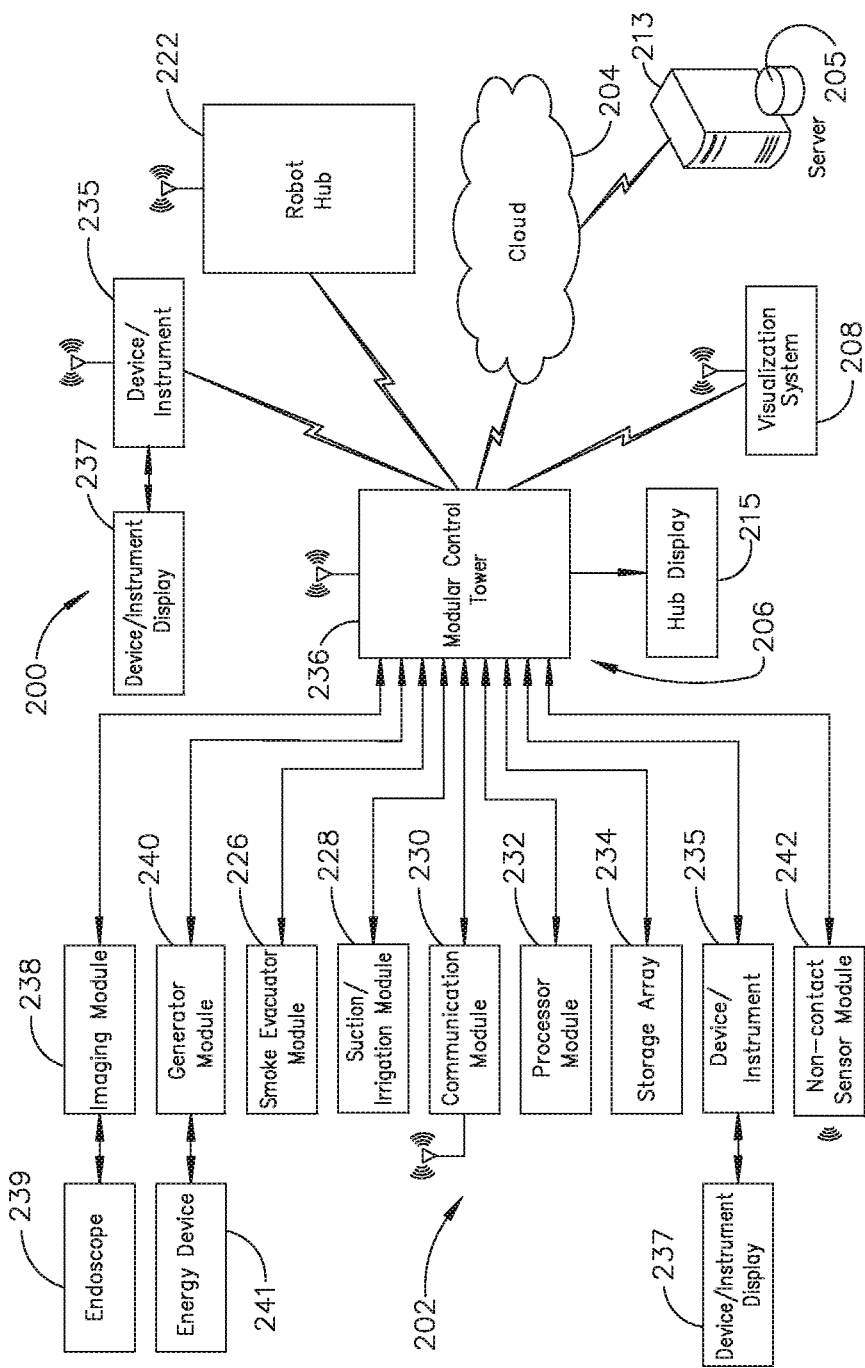
FIG. 9 illustrates a computer-implemented interactive surgical system, in accordance with at least one aspect of the present disclosure.
Figure 10:
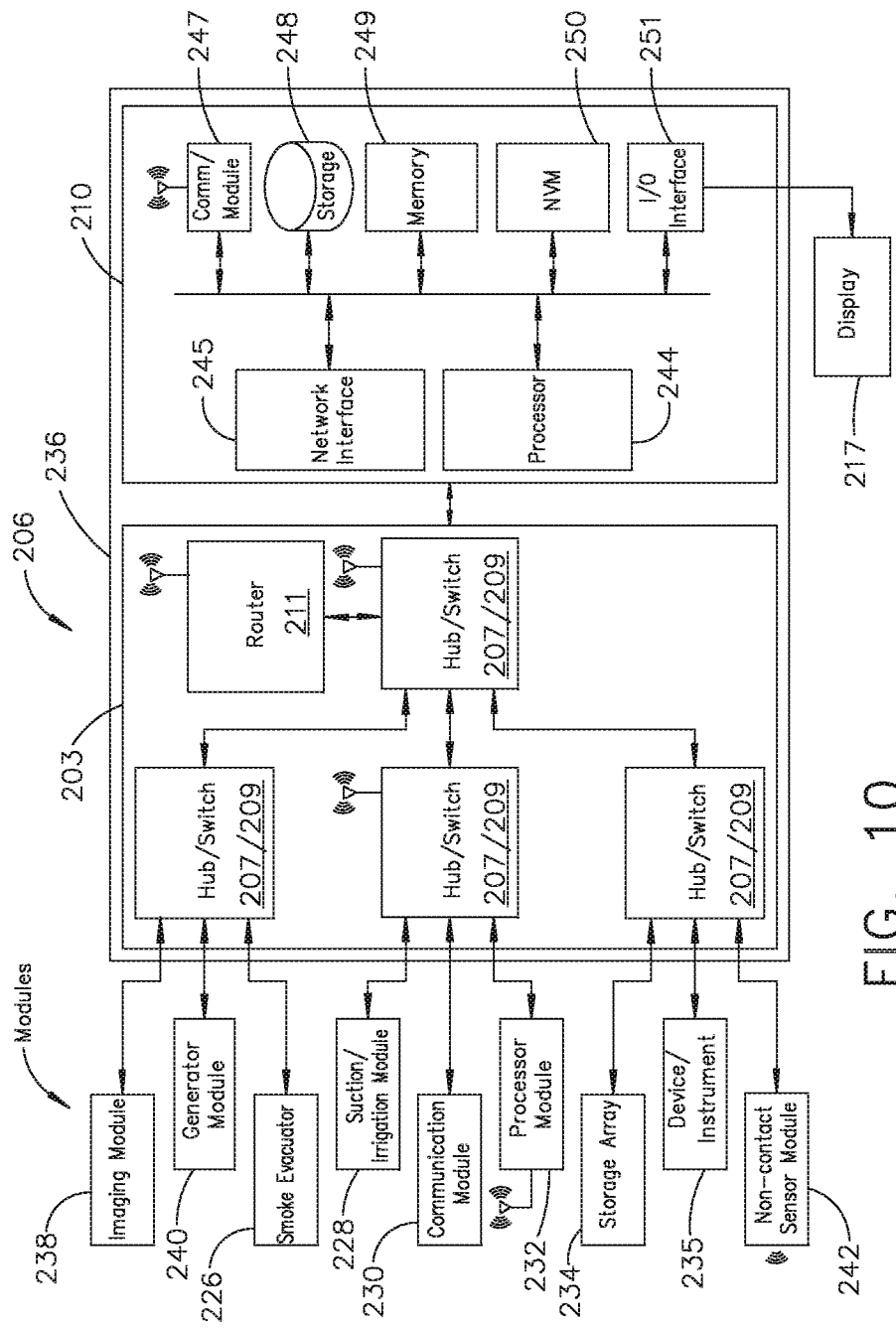
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, the disclosure of which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
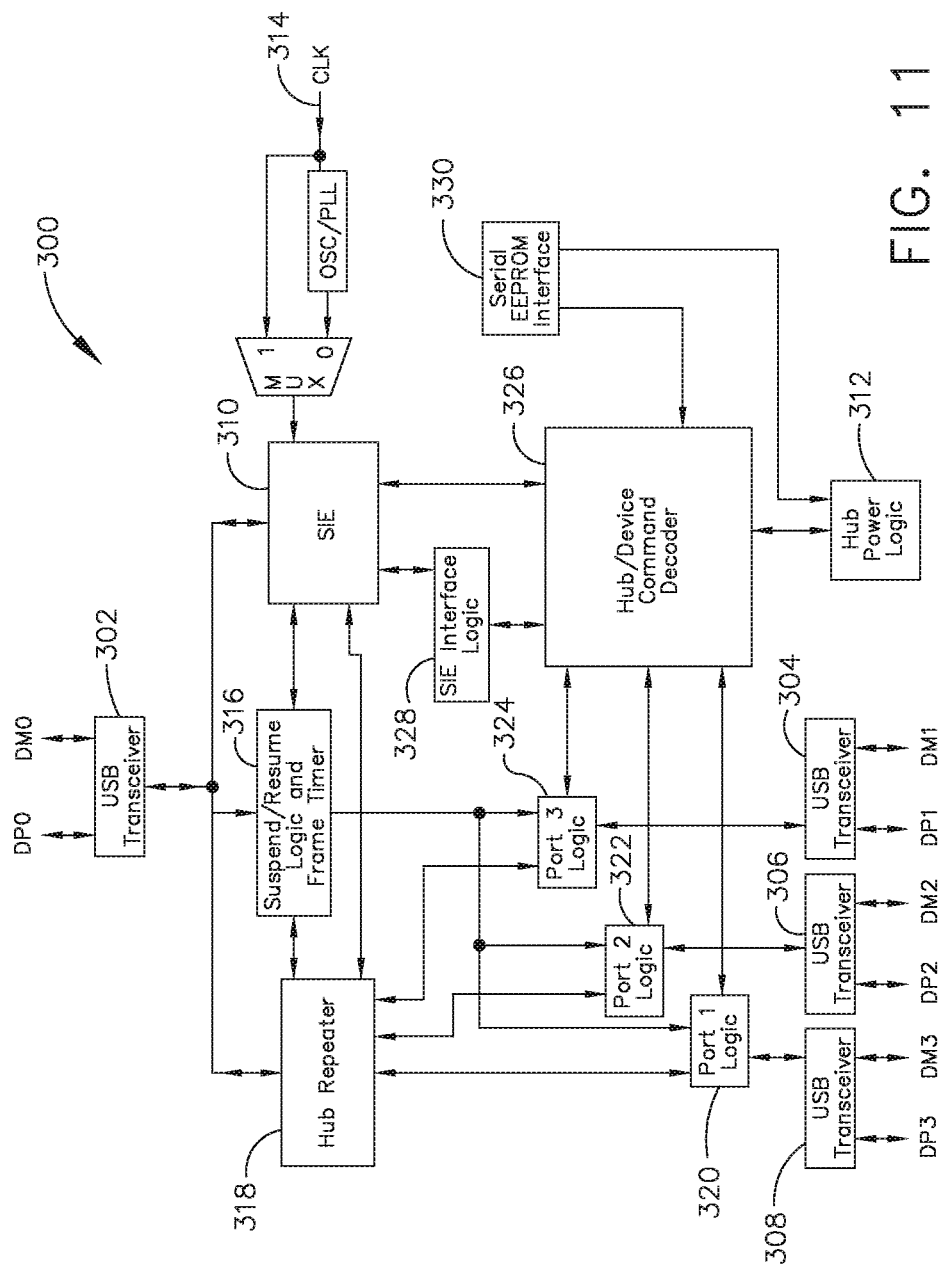
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
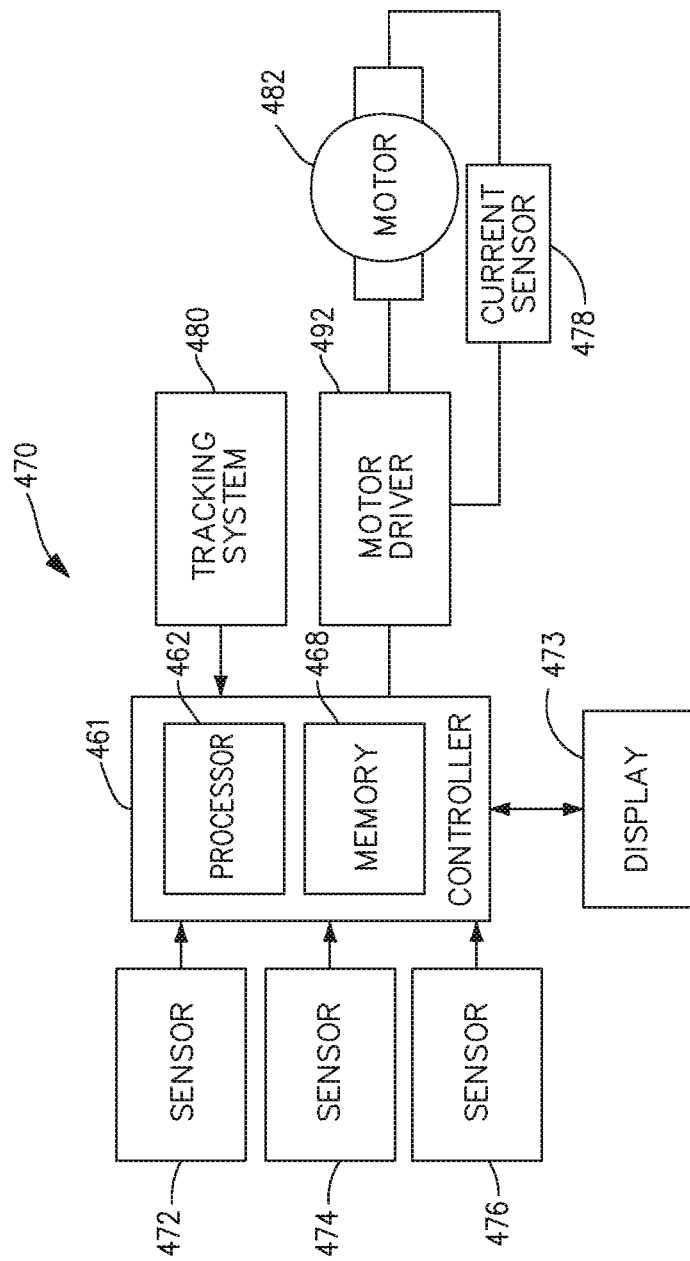
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
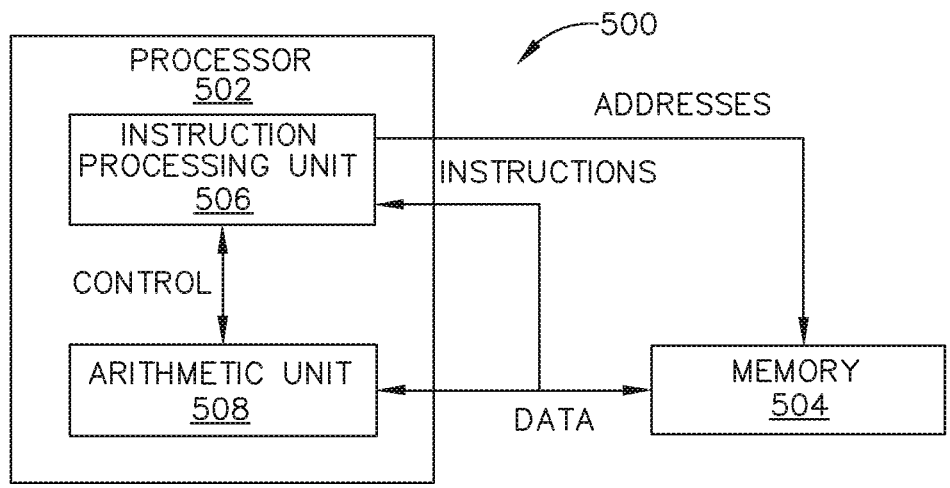
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
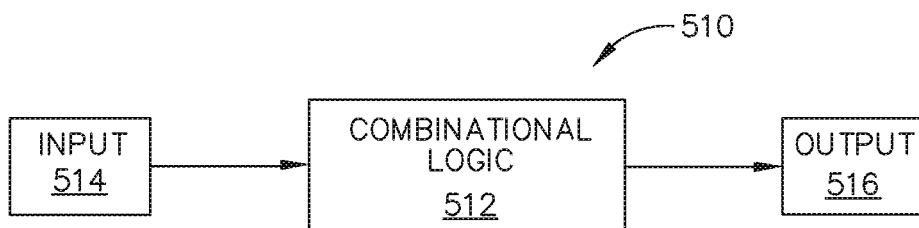
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
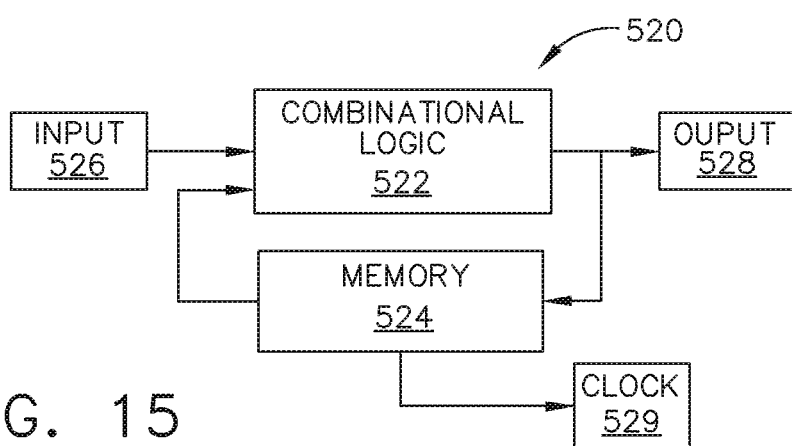
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
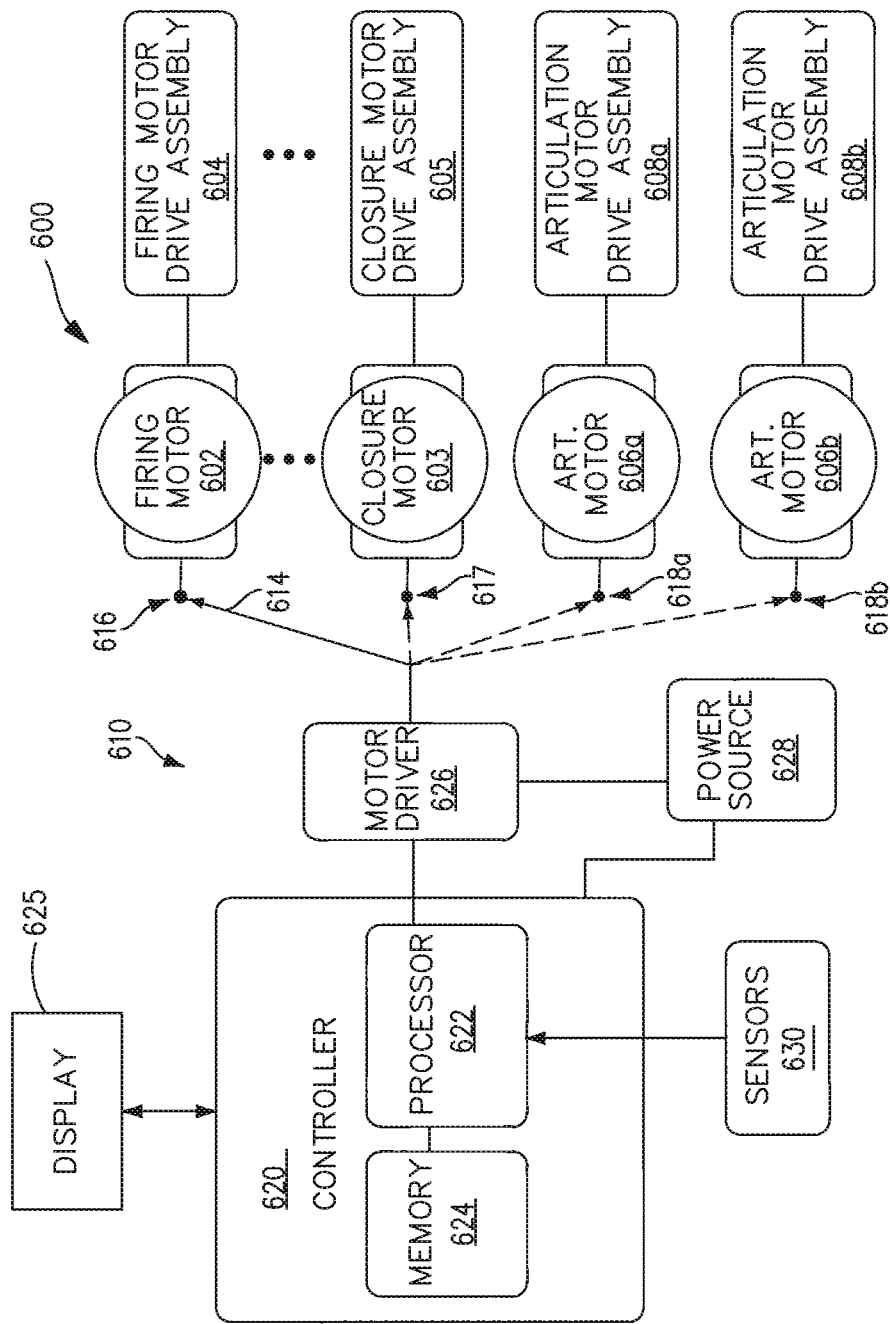
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
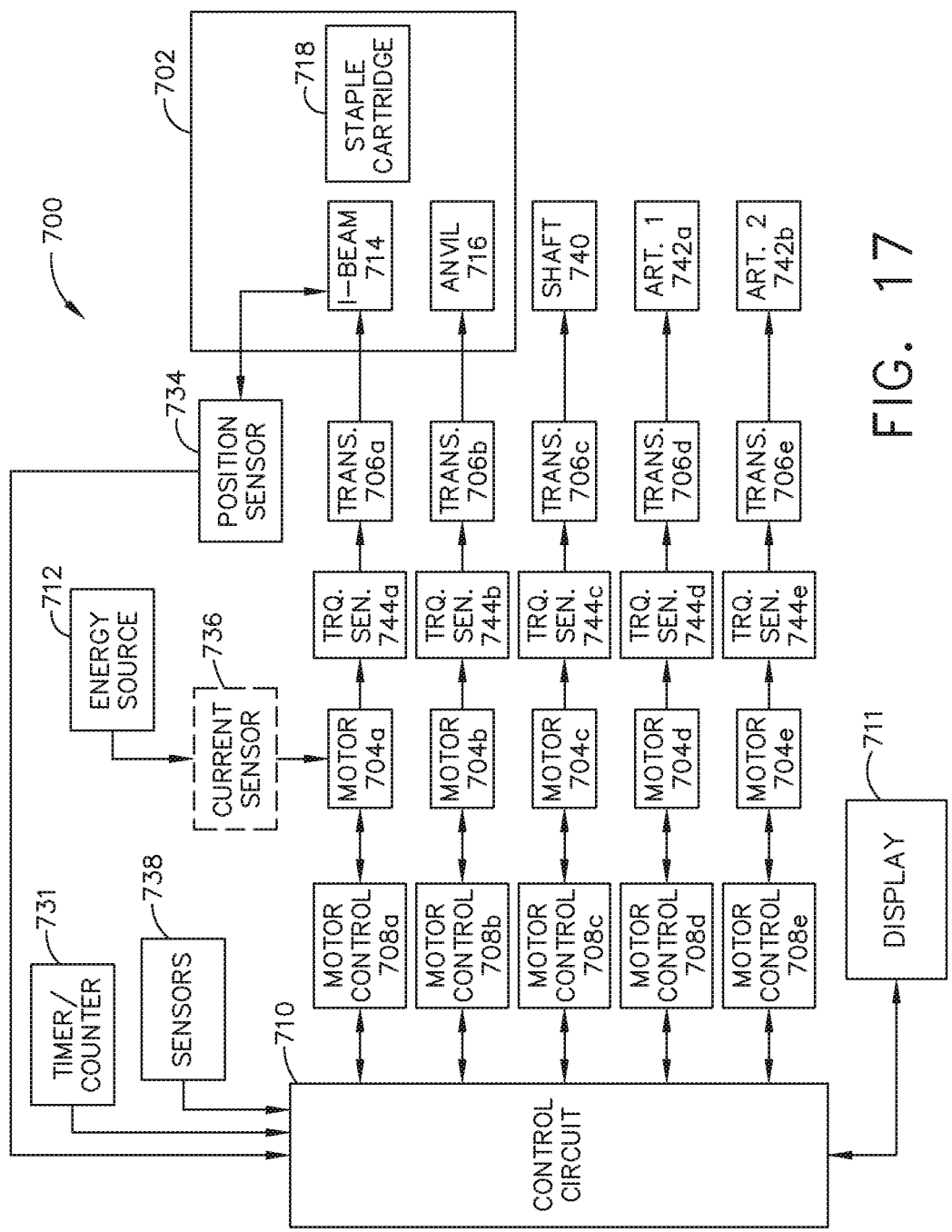
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
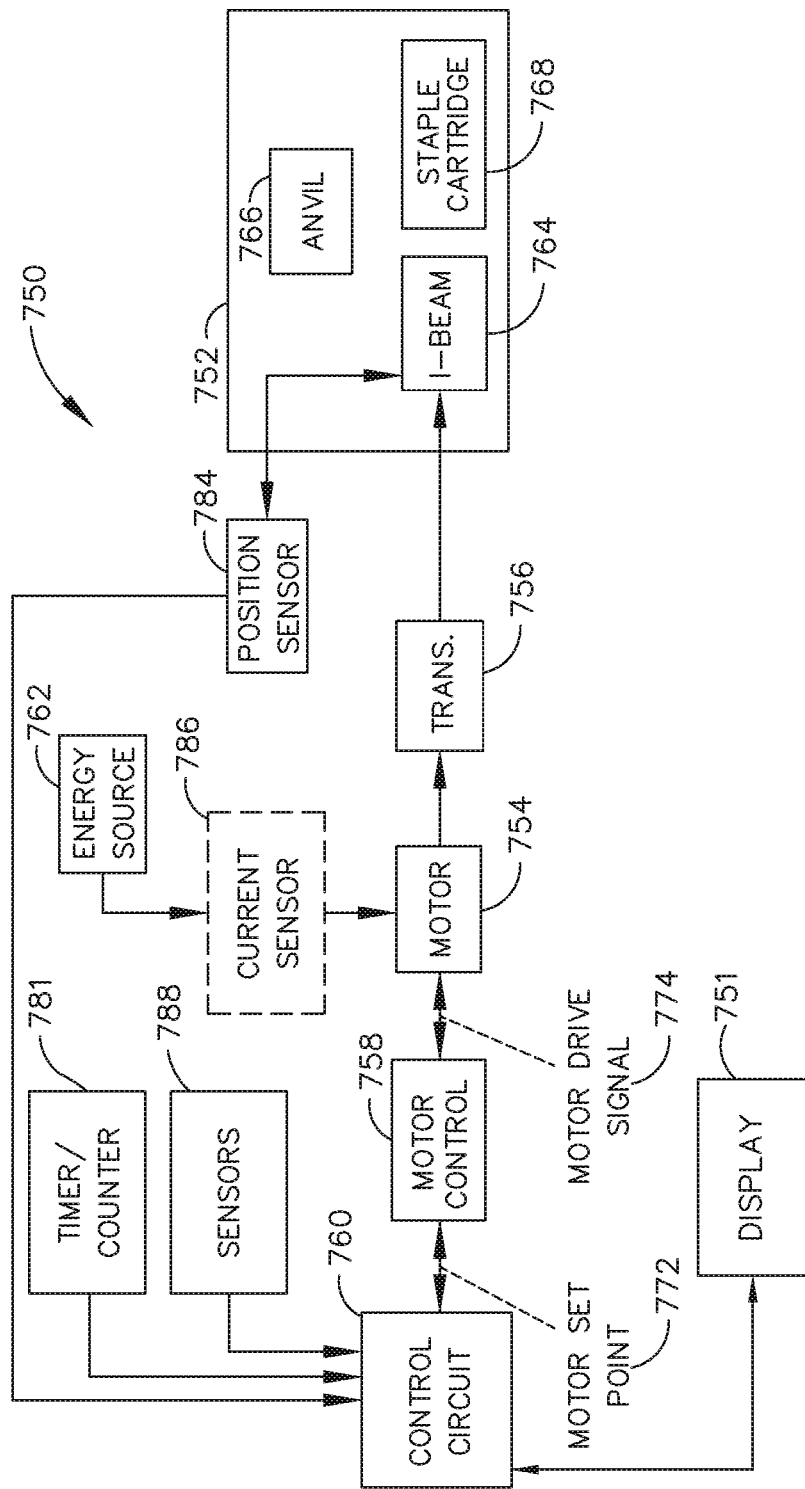
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
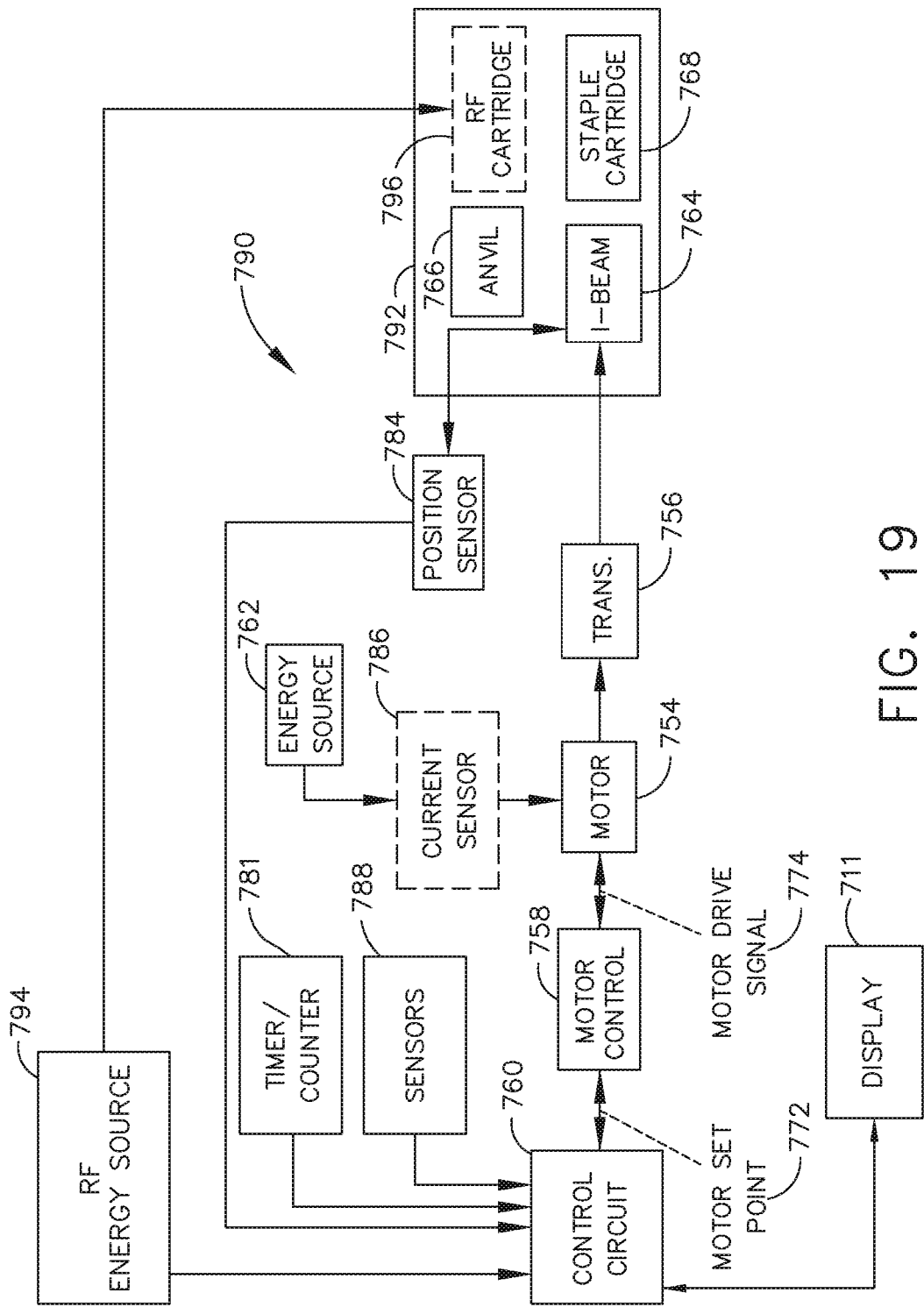
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 20:
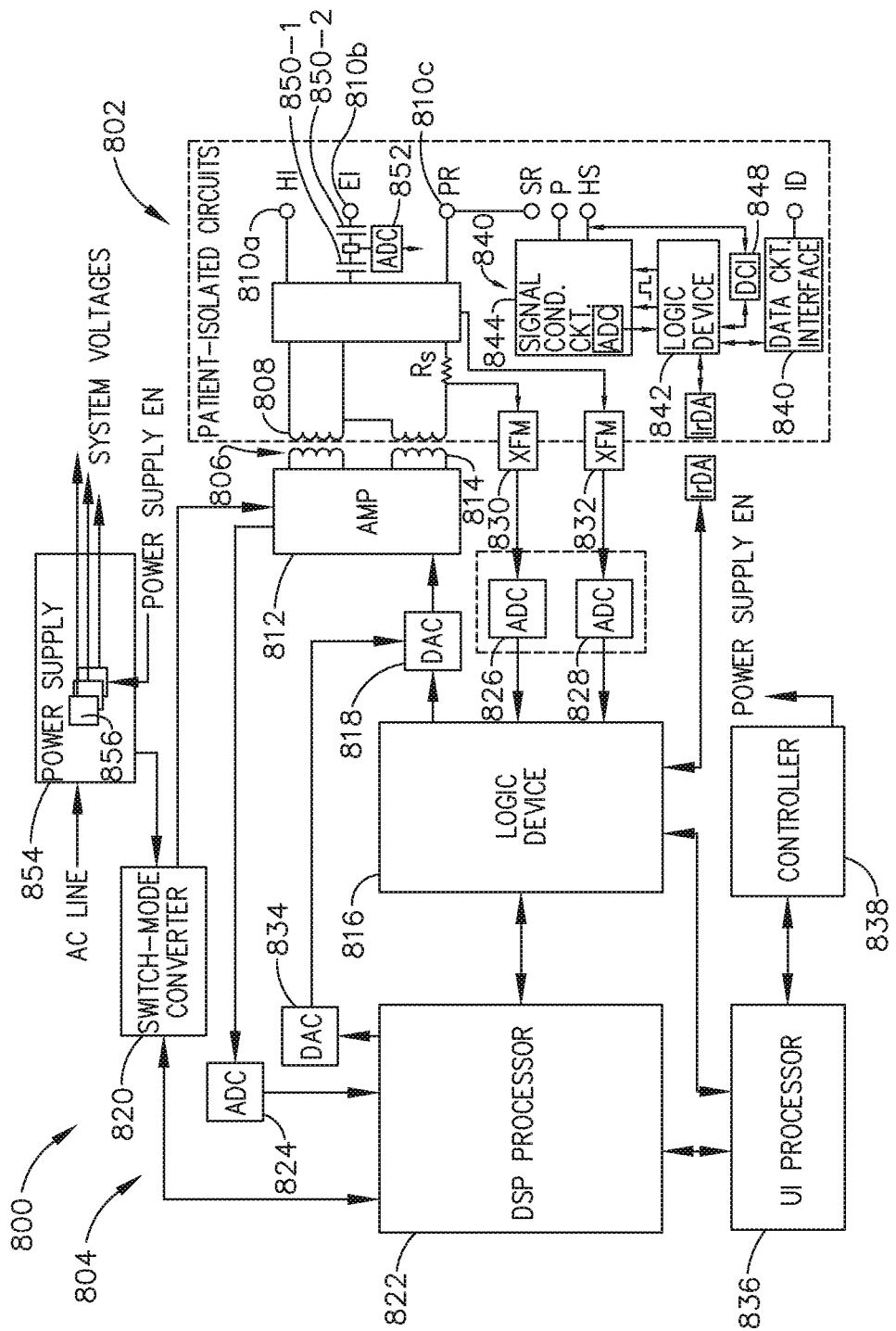
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810a, 810b, 810c for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810*b* to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
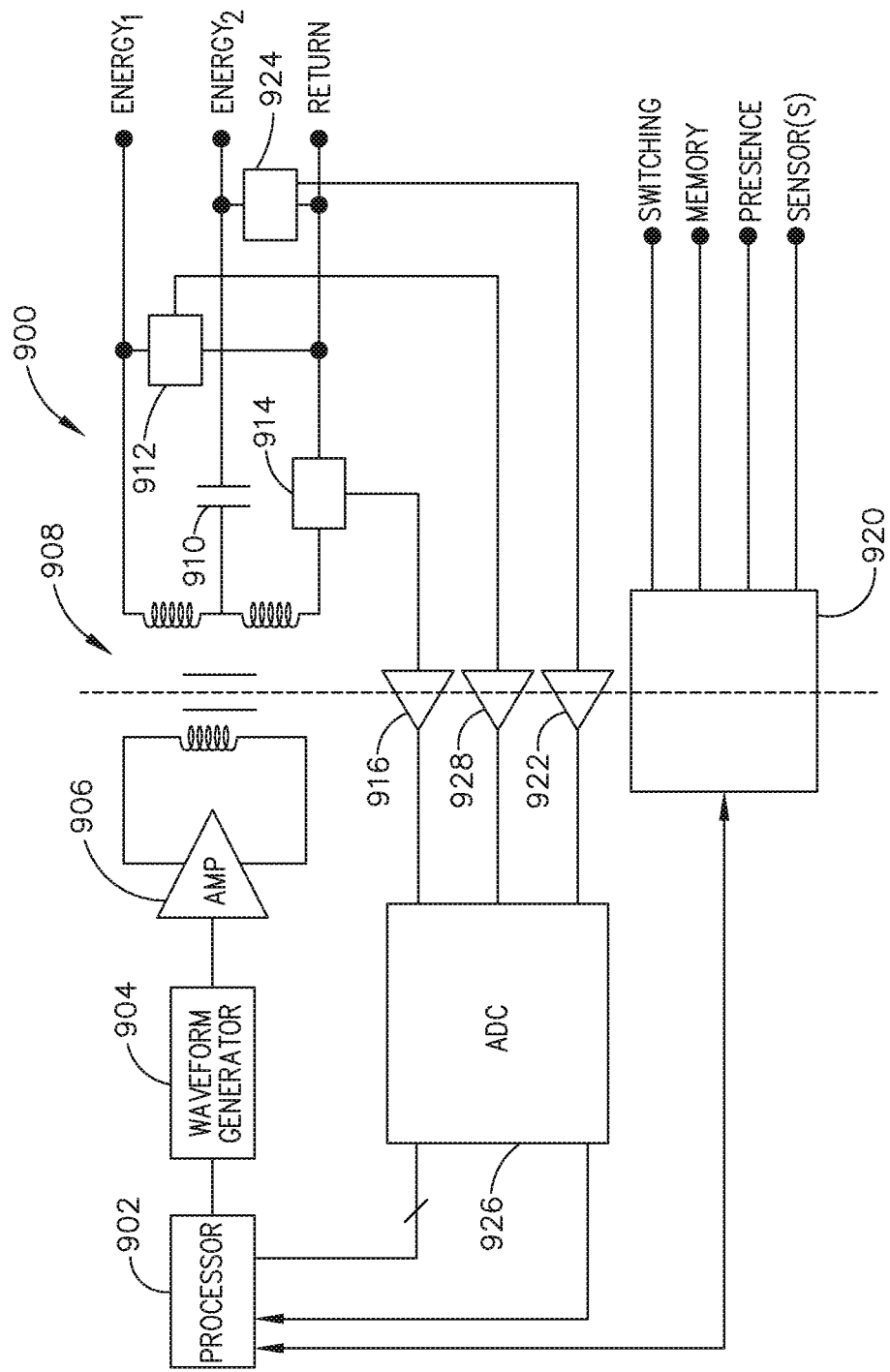
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 21). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Robotic surgical systems can be used in minimally invasive medical procedures. During such medical procedures, a patient can be placed on a platform adjacent to a robotic surgical system, and a surgeon can be positioned at a console that is remote from the platform and/or from the robot. For example, the surgeon can be positioned outside the sterile field that surrounds the surgical site. The surgeon provides input to a user interface via an input device at the console to manipulate a surgical tool coupled to an arm of the robotic system. The input device can be a mechanical input devices such as control handles or joysticks, for example, or contactless input devices such as optical gesture sensors, for example.

The robotic surgical system can include a robot tower supporting one or more robotic arms. At least one surgical tool (e.g. an end effector and/or endoscope) can be mounted to the robotic arm. The surgical tool(s) can be configured to articulate relative to the respective robotic arm via an articulating wrist assembly and/or to translate relative to the robotic arm via a linear slide mechanism, for example. During the surgical procedure, the surgical tool can be inserted into a small incision in a patient via a cannula or trocar, for example, or into a natural orifice of the patient to position the distal end of the surgical tool at the surgical site within the body of the patient. Additionally or alternatively, the robotic surgical system can be employed in an open surgical procedure in certain instances.

Figure 22:
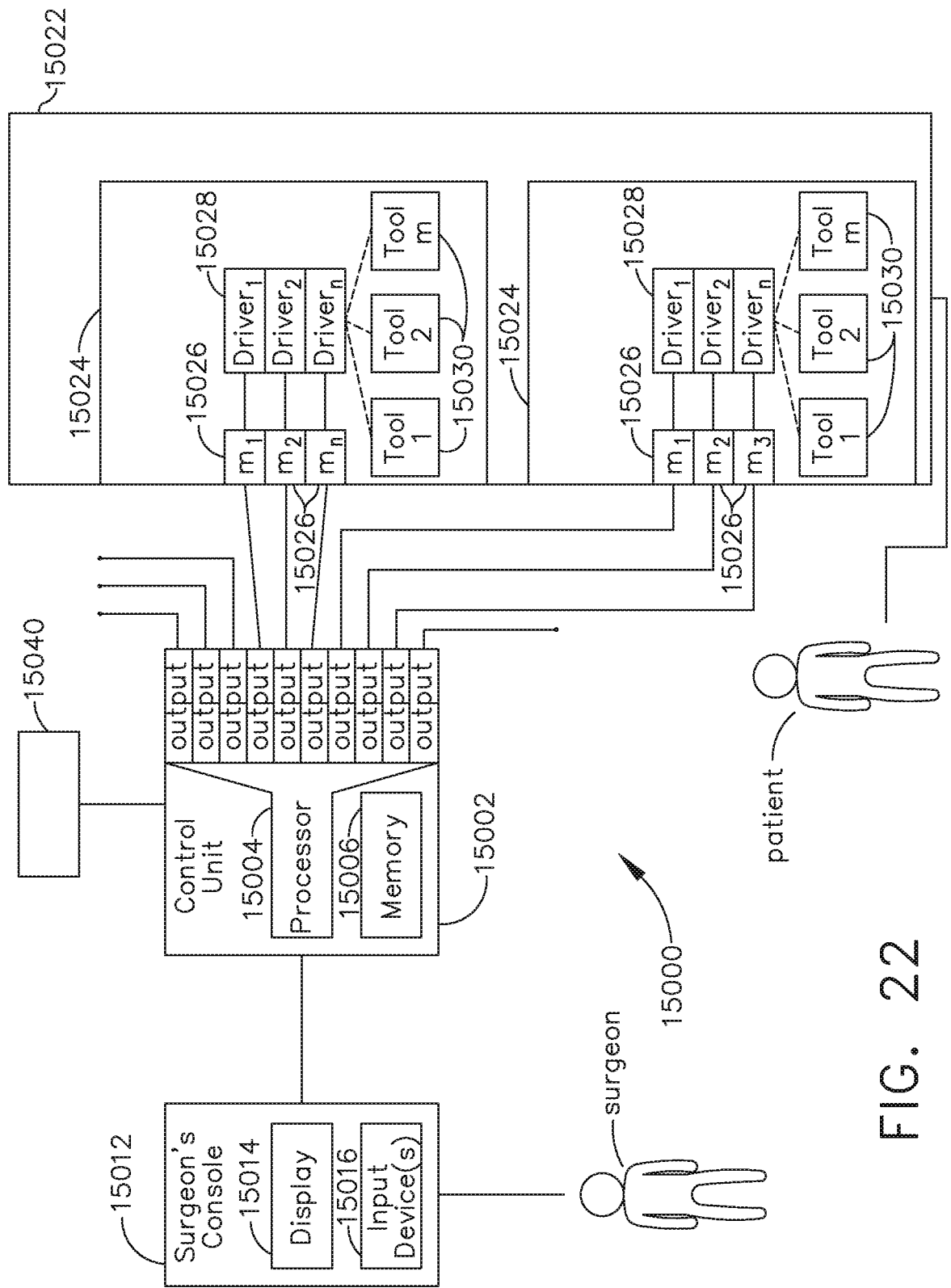
FIG. 22 is a schematic of a robotic surgical system, in accordance with one aspect of the present disclosure.

A schematic of a robotic surgical system 15000 is depicted in FIG. 22. The robotic surgical system 15000 includes a central control unit 15002, a surgeon's console 15012, a robot 15022 including one or more robotic arms 15024, and a primary display 15040 operably coupled to the control unit 15002. The surgeon's console 15012 includes a display 15014 and at least one manual input device 15016 (e.g., switches, buttons, touch screens, joysticks, gimbals, etc.) that allow the surgeon to telemanipulate the robotic arms 15024 of the robot 15022. The reader will appreciate that additional and alternative input devices can be employed.

The central control unit 15002 includes a processor 15004 operably coupled to a memory 15006. The processor 15004 includes a plurality of inputs and outputs for interfacing with the components of the robotic surgical system 15000. The processor 15004 can be configured to receive input signals and/or generate output signals to control one or more of the various components (e.g., one or more motors, sensors, and/or displays) of the robotic surgical system 15000. The output signals can include, and/or can be based upon, algorithmic instructions which may be pre-programmed and/or input by the surgeon or another clinician. The processor 15004 can be configured to accept a plurality of inputs from a user, such as the surgeon at the console 15012, and/or may interface with a remote system. The memory 15006 can be directly and/or indirectly coupled to the processor 15004 to store instructions and/or databases.

The robot 15022 includes one or more robotic arms 15024. Each robotic arm 15024 includes one or more motors 15026 and each motor 15026 is coupled to one or more motor drivers 15028. For example, the motors 15026, which can be assigned to different drivers and/or mechanisms, can be housed in a carriage assembly or housing. In certain instances, a transmission intermediate a motor 15026 and one or more drivers 15028 can permit coupling and decoupling of the motor 15026 to one or more drivers 15028. The drivers 15028 can be configured to implement one or more surgical functions. For example, one or more drivers 15028 can be tasked with moving a robotic arm 15024 by rotating the robotic arm 15024 and/or a linkage and/or joint thereof. Additionally, one or more drivers 15028 can be coupled to a surgical tool 15030 and can implement articulating, rotating, clamping, sealing, stapling, energizing, firing, cutting, and/or opening, for example. In certain instances, the surgical tools 15030 can be interchangeable and/or replaceable. Examples of robotic surgical systems and surgical tools are further described herein.

The reader will readily appreciate that the computer-implemented interactive surgical system 100 (FIG. 1) and the computer-implemented interactive surgical system 200 (FIG. 9) can incorporate the robotic surgical system 15000. Additionally or alternatively, the robotic surgical system 15000 can include various features and/or components of the computer-implemented interactive surgical systems 100 and 200.

In one exemplification, the robotic surgical system 15000 can encompass the robotic system 110 (FIG. 2), which includes the surgeon's console 118, the surgical robot 120, and the robotic hub 122. Additionally or alternatively, the robotic surgical system 15000 can communicate with another hub, such as the surgical hub 106, for example. In one instance, the robotic surgical system 15000 can be incorporated into a surgical system, such as the computer-implemented interactive surgical system 100 (FIG. 1) or the computer-implemented interactive surgical system 200 (FIG. 9), for example. In such instances, the robotic surgical system 15000 may interact with the cloud 104 or the cloud 204, respectively, and the surgical hub 106 or the surgical hub 206, respectively. In certain instances, a robotic hub or a surgical hub can include the central control unit 15002 and/or the central control unit 15002 can communicate with a cloud. In other instances, a surgical hub can embody a discrete unit that is separate from the central control unit 15002 and which can communicate with the central control unit 15002.

Robotic Surgical Assembly

Turning now to FIGS. 23-25 and 27, the robotic surgical assembly 40100 is connectable to an interface panel or carriage 40042, which is slidably mounted onto the rail 40040. The carriage 40042 supports or houses a motor "M" (FIG. 26) that receives controls and power from the control device 13004 (FIG. 4). The carriage 40042 may be moved along the rail 40040 via a motor driven chain or belt 40041 or the like. Alternatively, the carriage 40042 may be moved along the rail 40040 via a threaded rod/nut arrangement. For example, the carriage 40042 may support a threaded nut or collar, which receives a threaded rod therethrough. In use, as the threaded rod is rotated, the threaded collar, and in turn, the carriage 40042 are caused to be translated along the rail 40040. A coupling, or the like, is connected to a drive shaft of the motor M, and may be rotated clockwise or counter clockwise upon an actuation of the motor M. While a chain/belt 40041 or threaded rod and collar arrangement are described, it is contemplated that any other systems capable of achieving the intended function may be used (e.g., cable drives, pulleys, friction wheels, rack and pinion arrangements, etc.).

The carriage 40042 includes a coupling flange 40043 extending or projecting from a rear panel thereof and from the rail 40040. The coupling flange 40043 of the carriage 40042 defines an opening or bore 40043*a* therethrough and rotatably supports an instrument rotation gear or pulley 40048. The pulley 40048 has ring-shaped, non-circular, transverse cross-sectional profile passage or opening therethrough (e.g., substantially D-shaped, or the like) which defines a key-way for non-rotational receipt of a drive transfer assembly 40140 of the sterile barrier housing 40130. The pulley 40048 is rotatably supported in the coupling flange 40043 by journal bearings or the like.

A sterile shell or barrier 40060 is provided, which shrouds or covers the carriage 40042. Shell 40060 includes a rear shell portion 40060*a* configured and adapted to cover the rear panel of the carriage 40042 and an annular shell portion 40060*b* extending from rear shell portion 40060*a* and configured to cover the coupling flange 40043 of the carriage 40042. The annular shell portion 40060*b* of the shell 40060 defines an opening 40060*c* in registration with a passage or opening 40048*a* of the pulley 40048 having a non-circular, transverse cross-sectional profile (e.g., substantially D-shaped, or the like). A sterile drape 40061 or the like may be secured or adhered to the shell 40060 and may be pulled over the rail 40040 and the robotic arms 13002, 13003 (FIG. 4) to establish and maintain a sterile barrier between the patient 13013 (FIG. 4), the surgical field, and/or the robotic surgical system 13000 (FIG. 4).

The robotic surgical assembly 40100 includes a sterile barrier housing 40130 configured to mate with or otherwise connect to the shell 40060. The sterile barrier housing 40130 includes a hollow shell or body 40132 defining a cavity therein. The sterile barrier housing 40130 pivotally or hingedly supports a proximal cap or cover 40134 configured and adapted to selectively close a proximal end of the body 40132. The sterile barrier housing 40130 further includes a drive transfer assembly 40140 supported on, or connected to, a distal end of the body 40132.

The cavity of the body 40132 of the sterile barrier housing 40130 is configured to slidably receive a motor pack 40050 or the like therein. The motor pack 40050 may include four motors 40052, 40054, 40056, 40058 arranged in a rectangular formation such that respective drive shafts 40052*a*, 40054*a*, 40056*a*, 40058*a* thereof are all parallel to one another and all extend in a common direction. The drive shaft 40052*a*, 40054*a*, 40056*a*, 40058*a* of each motor 40052, 40054, 40056, 40058, respectively, may operatively interface with a respective drive coupler (of which only driver coupler 44144*a* is shown in FIG. 81B) of the drive transfer assembly 44140 (FIG. 81A) of the sterile barrier housing 40130. The motor pack 40050 may include four canister motors or the like, each having a drive shaft having a non-circular transverse cross-sectional profile (e.g., substantially D-shaped, or the like).

For an exemplary motor pack 40050 for use in the robotic surgical assembly 40100, reference may be made to U.S. Provisional Patent Application Ser. No. 62/181,817, filed on Jun. 19, 2015, entitled "Robotic Surgical Assemblies," the entire contents of which are incorporated by reference herein.

The motor couplers 40052*b*, 40054*b*, 40056*b*, 40058*b* may be non-rotatably connected to a respective drive shaft 40052*a*, 40054*a*, 40056*a*, 40058*a* of each motor 40052, 40054, 40056, and 40058, respectively. Each motor coupler 40052*b*, 40054*b*, 40056*b*, 40058*b* may have a substantially tubular configuration defining a lumen therethrough having a non-circular, transverse cross-sectional profile. The lumen of each motor coupler 40052*b*, 40054*b*, 40056*b*, 40058*b* is configured to non-rotatably engage and/or receive respective drive shaft 40052*a*, 40054*a*, 40056*a*, 40058*a* of each motor 40052, 40054, 40056, 40058, respectively, wherein the lumens may have a substantially D-shaped, transverse cross-sectional profile.

Each motor coupler 40052*b*, 40054*b*, 40056*b*, 40058*b* includes one or more distally extending tab 40052*c*, 40054*c*, 40056*c*, 40058*c*, which is/are configured to engage a respective mating feature or slot of the drive couplers (e.g., drive coupler 44144*a*) of the drive transfer shafts 44144, 44146, 44148, 44150 (FIG. 81A) of the sterile barrier housing 40130 to transmit rotational forces from the motors 40052, 40054, 40056, 40058 to respective drive transfer shafts 44144, 44146, 44148, 44150 of the drive transfer assembly 44140 in the manner of an "Oldham coupling." This Oldham-type coupling limits backlash and enables autocorrecting when components thereof are slightly misaligned with one another. In some embodiments, one or more of these tabs and/or slots may have complementary V-shaped configurations. It is contemplated that any rotational force transmitting feature may be provided at the distal end of the motor couplers 40052*b*, 40054*b*, 40056*b*, 40058*b*. In use, as any one of the motors 40052, 40054, 40056, 40058 is activated to rotate a respective drive shaft 40052*a*, 40054*a*, 40056*a*, 40058*a*, the particular drive shaft drive shaft 40052*a*, 40054*a*, 40056*a*, 40058*a* transmits the rotation to the respective motor coupler 40052*b*, 40054*b*, 40056*b*, 40058*b*, which in turn, transmits the rotation (via tabs 40052*c*, 40054*c*, 40056*c*, 40058*c*) to the respective drive couplers (e.g., drive coupler 44144*a*) of the drive transfer shafts 44144, 44146, 44148, 44150 of the drive transfer assembly 400140. Such an arrangement and coupling permit a degree of flotation of the motor couplers 40052b, 40054b, 40056b, 40058b and the drive couplers (e.g., drive coupler 44144a) in any radial direction relative to a longitudinal axis thereof.

The robotic surgical assembly 40100 includes a lock ring or collar 40160 rotatably supported on the distal end of the body 40132 of the sterile barrier housing 40130. The lock collar 40160 projects distally from the body 40132 of the sterile barrier housing 40130 and defines an internal thread configured for threadable connection to a proximal ring connector 40171 of the sterile barrier collar assembly 40170, which is described below.

The robotic surgical assembly 40100 includes a sterile barrier collar assembly 40170 connectable to the annular shell 40060b of the shell 40060 and extendable through the D-shaped passage or opening of the pulley 40048. Specifically, the sterile barrier collar assembly 40170 includes a tubular sleeve body 40172 having a non-circular, transverse cross-sectional outer profile (e.g., substantially D-shaped, or the like) and an inner bore 40172a having a complementary non-circular, transverse cross-sectional profile (e.g., substantially D-shaped, or the like).

The sterile barrier collar assembly 40170 further includes a semi-annular coupling cuff 40176 supported on or otherwise secured to a distal end of the tubular sleeve body 40172. The coupling cuff 40176 includes a U-shaped body portion having an open side edge or instrument opening that opens distally and laterally and a pair of opposed side arms. Each side arm of the body portion includes a ramp surface formed in or projecting from an inner juxtaposed surface thereof. Each ramp increases in height from a distal end (near the open side edge) to a proximal end (near a back span of the body portion). It is contemplated that each ramp may be angled at approximately 10° relative to a planar distal surface of the coupling cuff 40176. Each side arm of the body portion further includes a recess or channel formed in a surface thereof that is configured to slidably receive a respective arm or tab of a distal floating plate that is connected to or otherwise extending from a distal end of the tubular sleeve body 40172.

Figure 26:
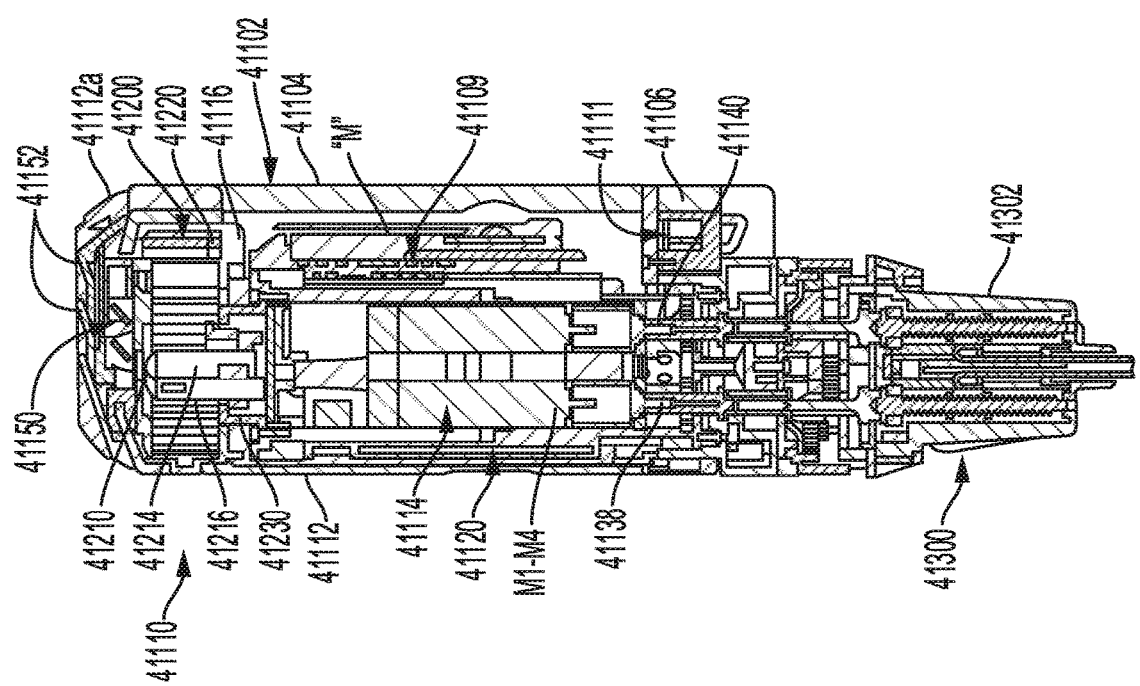
FIG. 26 is a sectional view of an instrument drive unit, in accordance with at least one aspect of the present disclosure.
Figure 28:
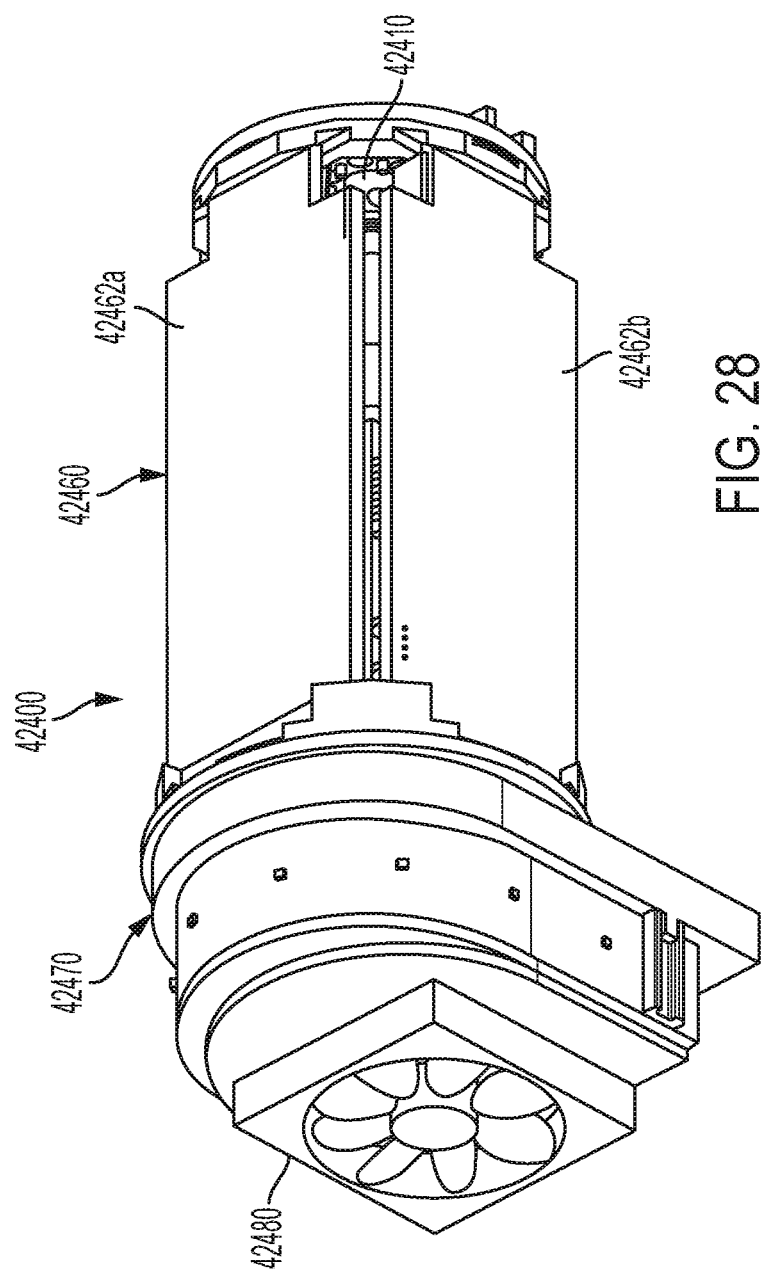
FIG. 28 is a perspective view of an instrument drive unit comprising a cooling unit, in accordance with at least one aspect of the present disclosure.

Turning now to FIGS. 26 and 28-29, various views of a robotic surgical assembly, also referred to as an instrument drive unit (IDU) 41110, are shown. As described above, the IDU 41110 transfers power and actuation forces from its motors to driven members (not shown) of electromechanical surgical instrument 41300 to ultimately drive movement of components of the end effector of electromechanical surgical instrument 41300, for example, a movement of a knife blade (not shown) and/or a closing and opening of jaw members of the end effector, the actuation or firing of a stapler, and/or the activation or firing of an electrosurgical energy-based instrument, or the like. The motor assembly 41114 of the IDU 41110 is rotated by a motor "M" supported in the IDU holder 41102 and transfers its rotational motion to electromechanical surgical instrument 41300.

The IDU holder 41102 of surgical assembly 41100 functions both to actuate a rotation of motor assembly 41114 of the IDU 41110 and to effect axial translation of IDU 41110 along the rail 40040 (FIG. 24) of the robotic arms 13002, 13003 (FIG. 4). The IDU holder 41102 includes a back member or carriage 41104 and an outer member or outer housing 14106, also referred to as a sterile shell or barrier 40060 (FIG. 23), extending laterally (e.g., perpendicularly) from a distal end 41107 of carriage 41104. In some embodiments, the housing 41106 may extend at various angles relative to carriage 41104 and from various portions of carriage 41104. The carriage 41104 has a first side and a second side, opposite the first side. The first side of the carriage 41104 is detachably connectable to the rail 40040 of the robotic arms 13002, 13003 to enable the IDU holder 41102 to slide or translate along rail 40040 of the robotic arms 13002, 13003. The second side of the carriage 41104 is configured to support a housing 41112 or the like of the IDU 41110.

The carriage 41104 of the IDU holder 41102 supports or houses a motor, such as, for example, canister motor "M" therein. Motor "M" receives controls and power from control device 13004 (FIG. 4) to ultimately rotate internal motor assembly 41114 of IDU 41110. Carriage 41104 includes a printed circuit board 41109 in electrical communication with motor "M" of carriage 41104 to control an operation of motor "M" of carriage 41104. Carriage 41104 further includes a belt or gear drive mechanism 41111 that extends distally from motor "M." Drive mechanism 41111 is configured to operably interface with motor assembly 41114 of IDU 41110 to effect a rotation of motor assembly 41114 upon actuation of motor "M" of carriage 41104.

The housing 41112 of IDU 41110 is engaged to the second side of carriage 41104 of IDU holder 41102 so as to shroud, cover, and protect the inner components of IDU 41110 and carriage 41104. Housing 41112 of IDU 41110 may have a generally cylindrical configuration, but in some embodiments, housing 41112 may assume a variety of configurations, such as, for example, squared, triangular, elongate, curved, semi-cylindrical, or the like. As mentioned above, housing 41112 protects or shields various components of IDU 41110 including motor assembly 41114 and a flex spool assembly 41200 for transferring power and data to components of IDU 41110. Housing 41112 also provides a platform 41116 on which the inner components of IDU 41110 are attached.

IDU 41110 includes a fan 41150 disposed within a top portion thereof and is located above flex spool assembly 41200. Fan 41150 is connected to flex spool assembly 41200 via a connector (not explicitly shown) to provide adjustable power to fan 41150. A top portion 41112a of housing 41112 may define a plurality of vents or slits 41152 therein to allow for air to transfer out of IDU 41110. Fan 41150 is configured to draw air through flex spool assembly 41200 and out of top portion 41112a of housing 41112 through slits 41152 to cool electronics during operation thereof and to maintain a negative pressure through IDU 41110. The flex spool assembly 41200 is configured to adjust the amount of power delivered to fan 41150 based on the temperature within IDU 41110. Speed controllers (not shown) associated with flex spool assembly 41200 and/or integrated circuit 41120 may be provided to control a speed of fan 41150 to adjust a cooling rate. For example, the speed control may adjust the electrical current that is delivered to fan 41150 to adjust a speed thereof.

The IDU 41110 includes the integrated circuit 41120 and the motor assembly 41114 each rotatably disposed therewithin. In some embodiments, IDU 41110 may include brackets and/or stops configured to compensate for loads directed on motor assembly 41114 and/or integrated circuit 41120 in a direction that is perpendicular or transverse to the longitudinal axis defined by IDU 41110. Integrated circuit 41120 includes a top rigid printed circuit board or nexus and four elongate rigid printed circuit boards 41124a, 41124b, 41126a, 41126b that extend perpendicularly from top printed circuit board 41122. Top printed circuit board 41122 has one or more male electrical connectors 41128 for coupling to one or more female electrical connectors 41216*a* of flex spool assembly 41200.

The elongate printed circuit boards 41124*a*, 41124*b*, 41126*a*, 41126*b* are parallel with one another and are disposed along a longitudinal axis of IDU 41110. Elongate printed circuit boards 41124*a*, 41124*b*, 41126*a*, 41126*b* include a first pair of elongate printed circuit boards 41124*a*, 41124*b* that oppose one another and a second pair of elongate printed circuit boards 41126*a*, 41126*b* that oppose one another. Elongate printed circuit boards 41124*a*, 41124*b*, 41126*a*, 41126*b* cooperatively form a rectangular configuration and define a cavity therein configured for slidable receipt of motor assembly 41114. It should be appreciated that circuit boards 41124*a*, 41124*b*, 41126*a*, 41126*b* and nexus 41122 of integrated circuit 41122 may be configured in any number of structural combinations, such as, for example, first, second, third, and fourth circuit boards 41124*a*, 41124*b*, 41126*a*, 41126*b* being coupled, side-by-side, where one of first, second, third, or fourth circuit board 41124*a*, 41124*b*, 41126*a*, 41126*b* is further coupled to one side of a first, second, third, or fourth side of nexus 41122. In some embodiments, integrated circuit 41120 may have various connectors, flex cables, or wires used to interconnect elongate printed circuit boards 41124*a*, 41124*b*, 41126*a*, 41126*b* to one another and/or to nexus 41122.

First pair of elongate printed circuit boards 41124*a*, 41124*b* have a first end portion in electrical communication with nexus 41122 and a second end portion in electrical communication with motor assembly 41114 to transfer power from printed circuit assembly 41200 to motor assembly 41114, as will be described in detail below. Second pair of elongate printed circuit boards 41126*a*, 41126*b* have a first end portion in electrical communication with nexus 41122 and a distal end in electrical communication with various electrical components of IDU 41110 and/or surgical instrument 41300 to transfer communication signals and/or power to the various electrical components of IDU 41110 and surgical instrument 41300.

The electrical components of IDU 41110 may include, but are not limited to, transducers, encoders, gyroscopes, magnetometers, distal limit sensors, pressure sensors, torsional sensors, load cells, optical sensors, position sensors, heat sensors, illumination elements, cameras, speakers, audible emission components, motor controllers, LED components, microprocessors, sense resistors, accelerometers, switches to monitor, limit and control positional limits, etc. In some embodiments, each of these electrical components may be incorporated into flex spool assembly 41200 of IDU 41110.

Motor assembly 41114 of IDU 41110 is non-rotatably disposed within the cavity of integrated circuit 41120. Motor assembly 41114 may include four motors "M1-M4," for example, canister motors or the like, each having a drive shaft 41138, 41140 (only drive shafts of two motors of motors "M1-M4" being shown in FIG. 26) having a non-circular, transverse cross-sectional profile (e.g., substantially D-shaped, or the like), as is described above. The four motors "M1-M4" are arranged in a rectangular formation such that respective drive shafts 41138, 41140 thereof are all parallel to one another and all extending in a common direction. As the motors "M1-M4" of the motor assembly 41114 are actuated, rotation of the respective drive shafts 41138, 41140 of the motors "M1-M4" is transferred to gears or couplers of drive assemblies of surgical instrument 41300 via respective drive transfer shafts to actuate various functions of surgical instrument 41300.

Flex spool assembly 41200 of IDU 41110 is configured to transfer power and information (e.g., signals that direct actuation of certain functions of IDU 41110 and surgical instrument 41300) from control device 13004 to an integrated circuit 41120 of IDU 41110. Flex spool assembly 41200 generally includes a first flex circuit 41210 and a second flex circuit 41220. First flex circuit 41210 is configured to electrically interconnect control device 13004 and a plurality of electrical components (e.g., motors, various sensors, transducers, etc.) of IDU 41110 and/or surgical instrument 41300.

IDU 41110 further includes a spindle assembly 41230 for transferring rotational motion from motor assembly 41114 to first flex circuit 41210. Spindle assembly 41230 includes an outer annular member 41232, and an inner annular member or ring member 41234. Outer annular member 41232 is fastened to a proximal end portion of motor assembly 41114 via fasteners 41236. Inner annular member 41234 is fastened to outer annular member 41232 via fasteners 41238 and is rotatable relative to platform 41116 such that outer annular member 41234 rotates relative to platform 41116. In embodiments, outer and inner annular members 41232, 41234 of spindle assembly 41230 may be of a single integral construction. A lubricious coating may be applied to surfaces of spindle assembly 41230 that contact platform 41116 or to the surfaces of platform 41116 that contact spindle assembly 41230, such that spindle assembly 41230 rotates relative to platform with limited friction. Accordingly, the lubricious coating may include any suitable material, such as, for example, ultra-high molecular weight polyethylene, nylon, acetal, or polytetrafluoroethylene.

Robotic Surgical Assembly Cooling

Cooling the IDU 40110 (FIG. 23) of a robotic surgical assembly 41100 (FIG. 23) for a robotic surgical system 13000 (FIG. 4) can be challenging because of the fact that the instrument drive unit can be located at least partially within the sterile field during the course of a surgical procedure. As described above, the IDU 40110 can include a fan 41150 (FIGS. 26 and 28-29) to promote air transfer out of the IDU 40110 for cooling the IDU 40110 during use; however, this can create two issues. First, if the air intake of the fan 41150 is from outside of the sterile field and the fan 41150 releases the circulated air into the sterile field, then the fan 41150 can be releasing nonsterile air into the sterile field, which can result in contamination of the sterile field. Second, if the air intake of the fan 41150 is from inside of the sterile field, then the fan 41150 could potentially intake a contaminant from the sterile field and then cause that contaminant to be proliferated through the surgical theater, outside of the bounds of the sterile field. Therefore, there is a need for robotic surgical assembly cooling systems that address these and other issues.

In various aspects, contamination of the surgical site, sterile field, and/or surgical theater by air-circulating cooling systems can be prevented by controlling heat transfer and air circulation within the robotic surgical system 13000 and/or IDU 40110. For example, an air filter (e.g., an ultra-low particular air (ULPA) filter) can be integrated into or otherwise positioned at the air intake manifold to ensure that air exhausted from the robotic surgical system 13000 is sterile. As another example, the robotic surgical system 13000 can include a circulation path where the air intake and the exhaust are both directed to an area of the robotic surgical system 13000 outside of the sterile surgical area. In one aspect, the air circulation path could be directed towards or connected to the smoke evacuation system in order to leverage the smoke evacuation system's integral, high-quality air filters. As yet another example, the robotic surgical system 13000 can be configured to ionically collect particulates from air that is drawn into or exposed to the cooling system. In one aspect, the robotic surgical system 13000 can include an ionizing air filter configured to capture particulates within the air drawn into the cooling system. The ionizing air filter can include plates that are configured to collect charged particles that are drawn into the device. The removable charged plates could be cleaned and reused. Further, the charged plates could permit testing and identification of particulates captured from the indrawn air. The charged plates could have the capability of actively attracting a variety of different contaminants and particulates from the air passing through the ionizing air filter, including bacterial contaminants. These systems and other examples will be discussed in greater detail below.

In such aspects, dedicated heat management systems can be implemented within or in conjunction with the sterile barrier, such as by integrating a cooling apparatus within the air circulation flow path or coupling the cooling apparatus to the IDU 40110. For example, the cooling system can be in thermal cooperation with the IDU 40110 and/or components thereof (including, for example, the motor assembly), but the cooling air circulation path can be isolated from the internal air of the IDU 40110. As another example, the cooling system can include a cooling circulation system that can include fluid and/or vaporous aspects in order to transfer heat from the IDU 40110 to a location for venting to the atmosphere remote from the robotic arm 13120. As another example, the cooling system can include a Peltier cooling element to extract heat from the IDU 40110 and other heat-generating components of the robotic surgical system 13000 for transfer to other surfaces exposed to convection from dedicated air-flow pathways.

Figure 23:
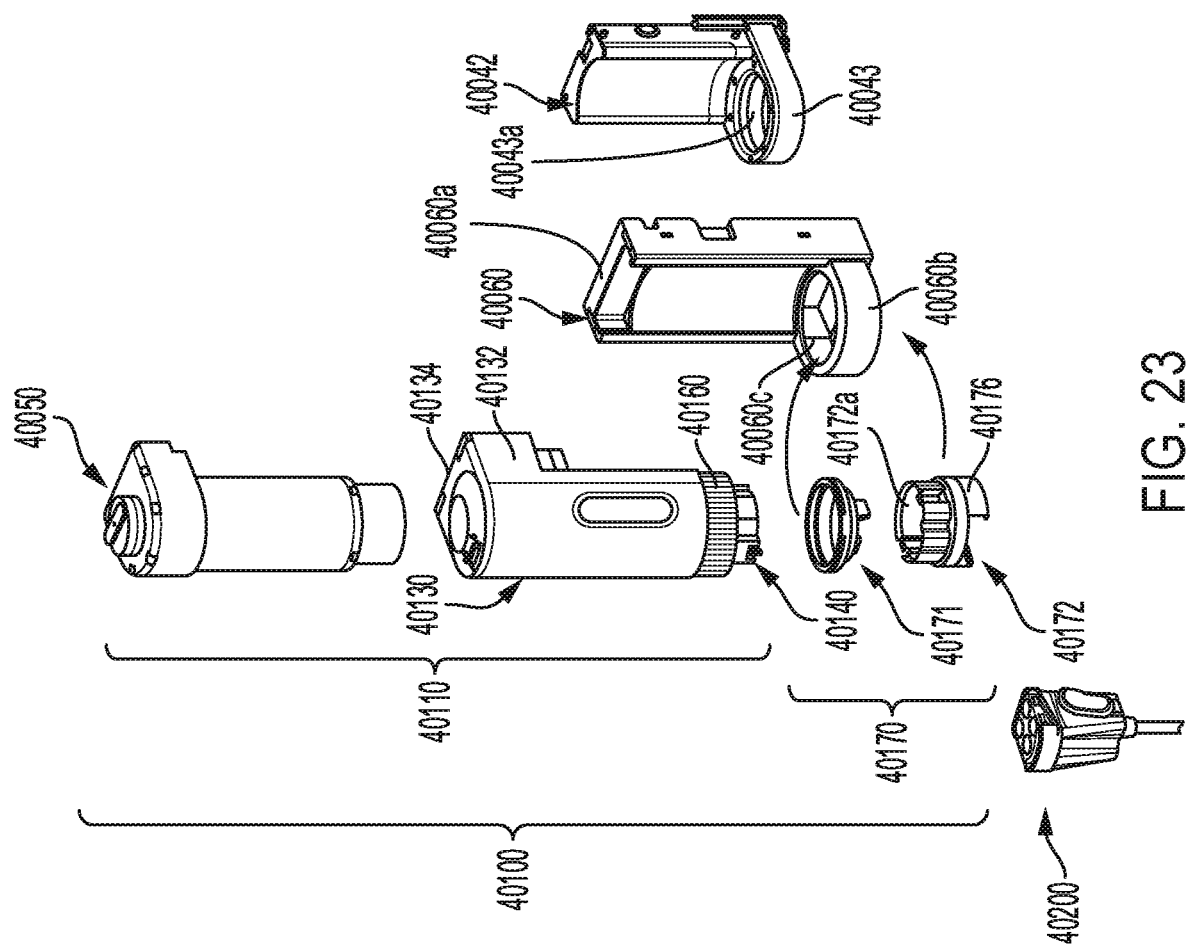
FIG. 23 is an exploded view of a robotic surgical assembly, in accordance with at least one aspect of the present disclosure.
Figure 24:
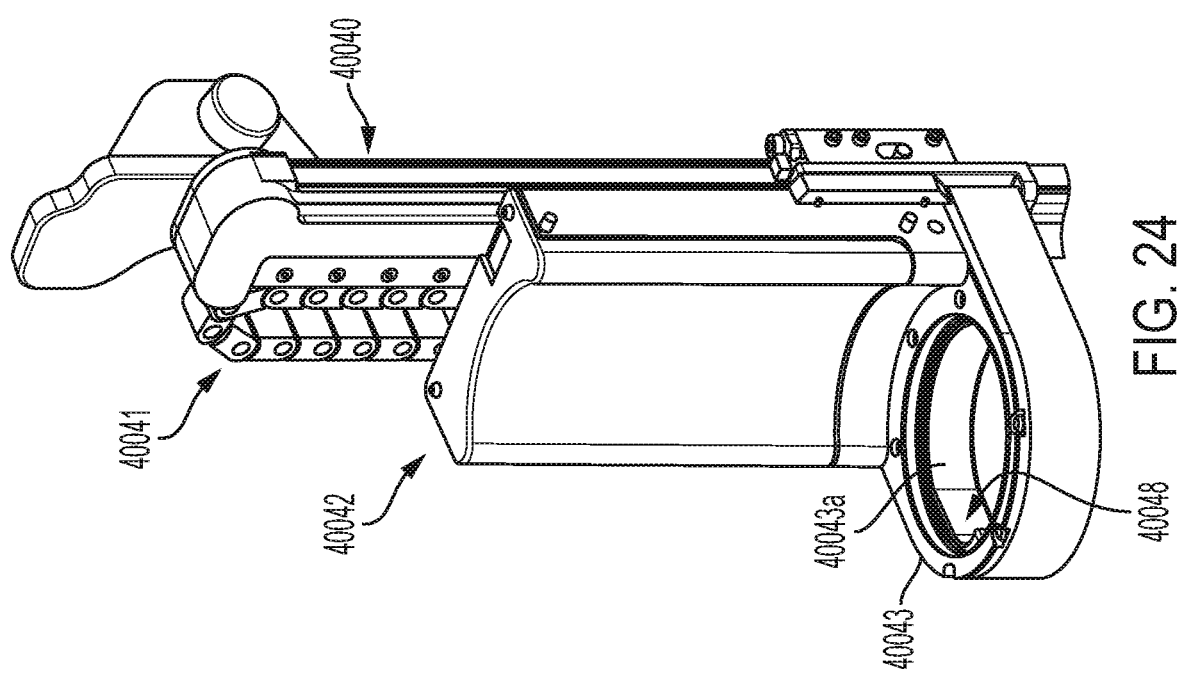
FIG. 24 is a perspective view of a carriage and a slide rail of a robotic surgical assembly, in accordance with at least one aspect of the present disclosure.
Figure 25:
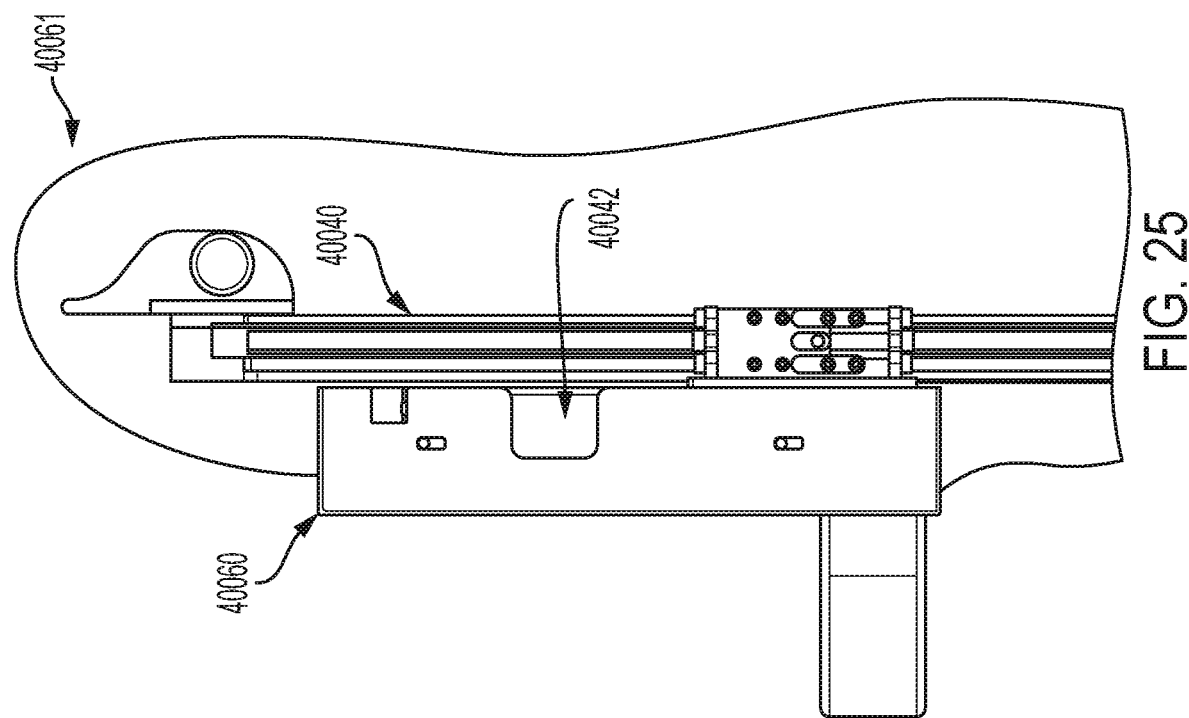
FIG. 25 is a side elevational view of a carriage and a slide rail of a robotic surgical system, in accordance with at least one aspect of the present disclosure.
Figure 31:
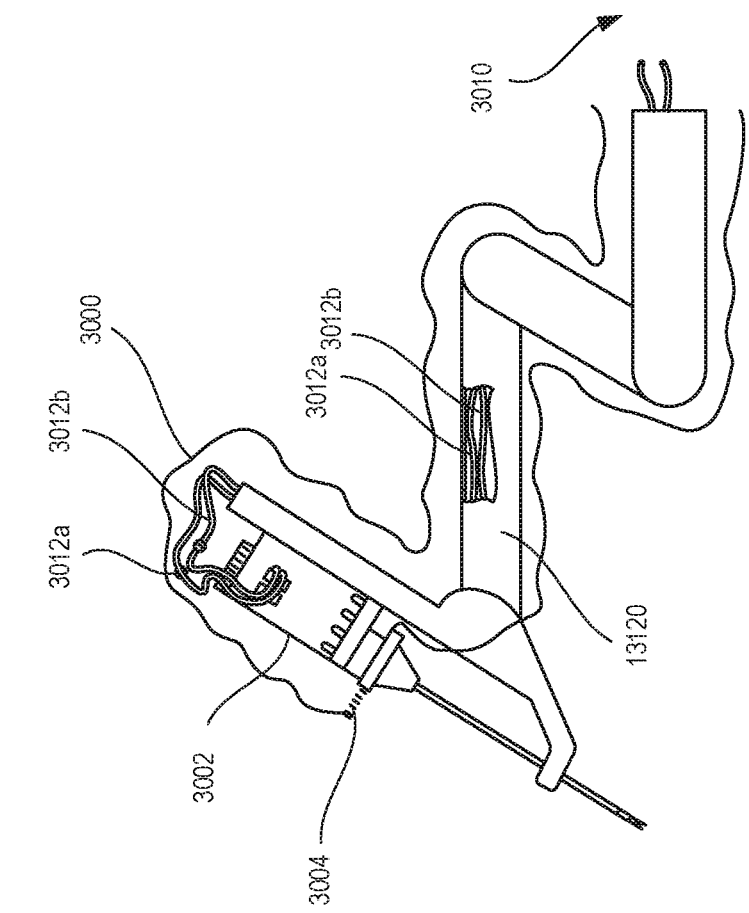
FIG. 31 is a side elevational view of a robotic arm comprising a fluid-based cooling system for an instrument drive unit, in accordance with at least one aspect of the present disclosure.
Figure 30:
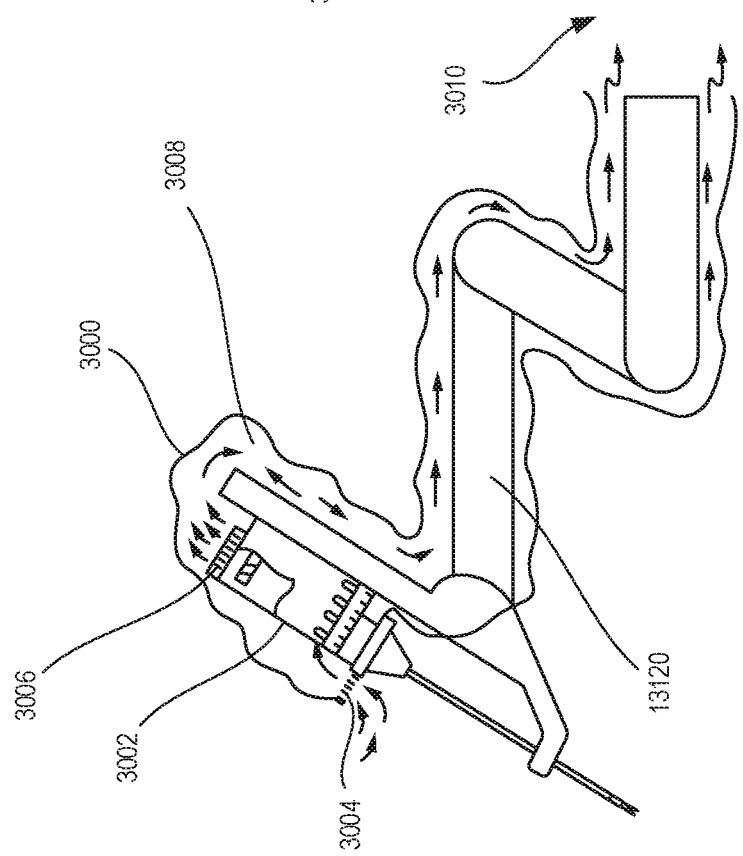
FIG. 30 is a side elevational view of a robotic arm comprising an air-based cooling system for an instrument drive unit, in accordance with at least one aspect of the present disclosure.

Referring now to FIGS. 30 and 31, in some aspects the sterile drape 3000 can be dimensioned or configured to cover the IDU 3002 when affixed to the robotic arm 13120, as opposed to the IDU 3002 being exposed to the sterile field, as shown in FIGS. 23-25. For example, FIG. 30 is a side elevational view of a robotic arm 13120 comprising an air-based cooling system for an IDU 3002 positioned within the sterile drape 3000. In this aspect, the sterile drape 3000 includes an air intake filter 3004 through which ambient air (e.g., air from the sterile field) is indrawn into the interior 3008 of the sterile barrier 3000. The filter 3004 can include, for example, an ULPA filter or an ionizing air filter. The filter 3004 is configured to remove contaminants and other particulates from the indrawn ambient air. Once it has been drawn through the filter 3004, the air can pass into the IDU 3002 (e.g., through a port thereon) at which point it is heated by the electronics, motors, and other interior components of the IDU 3002 and then exhausted by the IDU fan 3006 (e.g., the fan 41150 from FIGS. 26, 28, and 29) into the interior 3008 of the sterile drape 3000, carrying thermal energy away from the IDU 3002. The heated air is then drawn through the interior 3008 of the sterile drape 3000 and exhausted into or at a secondary location 3010 remote from the robotic surgical arm 13120. The secondary location 3010 can include, for example, an enclosure. In one aspect, the secondary location 3010 can include a smoke evacuation system to which the interior 3008 of the sterile drape 3000 is fluidically coupled. In another aspect, the secondary location 3010 can include atmosphere within a room or another such enclosure.

In addition to air-based cooling systems, the robotic surgical system 13000 could also include fluid-based cooling systems. For example, FIG. 31 is a side elevational view of a robotic arm 13120 comprising a fluid-based cooling system for an IDU 3002 positioned within the sterile drape 3000. In this aspect, the robotic surgical system 13000 can define a fluid circulation path coupled to the IDU 3002 and that extends at least partially through the robotic arm 13120. The fluid circulation path can include a first tube 3012*a* configured to transport a cooling fluid (e.g., water) to the IDU 3002 and/or a heat exchanger coupled to the IDU 3002 and a second tube 3012*b* configured to transport the fluid heated by the IDU 3002 to a secondary location 3010, as described above.

Figure 32:
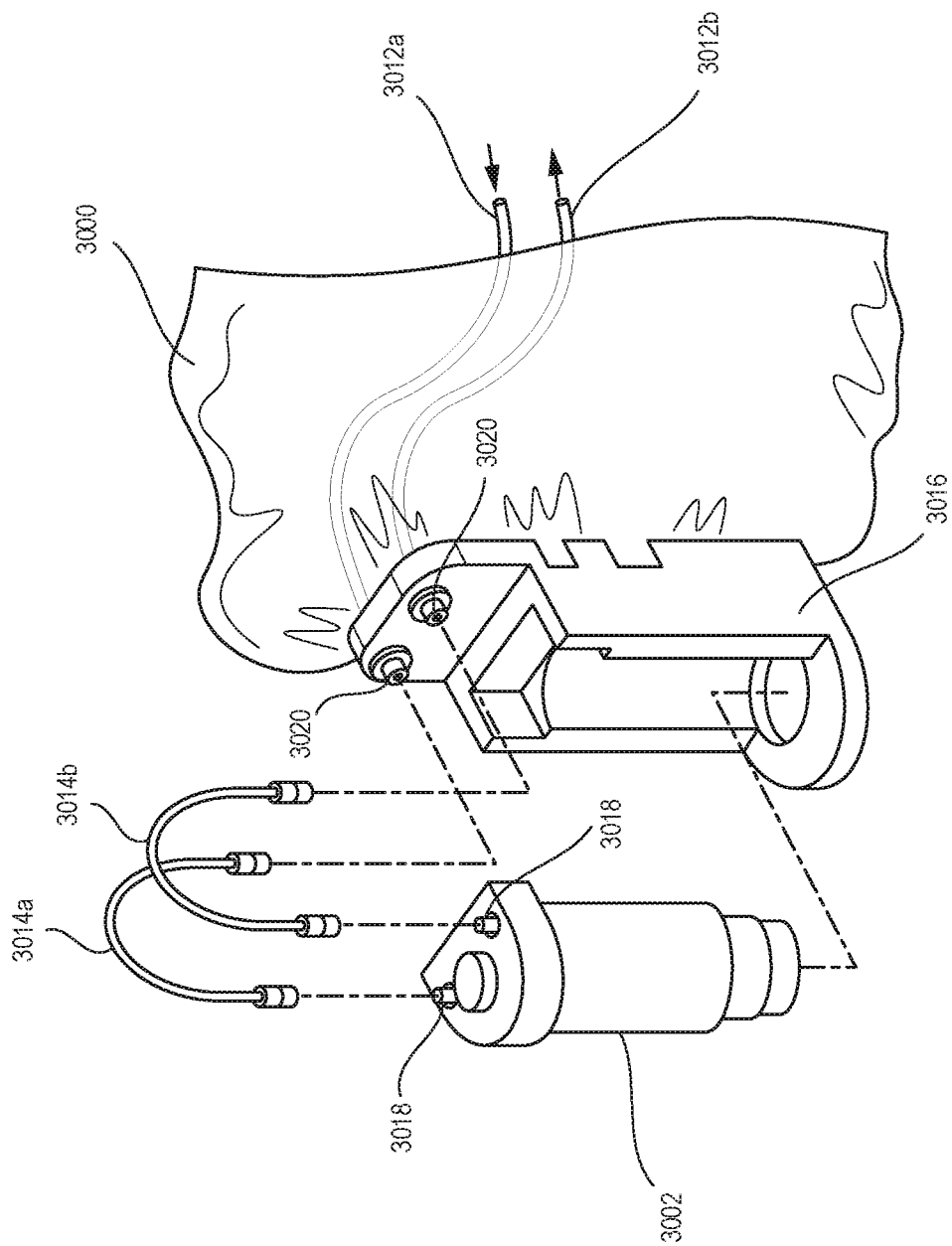
FIG. 32 is a perspective view of a fluid-based, enclosed cooling system for an instrument drive unit, in accordance with at least one aspect of the present disclosure.

In other aspects, the IDU 3002 can be positioned externally to the sterile drape 3000 and can be configured to include a sealed cooling system enclosed from the sterile field. For example, FIG. 32 is a perspective view of a fluid-based, enclosed cooling system for an IDU 3002 positioned externally to the sterile drape 3000. In this aspect, the first tube 3012*a* and the second tube 3012*b* are fluidically coupled to a pair of connectors 3020 disposed on the carriage 3016 (or the sterile barrier thereof) that is configured to receive and secure the IDU 3002. Further, the IDU 3002 likewise includes a pair of connectors 3018 disposed thereon. The IDU connectors 3018 can be fluidically coupled to the carriage connectors 3020 via a first connector tube 3014*a* and a second connector tube 3014*b*, in order to fluidically couple the first tube 3012*a* and the second tube 3012*b* to the IDU 3002 for providing cooling fluid thereto and removing heated fluid therefrom for cooling the IDU 3002. In operation, the first tube 3012*a* can transport cooling liquid through the sterile drape 3000 to the first connector tube 3014*a* via a carriage connector 3020, which in turn transports the cooling liquid to the IDU 3002 through the corresponding IDU connector 3018. The cooling fluid is then passed through a heat exchanger or other assembly for transferring thermal energy from the motors, electronics, and/or other components of the IDU 3002 to the cooling liquid. At that point, the heated liquid is transported to the second connector tube 3014*b* via the corresponding IDU connector 3018, which in turn transports the heated liquid to the second tube 3012*b* via the corresponding carriage connector 3020. The second tube 3012*b* then carries then heated liquid to the secondary location 3010, as described above. The cooling system can thus be entirely fluidically isolated from the sterile environment.

In various aspects, the robotic surgical system 1300 could also be configured to include cooling air inlets and outlets within the robotic surgical assembly 40100 that are oriented to mitigate the intake of contaminants from the sterile field. For example, the air inlets and outlets can be oriented so that the air drawn into the cooling system is directed either obliquely relative to or away from the surgical site so as to not create a substantial air differential within the sterile field, reducing the intake of fluids or aerosols that may be present within the sterile field.

Figure 33:
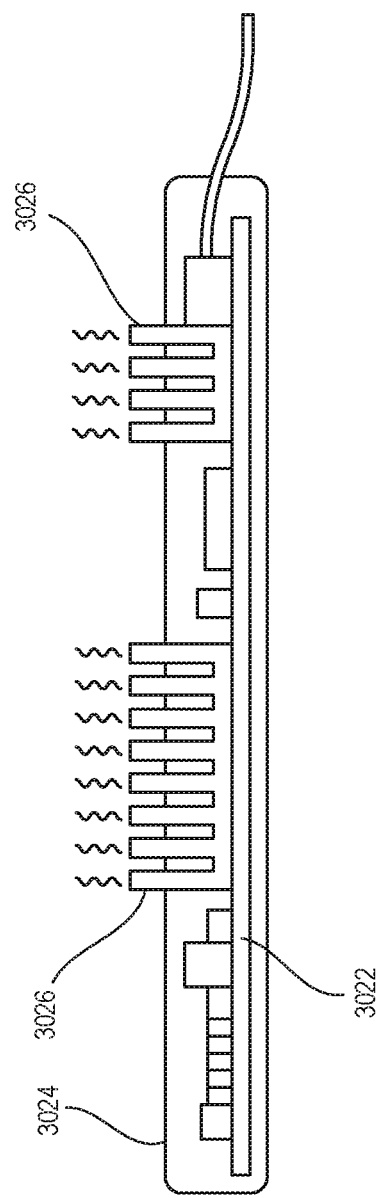
FIG. 33 is a schematic view of robotic surgical assembly circuitry comprising a heat sink assembly, in accordance with at least one aspect of the present disclosure.
Figure 34:
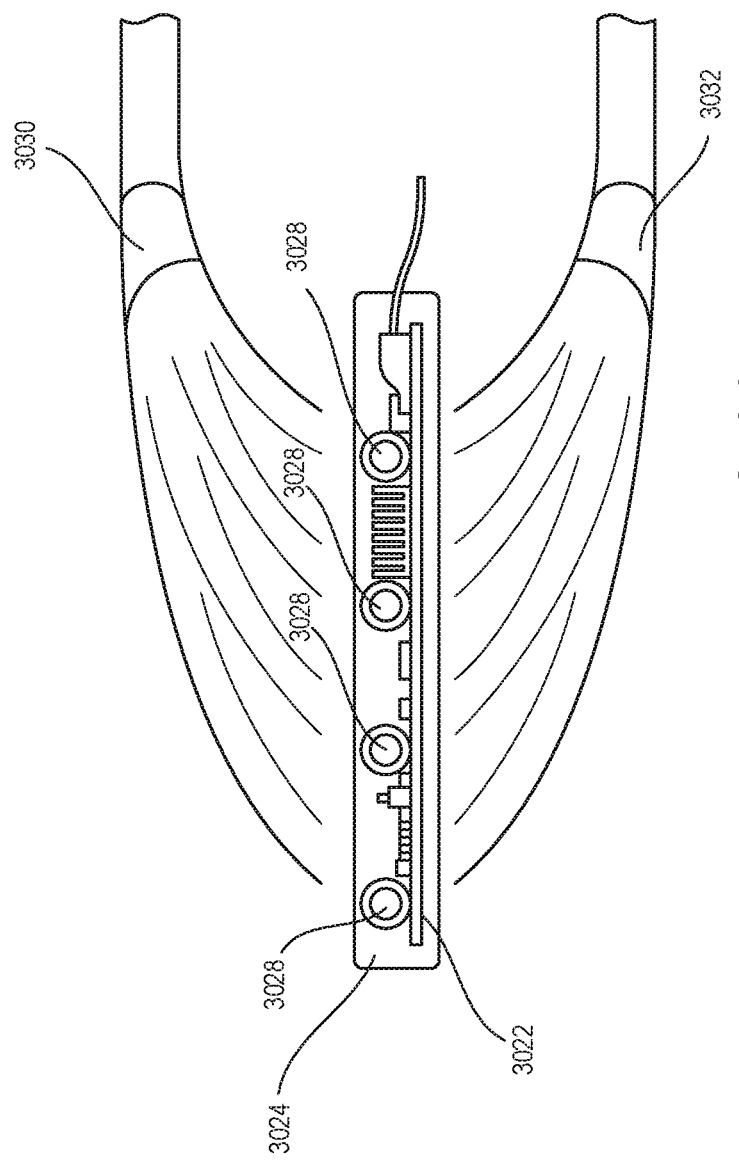
FIG. 34 is a schematic view of robotic surgical assembly circuitry comprising a fluid cooling system, in accordance with at least one aspect of the present disclosure.

In various aspects, contamination of the surgical site, sterile field, and/or surgical theater by air-circulating cooling systems can be prevented by integrating thermal management elements within the electronics systems of the robotic surgical system 13000 and/or IDU 3002 that are sealed and/or isolated from the sterile field. Referring now to FIGS. 33 and 34, the electronics 3022 of the IDU 3002 (e.g., the integrated circuit 41120 in FIG. 26) can be fluidically sealed to prevent contamination and/or exposure to particulates from air and/or fluid circulated through the IDU 3002 for cooling. In various aspects, a sealing layer 3024 can thus be defined about the IDU electronics 3022. The sealing layer 3024 can include, for example, epoxy, acrylate, ultravioletcurable adhesive, polyurethane, polysulfide (or other solidifying resin), silicone, fluorosilicone (or other suitable polymers or elastomers), or combinations thereof. The materials of the sealing layer 3024 can be deposited via potting or encapsulation techniques, for example. Sealing the electronics 3022 can inhibit cooling and/or exacerbate thermal buildup; therefore, the IDU 3002 can include various cooling elements to mitigate these deleterious effects.

As one example, FIG. 33 illustrates an aspect including heat sink fins 3026 in thermal communication with the electronics 3022 and extending through the sealing layer 3024 for dispersing heat generated from the electronics 3022. The heat radiated by the fins can then be dispersed from the IDU 3002 via air- or fluid-based cooling systems, as described above. In one aspect, the illustrated assembly could be fabricated by adhesively bonding the heat sink fins 3026 to the electronics 3022 via a thermally conductive material (in order to promote thermal communication between the electronics 3022 and the heat sink fins 3026) and the sealing layer 3024 can then be applied thereover to cover the electronics 3022 to create a fluid and air barrier, while still enabling the heat sink fins 3026 to be placed into an air- or fluid-based circulation path to allow for thermal transfer from the electronics 3022. In one aspect, the heat sink fins 3026 can be positioned at or adjacent to a particular structure or set of structures for which additional cooling is desired. In yet another aspect, the heat sink fins 3026 can be positioned at or adjacent to components of the IDU 3002 other than or in addition to the electronics 3022. For example, the heat sink fins 3026 could be integrated into the housing of the motor pack 40050 such that they are in thermal communication with the motors 41052, 41054, 41056, 41056 (FIG. 27), or other components of the motor assembly 41114 (FIG. 26).

As another example, FIG. 34 illustrates as aspect including one or more conduits 3028 extending through the sealing layer 3024 and in thermal communication with the electronics 3022. The conduits 3028 can be part of the circulation path of the cooling system and thus be fed cooling fluid from an inlet 3030 (e.g., coupled to the first tube 3012a) and remove the heated fluid via an outlet 3032 (e.g., coupled to the second tube 3012b). The conduits 3028 can extend through the sealing layer 3024 such that at least a portion of the walls of the conduits 3028 are in contact or thermal communication with the electronics 3022. Accordingly, as the cooling fluid travels through the conduits 3028, thermal energy is transferred from the electronics 3022 to the fluid, which is then removed from the IDU 3002 via the outlet 3032. In one aspect, a cleaning solution can be introduced through the conduits 3028 to clean and sterilize the air or fluid circulation path of the cooling system, without contacting the electronics 3022, motor assembly 41114, and/or other components of the IDU 3002.

In any of the aspects described above where the cooling systems include air or fluid circulated through the IDU 3002, the cooling systems can additionally include pumps, blowers, tubing, and other components necessary for driving the air or fluid through the circulation path. The pumps, blowers, and other such components can be located locally with respect to the robotic arm 13120 or positioned remotely therefrom.

As another example, a Peltier cooling element could be integrated into the sealing layer 3024. In one aspect, the Peltier cooling element could be positioned in proximity to a critical structure within the IDU 3002 for which it was especially desirable or difficult (e.g., due to engineering constraints) to cool. Thus, the Peltier cooling element could be used to extract heat from the critical structure and transfer the heat to areas, either within the IDU 3002 and/or outside of the IDU 3002, with a higher convective heat transfer rate than the area at or around the critical structure.

Figure 36:
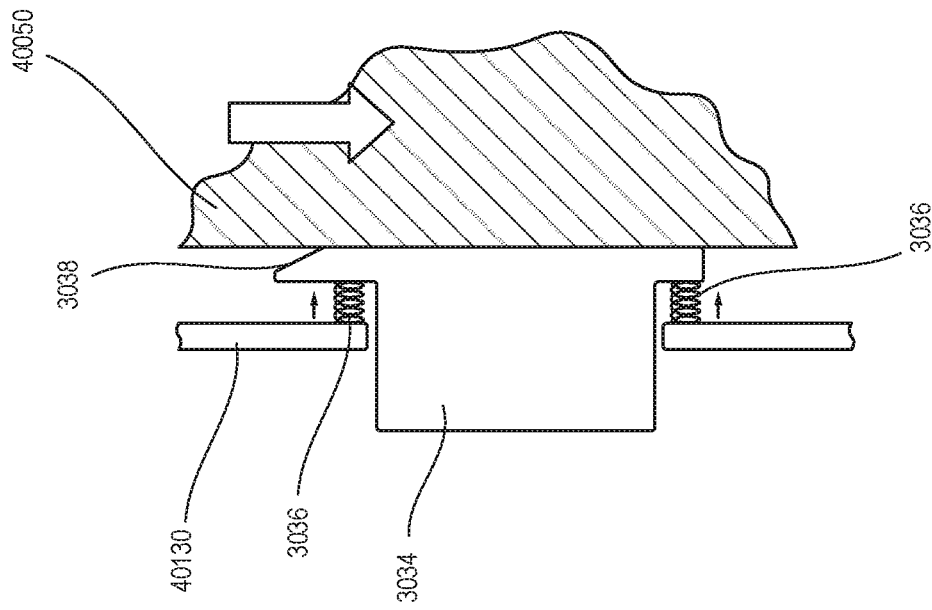
FIG. 36 is a sectional view of the instrument drive unit and heat sink assembly of FIG. 35, in accordance with at least one aspect of the present disclosure.
Figure 35:
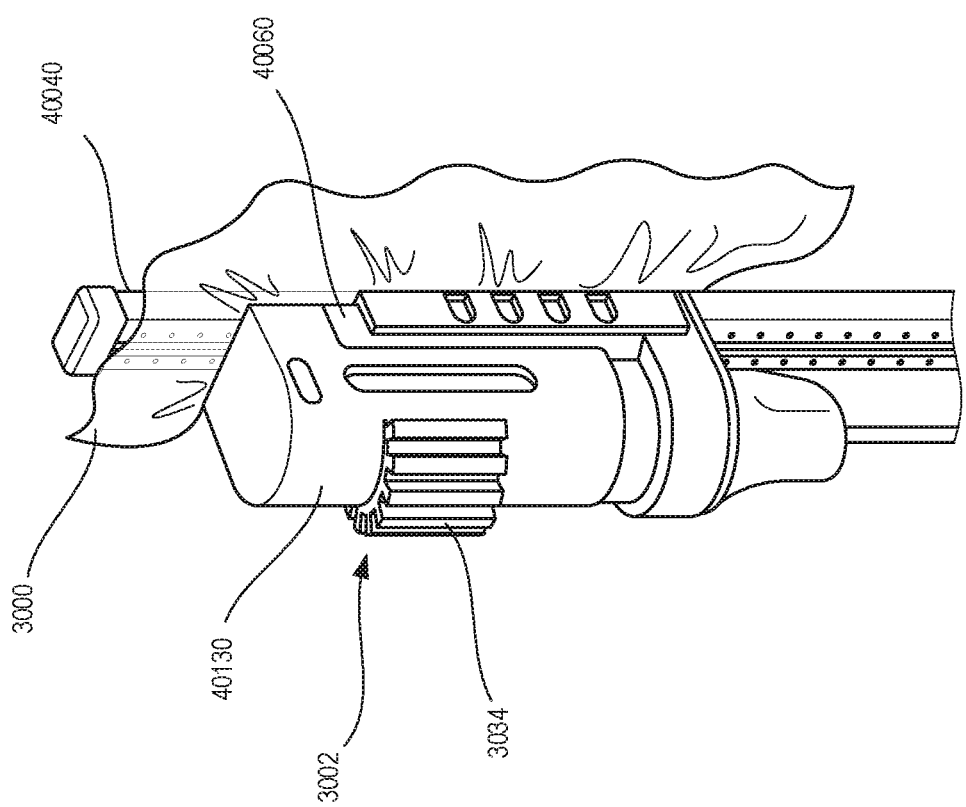
FIG. 35 is a perspective view of an instrument drive unit comprising a heat sink assembly, in accordance with at least one aspect of the present disclosure.

In other aspects, cooling systems for the IDU 3002 can be integrated into the sterile barrier components of the robotic surgical assembly 40100 for cooling the nonsterile components housed thereby. For example, in an aspect illustrated in FIGS. 35 and 36 the sterile barrier housing 40130 configured to receive a motor pack 40050 can include one or more heat sink fins 3034 that extend through the wall of the sterile barrier housing 40130 and contact the motor pack 40050 (when the motor pack 40050 is positioned therein) for dispersing heat generated by the motor pack 40050. In one aspect, the heat sink fins 3034 can further be biased towards the interior of the sterile barrier housing 40130 via, for example, springs 3036. The biasing of the heat sink fins 3034 ensures that they physically contact, and are thus in thermal communication with, the motor pack 40050 to maintain heat conduction from the motor pack 40050 to the heat sink fins 3034. The portion of the heat sink fins 3034 interior to the sterile barrier housing 40130 can further include a chamfered edge 3038 in order to slidably direct the motor pack 40050 into position within the sterile barrier housing 40130 as the motor pack 40050 is received thereby. Due to the physical contact between the heat sink fins 3034 and the motor pack 40050, the heat sink fins 3034 absorb heat generated by the motor pack 40050 and then convectively disperse the absorb heat into the surrounding environment (e.g., the surgical theater) to cool the motor pack 40050 and the IDU 3002 as a whole.

Sterile Drape

As described above, a sterile drape 3000 may be utilized in conjunction with the robotic arm 13120 and/or robotic surgical assembly 40100 (FIG. 26) to establish and maintain a sterile barrier between the patient 13013 (FIG. 4), the surgical field, and/or the robotic surgical system 13000 (FIG. 4). The sterile drape 3000 can be deployable in a variety of different manners for enshrouding the robotic arm 13120 and/or various components of the robotic surgical assembly 40100. Furthermore, the sterile drape 3000 can include a variety of different materials and structures for communicating information to the surgical staff, such as whether the sterile drape 3000 has suffered a breach (due to, e.g., a puncture or abrasion).

In one aspect illustrated in FIG. 37, a sterile drape 3000 can include one or more first connectors 3040 positioned along a first edge 3039 and one or more second connectors 3042, which are configured to removably engage the first connectors 3040, positioned along an opposing second edge 3041. The first connectors 3040 can include male connectors and the second connectors 3042 can include corresponding female connectors, or vice versa, for example. The first connectors 3040 and the second connectors 3042 can be arranged such that, when they are joined together, the sterile drape 3000 can form a generally tubular structure that is shaped and dimensioned to enshroud a robotic arm 13120 and/or other component(s) of the robotic surgical assembly 40100. The removable connectors 3040, 3042 can thereby allow the sterile drape 3000 to be secured about the robotic arm 13120 and/or robotic surgical assembly 40100 after the sterile components of the robotic surgical assembly 40100 (i.e., the sterile barrier housing 40130 for the motor pack 40050 and the sterile shell or barrier 40060 for the carriage 40042) are secured in place. The connectors 3040, 3042 can include a variety of different types and configurations of connectors or closure elements. For example, in the aspect illustrated in FIG. 38A, the connectors 3040, 3042 can define a single, inter-meshable closure positioned longitudinally along the edges 3039, 3041 of the sterile drape 3000 that is joinable in the manner of a zip fastener. As another example, in the aspect illustrated in FIG. 38A, the connectors 3040, 3042 can define corresponding male and female snap features that are positioned at discrete locations along the edges 3039, 3041 of the sterile drape 3000.

In one aspect, the sterile drape 3000 can further include an adhesive layer positioned along at last one of the edges 3039, 3041 of the sterile drape 3000. In operation, the adhesive layer could be exposed and then adhered over the connectors 3040, 3042 to provide additional securement to the line of connection of the sterile drape 3000. In another aspect, the sterile drape 3000 can further include protuberances or grips located at or adjacent to the connectors 3040, 3042 in order to assist users in bringing the opposing edges 3039, 3041 of the sterile drape 3000 together and aligning the respective connectors 3040, 3042 while maintaining sterile technique.

In one aspect, the sterile drape 3000 can include a plurality of interlocking segments that are detachably connectable together to conform to a robotic arm 13120. Such combinations of interlocking segments can allow a robotic arm 13120 to be progressively barriered off, for example. For example, FIGS. 39A and 39B illustrate a sterile barrier 3000 that includes a first segment 3000a, a second segment 3000b, a third segment 3000c, and a fourth segment 3000d that are detachably connectable together at connection points 3044. Each of the segments 3000a, 3000b, 3000c, 3000d of the sterile drape 3000 can be dimensioned or otherwise configured to conform to a specific portion or component of the robotic arm assembly. Further, although the sterile drape 3000 is illustrated as including four segments 3000a, 3000b, 3000c, 3000d in FIGS. 39A-39C, this is simply for illustrative purposes and the sterile drape 3000 can, in various aspects, have any number of segments 3000a, 3000b, 3000c, 3000d. In one aspect, the corresponding segments can be connected both to each other and the robotic arm 13120 at the connection points 3044. For example, the robotic arm 13120 can include a first connector 3046 (e.g., a male connector) that is configured to engage with a corresponding second connector 3048 (e.g., a female connector) disposed on one of the sterile drape segments (which is the second segment 3000b in the detail view shown in FIG. 39B). That sterile drape segment can then also include a third connector 3050 (e.g., a male connector) that is configured to engage with a corresponding fourth connector (e.g., a female connector) disposed on the corresponding sterile drape segment (which is the first segment 3000a in the detail view shown in FIG. 39B). Further, the sterile drape segments can be constructed in different manners. For example, some of the sterile drape segments could include tubular structures (e.g., the first segment 3000a and the third segment 3000b), whereas other sterile drape segments could include flat structures that are folded over and sealed together (e.g., the second segment 3000b could include a flat segment that with opposing ends that are sealed around the Y-shaped junction between opposing members of the robotic arm 13120).

In other aspects, the sterile barrier 3000 can include segments having elastic sleeves at their the open ends, which enable a tight fit around the robotic arm 13120 in the regions where the sterile drape segments overlap and allow for attachment to hard plastic barrier component. The hard plastic barrier component(s) could include a circular groove that could serve as an attachment point for the elastic sleeve portion and would prevent slippage of the elastic sleeve with respect thereto. In still other aspects, the sterile barrier 3000 can include segments having accordion-like folds at joint and elbow locations, which can provide flexibility to the sterile drape 3000 without stretching or potentially damaging the sterile drape 3000.

In one aspect, one or more sterile drape modules can be detachably connected to the sterile drape 3000 for supplementing or augmenting the sterile drape 3000. For example, FIGS. 39A and 39C illustrate a module 3054 including a blower 3056 that is configured to transport air from a first location (e.g., within the sterile barrier 3000) to a second location via an outlet 3058. The module 3054 can be configured to facilitate air movement through the sterile barrier 3000 for cooling of the robotic surgical assembly, for example.

The sterile barrier 3000 can include a variety of different modules and attachment points for facilitating the attachment of devices thereto. For example, in one aspect illustrated in FIG. 40, the sterile drape 43704 may be provided between a patient side cart (not shown), particularly over the manipulator arms 43140, and the surgical instrument (not shown) in order to create a sterile boundary between the sterile field, which may include a sterile adapter 43700 of the actuation interface assembly 43706 to which a sterile surgical instrument is attached, and the non-sterile patient side cart. The sterile adapter 43700 of the sterile drape 43704 can include actuation interface assemblies 43706 that are configured to engage with transmission mechanisms provided at a proximal end of the surgical instruments. The surgical instrument and the actuation interface assembly 43706 may be mechanically and electrically connected to be able to operate the instrument.

In one aspect illustrated in FIGS. 41A-41D, multiple sterile drapes 3000 can be provided as a set that are detachably connected to each other at their proximal ends 3066 via, for example, perforated edges, zip fasteners, and other connectors or lines of connection. Accordingly, users can deploy a sterile drape 3000 on a robotic arm 13120 by drawing one of sterile drapes 3000 from the set over the robotic arm 13120 and then detaching the deployed sterile drape 3000 from the remaining members of the set, as is shown in FIGS. 41B-41D. The sterile drape 3000 can further include a rip cord 3060 coupled to a line of connection 3062 extending longitudinally along the sterile drape 3000. The rip cord 3060 can be configured to release the line of connection 3062 (as shown in FIG. 41B), opening the sterile drape 3000 lengthwise and thereby allowing the sterile drape 3000 to be released from the robotic arm 13120 on which it is deployed (as shown in FIG. 41C) in a convenient manner. Thereafter, a replacement sterile drape 3000 can be deployed along the robotic arm 13120 (as shown in FIG. 41D).

In one aspect illustrated in FIGS. 42A-42C, the sterile drape 3000 can be deployable from a container 3064 or cartridge that is positionable at the base of the robotic arm 13120 or is integral to the robotic arm 13120. In this aspect, the container 3064 can house a set of sterile drapes 3000 that are detachably connected to each other at their proximal ends 3066 via, for example, perforated edges, zip fasteners, a rip cord (such as the rip cord 3060 described above), and other connectors or lines of connection. Accordingly, users can replace a sterile drape 3000 deployed on a robotic arm 13120 by withdrawing a new sterile drape 3000 from the container 3064 after or as the currently deployed sterile drape 3000 is removed, as is shown in FIGS. 42B and 42C.

The sterile drape 3000 can further include a rip cord 3060, as described above in connection with FIGS. 41A-41D.

In one aspect illustrated in FIGS. 43A and 43B, the sterile drape 3000 a skeleton 3068 configured to structurally reinforce the sterile drape 3000. The skeleton 3068 can include structures that are positioned along an interior surface, along an exterior surface, and/or positioned between layers of the sterile drape 3000. In the illustrated aspect, the skeleton 3068 includes a rigid or semi-rigid helical structure oriented coaxially with the sterile drape 3000. The helical structure can be circular, ellipsoidal, rectangular, or any other shape in cross-section that conforms to the profile of the robotic arm 13120 with which the sterile drape 3000 is to be utilized. The skeleton 3068 can be beneficial in order to, for example, make the sterile drape 3000 easier to snake around joints than sterile drapes 3000 lacking the skeleton 3068. Further, in aspects where the skeleton 3068 is utilized in conjunction with a segmented sterile barrier (e.g., such as the sterile barrier 3000 illustrated in FIG. 39A), the shape, structure, and/or configuration of the skeleton 3068 can be customized for the particular section of the robotic arm 13120 and/or robotic surgical assembly 40100 over which that section is to be deployed.

In one aspect illustrated in FIG. 44, the sterile barrier 3000 can include one or more joint sections 3070. The joint sections 3070 can be constructed from a material, have a particular arrangement or structure, or otherwise be configured to promote bending of the sterile drape 3000 at their locations as compared to the remaining portions of the sterile drape 3000. For example, the joint sections 3070 can define gaps or a lack of the presence of a skeleton 3068. Further, the joint sections 3070 can be positioned at regular or irregular intervals along the length of the sterile drape 3000, for example. In one aspect, the joint sections 3070 can be positioned at locations corresponding to the locations of the joints of the robotic arm 13120 for which the sterile drape 3000 is intended to be utilized, thereby allowing the sterile drape 3000 to closely conform to the arrangement of the arm sections of the robotic arm 13120.

Figure 45B:
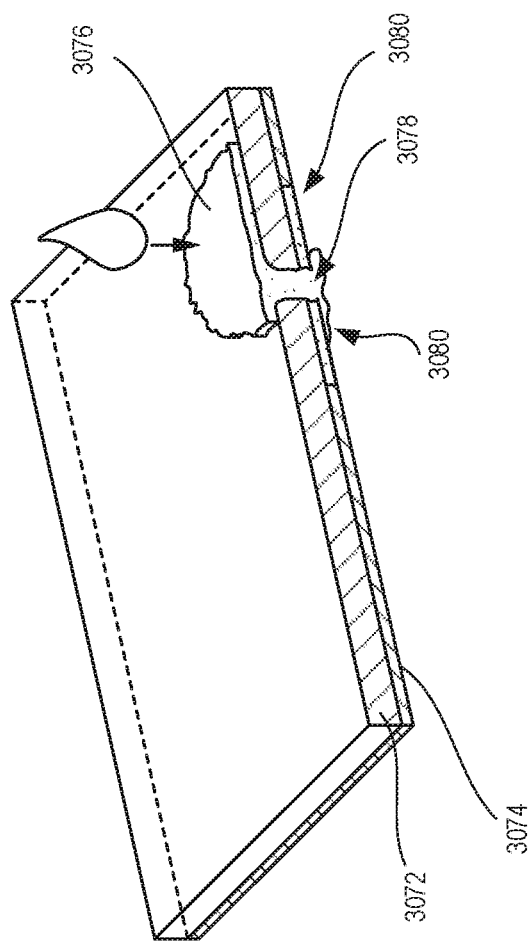
FIG. 45B is a perspective view of the sterile drape of FIG. 45A positioned on a robotic arm, where the sterile drape has been breached, in accordance with at least one aspect of the present disclosure.
Figure 45A:
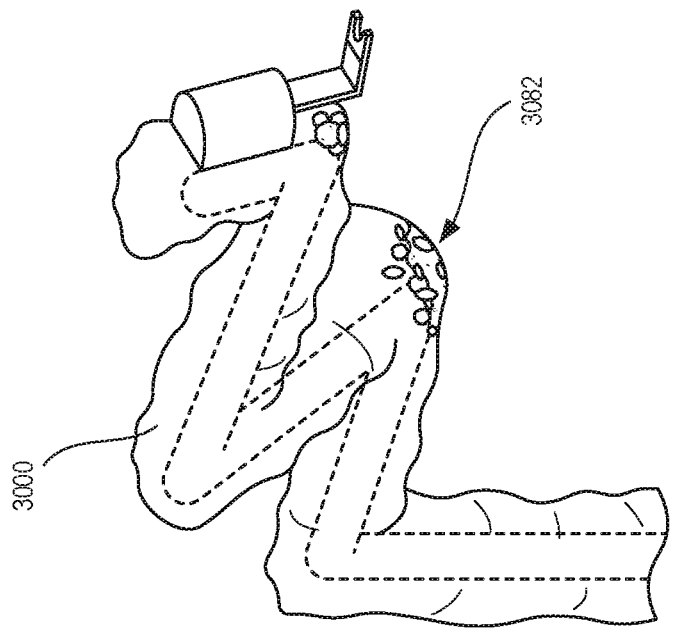
FIG. 45A is a detail view of a sterile drape comprising a moisture-detecting layer, in accordance with at least one aspect of the present disclosure.
Figure 46A:
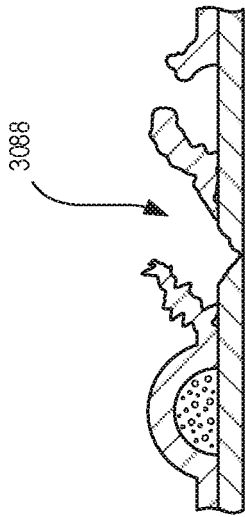
FIGS. 46A-46B are detail views of a sterile drape comprising pressurized air pockets, in accordance with at least one aspect of the present disclosure.
Figure 46B:
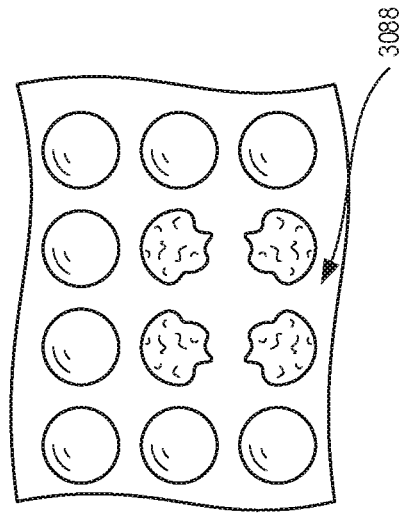
Figure 46C:
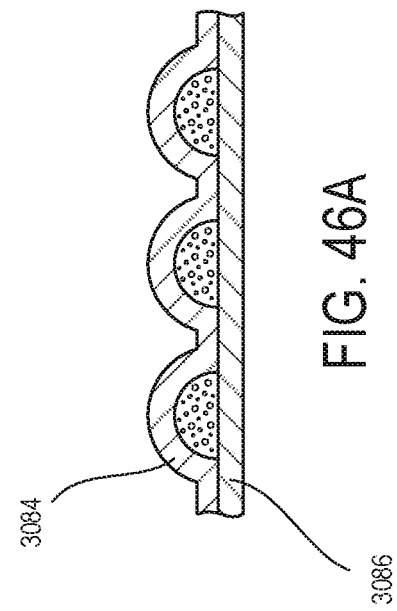
FIGS. 46C-46D are detail views of the sterile drape of FIGS. 46A-46B, where the sterile drape has been breached, in accordance with at least one aspect of the present disclosure.
Figure 46D:
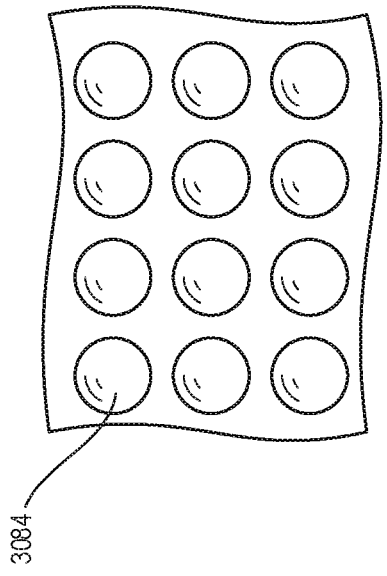

In one aspect illustrated in FIGS. 45A and 45B, the sterile barrier 3000 can be configured to indicate when a liquid 3076 (e.g., body fluid) has breached the sterile barrier 3000. In the illustrated example, the sterile barrier 3000 includes a first or exterior layer 3072 and a second or interior layer 3074. The exterior layer 3072 can include a clear or translucent material. The interior layer 3074 can be configured to change color upon contact with moisture. For example, the interior layer 3074 can include a moisture-detecting dye. Accordingly, when a breach 3078 has formed in at least the exterior layer 3072 and liquid 3076 has come in contact with the interior layer 3074, the portions 3080 of the interior layer 3074 coming in contact with the liquid 3076 are configured to change color. Therefore, the sterile barrier 3000 creates a visual indication 3082 that the sterile barrier 3000 has been breached and potentially contaminated by a liquid 3076 so that users can take corrective action (e.g., sealing the breach or having the robotic arm 13120 and/or other components of the robotic surgical system 13000 cleaned).

In one aspect illustrated in FIGS. 46A-46D, the sterile barrier 3000 can be configured to visually indicate when a breach 3088 has occurred in the sterile barrier 3000 or the surface of the sterile barrier 3000 has otherwise been physically disturbed. In the illustrated example, the sterile barrier 3000 includes a plurality of air- or fluid-filled pockets 3084 positioned along a surface 3086 of the sterile barrier 3000. The pockets 3084 can include, for example, regularly spaced, protruding, air-filled hemispheres. Accordingly, when a breach 3088 has formed in the sterile barrier 3000, the pockets 3084 deflate or collapse and thereby create a visual indication that the sterile barrier 300 has been breached so that users can take corrective action.

Figure 47C:
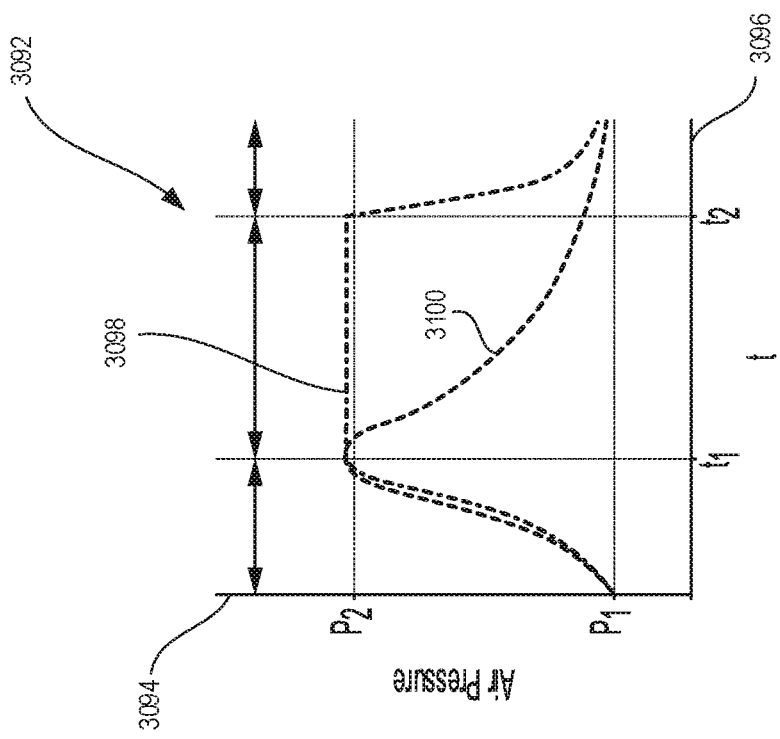
FIG. 47C is a graph of sterile drape air pressure verse time for breached and non-breached sterile drapes, in accordance with at least one aspect of the present disclosure.
Figure 47B:
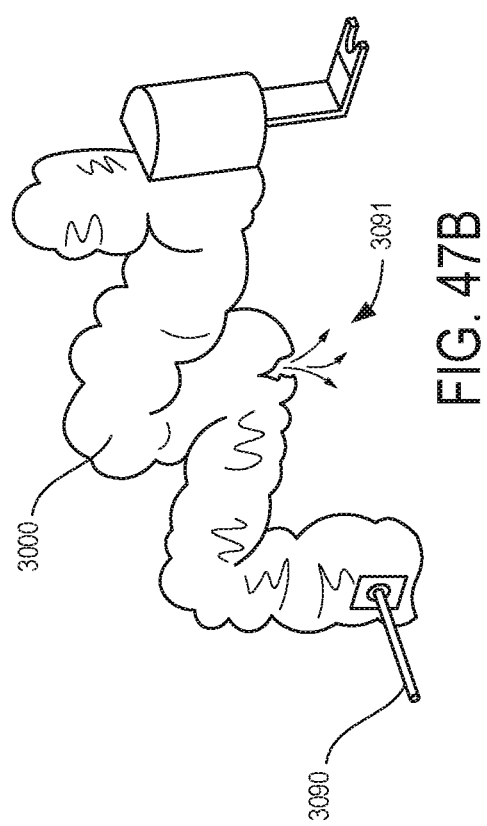
FIG. 47B is a perspective view of the sterile drape of FIG. 47A, where the sterile drape has been breached, in accordance with at least one aspect of the present disclosure.
Figure 47A:
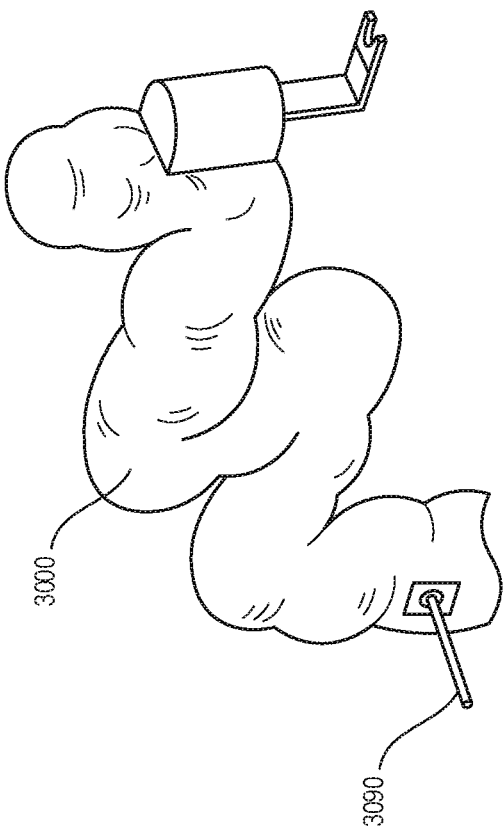
FIG. 47A is a perspective view of a pressurized sterile drape positioned on a robotic arm, in accordance with at least one aspect of the present disclosure.

In one aspect illustrated in FIGS. 47A-47C, the sterile barrier 3000 can be configured to be pressurized or inflated from an air source 3090 in order to indicate when a breach 3091 has occurred in the sterile barrier 3000. In the illustrated example, the sterile barrier 3000 can be configured to be airtight (or substantially airtight) when deployed on a robotic arm 13120 and can be pressurized via an air source 3090 that is fluidically couplable to the sterile barrier 3000. In various aspects, the air source 3090, sterile barrier 3000, robotic arm 13120, and/or another component of the robotic surgical system 13000 can include an air pressure sensor for sensing the internal air pressure of the sterile barrier 3000. Accordingly, when a breach 3091 has formed in the sterile barrier 3000, the sterile barrier 3000 can be depressurized and at least partially deflate, as illustrated in FIG. 47B. The robotic surgical system 13000 can be configured to sense this depressurization based on the sensed air pressure profile of the sterile barrier. In one aspect, the control device 13004 (FIG. 4) can be communicably connected to the air pressure sensor for receiving air pressure data therefrom. For example, FIG. 47C illustrates a prophetic graph 3092 where the vertical axis 3094 represents air pressure and the horizontal axis 3096 represents time. A first line 3098 indicates a surgical procedure where the sterile barrier 3000 was inflated from an initial pressure $P_1$ until it reached an operating pressure $P_2$ at $t_1$. As can be seen, the first line 3098 maintains a flat profile until the sterile barrier 3000 begins being deflated at $t_2$ (which can represent the completion of the surgical procedure, for example). Therefore, it can be determined that the sterile barrier 3000 did not suffer a breach during the surgical procedure. Conversely, a second line 3100 indicates a surgical procedure where the sterile barrier 3000 was inflated to an operating pressure $P_2$, but then suffered a breach at a point after $t_1$, resulting in the air pressure of the sterile barrier 3000 decreasing prematurely. Therefore, it can be determined that the sterile barrier 3000 did suffer a breach 3091 during the surgical procedure. In this way, monitoring the internal air pressure of a pressurized sterile barrier 3000 can be utilized to monitor for breaches 3091. Once a breach 3091 has been detected, the robotic surgical system 13000 (or a control device 13004 thereof) can be configured to provide a notification to the users (e.g., via a display device 13006 (FIG. 4)) or take some other corrective action (e.g., increase the air-flow rate provided by the air source 3090 to attempt to compensate for the breach 3091).

Figure 48B:
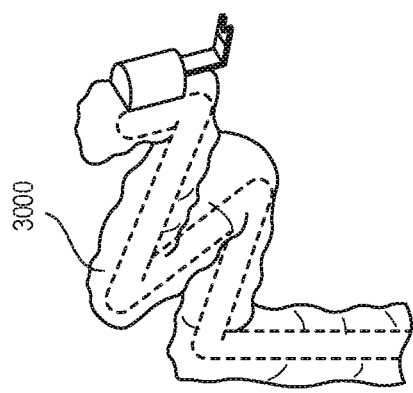
FIG. 48B is a perspective view of the sterile drape of FIG. 48A, where the sterile drape has not been experienced a temperature above a threshold temperature, in accordance with at least one aspect of the present disclosure.
Figure 48C:
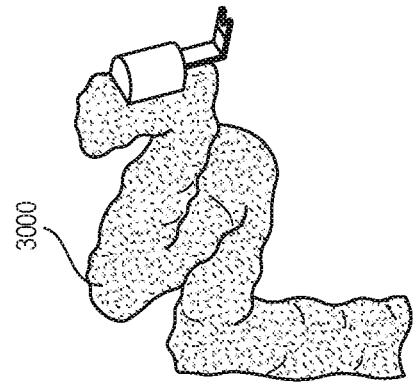
FIG. 48C is a perspective view of the sterile drape of FIG. 48A, where the sterile drape has been experienced a temperature above a threshold temperature, in accordance with at least one aspect of the present disclosure.
Figure 48A:
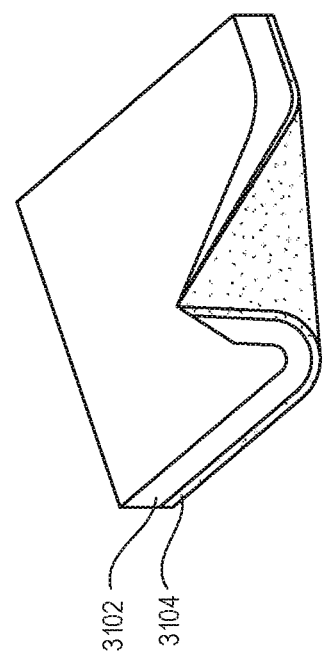
FIG. 48A is a detail view of a sterile drape comprising a color-changing layer, in accordance with at least one aspect of the present disclosure.
Figure 48D:
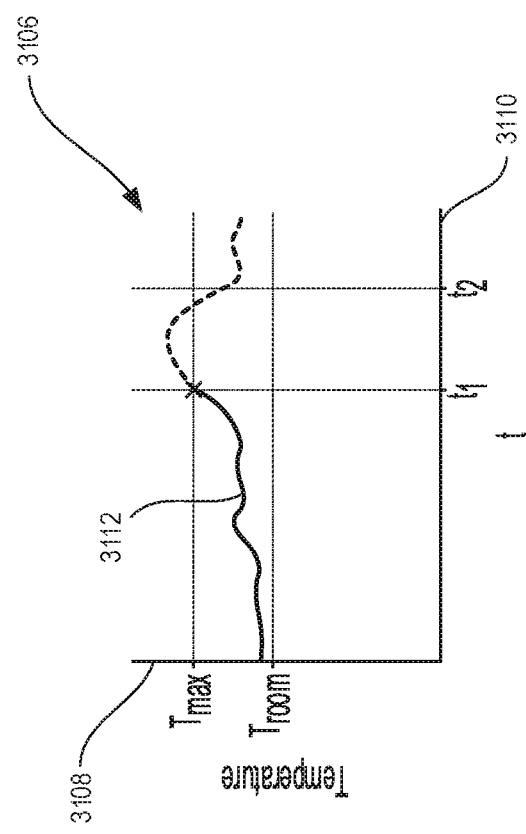
FIG. 48D is a graph of temperature verse time for a color-changing sterile drape, in accordance with at least one aspect of the present disclosure.

In one aspect illustrated in FIGS. 48A-48D, the sterile barrier 3000 can be configured to indicate whether a threshold temperature was reached or exceeded. In the illustrated example, the sterile barrier 3000 includes a first or exterior layer 3102 and a second or interior layer 3104. The exterior layer 3102 can include a clear or translucent material. The interior layer 3104 can be configured to change color upon reaching or exceeding a threshold temperature $T_{max}$. For example, the interior layer 3074 can include a thermosensitive or thermochromic dye that is configured to change color upon reaching the threshold temperature $T_{max}$. The thermochromic dye can be applied to the interior layer 3074 in the form of microcapsules, for example. In one aspect, the thermosensitive dye can be configured to permanently change color upon reaching the threshold temperature $T_{max}$ to visually alert users as to whether the sterile shield 3000 has ever been exposed to a temperature reaching the threshold temperature $T_{max}$. For example, FIG. 48D illustrates a prophetic graph 9106 where the vertical axis 3108 represents the temperature experienced by the sterile barrier 3000 and the horizontal axis 3110 represents time. A line 3112 indicates the temperature experienced by the sterile barrier 3000 during the course of a particular surgical procedure. At time $t_1$ the temperature reaches or exceeds the temperature threshold $T_{max}$, thereby causing the sterile barrier 3000 to transition from a first color (or translucent), as shown in FIG. 48B, to a second color, as shown in FIG. 48C. The color change can visually indicate that the sterile barrier 3000 has been exposed to temperatures outside of its acceptable operating range so that users can, for example, take corrective action.

In one aspect illustrated in FIGS. 49A-48C, the sterile barrier 3000 can be configured to self-heal breaches 3120. In the illustrated example, the sterile barrier 3000 includes a first or interior layer 3114, a third or exterior layer 3118, and a second layer 3116 sandwiched between the first and third layers 3114, 3118. The second layer 3116 can include a material that is configured to heal breaches 3120, such as a liquid or gel polymer that is configured to crosslink and solidify when exposed to air. Accordingly, when a breach 3120 has formed in at least one of the first or second layers 3114, 3118 of the sterile barrier 3000 (as shown in FIG. 49B), the material from the second layer 3116 advances into the space opened by the breach 3120, at which point it is exposed to air and forms a plug 3122 and thereby heals the breach 3120 (as shown in FIG. 49C). It can be useful for sterile barriers 3000 to include some type of self-healing mechanism in order to prevent or mitigate contamination of components enshrouded by the sterile barrier 3000 when a breach 3120 has occurred.

Figure 50:
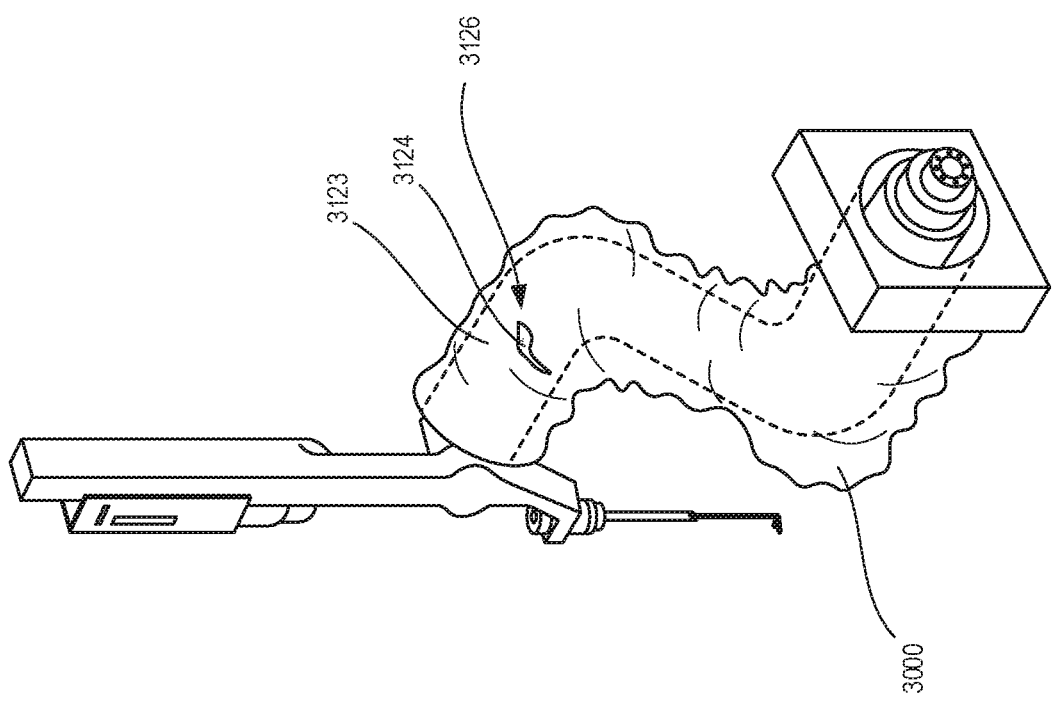
FIG. 50 is a perspective view of a sterile drape comprising a colored underlayer, in accordance with at least one aspect of the present disclosure.

In one aspect illustrated in FIG. 50, the sterile barrier 3000 can be configured to visually indicate when a breach 3126 has occurred in the sterile barrier 3000. In the illustrated example, the sterile barrier 3000 can include a first or exterior layer 3123 that is a first color and a second or interior layer 3124 that is a second color. The exterior layer 3123 can additionally be constructed from an opaque material such that the interior layer 3124 is not visible unless a breach 3126 is formed in the exterior layer 3123. Accordingly, when the sterile barrier 3000 suffers a breach 3126, the interior layer 3124, which is a different color from the exterior layer 3123, is revealed, visually indicating the presence of the breach 3126. In one aspect, the color of the interior layer 3124 can be selected such that it highly contrasts or is especially visible against the color of the exterior layer 3123.

Robotic Surgical Attachment Assemblies

Figure 51:
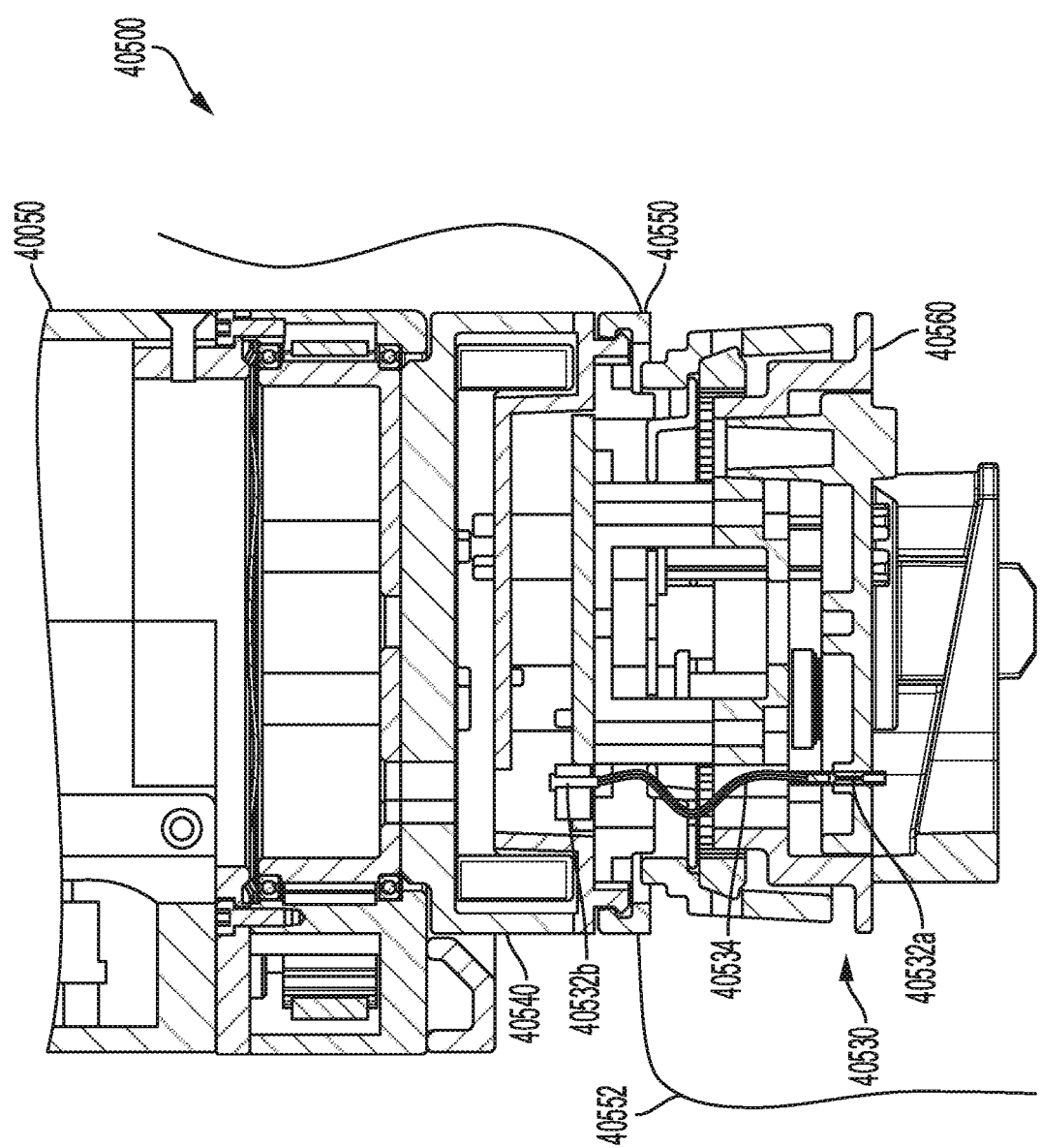
FIG. 51 is a sectional view of a portion of a robotic surgical assembly, in accordance with at least one aspect of the present disclosure.
Figure 52:
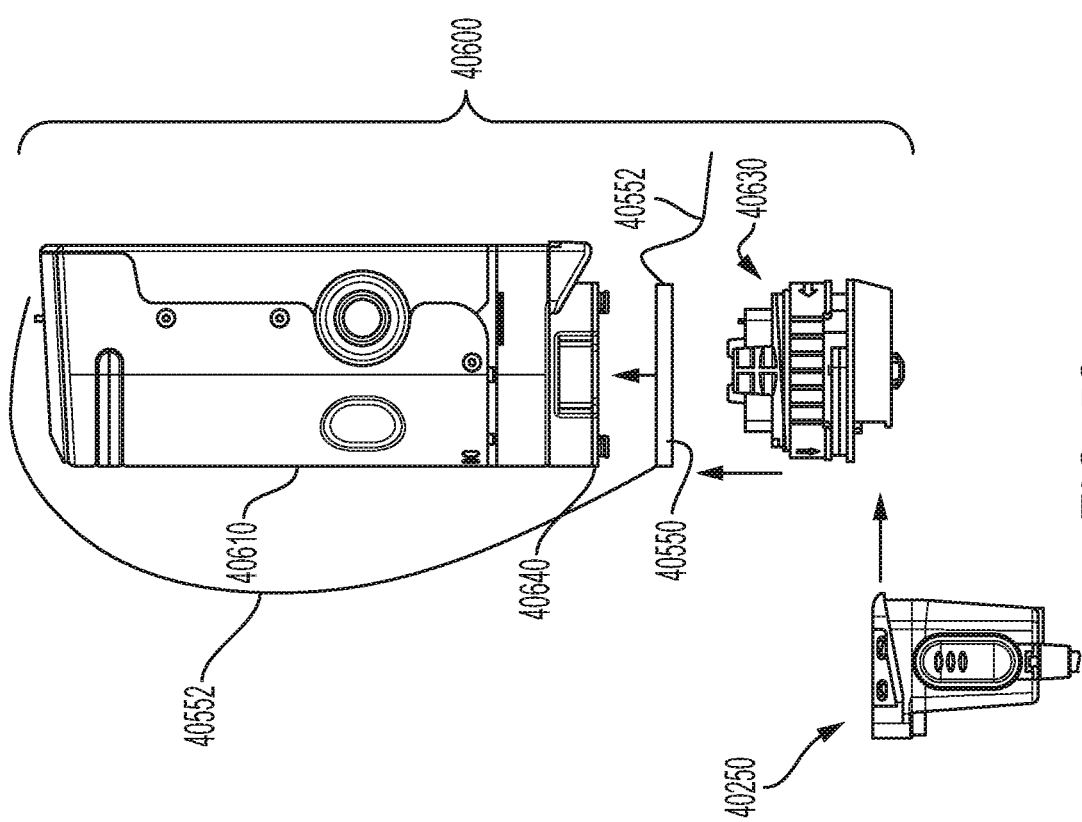
FIG. 52 is an exploded view of a robotic surgical assembly, in accordance with at least one aspect of the present disclosure.
Figure 53:
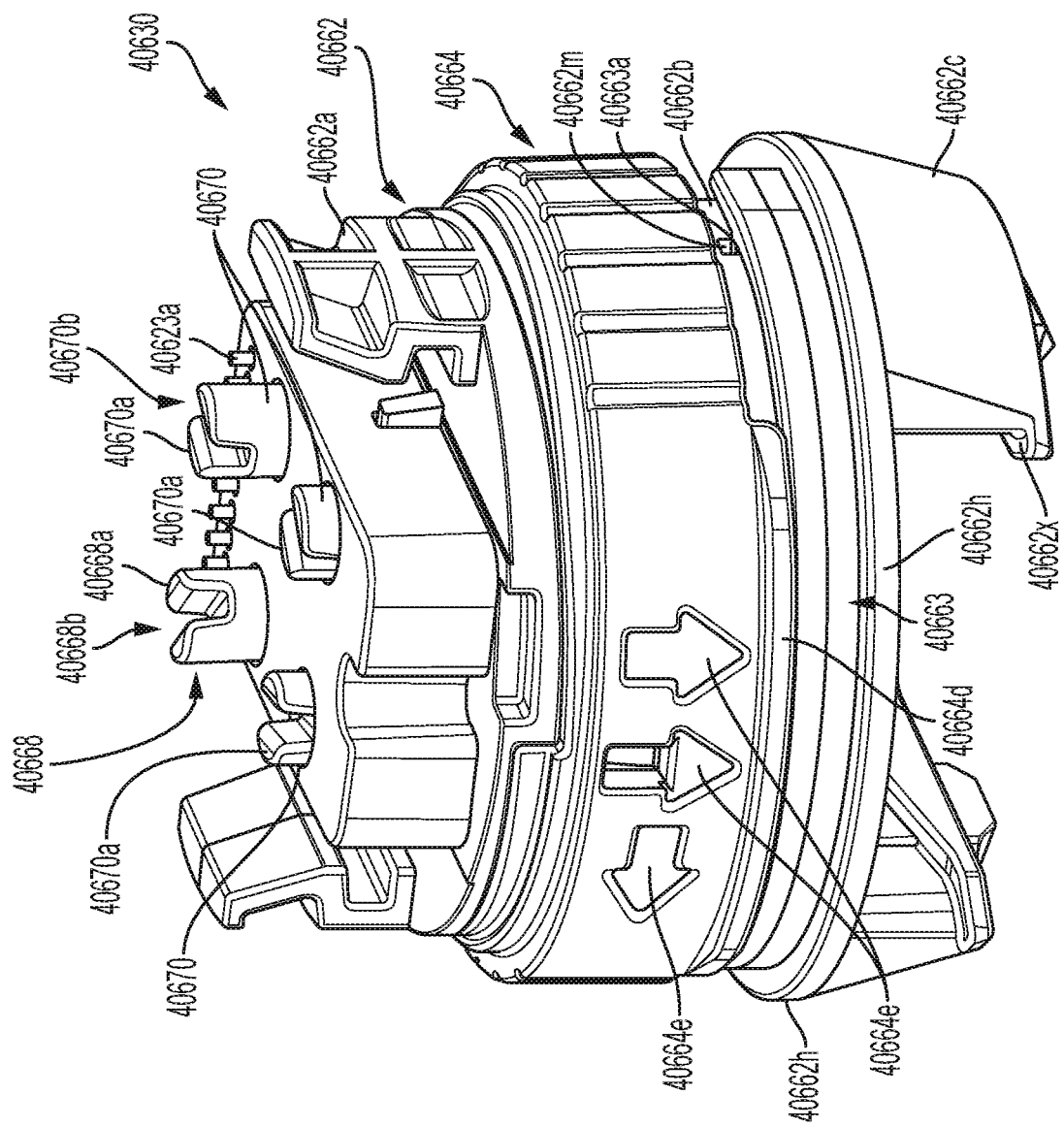
FIG. 53 is a perspective view of a sterile interface module of a robotic surgical assembly, in accordance with at least one aspect of the present disclosure.

Turning now to FIGS. 51-53, the robotic surgical assembly 43600 of the robotic surgical system 13000 (FIG. 4) includes an instrument drive unit or housing 43610 supporting a motor assembly or motor pack 43050, as described above under the heading ROBOTIC SURGICAL ASSEMBLY. The housing 43610 of the robotic surgical assembly 43600 includes a connector assembly 43540.

A collar assembly or sterile interface module 43630 is provided for selectively interconnecting the robotic surgical assembly 43600 and an electromechanical surgical instruments 43250. In general, the sterile interface module 43630 functions to provide an interface between the instrument drive unit or housing 43610 and an electromechanical surgical instrument 43250. This sterile interface module 43250 advantageously maintains sterility, provides a means to transmit electrical communication between the robotic surgical assembly 43600 and the electromechanical surgical instrument 43250, provides a means for transferring rotational force from the robotic surgical assembly 43600 to the electromechanical surgical instrument 43250 for performing a function with the electromechanical surgical instrument 43250, and/or provides a means to selectively attach/remove the electromechanical surgical instrument 43250 to the robotic surgical assembly 43600 (e.g., for rapid instrument exchange).

The collar assembly or sterile interface module 43630 includes electrical connectors 43532a, 43532b and an electrical ribbon 43534 coupled between the electrical connectors 43532a, 43532b to provide electrical communication between the robotic surgical assembly 43600 and any electromechanical surgical instrument, such as electromechanical surgical instrument 43250, coupled thereto.

Ring member 43550 is configured for rotatable attachment to a distal end of the connector assembly 43640 (e.g., via snap fit) of the IDU or housing 43610. The sterile drape 43552 can be arranged as desired about the housing 43610, the robotic surgical assembly 43600 and the robotic arms 13002, 13003 (FIG. 4) to provide a sterile barrier between the various aforementioned components and/or the surgical site/fluids and the electromechanical surgical instruments 43250, as is described above.

The first and second drive transfer assemblies 43668, 43670 of the sterile interface module 43630 include respective drive couplers 43668a, 43670a defining coupling ends 43668b, 43670b engageable with coupling ends 41052c, 41054c, 41056c, 41058c (FIG. 27) of respective motor couplers 41052b, 41054b, 41056b, 41058b (FIG. 27) of the motor assembly 41114 (FIG. 26) supported within the housing 43610. The first and second drive transfer assemblies 43668, 43670 further include transfer shafts (not shown) that extend to a respective instrument engagement end (e.g., a gear or the like with distally extending teeth) at a distal end thereof for transmitting drive motions from the motor assembly 41114 to the electromechanical surgical instrument 43250 for driving various functions thereof.

Additional detail regarding coupling arrangements for robotic surgical assemblies and/or IDUs can be found in U.S. International Patent Application No. PCT/US2017/033899, published as WO2017205308A1, titled ROBOTIC SURGICAL ASSEMBLIES, which is incorporated by reference herein in its entirety.

As can be seen, the surgical system 13000 includes a number of different connection points between components of the robotic surgical assembly 43600 and between the electromechanical surgical instrument 43250 and the robotic surgical assembly 43600. If any one of these components is not fully connected or seated to the corresponding component or components to which it is connectable, such incomplete connections can cause failures of the surgical system 13000 and unsafe operational conditions. Therefore, it can be desirable for various attachment assemblies of the robotic surgical assembly 43600 to promote connections between the components, only permit activation of the robotic arm 13120 or other powered components of the surgical system 13000 until all of the components are properly connected together, and otherwise ensure that each of the components and/or the electromechanical surgical instrument 43250 are fully connected together.

In one aspect, the various components of the robotic surgical assembly 43600 and/or surgical instrument 43250 can include connectors biased to resist connection between the corresponding connectable components (i.e., driving the components apart) up to a point at which the bias reverses, biasing the components into complete coupling between each other. For example, the aspect illustrated in FIGS. 54A-54D demonstrates a biased coupling arrangement between the sterile interface module 43630 and the surgical instrument 43250. In this example, the sterile interface module 43630 includes a ramped surface 2300 that is dimensioned to receive a corresponding ramped surface 2302 of the surgical instrument 43250. Further, the module ramped surface 2300 includes a biasing element 3204 and the instrument ramped surface 3202 includes a corresponding recess 3206 that is configured to receive and retain the biasing element 3204 therein when the surgical instrument 43250 is fully seated to the sterile interface module 43630. It should be noted that in other aspects, the positions of the biasing element 3204 and the recess 3206 can be interchanged with each other. Accordingly, as the instrument ramped surface 3202 begins to be slid into position relative to the module ramped surface 3200 (as shown in FIG. 54B), the biasing element 3204 is configured to bear against a portion of the instrument ramped surface 3202 and provide a physical resistance to the continued insertion of the instrument ramped surface 3202 (as shown in FIG. 54C). However, as the biasing element 3204 gives way under an increased load from the insertion of the instrument ramped surface 3202, the instrument ramped surface 3202 reaches a point at which it can be slid further past the module ramped surface 3200 without restriction from the biasing element 3204. At that point, the biasing element 3204 snaps into engagement with the recess 3206 and thereby securely holds the surgical instrument 43250 in firm engagement with the sterile interface module 43630 (as shown in FIG. 54D). In one aspect, the position at which the biasing element 3204 securely engages the recess 3206 of the surgical instrument 43250 can correspond to the position at which the module electrical contacts 3210 are aligned and communicatively coupled to the corresponding instrument electrical contacts 3212 to ensure proper data and signal transmission between the sterile interface module 43630 and the surgical instrument 43250. It should be noted that although this example depicts a biased coupling arrangement between the sterile interface module 43630 and the surgical instrument 43250, this example was simply for illustrative purposes and the above concepts apply equally to coupling arrangements between any other components of the robotic surgical assembly 43600.

In one aspect, the various components of the robotic surgical assembly 43600 and/or surgical instrument 43250 can include connectors having electronic or electrical lockouts for detecting when components are fully connected together. For example, the aspect illustrated in FIGS. 55A-55C demonstrates a biased coupling arrangement between the sterile interface module 43630 and the surgical instrument 43250. In this example, the surgical instrument 43250 includes a first electrical contact 3214 disposed at its module engagement end and the sterile interface module 43630 includes a second electrode contact 3216 positioned such that it physically contacts the first electrical contact 3214 only when the surgical instrument 43250 is fully seated to the sterile interface module 43630. In one aspect, one or more of the electrical contacts 3214, 3216 can be biased to make contact with the opposing electrical contact 3214, 3216. In another aspect, the electrical contacts 3214, 3216 can be oriented such that they are the last electrical connection that is made between the components being coupled together (in this case, the sterile interface module 43630 and the surgical instrument 43250) during the attachment process. Therefore, as soon as the electrical circuit between the electrical contacts 3214, 3216 is completed, the robotic surgical system 13000 can be assured that the surgical instrument 43250 is fully seated on the sterile interface module 43630. In one aspect, an ID chip or control circuit of the surgical instrument 43250 can be powered on by the contact between the electrical contacts 3214, 3216 and the control device 13004 of the robotic surgical system 13000 can be configured to transmit a query for response by the ID chip. Accordingly, once the control device 13004 receives a response to its query, the control device 13004 can be assured that the surgical instrument 43250 is fully seated on the sterile interface module 43630. The control device 13004 can thereafter permit the robotic surgical system 13000 to be fully activated or operated. In another aspect, the surgical instrument 43250 can include a control program and/or set of parameters defining how the surgical instrument 43250 is to be operated by the robotic surgical system 13000. The control program and/or set of parameters can be required for operation of the surgical instrument 43250, for example. Since transmission of the control program and/or set of parameters is/are required to operate the surgical instrument 43250 in this example, the control device 13004 can therefore prevent the surgical system 13000 from being activated or operated until the electrical circuit between the electrical contacts 3214, 3216 is completed. Once the control program and/or set of parameters is/are received, then the control device 13004 can customize the motor controllers for the surgical instrument 43250 as dictated by the control program and/or set of parameters and then permit the activation or operation of the robotic surgical system 13000. It should be noted that although this example depicts a lockout coupling arrangement between the sterile interface module 43630 and the surgical instrument 43250, this example was simply for illustrative purposes and the above concepts apply equally to coupling arrangements between any other components of the robotic surgical assembly 43600.

Figure 56:
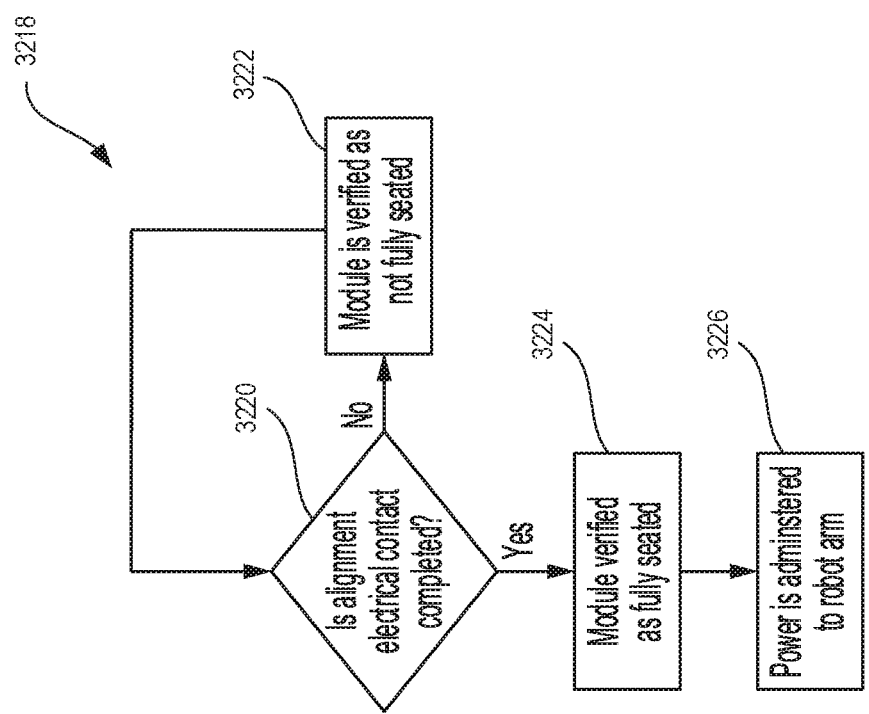
FIG. 56 is a logic flow diagram of a process for verifying that a surgical instrument is fully coupled to the robotic surgical assembly, in accordance with at least one aspect of the present disclosure.
Figure 55A:
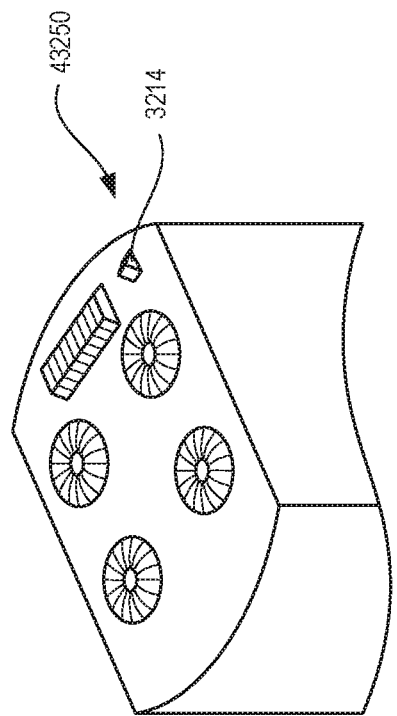
FIG. 55A is a perspective view of a proximal end of a surgical instrument comprising an alignment electrical contact, in accordance with at least one aspect of the present disclosure.
Figure 55B:
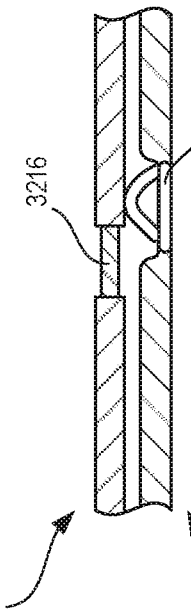
FIG. 55B is a sectional view of the surgical instrument of FIG. 55A uncoupled to a sterile interface module, in accordance with at least one aspect of the present disclosure.
Figure 55C:
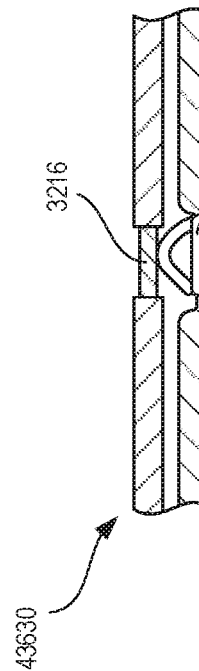
FIG. 55C is a sectional view of the surgical instrument of FIG. 55A coupled to a sterile interface module, in accordance with at least one aspect of the present disclosure.

A control circuit, such as the processor 15004 of the robotic surgical system 15000 illustrated in FIG. 22, can be configured to monitor an attachment assembly, such as the attachment assembly illustrated in FIGS. 55A-55C, for connecting two modules and control power to the robotic arm 13120 accordingly. The modules monitored by the control circuit can include any combination of components of the surgical robotic assembly 43600 and/or a surgical instrument 43250. For example, the processor 15004 can be configured to execute the process 3218 illustrated in FIG. 56. The process 3218 can be embodied as, for example, instructions stored in a memory 15006 coupled to the processor 15004 that, when executed by the processor 15004, cause the robotic surgical system 15000 to perform the process 3218.

Accordingly, the processor 15004 executing the process 3218 can determine whether alignment of the electrical contact(s) has been completed. For example, the processor 15004 can determine whether a circuit has been completed by opposing electrical contacts 3214, 3216 or whether a module (e.g., a surgical instrument 43250) is responsive to a query generated by the processor 15004, as described above. If the electrical contacts have not been aligned, then the process 3218 proceeds along the NO branch and the processor 15004 determines 3222 that the module is not fully seated and then continues monitoring for alignment of the electrical contacts. If the electrical contacts have been aligned, then the process 3218 proceeds along the YES branch and the processor 15004 determines 3224 that the module is fully seated. Accordingly, the processor 15004 then administers power 3226 to the robotic arm 13120 or otherwise permits the robotic arm 13120 to be operated by a user.

Robotic Surgical Detection Assemblies

As noted above with respect to FIGS. 51-53, the robotic surgical system 13000 includes a number of different connection points between components of the robotic surgical assembly 43600 and between the electromechanical surgical instrument 43250 and the robotic surgical assembly 43600. Each of these connection points represents a potential failure point if a component of the robotic surgical system 13000 or the surgical instrument 43250 is improperly connected or misaligned. Improperly connected or misaligned components can cause failures of the surgical system 13000 and unsafe operational conditions. Therefore, it can be desirable for the robotic surgical system 13000 to include detection systems to ensure proper connections and alignment of components. In response to detecting an improper or misaligned connection, the robotic surgical system 13000 can take various actions, including providing alerts or prompts to users or preventing the robotic surgical system 13000 (or components thereof) from being activated until all components or the relevant components of the robotic surgical system 13000 are properly connected together. For example, the robotic surgical system 13000 can prevent the motor pack 40050 from activating until the electromechanical surgical instrument 43250 is properly connected to the robotic surgical assembly 43600. The robotic surgical system 13000 can, in various aspects, be configured to detect coupling between corresponding components based upon detecting the presence of the components with respect to each other, detecting an actual coupling between components (e.g., via a continuity circuit, as described below), or a combination thereof. In one aspect, the robotic surgical system 13000 can control the components and/or provide alerts based on the detection of proper coupling between the components and knowledge of at least one more piece of information, such as firing status, cartridge authentication, cartridge identification, analysis for suitability of cartridge selection (e.g., based on situational awareness, as is described above), and so on.

In one aspect, the various components of the robotic surgical assembly 43600 and/or surgical instrument 43250 can include sensors configured to detect proximity and physical mating between corresponding components thereof. For example, in the aspect illustrated in FIGS. 57A and 57B, the sterile shell or barrier 40060 can include a sensor assembly configured to detect whether a corresponding detection element is within a threshold proximity to the sensor assembly (or a particular sensor thereof). In the illustrated aspect, the sterile shell 40060 comprises a set of four sensors 3230a, 3230b, 3230c, 3230d. This aspect further includes a corresponding detection element assembly that is configured to be detected by the sensor assembly. In the illustrated aspect, the IDU 43610 includes a first detection element 3228a, the ring member 43550 includes a second detection element 3228b, the sterile interface module 43630 includes a third detection element 3228c, and the surgical instrument 43250 includes a fourth detection element 3228d disposed thereon. The first sensor 3230a is configured to detect the first detection element 3228a, the second sensor 3230b is configured to detect the second detection element 3228b, and so on. It should be understood that the sensor assembly is not limited to this particular number and arrangement of the sensors 3230a, 3230b, 3230c, 3230d and/or detection elements 3228a, 3228b, 3228c, 3228d as this aspect is simply for purposes of illustrating the concepts discussed herein. The sensors 3230a, 3230b, 3230c, 3230d can include any type of sensor configured to detect the presence of a corresponding detection element within a threshold proximity thereof. For example, the sensors 3230a, 3230b, 3230c, 3230d can include Hall effect sensors and the detection elements 3228a, 3228b, 3228c, 3228d can include magnets. As another example, the sensors 3230a, 3230b, 3230c, 3230d can include RFID readers and the detection elements 3228a, 3228b, 3228c, 3228d can include (passive or active) RFID tags. In certain examples, the sensors may comprise proximity sensors (e.g., ultrasonic, IR, inductive, capacitive, photoelectric, Hall effect sensor, etc.). In certain examples the sensors comprise pressure sensors such as, for example, piezoresistive, capacitive, strain gauges, or any other suitable sensor type, including combinations thereof.

Figure 57B:
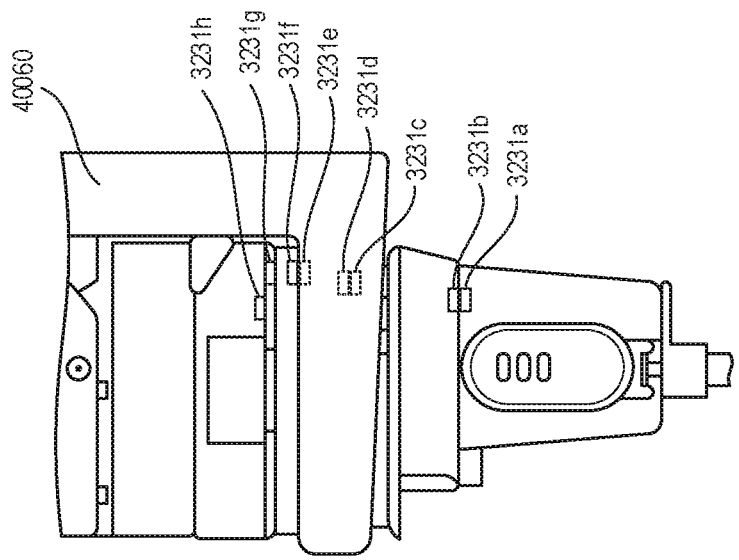
FIG. 57B is a side elevational view of a surgical instrument coupled to the robotic surgical assembly of FIG. 57A, in accordance with at least one aspect of the present disclosure.

Further, the components of the robotic surgical assembly 43600 and/or surgical instrument 43250 can include corresponding sets of electrical contacts 3231a-3231h are properly paired that are configured to detect proper mating and alignment between the components described above in connection with FIGS. 55A-55C. As illustrated in FIG. 57B, for example, proper pairing is achieved between the electrical contacts 3231a, 3231b, between the electrical contacts 3231c, 3231d, and between the electrical contacts 3231e, 3231f, but not the electrical contacts 3231g, 3231h. In various aspects, proper pairing, or lack of proper pairing, between corresponding ones of the electrical contacts 3231a-3231h can be detected by applying a voltage to electrical circuits that are formed by proper pairing of the electrical contacts 3231a-3231h, and detecting current through the electrical circuits. Other suitable techniques for detecting proper pairing of the electrical contacts 3231a-3231h are contemplated by the present disclosure.

In one aspect, the interfaces between the surgical instrument 43250 and/or the robotic surgical assembly 40100 can be temperature-dependent. For example, the electrical contacts 3231a-3231h can include conductive rings disposed on the surgical instrument 43250 and/or the components of the robotic surgical assembly 40100. The conductive rings can be separated by a gap, but electrically coupled with a shape memory alloy that is configured to operate within a certain operating temperature, for example. If the component on which the conductive rings are disposed is heated beyond the operating temperature of the shape memory alloy, the shape memory alloy changes shape, thereby breaking the electrical coupling between the components and disengaging the components from each other.

In one aspect, the electrical contacts 3231a-3231h can include a series of springs configured to contact the corresponding components of the robotic surgical assembly 40100 and/or the surgical instrument 43250 and inductance can be measured on the springs to determine proper coupling of the components. In particular, when the components are properly coupled, the components can compresses the springs, thereby changing the inductance, which can be measured by a control circuit coupled to the electrical contacts 3231a-3231h. Accordingly, the control circuit can compare the change in inductance between the various springs of the electrical contacts 3231a-3231h and then control could various components of the robotic surgical system 13000 based on whether an inductance change for a spring or set of springs differs from the average of the springs and/or a baseline or threshold change in value. For example, the control circuit could determine or measure the inductance associated with a given spring for an electrical contact, compare the determined inductance to a threshold, and then enable or disable the motor pack 40050 according to the comparison between the determined inductance and the threshold. In this way, the springs could serve as switches to enable or disable the motor pack 40050.

Figure 57A:
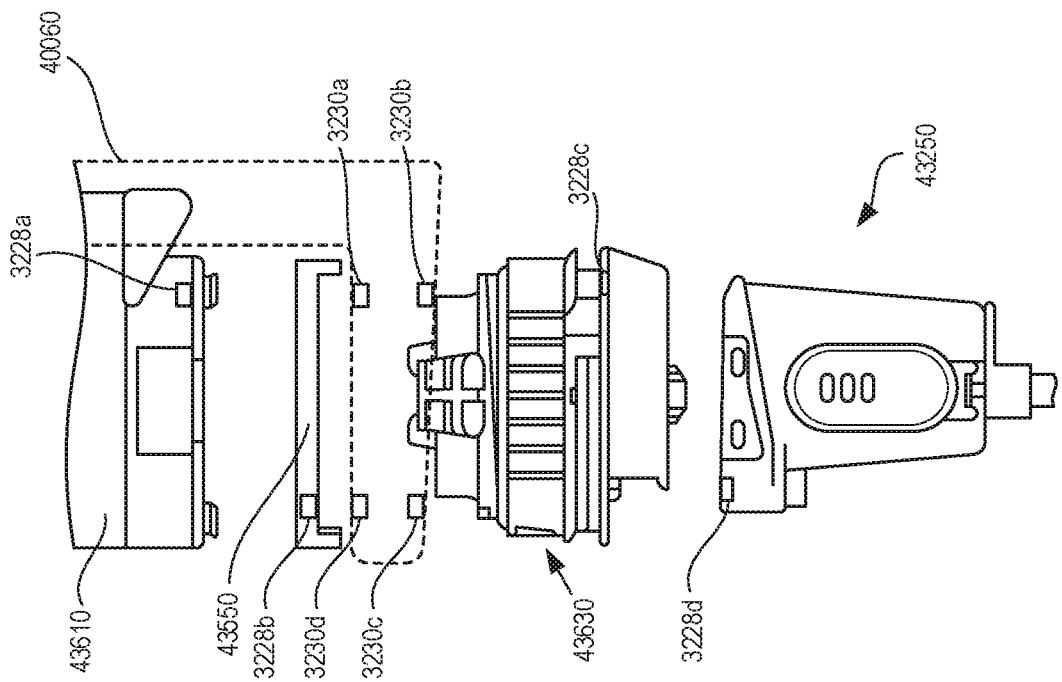
FIG. 57A is an exploded view of a robotic surgical assembly and surgical instrument comprising coupling sensors, in accordance with at least one aspect of the present disclosure.
Figure 58:
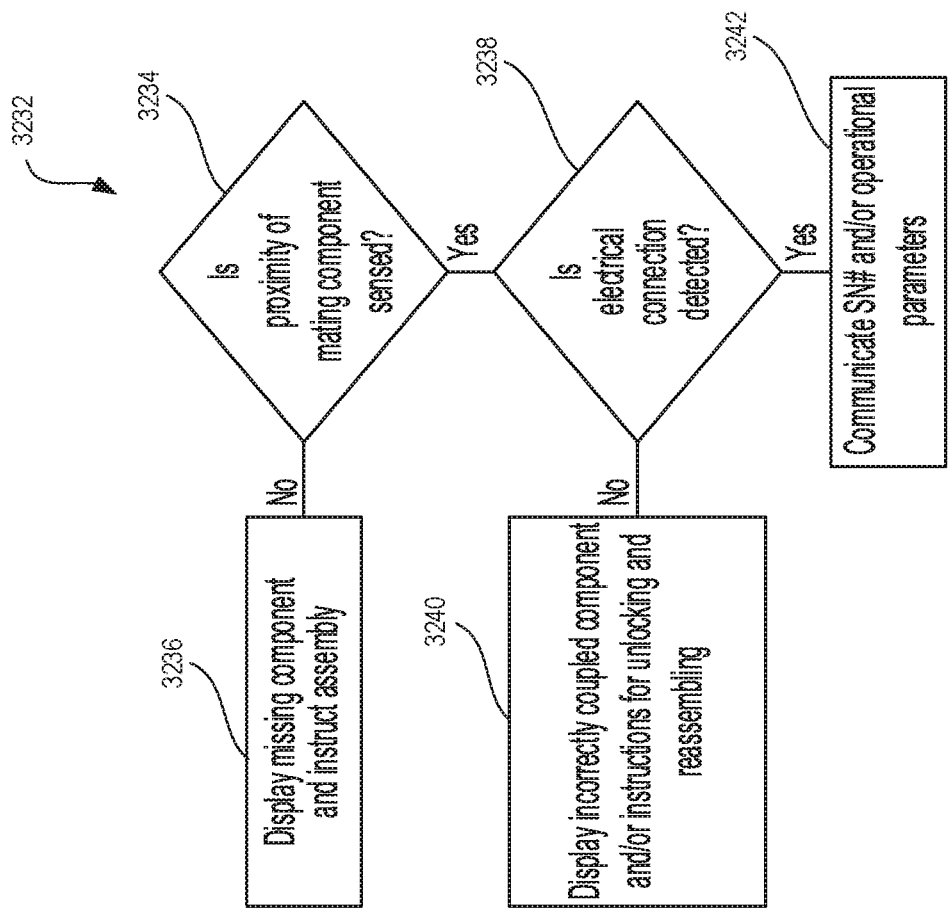
FIG. 58 is a logic flow diagram of a process for verifying that a surgical instrument is fully coupled to the robotic surgical assembly, in accordance with at least one aspect of the present disclosure.

A control circuit, such as the processor 15004 of the robotic surgical system 15000 illustrated in FIG. 22, can be configured to monitor a detection assembly, such as the detection assembly illustrated in FIGS. 57A and 57B. For example, the processor 15004 can be communicatively coupled to the sensors 3230*a*, 3230*b*, 3230*c*, 3230*d* described above. The modules monitored by the control circuit can include any combination of components of the surgical robotic assembly 43600 and/or a surgical instrument 43250. For example, the processor 15004 can be configured to execute the process 3232 illustrated in FIG. 58. The process 3232 can be embodied as, for example, instructions stored in a memory 15006 coupled to the processor 15004 that, when executed by the processor 15004, cause the robotic surgical system 15000 to perform the process 3232.

Accordingly, the processor 15004 executing the process 3232 can determine 3234 whether mating components (e.g., the IDU 43610, ring member 43550, sterile interface module 43630, or surgical instrument 43250) are within a sensed proximity to one another based on signals from the sensors 3230*a*, 3230*b*, 3230*c*, 3230*d*. If proximity of mating components is not sensed, then the process 3232 proceeds along the NO branch and the processor 15004 causes 3236 a display (e.g., a surgeon console's display 15014 (FIG. 22)) to display that the component is missing and/or instructions for assembling the robotic surgical system 13000.

If proximity of mating components is sensed, then the process 3232 proceeds along the YES branch and the processor 15004 determines 3238 whether an electrical connection is detected by determining whether electrical connections 3231*a*-3231*h* are properly paired. The processor 15004 can make this determination via the attachment assembly described in FIGS. 55A-55C, for example. If an electrical connection is not detect, but proximity of mating components is sensed, the process concludes that the components are improperly connected, and the process 3232 proceeds along the NO branch causing 3240 a display to alert a user that the component is incorrectly coupled and/or instructions for unlocking and reassembling the components. If an electrical connection is detected, then the process 3232 proceeds along the YES branch and the processor 15004 receives 3242 the serial number and/or operational parameters from the surgical instrument 43250 for the operation of the surgical instrument 43250 by the surgical system 13000.

In one aspect, various components of the robotic surgical assembly 43600 and/or surgical instrument 43250 can include a continuity circuit to determine when the components of the robotic surgical assembly 43600 and/or surgical instrument 43250 are coupled together. For example, the aspect of the robotic surgical assembly 40100 illustrated in FIG. 59 includes a continuity circuit assembly configured to detect when the carriage shell 40060 is seated to the carriage 40042, the ring connector 40171 (or another component of the sterile barrier collar assembly 40170 illustrated in FIG. 23 or the collar assembly 43630 illustrated in FIGS. 51-53) is seated to the carriage shell 40060, the sterile barrier housing 40130 is seated to the ring connector 40171, and the cap 40134 of the sterile barrier housing 40130 is closed.

In the example illustrated in FIG. 59, the carriage 40042 includes a first continuity circuit portion 3250; the carriage shell 40060 includes second, third, and fourth continuity circuit portions 3252, 3254, 3256; the ring connector 40171 includes a fifth continuity circuit portion 3258; and the sterile barrier housing 40130 includes sixth, seventh, eighth, and ninth continuity circuit portions 3260, 3262, 3264, 3266. The second, third, and fourth continuity circuit portions 3252, 3254, 3256 of the carriage shell 40060 are electrically coupled together. In one aspect, the second, third, and fourth continuity circuit portions 3252, 3254, 3256 can be different portions of a single continuity circuit extending through the carriage shell 40060. Likewise, the sixth, seventh, and eighth continuity circuit portions 3260, 3262, 3264 of the sterile barrier housing 40130 are electrically coupled together. In one aspect, the sixth, seventh, and eighth continuity circuit portions 3260, 3262, 3264 can be different portions of a single continuity circuit extending through the sterile barrier housing 40130.

The first continuity circuit portion 3250 is positioned to contact and electrically connect to the second continuity circuit portion 3252 disposed on the carriage shell 40060 when the carriage shell 40060 is seated on the carriage 40042. The third continuity circuit portion 3254 is positioned to contact and electrically connect to the fifth continuity circuit portion 3258 disposed on the ring connect 40171 when the ring connect 40171 is seated on the carriage shell 40060. The fourth continuity circuit portion 3256 is positioned to contact and electrically connect to the seventh continuity circuit portion 3262 disposed on the sterile barrier housing 40130 when the sterile barrier housing 40130 is seated on the carriage shell 40060. The fifth continuity circuit portion 3258 is positioned to contact and electrically connect to the sixth continuity circuit portion 3260 disposed on the sterile barrier housing 40130 when the sterile barrier housing 40130 is seated on the ring connector 40171. The eighth continuity circuit portion 3264 is positioned to contact and electrically connect to a ninth continuity circuit portion 3266 disposed on the cap 40134 of the sterile barrier housing 40130 when the cap 40134 is in the closed position. Accordingly, when each of the illustrated components of the robotic surgical assembly 40100 are properly seated together and the cap 40134 of the sterile barrier housing 40130 is in the closed position, the various circuit portions form a continuous electrical connection.

Accordingly, in one aspect, a control circuit coupled to the illustrated continuity circuit assembly can be configured to transmit a signal through the continuity circuit assembly at a first point and then control the robotic surgical system 15000 according to whether the signal is received at a second point. If the control circuit does not receive the input signal, which would indicate that one or more components of the robotic surgical assembly 40100 are not properly seated to each other and/or that the cap 40134 of the sterile barrier housing 40130 is open. If the control circuit does receive the input signal, that would indicate that all of the components of the robotic surgical assembly 40100 are properly connected and the cap 40134 is closed. In another aspect, the control circuit can be configured to apply a voltage to the continuity circuit assembly and determine whether the continuity circuit assembly is an open circuit or a closed circuit. An open circuit would indicate that one or more components of the robotic surgical assembly 40100 are not properly seated to each other and/or that the cap 40134 of the sterile barrier housing 40130 is open. A closed circuit would indicate that all of the components of the robotic surgical assembly 40100 are properly connected and the cap 40134 is closed. The control circuit can then control the robotic surgical system 15000 according to the engagement status between the components of the robotic surgical assembly 40100. For example, the control circuit could prevent the robotic arm to which the robotic surgical assembly 40100 is coupled from activating or moving unless it determines that all of the components of the robotic surgical assembly 40100 are properly connected together.

In various examples, each of the continuity circuit portions described above comprises a unique resistive element with a different resistance, which can be connected in parallel or in series circuit. The resistive elements are configured to form a part of the continuity circuit only when their respective components of the robotic surgical assembly 40100 are properly connected. Accordingly, the resistive elements form a series of interruptible interconnections that provide a different detected value depending on which portion of the series is interrupted. A control circuit can determine which control circuit portion is interrupted based on the detected value. In at least one example, the detected value can be a current value. A predetermined voltage can be applied to the continuity circuit, and a current value can be measured to determine which, if any, of the components of the robotic surgical assembly 40100 is not properly connected thereby causing its control circuit portion to be interrupted.

In various examples, the continuity circuit portions are interrupted when their respective components of the robotic surgical assembly 40100 are properly connected. In other examples, the continuity circuit portions are interrupted when their respective components of the robotic surgical assembly 40100 are improperly connected.

In one aspect, various components of the robotic surgical assembly 43600 and/or surgical instrument 43250 can include one or more detection elements that are detectable by a sensor assembly 3270 to determine the location and orientation of each component. For example, the aspect of the robotic surgical assembly 40100 illustrated in FIG. 60 includes a first detection element 3274 disposed on the carriage 40042 (or the sterile shell thereof), a second detection element 3276 disposed on the IDU 40110 (e.g., the motor pack assembly), a third detection element disposed on the sterile barrier collar assembly 40170 (which can include the collar assembly 40170 illustrated in FIG. 23 or the collar assembly 43630 illustrated in FIGS. 51-53), and a set of detection elements 3280, 3282, 3284 disposed on the surgical instrument 40200. In the particular example shown in FIG. 60, the surgical instrument 40200 is a trocar 3273. The same or different detection element assemblies or arrangements can be utilized in connection with other trocars 3273 or different surgical instruments 40200. In particular, the trocar 3273 can include a fourth detection element 3280 disposed adjacently to its proximal engagement end, a fifth detection element 3282 disposed at its collar at which it is gripped by the grasper 3272 of the robotic arm 13120, and a sixth detection element 3284 likewise disposed at its collar. Further, in this aspect the sensor assembly 3270 is located on the robotic arm 13120. The sensor assembly 3270 can include a set of sensors configured to sense the detection elements disposed on the robotic surgical assembly 43600 and/or surgical instrument 43250. In this particular aspect, the sensor assembly 3270 includes a first set of sensors 3270a, 3270b that are configured to detect the detection elements 3274, 3276, 3278 disposed on the robotic surgical assembly 40100 and a second set of sensors 3271a, 3271b that are configured to detect the detection elements 3280, 3282, 3284 disposed on the surgical instrument 40200. The first set of sensors 3270a, 3270b can be positioned at or adjacently to the position on the robotic arm 13120 near which the carriage is secured 40042, for example. The second set of sensors 3271a, 3271b can be positioned at or adjacently to the grasper 3272 for holding the surgical instrument 40200, for example. The sensor assembly 3270 can include any type of sensor configured to detect the presence of a corresponding detection element within a threshold proximity thereof. For example, the sensors 3270a, 3270b, 3271a, 3271b can include RFID readers and the detection elements 3274, 3276, 3278, 3280, 3282, 3284 can include (passive or active) RFID tags.

In certain examples, the sensors of the sensor assembly 3270 comprise limited detection ranges that are capable of detecting their corresponding detection elements only when their respective components of the robotic surgical assembly 40100 are in properly assembled, or at least partially assembled, configurations. In other words, placing the components of the robotic surgical assembly 40100 in properly assembled configurations causes the detection elements of such components to be in the detectable ranges of their corresponding sensors of the sensor assembly 3270. In certain examples, the signals from RFID tags are detected by the RFID readers at predetermined signal strengths in the properly assembled configurations of their respective components of the robotic surgical assembly 40100. Accordingly, a control circuit coupled to the RFID readers can assess proper assembly of the robotic surgical assembly 40100 by comparing signal strength of the signals transmitted from the RFID tags to predetermined signal strengths associated with properly assembled configurations of corresponding components of the robotic surgical assembly 40100.

Figure 61C:
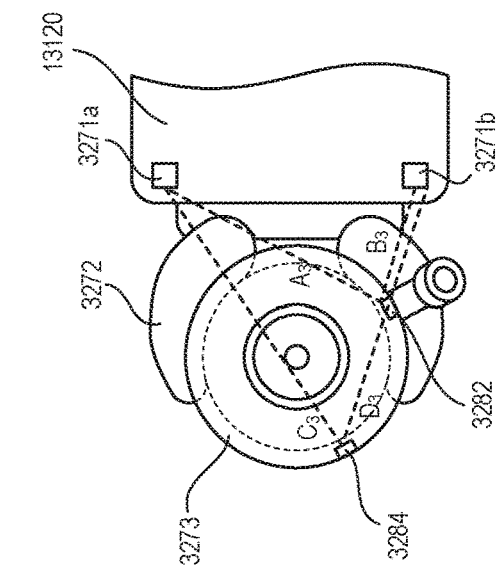
FIG. 61C is an overhead elevational view of the robotic surgical assembly of FIG. 60, where the surgical instrument is in a third orientation, in accordance with at least one aspect of the present disclosure.
Figure 61B:
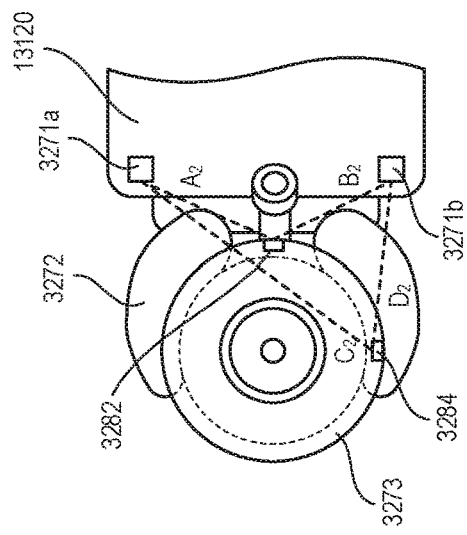
FIG. 61B is an overhead elevational view of the robotic surgical assembly of FIG. 60, where the surgical instrument is in a second orientation, in accordance with at least one aspect of the present disclosure.
Figure 61A:
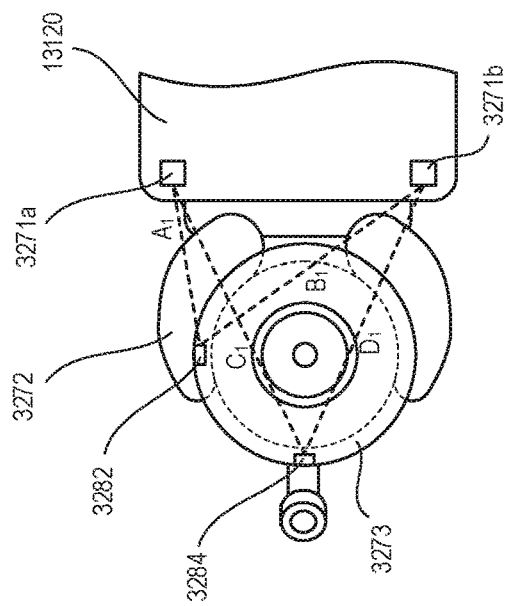
FIG. 61A is an overhead elevational view of the robotic surgical assembly of FIG. 60, where the surgical instrument is in a first orientation, in accordance with at least one aspect of the present disclosure.

Accordingly, the sensor assembly 3270 can detect the presence of each of the components of the robotic surgical assembly 40100 and the surgical instrument 40200 based on whether the corresponding detection element(s) for the component are within detection range of the sensor assembly 3270. However, as is illustrated in FIGS. 61A-61C, the sensor assembly 3270 can also detect the orientation or arrangement of the components of the robotic surgical assembly 40100 and the surgical instrument 40200 based on the locations of the detection elements with respect to one or more sensors within the sensor assembly 3270. For example, FIG. 61A illustrates the trocar 3273 in a first orientation where the distance from the third sensor 3271a and the fourth sensor 3271b to the fifth detection element 3282 is $A_1$ and $B_1$, respectively. Further, the distance from the third sensor 3271a and the fourth sensor 3271b to the sixth detection element 3284 is $C_1$ and $D_1$, respectively. By comparing the values for $A_1$ and $B_1$, a control circuit coupled to the sensor assembly 3270 can triangulate the location of the fifth detection element 3282 and accordingly determine the orientation of the portion of the trocar 3273 to which the fifth detection element 3282 is attached. Likewise, by comparing the values for $C_1$ and $D_1$, a control circuit coupled to the sensor assembly 3270 can triangulate the location of the sixth detection element 3284 and accordingly determine the orientation of the portion of the trocar 3273 to which the sixth detection element 3284 is attached (which, in the illustrated aspect, is the insufflation port attachment point). Therefore, the control circuit can determine that the trocar 3273 is in the first orientation. Further, FIGS. 61B and 61C illustrate the trocar 3273 in a second orientation and third orientation, respectively, and the corresponding detectable distances between the sensors 3271a, 3271b and the detection elements 3282, 3284. By detecting the distances, the control circuit can differentiate between these different orientations and thereby determine whether the trocar 3273 is oriented correctly with respect to the robotic arm 13120.

The sensor assembly 3270 can be communicably coupled to a control circuit, such as the processor 15004 of the robotic surgical system 15000 illustrated in FIG. 22, for receiving the sensor data from the sensor assembly 3270. The control circuit can monitor the presence and orientation of the components of the robotic surgical assembly 40100 and the surgical instrument 40200 and control the robotic surgical system 15000 accordingly, such as by providing warnings and/or instructions to the users or only permitting the activation or operation of the robotic arm 13120 in the event that each of the components is connected and oriented correctly.

In one aspect, a surgical instrument 40200 (e.g., a trocar 3273) can include an electrical continuity circuit for detecting the orientation of the surgical instrument 40200. For example, the grasper 3272 of the robotic arm 13120 could include one or more sensors that senses contact with the surgical instrument 40200. The grasper 3272 could seek to establish electrical continuity from a first point on the surgical instrument 40200 to a second point on the surgical instrument 40200 via the current passing from the grasper 3272, through the surgical instrument 40200, and then back to the grasper 3272. For example, in the aspect illustrated in FIGS. 62A and 62B, the grasper 3272 includes a sensor 3290 configured to detect the presence of the trocar 3273 and a pair of electrical contacts 3292 disposed at a first location and a second location. The sensor 3290 can include an image sensor configured to read a detection element (e.g., a barcode or QR code) disposed on the trocar 3273 for identifying the trocar 3273, for example. Further, the trocar 3273 can include an electrical contact 3296 that is sized and dimensioned to be contacted by both of the grasper electrical contacts 3292 when trocar 3273 is oriented correctly within the grasper 3272 when gripped thereby. Accordingly, when the trocar 3273 is oriented correctly within the grasper 3272, the trocar electrical contact 3296 and the grasper electrical contacts 3292 establish electrical continuity, which can be detected via a control circuit coupled thereto, for example. When the trocar 3273 is not oriented correctly within the grasper 3272, at least one of the grasper electrical contacts 3292 will not physically contact the trocar electrical contact 3296 and thus electrical continuity will not be established (which can likewise be detected via the control circuit).

The sensor 3290 can be communicably coupled to a control circuit, such as the processor 15004 of the robotic surgical system 15000 illustrated in FIG. 22, for receiving the sensor data from the sensor 3290 via, e.g., a first connection 3300. Likewise, the electrical contacts 3292 can be coupled to the control circuit via, e.g., a second connection 3298 for transmitting a signal therethrough. If the control signal can receive the transmitted signal, then it can determine that there is electrical continuity between the trocar electrical contact 3296 and the grasper electrical contacts 3292 and that the trocar 3273 is therefore oriented correctly within the grasper 3272. The control circuit can monitor the presence and orientation of a surgical instrument 40200 (or any other components of the robotic surgical assembly 40100 that are gripped by a grasper 3272) and control the robotic surgical system 15000 accordingly, such as by providing warnings and/or instructions to the users or only permitting the activation or operation of the robotic arm 13120 in the event that the surgical instrument 40200 is connected and oriented correctly.

In one aspect, a surgical instrument 40200 (e.g., a trocar 3273) can include detection elements 3304 that indicate the identity or type of the surgical instrument 40200. For example, in the aspect illustrated in FIG. 63A, the grasper 3272 can include a sensor 3302 that is configured to sense the detection element 3304 disposed on the trocar 3273 when the trocar 3273 is grasped by or within a proximity to the grasper 3272. The particular arrangement or type of the detection element 3304 can be configure to identify the type or identity of the trocar 3273. Further, the detection element 3304 can be positioned or configured such that it is only detectable by the sensor 3302 when the trocar 3273 is oriented correctly within the grasper 3272. In one aspect, the sensor 3302 can include a Hall effect sensor and the detection element 3304 can include one or more magnets that create a magnetic signature detectable by the Hall effect sensor, for example. In another aspect, the sensor 3302 can include an image sensor and the detection element 3304 can include a set of markings, barcode, or QR code that is visually distinguishable by the image sensor. For example, FIG. 63B illustrates a detection element 3304 in a first configuration, FIG. 63C illustrates a detection element 3304 in a second configuration, and FIG. 63D illustrates a detection element 3304 in a third configuration. The first configuration of the detection element 3304 can indicate that the trocar 3273 is an 8 mm trocar with a stop cock, the second configuration of the detection element 3304 can indicate that the trocar 3273 is an 8 mm trocar without a stop cock, and the third configuration of the detection element 3304 can indicate that the trocar 3273 is a 5 mm trocar without a stop cock, for example. Further, if the detection element 3304 is not detectable by the sensor 3302, then that can indicate that an incompatible trocar 3273 is being utilized or that the trocar 3273 is not oriented correctly within the grasper 3272. Accordingly, a control circuit communicably coupled to the sensor 3302, such as the processor 15004 of the robotic surgical system 15000 illustrated in FIG. 22, can monitor the presence of a surgical instrument 40200 (or any other components of the robotic surgical assembly 40100 that are gripped by a grasper 3272) and control the robotic surgical system 15000 accordingly, such as by providing warnings and/or instructions to the users or only permitting the activation or operation of the robotic arm 13120 in the event that the surgical instrument 40200 is connected and oriented correctly.

Figure 64:
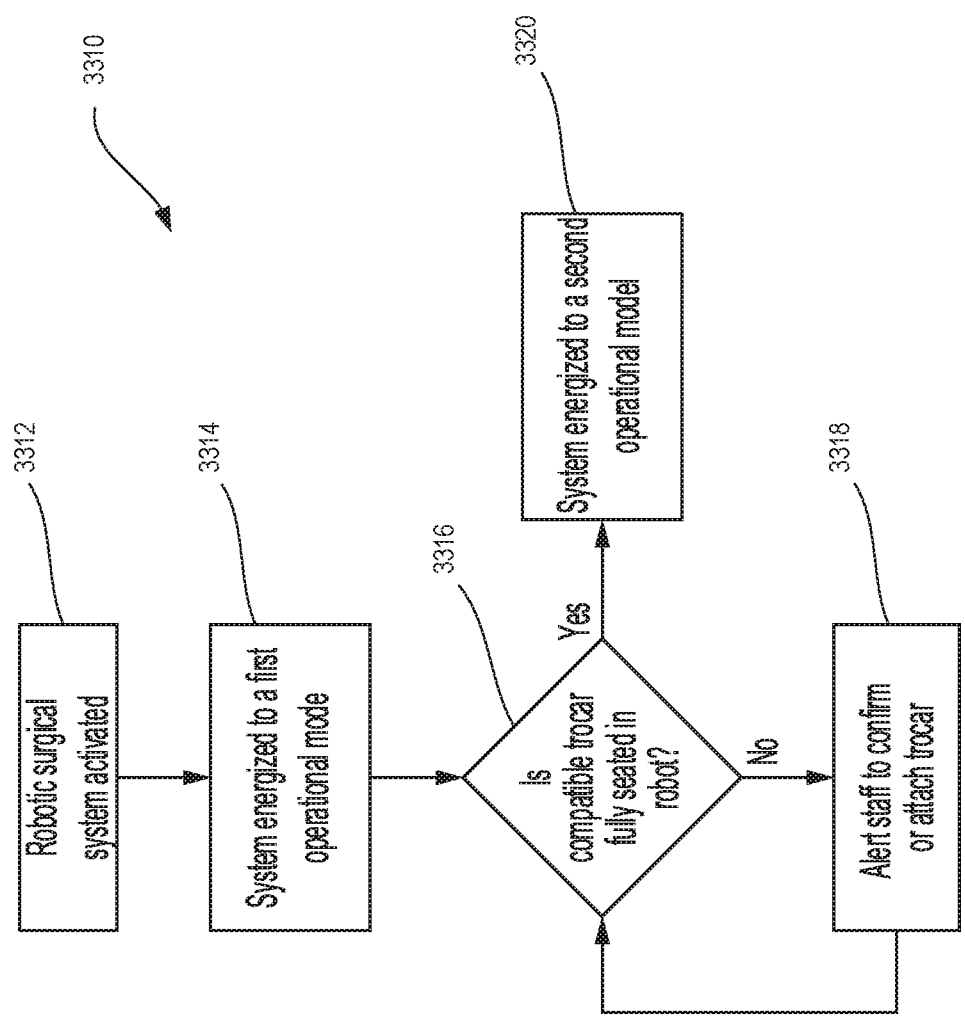
FIG. 64 is a logic flow diagram of a process for determining whether a compatible trocar is coupled to the robotic surgical assembly, in accordance with at least one aspect of the present disclosure.

In various aspects discussed above and below, a control circuit can be configured to take various actions in response to detecting the presence and orientation of a surgical instrument 40200 and/or components of a robotic surgical system 40100, such as providing instructions to users or only permitting activation or operation of the robotic surgical system 15000 when all components are properly connected together. In another aspect, a control circuit, such as the processor 15004 of the robotic surgical system 15000 illustrated in FIG. 22, can operate the robotic surgical system 15000 in different modes according to whether a compatible surgical instrument 40200 (e.g., a trocar) are connected to the robotic surgical system 15000 by, for example, executing the process 3310 illustrated in FIG. 64.

Accordingly, a processor 15004 executing the process 3310 can determine 3312 that the robotic surgical system 15000 has been activated and then energize 3314 or operate the robotic surgical system 15000 in an initial or first operational mode. Accordingly, the processor 15004 can determine 3316 whether a compatible surgical instrument 40200, such as a trocar, is seated within the robotic surgical system 15000. The processor 15004 can make this determination by reading a barcode or QR code via an image sensor as described in connection with FIGS. 62A and 62B, identifying detection elements via a sensor as described in connection with FIGS. 63A-63D, and so on, and then determining whether those elements correspond to a compatible surgical instrument 40200. If the surgical instrument 40200 is compatible, then the process 3310 proceeds along the YES branch and the processor 15004 energizes 3320 the robotic surgical system 15000 to a second operational mode. In the second operational mode, the processor 15004 can control the surgical instrument 40200 according to parameters (e.g., grip strength or expected grip stroke) specific to the identified surgical instrument 40200, for example. If the surgical instrument 40200 is not compatible or the processor 15004 is not able to determine whether the surgical instrument is compatible 40200 (e.g., due to the instrument being improperly oriented with respect to the robotic arm 13120, causing the detection elements to not be identifiable), then the process 3310 proceeds along the NO branch and the processor 15004 alerts 3318 the surgical staff to attach the surgical instrument 40200 or confirm that the surgical instrument 40200 is attached properly. The processor 15004 can provide the alert via the surgeon console's display 15014, for example. The processor 15004 can thereafter continue monitoring to determine 3316 whether the surgical instrument 40200 is fully seated and respond accordingly.

Figure 65:
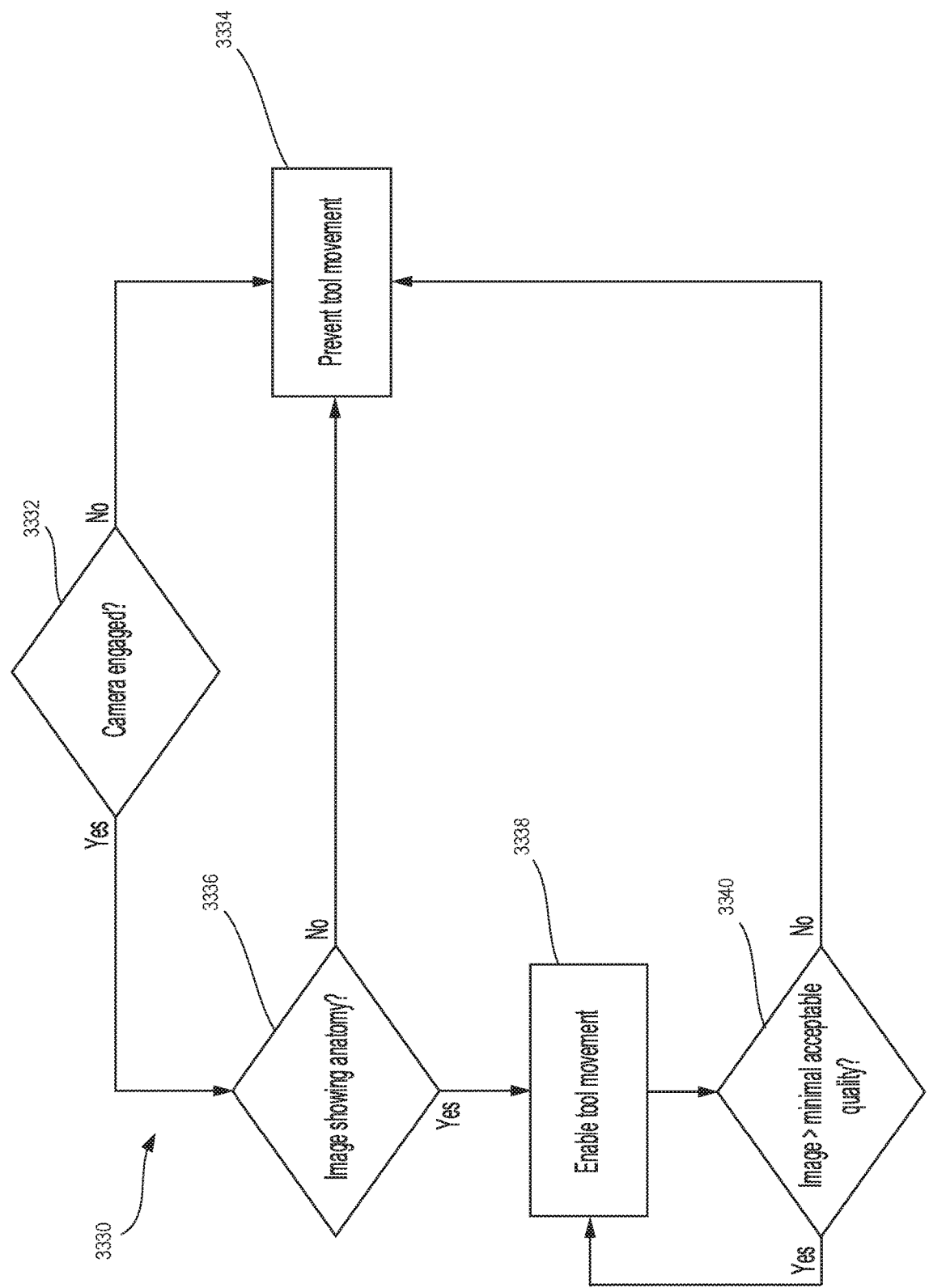
FIG. 65 is a logic flow diagram of a process for controlling surgical tool movement according to scope visualization, in accordance with at least one aspect of the present disclosure.

In addition to controlling the robotic surgical system 15000 according to the presence, position, orientation, and/or type of surgical instrument 40200 connected to the robotic surgical system 15000, the robotic surgical system 15000 could also be controlled according to whether a camera (i.e., a scope, such as an endoscope 239 as shown in FIG. 9) is engaged, what is being viewed by the camera, and/or image quality of the video feed provided by the camera. Controlling the robotic surgical system 15000 according to the camera status can be beneficial because insufficient visualization (i.e., no camera being attached or the camera having poor image quality) is indicative of situations where it would be desirable to prevent surgical instruments 40200 (or other components of the robotic surgical system 15000) from moving inadvertently. For example, a camera having poor image quality can indicate that the camera is being cleaned, either internally within the patient during a surgical procedure or externally to the patient. As another example, a camera not being connected to the robotic surgical system 15000 can indicate that the camera has been detached for cleaning or that the initial setup process for the robotic surgical system 15000 is ongoing. In any of these cases, it should not be necessary for the surgical instrument 40200, robotic arm, or other components of the robotic surgical system 15000 to move. Therefore, it can be desirable to prevent movement of the robotic surgical system 15000 in these instances by locking out users from moving the surgical instruments 40200 and/or robotic arms until the camera status is resolved and sufficient image quality within the body of the patient has been (re)established. In one aspect, a control circuit, such as the processor 15004 of the robotic surgical system 15000 illustrated in FIG. 22, can operate the robotic surgical system 15000 according to what is being viewed by the camera by, for example, executing the process 3330 illustrated in FIG. 65. In one aspect, the control circuit could be coupled to a proximity sensor configured to detect the position of the camera and/or the robotic arm on which the camera is supported. In another aspect, the control circuit can be configured to execute various image processing algorithms for determining image quality and/or performing image recognition.

Accordingly, a processor 15004 executing the process 3330 can determine 3332 whether a camera is engaged to the robotic surgical system 15000. The processor 15004 can make this determination by monitoring whether the robotic surgical system 15000 is actively receiving a video feed, by sensing for the presence of a camera using various detection arrangements (e.g., as described in connection with FIGS. 62A-63D), and so on. If a camera is not engaged, then the process 3330 proceeds along the NO branch and the processor 15004 prevents 3334 movement of a surgical tool, such as a surgical instrument 40200, coupled to the robotic surgical system 15000. If a camera is engaged, then the process 3330 proceeds along the YES branch and the processor 15004 determines whether the image or video feed from the camera are showing anatomy. The processor 15004 can identify anatomical structures using a variety of image recognition techniques, such as image overlay. If the image or video feed from the camera is not showing anatomy, then the process 3330 proceeds along the NO branch and the processor 150004 prevents 3334 movement of a surgical tool. If the image or video feed is showing anatomy, then the process 3330 proceeds along the YES branch and the processor 15004 enables 3338 movement of the coupled surgical tool. Thereafter, the processor 15004 monitors the quality of the image or video feed to ensure that it is maintained within acceptable bounds. Accordingly, the processor 15004 determines 3340 whether the image quality meets or exceeds a threshold image quality. The processor 15004 can make this determination by, for example, algorithmically analyzing the image or video feed data to ascertain the degree or noise or blur present in the data and then comparing the calculated noise or blur relative to a threshold. If the image quality does not satisfy the threshold, then the process 3330 proceeds along the NO branch and the processor 15004 prevents 3334 movement of a surgical tool. If the image quality does satisfy the threshold, then the process 3330 proceeds along the YES branch and the processor 15004 continues to enable 3338 movement of the surgical tool. In sum, this process 3330 only permits a surgical tool to be operated via the robotic surgical system 15000 when a camera is engaged and showing anatomy with an appropriate image quality. Therefore, this process 3330 prevents the surgical tool from being operated outside of the scope of the surgical procedure, during when there should be no or little reasons to operate the surgical tool.

In one aspect, a surgical instrument 40200 (e.g., a trocar 3273) can include a grip surface 3342 configured to cause differential vacuum pressure depending upon the orientation of the surgical instrument 40200 within a grasper 3272. For example, in the aspect illustrated in FIGS. 66A-66C, the grasper 3272 and/or robotic arm 13120 includes a vacuum source 3344 that is configured to cooperate with a grip surface 3342 of a trocar 3273 to generate a vacuum pressure when the trocar 3273 is gripped by the grasper 3272. The vacuum source 3344 can include an opening that is configured to sealingly engage with the grip surface 3342 of the trocar 3273. The grip surface 3342 can be irregular or non-uniform such that the grip surface 3342 causes different vacuum pressures to be generated depending upon the orientation of the trocar 3273. For example, the grip surface 3342 can include a roughened portion 3342a that is not configured to create an air-tight seal with the vacuum source 3344 and a smooth portion 3342a that is configured to create an air-tight (or substantially air tight) seal with the vacuum source 3344. To demonstrate these concepts, in FIG. 66B the roughened portion 3342a of the grip surface 3342 overlaps partially with the opening of the vacuum source 3344, causing a pressure $V_1$ to be generated. Correspondingly, in FIG. 66C the smooth portion 3342b of the grip surface 3342 is aligned with the opening of the vacuum source 3344, with no overlap from the roughened portion 3342a, which thus causes a pressure $V_2$ to be generated. These pressures can be detected by a control circuit coupled to the vacuum source 3344 and/or a pressure source configured to detect the air pressure generated at the interface between the grip surface 3342 and the vacuum source 3344 to identify the orientation of the trocar 3273 relative to the grasper 3272.

FIG. 66D further illustrates a prophetic set of graphs 3350 indicating control of the robotic surgical system 15000 via a control circuit monitoring vacuum pressure from the aspect illustrated in FIGS. 66A-66C. The graphs 3350 include a first vertical axis 3352 representing vacuum pressure and a second vertical axis 3354 representing power to a device coupled to or a component of the robotic surgical system 15000 (e.g., a surgical instrument or a robotic arm). Further, the graphs 335 include a horizontal axis 3356 representing time. A first line 3358 represents the vacuum pressure over time and a second line 3360 represents device power over time. In this example, a pressure value of $V_2$ indicates that the trocar 3273 (or other surgical instrument) is oriented properly within the grasper 3272 (as shown in FIG. 66C) and thus can serve as a threshold for powering the device. As indicated by the first line 3358, the vacuum pressure initially increases to a first peak at or near $V_1$, which indicates that the trocar 3273 is not correctly oriented at that time (as shown in FIG. 66B). Accordingly, the control circuit coupled to the vacuum source 3344 and/or pressure sensor can identify that the trocar 3273 is not oriented properly and present an alert or instructions to the surgical staff, for example. As further indicated by the first line 3358, the surgical staff correct the orientation of the trocar 3273 and at time $t_1$ the vacuum pressure reaches or exceeds the pressure threshold $V_2$ indicative of the trocar 3273 being oriented correctly. Accordingly, the control circuit can activate, energize, or otherwise permit operation of the device controlled thereby, as indicated by the second line 3360 increasing from zero to a define value at time $t_1$. The control circuit continues energizing the device until, at time $t_2$, the vacuum pressure drops steeply (potentially indicating that the trocar 3273 has been disconnected from the grasper 3272). Accordingly, the control circuit deactivates the device, as indicated by the second line 3360 decreasing from the defined value to zero at time $t_2$. In this way, a control circuit can control the operation of a surgical instrument and/or a component of the robotic surgical system 15000 according to detected vacuum pressure indicative of the orientation of a surgical tool, such as a trocar 3273.

Robotic Detection Zones and Safety Thresholds

In various aspects, the movement and functions of the robotic surgical systems can be controlled based on the proximity of components of the robotic surgical systems to individuals or objects located within the operating room or the presence of individuals or objects located within the operating room within detection or safety zones defined within the operating room. For example, FIGS. 67A-74 illustrate a variety of different illustrative detection arrangements for monitoring the position of surgical staff members, the patient 3380, components of the robotic surgical systems 3370, and/or surgical tools and controlling the robotic surgical systems 3370 accordingly. Further, each of these aspects can be utilized in conjunction with situationally aware systems, which are described above under the heading ROBOTIC SURGICAL SYSTEM.

In other aspects, various other activities occurring within the operating room can be visually monitored to provide additional information to the robotic surgical system regarding the placement and location of individuals and objects within the operating room. For example, the functional or operational workspace over or about the patient could be monitored by a camera or series of cameras positioned outside the patient's body (e.g., on the robotic arm(s) or throughout the operating room space). Further, the cameras configured to record the activities occurring outside the patient's body could be synchronized with the image or video feed from scopes positioned within the patient's body. By synchronizing the video feeds, the external cameras could provide the robotic surgical system with situational awareness regarding activities occurring in preparation for the next surgical task, tools being changed, or other devices used in tandem with the robot tools. Still further, the external cameras could be configured to track non-robotic instruments (e.g., handheld surgical instruments) utilized by the surgical staff during the course of the surgical procedure. The external cameras could also establish a detection zone or safety envelope around the surgical staff with respect to the range of motion of the robotic arm(s) and ensure the robotic arms never violate this space. The safety envelope can be updated real time (e.g., with a safety threshold) to ensure safety of the staff. Sensors or specialized equipment may be worn by the surgical staff to identify themselves and aid in their detection by the robotic surgical system.

In other aspects, various non-camera sensors can be utilized to detect and monitor the detection zones. For example, an alternative to optical mapping of the operating room and/or individuals within the operating room could include RF, acoustic, or millimeter radar detection mediums. For example, the functional or operational workspace could be acoustically mapped by generating a baseline acoustical map and then monitoring to detect changes in the acoustical characteristics of the mapped area, which could indicate the proximity of individuals or objects within the mapped area. As another example, antennae could be positioned at specific locations of the surgical tools, components of the robotic surgical system, and other devices. The antennae can be connected to fixed frequency oscillators in an LC circuit, for example. Accordingly, if an object is sufficiently distant from the given antenna, the inductive and capacitive reactance match, and the voltage through the inductor is at maximum. Moving a grounded object closer to the antenna (such as a person moving closer to the antenna) changes the capacitance, which lowers the voltage through the inductor. The change in voltage can be used to drive an amplifier and thus be utilized to detect the movement of individuals or objects through the operating room. A control circuit could then control the movement of the robotic arms and other components or the robotic surgical system accordingly.

Figure 67B:
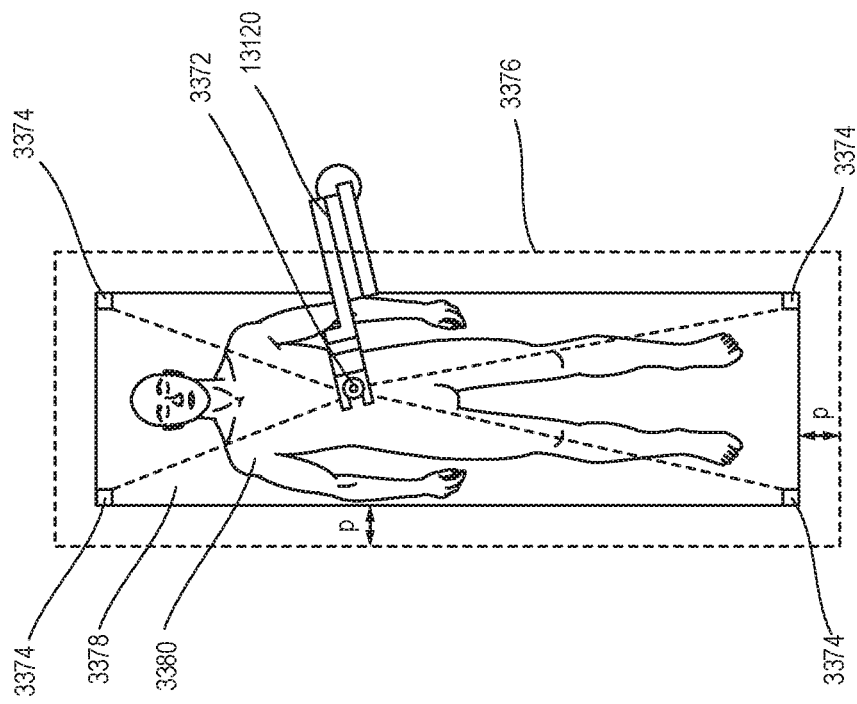
FIG. 67B is an overhead elevational view of the robotic surgical system of FIG. 67A, in accordance with at least one aspect of the present disclosure.
Figure 67A:
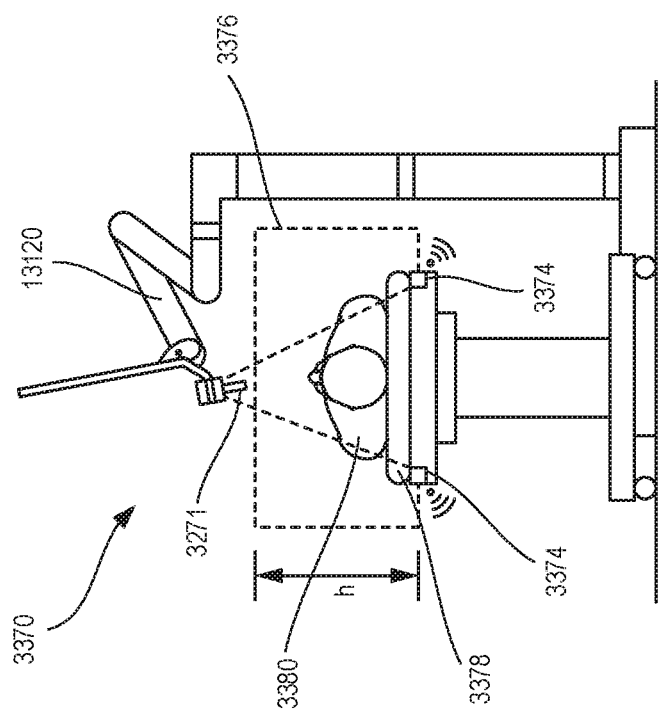
FIG. 67A is a side elevational view of a safety envelope defined about a patient for a robotic surgical system, in accordance with at least one aspect of the present disclosure.
Figure 73:
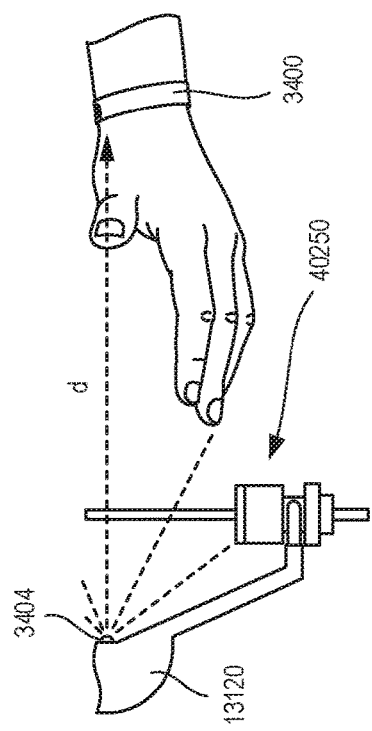
FIG. 73 is a schematic view of a robotic surgical system comprising a sensor to sense an identifier position, in accordance with at least one aspect of the present disclosure.

In one aspect, a detection zone can be defined with respect to the operating table. For example, FIGS. 67A and 67B illustrate a robotic surgical system 3370 including a sensor 3271 actuated by a robotic arm 13120. In one aspect, the sensor 3271 can be positioned adjacently to a surgical tool coupled to the robotic arm 13120. The sensor 3271 is configured to detect a set of detection elements 3374 positioned at the corners of an operating table 3378. The sensor 3271 can include any sensor type capable of identifying and determining the relative position or location of the corresponding detection elements 3274. For example, the sensor 3271 can include an image sensor and the detection elements 3374 can include visually identifiable elements, for example. As another example, the sensor 3271 can include an RFID reader and the detection elements 3374 can include RFID tags, for example. In other examples, the sensor 3271 can include a Hall effect sensor and the detection elements 3274 can include magnets. In various other examples, the sensor 3271 can include a reed sensor, an ultra-high frequency RF sensor, and so on and the detection elements 3274 can include corresponding elements.

Further, the robotic surgical system 3370 can define a detection zone 3376 based on the position of the detection elements 3274 detected by the sensor 3271. In one aspect, the detection zone 3376 can be coextensive with the detected boundary of the operating table 3378 as delineated by the detection elements 3274. In other aspects, such as the aspect illustrated in FIGS. 67A and 67B, the detection zone 3376 can be non-coextensive with the operating table. For example, the detection zone 3376 can be defined as extending a distance p from the detected boundary of the operating table 3378 and a height h thereabove. The detection zone 3376 can define a volume about the operating table 3378 and/or patient 3380 in which the robotic surgical system 3370 monitors for the presence of objects and/or individuals and then controls the surgical tools or components of the robotic surgical system 3370 accordingly. For example, if an individual (other than the patient 3380) is detected as being present within the detection zone 3376, a control circuit coupled to the sensor 3271 can cause the robotic arm 13120 to cease movement, thereby preventing the robotic arm 13120 and/or a surgical tool coupled thereto from contacting the individual. As another example, if a surgical tool is detected as being present within the detection zone 3376, the control circuit can slow the movement of the robotic arm 13120 or decrease the maximum allowable movement speed of the robotic arm 13120, thereby seeking to mitigate the risk of the surgical tool being inadvertently brought into contact against the patient 3380.

In one aspect, a detection zone can be defined with respect to removably attachable tags, thereby allowing users to freely define the scope and bounds of the detection zone. For example, FIG. 68 illustrates a tag 3384 detectable by a sensor, as described above. The tags 3384 can be utilized to identify the space occupied by the patient 3380 or to establish other safety thresholds to ensure that the components of the robotic surgical system 3370 and/or surgical tools supported thereby do not violate that space or function differently within that space. The tags 3384 can be disposable or reusable. In operation, the tags 3384 could be placed by the user (e.g., a surgeon or nurse) on or around the patient 3380 to provide feedback to the robotic surgical system 3370 regarding the patient location or a desired safety zone (which may not necessarily be limited to a space defined by the patient's location). Accordingly, users can flag the operating table 3378, the patient 3380, the limbs or other body parts of the patient 3380, and/or other critical or interfering objects within the operating envelope. In one aspect, the tags 3384 can include a detection element 3374 coupled to an attachment surface 3386, such as an adhesive surface, affixable to the patient or objects. As shown in FIG. 69A, a sensor 3382 supported by a robotic arm 13120 adjacently to the surgical tool (e.g., a trocar 3273) can detect the detection elements 3374 of the tags 3384 as they are positioned on the patient 3380 or other objects. Further, as shown in FIGS. 69B-69D, the tags 3384 can be utilized to identify a detection zone or safety thresholds with respect to patients 3380 of different body dimensions. Such customizable detection zones or safety thresholds can be much safer than statically defined detection zones due to the inherent variation in patients' 3380 anatomy.

In one aspect, a detection zone can be defined with respect to a component of the robotic surgical system itself, such as a robotic arm 13120. For example, in FIG. 70 the robotic surgical system includes a sensor 3388 (e.g., an image sensor) that is configured to detect the position of a surgical instrument 40250 or another surgical tool supported by a robotic arm 13120 with respect to a detection zone 3390 corresponding to the range of movement of the surgical instrument 40250. In various aspects, the sensor 3388 can be mounted to the robotic arm 13120 or positioned at another location within the operating room. In one aspect, the scrubs 3394 provided to the surgical staff members can include reflective material 3393 to assist the camera 3388 or other image sensor in visually distinguishing the surgical staff members from the surrounding environment and thereby detecting when they are present within a detection zone 3390.

In one aspect, the robotic surgical system can be configured to define multiple detection zones that delineate different manners in which the robotic arm 13120, surgical instrument 40250, or other components of the robotic surgical system are controlled. For example, FIG. 72 illustrates an example where the sensor 3388 is configured to monitor both a first detection zone 3390 (which is also shown in FIG. 70) and a second detection zone 3396 defined about the first detection zone 3390. The first detection zone 3390 can correspond to the range of movement of the surgical instrument 40250 supported by the robotic arm 1310 and the second detection zone 3396 can correspond to a threshold distance about the first detection zone 3390, for example. However, the various detection zones 3390, 3396 do not necessarily be defined in relation to each other and, in some aspects, can instead be separately defined from each other or defined according to separate locations, objects, or individuals. Further, as noted above, the robotic arm 13120 could be controlled differently depending upon which of the detection zones 3390, 3396 an individual is present within. For example, the sensor 3388 does not detect an individual in either of the detection zones 3390, 3396, then a control circuit coupled to the sensor 3388 can permit the robotic arm 13120 and/or surgical instrument 40250 to operate normally. If the sensor 3388 detects an individual present within the second detection zone 3396, but not the first detection zone 3390, the control circuit can take a first action, such as slowing or limiting the maximum movement speed of the robotic arm 13120. Finally, if the sensor 3388 detects an individual present within the first detection zone 3390, the control circuit can take a second action, such as deactivating or preventing movement of the robotic arm 13120 and/or the surgical instrument 40250. Therefore, the robotic surgical system can dictate its behavior based on the position of the surgical staff relative to the detection zones 3390, 3396.

In another aspect, the robotic surgical system can be configured to detect an object or reference worn by surgical staff members during a surgical procedure. For example, the robotic surgical system in FIG. 73 can include a sensor 3404 to sense the location and/or presence of a band 3400 worn by the surgical staff in the operating room and then control the robotic arm 13120 and/or the surgical instrument 40250 accordingly. The bands 3400 can include an elastomeric material, for example, and could be worn on the wrist, forearm, bicep, and so on. Further, the bands 3400 could be disposable or reusable. In one aspect, the sensor 3404 can include a thermal camera and the band 3400 can include a thermal band that is configured to emit thermal energy or has been heated to a particular temperature, for example. The thermal band can be set to a predefined temperature, such as 99° F. Having the bands 3400 set to a predefined temperature could be beneficial because it would allow the sensor 3404 to be calibrated to detect objects specifically at that temperature, thereby improving detection accuracy. On benefit of utilizing thermal data is that the operating room is often dimmed or dark during setup for a surgical procedure, which can interfere with the function of image sensors configured to work within the visual light spectrum. In another aspect, the sensor 3404 can include a magnetic or RF sensor and the band 3400 can include a magnetic or RF band, respectively. As noted above with respect to the robotic surgical system including a thermal camera for detecting a thermal band, such magnetic or RF detection mediums can be beneficial in situations where the room is darkened or dim.

In various other aspects, the robotic surgical system could also be configured to utilize multi-spectral imaging, passive IR, visual light, multi-spectral RF, and/or ultrasound and other detection mediums to monitor the operating room and its inhabitants and surgical tools. Such sensor data could also be utilized by the robotic surgical system to complement or augment contact sensor data (e.g., as described in connection with FIGS. 54A-66D).

Figure 74:
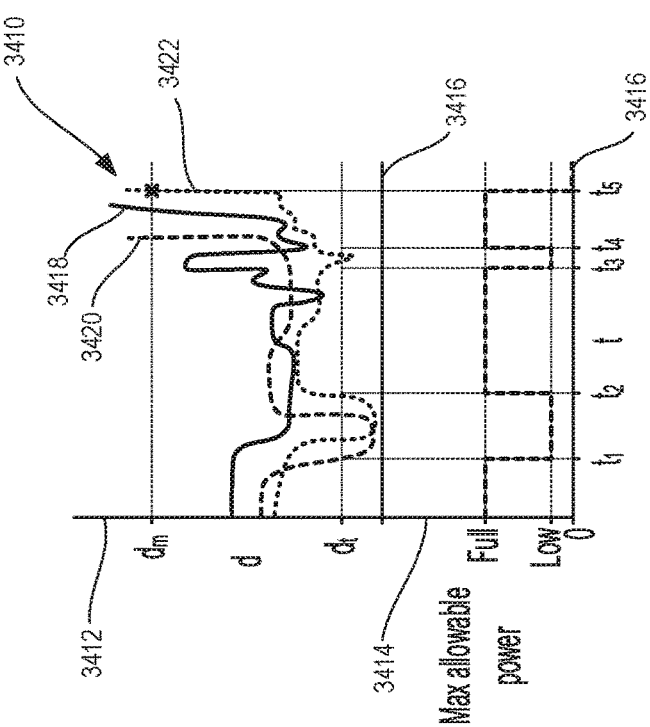
FIG. 74 is a graph of object distance and robotic surgical system power verse time, in accordance with at least one aspect of the present disclosure.

As noted above, a control circuit coupled to the various described sensor assemblies can control the actions or operations of the robotic surgical system or surgical instruments coupled to the robotic surgical system in a variety of different manners. Such control circuits can include the processor 15004 of the robotic surgical system 15000 illustrated in FIG. 22, for example. Accordingly, the control of one such control algorithm executed by a control circuit is illustrated by FIG. 74, which is a set of graphs 3410. The graphs 3410 include a first vertical axis 3412 representing distance between the detected object and a reference (e.g., the distance between a thermal band 3400 and a thermal camera 3404 or the distance between a surgical staff member and a defined detection zone), a second vertical axis 3414 representing power provided to the robotic surgical system, and a horizontal axis 3416 representing time. In this particular prophetic example, the relative position of three objects within the operating room are being monitored, one of which is represented by each of the first line 3418, the second line 3420, and the third line 3422. In this implementation, the control circuit is configured to modulate the maximum allowable power providable to the robotic surgical system according to the relative positions of the objects. The distance $d_m$ represents the maximum detection distance for the robotic surgical system and the distance $d_1$ represents the safety or threshold distance between the monitored objects and the reference. As can be seen by the first line 3418, the first object never violates the distance $d_r$. As can be seen by the second line 3420, the second object is detected as being within the threshold distance $d_r$ at time $t_1$ (i.e., is within a safety zone or safety envelope defined with respect to the reference). Accordingly, the control circuit reduces the maximum allowable power to the robot from the "full" to the "low" value. As can be seen by the third line 3422, the third object likewise moves within the distance $d_r$ after $t_1$ and both of the second and third objects are within the distance $d_r$ for a time period, prior to the second object moving away by at least the distance $d_r$. However, at the time that the second object moves away by at least the distance $d_r$, the third object is nonetheless still within the threshold distance $d_r$ from the reference; therefore, the control circuit maintains the maximum allowable power at the "low" value. However, at time $t_2$, the second object likewise moves away from the reference by at least the threshold distance $d_r$. As there are no objects violating the threshold distance $d_r$, the control circuit increases the maximum allowable power to the "full" value. The third object once again violates the threshold distance $d_r$ between time $t_3$ and $t_4$. In response, the control circuit once again decreases the maximum allowable power to the robotic surgical system to the "low" period during that time period. Further, at time $t_5$, all three objects have moved past the maximum detection distance $d_m$. Accordingly, the control circuit can determine that the surgical procedure has been completed and deactivates the robotic surgical system (as indicated by the maximum allowable power being decreased to zero). In sum, one or more functions of the robotic surgical system (e.g., the maximum allowable power) can be controlled according to the presence of one or more objects or individuals within particular zones or within particular proximities defined according to various reference objects.

Motor Pack Assemblies

Referring back to FIGS. 23 and 25-27, the robotic surgical assembly 40100 can include a motor pack 40050 configured to be received within the sterile barrier housing 40130. The motor pack 40050 may include four motors 40052, 40054, 40056, 40058 with respective drive shafts 40052a, 40054a, 40056a, 40058a for driving various operations of a surgical instrument 40100 coupled to the robotic surgical assembly 40100. Various alternative motor packs 40050 are described herebelow.

Figure 75:
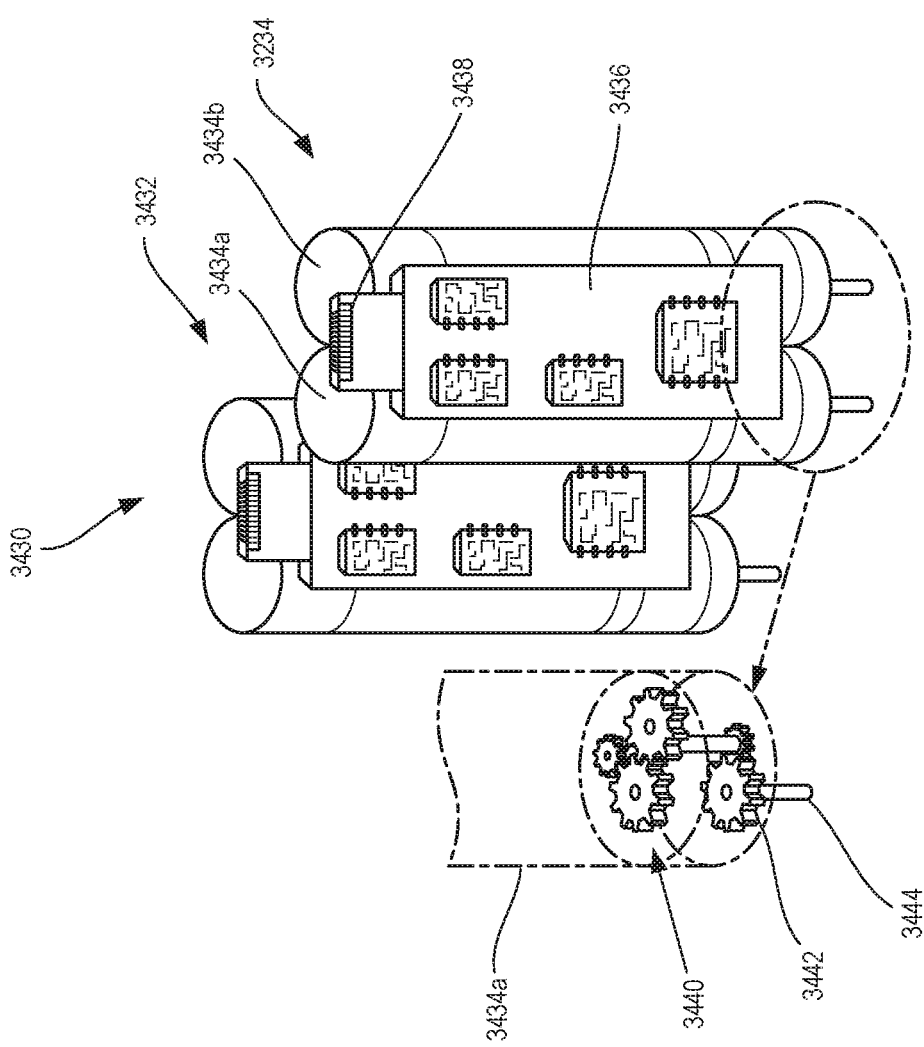
FIG. 75 is a schematic view of a motor pack comprising interchangeable motor assemblies, in accordance with at least one aspect of the present disclosure.

In one aspect, the motors of the motor pack 40050 may be reconfigurable or interchangeable. For example, FIG. 75 illustrates a motor assembly 3430 supportable within a motor pack 40050, wherein the motor assembly 3430 includes a set of modular motor units 3432. In this aspect, the motor pack 40050 can be configured to support sets of modular motor units 3432, as opposed to a singular set of motors, where each of the modular motor units 3432 could be individually swapped out of the motor pack 40050. In the illustrated example, the modular motor units 3432 include a first motor 3434a and a second motor 3434b coupled to control circuitry 3436 and electrical connector 3438 for receiving control signals. However, the modular motor units 3432 can include any number of motors. Configuring the motor assembly 3430 as a collection of modular motor units 3432 provides several benefits compared to utilizing a singular, integral motor assembly, including improving the modularity of the motor pack 40050, improving the ease with repairs can be performed on the motor pack 40050, and permitting new or updated technologies to be integrated into previous versions of the motor pack 40050. For example, the modular motor units 3432 could be swapped between a handheld surgical instrument (e.g., the surgical instrument shown in FIGS. 79-80) and a robotically controlled surgical instrument (e.g., the surgical instruments 400200, 400250 shown in FIG. 23 or 52). As another example, if there is a failure with one of the motors or the control circuitry of the motor pack 40050, then the malfunctioning modular motor unit 3432 can be removed and repaired, without necessitating that the entire motor pack 40050 be disassembled or serviced. As yet another example, because each of the interchangeable modular motor units 3432 includes its own control circuitry 3436, the control circuitry 3436 could include the necessary logic for controlling the modular motor unit 3432 and thus new versions of modular motor units 3432 could be integrated into prior versions of motor packs 40050 without requiring any further hardware upgrades to the robotic surgical system. Therefore, motors that are more efficient (e.g., requiring less power or providing more torque for the same amount of power), provide more torque, have higher hold loads, quieter drives, have longer operational lifespans, generate higher output speeds, have smaller external footprints, generate less heat, have improved water tight configurations, and so on could be integrated into prior versions of motor packs 40050 as these updated motor configurations are developed, without requiring any other hardware updates or other changes to the robotic surgical system architecture. Further, modular motor units 3432 from different manufacturers or even containing different types of motors could be swapped into a motor pack 40050.

Figure 76:
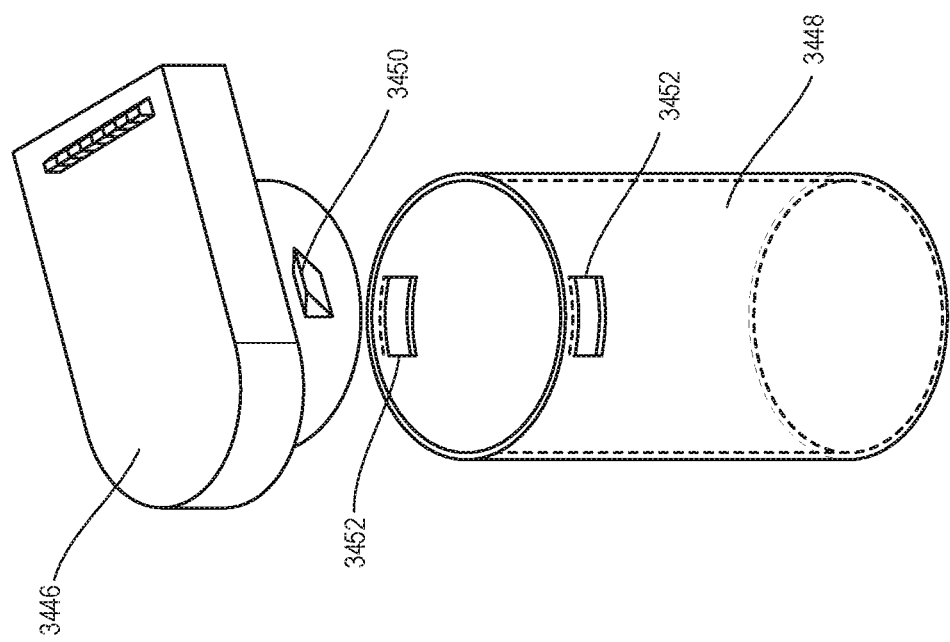
FIG. 76 is a perspective view of a motor pack housing comprising a removable cap, in accordance with at least one aspect of the present disclosure.

In one aspect, the motor pack 40050 can further be configured to assist in swapping out or servicing the modular motor units 3432. For example, FIG. 76 illustrates a motor pack 40050 that includes a body 3448 configured to receive a motor assembly therein, such as a motor assembly 3430 including one or more modular motor units 3432 as shown in FIG. 75 or the motor assembly shown in FIG. 27, and a lid 3446 that is removably affixable to the body 3448. Accordingly, users could remove the lid 3446 from the body 3448, replace and/or service any modular motor units 3432 or other motor assemblies therein, and then replace the lid 3446. The lid 3446 can be removably connectable to the body 3448 via one or more detents 3450 that are configured to engage corresponding slots 3452 disposed on the body 3448, for example.

Figure 27:
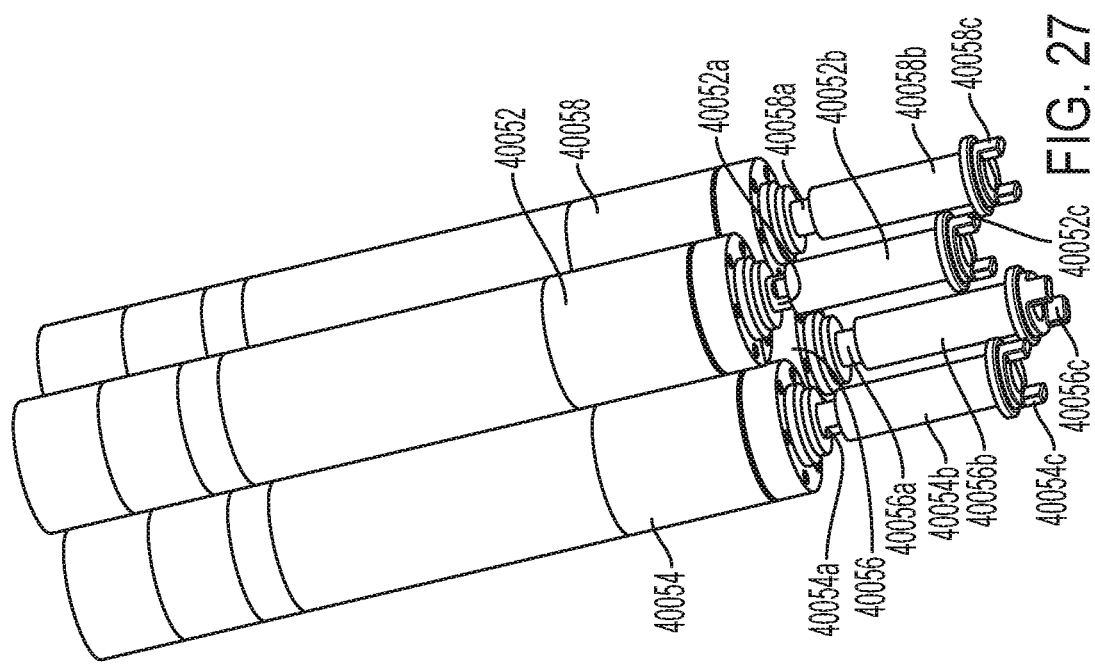
FIG. 27 is a perspective view of motors and respective motor couplers of a motor pack, in accordance with at least one aspect of the present disclosure.

In another aspect, the motors of the motor pack 40050 may be re-orientable or reconfigurable into different configurations. For example, the motors can be swapped between a first configuration or a second configuration, which can in turn cause the motor to produce different effects or provide different functions. Referring again to FIG. 75, one of the motors (e.g., the first motor 3434*a*) within a modular motor unit 3432 can include a gear drive 3440 wherein the last stage 3442 drives an output shaft 3444 (e.g., a drive shaft 52*a*, 54*a*, 56*a*, and 58*a* as illustrated in FIG. 27) that is offset from or not aligned with the longitudinal axis of the motor 3434*a*. Accordingly, the output shaft 3444 of the motor 3434*a* can positioned a first orientation or a second orientation with respect to the motor pack 40050 depending upon the orientation of the modular motor unit 3432 within the motor pack 40050. In various aspects, one or multiple of the motors within a motor pack 40050 and/or a modular motor unit 3432 can be reconfigurable in this manner. Such reconfigurable motors could be utilized to, for example, allow users to configure which drive disk or sterile shell drive coupler (such as the drive coupler 44144*a* shown in FIG. 81B) is coupled to which modular motor unit 3432, which would in turn change which function of the surgical instrument each motor was driving. Further, the use of reconfigurable motor packs 40500 within the IDU 40110 (FIG. 23) would allow users to customize the IDU 40110 for different, more advance, and/or new surgical tools. Further, the motors within the motor pack 40500 could be constructed to have different sizes and/or different power outputs. Therefore, reconfigurable motors within the motor pack 40500 could allow users to align the differently sized motors with particular drive couplers depending upon the type of surgical instrument being coupled to the IDU 40110. Having differently sized motors could be beneficial because not all surgical instrument functions require the same torque thresholds. Therefore, the motor within the motor pack 40050 could be constructed so that some of the motors were larger to produce higher output power/torque and some motors were smaller to produce lower output power/torque, without altering the overall size of the motor pack 40050. During use, the motor pack 40050 could then be reconfigured to align the motors based on the particular desired or required output power/torque for the surgical instrument. In another aspect, for motor packs 40050 that include differentially sized motors or motors have offset output shafts 3444, the motor pack 40050 could additionally include a gearing assembly that engages with the differentially aligned output shafts of the motors and places the output of the motor pack 40050 back on the centerline of the motors.

Figure 77:
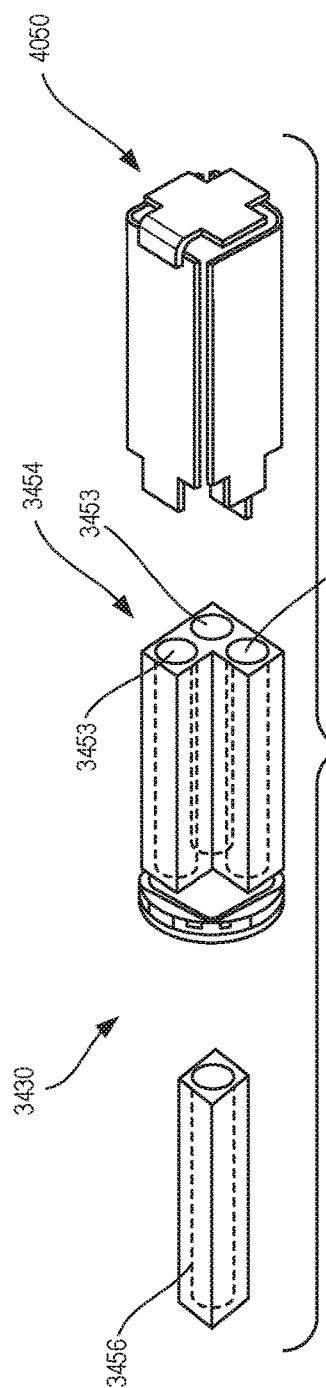
FIG. 77 is an exploded view of a motor pack assembly comprising a removable motor, in accordance with at least one aspect of the present disclosure.
Figure 78:
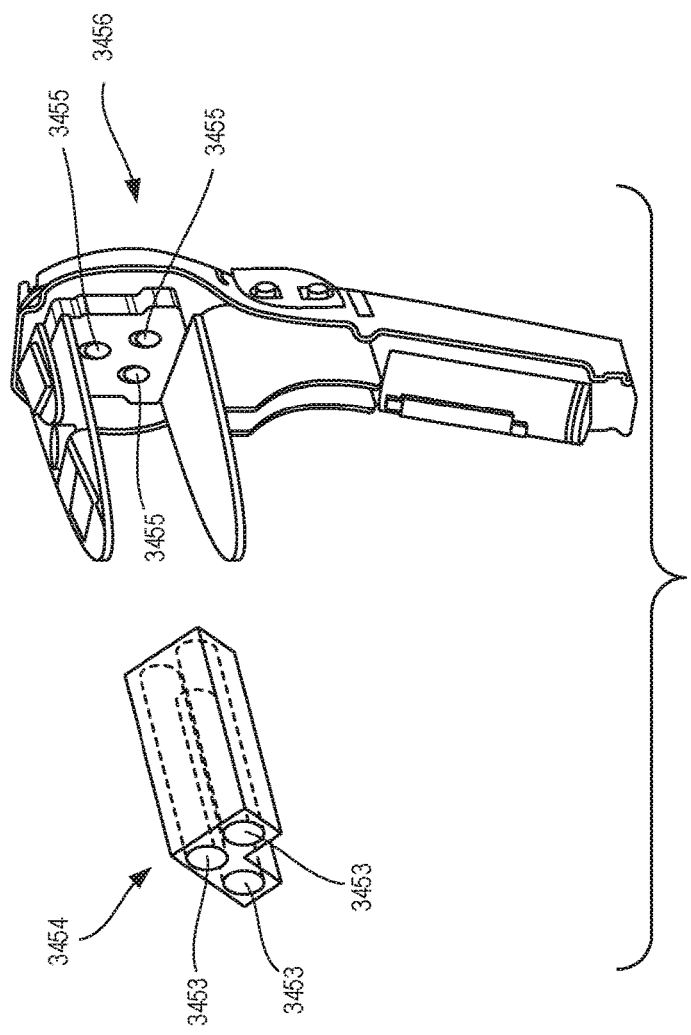
FIG. 78 is an exploded view of the motor pack assembly of FIG. 77 being coupled to a surgical instrument handle, in accordance with at least one aspect of the present disclosure.

Generally speaking, the motor pack 40500 for a robotic surgical system includes a four-motor configuration (see, e.g., FIG. 27), whereas a motor assembly for a handheld surgical instrument is driven by a three-motor configuration. Therefore, motor assemblies for robotic surgical systems and handheld surgical instruments can be incompatible with each other. However, in one aspect, the motor assembly 3430 can be reconfigurable for use in connection with a robotic surgical system 13000 or a handheld surgical instrument. For example, FIG. 77 illustrates a motor assembly 3430 supportable within a motor pack 40050, wherein the motor assembly 3430 includes a first modular motor unit 3456 including a single motor and a second modular motor unit 3454 including three motors 3453. In this example, the motor assembly 3430 can be provided in a first configuration where the first modular motor unit 3456 is utilized in conjunction with the second modular motor unit 3456 and a second configuration where the first modular motor unit 3456 is removed and the second modular motor unit 3454 is utilized alone. When in the first configuration, the motor assembly 3430 can be utilized to drive a robotic surgical system, for example. When in the second configuration, the motor assembly 3430 can be utilized to drive a handheld surgical instrument 3458, as illustrated in FIG. 79, for example. In particular, the second modular unit 3454 can be arranged such that its motors 3453 are aligned with corresponding connectors 3455 or drive shafts of a handpiece 3457 for receiving and/or coupling the handpiece 3457 to the motors 3453. Correspondingly, the motors 3453 of the second modular unit 3454 can be configured to engage and drive the proximal couplers 3461 of the drive assemblies of an electromechanical surgical instrument 3460, as illustrated in FIG. 80, when the electromechanical surgical instrument 3460 is coupled to the handpiece 3457 (e.g., via a coupling collar 3462). Accordingly, depending upon which configuration the motor assembly 3430 is in (i.e., whether the first modular motor unit 3456 is present or remove), the motor assembly 3430 can interchangeably drive either a robotic surgical system or a handheld surgical instrument 3458.

In another aspect, a handheld surgical instrument 3458 could be configured to have a single a non-replaceable, permanent, or integral motor and be configured to receive a modular motor unit containing two motors, such as the modular motor unit 3432 illustrated in FIG. 75. Accordingly, a modular motor units 3432 could interchangeably drive a handheld surgical instrument 3458 in combination with its integral motor or drive a robotic surgical system in combination with a second modular motor unit 3432. The non-replaceable motor for the handheld surgical instrument 3458 could be utilized to drive a particular selected function for the handheld surgical instrument 3458, such as rotation of the instrument's shaft. Further, the motors 3434*a*, 3434*b* of the modular motor unit 3432 could be higher capacity (i.e., capable of producing higher output powers or torques) and could therefore be utilized to drive the surgical functions of the handheld surgical instrument 3458. In yet another aspect, a handheld surgical instrument 3458 could be configured to receive a motor pack 40050 comprising four motors, but lock out or not engage one of the motors that is unneeded. Alternatively, a handheld surgical instrument 3458 that is normally driven by three motors, but includes some manual function (e.g., manual rotation of the instrument's shaft), could engage all four motors of the motor pack 40050 and then convert the manual operation to a motor-driven operation. This aspect could include various adapters and/or additional controls for controlling the motor-driven operation.

Referring now to FIGS. 81A and 81B, the robotic surgical assembly 44100 includes a sterile barrier housing 40130 configured to mate with or otherwise connect to the shell 44060. The sterile barrier housing 40130 includes a hollow shell or body 44132 defining a cavity 44132a therein. The sterile barrier housing 40130 pivotally or hingedly supports a proximal cap or cover 40134 configured and adapted to selectively close a proximal end of the body 44132. The sterile barrier housing 40130 further includes a drive transfer assembly 44140 supported on, or connected to, a distal end of the body 44132. The cavity of the body 44132 of the sterile barrier housing 40130 is configured to slidably receive a motor pack 40050 (FIG. 23) or the like therein.

The drive transfer assembly 44140 of the sterile barrier housing 40130 includes a body portion 44142 extending from the distal end of the body 44132. The body portion 44142 of the drive transfer assembly 44140 has a non-circular form (e.g., substantially D-shaped, as illustrated) outer profile for keyed receipt within a complementary non-circular (e.g., D-shaped, as illustrated) passage or opening of the pulley 40048 (FIG. 23) of the carriage 40042 (FIG. 23). While a D-shaped, transverse cross-sectional profile is shown and described, any non-circular, transverse cross-sectional profile may be used to provide a keyed connection, including and not limited to hex, Allen, star, cross, double "D", "T", torx, val, phillips, helix profiles.

The drive transfer assembly 44140 rotatably supports at least one, and as shown in FIGS. 81A and 81B, four drive transfer shafts 44144, 44146, 44148, 44150. As illustrated, a proximal end of each drive transfer shaft 44144, 44146, 44148, 44150 non-rotatably supports a respective drive coupler (of which only driver coupler 44144a is shown in FIG. 81B) that, via the motor couplers 41052b, 41054b, etc. (FIG. 27), are configured and adapted for non-rotatable connection to a drive shaft 41052a, 41054a, 41056a, 41058a (FIG. 27) of a respective motor 41052, 41054, 41056, 41058 (FIG. 27) of motor pack 40050. In particular, each drive coupler is translatably supported on respective drive transfer shaft 44144, 44146, 44148, 44150 via a pin-slot arrangement such that the couplers may float on respective drive transfer shaft 44144, 44146, 44148, 44150. Each drive coupler defines a respective mating feature configured to receive and transmit rotational forces from respective drive shafts 41052a, 41054a, 41056a, 41058a of the motors 41052, 41054, 41056, 41058 of the motor pack 40050. A distal end of each drive transfer shaft 44144, 44146, 44148, 44150 supports a respective drive coupler 44144b, 44146b, 44148b, 44150b, which are configured and adapted for non-rotatable connection to proximal couplers 3461 (FIG. 80) of the drive assemblies of the electromechanical surgical instrument (e.g., the surgical instrument 40200 illustrated in FIG. 23, the surgical instrument 43250 illustrated in FIG. 57A, or the surgical instrument 3460 illustrated in FIG. 80). It is contemplated that each drive coupler 44144b, 44146b, 44148b, 44150b may resemble a crown gear or the like.

The motor pack 40050 and the sterile barrier housing 40130 can have different shapes and configurations than those illustrated in FIGS. 81A and 81B, however. In one aspect, the motor pack 40050 and/or sterile barrier housing 40130 can be dimensioned or include alignment features configured to urge the motor pack 40050 into proper alignment with the sterile barrier housing 40130 when the motor pack 40050 is being inserted into the sterile barrier housing 40130 and/or when the sterile barrier housing 40130 is being closed, as opposed to the cavity 132a of the sterile barrier housing 40130 having a cylindrical profile as illustrated in FIGS. 81A and 81B. For example, FIGS. 82A-82C illustrate a motor pack 40050 and a corresponding sterile barrier housing 40130 including a variety of characteristics to promote the alignment of the motor pack 40050 within the sterile barrier housing 40130.

In one aspect, the body 3471 of the motor pack 40050 and the cavity 44132a of the sterile barrier housing 40130 can have a complementary non-radially symmetric shape, such as an oval. The protrusion body 3471 and/or cavity 44132a can have a symmetric profile or may be tapered, for example, to improve ease of use by allowing for the keyed interaction between the protrusion body 3471 and the cavity 44132a to get tighter the farther the motor pack 40050 is inserted into the sterile barrier housing 40130.

In another aspect, the motor pack 40050 can include a protrusion 3470 or alignment feature extending from its body 3471 and the sterile barrier housing 40130 can include a corresponding recess 3472 that is configured or keyed to receive the protrusion 3470. The protrusion 3470 can be dimensioned to physically prevent the motor pack 40050 from being inserted into the sterile barrier housing 40130 in any orientation except where the protrusion 3470 is aligned with the keyed recess 3472. The protrusion 3470 and/or recess 3472 can have a symmetric profile or may be tapered, for example, to improve ease of use by allow for the keyed interaction between the protrusion 3470 and the recess 3472 to get tighter the farther the motor pack 40050 is inserted into the sterile barrier housing 40130.

In another aspect, the motor pack 40050 can include a protrusion 3473 or alignment feature extending from its body 3471 and the cap 40134 of the sterile barrier housing 40130 can include a corresponding recess 3475 configured or keyed to receive the protrusion 3473 when the motor pack 40050 is positioned within the sterile barrier housing 40130 and the cap 40134 is being closed. The recess 3475 could thus be configured to physically interact with the protrusion 3473 of the motor pack 40050 as the cap 40134 is closed, aligning or seating the motor pack 40050 within the sterile barrier housing 40130. In one further aspect, the protrusion 3473 can include an electrical connector and the recess 3475 can include a corresponding electrical connector configured to electrically and communicably couple the motor pack 40050 to the sterile barrier housing 40130 when the cap 40134 is closed, thereby allowing electrical signals and other controls signals to be transmitted to the motor pack 40050 through the corresponding electrical connectors.

Although the particular example illustrated in FIGS. 82A-82C includes all three of the aforementioned aspects, this example is merely for illustrative purposes and the motor pack 40050 and/or sterile barrier housing 40130 can include any combination of one or multiple of these aspects.

In various aspects, the motors of the various motor assemblies described herein can be inline or offline from the surgical tool, the IDU 40110, and/or any other component of the robotic surgical system. In one aspect, if a particular type of motor pack 40500 is incapable of driving a desired function of a robotic surgical system and/or a handheld surgical instrument, then the motor pack 40500 could be supplemented with more than one motor operating in parallel to one another to increase the capabilities of the motor pack 40500. Accordingly, a motor and/or motor pack 40500 could be configured to piggyback another primary motor pack 40500 being utilized to drive a robotic surgical system, allowing the robotic surgical system 40100 to operate inline from the macro perspective of the overall system and the motor pack 40500 relative to the surgical tool, but allow the offset motor and/or motor pack 40500 to boost the primary drive motor pack 40500 to which it is coupled and thereby preform at a level beyond the standard output configuration of that size and type of motor pack 40500. Various inline motor assembly configurations are described in connection with PCT Application Publication No. WO2017/210516, titled ROBOTIC SURGICAL ASSEMBLIES AND INSTRUMENT DRIVE UNITS THEREOF; PCT Application Publication No. WO2017/205308, titled ROBOTIC SURGICAL ASSEMBLIES; and U.S. Patent Application Publication No. US2018/0168748, titled ROBOTIC SURGICAL ASSEMBLIES, each of which is hereby incorporated by reference herein in its entirety. Various offline motor assembly configurations are described in connection with PCT Application Publication No. WO2016/183054, titled COUPLING INSTRUMENT DRIVE UNIT AND ROBOTIC SURGICAL INSTRUMENT; U.S. Patent Application Publication No. US2018/0153628, titled OFFSET INSTRUMENT DRIVE UNIT; and PCT Patent Application Publication No. WO2016/043845, titled ROBOTICALLY CONTROLLING SURGICAL ASSEMBLIES, each of which is hereby incorporated by reference herein in its entirety.

Robotic Surgical Assembly Adapter and Bailout Assemblies

Referring back to FIGS. 23-27, the robotic surgical assembly 40100 can include an IDU 40110 that is drivingly couplable to a sterile barrier collar assembly 40170 (or the sterile barrier collar assembly 43630 described in connection with FIGS. 51-53), a carriage 40042 (or a sterile shell 40060 situated thereover), and an electromechanical surgical instrument 40200 for driving the various functions of the surgical instrument 40200 via a motor assembly supported within the IDU 40110. The robotic surgical assembly 40100 described above can additionally include various integrated adapters, bailouts, or other mechanisms for limiting damage to the robotic surgical assembly 40100 and/or robotic surgical system 15000 (FIG. 22), returning a damaged surgical instrument 40200 to a removal state, and performing various other functions.

In one aspect, the robotic surgical assembly 40100 can include motor torque fuses that are configured to limit the maximum force exertable from the motor pack 40050 on the surgical instrument 40200. For example, the sterile barrier collar assembly 43630 could be configured to function as both a coupling mechanism (e.g., between the IDU 40100 and the surgical instrument 40200) and a fuse to prevent over torqueing of an attached surgical instrument 40200. In particular, one or both of the drive transfer assemblies 43668, 43670 of the sterile interface module 43630 could have reduced cross-section along their length that would encourage the drive transfer assemblies 43668, 43670 to fusably fail before either the motor gear train of the motor pack 40050 or the drive train of the surgical instrument 40200 in the event that a high torque condition occurs. Accordingly, this would reduce the possibility of damage to the reusable components of the robotic surgical assembly 40100 and the surgical instrument 40200. Preventing damage to the surgical instrument 40200 in the event that a high torque condition occurs is especially desirable because if the drive train of the surgical instrument 40200 is damaged or jams during a surgical procedure, the surgical instrument 40200 could cause damage to any tissue grasped or being treated by the surgical instrument 40200. Therefore, having the sterile barrier collar assembly 43630 or a component thereof fail is a much more desirable alternative.

In one aspect, the drive transfer assemblies 43668, 43670 of the sterile barrier collar assembly 43630 could be configured to reduce or eliminate built-up torque in the rotary driver due to the motor pack 40050. For example, FIGS. 83A and 83B illustrate a sterile barrier collar assembly 43630 engaged with the rotary drivers 3480 from the motor pack 40050 (e.g., drive shafts 41052a, 41054a, 41056a, 41058a illustrated in FIG. 27) or sterile barrier housing 40130 (e.g., the drive transfer shafts 44144, 44146, 44148, 44150 of the drive transfer assembly 44140 illustrated in FIG. 81A). In this aspect, the rotary drivers 3480 each include a tab 3482 having a tapered profile with beveled edges 3483. Further, the drive couplers 3484 each include a recess 3486 and that is configured or keyed to receive the tab 3482 from a corresponding rotary driver 3480 and likewise includes beveled edges 3487. This profile of the tabs 3482 of the rotary drivers 3480 and the corresponding recesses 3486 of the drive couplers 3484 allows for the reduction of built-up pressure in the robotic surgical assembly 40100 if the motor pack 40500 were to fail when the sterile barrier collar assembly 43630 is released from the driver carriage of the surgical instrument 40200. In particular, the illustrated profile allows for complete engagement between the rotary drivers 3480 and the drive couplers 3484 when there is no force driving them apart, thereby allowing the rotary drivers 3480 and the drive couplers 3484 to function as normal. However, when the sterile barrier collar assembly 43630 is released from the surgical instrument 40200, the distally slidable motion allows built up torque to be released from the coupling between the rotary drivers 3480 and the drive couplers 3484 because the tabs 3482 partially disengage from the corresponding recesses 3486 and the beveled edges 3483, 3487 allow for the rotary drivers 3480 and/or drive couplers 3484 to slip or move with respect to each other. The slippage thereby allows for the release of any built-up torque, which in turn allows for easy removal of the components of the robotic surgical assembly 40100.

In one aspect, the robotic surgical assembly 40100 can include a mechanism for physically actuating or manipulating a surgical instrument 40100 coupled to the robotic surgical assembly 40100 (or a portion thereof) during the operation thereof. In some situations, the motor pack 40050 can become jammed or suffer an electrical or mechanical failure that results in the surgical instrument 40200 not responding to the surgeon's controls, which can be especially problematic when the surgical instrument 40200 is inserted within a patient during a surgical procedure. In one aspect, the motor pack 40050 can be disengaged from the sterile interface module 43630, leaving the sterile interface module 43630 connected to the surgical instrument 40200 such that the drive couplers 3484 (which are normally driven by the motor pack 40500) are visible and able to be accessed. When exposed, the drive couplers 3484 could be manually drivable to actuate the surgical instrument 40200 connected thereto. For example, in FIGS. 84A-84C the robotic surgical assembly 40100 can further include an interface module 3492 that is configured to engage with the drive couplers 3484 of the sterile interface module 43630 and allow the drive couplers 3484 to be manually driven by standard sterile OR tools (e.g., hemostats 3498) to manually actuate various functions of the surgical instrument 40200, including allowing the surgical instrument 40200 to be manipulated such that it can be extracted from the patient. In one aspect, the interface module 3492 includes a driver 3490 that is configured to be manually actuatable drive a drive coupler 3484 that is coupled to the interface module 3492. In the illustrated example, the driver 3490 includes a first end 3494 that is configured to engage with a corresponding mating portion of a driver coupler 3484 (e.g., the recess 3486 of the drive coupler 3484 as illustrated in FIGS. 83A and 83B) and a second end 3496 that is configured to extend to be manually grippable to actuatable by tools. The second end 3496 can include a tab or projection. In one aspect, the driver 3490 is positioned on the interface module 3492 to engage with a particular driver coupler 3484 of the sterile interface module 43630. For example, the driver 3490 can be positioned in the interface module 3492 to engage with the drive coupler 3484 that is configured to control a critical function of the surgical instrument 43250, such as the driver coupler 3484 that controls the I-beam shaft for a surgical stapling and cutting instrument. Although illustrated as including a single driver 3490, in other aspects the sterile interface module 3492 can include multiple drivers 3490.

Figure 85B:
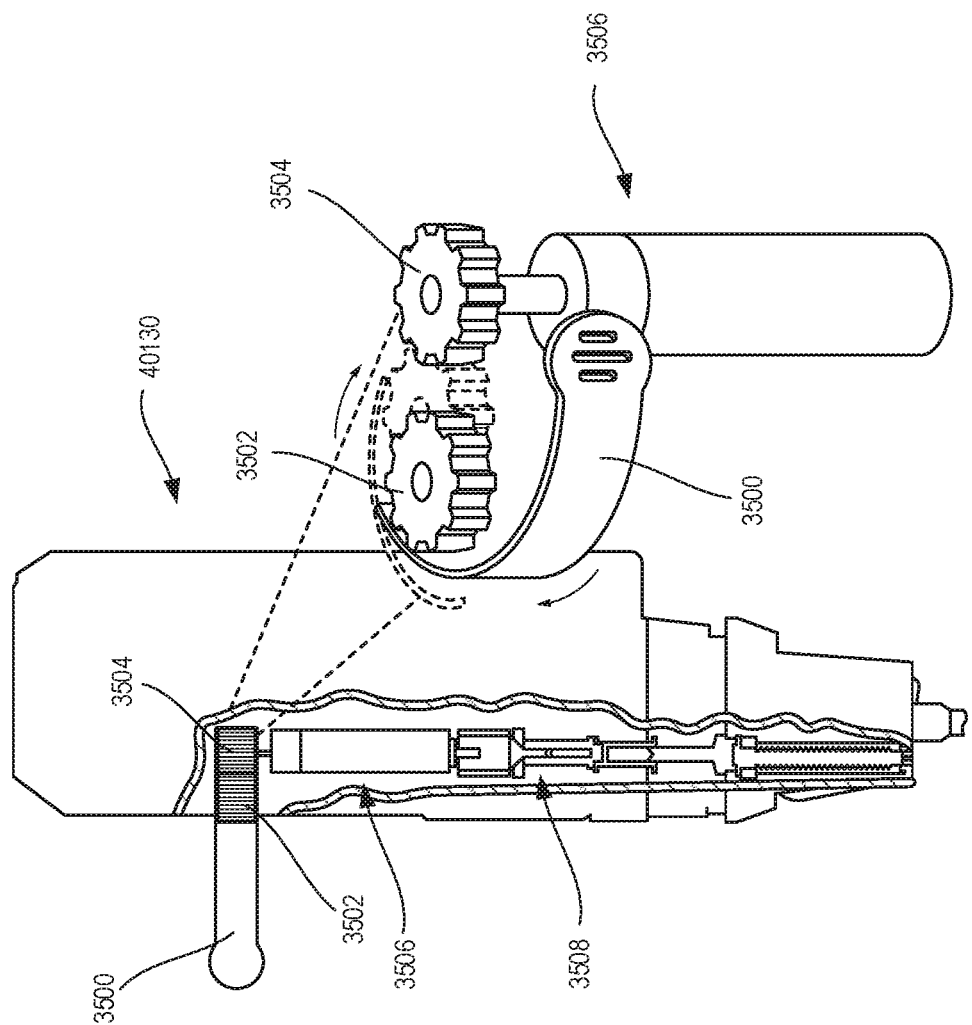
FIG. 85B is a cutaway view of the instrument drive unit of FIG. 85A, in accordance with at least one aspect of the present disclosure.
Figure 85A:
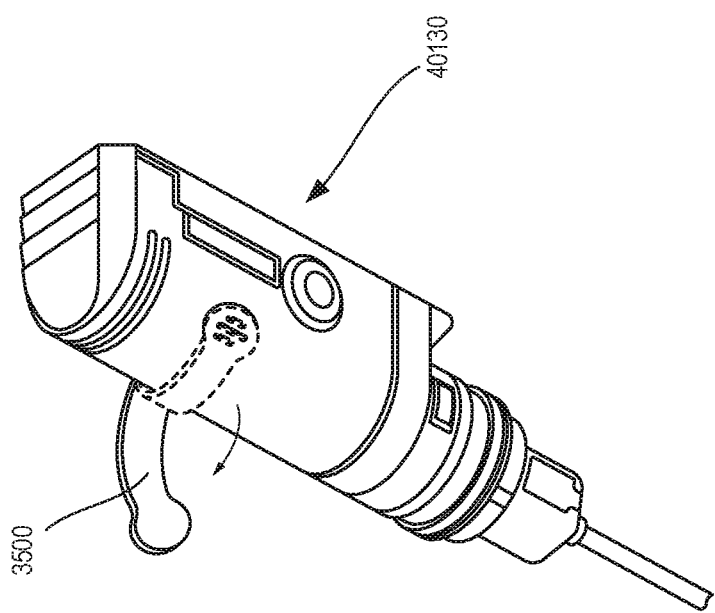
FIG. 85A is a perspective view of an instrument drive unit comprising a bailout lever, in accordance with at least one aspect of the present disclosure.

In one aspect, the robotic surgical assembly 40100 can include a mechanism for manually bailing out the robotic surgical assembly 40100 during operation. For example, the robotic surgical assembly 40100 could include a bailout lever that, when actuated, either interrupts the drive train between the motor pack 40500 and the sterile collar assembly 43630 or causes the motor pack 40500 and the sterile collar assembly 43630 to counter-rotate. On such example is illustrated in FIGS. 85A and 85B, which shows a sterile barrier housing 40130 including a bailout lever 3500 that is actuatable between a first position that permits normal operation of the robotic surgical assembly 40100 and a second position that interrupts the operation of the robotic surgical assembly 40100. In particular, the bailout lever 3500 is coupled to a first or bailout gear 3502 that is transitioned from a first position that is disengaged from the drive train 3508 between the motor pack 40500 and the sterile collar assembly 43630 and a second position that is engaged with the drive train 3508 such that the operation of the drive train 3508 is interrupted as the bailout lever 3500 is actuated from its first position to its second position. As the bailout gear 3502 is transitioned to the second position, the bailout gear 3502 engages with a corresponding second or motor gear 3504, as shown in FIG. 85B. The engagement between the bailout gear 3502 and the motor gear 3504 locks the motor gear 3504, which in turn prevents actuation or operation of the motor 3506 to which the motor gear 3504 is coupled and/or the motor assembly 41114 (FIG. 26) as a whole.

In one aspect, the bailout lever 3500 could be configured such that actuating the bailout lever 3500 (i.e., transitioning the bailout lever 3500 to the second position) could permanently deform or otherwise render the sterile barrier housing 40130 no longer usable. In another aspect, the bailout lever 3500 could include a resettable feature that allows the bailout lever 3500 to be reset (and the sterile barrier housing 40130 utilized again) after it has been actuated, unless an excessive load was imparted upon the bailout gear 3502 when engaged with the motor gear 3504 and/or drive train 3508. In one aspect, the bailout lever 3500 could have ergonomic features that are easily gripped. In another aspect, the bailout lever 3500 could include a connector that is configured to engage with a second lever member that allows the second lever member to be attached to the bailout lever 3500 to extend the length of the bailout lever 3500 and thereby provide an improved mechanical advantage. In one aspect, the bailout lever 3500 could include a unidirectional mechanism (e.g., a ratchet mechanism) that is configured to prevent the bailout lever 3500 from being actuated in the incorrect direction. The unidirectional mechanism could be engaged or disengaged according to the type of drive train 3508 to which the bailout lever 3500 is coupled (e.g., a drive train for articulating a surgical instrument 40200 or a drive train for actuating the jaw(s) of a surgical instrument). Further, the unidirectional mechanism could be configured selectably constrain counter-rotating movement of the drive train 3508 (or a component thereof). For example, in robotic surgical assemblies 40100 that permit manual actuation (e.g., for resetting the robotic surgical assembly 40100, as illustrated in FIGS. 84A-84C), the unidirectional mechanism could be configured to constrain counter-rotating movement in the direction in which the robotic surgical assembly 40100 is manually actuatable.

In one aspect, the robotic surgical assembly 40100 can include interchangeable or replaceable bailout systems to allow for jammed or broken components of the robotic surgical assembly 40100 to be reset. The interchangeable bailout assemblies could be couplable to the sterile collar assembly 43630, for example. In use, users could disconnect the sterile collar assembly 43630 from the IDU 41110, couple an interchangeably bailout assembly to the sterile collar assembly 43630, and then manually actuate the bailout assembly to reset the sterile collar assembly 43630 and/or a surgical instrument 40200 coupled thereto to a particular position (e.g., full retraction or centering of the drive assembly of the sterile collar assembly 43630). In one aspect, the bailout assembly could be configured to actuate all of the drive assembly members to their home positions simultaneously. In one aspect, the bailout assembly could include a return or resetting lever that is selectively couplable to a specific drive member, thereby allowing the user to individually actuate or retract each drive member to its home state. In one aspect, the bailout assembly could include a sensor configured to sense a parameter of the bailout assembly to know where the home position is of the drive assemblies are and controllably retract to the drive assemblies to their home positions, preventing and over-retraction or centering of the drive assemblies. In one aspect, the bailout assembly could include a control circuit configured to communicably connect to the surgical instrument 40200 when coupled to the robotic surgical assembly 40100 (e.g., through electrical contacts disposed on surgical instrument 40200 and the components of the robotic surgical assembly 40100). The control circuit could be configured to identify the surgical instrument 40200 and then control the bailout assembly according to the surgical instrument type (i.e., configure its parameters to return the drive assemblies to the home positions particular for that surgical instrument type). The control circuit could also be configured to mark the surgical instrument 40200 as damaged to prevent reuse of the surgical instrument 40200. For example, the control circuit could write to a value to an EEPROM within the surgical instrument 40200 that marks the surgical instrument 40200 as damaged and thereby prevents the surgical instrument 40200 from operating thereafter. In one aspect, the bailout assembly could include a motor or other powered system for automatically actuating the drive assembly to which it is connected to its home position, rather than requiring that users manually actuate the bailout assembly to reset the robotic surgical assembly 40100. Further, the bailout assembly could include controls or be communicably coupled to controls, such that users can cause the bailout assembly to reset the robotic surgical assembly 40100 to the desired position via actuation of the controls.

Detachable Surgical Device Motor Pack

As previously disclosed above with respect to FIGS. 4 and 4A, a surgical environment may incorporate a robotic surgical system. The robotic surgical system 13000 includes robotic arms 13002, 13003, a control device 13004, and a console 13005 coupled to the control device 13004. As illustrated in FIG. 4, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Each of the robotic arms 13002, 13003 is made up of a plurality of members connected through joints and includes a surgical assembly 13010 connected to a distal end of a corresponding robotic arm 13002, 13003.

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor I . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. In some instances, more than one surgeon may be required during a surgical procedure and it may be difficult to coordinate separate tasks among the surgeons. Alternatively, a robotic system may not have sufficient arms to carry out multiple tasks. Such a handheld device may also have the capability of using multiple detachable end effectors or surgical tools, and may also have other modular capabilities. Examples of such a modular hand-held surgical instrument may be found in U.S. patent application Ser. No. 15/382,285, titled MODULAR BATTERY POWERED HANDHELD SURGICAL INSTRUMENT WITH VOLTAGE SAG RESISTANT BATTERY PACK and filed Dec. 16, 2016, the disclosure of which is herein incorporated by reference in its entirety and for all purposes.

For cost effectiveness, it may be useful to have the modular end effectors or surgical tools usable by the hand-held device also to be employed by the robotic device. Thus, a single modular end effector or surgical tool may be installed in either the modular hand-held device or the robotic device. In such cases, all electrical and mechanical interfaces for the modular end effectors must be consistent between the hand-held and the robotic platforms. In some aspects, this consistency may be obtained by using a detachable surgical device motor pack. This detachable motor pack may be installed on an end of a robotic surgical device arm or within a housing of the modular hand-held device. The modular end effector may then mate with the detachable motor pack in either of the hand-held instrument or the robotic instrument. Some exemplary aspects of a detachable motor pack may be found in U.S. Pat. No. 8,912,746 titled SURGICAL INSTRUMENT MOTOR PACK LATCH filed Oct. 26, 2012, the disclosure of which is herein incorporated by reference in its entirety and for all purposes.

The detachable motor pack may comprise a housing, a plurality of motors retained within the housing, a controller configured to control one or more operations of the plurality of motors, a first interface portion configured to releasably attach to a hand-held surgical instrument and to a robotic surgical instrument, and a second interface portion configured to releasably attach to a first surgical end effector of the hand-held surgical instrument and to a second surgical end effector of the robotic surgical instrument. In some aspects, the end effector of the hand-held surgical instrument may be the same as the end effector of the robotic surgical instrument. In other aspects, the end effector of the hand-held surgical instrument may differ from the end effector of the robotic surgical instrument.

The first interface portion of the detachable motor pack may comprise mechanical and electrical interface components that, when releasably attached to the hand-held surgical instrument, are configured to operate with a handle assembly interface. The handle assembly interface may communicate mechanical, electrical, or both mechanical and electrical outputs to control the detachable motor pack operations. Mechanical outputs may be derived from one or more buttons, slides, triggers, or other mechanically operated components to direct the operation of the detachable motor pack. Electrical outputs to control the detachable motor pack operations may include electrical signals to the detachable motor pack controller. The detachable motor pack control may also provide status and operational signals in return to the handle assembly interface to provide status information to controller electronics in the hand-held surgical device.

The first interface portion of the detachable motor pack may comprise mechanical and electrical interface components that, when releasably attached to the robotic surgical instrument, are configured to operate with a robotic arm interface. In some aspects, the robotic arm interface may be part of the electrical drives connected to the robotic control device. In some aspects, the robotic arm interface may be configured to conduct one or more drive signals or one or more control signals to the first interface portion of the detachable motor pack. The robotic arm interface may be in electrical and data communication with robotic system control device. Electrical outputs from the robotic arm interface may control the detachable motor pack operations and may include electrical signals to control the detachable motor pack controller. In some aspects, the control device may control the plurality of motors disposed within the detachable motor pack, with each motor configured to drive a pushing or a pulling of one or more cables, such as cables coupled to the modular end effector. The detachable motor pack control may also provide status and operational signals to the robotic surgical system control device to provide status information to the robotic system.

The second interface portion of the detachable motor pack is configured to mate with an interface of the modular end effector or surgical tool. The second interface portion may include mechanical components configured to drive the mechanical drive portions of the modular end effector. The drive portions of the modular end effector may control a variety of mechanical functions of the end effector including, without limitation, a grasping jaw, a cutting implement, or a stapling anvil. Each mechanical component of the second interface portion may be mechanically coupled directly to a motor shaft, or to one or more gears comprising a mechanical drive train. The second interface portion may include electrical components configured to deliver electrical energy to the modular end effector. Such energy may be used to power one or more RF electrodes for sealing or cutting operations, or the energy may be delivered to a high frequency component such as a piezoelectric stack used by an ultrasonic cutter or tissue sealer. The electrical components of the second interface may also be used to receive sensor information from the end effector. Such sensor information may be relayed to control components of either the hand-held device or the robotic device. Sensor data received from the end-effector or surgical tool may include, without limitation, limit signals indicating that a desired mechanical motion has reached an end of travel for safe operation.

The first interface portion may incorporate features designed to secure the detachable motor pack to either the robotic device or the hand-held device. Such features may include latching features, such as bolt holes or hooks, and alignment features such as dove-tails or alignment pins. The second interface portion may incorporate features designed to secure the detachable motor pack to a modular end effector or surgical tool. The features for securing the detachable motor pack to either the robotic device or the handheld device may be the same as or different from the features for securing the detachable motor pack to the modular end effectors. In one aspect, the features for securing the detachable motor pack to the end effectors and to the hand-held surgical device or robotic surgical device may be included in either the first interface portion or the second interface portion. In another aspect, the features for securing the detachable motor pack to the end effectors and to the hand-held surgical device or robotic surgical device may be incorporated into the motor pack housing. It is understood that the features for securing the detachable motor pack to the end effectors and to the hand-held surgical device or robotic surgical device may be incorporated in both the housing and in the first and second interface portions.

As disclosed above, the detachable motor pack includes a plurality of motors. The detachable motor pack may include one, two, three, four, or more motors as required to drive the functions of the end effectors. Such motors may include any type of motor appropriate for the use with the detachable end effectors. Examples of such motors may include, without limitation, DC brushed motors, DC brushless motors, servo motors, direct drive motors, and stepper motors. Such motors may also incorporate components capable of sensing the rotational position of the motor shaft such as optical encoders, magnetic encoders, or resistive encoders. The encoders may be incremental or absolute. The detachable motor pack may also include electronics required to power the encoders and transmit positional and velocity data obtained from the encoders. In this manner, the detachable motor pack may provide motor positional and velocity data to the platform to which it is attached (the hand-held device or the robotic device) via the first interface portion. The motors may be mechanically linked to one or more gears or drive trains. The motors may be mechanically coupled to the mechanical components of the second interface portion. In this manner, the motors of the detachable motor pack may be able to drive the mechanical components of the detachable end-effectors or surgical tools when the end-effectors are detachably linked to the motor pack.

The detachable motor pack may also include a controller. The controller may comprise any one or more digital, analog, mixed analog-digital, and integrated circuit components. The controller may further include a processor unit, one or more dynamic memory components, one or more static memory components, and one or more interface components. The static memory components may store instructions, that when executed by the processor, will cause the processor to direct the motion of the plurality of motors.

The controller interface components may include input components and output components. In one aspect, the controller input components may be used by the controller to receive instructions for the operation of the detachable motor pack from the instrument platform (either the hand-held device or the robotic device). In one non-limiting example, the controller may be configured to receive identification information from the surgical platform (either the hand-held device or the robotic device). In some aspects, the detachable motor pack may have independent usage configurations depending on whether it is attached to the robotic device or the hand-held device. The motor pack may have different or fewer functions when attached to the hand-held device than when used with the robot tool driver. In one non-limiting example, functionality changes may include changing the use of a multi-axis articulating surgical tool shaft from multi-axis articulation (for the robotic platform) to single axis articulation (for the hand-held surgical device). The multi-axis articulation of the end-effector may result in more robust independently controllable jaw motions than the single-axis articulation. In another non-limiting example, the instrument platform may provide instructions to move a motor associated with a grasping jaw of an end-effector to a certain position. It may be recognized that the use of a detachable motor pack would permit the platforms to have the modular capability regarding the type of surgical tool used at any time along with the plasticity of how the surgical tool is controlled by each platform.

The input components may also receive data from the motor encoders to allow the processor to properly drive the motors based on their speed and rotary position. The input components may also receive data from sensors on the detachable end-effectors (via the second motor pack interface portion). Such sensor data may also be used to control the motion of the motors. In one non-limiting example, limit switch sensor data may be provided by the end-effectors to notify the controller that a mechanical component on the end-effector has attained a limiting position beyond which it may not safely move, for example a tissue grasping jaw. The input components may also receive device identifying information from the detachable end-effectors. Such identifying information may be used by the controller to associate one of the plurality of motors with a single mechanical activation of the end-effector (such as a grasping jaw). As one non-limiting example, the identifying information from an RF tissue sealing device may be used by the motor pack controller to associate a first motor with a grasping jaw motion, and a second motor with a sliding knife motion.

The controller output interface components may be used to direct the rotary action of the plurality of motors. For example, the output interface components may control the action of the drive electronics for powering the motor windings. The output interface components may also be used to transmit status data to the surgical device platform (the hand-held device or the robotic device). Such status data may relate to the position, direction, and/or velocity of the plurality of motors. The status data may also provide error information, for example that one of the motors is not responsive. The status data may also provide information regarding the state of the coupling of the motor pack first interface portion with the surgical platform (the hand-held device or robotic device) or the state of coupling of the detachable end-effector with the second interface portion. Such information may be useful to determine that the detachable motor pack is properly affixed to the surgical platform or that the end-effector is properly affixed to the motor pack.

In addition to the disclosure above, additional configurations related to the use of the detachable motor pack with a hand-held surgical device may be further described. In one aspect, the hand-held surgical tool may be configured to accept a sterile barrier between a handle component and the detachable motor pack. Accordingly, sterility of the handle component may be maintained while the detachable motor pack is changed. In another aspect, the end-effector or surgical tool may be detachably mounted on the hand-held device frame directly while the detachable motor pack is inserted or exchanged. In yet another aspect, the detachable end-effector or surgical tool may transmit identifying information or operational parameters to the hand-held device controller. Such information or parameter transfer may be effected either directly to the hand-held device controller or indirectly via the interfaces of the detachable motor pack. In this manner, the operation of the detachable end-effector or surgical tool may be controlled by a combination of instructions received from one or more of the hand-held device controller and the motor pack controller.

Additional aspects of the detachable motor pack are further disclosed herein.

In one aspect, the detachable motor pack may include a user display unit, in which the controller is configured to control the user display unit. The display unit may display information related to the velocity and/or position of each of the motors. The display unit may further display fault information. Non-limiting examples of fault information may include mis-alignment of the motor pack with an interface on the surgical platform (hand-held device or robotic device), mis-alignment of the detachable end-effector with the motor pack, or fault data related to malfunctions of the motors. The display unit may additionally display identification information received by the motor pack from the end-effector.

In another aspect, the detachable motor pack may further comprise one or more electrical contacts configured to source electrical signals to one or more mating electrical contacts of the hand-held surgical instrument thereby providing the data to a user display unit of the hand-held surgical instrument. The electrical contacts may form part of the electrical components of the first interface portion of the motor pack. Such information may include, without limitation, identification information from the end-effector, motor operation information (velocity and position) of the motors, and fault information as disclosed above.

In another aspect, the controller of the motor pack may be configured to control a first set of operations of the plurality of motors when the detachable motor pack is releasably attached to the hand-held surgical instrument, and to control a second set of operations of the plurality of motors when the detachable motor pack is releasably attached to the robotic surgical instrument.

In yet another aspect, the controller of the detachable motor pack may be configured to receive one or more operating parameters from a first surgical tool, such as a first detachable end-effector, and a second surgical tool such as a second detachable end-effector. The detachable motor pack controller may be configured to control the first set of operations based on the one or more operating parameters received from the first surgical tool or end-effector and the controller may be configured to control the second set of operations based on the one or more operating parameters received from the second surgical tool or end effector.

FIGS. 86A-88 depict a non-limiting example of a detachable motor pack that may be used in concert with an exemplary detachable surgical tool.

Figure 86A:
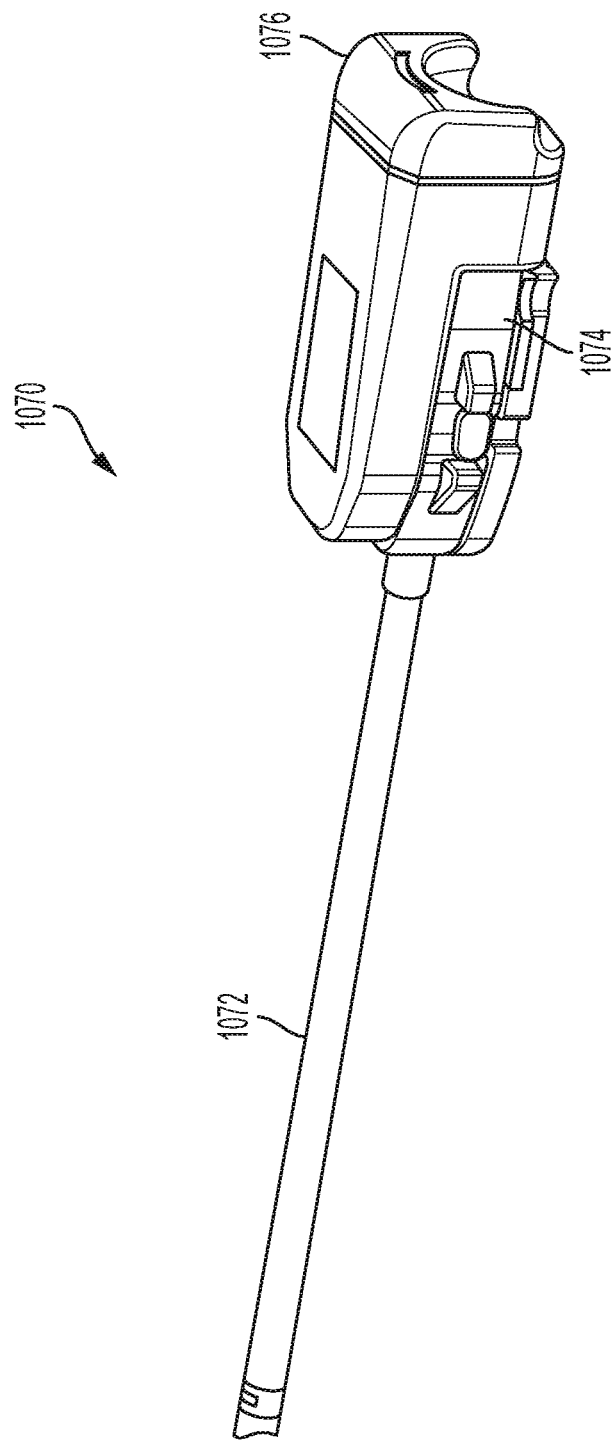
FIG. 86A is a perspective view of a detachable motor pack is mounted to a proximal surgical tool interface, in accordance with at least one aspect of the present disclosure.

FIG. 86A depicts an aspect of a surgical tool/detachable motor pack assembly 1070. The surgical tool/detachable motor pack assembly 1070 includes an elongate surgical instrument shaft 1072 supporting an end effector (not shown) at a distal end of the instrument shaft 1072, a proximal surgical tool interface 1074 supporting the proximal end of the instrument shaft 1072, and a detachable motor pack 1076 mounted and latched to the proximal surgical tool interface 1074. The motor pack 1076 includes electric motors that are drivingly coupled with drivable features of the end effector.

Figure 86B:
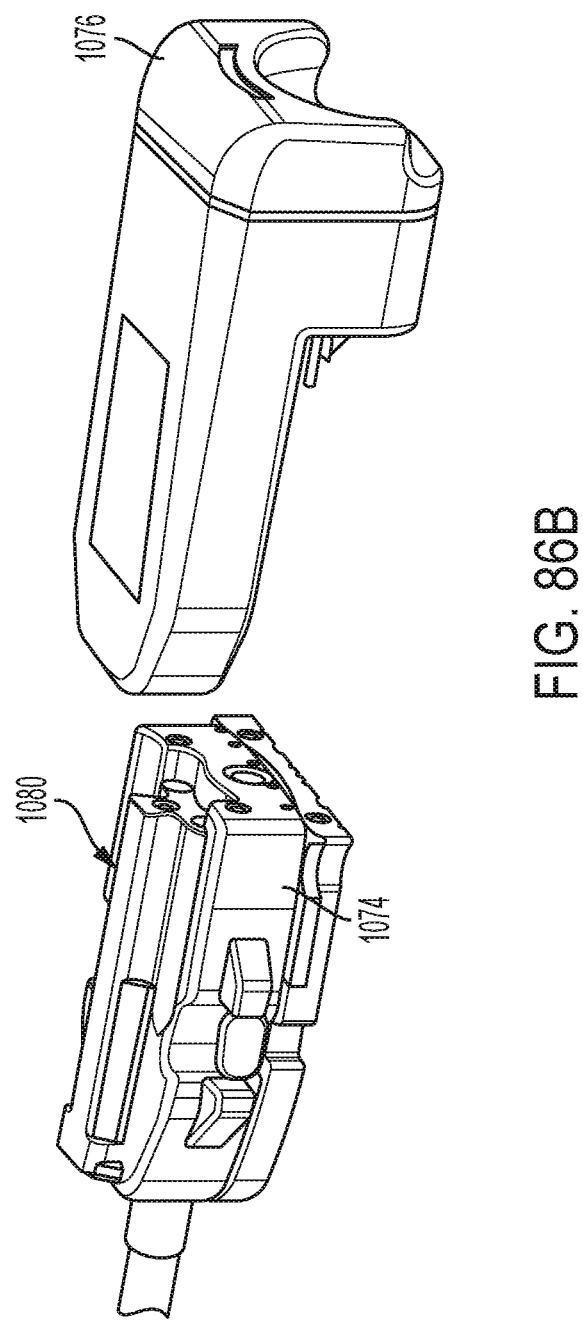
FIG. 86B is a perspective view of the detachable motor pack of FIG. 6A separated from the proximal surgical tool interface.

FIG. 86B shows the motor pack 1076 separated from the proximal surgical tool interface 1074. The top of the proximal surgical tool interface 1074 includes a longitudinally-oriented dovetail alignment feature 1080 that interfaces with a complementarily-shaped dovetail alignment feature of the motor pack 1076 to provide for sliding engagement between the motor pack 1076 and the proximal surgical tool interface 1074 about a longitudinally-oriented engagement axis.

FIG. 87 shows interfacing features of the motor pack 1076. A control cable may electrically connect the motor pack 1076 to a controller. Examples of suitable controllers are described elsewhere herein. The dovetail alignment feature 1086 of the motor pack 1076 interfaces with the dovetail alignment feature 1080 of the proximal surgical tool interface 1074. Precision alignment pins 1088 are received by corresponding alignment receptacles in the proximal surgical tool interface 1074. A roll drive coupling 1090, a clamp drive coupling 1092, and a fire drive coupling 1094 interface with corresponding input couplings of the proximal surgical tool interface 1074. The roll drive coupling 1090 is rotationally coupled with rotation of the instrument shaft 1072. A clamp drive coupling 1092 is used to transfer a rotary actuation motion from an electric motor in the motor pack 1076 to a clamping mechanism in the end effector. The fire drive coupling 1094 is used to transfer a rotary actuation motion from an electric motor in the motor pack 1076 to the end effector, for example, to deploy staples into clamped tissue and to articulate a knife to cut the clamped and stapled tissue. A latch shaft 1096 of the latch mechanism is configured to provide for automated latching of the motor pack 1076 to the proximal surgical tool interface 1074 in response to pushing the motor pack 1076 onto the proximal surgical tool interface 1074 along the engagement axis. Motor pack electrical contacts 1098 are positioned to interface with corresponding proximal surgical tool interface electrical contacts when the motor pack 1076 is mounted and latched to the proximal surgical tool interface 1074.

Figure 88:
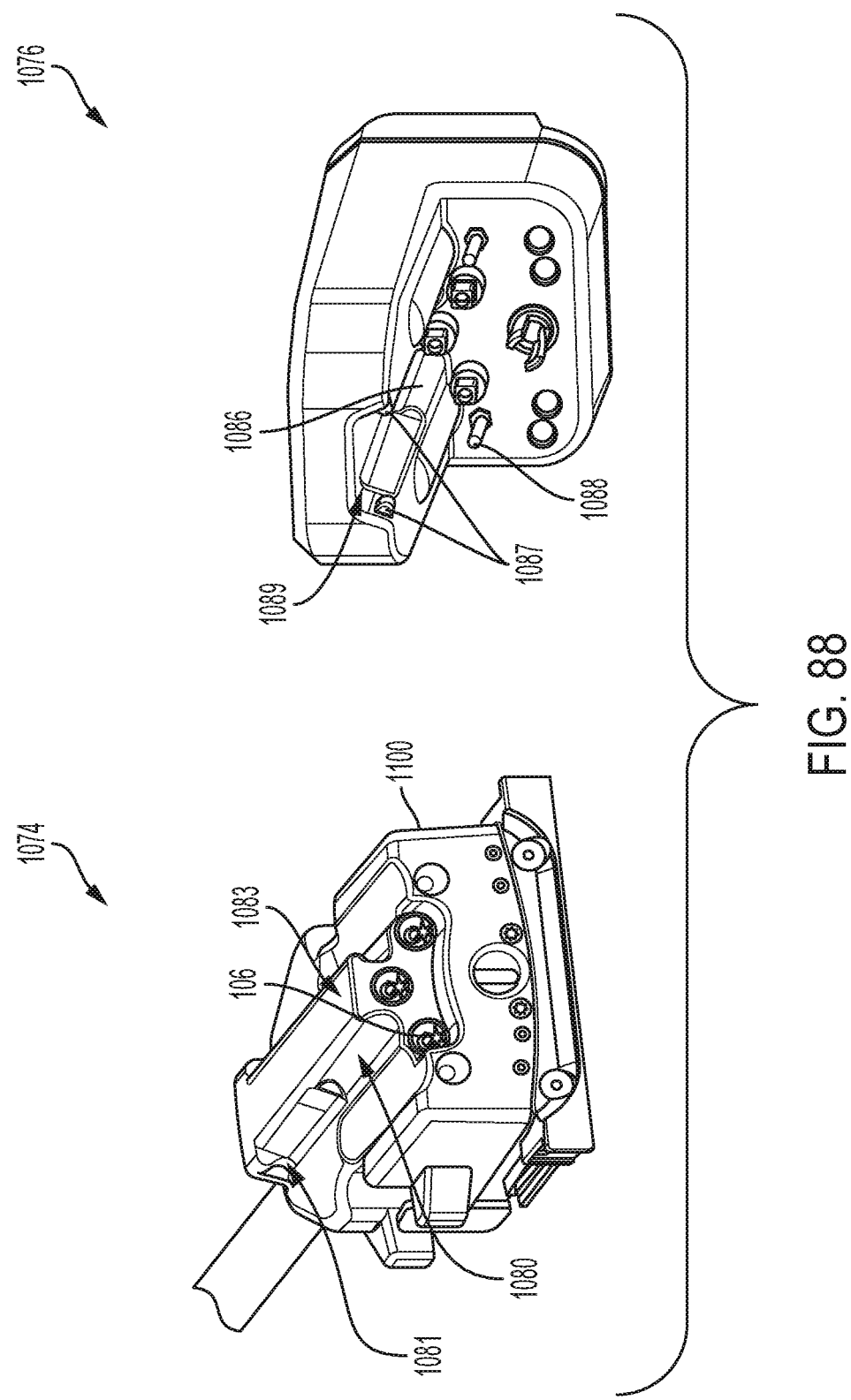
FIG. 88 is a perspective view of the robotic surgical tool of FIG. 6A depicting the proximal surgical tool interface and the second interface portion of the detachable motor pack.

FIG. 88 depicts corresponding interfacing features of the proximal surgical tool interface 1074 and the second interface portion of the motor pack 1076 that provide progressive engagement during the mounting of the motor pack 1076 on to the proximal surgical tool interface 1074 for easy, precise alignment. Easy initial engagement between the motor pack 1076 and the proximal surgical tool interface 1074 is provided by double-dove tail features of the motor pack 1076 and the proximal surgical tool interface 1074. The double-dovetail features of the proximal surgical tool interface 1074 include a pair of proximal recesses 1080, a pair of distal recesses 1081, and a flattop surface 1083 disposed over and between the proximal recesses 1080 as well as over and between the distal recesses 1081. The double-dovetail features of the motor pack 1076 include a pair of elongated proximal protrusions 1086, a pair of distal protrusions 1087, and a flat surface 1089 disposed over and between the proximal protrusions 1086 as well as over and between the distal protrusions 1087. When the motor pack 1076 is fully mounted to the proximal surgical tool interface 1074, the distal protrusions 1087 are received by the distal recesses 1081 and the proximal protrusions 1086 are received by the proximal recesses 1080, thereby securing the motor pack 1076 to the proximal surgical tool interface 1074 against all relative motion except proximal translation of the motor pack 1076 relative to the proximal surgical tool interface 1074. The gap between the proximal protrusions 1086 and the distal protrusions 1087 facilitates a coupling sequence in which the motor pack 1076 is partially overlapped with the proximal surgical tool interface 1074 so that the motor pack flat surface 1089 interfaces with the proximal surgical tool interface top surface 1083 and the proximal protrusions 1086 are disposed proximal of the proximal chassis proximal recesses 1080. The motor pack 1076 is then slid distal relative to the proximal surgical tool interface 1074, thereby causing the proximal protrusions 1086 to be slidingly received by the proximal recesses 1080. During a final portion of distal movement of the motor pack 1076 relative to the proximal surgical tool interface 1074 the distal protrusions 1087 are then received by the distal recesses 1081. The double-dovetail features accommodate a range of initial misalignment between the motor pack 1076 and the proximal surgical tool interface 1074, thereby making it easy to accomplish the initial mating between the double-dovetail features. Once initially mated, relative motion of the motor pack 1076 toward the proximal surgical tool interface 1074 results in progressively less possible misalignment between the motor pack 1076 and the proximal surgical tool interface 1074 due to the progressively longer interfacing portions of the double-dovetail features. At the end of the relative movement of the motor pack 1076 toward the proximal surgical tool interface 1074, the precision alignment pins 1088 on the motor pack 1076 engage the precision alignment receptacles 1100 in the proximal surgical tool interface 1074, thereby precisely positioning the motor pack 1076 relative to the proximal surgical tool interface 1074.

In another aspect, the detachable motor pack may include a releasably attachable power source. The controller of the detachable motor pack may be configured to detect a presence of a primary power source of the hand-held surgical instrument and to detect a presence of a primary power source of the robotic surgical instrument. In some aspects, the controller may be configured to detect the presence of a primary battery pack comprising the primary power source of the hand-held surgical instrument. In another aspect, the controller of the detachable motor pack may be configured to detect the presence of a wired power source comprising the primary power source of the robotic surgical instrument. In still another aspect, the controller may be configured to cause the releasably attached power source to source power to the hand-held surgical instrument upon a determination of a lack of presence of a primary power source of the hand-held surgical instrument. In yet another aspect, the releasably attachable power source is rechargeable.

The releasably detachable power source disclosed above may include a number of aspects. In one example, a releasably attachable power source for a detachable motor pack for use with a hand-held surgical device and a robotic surgical device, may include a housing, a plurality of batteries, and a controller, in which the controller is configured to control a voltage output and a current output of the power source. The controller may further be configured to determine if the detachable motor pack is in communication with the hand-held surgical device or in communication with the robotic surgical device. In one example, the controller of the releasably detachable power source may receive data parameters from the detachable motor pack. The data parameters may include information indicative of an attachment of the detachable motor pack to a hand-held surgical device or to a robotic surgical device. The controller of the power source may be configured to source power directly from the plurality of batteries to the detachable motor pack. The power source controller may further be configured to source power to the detachable motor pack having a voltage differing from a voltage of the plurality of batteries. In another aspect, the controller of the power source may be configured to control a voltage output and a current output of the power source based on data parameters received from the detachable motor pack.

In some instances, it may be desirable to have detachable battery packs that differ in their output characteristics. As an example, a first hand-held surgical device may require a motor pack having a first voltage output and a first output capacity, and a second hand-held surgical device may require a motor pack having a second voltage output and a second output capacity. In a second example, a first detachable surgical tool may require a power source having a first voltage output and a first output capacity, while a second detachable surgical tool may require a power source having a second voltage output and a second output capacity.

In one aspect, a single detachable battery pack may include voltage and current controls to change the output characteristics of the battery pack to meet the power requirements of either the hand-held devices or surgical tools. In another aspect, a battery pack may operate in a "native mode" to source power to the hand-held device directly from the batteries. The battery pack may also operate in a second "conditioned mode" to condition the battery power according to a variety of electronics and to source the "conditioned" power (having a voltage and/or current that differs from the native mode) to the hand-held device. Different battery packs may have different "native modes" based on the types of batteries inserted within them.

In another aspect, a detachable battery pack may be configured to accept rechargeable batteries or non-rechargeable batteries having similar form factors. In one example of the use of such a battery pack, non-rechargeable batteries may be inserted into the battery pack and the surgical instrument may be used while the rechargeable batteries are charging.

In one aspect, a detachable motor pack for use with multiple electrical surgical instruments may include a housing, a plurality of motors retained within the housing, a controller configured to control one or more operations of the plurality of motors, in which the controller includes a processor and a memory unit, a power supply interface configured to receive a releasably attachable power source, a first interface portion, in which the first interface portion is configured to releasably attach to a hand-held surgical instrument and to a robotic surgical instrument, and a second interface portion, in which the second interface portion is configured to releasably attach to a first surgical tool of the hand-held surgical instrument and to a second surgical tool of the robotic surgical instrument.

In some examples, the memory unit of the motor pack may include instructions that, when executed by the motor pack processor, cause the processor to determine one or more output parameters of a (first) power source releasably attached to the power supply interface. In some examples, the one or more output parameters may include a voltage output and a current output of the (first) power source. The memory unit of the motor pack may further include instructions that, when executed by the motor pack processor, cause the processor to store the one or more output parameters of the (first) power source in the motor pack memory unit. Additionally, the memory unit of the motor pack may include instructions that, when executed by the processor, cause the processor to determine one or more output parameters of a second power source releasably attached to the power supply interface, compare the one or more output parameters of the second power source to the one or more output parameters of the first power source, and cause the second releasably attached power source to output a voltage or a current equal to the voltage output or current output, respectively, of the first releasably attached power source. In one example, the controller of the motor pack may transmit data to a controller within the second releasably attached power source. The controller of the second power source may use those data to condition the output voltage or current of the second power source so that they are equal to those of the first power source.

Figure 89A:
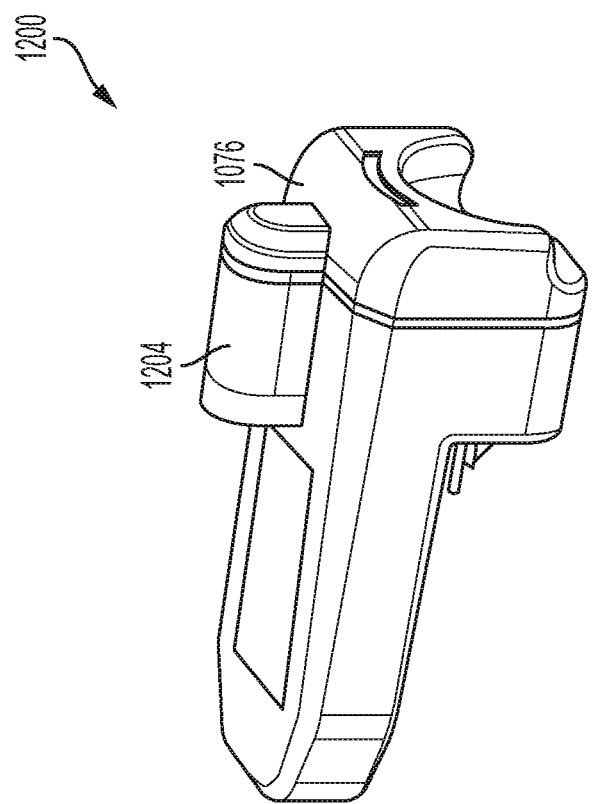
FIG. 89A is a perspective view of a detachable motor pack to which is mounted a detachable battery pack, in accordance with at least one aspect of the present disclosure.
Figure 89B:
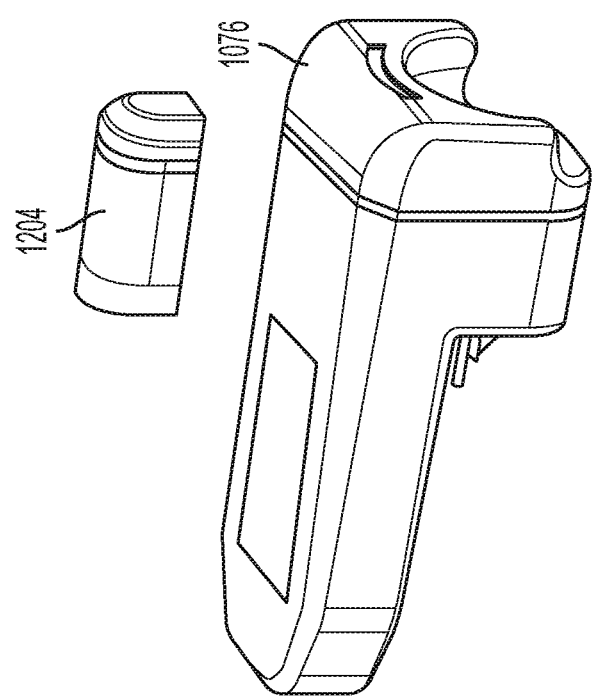
FIG. 89B is a perspective view of the detachable battery pack separated from the detachable motor pack, in accordance with at least one aspect of the present disclosure.

FIGS. 89A, 89B illustrate an example of a detachable motor pack and an associated detachable battery pack. FIG. 89A illustrates the assembled motor pack/battery pack 1200 which may include the detachable motor pack 1076 having a detachable battery pack 1204 releasably affixed to a surface of the motor pack 1076. FIG. 89B depicts the releasable motor pack 1076 separated from the detachable battery pack 1204.

In various aspects, Integrity of communications between the robotic surgical instrument and a surgical hub (e.g. surgical hub 106) such as, for example, data communications indicative of positions and/or motions of an end effector of the robotic surgical instrument are verified. In at least one aspect, accurate communications between the robotic surgical instrument and the surgical hub can be ensured using security codes such as, for example, cyclic redundancy checks (CRC) which are error-detecting codes attached to data communications to detect accidental changes in communicated data which may occur during data transmission. Blocks of data entering these systems get a short check value attached, based on the remainder of a polynomial division of their contents.

In various instances, a safety processor is configured to stop the motor pack from running if a computed CRC, which is computed from the received data, does not match the received CRC. A CRC verification module can be employed by the safety processor to compute a CRC from the received data and compare the computed CRC with the received CRC. In various instances, processors of the robotic surgical instrument and/or the surgical hub may comprise security code generator modules and/or security code verification modules. Security codes can be generated by CHECK-SUM, HASH, or other suitable protocols. The security code generation module and/or the security code verification module may be implemented in hardware, firmware, software or any combination thereof.

Cooperative Robotic Surgical Systems

As previously disclosed above, with reference to FIG. 4, the robotic surgical system 13000 includes robotic arms 13002, 13003, a control device 13004, and a console 13005 coupled to the control device 13004. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003.

Each of the robotic arms 13002, 13003 is made up of a plurality of members connected through joints and includes a surgical assembly 13010 connected to a distal end of a corresponding robotic arm 13002, 13003. In an exemplification, the surgical assembly 13010 includes a surgical instrument 13020 supporting an end effector 13023. Accordingly, one or more additional surgical assemblies 13010 and/or surgical instruments 13020 may also be attached to the additional robotic arm(s). The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008.

The control device 13004 may control a plurality of motors (for example, Motor I . . . n) with each motor configured to drive a pushing or a pulling of one or more cables, such as cables coupled to the end effector 13023 of the surgical instrument 13020. The control device 13004 coordinates the activation of the various motors to coordinate a pushing or a pulling motion of one or more cables in order to coordinate an operation and/or movement of one or more end effectors 13023. In an exemplification, each motor is configured to actuate a drive rod or a lever arm to affect operation and/or movement of end effectors 13023 in addition to, or instead of, one or more cables.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

A simplified functional block diagram of a system architecture 13400 of the robotic surgical system 13010 is depicted in FIG. 5. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. The surgeon master module 13430 communicates with surgeon control devices at the console 13005 and relays inputs received from the console 13005 to the core module 13420. The robotic arm module 13440 coordinates operation of a robotic arm subsystem, an arm cart subsystem, a set up arm, and an instrument subsystem in order to control movement of a corresponding arm 13002, 13003. The instrument module 13450 controls movement of an instrument and/or tool component attached to the arm 13002, 13003. The instrument module 13450 is configured to correspond to and control a single instrument. The position data collected by the instrument module 13450 is used by the core module 13420 to determine when the instrument is within the surgical site, within a cannula, adjacent to an access port, or above an access port in free space.

The robotic surgical systems and features disclosed herein can be employed with the robotic surgical system of FIGS. 4 and 5. One may further appreciate that various systems and/or features disclosed herein can also be employed with alternative surgical systems including the computer-implemented interactive surgical system 100, the computer-implemented interactive surgical system 200, the robotic surgical system 110, the robotic hub 122, and/or the robotic hub 222, for example.

In various instances, a robotic surgical system can include a robotic control tower, which can house the control unit of the system. For example, the control unit 13004 of the robotic surgical system 13000 (FIG. 4) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

In some examples (see FIG. 2), a single surgeon may direct a robotic surgical operation from a surgical console 118. The surgical console 118 may interface with a surgical hub 122 which may control the motions of the robotic arms and end effectors. The surgical hub 122, for example, may be housed in a robotic control tower.

Additional examples of robotic surgical systems and components—including, for example, user control arms and control arm mechanisms, including hand or finger-tip controls—may be found in the following references that are incorporated herein by reference in their respective entireties and for all purposes:

U.S. Pat. No. 7,955,322 filed on Dec. 20, 2006 and entitled WIRELESS COMMUNICATION IN A ROBOTIC SURGICAL SYSTEM;

International Patent Application Serial No. PCT/US2017/ 034619 filed on May 26, 2017 and published as International Patent Application Publication No. WO2017/ 210101 entitled SYSTEMS, METHODS, AND COMPUTER-READABLE STORAGE MEDIA FOR CONTROLLING ASPECTS OF A ROBOTIC SURGICAL DEVICE AND VIEWER ADAPTIVE STEREOSCOPIC DISPLAY;

International Patent Application Serial No. PCT/US2017/ 035580 filed on Jun. 2, 2017 and published as International Patent Application Publication No. WO2017/ 210499 entitled CONTROL ARM FOR ROBOTIC SURGICAL SYSTEMS; and International Patent Application Serial No. PCT/US2017/ 034619 filed on May 26, 2017 and published as International Patent Application Publication No. WO2017/ 210101 entitled SYSTEMS, METHODS, AND COMPUTER-READABLE STORAGE MEDIA FOR CONTROLLING ASPECTS OF A ROBOTIC SURGICAL DEVICE AND VIEWER ADAPTIVE STEREOSCOPIC DISPLAY.

In some examples, the surgical suite may include multiple robotic hubs and/or control towers. In some instances, multiple surgeons operating the multiple robotic hubs may assist each other during a difficult or long surgical procedure. In some cases, the multiple robotic hubs may act independently, although may share robotic arm and end effector location data to prevent mechanical conflict. In alternative examples, multiple surgical suites may be located in the same health care facility, in which each surgical suite may have its own robotic hub or tower. Regardless of the disposition of multiple robotic hubs, it may be understood that during a particular surgical procedure, one or more of the multiple robotic hubs may be idle and not associated with a surgical procedure. Under such conditions, it may be desirable for a surgeon operating a single surgical hub to harness the capabilities of an idle surgical hub during a surgical procedure.

Figure 90:
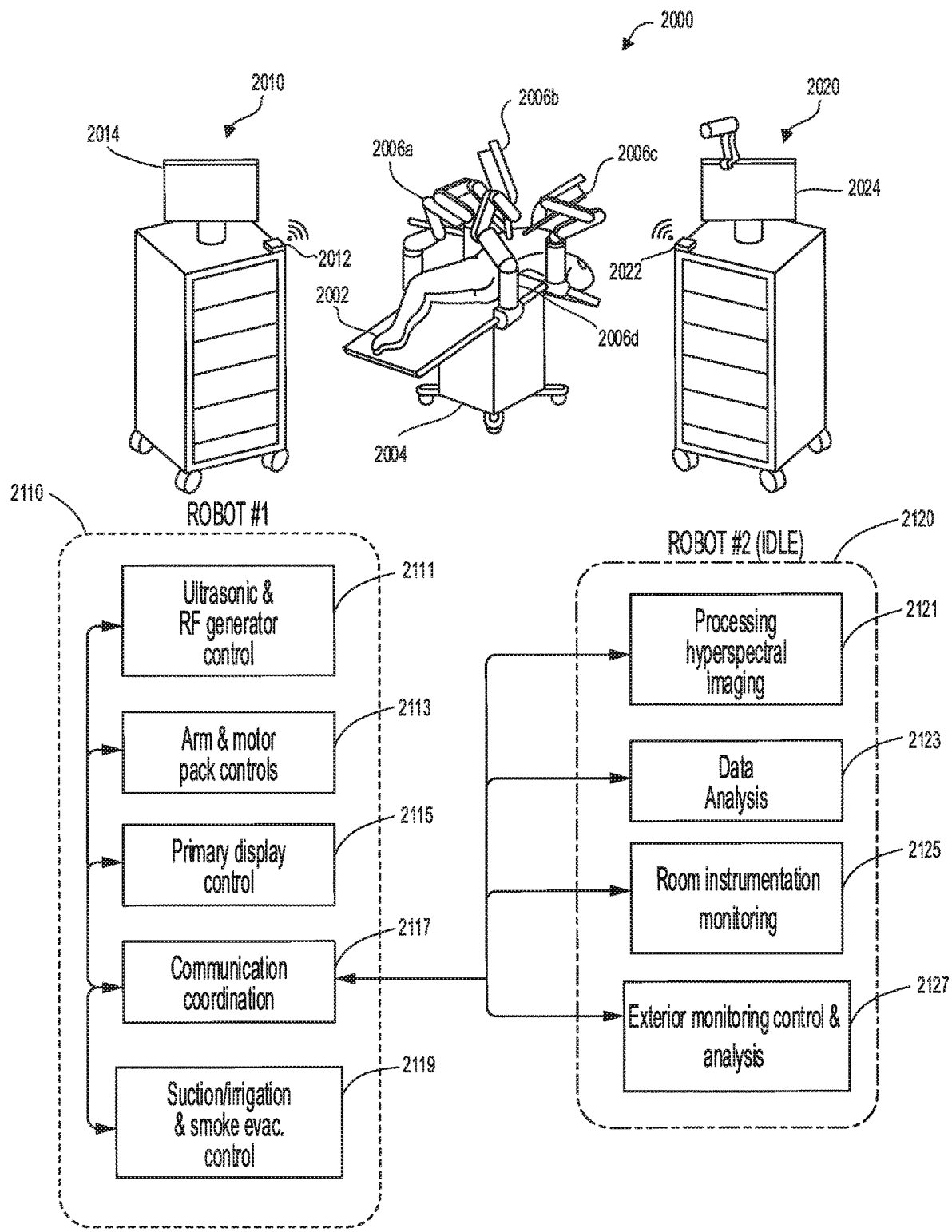
FIG. 90 depicts an automated surgical system having two automated surgical systems that are configured to operate in a cooperative manner, in accordance with at least one aspect of the present disclosure.

FIG. 90 depicts an example of a surgical suite 2000 having multiple surgical hubs or towers (2010 and 2020). As depicted in FIG. 90, a patient 2002 lies on an operating table 2004 and is surrounded by multiple robotic surgical arms 2006*a-d*. The multiple robotic surgical arms 2006*a-d* may be controlled by a surgeon using a control console associated with surgical tower 2010. Surgical tower 2010 and surgical tower 2020 may be in communication with each other via communication links. In one non-limiting example, surgical tower 2010 may communicate with surgical tower 2020 via paired wireless transmitters/receivers, for example wireless transmitter/receiver 2012 associated with surgical tower 2010, and wireless transmitter/receiver 2022 associated with surgical tower 2020. The wireless transmitters/receivers 2012, 2022 may employ any useful wireless technology including, without limitation, WiFi, Blue Tooth, or other such technology. It may be understood that communications between the surgical tower 2010 and surgical tower 2020 may also be accomplished by the use of wired technology such as, for example, Ethernet communication or fiber-optic communication.

Block diagrams 2110 and 2120 depict functional modules that may be part of surgical towers 2010 and 2020, respectively.

As depicted in FIG. 90, surgical tower 2010 may be considered the "primary" surgical tower defining a primary surgical hub. The primary hub may be configured to perform, without limitation, the functions directly related to the operation of the surgical robotic arms 2006a-d. The primary surgical tower 2010 may include a user control console at which the surgeon may direct the robotic arms 2006a-d. The primary surgical hub may also include a primary display 2014 to provide the surgeon with graphical information regarding the procedure including, without limitation, a display of relevant surgical data (such as patient blood pressure, temperature, and $SpO_2$), graphical images of the surgical site (by means of a camera disposed within or near the surgical field), or analytical data derived from parameters obtained regarding the patient (such as historical data related to the patient's physiology). In some aspects, the display may include a stereoscopic display. The stereoscopic display may be an autostereoscopic display that may be generated based on eye tracking of the surgical user. The display may include user concentric overlays to depict images of the surgical site along with graphical annotations related to an analysis of the tissue being displayed. The display may also be a unified display of all images and data related to the surgical site.

The surgeon at the primary surgical tower 2010 may operate any haptic interface devices at the user control console to manipulate the surgical robotic arms 2006a-d. The haptic interface devices may include any type of remote manipulator using one or more electronic, hydraulic, or mechanical linkages to cause the robotic arms 2006a-d to operate. The haptic interface devices may include joysticks, triggers, or more complicated control devices. Some examples of more complex surgical haptic interface and control devices may also be found in the following references that are incorporated herein by reference in their respective entireties and for all purposes:

International Patent Application Serial No. PCT/US2017/035583 filed on Jun. 2, 2017 and published as International Patent Application Publication No. WO2017/210501 entitled CONTROL ARM ASSEMBLIES FOR ROBOTIC SURGICAL SYSTEMS;

International Patent Application Serial No. PCT/US2017/034435 filed on May 25, 2017 and published as International Patent Application Publication No. WO2017/210073 entitled PASSIVE AXIS SYSTEM FOR ROBOTIC SURGICAL SYSTEMS;

International Patent Application Serial No. PCT/US2017/058973 filed on 27 Oct. 2016 and published as International Patent Application Publication No. WO2017/075122 entitled INPUT HANDLES FOR ROBOTIC SURGICAL SYSTEMS HAVING VISUAL FEEDBACK; and International Patent Application Serial No. PCT/US2016/057784 filed on Oct. 20, 2016 and published as International Patent Application Publication No. WO2017/070266 entitled VARIABLE SWEEPING FOR INPUT DEVICES.

Additional components of the primary surgical tower 2010, may include one or more of a robotic actuator, a surgical system controller comprising a processor and a memory component configured to store a set of processor instructions and a processor data, and communication interface for data transmission and reception from, for example, the wireless transmitter/receiver 2012. In one aspect, the communication interface may include a communication controller 2117. The primary surgical tower 2010 may incorporate the functions associated with the direct control of the robotic arms 2006a-d along with the control of other devices used throughout the surgery. Thus, for example, functional components may include those related to control of electrosurgical instruments 2111 (either ultrasonic or radio frequency devices). Such controls may include the control of energy delivered to the instruments and control of mechanical features of such instructions, such as the activation of knives and grasping jaws. Additional functions may include those related to control of the mechanical arms and motor packs 2113 (linkages and drivers) to position the surgical end effectors attached to the robotic arms 2006a-d. During a surgical procedure, suction or fluid irrigation at the surgical site may be needed or smoke generated during an electrocautery procedure may have to be removed. The primary surgical tower 2010 may also have a control function 2119 associated with these processes. The primary surgical tower 2010 may also include a display controller 2115 configured to control the primary display 2014.

In a surgical procedure using a single surgical tower, in addition to the functions disclosed above, may also be required to carry out functions not associated with the direct control of the surgical tools. Such functions may include, without limitation, the processing of imaging data (such as hyperspectral imaging), monitoring the presence and location of additional surgical tools within the surgical suite, and monitoring, control, and analysis of environmental factors. The second surgical tower may provide support processing and control aspects to the first surgical tower in order to improve visualization, deformed state organ modeling or simulation, or even provide sub-processed control signals for a system using more complicated or more electrodes than it is capable of controlling alone. It may be recognized that there may be computational costs associated with such additional functions, and such costs may result in a slowing down in the response of the primary surgical tower during a procedure. It may therefore be useful to off-load such functions onto an idle, second surgical tower. Functionally, the primary surgical tower may act as a multiprocessor system when it cooperatively couples with a second, idle, tower. Again, turning to FIG. 90, the second surgical tower 2020 may be used to this purpose.

In some aspects, the second (or secondary) surgical tower 2020 may include a user control console, a robotic actuator, a surgical system controller comprising a processor and a memory component configured to store a set of processor instructions and a set of processor data, and a surgical system communication interface. The communication interface of the secondary surgical tower 2020 may control the wireless transmitter/receiver 2022 of the secondary surgical tower 2020. The secondary surgical tower 2020 may also have a secondary display 2024. In some aspects, the secondary display 2024 may display status information regarding the operation of the secondary surgical tower 2020 or other information.

As disclosed above, and in some aspects, some functions of the primary surgical tower 2010 may be off-loaded for computational efficiency onto the secondary surgical tower 2020. Block diagram 2120 illustrates some examples of functions performed by the secondary surgical tower 2020 in coordination with the primary surgical tower 2010. Thus, for example, the secondary surgical tower 2020 may incorporate functions to process hyperspectral imaging data 2121, monitor and track surgical instrument location and uses 2125 in the surgical suite, or monitor, control, and analyze environmental conditions 2127. The secondary surgical tower 2020 may be configured to carry out such functions when performing such functions does not interfere with its ability to perform its core functions. For example, the secondary surgical tower 2020 may be configured to carry out such functions when its robotic actuator is inactive or idle.

The secondary surgical tower 2020 may also include additional functions associated with the analysis of additional data 2123. As one example, a surgical system including the primary surgical tower 2010 and the surgical robotic arms 2006a-d may include a variety of sensors. Such sensors may sense the position and velocity of motors associated with the surgical robotic arms 2006a-d. In another example, there may be sensors associated with the functions of surgical end effectors, including, without limitation, jaw positions, electrode or tissue temperatures. There may also be sensors configured to obtain physiological data from a patient. Such sensors may be in data communication with the processor of the primary surgical tower 2010. The memory component of the primary surgical tower 2010 may include instructions, that when executed by the processor, causes the sensor data received by the processor to be transmitted, via the primary tower communication controller 2117, to a communication interface of the secondary surgical tower 2020. A memory component of the secondary surgical tower 2020 may include instructions, that when executed by the secondary surgical tower 2020 processor, causes the processor to calculate one or more analytical functions based on the sensor data received from the primary tower communication controller 2117 when the second robotic actuator is inactive. In addition, the memory component of the secondary surgical tower 2020 may include instructions, that when executed by the second tower processor, causes the processor to transmit the results of the one or more calculated analytical functions to the communication interface of the primary tower 2010 via the secondary tower 2020 communication interface. Upon receipt by the communication interface of the primary tower 2010 of the results of the calculated analytical functions from the secondary tower 2020, the primary tower 2010 memory component may include instructions to display the results on the primary display 2014.

In some other aspects, some control of the surgical robotic arms 2006a-d may also be off-loaded onto the secondary surgical tower 2020. In this aspect, the robotic actuators associated with the secondary surgical tower 2020 may be used to control some of the surgical robotic arms 2006a-d. For example, the robotic actuator controls associated with the primary surgical tower 2010 may control an operation of a first surgical tool and the robotic actuator controls of the secondary surgical tower 2020 may control an operation of a second surgical tool in concert with the first surgical tool. The user console of the primary surgical tower 2010, when operated by the surgeon, may generate data, a first portion of which may be used by the processor of the primary surgical tower 2010 to control the robotic actuator of the primary surgical tower 2010. The processor of the primary surgical tower 2010 may transmit a second portion of the data received from the user console to the secondary surgical tower 2020 over the primary surgical tower 2010 communication interface. In turn, the processor of the secondary surgical tower 2020 may use the second portion of the data, received from the primary surgical tower 2010, to control a function of the robotic actuator of the secondary surgical tower 2020.

As disclosed above, a surgeon or operator may sit at an operator control of a first surgical tower, allowing the first surgical tower to operate one or more robotic arms and/or surgical tools or end effectors to carry out a sequence of operations. At the same time, one or more additional or alternative operations of the robotic arms and/or surgical tools may be controlled by a second surgical tower. It may be understood that the first surgical tower may be considered a primary surgical tower, while the second surgical tower may be considered a secondary surgical tower. The two surgical towers may communicate with each other regarding their respective operations. Thus, the second surgical tower may receive communication indicating its secondary status, and that the first surgical tower may be recognized as being the primary. Additionally, each surgical tower may receive communications indicating what operations are being controlled by the other surgical tower. In some aspects, the user at the first surgical tower may transmit commands to the two surgical towers indicating that an operation of the first surgical tower is to be transferred to the second surgical tower, or vice versa. In some aspects, a central hub controller may receive communications indicating the status and operations of each of the surgical towers. As an example, a surgical tool may comprise an electrosurgical tool, for example a device that uses RF energy to cauterize or cut tissue. A single energy source may provide RF energy to the electrosurgical tool. The operator may control the first surgical tower to apply the energy to the electrosurgical tool while the electrosurgical tool is operated by a robotic arm controlled by the first surgical tower. Alternatively, the operator may transfer the electrosurgical tool to a robotic arm controlled by the second surgical tower transmit instructions for the second surgical tower to apply the energy to the electrosurgical tool.

As disclosed above, multiple surgical towers may coordinate their operations during a surgical procedure. The multiple surgical towers may each include functions to automatically coordinate its operations with the other surgical towers. In one example, a first or primary surgical tower may guide ablation electrodes for a catheter procedure. A second surgical tower may receive imaging information which may be processed and presented to the operator at a display associated with the primary surgical tower, thereby allowing the operator of the primary surgical tower to visualize the positioning of the ablation electrodes. A microwave, ultrasonic, or RF ablation system which controls the activation, energy modality, and electrode orientation of a surgical tool could be synchronized with a larger robotic system that could include visualization, retraction, patient positioning, biopsy systems. The control console of the first surgical tower could display visualization information received from the second surgical tower, thereby providing the operator of the first surgical tower one or more visual overlays of different visualization system, or even position and assist the first system in being setup and used. The first surgical tower could be operated by or operated through the second surgical tower.

In another aspect, a first surgical tower may control a first set of robotic arms and surgical tools and a second surgical tower may control a second set of robotic arms and surgical tools. Each surgical tower may receive data related to the positioning of the robotic arms controlled by the other surgical tower. In this way, conflicting motion of the surgical arms may be avoided. In some aspects, the robotic arms of the two surgical towers may share a common coordinate system for the motion control kinematics. In one example, the surgical table may be referenced as a common coordinate center. Each surgical tower may establish the position/orientation of its robotic arms relative to the table. With the position of the reference center known, the subsequent positioning of the arm(s) can be known relative to the table. Each surgical tower can track the kinematics of the arm positions and motions through its own control and verification systems based on the kinematic data received from the other surgical tower. These positions can be mapped to the global coordinate system to improve procedure efficiency (e.g., eliminate arm collisions, improve the cooperative control of each system, etc.). This establishes the overall footprint and positioning of all components of the robotic arms under one system.

Figure 91:
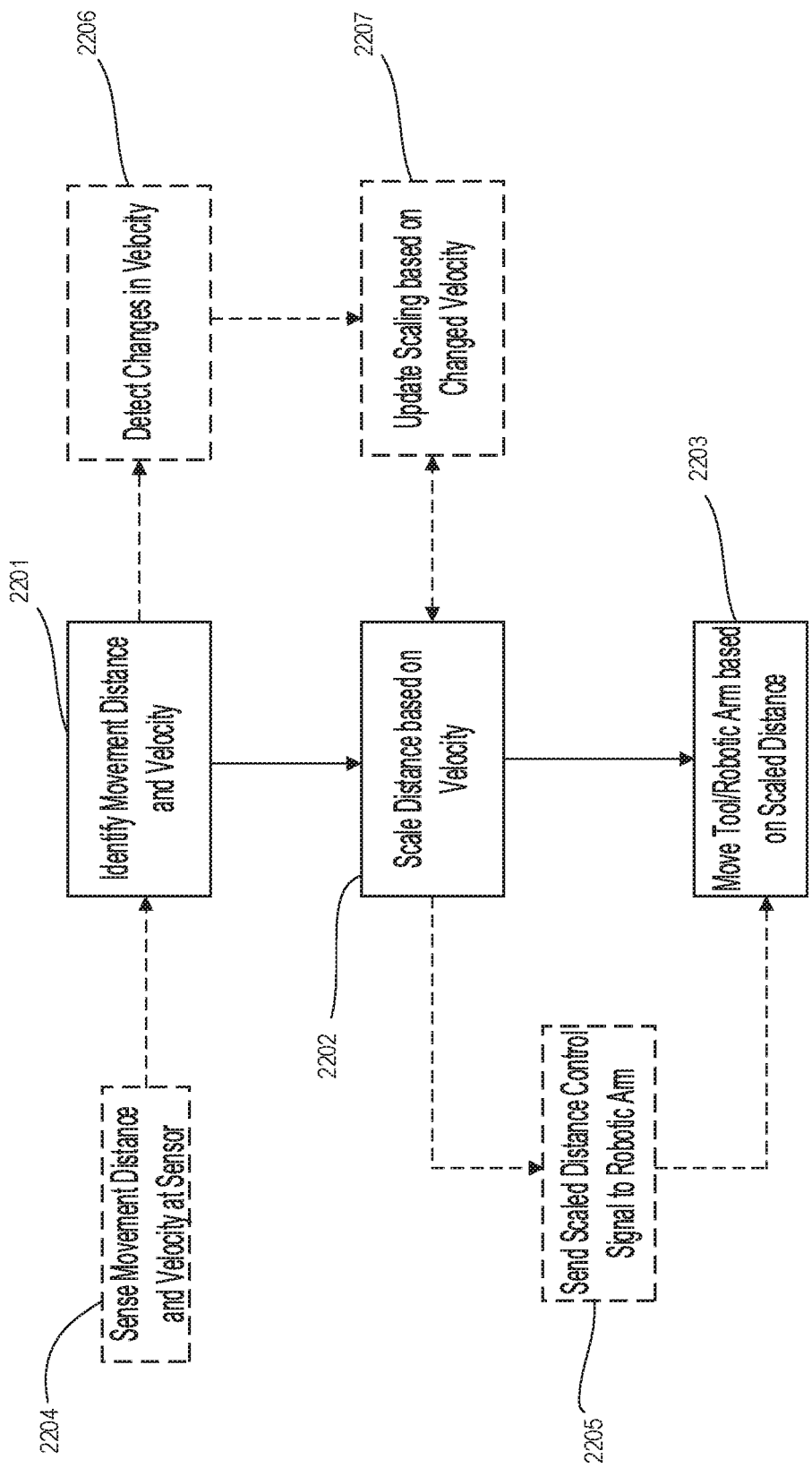
FIG. 91 depicts a block diagram of functions for controlling a robotic arm, in accordance with at least one aspect of the present disclosure.

Kinematic control of the robotic arms may be accomplished through proper scaling of the motions of the user control interfaces, including, without limitation, joystick controls, hand and arm controls, and fingertip controls. FIG. 91 depicts a block diagram of functions that may be used to scale the motion of the user control interfaces to the equivalent motions of the robotic arms. In box 2201, a movement distance, velocity, and/or acceleration of an input controller of a robotic surgical system moveable in at least three dimensions is identified. In box 2204, the movement distance, velocity, and/or acceleration of the input controller may be sensed from one or more sensors that may be integrated into the input controller or separate from the input controlled.

In box 2202, the identified movement distance is dynamically scaled based on at least one of the identified movement velocity and acceleration. In box 2205, a control signal based on the dynamically scaled movement distance may be sent to the robotic arm. The dynamic scaling may include one or more of the algorithms discussed herein and/or other algorithms. For example, dynamic scaling may include multiplying the identified movement distance by the identified movement velocity and/or acceleration. The dynamic scaling may also include dividing the identified movement velocity by a velocity scaling factor. The dynamic scaling may also include dividing the identified movement distance by a distance scaling factor. At least one of the distance scaling factor or the velocity scaling factor may be adjusted based on a predetermined criterion. The criterion may include a type of tool attached to a robotic arm, a type of robotic arm coupled to the input controller, a user selected function or feature associated with a predetermined scaling factor, or other predetermined criterion.

The dynamic scaling may include calculating a product of the movement distance divided by a distance scaling factor and the movement velocity and/or acceleration divided by a velocity scaling factor.

In box 2203, a surgical tool coupled to a robotic arm is moved based on the dynamically scaled movement distance. In some instances, the robotic arm may be moved based on the control signal received at the robotic arm, the moving of the robotic arm moving the surgical tool.

In box 2206, two or more different movement velocities of the input controller may be detected over a predetermined time. This may occur if a user changes the speed at which they are moving the input controller by, for example, suddenly accelerating or decelerating. In box 2207, the scaling of the movement distance may be dynamically updated for each of the respective detected movement velocity changes. In some instances, the surgical tool may be moved by different relative amounts according to the updated dynamic scaling, so that the relative movement amount changes as a dynamic scaling value changes.

Additional disclosures regarding such input scaling control of surgical robotic arm motions may be found in International Patent Application Serial No. PCT/US2015/051130 filed on Sep. 21, 2015 and published as International Patent Application Publication No. WO2016/053657 entitled DYNAMIC INPUT SCALING FOR CONTROLS OF ROBOTIC SURGICAL SYSTEM, the disclosure of which is incorporated herein by reference in its entirety and for all purposes.

It may be recognized that communication between multiple surgical towers and the surgical towers and the central hub must be kept secure to prevent unauthorized communications. These communications may include wired or wireless communications among the hub, the surgical towers, and the smart surgical tools operated by the surgical towers. In some aspects, all such communications may include encryption functions to maintain communication security. Data stored in the surgical towers may also be encrypted for security.

Robotic Arm Kinematics and Control System

Figure 92:
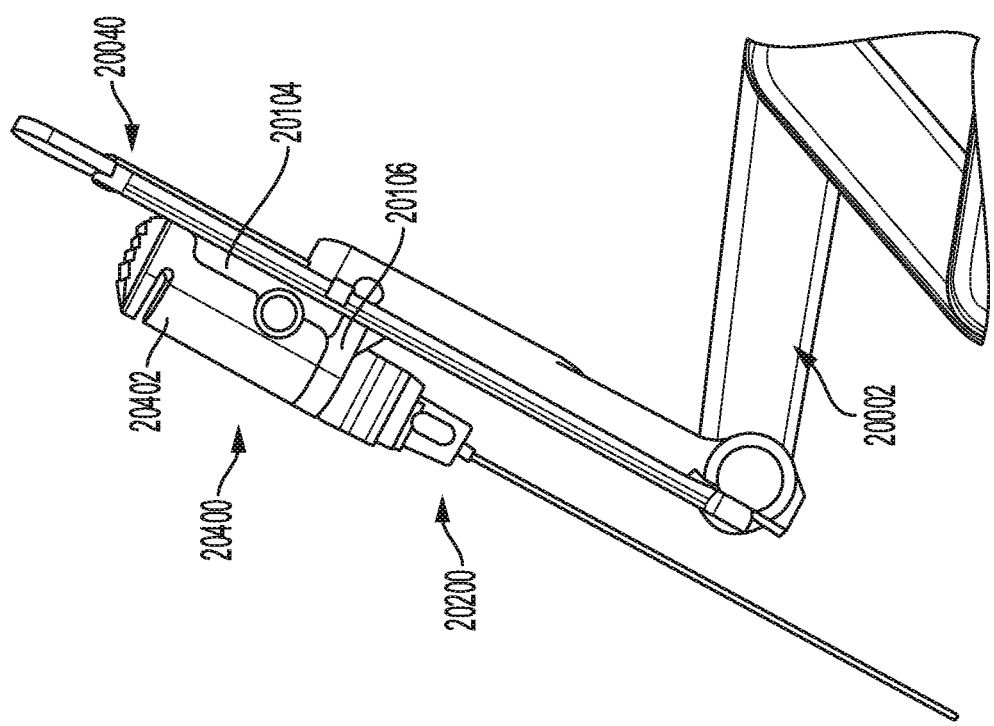
FIG. 92 is a side, perspective view of a surgical assembly including a surgical instrument holder, an instrument drive unit (IDU), an adapter assembly, and a surgical instrument, in accordance with at least one aspect of the present disclosure.

As discussed above, robotic control systems of the present disclosure described herein such as robotic surgical system 13000 of FIG. 4 may include robotic arms such as robotic arms 13002, 13003. The robotic arms can be capable of performing various kinematic functions. One example of such kinematic functions is linear slide kinematics. In FIG. 92, a surgical robotic arm 20002 which is similar to robotic arms 13002, 13003 is depicted. As discussed above, the robotic arm 20002 is configured to releasably secure a robotic surgical assembly such as surgical assembly 13010 or others described herein. The robotic arm 20002 may also be configured to secure and/or control surgical instruments described herein such as surgical instrument 13020 or end effectors described herein such as end effector 13023. In FIG. 92, the robotic arm 20002 controls surgical instrument 20200, which could be part of the robotic surgical assembly 13010, for example. The robotic arm 20002 can be driven by electric drives (not shown) that are connected to a control device which may be similar to the common control module 610 of FIG. 16, for example. The control device could be communicatively coupled to a control circuit of the surgical instrument 20200, such as control circuit 710 of FIG. 17, for example. As shown in FIG. 922, a surgical instrument holder can include a housing 20106 and a carriage 20104. The surgical instrument holder may slide along a rail 20040 of the robotic arm 20002. In this way, the surgical instrument holder can implement the linear slide kinematics of the robotic arm 20002. For example, when the motor (which could be similar in operation to a motor of the surgical instrument 20200 such as motor 754) that is coupled to the robotic arm 20002 is actuated, the surgical instrument 20200 can be linearly moved along the robotic arm 20002 towards a desired location such as treatment area of a patient.

The motor may also be used to cause the robotic arm to move in a linear direction or movement. The surgical instrument 20200 can also be rotated by the robotic arm 20002 based on transferring power from the motor. To this end, an instrument drive unit 20400 can transfer power and actuation forces from the motor to a drive assembly of an adapter assembly to drive a rotation of surgical instrument 20200 (such as an endoscope) up to least about 180 degrees about its longitudinal axis. The carriage 20104 may be configured to non-rotatably support an outer shell 20402.

Further details about the surgical assembly depicted in FIG. 92 may be found in U.S. Patent Publication 2018/0153634, which is hereby incorporated by reference.

Figure 93:
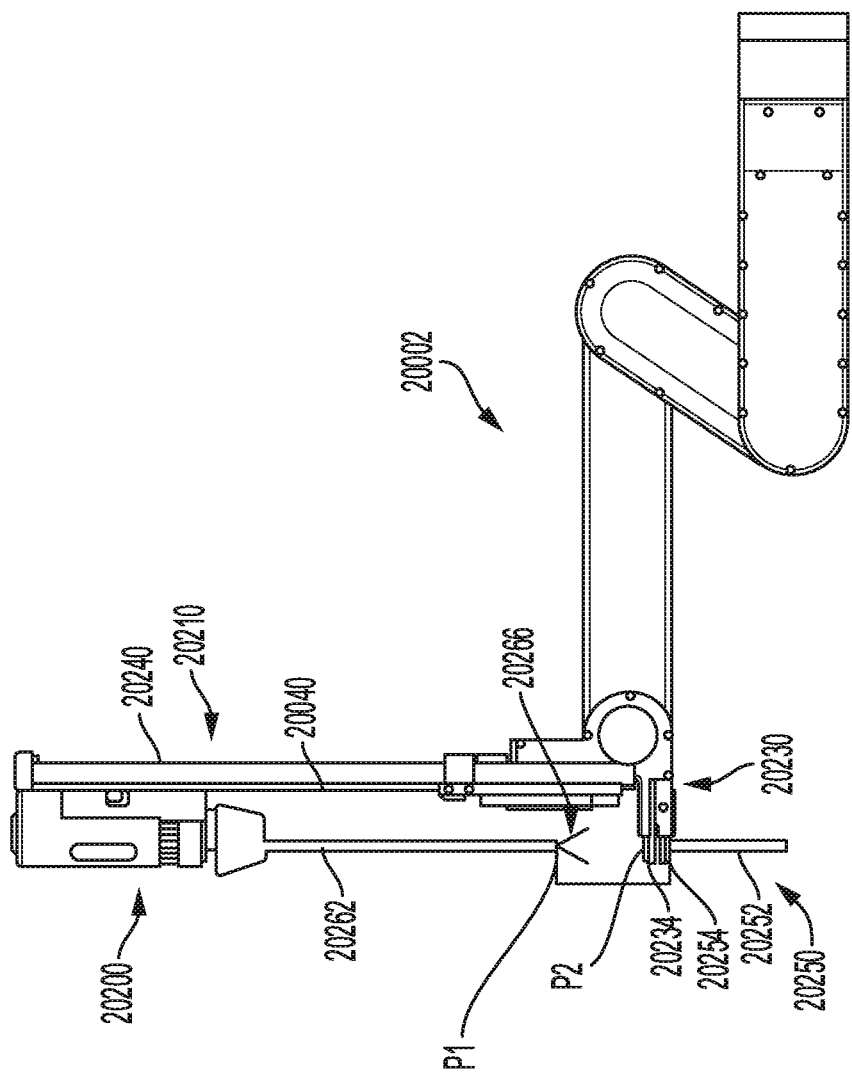
FIG. 93 is a side view of an arm that may be included in a robotic surgical system in an open position, in accordance with at least one aspect of the present disclosure.

The robotic arm 20002 can also releasably control surgical instruments relative to a trocar placed relative to a surgical site. FIG. 93 illustrates a side view of the robotic arm 20002, including a mounting assembly 20210 for securing surgical tools thereto. The robotic arm 20002 can be constructed of three members connected via joints, as shown in FIG. 93. The mounting assembly 20210 is coupled to a distal end of the arm 20002 and includes a mounting device 20230 and a longitudinally-extending support 20240. The mounting device 20230 may support a clamping and release assembly 20234. The mounting device 20230 is also configured to selectively secure a variety of surgical instruments or tools therein to thereby secure a surgical tool to the robotic arm 20002. The mounting device 20230 also may be designed to receive a trocar 20250. The trocar 20250 is releasably secured within the mounting device 20230 through a transition between an open configuration and a closed configuration of the clamping assembly 20234. The trocar 20250 can include a cannula 20252 configured to provide a pathway to a surgical site within the patient and has an access port 20254 for receiving an end effector of the surgical instrument 20200, which may be similar to end effectors (e.g., end effector 13023) described herein to perform the surgical operation on the patient. The end effector could include a jaw assembly 20266.

The longitudinally-extending support 20240 can support a vertical rail 20040. The vertical rail 20040 is coupled to the support 20240 and extends along a length of the support 20240. The vertical rail 20040 is configured such that the surgical instrument 20200 may be slideably coupled thereto and aligned with the trocar 20250. In particular, the jaw assembly 20266 extending from a shaft 20262 (which may be similar to shafts described herein such as shaft 740) of the instrument 20200 is substantially aligned with the trocar 20250 so that it can be inserted into or removed from the access port 20254 of the trocar 20250. The vertical rail 20040 can be configured for positioning the jaw assembly 20266 of the surgical instrument 20200 at least between a position P1 located just prior to entry into the access port 20254 and a position P2 located a distance from the access port 20254. Further details about the surgical assembly depicted in FIG. 93 may be found in International Patent Publication 2017/044406, which is hereby incorporated by reference herein in its entirety.

Figure 94:
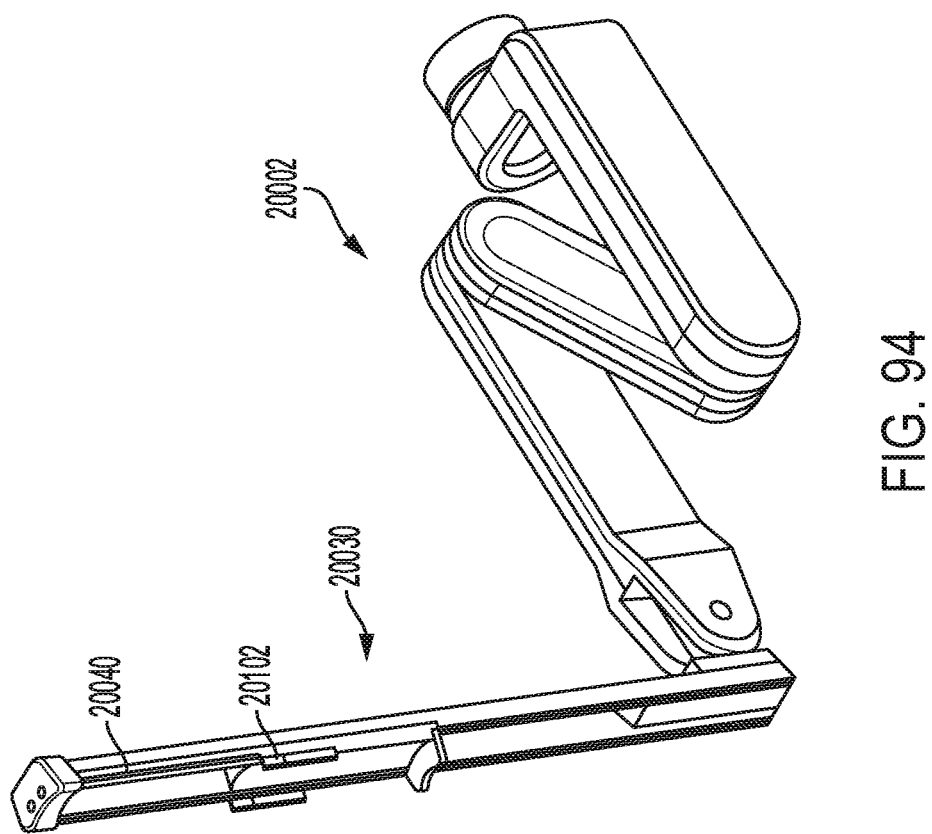
FIG. 94 is a front perspective view of a robotic arm of a robotic surgical assembly including an IDU holder, in accordance with at least one aspect of the present disclosure.
Figure 95:
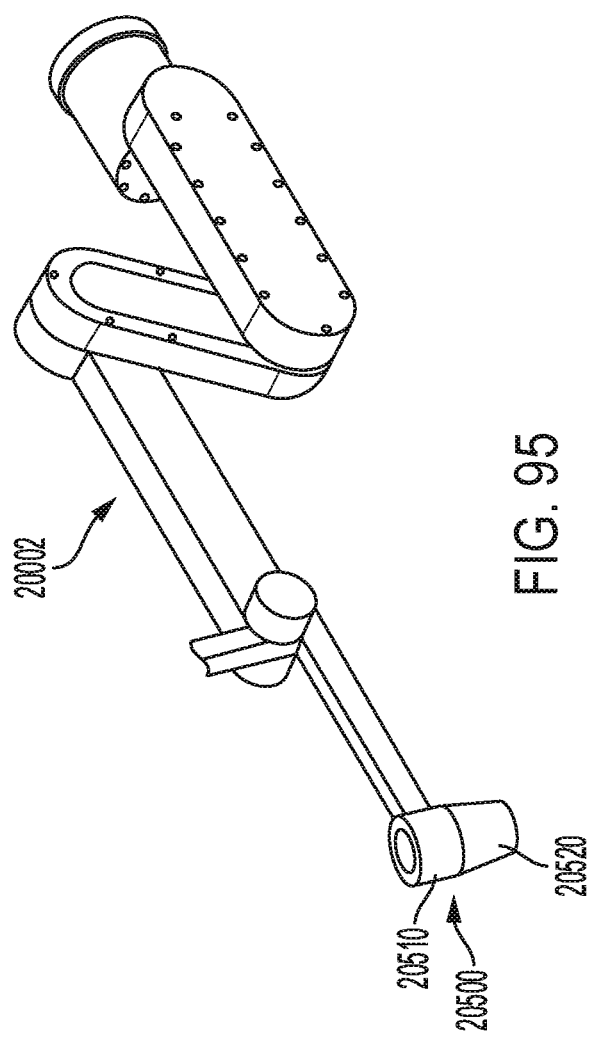
FIG. 95 is a perspective view of an arm of an medical work station including a mounting structure thereon, in accordance with at least one aspect of the present disclosure.

As shown in FIG. 94, the robotic arm 20002 can also be configured to implement robotic spherical kinematics of a robotic surgical assembly 20030 releasably secured by the robotic arm 20002. That is, robotic arm 20002 can be connected to the control device, which may control a plurality of motors, with each motor configured to drive movement of the robotic arm 20002 in a plurality of directions. The plurality of motors can form a motor pack. These directions including rotational as well as linear direction. Also, the motors could be connected to more than one robotic arm 20002, such as the two robotic arms 13002, 13003 of FIG. 4, for example. The control device may control the motor pack of an instrument drive unit (IDU) to drive various operations of surgical instrument 20200, and may control a rotation of the motor pack to ultimately rotate surgical instrument 20200 along a longitudinal axis of the IDU. Each motor of the motor pack can be configured to actuate a drive rod or a lever arm to effect operation and/or movement of each end effector (not shown) of the surgical instrument(s) 20200. The motors can be supported by the carriage 20104, which is slidably mounted on the rail 20040. The carriage 20104 may be part of an IDU holder 20102. FIG. 95 shows the robotic arm 20002 supporting a mounting structure 20500 with spherical robotic kinematic capabilities. The mounting structure 20500 could be removably or fixedly coupled to robot arm 20002. Furthermore, a portion (e.g., a proximal housing 20510) of mounting structure 20500 may be rotatable with respect to another portion (e.g., a distal housing 20520) of mounting structure 20500, such that at least a portion of the mounting structure 20500 is rotatable with respect to robot arm 20002. The mounting structure 20500 can be configured to accept a cannula assembly at least partially therein. In general, the robotic arm 20002 could support multiple types of components usable with surgical or medical procedures, in which these components are rotatably movable based on the associated motor(s). Further details about the surgical assembly depicted in FIGS. 94 and 95 may be found in World Intellectual Patent Organization Patent Publication WO 2017/205576 and World Intellectual Patent Organization Patent Publication WO 2017/205467, each of which is hereby incorporated by reference herein in its entirety.

The motors of the motor pack housed within the IDU can be configured to power the surgical instrument 20200 to drive various operations of the attached end effector (e.g., jaw assembly 20266). The jaw assembly 20266 could include a staple cartridge, knife blade or other suitable tissue effecting components such as fastening, cutting, clamping elements for driving one or more of the various operations. The jaw assembly 20266 could be directly coupled to an instrument drive connector (which can be coupled to the IDU) or alternatively to a surgical loading unit of the robotic surgical assembly 20030. The IDU can be supported or connected to a slider that is movably connected to a track (e.g., vertical rail 20040) of the robotic arm 20002. In this way, the slide may move, slide, or translate along a longitudinal axis defined by the track of the robotic arm 20002 upon a selective actuation by motors. Thus, the slider can move to selected locations along the track and provide positional feedback to the clinician. Further details can be found in U.S. Patent Publication U.S. 2018/0250080, which is hereby incorporated by reference herein in its entirety.

In some aspects, the robotic surgical assembly 20030 including robotic arm 20002 and a motor pack comprising multiple motors each configured to actuate a lever arm of the robotic surgical assembly 20030 could be considered an underactuated system. In other words, the number of lever arm or actuators of the robotic surgical assembly 20030 could be less than the number of degrees of freedom such that there are fewer motor actuators than the number of joints in the robotic surgical assembly 20030. The robotic surgical assembly 20030 could be considered to have at least two joints, for example, but there might be only one motor actuator. In such situations, the control device could be programmed to control coupled joint motion of a multi-bar linkage system. The linkages can be understood as part of particular robotic arms, such as the robotic arm 20002 having n number of linkages, for example. In particular, the control device could control the sum of linked joints to keep the location or pivot of the trocar 20250 in the same location while the several linked joints of the robotic surgical assembly 20030 simultaneously move together. The multi-bar linkage system could be subdivided into different operative sections. For example, some sections of the robot control arm(s) 20002 could be linked and cooperatively moved by the control device while the control device also maintains another set of linked joints that can be held or moved autonomously to the first set. In one aspect, one control device could control a first set of linked joints while another control device could control a second set of linked joints.

Multiple different types of multi-bar linkage system are contemplated, including four-bar linkages. Such four-bar linkages could enable continuous motion, such as parallelogram linkage, drag-link, and crank-rocker linkages, or they could be characterized as having no continuous motion, such as double-rocker linkages. The parallelogram linkage may be characterized by equal length paired linkage legs coupled in a manner in which the motion of one set is mirrored by the other set to establish paired motion with constant endpoints. The drag-link may be characterized by the presence of one or more primary links. In the drag-link, a first spherical rotation of a primary link could result in a second spherical rotation of a second primary link at a rate that is proportionate to the differences in length of the two primary links (i.e., first and second primary link). The crank-rocker can be characterized by a full circular sweep of a first shorter primary link that results in a limited arc of a larger radius than the follower path of the second primary link. The double-rocker can be characterized by a connection link that is significantly shorter than the link between the end-points. Accordingly, for the double-rocker, this results in two arcuate paths for the two primary link motions that only work within a limited angle of operation.

Multiple control methodologies by the control device to control the robotic surgical assembly 20030 including the robotic arm 20002 are also contemplated, including forward kinematics, inverse kinematics, Jacobian transpose, and teleoperation as well as force controlled actuation. Forward kinematics may include Jacobian coordinates to represent elliptic curve points, since the robotic arm 20002 can be capable of spherical kinematic capabilities. Using position sensors that can be similar in operation to position sensor 472 of FIG. 12, for example, the control device may determine the end point position of the robotic arm 20002 such as relative to the trocar 20250. With forward kinematics obtained by the control device using the integration of a kinematic model, the control device can solve for the pose (position and orientation) of the robotic arm 20002. This way, the control device may determine the endpoint and joint position or derivatives thereof of the robotic surgical assembly 20030 including the robotic arm 20002 in both situations where the robotic arm 20002 continues forward movement in its current direction or rotates. The forward kinematics could also be approached from an opposing perspective. Using inverse kinematics, the control device can solve for the robotic joint velocities necessary for a particular desired end effector (e.g., end effector 13023) velocity. In other words, the control device may control the joint of the robotic surgical assembly 20030 to determine the joint positions required for a particular endpoint placement and orientation (pose) corresponding to a desired pose of the end effector of the surgical instrument 20200 or surgical tool securably controlled by the robotic surgical assembly 20030.

The Jacobian transpose is a control methodology to control the robotic surgical assembly 20030 and robotic arm 20002 in a specific task space. In particular, the Jacobian transpose may relate the pose of the secured end effector to a corresponding set of joint angles; that is, how movement of the joint angles causes movement of the end effector. This way, the control device can determine the applicable force-torque requirements and control the torque applied by the motor actuators/pack to the set of joint angles based on the respective workspace coordinates and end effector force constraints. The control device may also use teleoperation to remotely control and operate the end effector securably held by the robotic arm 20002. Teleoperation may involve a master-slave type relationship in which the master controller controls motion of the slave end effector. The master controller can be used by a clinician, in which the master controller may be joystick controller, virtual reality controller, some controller similar to manual input devices 13007, 13008, or some other suitable controller. The master controller might constitute a unilateral control model in which motion as indicated by user control signals input into the master controller for example, are translated to the robotic end effector. Thus, although there could be a display device such as display device 13006 to display images of the surgical site, the joystick controls of the master controller may not comprise any feedback. Alternatively, the master controller might constitute a bilateral control model with haptic or force based feedback control, for example. Thus, any force or interactions made for the master controller or slave end effector are reflected in the control and operation of the other. Moreover, when the motions of the master controller are reflected in the end effector, the location of the end effector can be proportionate to the motions input into the master controller. Accordingly, when the master controller's position is recorded, the slave end effector or slave robot may follow the master controller's position in a corresponding fashion.

The control device could also implement a force controlled actuation control methodology. In such a methodology, the motor(s) associated with the robotic arm 20002 can be directly controlled by the control device to directly incorporate force and motion into control of the robotic arm 20002 and the robotic surgical assembly 20030. The force and motion components of the robotic control could be performed in isolation or simultaneously. In a hybrid force and position control approach, the control device could operate in six axes, such as a three x-, y-, and z-direction axes for force and three x-, y-, and z-directions for torque. With the six axes, the control device may separately apply a motion based control or a force based control onto each of the axes. That is, the control device could send control signals in each axis to the motor pack for this purpose. In a parallel force and position control approach, the control device could implement motion based control and force based control simultaneously. Alternatively, the control device may implement indirect force control in which force constraints, admittance control, or impedance control, for example, could be used to indirectly control motion. For example, the force constraints could be applied by the control device when position of the robotic arm 20002 deviates from the target position beyond a deviation threshold. These constraints can be different from a closed force feedback loop. The impedance control could comprise the control device implementing a maximum biasing response force, so that applied force to the robotic arm 20002 could be modified depending how much progress is being made in the motion of the robotic arm 20002. Admittance control can refer to the control device implementing a relationship between the amount of applied force and motion; for example, the more force is applied, the greater the amount of position change that is caused. Accordingly, a force sensor such as one similar in operation to force sensor 788 of FIG. 19 may be used to measure the extent of an applied input force so that the robotic arm 20002 can be controlled by the control device to move proportionally to the applied input force.

Figure 96:
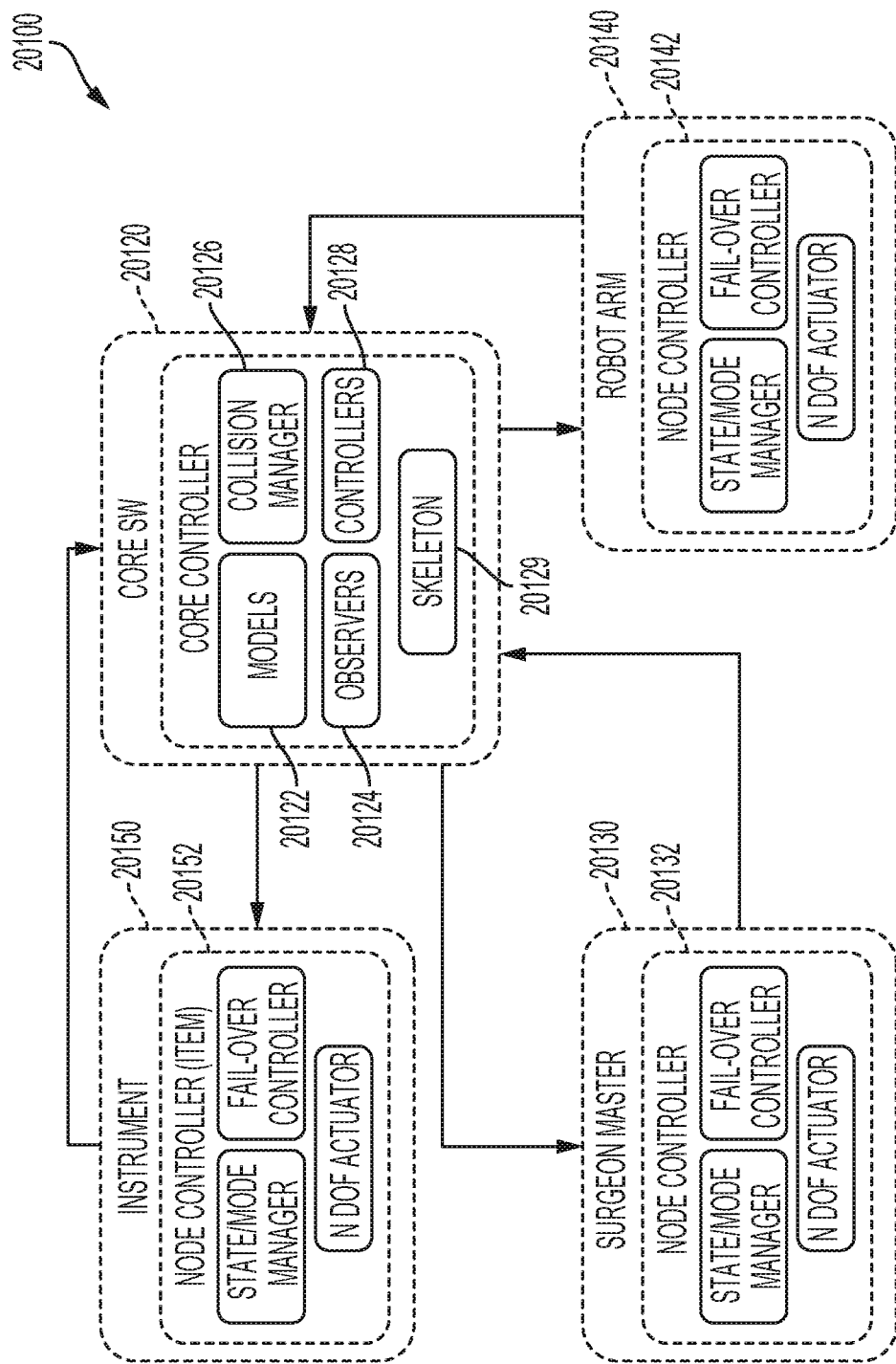
FIG. 96 is a block diagram of control components for controlling a robotic surgical system, in accordance with at least one aspect of the present disclosure.

As shown in FIG. 96, a system architecture 20100 for the robotic surgical system 13000 to implement this force controlled actuation is depicted. The system architecture 20100 comprises a core module 20120, a surgeon master module 20130, a robot arm module 20140, and an instrument module 20150. The core module 20120 may serve as a central controller for the robotic surgical system 13000 and coordinate operations of all of the other modules 20130, 20140, 20150. For example, there could be more than one robotic arm 20002, and the core module 20120 could map control devices to each of the robotic arms, determine current status, perform all kinematics and frame transformations, and relay resulting movement commands. In this regard, the core module 20120 may receive and analyze data from each of the other modules 20130, 20140, 20150 in order to provide instructions or commands to the other modules 20130, 20140, 20150 for execution within the robotic surgical system 13000. The relayed movement commands may be based on a measured extent of the applied input force, as discussed above. This way, the core module 20120 can specifically control a robotic arm such as robotic arm 20002 to apply a controlled force to an object.

The controlled force could be tailored for specific operations such as deburring, grinding, pushing an object, or some other suitable operation. Although depicted as separate modules, one or more of the modules 20130, 20140, and 20150 are a single component in other aspects. The core module 20120 includes models 20122, observers 20124, a collision manager 20126, controllers 20128, and a skeleton 20129. The models 20122 may include units that provide abstracted representations (base classes) for controlled components, such as the motors of the motor pack and/or the arm(s) 20002. The observers 20124 create state estimates based on input and output signals received from the other modules 20130, 20140, 20150. The collision manager 20126 can prevent collisions between components that have been registered within the system 13000. The skeleton 20129 may track the system 13000 from a kinematic and dynamics point of view, including forward, inverse kinematics etc. as discussed above. The dynamics item may be implemented as algorithms used to model dynamics of the components of the system 13000. This tracking and modeling can be used to address the geometric uncertainty involved with controlling the robotic surgical assembly 20030. Aside from monitoring the robotic surgical assembly 20030, the collision manager 20126 and skeleton 20129 could monitor the applied force and corresponding movement of various components within the system 13000 to avoid high or excessive forces applied to the surgical environment, which may improve safety of the system 13000. The surgeon master module 20130 may communicates with clinician control devices (e.g., master controller) and relays inputs received from these devices to the core module 20120.

In one aspect, the surgeon master module 20130 communicates button status and control device positions to the core module 20120 and includes a node controller 20132. The robot arm module 20140 may coordinate operation of a robot arm subsystem including robotic arms (e.g., robotic arm 20002), an arm cart subsystem, a set up arm, and an instrument subsystem in order to control movement of the corresponding robotic arms. Each robot arm module 20140 may correspond to and control a single arm. As such, additional robot arm modules 20140 are included in configurations in which the system 13000 includes multiple arms rather than only the robotic arm 20002. The instrument module 20150 controls movement of the surgical instrument 20200 attached to the robotic arm 20002. The instrument module 20150 may be configured to correspond to and control the single surgical instrument 20200. Accordingly, in aspects in which more than one surgical instrument are included, additional instrument modules 20150 may likewise be included. The instrument module 20150 can obtain and communicate data related to the position of the end effector of the surgical instrument 20200 (which may include the pitch and yaw angle of the end effector jaws), the width of or the angle between the jaws, and the position of an associated access port.

Each of the node controllers 20132, 20142, 20152 comprises a state/mode manager, a fail-over controller, and a N degree of freedom ("DOF") actuator, respectively. The position data collected by the instrument module 20150 can be used by the core module 20120 to determine when the instrument 20200 is within the surgical site (e.g., within an associated cannula, adjacent to the access port, or above the access port in free space). The core module 20120 may determine whether to provide instructions to open or close the jaws of the surgical instrument 20200 based on the positioning of the instrument 20200. For example, when the position of the instrument 20200 indicates that the instrument 20200 is within the cannula, instructions may be provided to maintain the end effector in a closed position. When the position of the instrument 20200 indicates that the instrument 20200 is outside of the access port, instructions may be provided to open the closed end effector. Based on this position data and corresponding force applied to the robotic arm 20002 or other movable component of the robotic surgical assembly 20030, the surgeon master module 20130 could provide improved force feedback to clinician users in bilateral teleoperation. Further details about the surgical assembly depicted in FIG. 96 may be found in U.S. Patent Publication 2018/0153634, which is hereby incorporated by reference herein it its entirety.

Figure 97:
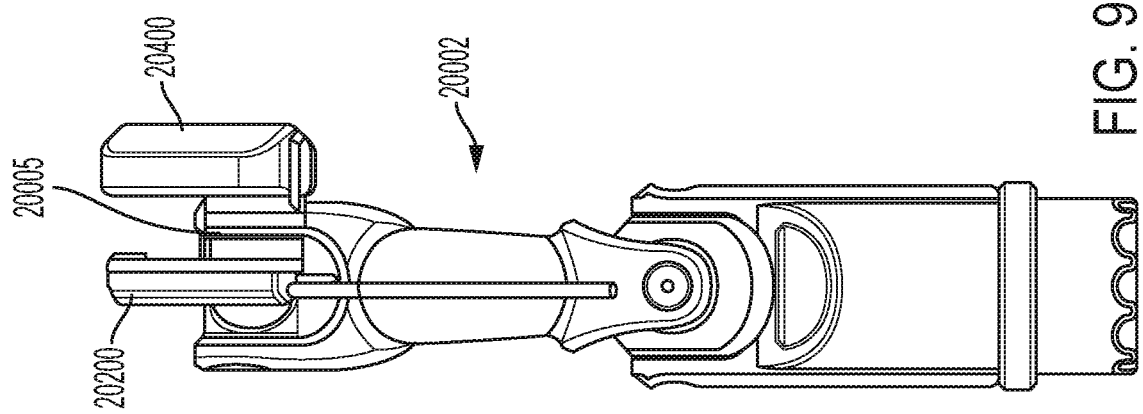
FIG. 97 is a perspective view of a torque sensor assembly for use with the robotic arm, in accordance with at least one aspect of the present disclosure.
Figure 98:
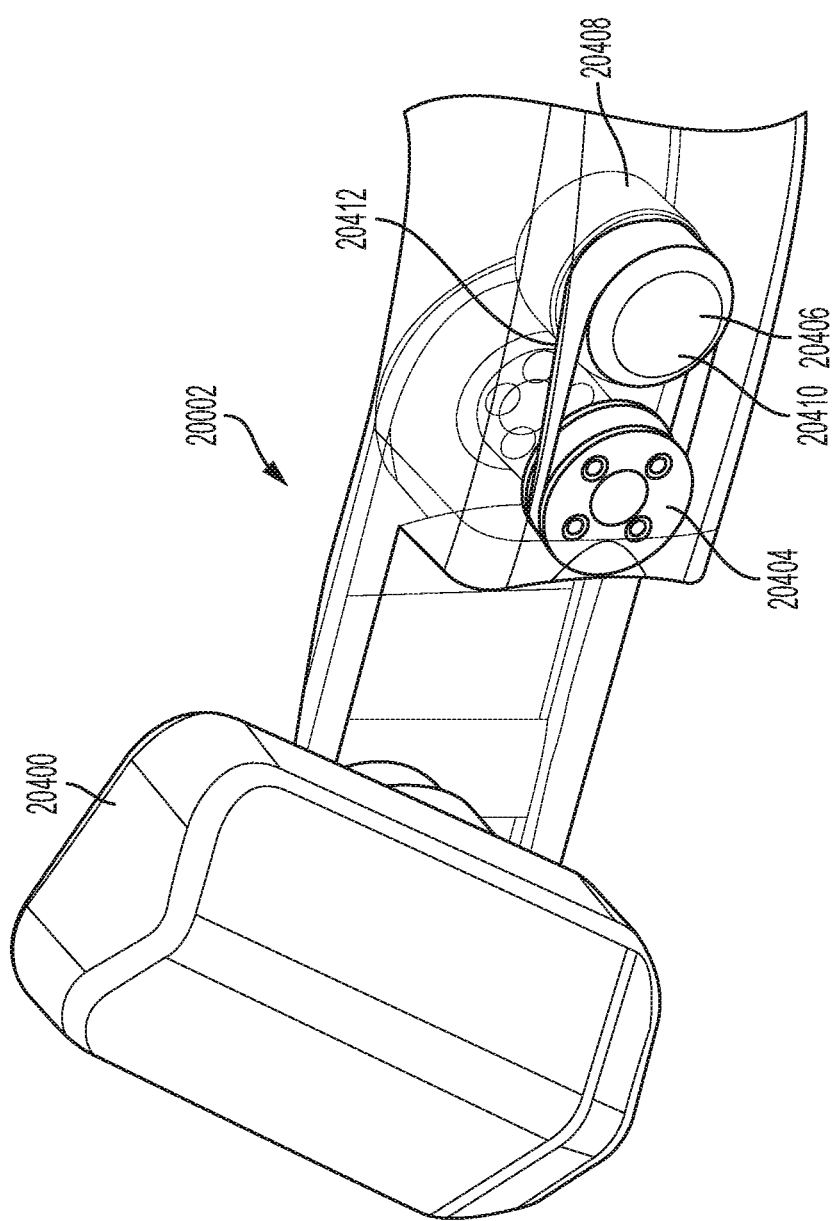
FIG. 98 is a perspective view of a torque sensor assembly for use with a robotic arm, in accordance with at least one aspect of the present disclosure.

The motors of the motor pack could involve different types of motor drive mechanisms. For example, the motors could be local to the robotic arm 20002. As illustrated in FIG. 97, the instrument drive unit (IDU) 20400 has an adapter portion to extend through the mount 20005. The adapter portion may have an engaging surface to operatively engage a portion of the surgical instrument 20200. Thus, the motor pack of the IDU 20400 is local to the robotic arm 20002 in FIG. 97. FIG. 98 shows that the robotic arm 20002 supports a rotatable torque sensor 20404 and a motor assembly 20406 that are coupled together by a drive belt 20412, in which the rotatable torque sensor 20404 and motor assembly 20406 may be operationally connected to the IDU 20400. The torque sensor 20404 can support various electrical components (e.g., resistors, wires, etc.) configured to communicate with the control device associated with the robotic arm 20002 to provide torque feedback data, for example. The torque sensor 20404 could be coupled to the mount 20005, which could be an arm mount 20005 to secure the torque sensor 20404. Additionally, the torque sensor 20404 may comprise a body defining a plurality of exposed gauges in which the body supports the various electrical components for communicating with the control device. The motor assembly 20406 includes at least one motor 20408 and a harmonic gear box 20410 that cooperate to impart rotation on torque sensor 20404 via drive belt 20412 to effect rotation of the IDU 20400. This rotation may involve rotating the arm mount 20005 about a transverse axis that is transverse relative to the robotic surgical assembly 20030.

In some aspects, the motor(s) 20408 of the motor assembly 20406 can be organized as a motor pack of the IDU 20400. The locally positioned motors 20408 can be arranged in a redundant coupling configuration between various joints of the robotic surgical assembly 20030 so that motion of the robotic arms could be synchronized. Alternatively, the motors 20408 could be controlled via a central location such as a hub control device to control each IDU 20400 and motor pack of each robotic arm. Accordingly, in one aspect, the motors 20408 of the motor pack can be centralized to a central location of the robotic surgical assembly 20030 in which various linkages and/or cables are used to interconnect to the various arm joints of the multiple robotic arms of the robotic surgical assembly 20030. Furthermore, the end effectors secured by each of the multiple robotic arms could be steerable. For example, a steerable portion of a hollow tubular structured end effector may be manipulated by the robotic arm 20002 relative to the trocar 20250. In particular, the cannula 20252 could be an active cannula 20252 capable of steering motions that can be adjusted depending on the progress of the surgical operation being performed on the patient. In one aspect, the steering mechanism could be a tendon-driven mechanism, which can comprise an elastic central backbone and a group of tendons arranged in parallel about this back. This tendon-drive mechanism may have a concise profile that is easy to control. The steering mechanism of the end effector can be remotely operated by the clinician. Further details regarding the motor drive mechanisms described herein may be found in World Intellectual Property Patent Organization Patent Publication WO 2016/043845, which is hereby incorporated by reference herein in its entirety.

In various aspects, the robotic surgical system 13000 can be used with an abdomen wall access port, which can be a type of the access port 20254 described above. There may be a virtual port pivot, around which various robotic arms such as the robotic arm 20002 can move. The kinematics about the virtual port pivot can be used as part of insertion of the surgical instrument 20200 secured by the robotic arm 20002 into the access port 20254 of the patient. Also, the robotic arm 20002 may comprise a surgical mounting device configured to releasably secure an access device therein, including the trocar 20250, cannula 20252, access port 20254 and other suitable access tools or instruments. The robotic arm 20002 can then pivot about the access device. The surgical mounting device might support a clamping assembly and a release mechanism, or release mechanisms. The surgical mounting device may be mechanically attached to the robotic arm 20002. Further details about this mounting device can be found in U.S. Patent Publication 2018/0177557, which is hereby incorporated by reference herein in its entirety. The rotation of the robotic arm 20002 may be rotation about a point that is not physically located at, or is remote to the robotic surgical assembly 20030. Restricted rotation about this remote point may be termed a remote center-of-motion (RCM) mechanism. Remote RCM mechanisms may include parallel RCM, spherical RCM, and hybrid RCM. FIG. 99 illustrates a parallel RCM system in which the remote RCM robotic surgical system 13000 comprises a base unit and multiple linking units coupled to each other. At least two of the linking units are kept parallel to each another during motion. In various aspects, a robotic module is provided that can be used to orient an end effector about two axes intersecting at a fixed geometric point located distal to the mechanism materializing a pivot point or a RCM. A robotic end effector mounted on a RCM module will rotate about the RCM point, which can be conveniently located on the end effector since this point is remote from the robotic module.

Figure 99A:
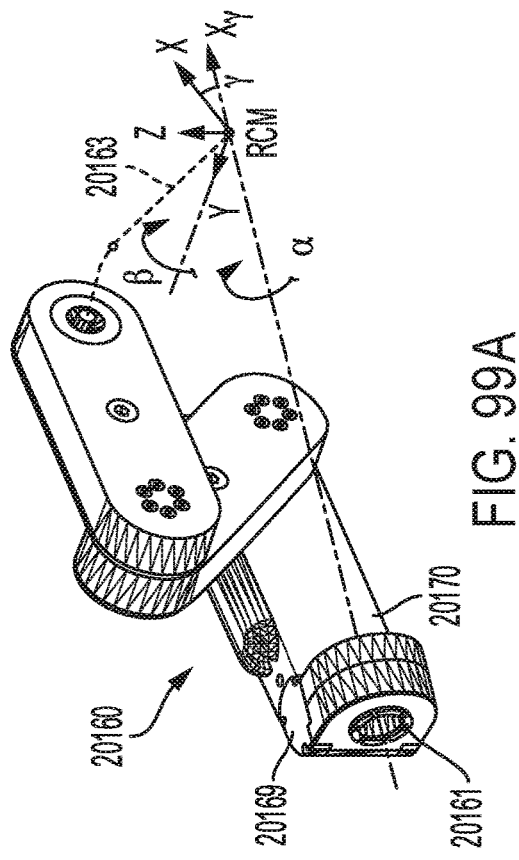
FIGS. 99A-99C are diagrams of a remote center of motion (RCM) robotic module, in accordance with at least one aspect of the present disclosure.
Figure 99C:
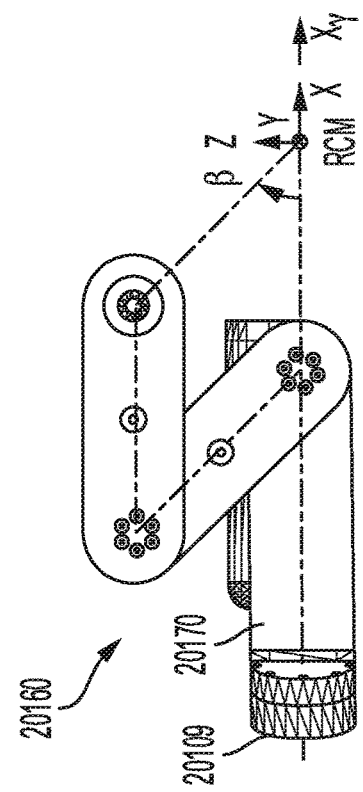
Figure 99B:
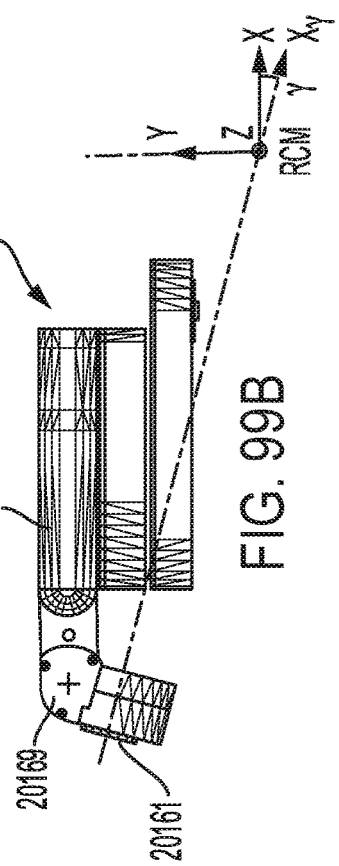
Figure 100:
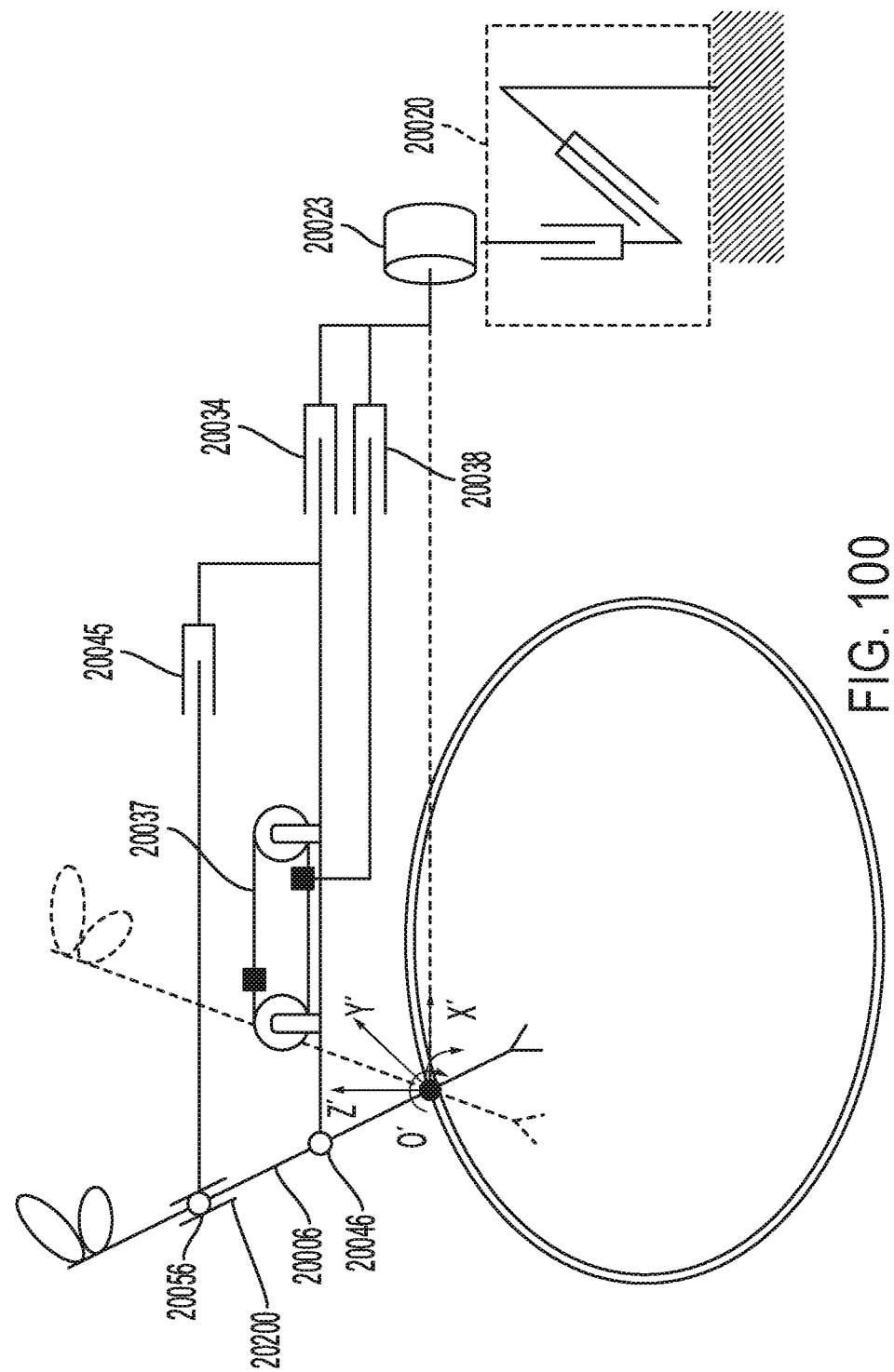
FIG. 100 shows motion about a remote center of motion (RCM) after adjusting the RCM, in accordance with at least one aspect of the present disclosure.

In FIGS. 99A-99C, the module or mechanism 20160 may include first, second and third arms (also referred to as links and linking units) and which may be similar in operation to all or a subset of the robotic arm 20002. One of the arms, such as the third arm could be configured to receive a holder/driver that holds an end effector 20163 (e.g., could be similar in operation to end effector 13023), depending on the applicable desired functionality. The RCM module 20160 is configured to allow two active parallel degree-of-freedom (DOF) RCM mechanisms: a) rotation $\alpha$ about axis $x_y$ of the base shaft 20161 representing a first pivoting axis; and b) rotation $\beta$ about axis y of the parallelogram structure formed by the second and third arms, and the end effector 20163, representing a second pivoting axis y. The two axes intersect at the center of the xyz coordinate system, representing the pivot point or RCM point of the mechanism. The RCM module 20160 is configured so that the adjustment angle $\gamma$ between the elements 20169 and 20170 can be adjusted, and the elements 20169 and 20170 can be locked in a desired relative orientation. The adjustment angle $\gamma$ changes the orientation of the axis $x_y$ and shifts the location of the RCM point along the second pivot axis y. This angular adjustment design may allow for conveniently setting the pivot point to accommodate different end effectors (e.g., end effector 20163) while maintaining a compact design. The RCM module 20160 may have a folded configuration in which $\beta_0=0°$. This folded operation mode may allow the module 20160 not just to clear the RCM pivot, but also to clear the region above the RCM. This is important in performing image-guided procedures, wherein the robotic surgical assembly 20030 should be distal from the active field of the image to allow unimpeded visualization of the target end effector 20163 during the procedure. Conversely, the RCM module 20160 may also have a folded configuration in which $\beta_0=90°$. In general, the module can operate about a folded ($\beta=0°$), normal ($\beta=90°$), inverted ($\beta=-90°$), extended ($\beta=180°$), or any unfolded position ($\beta\{-90°, 0°, 90°, 180°\}$), with end effector 20163 mounting on either side of the mechanism. Further details about parallel RCM mechanisms can be found in U.S. Patent Publication 2018/0177557, which is hereby incorporated by reference in its entirety.

Spherical RCM may involve a circular-guiding arc RCM mechanism, for example. As discussed above, RCM can be used to mechanically constrain the position of a certain point in the surgical operation space. A spherical RCM mechanism could involve more than 2 DOFs such as 3 DOF and could be placed inside or outside the patient's body. Circular-guiding arcs, semi-circular arches, or other spherical-based linkages can be used as part of spherical RCM to model the robotic kinematics involved in the insertion of surgical tools into an access or insertion port of the patient for surgery. Hybrid RCM mechanisms could enable 6 DOF surgical tool motion. For example, the robotic kinematic could include four segments: two parallel coupled joint elements, one prismatic and one optional revolute joint in the end effector 13023 to enable the 6 DOF motion. The robotic surgical system 13000 can implement any of the RCM mechanisms described above or some other suitable RCM mechanism. To this end, the robotic surgical system 13000 could implement an instantaneous and/or adjustable remote center of motion (ARCM) mechanism. That is, the fixed point in space (i.e., remote center of motion) about which the surgical instrument 20200 secured by the robotic surgical assembly 20030 can be adjusted or changed. An adjustment of the remote center of rotation (RCM) O in an X-direction can be achieved by simultaneous and equivalent movement in the prismatic joint 20034 and the prismatic joint 20038.

The RCM can be adjusted from O to O' by adjusting the position of the belt clamp 20037 and/or YZ table 20020, for example. The surgical instrument 20200 is held by instrument holder 20006 and supported by the CM mechanism on one side of the revolute joint 20023. When the RCM is shifted to O', the YZ table 20020 connected to the other side of the revolute joint 20023 also makes the adjustment of its respective Y and Z directions. The prismatic joint 20034 and prismatic joint 20038 move together while the prismatic joint 20045 stays static to perform the RCM adjustment in the X-direction. When the adjustment is completed, RCM is enabled when the prismatic joint 20038 is fixed. The orientation of the surgical instrument may be steered by the revolute joint 20023 to obtain its rotation around X-axis. The displacements of the joints 20046, 20056, which are identical to the motion on the prismatic joint 20034 and 20045 while the prismatic joint 20038 keeps static, can enable the surgical instrument 20200 to rotate around Y-axis. Further details about ARCM mechanisms can be found in U.S. Patent Publication 2012/0132018, which is hereby incorporated by reference herein in its entirety.

Figure 101:
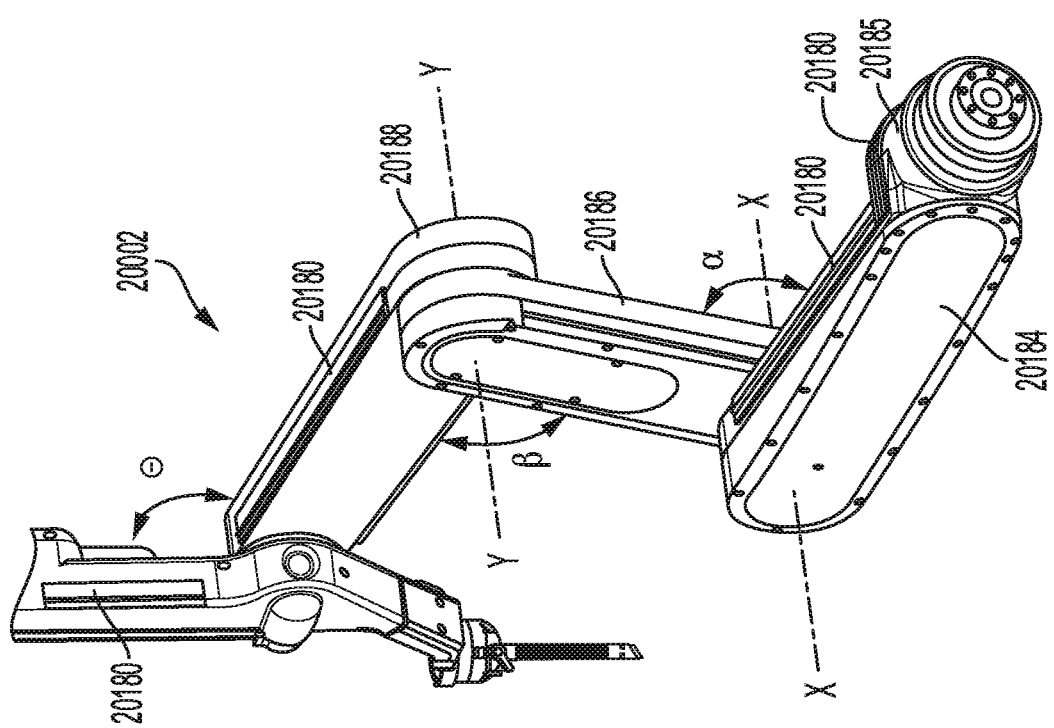
FIG. 101 is a perspective view of a surgical robotic arm of a robotic system, in accordance with at least one aspect of the present disclosure.

Moreover, RCM mechanics can be used with the robotic surgical system 13000 to provide rotation around the incision point into the patient to prevent potential damage of the patient's tissue being treated by the robot surgical assembly 20030. Also for prevention of damage to the patient, force feedback from the robotic arm 20002 can be provided to the control device to mitigate accident involving the interacting robotic arm(s) 20002. As discussed above, one or more control devices could be provided. The control device may control a plurality of motors (e.g., of a motor pack), each of which is configured to actuate the surgical instrument 20200 to effect operation and/or movement of surgical instrument 20200. Specifically, the control device may coordinate the activation of the various motors to coordinate a clockwise or counter-clockwise rotation of drive members to coordinate operation and/or movement of the surgical instrument 20200. As depicted in FIG. 101, the robotic arm 20002 may include a plurality of movable links including a first link 20184, a second link 20186, a third link 20188, and a holder such as instrument holder 20006, which are coupled to each other by actuators allowing for movement of the robotic arm 20002 into various configurations. The links 20184, 20186, 20188 can be rotatable about respective joints. The first link 20184 can comprise a curved base 20185 configured to secure the robotic arm 20002 to a movable base. Movement can occur via actuation forces transferred from the motors via the IDU, as discussed above.

Since the edges of the movable links of the robotic arm 20002, namely, the first and second links 20184 and 20186, the second and third links 20186 and 20188, etc., are capable of being flush with each other, there is a possibility of trapping and crushing various obstructions, such as user's appendages, fingers, etc., between the links 20184, 20186, 20188 as well as the holder. To address and mitigate such accidents, a sensor system may be provided to detect physical contact between the movable links of the robotic arm 20002 and to control the robotic arm 20002. The robotic arm 20002 may include one or more sensor assemblies 20180 disposed on any of the links or holder. The sensor assemblies 20180 could be similar in operation to one or more of the sensors described above, such as the sensors 738. The sensor assemblies 20180 may be disposed on any surface that present a high risk of crushing, shearing, or otherwise injuring body parts that may be caught by the robotic arm 20002 during its movement. In some aspects, the sensor assemblies 20180 may be disposed adjacent an inner edge (e.g., an edge that is closest to a neighboring link), or outer edge of the links 20184, 20186, 20188. A sensor assembly 20180 might also be disposed on a curved surface of the curved base 20185 of the first link 20184 to prevent a joint from crushing the user's appendages resting on the curved base 20185. Thus, the sensor assemblies 20180 and control device can beneficially reduce or eliminate injury from accidents involving the robotic arm 20002. Further details about such incident detection systems can be found in World Intellectual Property Organization Patent Publication WO 2018/18152141, which is hereby incorporated by reference herein in its entirety.

In one aspect, the sensor assemblies 20180 comprise a curved sensor assembly including: a base housing, a first and a second force sensing resistor assemblies disposed within the base housing, and an interface member disposed over the first and second force sensing resistor assemblies. The first and second force sensing resistor assemblies can have contacts to connect to an associated control device. The control device may continuously monitor signals from one or more sensor assemblies 20180 and control the robotic arm 20002 in response to the signals output by one of the assemblies 20180. Based on these signals, for example, the control device may determine or measure relationships between the various linkages 20184, 20186, 20188, such as positional relationships. This way, virtual interactions about the virtual port pivot can be monitored by the control device to avoid inadvertent accidents. Furthermore, the force sensing resistor assemblies may have any suitable shape, including but not limited to rectangular or circular. The interface member can a substantially curved shape and comprise a bridge to engage the first and second force sensing resistor assemblies.

Cooperative Engagement Between Robotic Arms

Figure 102:
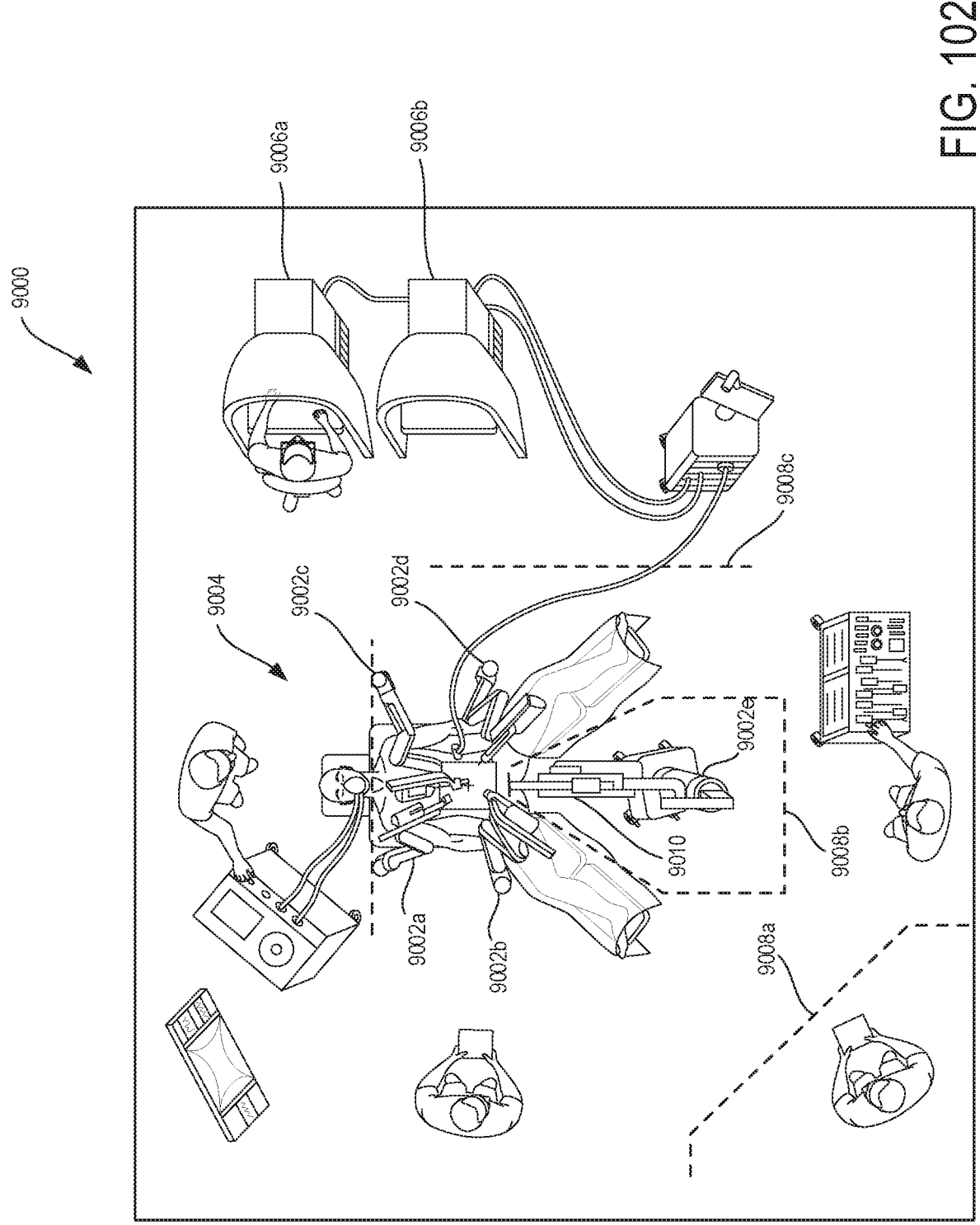
FIG. 102 is a top view of a surgical environment including a patient being treated by a robotic surgical assembly, in accordance with at least one aspect of the present disclosure.

In various aspects, a plurality of robotic arms can be attached to a surgical platform such as a surgical table, on which the patient may rest during a surgical operation. FIG. 102 depicts a top view of a robotic surgical system 9000 comprising a plurality of robotic arms 9002a, 9002b, 9002c, 9002d, 9002e each attached to the surgical platform 9004. The robotic surgical system 9000 can be similar to other robotic surgical systems described herein such as robotic surgical system 13000. Although four robotic arms 9002a-9002e are shown in FIG. 102, more or less than four arms can be used as desired for the particular operation being performed. As described above, each robotic arm of the 9002a-9002e could be controlled by its own control device. Alternatively, the robotics arms 9002a-9002e can be controlled in conjunction by a configurable selective arm base unit. This base unit might be connected to each of the control devices described above, or the base unit could control each of the robotic arms 9002a-9002e of the robotic directly. To this end, the base unit may be configured to control cooperative interactions between various ones of the robotic arms 9002a-9002e. The base unit may operate as a control circuit, which can be similar in some aspects to control circuits/units described herein. The base unit control circuit can be controlled by a clinician to selectively control a specific one or multiple of the robotic arms 9002a-9002e. In one aspect, the clinician may be a surgeon. Relatedly, there may be multiple medical personnel present in the surgical environment, such as physician assistants, anesthesiologists, and nurses (e.g., circulating nurse, scrub nurse, etc.).

The base unit control circuit may comprise a first central controller 9006a for a first surgical robot and a second central controller 9006b for a second surgical robot, in which the central controllers 9006a-9006b are operated together to implement the cooperative engagement of robotic arms 9002a-9002e. To this end, each surgical robot can control a subset of the robotic arms 9002a-9002e; for example, the first surgical robot could control the robotic arms 9002a-9002d while the second surgical robot controls the robotic arm 9002e. The cooperative engagement of the robotic arms 9002a-9002e might be controlled by the base unit control circuit autonomously, in conjunction with control inputs by the clinician/surgeon, or by a combination of autonomous and user control. The first and second controller 9006a-9006b could be arranged in a master-slave relationship so that the second surgical robot operates in response to the second controller 9006b receiving feedback of the operation of the first surgical robot by the first controller 9006a, for example. Accordingly, both of the controllers 9006a-9006b may have their own communication modules. Additionally or alternatively, the surgical instruments, tools, or devices attached to the respective robotic arm may comprise their own communication modules. These individual communication modules of the surgical instruments, tools, or devices can be used to control the cooperative interaction of the arms that these surgical implements are attached to. The base unit control circuit and/or controllers 9006a-9006b may have similar structural components as the control circuits (e.g., control circuit 760 shown in FIG. 18) described above, including programmable microcontrollers, processors, memory circuits, etc. as appropriate, for example.

In general, the base unit control circuit may enable cooperative operation of the robotic arms 9002a-9002e both within and outside of a sterile barrier. For example, the robotic arm 9002e could be operating in a non-sterile zone while the robotics arms 9002a-9002d operate in a sterile zone. Because some of the arms 9002a-9002e are operating in a sterile zone and others are operating in a non-sterile zone, it may be particularly important that the robotics arms 9002a-9002e operate in a cooperative fashion. As depicted in FIG. 102, a surgeon or clinician could be situated at a console to operate the one of the first and second controller 9006a-9006b. One surgeon could control the console for the first controller 9006a (e.g., that operates in a sterile field) while a different surgeon controls the console for the second controller 90006b (e.g., that operates in a non-sterile field). Each of the controllers 9006a-9006b could control a subset or all of the robotic arms based on a wired or a wireless connection, as applicable depending on the surgical procedure being performed. In one aspect, the area indicated by the sterile boundary demarcation 9008b is considered a non-sterile field. The areas indicated by non-sterile boundary demarcations 9008a, 9008c, respectively, in the direction extending further away from the patient are also considered non-sterile fields.

As discussed above, the robotic arms 9002a-9002e can each releasably hold, secure and/or control surgical tools, device or instruments for performing a surgical operation or procedure on the patient. In some aspects, one or more of the group of robotic arms 9002a-9002d controls an anvil of a stapling surgical instrument, which can be similar in operation to one of the surgical instruments described above such as surgical instrument 20200. The robotic arms 9002a-9002d can also implement other aspects of the surgical operation in the sterile abdominal cavity (e.g., other surgical tools or functions) such as using electrosurgical forceps or RF surgical instruments to cut and treat tissue during a gastrojejunostomy procedure, for example. That is, the surgical apparatuses held by each robotics arm 9002a-9002d can be passed through a cavity in the surgical environment, such as the sterile abdominal cavity of the patient, to assist in performing the desired operation. Conversely, the robotic arm 9002e controls a surgical device such as a surgical instrument 9010 and may pass through a natural orifice of the patient, such as the non-sterile anal orifice. As discussed above, each robotic arm may secure an access port, trocar, and/or cannula for insertion of the surgical tool, device or instrument(s) attached to the robotic arm. The surgical instrument 9010 could be a circular stapling surgical instrument. Thus, the base unit control circuit can be used to orient and align the surgical instrument 9010 and an anvil held by one of the robotic arms 9002a-9002d, for example, to properly align tissue to be compressed for forming an anastomosis between two types or pieces of tissue during a circular stapling operation. The base unit control circuit could comprise its own communication module to output control signals to the robotic arms 9002a-9002e or the control devices of the robotic arms 9002a-9002 based on this communicative coupling.

In particular, the first controller 9006a may communicate with the second controller 9006b to enable cooperative operation for forming the anastomosis, orienting a camera held by a robotic arm, aligning a tissue for an ultrasonic instrument to cut, or other suitable surgical operations requiring cooperative engagement of robotic arms, for example. Upon determining a position or adjusted position of each of the robotic arms 9002a-9002e, as described in further detail below, the base unit control circuit could control the robotic arms 9002a-9002e to cooperatively interact so that the associated circular stapler and anvil are properly aligned to staple tissue for performing a surgical operation. The robotic arms 9002a-9002e could be remotely operated. Also, more than one robotic arm can be used to control a surgical device, tool, or instrument, although one robotic arm can be sufficient to secure a single surgical device, tool, or instrument. Additionally to the robotic arms 9002a-9002e, there is also present in the surgical operating room of FIG. 102: an operating room monitor which can be similar to the primary display 119, an anesthesiologist, a physician assistant, a circulating nurse, a scrub nurse, a surgeon, and a control tower which can be similar to the hub 106 in FIG. 2. The control tower may comprise, for example: a camera (e.g., including endoscopic camera), generator like generator module 140, communications like communication module 130, smoke evacuation like smoke evacuation module 126, a module for the first surgical robot (first central controller 9006a), a module for the second surgical robot (second central controller 9006a), and an insufflator, for example.

In various aspects, the base unit control circuit may be configured to function as a control system for executing automated arm-to-arm adjustment of the robotic arms 9002a-9002e. That is, the base unit control circuit may change or modify the pose of each robotic arm 9002a-9002e, which includes height and attachment orientation relative to the surgical platform, as well as changing the spacing between various ones of the robotic arms 9002a-9002e (i.e., arm-to-arm spacing). This adjustment of arm position and/or orientation could be done autonomously by the base unit control circuit. Alternatively, this adjustment could be an assisted adjustment that functions as supplemental assistance to a surgeon that is controlling one of the surgical robots being used, such as via the console of the controllers 9006a-9006b. As discussed above, robotic arms 9002a-9002e can be coupled to each other and to their associated motor via different types of coupling, such as a dual rotary rod coupling, which can be part of the multi-bar linkage system of the robotic surgical assembly 20030. Using the dual rotary rod coupling, the robotic arms 9002a-9002e can be interconnected relative to each other, to the surgical platform, or a floor mount in the surgical environment. The two rods of the dual rotary rod coupling could rotate in synchronization with each other or out of sync, which in turn moves one or both of the two arms connected via the two rods. This movement may be relative to the bottom of the surgical platform, such as the location where the associated motors of the robotic arms 9002a-9002e are attached or housed to the surgical platform. The movement may refer to the entirety of a robotic arms or certain constituent linkages of the robotic arm such as the linkages 20184, 20186, 20188 described above. When the base unit control circuit determines whether two arms connected by a dual rotary rod coupling are rotating in sync or out of sync, the base unit control circuit may control one or both of the robotic arms to maintain a desired relative position or orientation between the two arms.

This control by the base unit control circuit may comprise an automated positional adjustment. To this end, the base unit control circuit may receive positional sensor measurements from sensors such as proximity sensors (e.g., ultrasonic, IR, inductive, capacitive, photoelectric, Hall effect sensor, etc.) or position sensors that can be similar to sensors described herein, such as the sensor assemblies 20180 disposed on any of the links or holder of a robotic arm. Based on the position or proximity signals, the base unit control circuit can determine the pose of each robotic arm, including the position and orientation of each arm, as well as the positional relationships between various arms such as a distance between a first robotic arm and a second robotic arm of the robotic arms 9002a-9002e. In some aspects, the base unit control circuit might comprise a powered adjustment tool, which can be powered by one or more dedicated motors of the robotic surgical assembly 20030. In other words, various motors of the motor pack could each correspond to a connection location of a robotic arm or a linkage of that robotic arm. Each motor could also correspond to a specific distance that a robotic arm or linkage thereof can be adjusted to. Thus, the user of the powered adjustment tool can use the tool to set up the positioning of each robotic arm considered alone or in relationship to another arm. For example, each dedicated motor could be used to transfer actuation forces to an associated adjustment member so that when all of the dedicated motors are activated, the various robotic arms 9002a-9002e are positioned at some specific distances therebetween. These specific distances could be user defined, such as some predetermined distance (e.g., 1 foot) between robotic arms or the some of the constituent linkages of these robotic arms. Moreover, the adjustment members could have integrated or connected sensors that function similarly to the sensor assemblies 20180, so that the surgical robot controlling the robotic arms being adjusted receives an indication of the specific distances between arms. Consequently, the surgeon controlling the respective controllers 9006a-9006b may be provided information indicating the specific distances that the arms are adjusted to.

As such, the powered adjustment tool may be controlled manually or automatically by the corresponding surgical robot. Also, the corresponding surgical robot could itself be controlled by the surgeon using the surgeon console for the controllers 9006a-9006. In configurations in which the powered adjustment tool is controlled by the surgical robot, an electronic lockout mechanism can be provided such as one comprising an electronically actuated fuse, electronic key, switch or other suitable mechanism. The electronic lockout, when activated, may prevent the robot from moving the corresponding robot arms controlled by it. In this manner, when the powered adjustment tool is adjusting arm-to-arm distances to the specific distance, the robot cannot otherwise move the arms. The lockout could also be applicable when arm movement is controlled by the surgeon. Alternatively, some arm movement as specified by the robot or the surgeon could be allowed, but the base unit control circuit may implement a lower force operational mode that compares the force required to move an arm to a force threshold. This way, when the arm(s) and adjustment member(s) of the powered adjustment tool are moved simultaneously, the arm(s) are moved at a slower rate or at a lower maximum force threshold. These functionalities of the base unit control circuit to adjust the various arms robotic arms 9002a-9002e can be used for cooperative engagement. Adjustment of arm-to-arm distances can improve the chance of success of the surgical operation. For example, the specific known arm-to-arm distances can help when one arm is holding a camera and the other arm is holding a surgical instrument that is being inserted into an access port, when one arm is holding an anvil that needs to be aligned with the surgical stapler secured by the other arm, or when one arm has forceps for gripping a tissue bite that needs to be inserted into the end effector of an RF surgical instrument held by the other arm.

In addition to arm-to-arm adjustments, the base unit control circuit may be configured to change the pivot position or orientation of any of the robotic arms 9002a-9002e relative to the surgical platform. This change in motion can be automated or an assist to such control by the surgeon. Adjustment of pivot position could comprise adjustment of the RCM relative to a virtual port pivot, as described above. Accordingly, the adjusted RCM could then restrain a corresponding arm to a different surgical operation space defined by a different pivot point. This adjustment to the different RCM could be made by the base unit control circuit because the position of the surgical platform has changed, such as from a horizontal position to a Tredenlenburg position, for example. Other changes in the position of the surgical platform are also possible and the positions of the respective robotic arms 9002a-9002e The precise change in incline or decline of the surgical platform could be used to determine the extent that the RCM should be adjusted. Additionally or alternatively, the adjustment of the position of the surgical platform could be used to change a pose (i.e., position and orientation) of any of the robotic arms 9002a-9002e. In this way, the robotic arms 9002a-9002e can be adjusted by the base unit control circuit to the desired height, orientation, and RCM rotation parameters for performing the surgical operation on the patient. Making these adjustments automatically or as an assist to the surgeon when the surgical platform moves can ensure the surgical procedure proceeds smoothly. These pose adjustments of the robotic arms 9002a-9002e can advantageously reduce or eliminate the risk of interruption when the surgical platform is inadvertently moved, for example. The initial positions of the robotic arms 9002a-9002e could be determined based on sensor measurements from the proximity or position sensor, for example.

The robotic arms 9002a-9002e might be mounted to the surgical platform/table as discussed above, or they be mounted to the floor of the surgical operating room. The precise mounting arrangement can be incorporated into the adjustment of the pose of the robotic arms 9002a-9002e. When the patient's head is raised based on the incline of the surgical platform, for example, kinematic calculations from the control device mapped to each of the robotic arms 9002a-9002e mounted on the surgical platform can be used to maintain the pivot and relative position of the trocars, access ports, tools, or other implements secured by the corresponding arm. Also, force thresholds as implemented by the control device or the base unit control circuit can be used based on force measurements by force sensors such as the sensor assemblies 20180 for maintaining pivot and relative position as well. Thus, the base unit control circuit could change the respective pivot positions of any robotic arm 9002a-9002e based on comparison to applicable force thresholds to maintain the pivot and relative position. When the arms 9002a-9002e are mounted to the floor, the arms can be automatically raised or lowered depending on the movement of the patient, such as when the patient's head is raised. For example, when the patient's head is raised based on the incline of the surgical platform, the subset of robotic arms 9002a-9002e located in an area corresponding to on that side of the table that is pivoting can be automatically raised. Conversely, the subset of robotic arms 9002a-9002e on the other side of the pivot may be automatically lowered.

The surgical platform 9054 can also be rotatably moved. When the platform is rotated, the patient could potentially move relative to the platform 9054. For example, gravity could cause the patient to subtly shift position. Accordingly, the access ports of the patient may move relative to the fixed position of the surgical robots and associated arms performing the procedure, which may result in transverse loads being applied to the associated arms 9002a-9002e. To address this undesired movement of the access ports, the base unit control circuit may control the motor pack to apply actuating forces to the arms 9002a-9002e to move so that these transverse loads stay below a certain threshold. If the actuating forces do not move the robotic arms 9002a-9002e sufficiently quickly, such that the threshold is exceeded, a safety stop could be triggered. For example, the safety stop could involve terminating providing power to the mechanical actuator that is causing the surgical platform to rotate. The robotic surgical system 13000 may inform the medical staff present in the operating room based on tactile or audible feedback, for example. As such, the base unit control circuit is designed to provide automated or assisted adjustment of arm support height, attachment orientation, and/or arm-to-arm spacing so that various arms 9002a-9002e maintain or adjust their pose so that the attached surgical tools, devices or instruments may operate properly on the patient, individually as well as cooperatively.

Figure 103A:
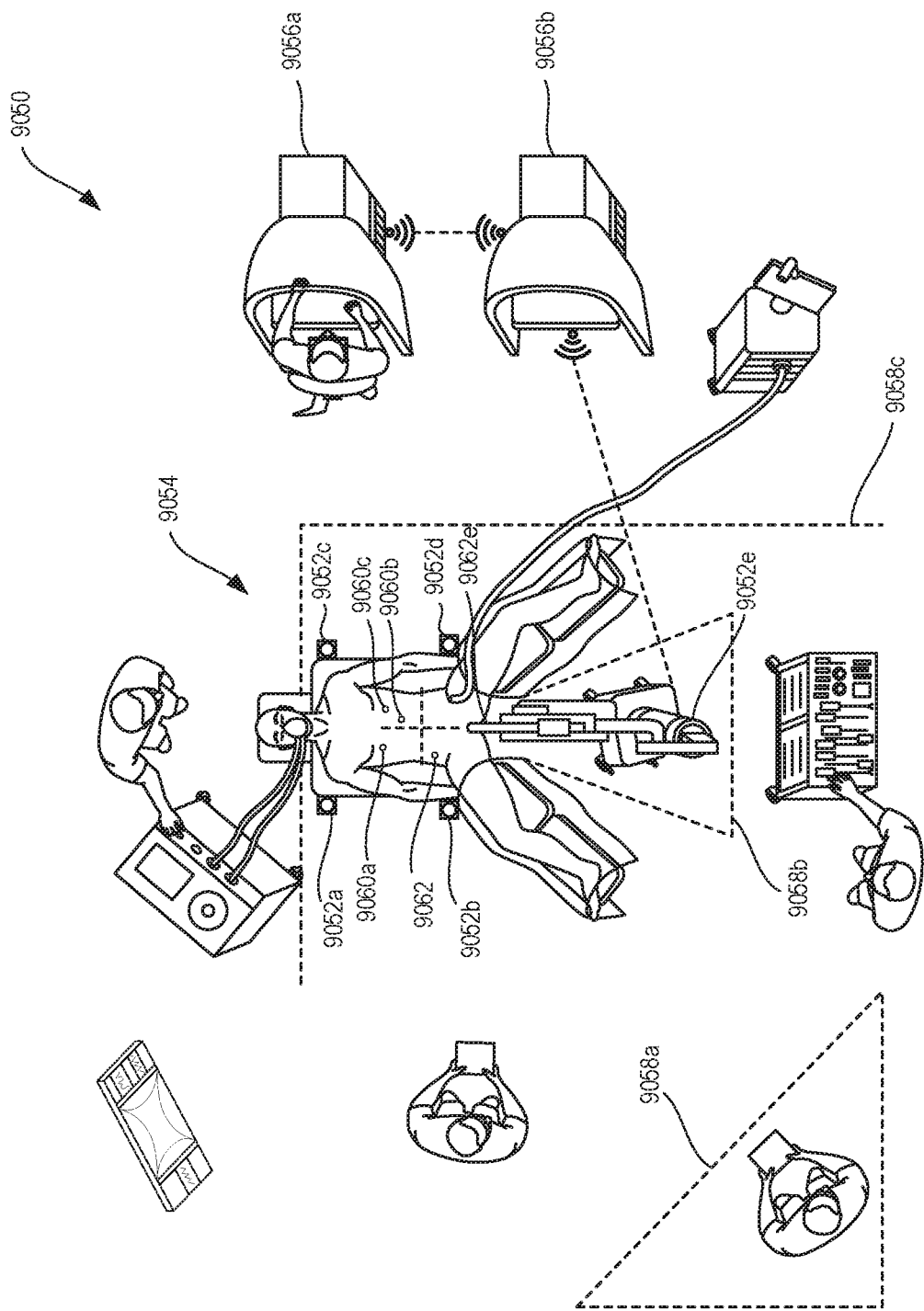
FIGS. 103A-103B are top views of a surgical environment including a patient being treated by a robotic surgical assembly, in accordance with at least one aspect of the present disclosure.
Figure 103B:
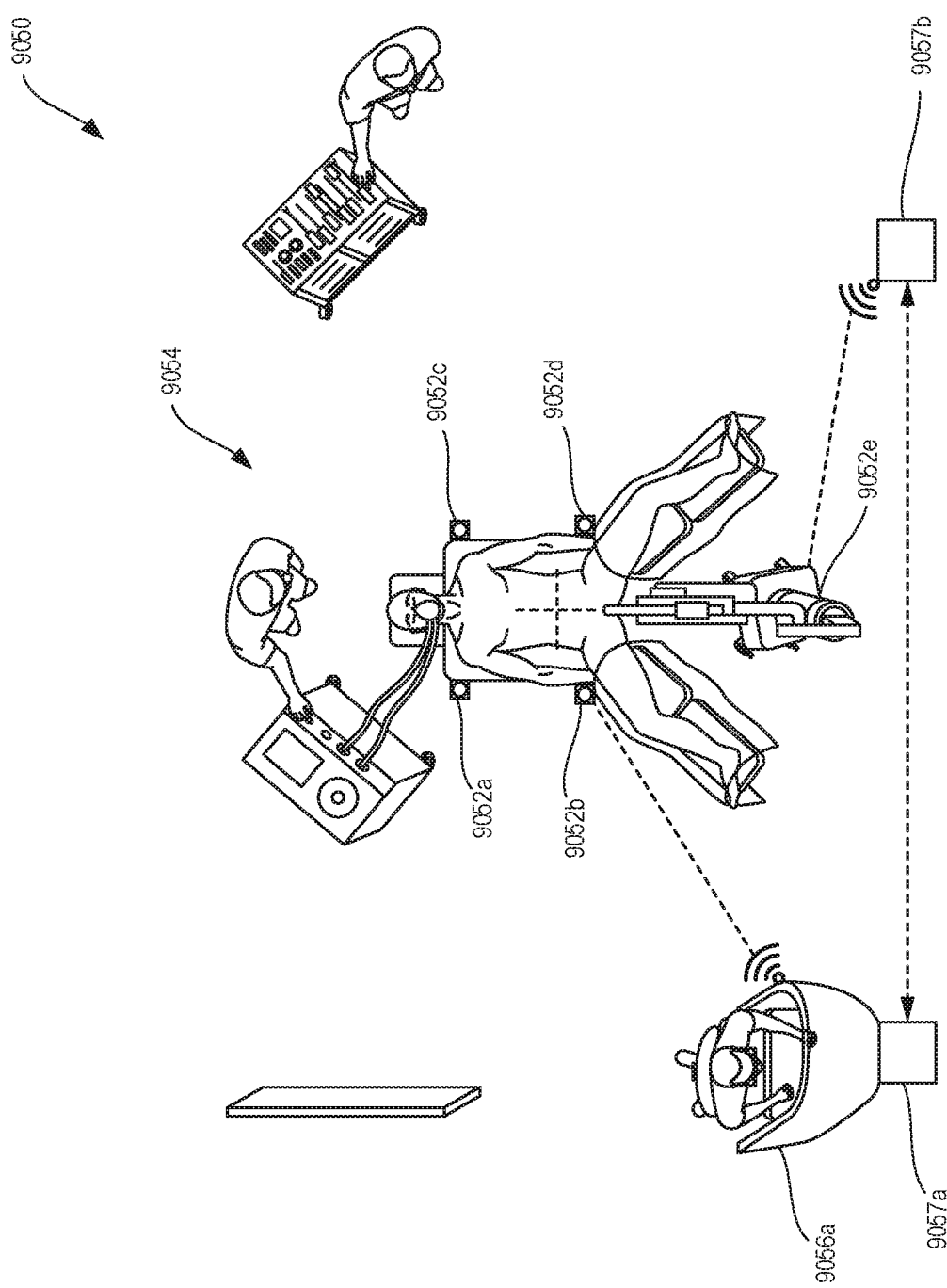

In various aspects, the robotic surgical system 13000 may include multiple individual trocar locations, in which the trocars can be operatively similar to the trocar 20250, for example. In addition, some of these multiple trocars and associated robotic arms can be either located within a sterile space or a non-sterile space. At least one of the robotic arms may be designed to operate outside of the sterile space, for example. FIGS. 103A-103B illustrate an example of such a robotic configuration. As shown in the top views of FIGS. 103A-103B, a robotic surgical system 9050 which can be similar to robotic surgical system 9000, comprising a plurality of robotic arms 9052a-9052e each attached to the surgical platform 9054. The robotic arms 9052a-9052e and surgical platform 9054 may be similar to the robotic arms 9002a-9002e and surgical platform 9002 described above. First and second central controllers 9056a-9056b can be similar to the first and second controller 9006a-9006b described above. Also, each of the non-sterile boundary demarcations 9058a-9058c demarcate sterile and non-sterile areas as described above. Similar to above, the surgical environment in FIGS. 103A-103B include an operating room monitor, an anesthesiologist, a physician assistant, a circulating nurse, a scrub nurse, a surgeon, and a control tower. FIG. 103A portrays multiple trocars 9060a-9060c positioned in various locations about the cavity of the patient, such as the abdominal cavity. The abdominal cavity may refer to an internal wall relative to a surgical incision. As indicated by the non-sterile boundary demarcations 9058a-9058c, the trocars 9060a-9060c are all located in a sterile zone. Conversely, the trocar 9060e is located in a non-sterile zone, as indicated by the non-sterile bounded area of non-sterile boundary demarcations 9058b.

Cooperative engagement of the robotic arms 9052a-9052e controlled by the base unit control circuit, therefore, can be used to ensure the sterile trocars do not intermingle with the non-sterile trocars. Such intermixing could be detrimental to the patient's health and therefore it is beneficial to avoid this intermixing via cooperative engagement of the arms. Additionally, for the same reason, the robotic arms can be cooperatively controlled so that robotic arms 9052a-9052d operating in a sterile field do not touch or come within undesirably close proximity to the robotic arm 9052e operating in a non-sterile filed, for example. The trocars 9060a-9060c, 9060e can each be coupled to their respective robotic arms 9052a-9052c, 9052e, which can be attached in a relationship like the trocar 20250 to robotic arm 20002 discussed above. An auxiliary trocar port 9062 may be provided and used, depending on the surgical incision and operation being performed. The placement of the trocars 9060a-9060c, 9062e and auxiliary trocar port 9062 shown in FIG. 103A is merely illustrative and such placement depends on the surgical operation being performed, such as a laparoscopic or gynecological operation, for example. The trocars may be placed or inserted within a lumen or other area relative to a surgical incision such as a semilunar or straight incision.

FIG. 103B shows one example of two surgical robots each controlling a subset of the robotic arms 9052a-9052e to perform a surgical procedure, such as a laparoscopic surgery. In one aspect, the first controller 9056a of the base unit control circuit may control a first surgical robot 9057a, which may control the subset of sterile robotic arms 9052a-9052d, for example. The controller 9056b of the base unit control circuit may control a second surgical robot 9057b, which may control the non-sterile robotic arm 9052e, for example. The controller 9056a-9056b can function as consoles for surgeons or might not be provided altogether such as controller 9056b in FIG. 1038. Consequently, the second surgical robot 9057b could be remotely or teleoperatively controlled or autonomously controlled. Each of the first and second controller 9056a-9056b and/or first and second surgical robot 9057a-9057b may have their own communication modules. In this way, they can communicate with their respective subset of robotic arms 9052a-9052e as well as with each other to implement the base unit control circuit for cooperative engagement as described above. In some aspects, the second surgical robot 9057b controls a circular stapling instrument (including the staple cartridge thereof) secured by the robotic arm 9052e in the non-sterile space while the first surgical robot 9057a controls the surgical tools, instruments, or devices secured by the robotic arms 9052a-9052d. For example, the robotic arm 9052a may secure a bipolar ultrasonic instrument, the robotic arm 9052b could securably hold another surgical stapler, the robotic arm 9052c securably hold a grasper or retractor, and the robotic arm 9052d securably hold a scope (e.g., endoscope). The robotics arm 9052a-9052e could cooperatively interact or engage with each other to treat tissue without mixing operations in sterile and non-sterile fields, respectively. Such tissue treatment can be for various surgical or medical procedures, as appropriate.

In one specific example, the cooperatively interacting robotic arms 9052a-9052e could be used for a colorectal configuration, such as that involving a multiquadrant arrangement with multiple surgical robots for a low anterior resection (LAR) procedure. The LAR procedure or colorectal configuration generally may be used for treating colorectal diseases such as colon/rectal polyps, diverticular disease, and cancer. The LAR procedure may be performed laparoscopically or as an open procedure. For a LAR procedure or a sigmoidectomy, for example, the surgical procedure may involve multi-quadrant manipulation and mobilization by the cooperatively engaging robotic arms 9052a-9052e. Upon properly placing the patient relative to the surgical platform and insufflating the patient's abdomen via an insufflator, it is necessary to place trocars 9060a-9060e and auxiliary trocar port 9062, as shown in FIG. 104.

Figure 104:
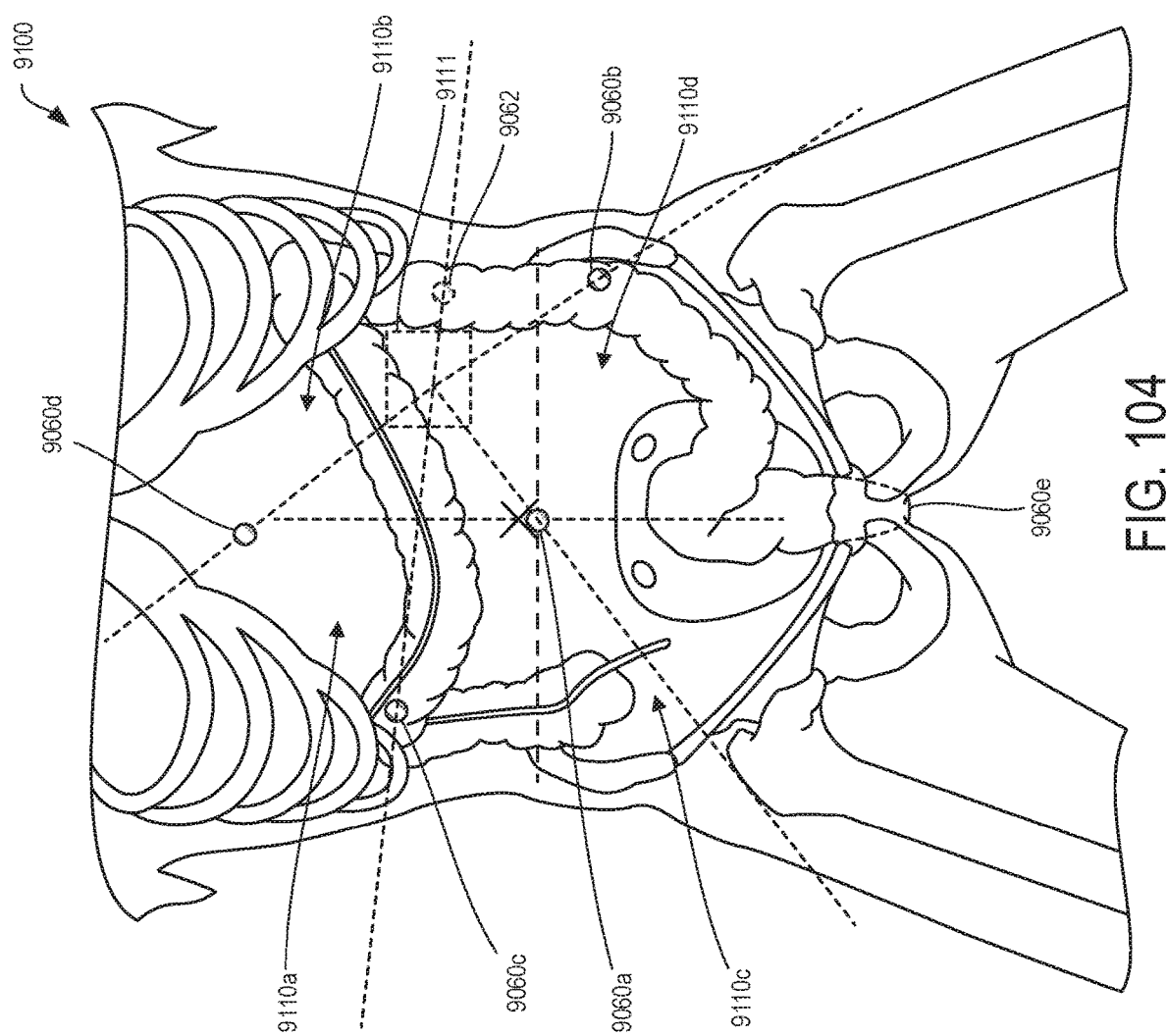
FIG. 104 is a diagram of a trocar port placement configuration, in accordance with at least one aspect of the present disclosure.

In the diagram 9100 of FIG. 104, trocar 9060a is positioned in the center of the abdominal cavity, trocar 9060b is positioned on a lower portion of the descending colon, trocar 9060c is positioned proximate to a junction of the transverse colon and the ascending colon, trocar 9060d is positioned proximate to the ribcage, trocar 9060e is positioned proximate to the rectum, and the auxiliary trocar port 9062 is positioned on an upper portion of the descending colon. The trocars 9060a-9060e and auxiliary trocar port 9062 function as access ports for their respective robotic arms 9052a-9052e. As discussed above and represented by the dashed lines passing through the trocars 9060a-9060e, each robotic arm 9052a-9052e secures a surgical implement. For example, the robotic arm 9052a may hold an electrosurgical energy surgical tool, the robotic arm 9052b may hold a grasper tool or a surgical stapling instrument, the robotic arm 9052c may hold a scope surgical tool, the robotic arm 9052d may hold a grasper tool, and the robotic arm 9052e may hold a circular surgical stapler. The robotic arms 9052a-9052e may cooperatively work within the delineated working area 9111 for performing surgical operations. In addition, for a colorectal procedure, the depicted portions of the patient's anatomy could be divided into four quadrants, as indicated by upper left quadrant 9110a, upper right quadrant 9110b, lower left quadrant 9110c, and lower right quadrant 9110d. The "x" in FIG. 104 represents the location of the patient's umbilicus.

Figure 105A:
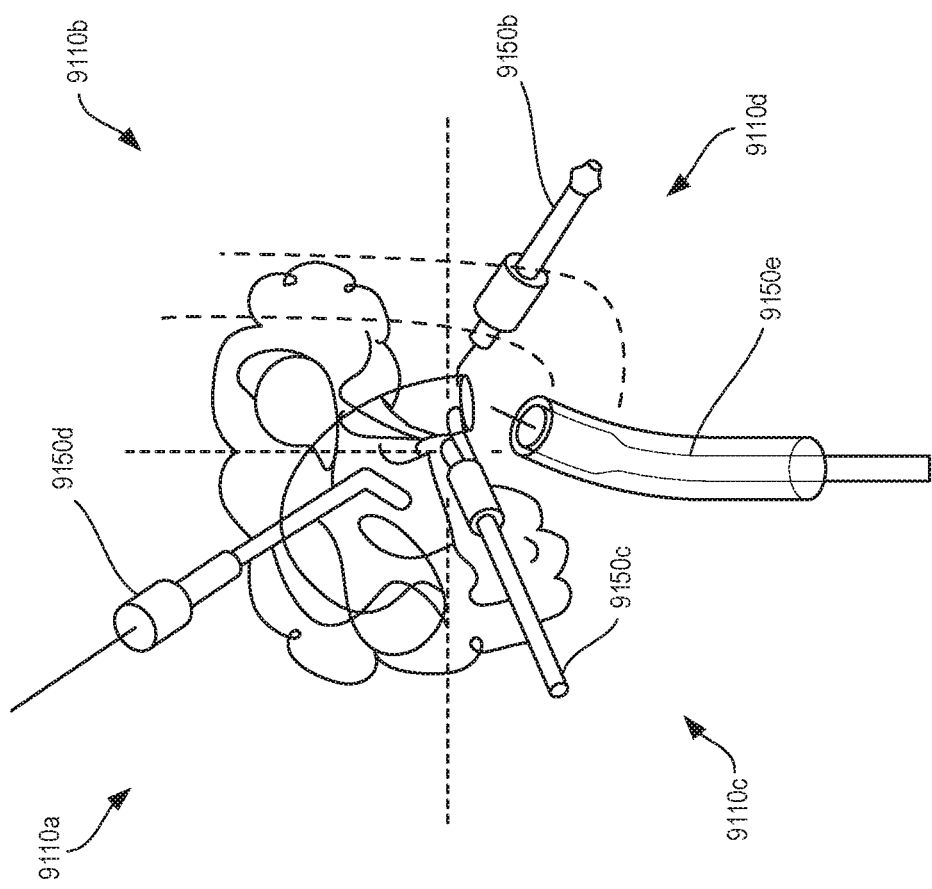

FIGS. 105A-105B depict an example of a resection and mobilization step of LAR procedure being performed, in which the resection and mobilization is performed in the upper quadrants 9110a-9110b. During the LAR, the surgeon may control the robotic arms 9052a-9052e to perform a small intestine/bowel relocation, retraction, and/or dissection step. Subsequently, the robotic arms 9052a-9052e may perform large intestine/colon. In particular, the robotic arms 9052a-9052e may execute complete mobilization of the splenic flexure as well as laterally or medially mobilize the transverse colon (or a portion thereof), for example. To this end, the grasper held by robotic arm 9052d may extend through trocar 9060b to grasp a portion proximate to the transverse colon in the upper right quadrant 9110b. The robotic arm 9052b may also be controlled by the base unit control circuit to grasp and retract another portion of the transverse colon in the upper left quadrant 9110a. Furthermore, the electrosurgical energy surgical instrument secured by the robotic arm 9052a could be used to treat tissue (e.g., coagulate, seal, cut, etc.) in support of the colon mobilization. The scope held by the robotic arm 9052c may be used for visualization.

Accordingly, the base unit control circuit can control the robotic arms 9052a-9052e in cooperative engagement to perform surgical steps across multiple surgical quadrants, in which the arms could be passable through different quadrants to perform different surgical operations. For example, one robotic arm could be passed through a first quadrant (e.g., via a trocar) for resection or cutting etc., while another robotic arm could be passed through a second different quadrant for moving or viewing tissue, etc. In particular, passing through the first quadrant could involve passing within a cavity of the patient while passing through the second quadrant could involve passing through an orifice of the patient. Also, the first quadrant could be a sterile quadrant while at least some portion of the second quadrant could be non-sterile or contain a non-sterile surgical implement. One or more robotic arms could be located in a sterile zone or a non-sterile zone, as appropriate, as discussed above. Similarly to the example operation in the upper quadrant, the robotic arms 9052a-9052e could be controlled to operate in conjunction in the lower quadrant. As part of a resection or dissection process, a first portion of the small bowel in the upper quadrant can be replaced and a second portion of the small bowel in the lower quadrant can be relocated. This could involve lateral mobilization of the descending and sigmoid colon and dividing the rectum, for example. Lower quadrant mobilization of the colon can occur for vascular isolation of a portion of tissue to be resected.

Figure 106:
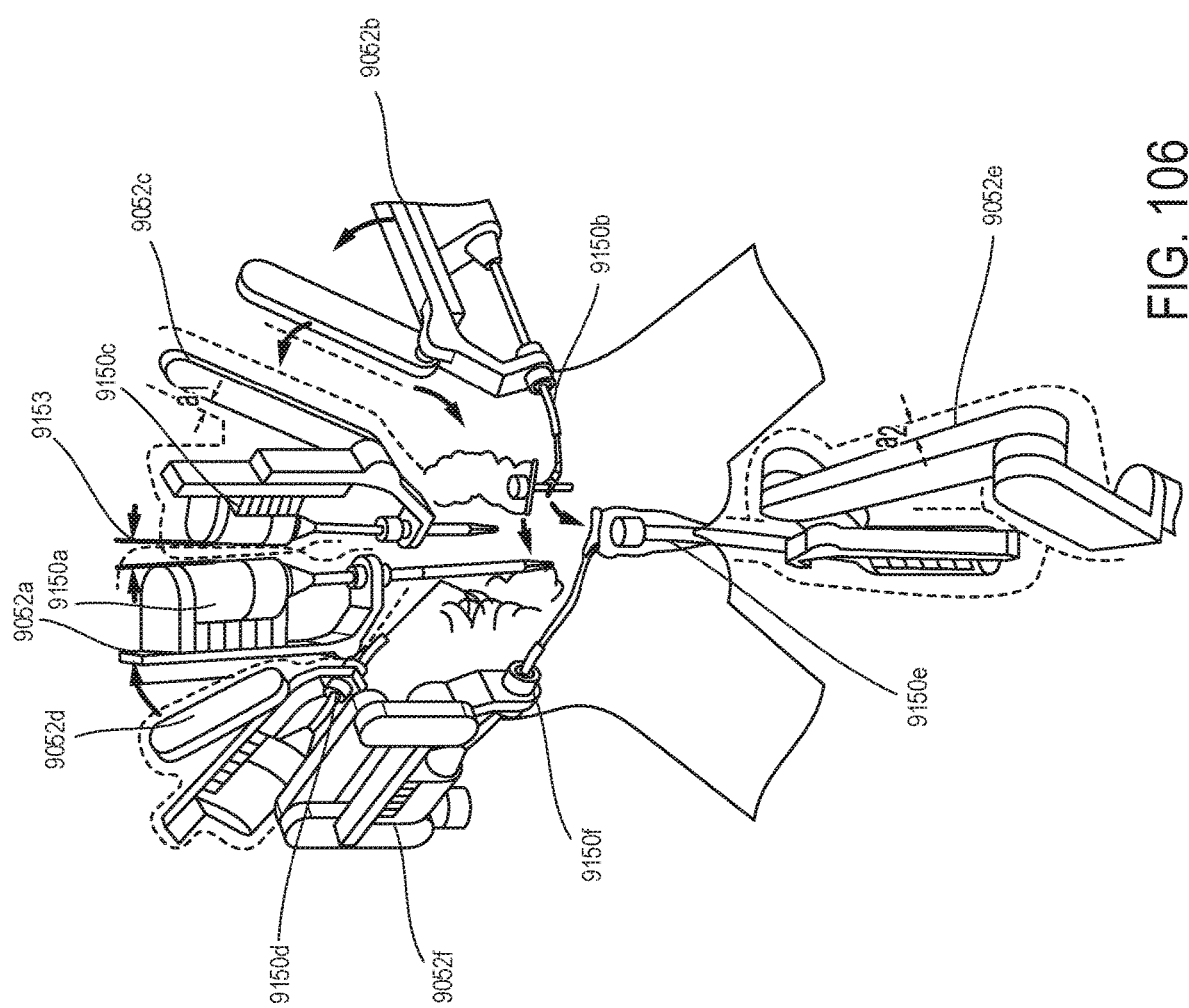
FIG. 106 illustrates positioning of a transected colon portion relative to a rectal portion of a patient for connection of an anvil to a circular stapler surgical instrument, in accordance with at least one aspect of the present disclosure.

FIGS. 105B and 106 show positioning by the robotic arms 9052a-9052e for a circular stapling operation for forming an anastomosis to rejoin portions of the colon and/or small intestine that were dissected for surgical treatment. In FIG. 105A, the grasper/retractor 9150d held by robotic arm 9052d grasps mobilized and/or resected portions of the colon, while the grasper 9150b held by robotic arm 9052d may grasp and/or pull down the detachable anvil of the circular stapling instrument 9150e held by the robotic arm 9052e. The scope 9150c held by robotic arm 9052c may be used to help visualize the circular stapling/anastomosis step. The operation as depicted in FIG. 105A may be primarily be performed in lower colorectal quadrants, such as in lower left quadrant 9110c and lower right quadrant 9110d. In one aspect, the proximal transected portion of the rectum is moved toward the rectum. The base unit control circuit and/or surgeon may then control the cooperatively interacting robotic arms 9052a-9052e for performing the stapling operation. The base unit control circuit may control the robotic arms 9052a-9052e so that they cooperatively reposition the transected upper colon portion to be adjacent to the rectal portion for connection to the circular stapler 9150e relative to a proposed anastomotic site.

Preceding this alignment and repositioning step may be a step for assessing the perfusion of the proposed anastomotic site. Once the robotic arms 9052a-9052e are controlled to properly align the anvil held by the grasper 9150b and the circular stapling instrument 9150e, the surgeon may determine the proper extent to compress the two pieces of tissue to be used to form the anastomosis. Subsequently, the circular stapling instrument 9150e may be fired and a ring of staples ejected from the staple cartridge of the circular stapling instrument 9150e relative to the anvil to form the anastomosis. The formed colorectal anastomosis may then be tested. Before performing the anastomosis, the electrosurgical energy surgical instrument 9150a held by robotic arm 9052a may be used to perform small bowel relocation and retraction as shown in FIG. 105B. Unlike FIG. 105A, this operation as depicted in FIG. 105B may be primarily be performed in upper colorectal quadrants, such as in upper left quadrant 9110a and upper right quadrant 9110b. The grasper/retractor 9150d held by robotic arm 9052d may grasp mobilized and/or resected portions of the large colon. The scope 9150c held by robotic arm 9052c may be used to for visualization and the grasper 9150b held by robotic arm 9052d may grasp tissue to assist treatment of tissue proximal to the transverse colon in the upper right quadrant 9110b by the electrosurgical energy surgical instrument 9150a. Accordingly, the robotic arms 9052a-9052e may be cooperatively controlled to work within or across multiple quadrants.

FIG. 106 illustrates how the base unit control circuit may control the robotic arms 9052a-9052f to cooperatively form the anastomosis while addressing the fact that robotic arms 9052a-9052d, 9052f are sterile while robotic arm 9052e is non-sterile, for example. As discussed above, the robotic arm 9052e could be controlled by a different surgical robot than the robotic arms 9052a-9052d, 9052f. Also as discussed above, the base unit control circuit may monitor and adjust arm pose and/or arm-to-arm spacing so that the multiple robotic arms 9052a-9052f do not entangle among themselves while lining up the anvil and/or trocar 9060b to the patient's rectum and/or the circular stapler 9150e prior to firing the circular stapling instrument 9150e. As shown in FIG. 106, the robotic arms 9052a-9052d, 9052f may each hold some sterile surgical tool, device, or instrument for assisting in the LAR procedure, including transecting and/or mobilizing the patient's colon across the upper and lower quadrants. The surgical implements 9150a-9150d, 9150f held by robotic arms 9052a-9052d, 9052f may each be sterile. Accordingly, when the base unit control circuit ensures surgical implements 9150a-9150d, 9150f or their corresponding robotic arms do not intermix with the circular stapling instrument 9150e, this may be beneficial to the patient's health and to the success of the surgical operation. As discussed above, the base unit control circuit may adjust robotic arm support height. For example, as shown in FIG. 106, the base unit control circuit may control the robotic arm 9052e to ensure the height, pose or other positional characteristic of the robotic arm 9052e or linkages thereof stay within the threshold a2.

Figure 107A:
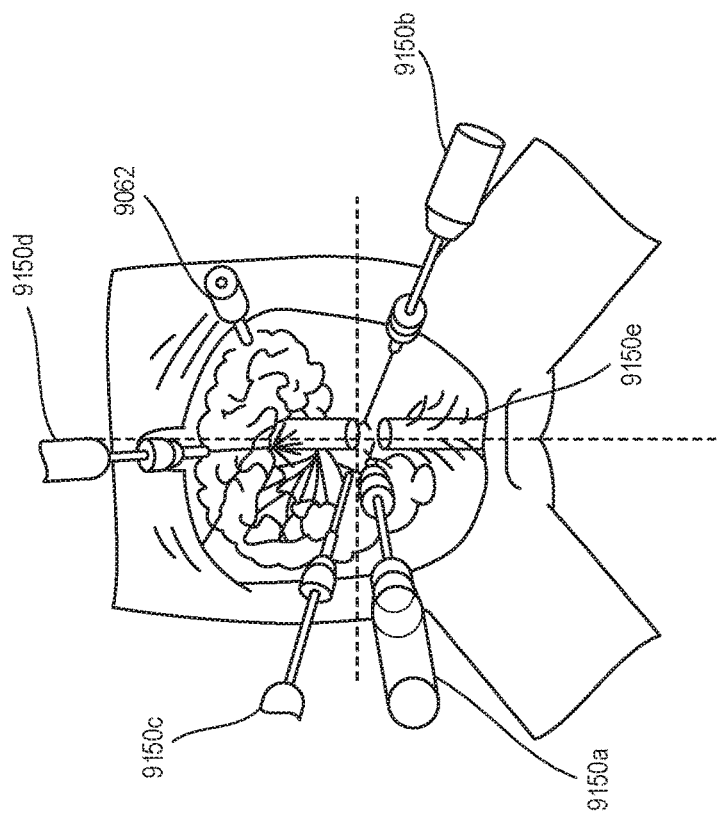
FIGS. 107A-107B depict the use of multiple surgical implements held by corresponding robotic arms to mobilize the colon of a patient and to perform anastomosis, respectively, in accordance with at least one aspect of the present disclosure.
Figure 107B:
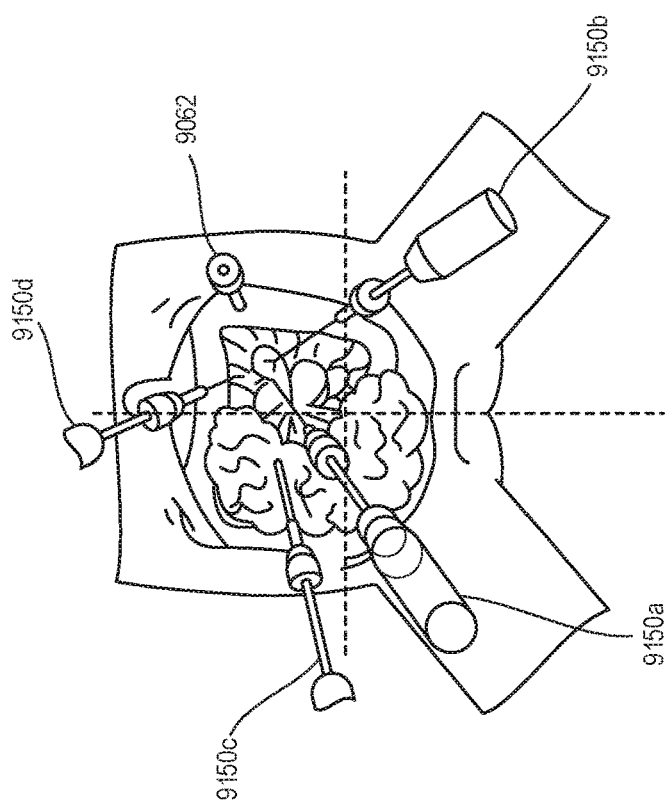

Similarly, the base unit control circuit may implement a safety threshold a2 or some other threshold to maintain a safe or desirable arm-to-arm spacing. To this end, the base unit control circuit may identify or determine when safety threshold a2 is violated, such as the safety margin violation 9153 represented between robotic arms 9052a and 9052c. Alternatively, the safety violation 9153 could refer to the distance between surgical implement 9150a and 9150c. Also, the safety violation 9153 could refer to problematic distances between various robotic arms 9052a-9052e and sterile zone boundaries. In all scenarios, the base unit control circuit may alert the surgeon/clinician that this violation 9153 has occurred, which can improve the safety and efficacy of the surgical operation being performed. This alert may take the form of audible or tactile feedback at the first and second central controllers 9056a-9056b, for example. FIGS. 107A-107B show example configuration of cooperating robotic arms 9152a-9152e to mobilize the colon and perform anastomosis, respectively, for a LAR operation. As described above, electrosurgical energy surgical instrument 9150a, grasper 9150b, scope 9150c, grasper 9150d, and circular stapling instrument 9150e may be secured or held by cooperatively interacting robotic arms 9152a-9152e. The surgical implements held by robotic arms 9152a-9152e described herein are merely examples and could be other surgical implements as appropriate and desired according to the surgical procedure being performed.

Determining or Adjusting Pose of Insufflation Ports

Figure 108:
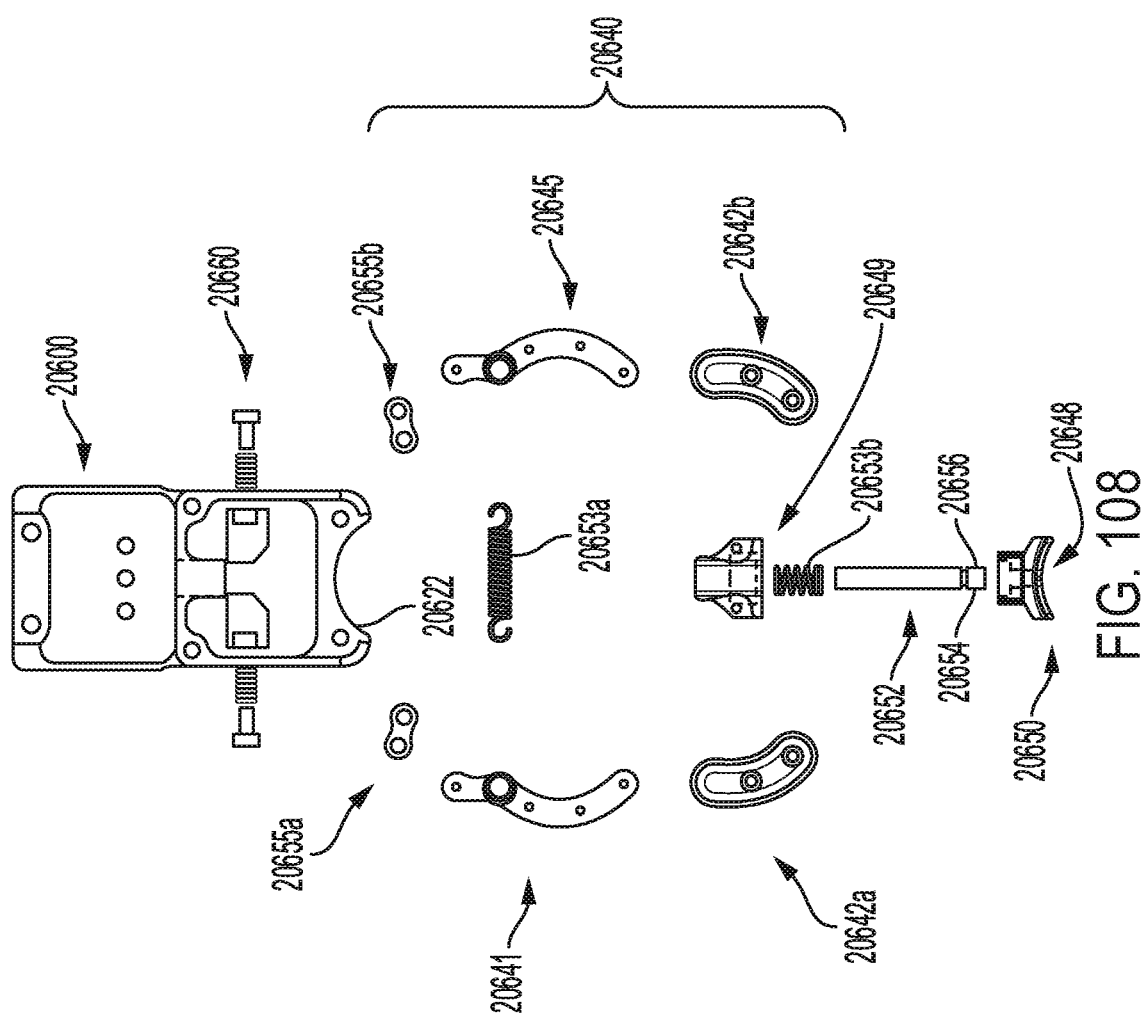
FIG. 108 is an exploded view of a surgical mounting device, in accordance with at least one aspect of the present disclosure.

In various aspects, the positioning, alignment, gripping, and/or pose of various access ports (e.g., access port 20254) and trocars (e.g., trocar 20250, 9060a-9060e) described herein may be controlled or adjusted to facilitate the performance of a surgical operation. As discussed above, any of the robotic arms (e.g., robotic arms 9152a-9152e) described herein may have a mounting device (e.g., mounting device 20230) and/or clamping assembly (e.g., clamping assembly 20234) securably attached to them. As shown in FIG. 108, mounting device 20600, which can be similar in operation to mounting device 20230, may includes a housing which supports a clamping assembly 20640 (which can be similar in operation to clamping assembly 20234) and a release mechanism 20660. A distal surface of the housing may further define a receiving recess 20622 which is configured to complement an exterior profile of an access device, such that the access device may be positioned in near abutment to, or approximated within the housing of the mounting device 20600. The release mechanism 20660 may be actuatable between an initial position and a release position, in which the release position enables the clamping assembly 20640 to transition to an open configuration so that an access device (e.g., trocar, surgical port) previously secured therein can be removed from surgical mounting device 20600.

Figure 109:
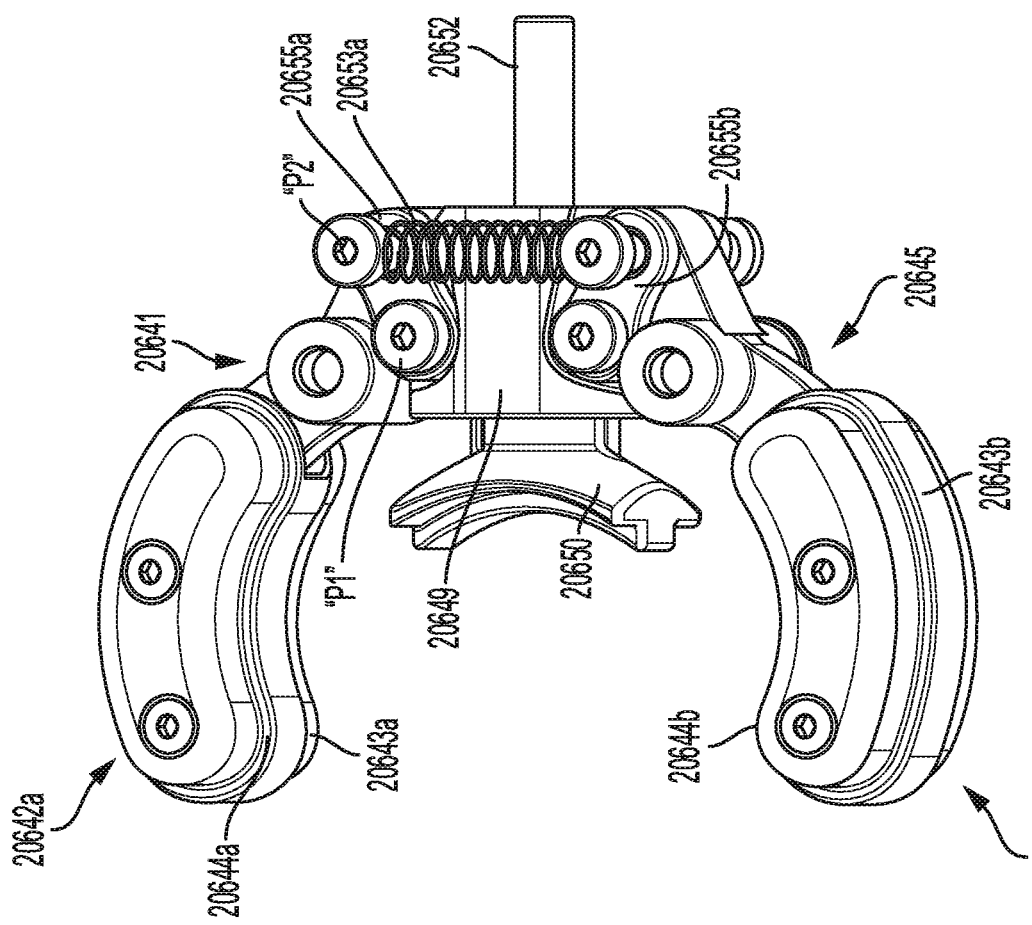
FIG. 109 is a perspective view of an embodiment of a clamping assembly of the mounting device of FIG. 108, in accordance with at least one aspect of the present disclosure.

As shown in FIG. 108, the clamping assembly 20640 includes a first clamping arm 20641 positioned opposite a second clamping arm 20645, and a plunger assembly 20648 positioned therebetween. The clamping links 20655a-20665b can have two throughholes and pivotably interconnect each of the first and second clamping arms 20641, 20645. A biasing member 20653a may act to bias the first and second clamping arms 20641, 20645 into the open position, which is overcome as the clamping assembly 20640 transitions into the closed configuration. Each of the first and second clamping arms 20641, 20645 may further include a cover or sleeve c configured to slidably engage with the respective distal portion of the clamping arms 20641, 20645. At least one of the clamping links 20655a-20665b may pivotably interconnect the first and second clamping arms 20641, 20645 to the drive member 20649. The plunger assembly 20648 may further include another biasing member 20653b to a bias a middle segment 20650 with respect to the drive member 20649. To this end, the drive member 20649 may be connected to the middle segment 20650 via a coupling bar 20652, which may further include a threaded post or stem 20656 extending distally from the coupling distal end 20654. FIG. 109 illustrates how a first pin P1 is disposed within a first through-hole and a second pin P2 is disposed within a second through-hole of the clamping links 20655a-20665b, such that clamping links 20655a-20665b are coupled to drive member 20649. Additional through-holes can be disposed on the clamping assembly 20640, including the cover or sleeve 20642a-20642b, as desired and as depicted in FIG. 109. The covers 20642a-20642b may further include a protruding ridge, rib, or shoulder 20643a-20643b disposed along the exterior contour 20644a-20644b configured to engage a corresponding channel or surface of an access device or trocar, for example.

Figure 110A:
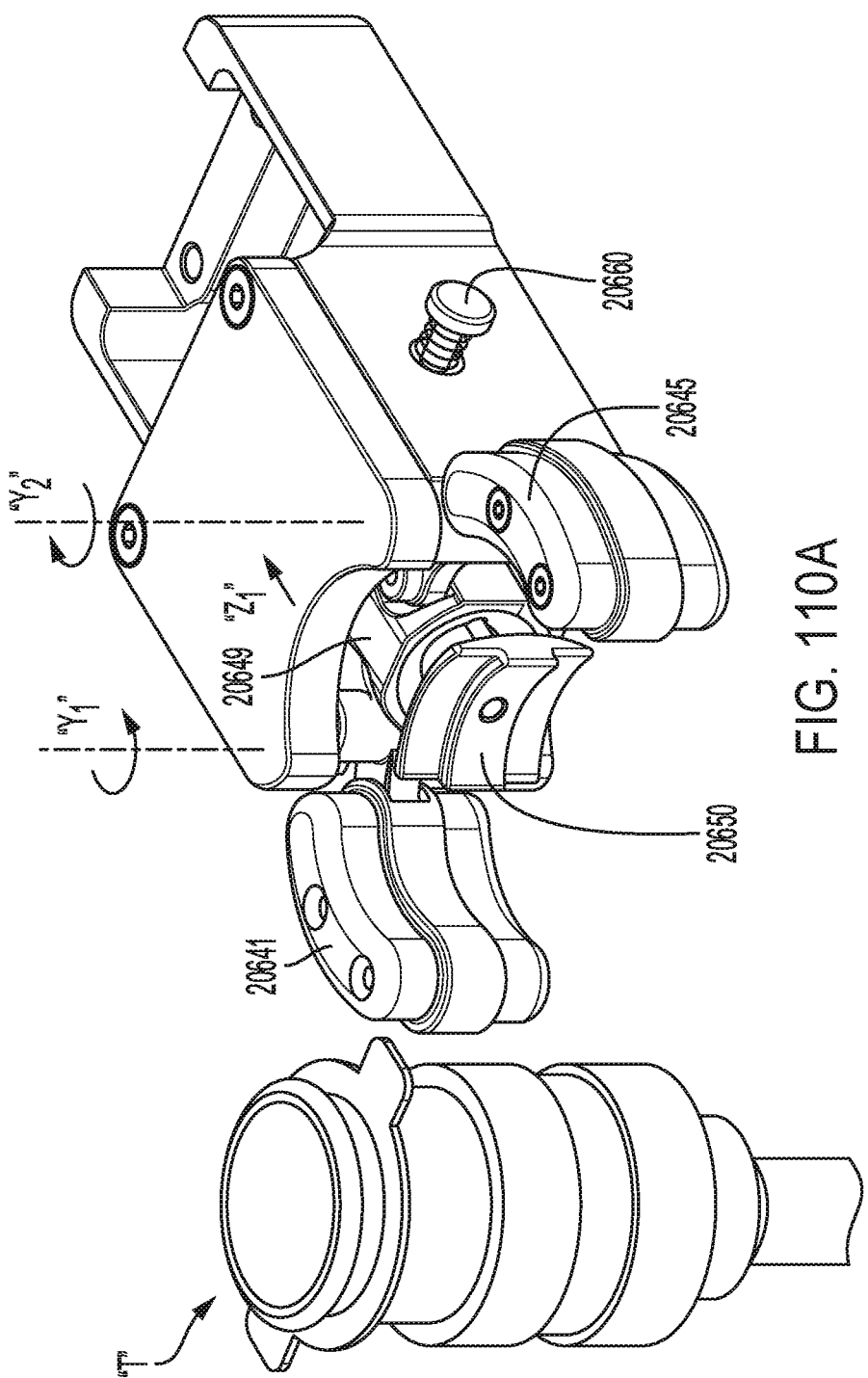
FIG. 110A is a perspective view of the mounting device of FIG. 108, with the clamping assembly in an unlocked configuration, for receipt of an access device therein, in accordance with at least one aspect of the present disclosure.
Figure 110B:
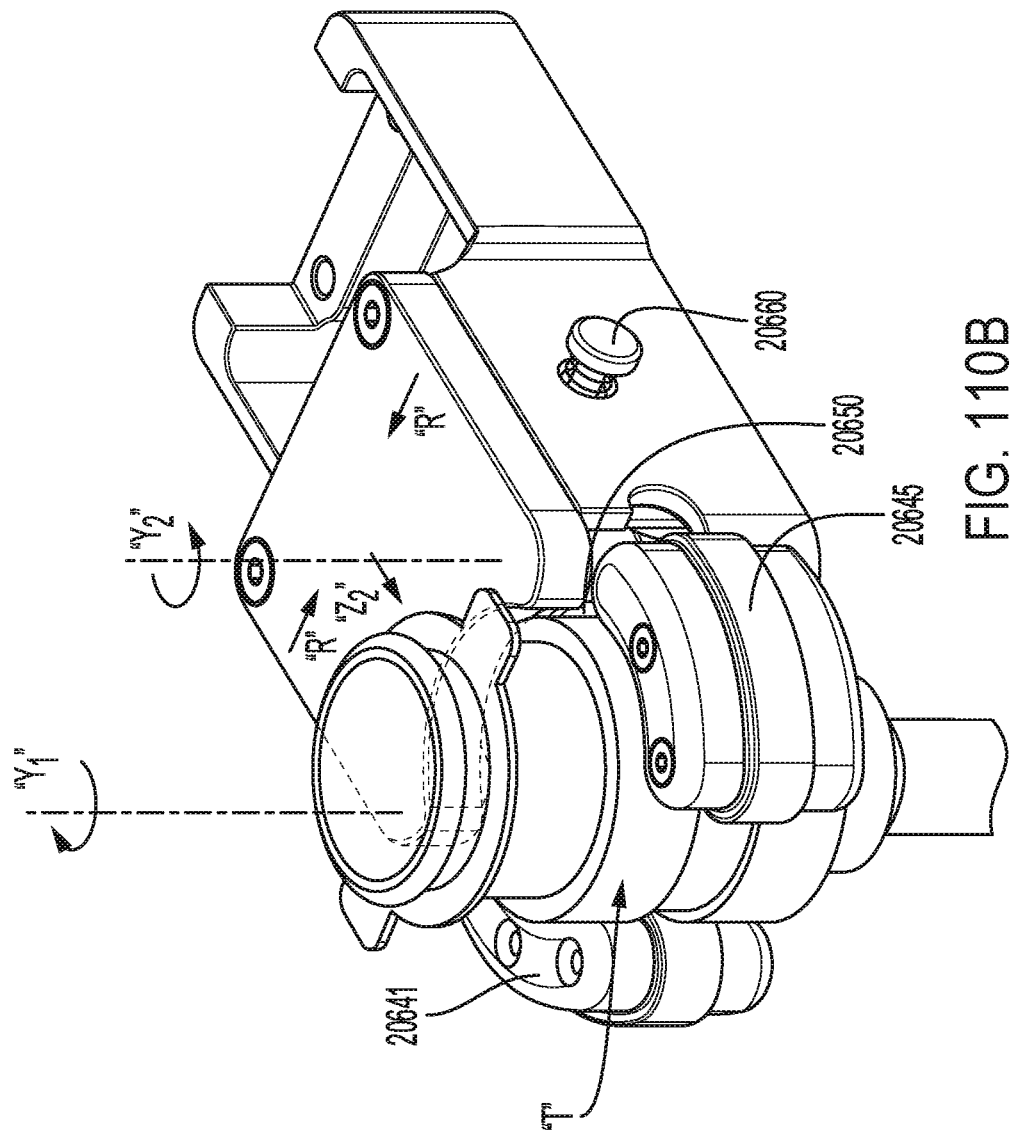
FIG. 110B is a perspective view of the mounting device of FIG. 108, with the clamping assembly in a locked configuration, and with the access device secured therein, in accordance with at least one aspect of the present disclosure.

FIGS. 110A-110B depict operation of the clamping assembly 20640 in an unlocked and a locked configuration respectively. In the unlocked configuration, an access device, such as the trocar T portrayed in FIGS. 110A-110B, can be received. Correspondingly, in the locked configuration, the trocar T is secured by the clamping assembly 20640 in FIG. 110B. The trocar T is merely an example trocar and may be similar in operation to any of the trocars described herein. The receiving surface of the first clamping arm 20641 may provide an arcuate profile which complements the external profile of trocar T, such that trocar T may be received therein, as can be seen in FIGS. 110A-110B. The clamping assembly 20640 is transitionable between an open, or unlocked, configuration of FIG. 110A and a closed, locked, configuration of FIG. 110B, for example. The pivoting of first and second clamping arms 20641, 20645 and the translation of drive member 20649 and middle segment 20650 correspond to the transition of the clamping assembly 20640 between the open and closed configurations. The first and second clamping arms 20641, 20645 may be pivotable about the through-hole(s) corresponding to axis $Y_1$ and $Y_2$ respectively, between a spaced apart position in FIG. 110A and an approximated position in FIG. 110B relative to one another. Additionally, the drive member 20649 and middle segment 20650 coupled therewith are translatable between a distal position in FIG. 110A and a proximal position in FIG. 110B, as indicated by arrows $Z_1$ and $Z_2$. In the open configuration of clamping assembly 20640, first and second clamping arms 20641, 20645 are in the spaced apart position and drive member 20649 and middle segment 20650 are in the distal position. In the closed configuration of clamping assembly 20640, first and second arms 20641, 20645 are in the approximated position and drive member 20649 and middle segment 20650 are in the proximal position.

The drive member 20649 may be connected to a motor or a motor pack (which can be similar in operation to motors described herein such as motor 20408), servo, electro-controller, or any other suitable means to achieve automated translation of drive member 20649 in the direction of arrow $Z_1$. That is, the motor may drive the translation of the drive member 20649 from the distal position to the proximal position. A controller could be included, such as on the associated robotic arm, to operate the motor remotely. As the drive member 20649 translates middle segment 20650 distally into the distal position and first and second arms 20641, 20645 are pivoted into the spaced apart position, the clamping assembly 20640 is thus translated into the open configuration. The release mechanism 20660 is actuatable between an initial position and a release position. In the release position, release mechanism 20660 is actuated in the direction of arrow R and the contact surface of release mechanism 600 comes into abutment with the drive member 20649, such that the drive member 20649 is urged to translate into the distal position in the direction of $Z_2$. As the drive member 20649 translates to the distal position, the middle segment 20650 concurrently translates into the distal position and the first and second arms 20641, 20645 pivot about axis $Y_1$ and $Y_2$ respectively into the spaced apart position. This transitions clamping assembly 20640 into the open configuration. With clamping assembly 20640 in the open configuration, the access device previously secured therein can be removed from surgical mounting device 20600. Further details about the mounting and clamping devices may be found in U.S. Patent Publication 2018/0177557, which is hereby incorporated by reference in its entirety.

In some aspects, the controller, control device, base unit control circuit, or other control means described herein can function as a tracking means for the access device or other portion of the robotic surgical assembly 20030. For the sake of clarity, the tracking means will be described herein as being performed by the base unit control circuit. To function as the tracking means, the base unit control circuit may control various tracking sensors, such as mechanical, optical, electromagnetic sensors, or other suitable tracking devices. These sensors could be designed to have high robustness such as resistance to impairment or negative effects by the surrounding environment. For example, the tracking sensors may include magnetic sensors constructed of amorphous ferromagnetic materials, which may improve the reliability of such magnetic sensors in harsh environments based on having a good response to changes to magnetic permeability or magnetization direction. Similarly, light and sound (e.g., ultrasonic sensors) may have weather resistant coatings or other chemically resistant coatings such as parylene coatings, for example, for protection in harsh environments. Preferably, the accuracy of the tracking sensors may also be high, such as at resolutions of less than 0.1 mm, for example. In one aspect, multiple tracking sensors may be disposed about the robotic surgical assembly 20030 and the base unit control circuit may track these multiple sensors concurrently. The refresh rate of the tracking means can be approximately 100 Hertz (Hz) with a latency of less than 1 millisecond (ms), for example.

The base unit control circuit could be configured to control the access devices' pose—position or orientation of the insufflation ports of the robotic arms used in a surgical procedure relative to the patient's abdominal wall and/or trocar gripping system—for a LAR procedure, for example. The insufflation ports' pose may be controlled to minimize constricting of the gas supply or pressure and inadvertent impingement on the adjacent body wall. The trocars of the robotic arms used for insufflation of the patient's abdomen could each have a trocar sleeve that includes a stop-cock valve mechanically interfitted between a trocar cannula (e.g., similar to cannula 20252) and a trocar housing. The stop-cock valve can be positioned in communication with the trocar cannula for selectively allowing and preventing the passage of an insufflation fluid, e.g. carbon dioxide, through flexible tubing into a portion of the trocar cannula. Each stop-cock valve may be mechanically or otherwise secured to each trocar; for example, ultrasonic welding or adhesives could be used for the attachment. During an LAR procedure as described above in which the robotic arms 9152a-9152e are used, for example, the base unit control circuit (or control device(s) described above) may be programmed to determine the orientation of each trocar attached to the corresponding robotic arms 9152a-9152e. To achieve this, the tracking sensors—could be similar in some aspects to the sensor assemblies 20180—may output sensor signals based on ultrasonic pulses, magnetic signatures, etc. depending on the tracking means used in order to sense the orientation of each trocar.

Thus, for each surgical robot controlling one or more of the robotic arms 9152a-9152e, the locations of the trocars and specifically the location of the attached stop-cock valves can be defined for the purposes of control by the base unit control circuit. This defined location may be advantageous for controlling the robotic arms 9152a-9152e and/or robotic surgical system 1300 generally so that unnecessary damage to the patient is reduced or avoided altogether. For example, the base unit control circuit may execute control algorithms to prevent surgical robots from pressing the stop-cock valves into the patient. For example, a control algorithm could be executed to limit motion of the robotic arms 9152a-9152e or linkages thereof in one or more directions. As such, position, proximity or other suitable sensors (could be similar to mounted sensor assemblies 20180) mounted on the robotic surgical assembly 20030 can provide data to the base unit control circuit to stop arm motions in a certain direction when the data indicates that the arm motion exceeds a certain limit or threshold. This way, the base unit control circuit can prevent the stop-cock valve from injuring the patient. Additionally, the base unit control circuit can be situationally aware to facilitate such a control algorithm. For example, information about the particular surgical procedure being performed and/or input information from operating room staff can be used to inform the positioning of the patient relative to the surgical platform and robotic surgical assembly 20030 during performance of the surgical procedure. This information may help the surgical robots involved in executing the procedure to set control limits on robotic motions.

FIGS. 111A-111D illustrate one example of a tracking means and controlled algorithm executed by the base unit control circuit to sense trocar pose and other useful positional information. At least one Hall effect sensor 9200, as indicated in FIG. 111A, can be provided to detect such information. For example, the hall effect sensor 9200 may detect the alignment and configuration of the trocar 9205, which can be similar in some aspects to trocars described above such as trocar 20250 and trocars 9060a-9062e. The Hall effect sensor 9200 may output an output signal that is a function of the surrounding magnetic field density that is affected by the one or more correlated field magnet(s) 9215. The external magnetic field of the correlated field magnets 9215 may be used to activate and cause the Hall effect sensor 9200 to generate an output Hall voltage. The correlated field magnets 9215 may be used for various magnet movements such as head-on, sideways, push-pull, pull-push, etc. in connection with the Hall effect sensor 9200 detecting proximity, movement, position etc. Also, the correlated field magnets 9215 may generate a magnetic signature in which the correlated field magnetic signature may be used to identity the type of the trocar 9205. Trocar type might include laparoscopic, bladed, optical trocar types, for example. Accordingly, the base unit control circuit may operate in conjunction with the Hall effect sensor 9200 to identify trocar type, trocar pose, and/or other relative positional information.

The magnetic signature varies depending on the number and placement of the correlated field magnet(s) 9215, for example. In FIG. 111B, the magnetic signature 9230 of the correlated field magnet(s) 9215 may indicate an 8 millimeter (mm) trocar 9205 with a stop-cock valve that is aligned. The magnetic signature 9235 in FIG. 111C could indicate a 8 mm trocar 9205 with no stop-cock valve. And in FIG. 111D, the magnetic signature 9240 could indicate a 5 mm trocar 9205 without a stop-cock valve. The Hall effect sensor 9200 may be disposed between the first and second clamping arms 9221, 9225 (can be similar to clamping arms 20641, 20645) and distal to the middle segment 9235 (can be similar to middle segment 2065). The first and second clamping arms 9221, 9225 may operate as part of a clamping device to secure the trocar 9205, as discussed above. FIGS. 112A-112E illustrate the Hall effector sensor 9200 being used to sense the particular magnetic signature of the trocar 9205, which enables the sensor 9200 to sense the number/pattern of magnets 9215 and their relative position to the sensor 9200. The configurations of FIGS. 112A-112C may correspond to the magnetic signatures of FIGS. 111B-111D. The magnetic signature 9230 of the correlated field magnet(s) 9215 may indicate an 8 millimeter (mm) trocar 9205 with a stop-cock valve 9250 that is aligned in FIG. 112A. The magnetic signature 9235 in FIG. 112B could indicate a 8 mm trocar 9205 without the stop-cock valve 9250. In FIG. 112C, the magnetic signature 9240 could indicate a 5 mm trocar 9205 without the stop-cock valve 9250.

Figure 113C:
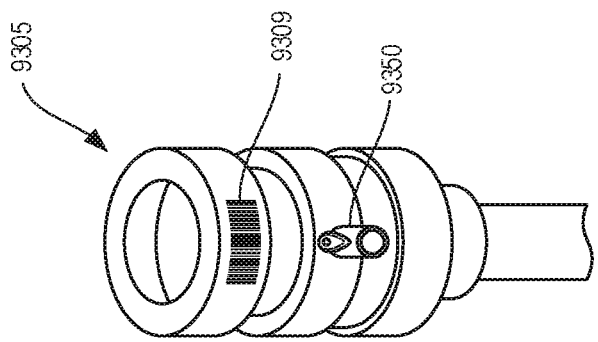
FIGS. 113A-113C depict various detections of visual cues by optical sensing means, in accordance with at least one aspect of the present disclosure.
Figure 113B:
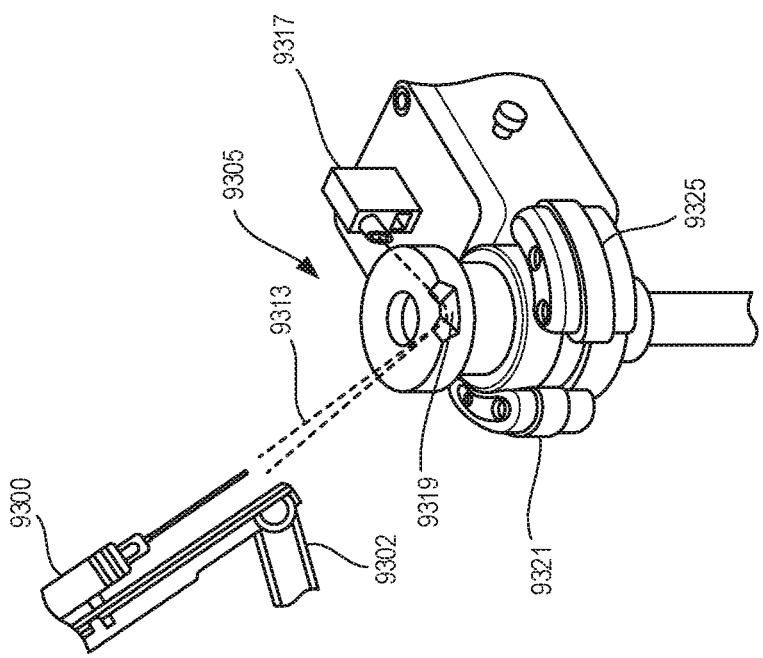
Figure 113A:
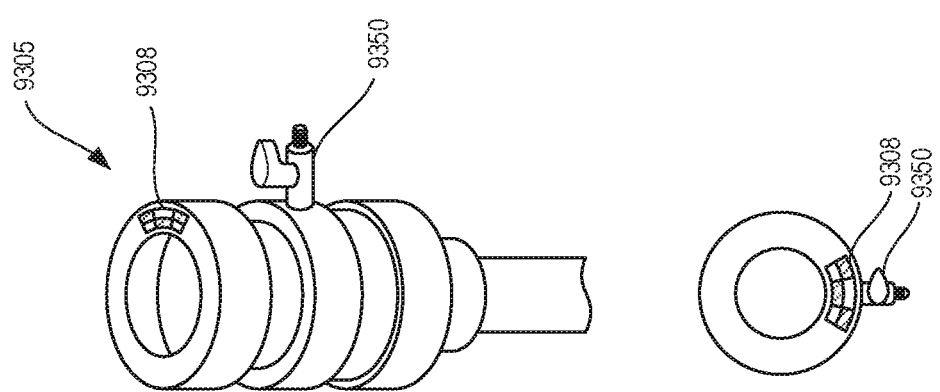

FIGS. 112D-112E depict the Hall effect sensor 9200 and base unit control unit may identify trocar alignment and trocar configuration so that this information is obtained to facilitate surgical treatment and to avoid injury to the patient based on the position of the trocar 9205, for example. FIGS. 113A-113C illustrate how visual cues could be provided for the tracking means and/or base unit control unit to determine the identity, orientation, and other positional information of the trocar 9305 (similar to trocars described herein) relative to robot arm 9302 (similar to robot arms described herein). In FIG. 113A, a tracking sensor such as an optical sensor could read/sense the matrix bar code 9308 in which the optical detection of 9308 is used to identify the identity and pose of trocar 9305, for example. The corresponding trocar 9305 with stop-cock valve 9350 and code 9308 is shown in FIG. 113A. In FIG. 113B, the robotic arm 9302 may secure a laser source 9300 attached to the arm 9302 and/or a linear slide such as the sliders or rails (e.g., rail 20040) described above. The laser source 9300 may emit a laser or some other form of light so that the light detector 9317 can be used for the trocar 9305 identification and detection described herein. In particular, the emitted light may contact recessed grooves 9319, which may cause a different diffraction or dispersal of light. The emitted light from laser source 9300 may reflect differently in such a way to encode trocar information that can be detected by the light detector 9317. The light emission and detection are indicated by the dashed lines in FIG. 113B. The trocar 9305 in FIG. 113B is gripped by the clamping arms 9321, 9325. In FIG. 113C, another bar code 9309 is shown as a method to optically sense and determine the type and positional information of the trocar 9305 as well as the presence and position of stop-cock valve 9350. The bar codes 9308-9309 could each be some suitable type of readable optical code, including quick response (QR) codes, for example.

Accordingly, the tracking means and base unit control circuit may be configured to determine the pose of the trocar 9305 and stop-cock valve 9350 for improving patient safety and the effectiveness of the surgical operation being performed, as described herein. Moreover, the control algorithm may be performed so that a history of the rotations made by a robotic arm is retained, such as by being stored within a memory circuit of the base unit control circuit. In this manner, the control algorithm may be executed to ensure an insufflation hose does not undesirably wrap around a tool, trocar, or other part of robotic surgical assembly 20030. Relatedly, the robotic arm holding the trocar may have the ability to rotate the trocar within the associated trocar holder to ensure the associated stop-cock valve is not in a position to accidentally injure the patient. Alternatively, the trocar may have a unique orientation when inserted into the corresponding robot arm. In such a scenario, the position of the stop-cock valve would be known based on this unique orientation. FIG. 114 illustrates an access device including a cannula 20700, which could be similar to cannulas described herein such as cannula 20252. The cannula 20700 may include an attachment portion 20761 having an array 20762 including a plurality of magnet positions 20764 for one or more magnets, as depicted in FIG. 114. An positioning identification device or other tracking means can be used to determine position of a stop-cock valve based on the plurality of magnet positions 20764, for example. Further details about the configuration depicted in FIG. 114 may be found in U.S. Patent Publication 2017/0105811, which is hereby incorporated by reference in its entirety.

In various aspects, the insulation tubing of an insufflator may be attached to the outside of a gripping member held by a robotic arm controlled by a surgical robot. The robotic arm or snap in features of a sterile feature can be provided to manage this insufflation tubing. The insufflation could be an abdominal insufflation for a LAR colorectal procedural, as described above. FIG. 115A-115B illustrate the management of the insufflation tubing 9403 which passes through the interior of the robotic arm 9402, in which the insufflation tubing 9403 is located within a sterile barrier 9409. Accordingly, it may be desirable to control the robotic arm 9402 to avoid entanglement with a non-sterile barrier, as discussed above. The sterile barrier 9409 may surround or encompass the robotic arm 9402, as depicted in FIG. 115A. Airflow or another suitable fluid may enter the insufflation tubing 9403 into a patient body cavity such as an abdominal cavity as part of surgical treatment. Clips 9417a-9417e may be used to attach to each segment/linkage 9484, 9486, 9488 of the robotic arm 9402 so that the insufflation tubing 9403 may be held in place. The robotic arm 9402 may secure a surgical implement 9450 at a distal end of the robotic arm 9402, in contrast to the proximal end of the robotic arm 9433.

FIG. 115B shows a sectional view of a section of the insufflation tubing 9403 with a clip 9417a used to secure the section of tubing 9403 against a section of housing 9423 of the robotic arm 9433. The attachment of the insufflation tubing 9403 to both the distal end of the linear slider/rail as well as the rest of the robotic arm 9433 may enable the base unit control circuit to move the robotic arm 9433 to move around the surgical environment for treating the patient while minimizing the likelihood of damage to the patient. For example, the configuration may allow the base unit control circuit to reduce or prevent instances causing potentially damage to the tissue such as addressing the risk of the insufflation port of the trocar being pinched against a wall of the patient's body. The configuration of FIG. 115B could also minimize the pinching of the insufflation tubing 9403 itself by the corresponding surgical robot. Similarly, potential pinching between the robot and the patient that may cause a loss of insufflation—insufflation fluid entering the tubing 9403—may be avoided. Also, a trocar with a vertically oriented insufflation port relative to the robot could the perimeter of the trocar from having extending elements that could be driven into the wall of the patient's body. In situations in which the insufflation is vertically oriented, the physical attachment of the tubing 9403 to the distal end of the linear slider of the robotic arm 9433 (where the trocar gripper is located) may help manage the tubing 9403 and prevent entanglement. Further attachments of the tubing 9403 to the arm 9433 would link management of the tubing with the sterile barrier attachment. Consequently this arrangement may minimize entanglement with any other movable joints and the robotic arm 9433 itself.

Figure 116:
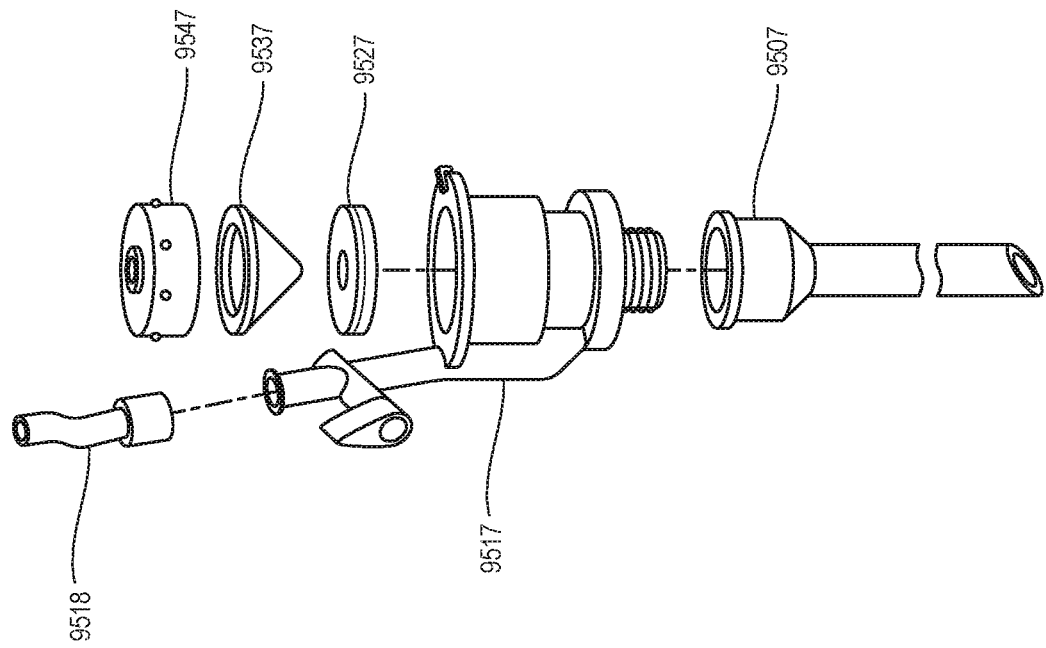
FIG. 116 shows a sealing system and reprocessable control housing for use with a cannula and insufflation valve, in accordance with at least one aspect of the present disclosure.

FIG. 116 shows an access device such as cannula 9507 (which can be similar in some aspects to other cannulas described herein) can be a screw-on cannula 9507 onto a robotic arm. The cannula 9507 could be disposable and plastic, for example. A robotic arm holding feature, such as a robotic clamp 9517 may be provided. The robotic clamp 9517 may be re-processable and metal, for example. The robotic clamp 9517 may be used so that a portion of the insufflation tubing 9518 is in an aligned position relative to the cannula 9507 and/or associated trocar, but the portion of the insufflation tubing 9518 is not fully coincident to the axis of the cannula 9507. This way, this may facilitate robotic arm cooperative engagement and management as described herein. Accordingly, the cannula 9507 may be parallel but not coincident to the insufflation tubing 9518. This parallel relationship may be for an aligned orientation of the cannula 9507 and/or trocar axis with the insufflation tubing 9518 so that the slide axis (e.g., sliders or rails of a robotic arm as described herein) of the surgical tool driver held by the robotic arm is aligned with the cannula 9507. Furthermore, three seals 9527, 9537, 9547 can be provided to seal the robotic clamp 9517. The seals 9527, 9537, 9547 may be disposable. The first seal 9527 may be a scraper that wipes, wicks, and absorbs fluid. The second seal 9537 may be a duckbill for the surgical instrument/tool held by the robotic arm for providing one way movement of the fluid. The third seal 9547 may be an instrument lip seal.

Figure 117:
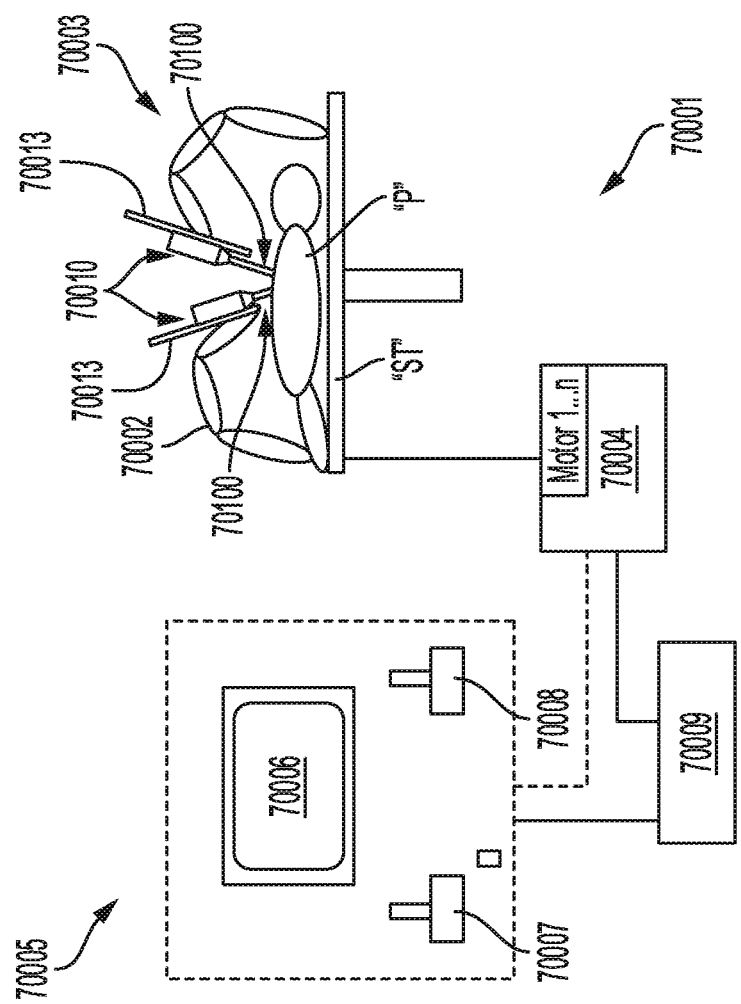
FIG. 117 is a schematic illustration of a robotic surgical system including a surgical assembly in accordance with the present disclosure.

Referring initially to FIG. 117, a robotic surgical system, such as, for example, medical work station 70001, generally includes a plurality of robot arms 70002 and 70003, a control device 70004, and an operating console 70005 coupled with control device 70004. Operating console 70005 includes a display device 70006, which is set up in particular to display three-dimensional images, and manual input devices 70007 and 70008, by means of which a clinician (not shown), for example a surgeon, is able to telemanipulate robot arms 70002 and 70003 in a first operating mode, as known in principle to a person skilled in the art.

Each of the robot arms 70002 and 70003 includes a plurality of members, which are connected through joints, to which may be attached, for example, a surgical assembly 70010. Robot arms 70002 and 70003 may be driven by electric drives (not shown) that are connected to control device 70004. Control device 70004 (e.g., a computer) is set up to activate the drives, in particular by means of a computer program, in such a way that robot arms 2 and 3, the attached surgical assembly 70010, and thus the surgical instrument 70100 (including the end effector, not shown) execute a desired movement according to a movement defined by means of manual input devices 70007 and 70008. Control device 70004 may also be set up in such a way that it regulates the movement of robot arms 70002 and 70003 and/or of the drives (not shown). Control device 70004 may control a plurality of motors, e.g., "Motor 1 . . . n," with each motor configured to drive movement of robotic arms 70002 and 70003 in a plurality of directions.

Medical work station 70001 is configured for use on a patient "P" lying on a surgical table "ST" to be treated in a minimally invasive manner by means of a surgical instrument 70100 of surgical assembly 70010. Medical work station 70001 may also include more than two robot arms 70002 and 70003, the additional robot arms likewise being connected to control device 70004 and being telemanipulatable by means of operating console 70005. A surgical assembly 70010 may also be attached to the additional robot arm. Medical work station 70001 may include a database 70009, in particular coupled to with control device 70004, in which are stored for example pre-operative data from patient "P" and/or anatomical atlases.

Reference may be made to U.S. Patent Application Publication No. 2012/0116416, entitled MEDICAL WORKSTATION, the entire disclosure of which is herein incorporated by reference in its entirety, for a detailed discussion of the construction and operation of medical work station 70001.

Figure 118:
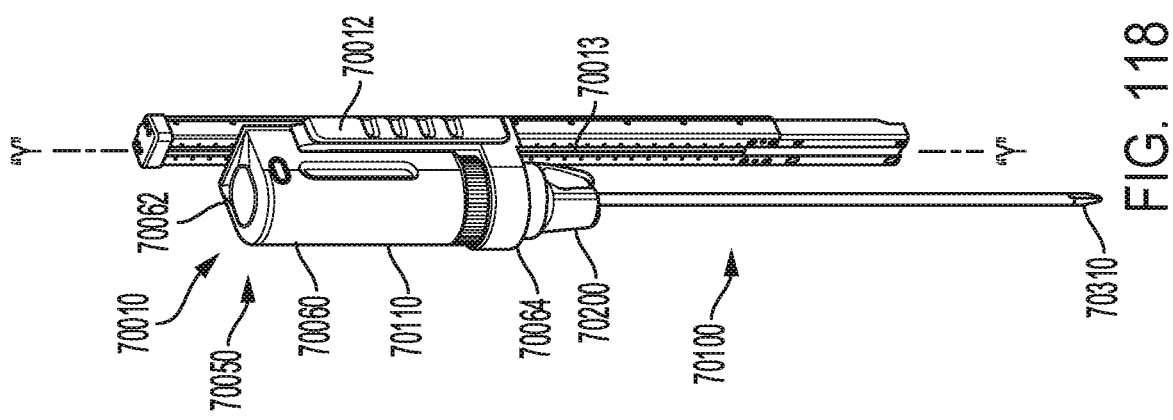
FIG. 118 is a perspective view of a surgical assembly of the robotic surgical system of FIG. 117.

Turning now to FIG. 118, in conjunction with FIG. 117, surgical assembly 70010 is shown coupled with or to robotic arm 70002. While surgical assembly 70010 is discussed singularly, a person of ordinary skill in the art can readily appreciate that the medical work station 70001 may also include a plurality of substantially identical surgical assemblies 70010 coupled with or to each of the robotic arms 70002 and 70003. Surgical assembly 70010 includes an instrument drive unit 70050 coupled to an instrument drive connector 70200 of a surgical instrument 70100 having an end effector 70310 disposed at a distal end thereof.

Instrument drive unit 70050 of surgical assembly 70010 may be supported on or connected to a slider 70012 that is movably connected to a track or slide 70013 of robotic arm 70002. Slider 70012 moves, slides, or translates along a longitudinal axis "Y" defined by track 70013 of surgical robotic arm 70002 upon a selective actuation by motors (not shown) disposed in track 70013 of robotic arm 70002 or motors (e.g., one or more of "Motor 1 . . . n") of control device 70004. As such, slider 70012, with instrument drive unit 70050 connected thereto, can be moved to a selected position along track 70013 of robotic arm 70002.

Figure 119:
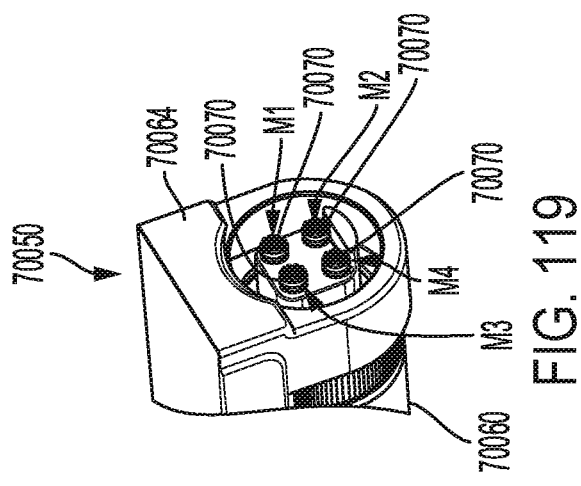
FIG. 119 is a perspective, end view of an instrument drive unit of the surgical assembly of FIG. 118.
Figure 120:
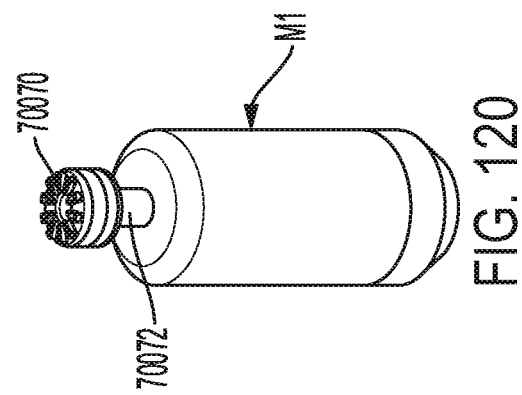
FIG. 120 is a schematic, perspective view of a motor of the instrument drive unit of FIG. 119.

With reference now to FIGS. 118 and 119, instrument drive unit 70050 of surgical assembly 70010 includes a housing 70060 having a proximal end 70062 and a distal end 70064 configured to be operably coupled to instrument drive connector 200 of surgical instrument 70100. Housing 70060 of instrument drive unit 70050 houses a plurality of motors "M1-M4" that are configured to drive various operations of end effector 70310 of surgical instrument 70100. Each motor "M1-M4" of instrument drive unit 70050, as shown in an exemplary illustration of motor "M1" in FIG. 120, includes an output drive coupler 70070 supported on a rotatable shaft 70072 extending distally from the motor. In some embodiments, output drive couplers 70070 are crown gears or the like, that are keyed to or non-rotatably supported on rotatable shafts 70072 of at least one of motors "M1-M4." In use, instrument drive unit 70050 transfers power and actuation forces from its motors (e.g., "M1-M4") to instrument drive connector 70200 of surgical instrument 70100 via rotation of output drive coupler(s) 70070 to ultimately drive movement of components of end effector 70310 of surgical instrument 70100, as described in further detail below.

Control device 70004 (FIG. 117) may control motors "M1-M4" of instrument drive unit 70050. In some embodiments, at least one motor "M1-M4" receives signals wirelessly (e.g., from control device 70004). It is contemplated that control device 70004 coordinates the activation of the various motors ("Motor 1 . . . n") to coordinate an operation and/or movement of surgical instrument 70100. It is envisioned that one or more motors correspond to a separate degree of freedom of surgical instrument 70100 engaged with instrument drive unit 70050.

Figure 122:
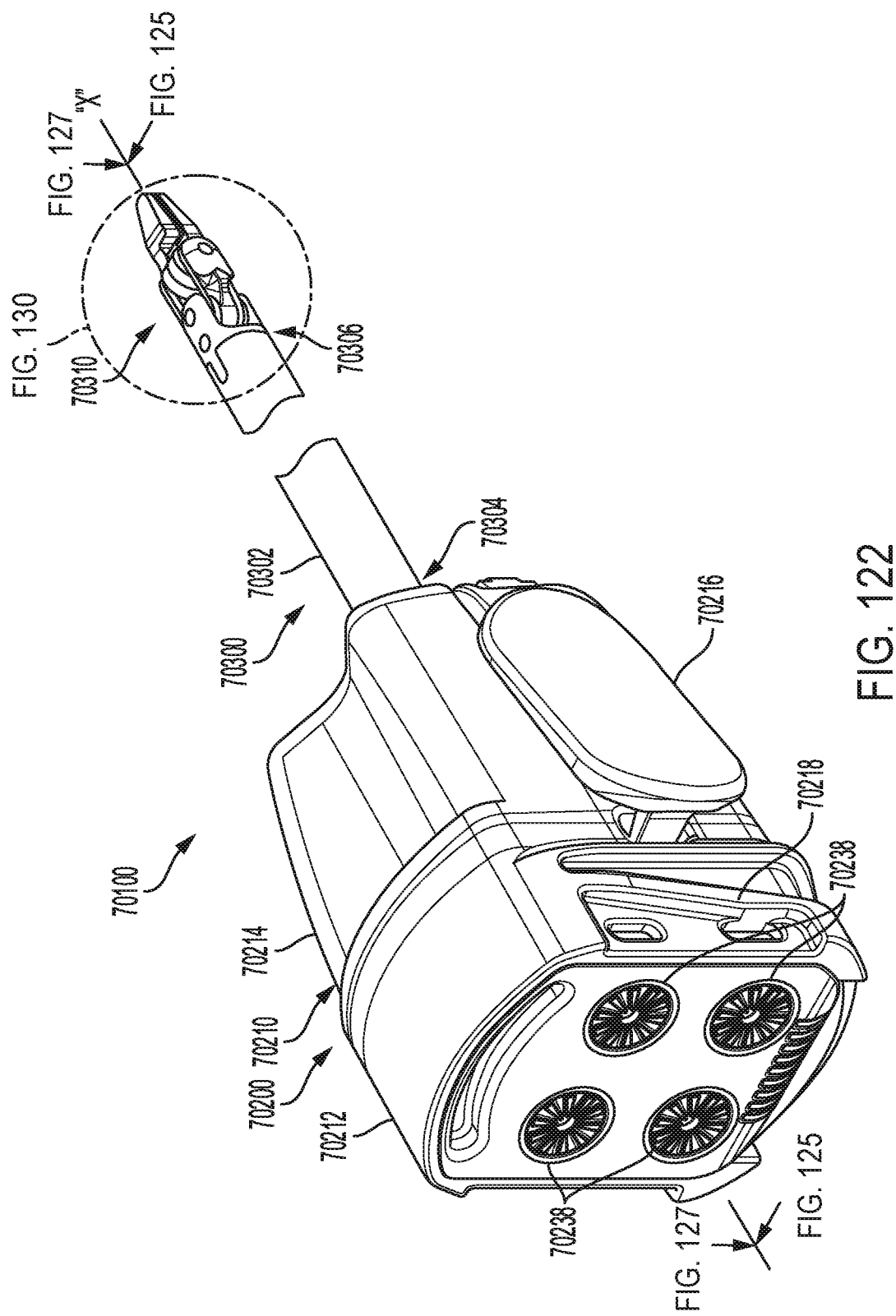
FIG. 122 is an enlarged perspective view of the surgical instrument of FIG. 121.
Figure 123:
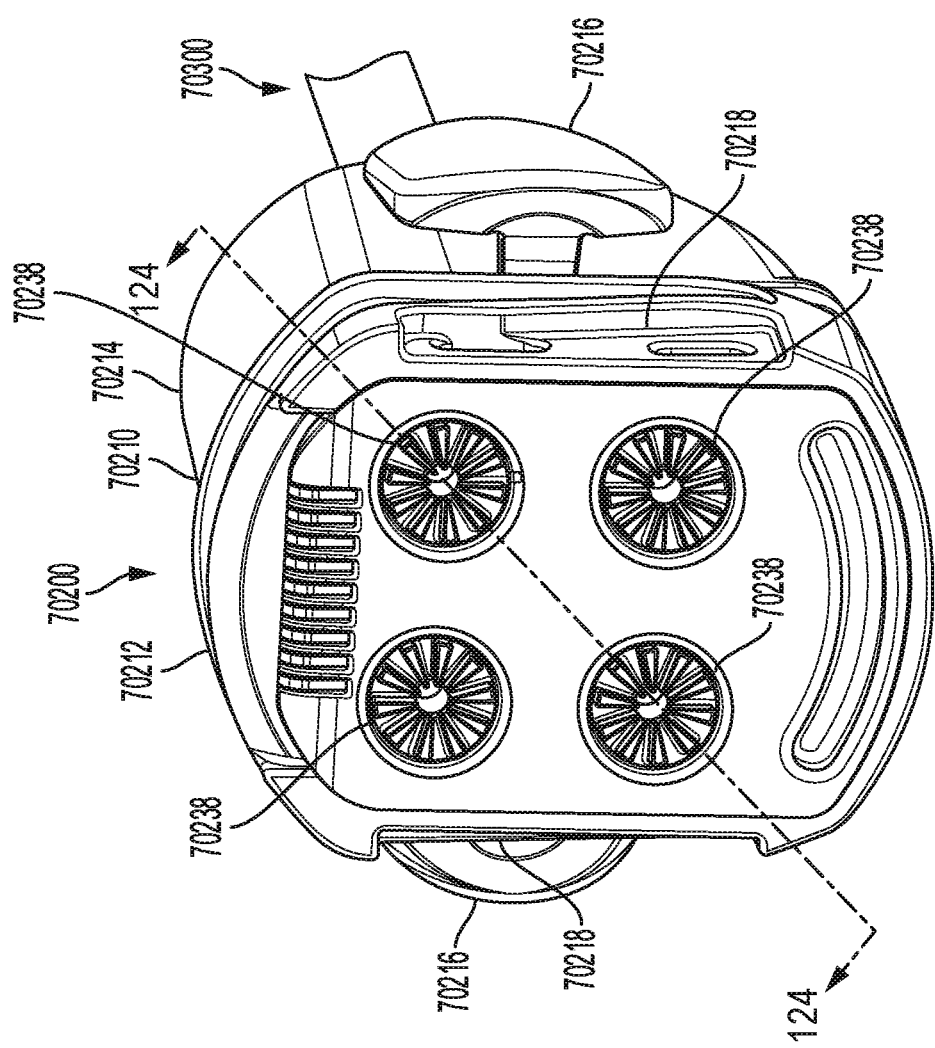
FIG. 123 is a perspective, end view of an instrument drive connector of the surgical instrument of FIGS. 121 and 28.

Referring now to FIGS. 121-123, instrument drive connector 70200 of surgical assembly 70010 includes a housing assembly 70210 which includes a proximal housing 70212 and a distal housing 70214. Proximal housing 70212 and distal housing 70214 are releasably coupled to each other, which may facilitate assembly of instrument drive connector 70200, and which may facilitate access, repair, and/or replacement of parts housed at least partially therein. Housing assembly 70210 may include cantilevered arms 70216 configured for use in disconnecting instrument drive connector 70200 from distal end 70064 of housing 70060 of instrument drive unit 70050. Proximal housing 70212 of housing assembly 70210 includes ramped camming surfaces 70218 disposed on opposed side surfaces thereof for transverse connection/disconnection with complementary mating surfaces (not shown) of instrument drive unit 70050 (FIG. 118).

With reference now to FIGS. 124-128, housing assembly 70210 defines a bore 70211 which houses a plurality of drive assemblies 70220 supported by a drive assembly frame 70270. Each drive assembly 70220 includes a drive screw 70230, a drive nut 70240, and a biasing element 70250, and is operatively connected to a drive member or rod 70260. Drive assembly frame 70270 includes a proximal end 70272 having a plurality of proximal bearings 70274 in which proximal ends 70232 of drive screws 70230 are retained. Each proximal bearing 70274 permits or facilitates rotation of drive screw 70230 with respect to housing assembly 70210. Additionally, proximal bearings 70274 may be configured to function as a proximal stop for drive nut 240. Proximal bearings 70274 are disposed radially around a proximal end of an elongated central shaft 70276. A plurality of longitudinally extending grooves 70278 (FIG. 126) are defined in an outer surface 70276a of central shaft 70276. Each groove 70278 is configured to slidingly engage a proximal end portion 70262 of drive members 70260 and second rail 70248 of drive nut 70240.

Figure 128:
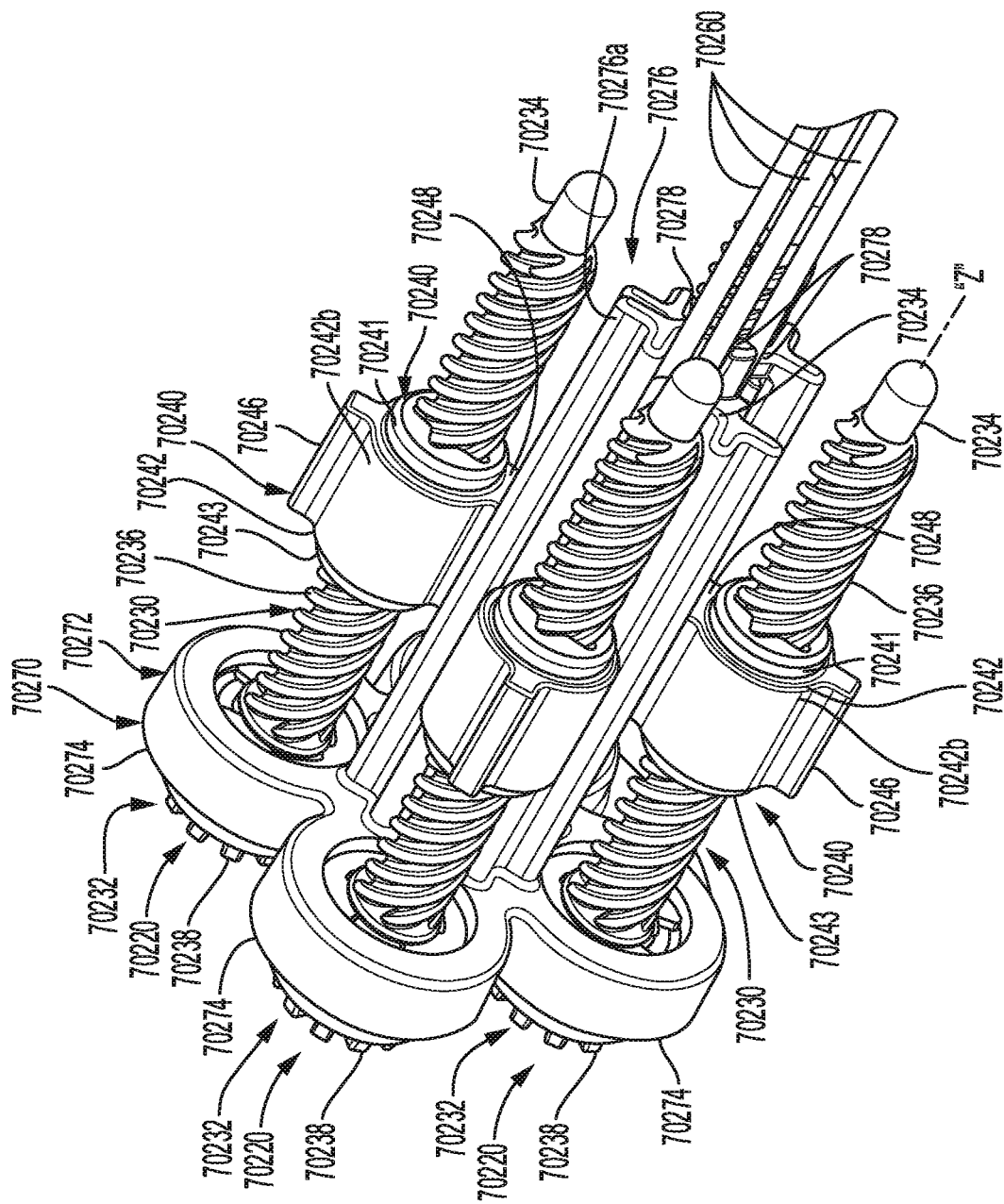
FIG. 128 is a perspective view of a drive assembly disposed within the instrument drive connector of FIGS. 121-127.

As shown in FIG. 128, drive screw 70230 includes a proximal end 70232, a distal end or tip 70234 that is non-threaded, and an elongated threaded body 70236 extending between proximal and distal ends 70232 and 70234, and defines a longitudinal axis "Z" through a radial center thereof. Proximal end 70232 of drive screw 70230 includes an input drive coupler 70238 that is configured to engage with respective output drive couplers 70070 of instrument drive unit 70050 (FIG. 119) such that movement of output drive couplers 70070 cause a corresponding movement of input drive coupler 70238. As input drive coupler 70238 is monolithically formed with elongated threaded body 70236, rotation of input drive coupler 70238 results in a corresponding rotation of elongated threaded body 70236. It should be understood that input drive coupler 70238 and elongated threaded body 70236 may be separate components that are keyed to one another. In some embodiments, input drive coupler 70238 may be a gear, such as a crown gear, that is configured to mate and/or mesh with a respective crown gear 70070 of motor "M1-M4" (FIG. 119), such that rotation of crown gear 70070 causes a corresponding rotation of crown gear 70238.

Figure 124:
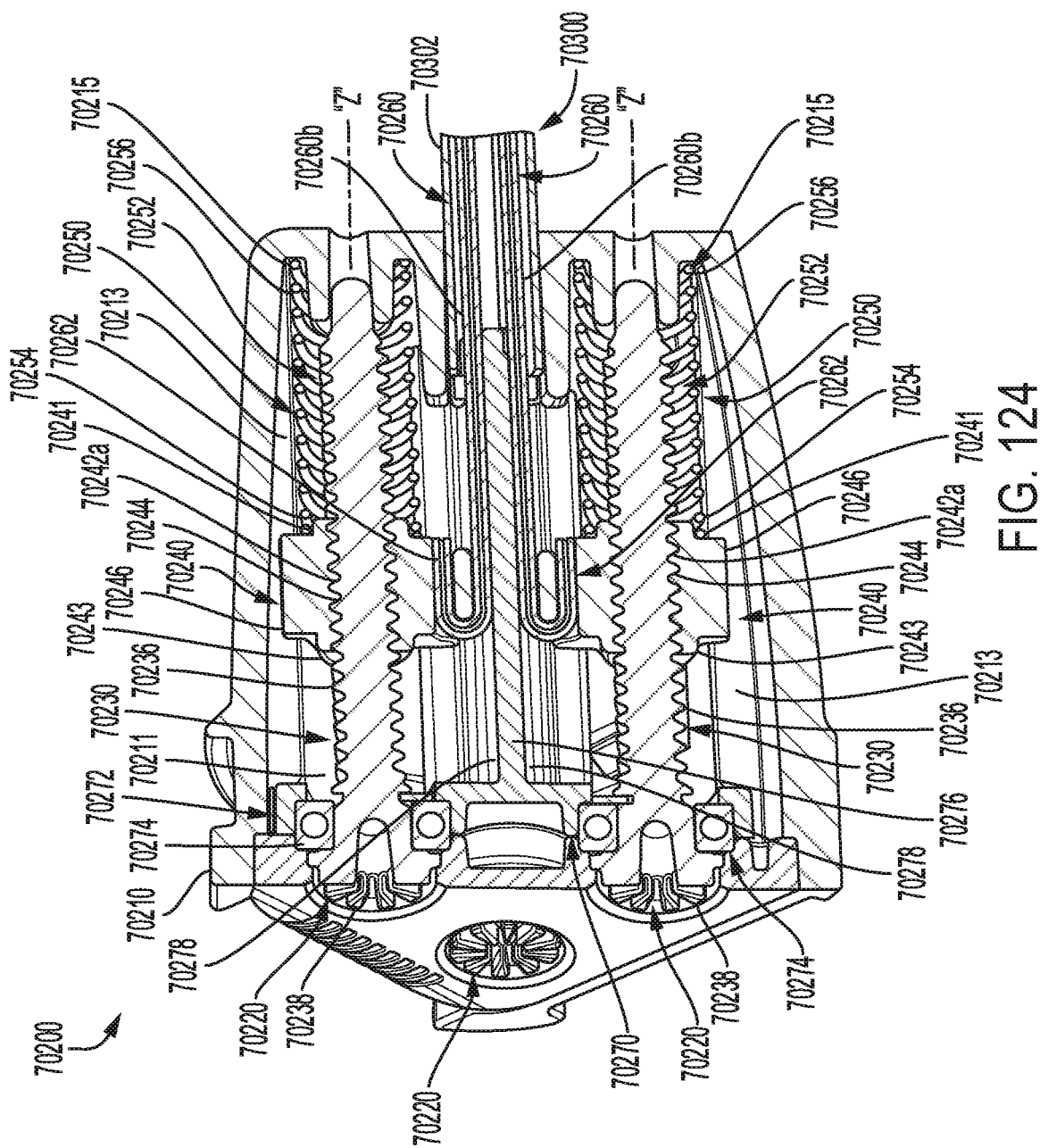
FIG. 124 is a cross-sectional view of the instrument drive connector of the surgical instrument of FIGS. 121-123, taken along line 124-124 of FIG. 123.

As shown in FIGS. 124 and 128, drive nut 70240 includes a body 70242 having a threaded aperture 70244 extending longitudinally through an inner surface 70242a thereof which is configured to mechanically engage the elongated threaded body 70236 of drive screw 70230. Drive nut 70240 is configured to be positioned on drive screw 70230 in a manner such that rotation of drive screw 70230 causes longitudinal movement of drive nut 70240. In embodiments, drive nut 70240 and drive screw 70230 are threadedly engaged with each other. Moreover, rotation of input drive coupler 70238 in a first direction (e.g., clockwise) causes drive nut 70240 to move in a first longitudinal direction (e.g., proximally) with respect to drive screw 70230, and rotation of input drive coupler 70238 in a second direction (e.g., counter-clockwise) causes drive nut 70230 to move in a second longitudinal direction (e.g., distally) with respect to drive screw 70230.

Drive nut 70240 includes a first rail 70246 extending longitudinally along an outer surface 70242b of body 70242, and which is configured to be slidably disposed in a longitudinally extending channel 70213 formed in bore 70211 of housing assembly 70210. First rail 70246 of drive nut 70240 cooperates with channel 70213 of bore 70211 of housing assembly 70210 to inhibit or prevent drive nut 70240 from rotating about longitudinal axis "Z" as drive screw 70230 is rotated. Drive nut 70240 also includes a second rail 70248 extending longitudinally along an outer surface 70242b of body 70242 which is configured to be slidably disposed in longitudinally extending groove 70278 formed in drive assembly frame 70270. Second rail 70248 is configured to mechanically engage a proximal end portion 70262 of drive member 70260.

Drive nut 70240 also includes a retention flange 70241 disposed at a distal end of body 70242. Retention flange 70241 has a smaller outer diameter than body 70242 of drive nut 70240 and is configured to engage a portion of biasing element 70250. Additionally or alternatively, a retention flange 70243 may be disposed at a proximal end of body 70242 of drive nut 70240.

A biasing element 70250, e.g., a compression spring, is configured to radially surround a portion of elongated threaded body 70236 of drive screw 70230. In embodiments, drive screw 70230 extends through an aperture 70252 defined by and extending longitudinally through biasing element 70250. Additionally, as seen in FIG. 124, a proximal portion 70254 of biasing element 70250 is configured and dimensioned to engage retention flange 70241 of drive nut 70230 and a distal portion 70256 of biasing element 70250 is configured and dimensioned for reception at least partially within a retention pocket 70215 formed in bore 70211 of housing assembly 70210. While the illustrated embodiment shows a particular type of biasing element (i.e., a compression spring), other types of biasing elements are contemplated by the present disclosure. Further still, it is contemplated that other retaining structures may be utilized for engagement with a biasing element.

Figure 125:
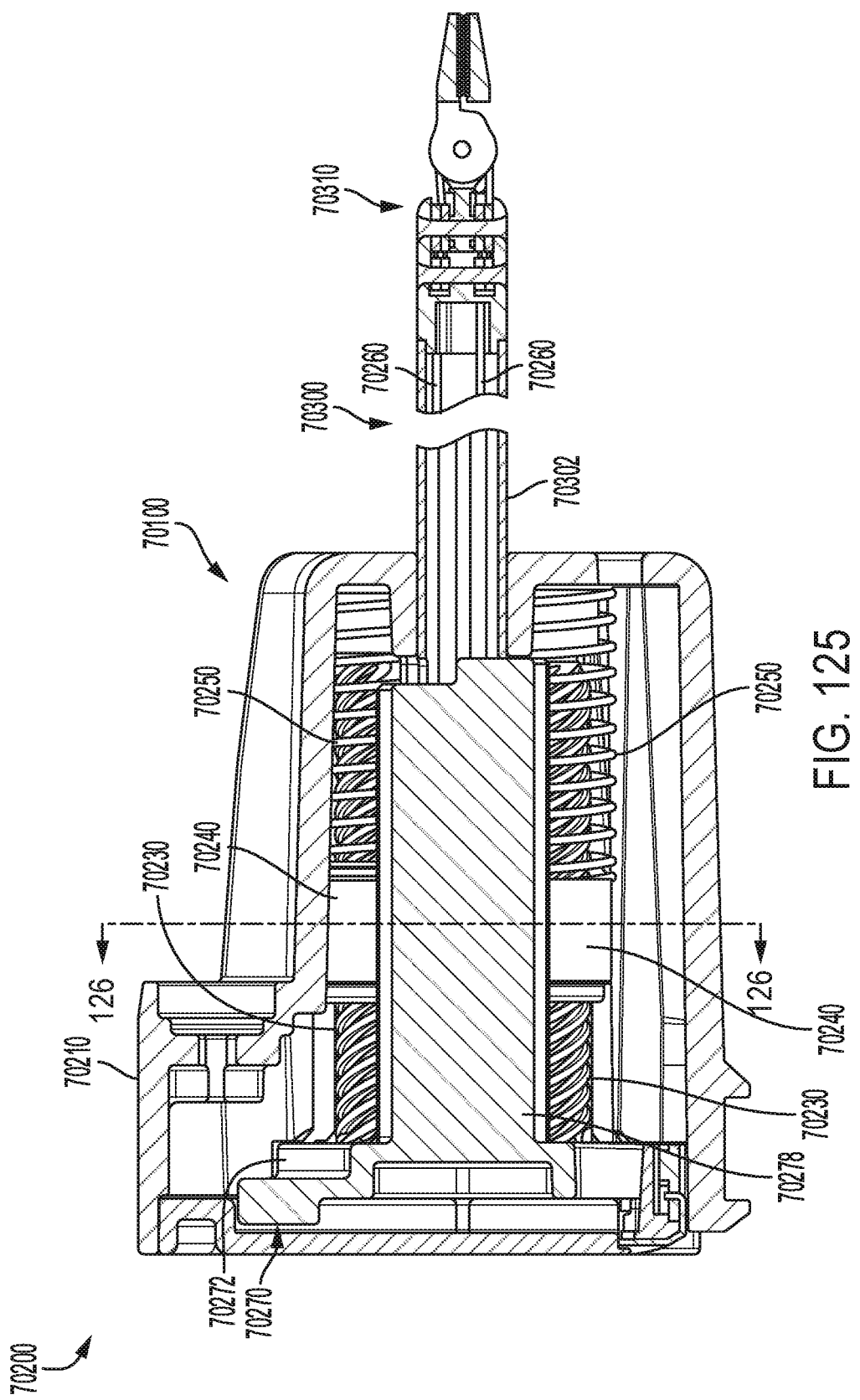
FIG. 125 is a cross-sectional view of the instrument drive connector of the surgical instrument of FIGS. 121-30, taken along line 125-125 of FIG. 122.
Figure 126:
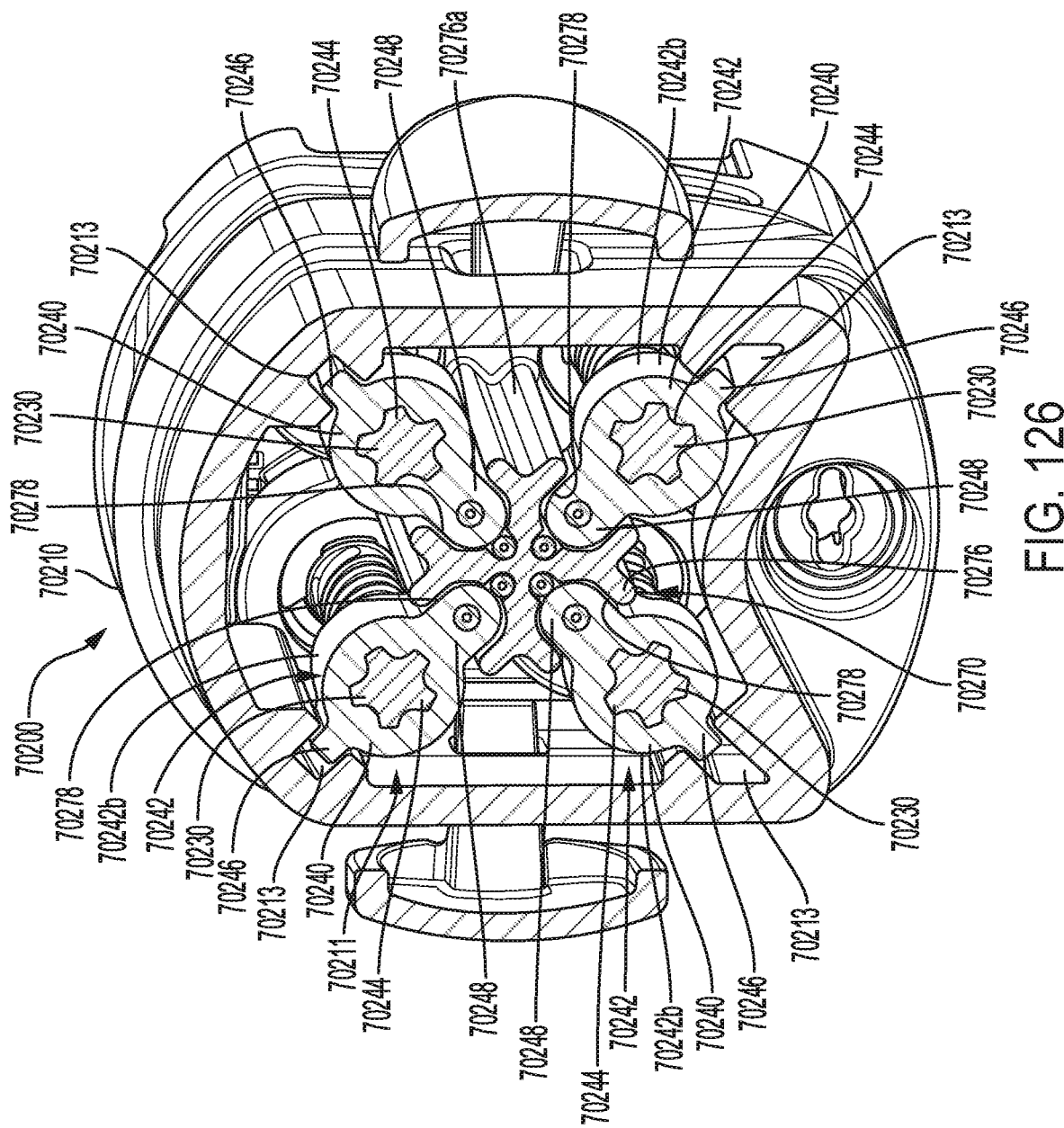
FIG. 126 is a perspective, cross-sectional view of the instrument drive connector of the surgical instrument of FIGS. 121-125, taken along line 126-126 of FIG. 125.
Figure 127:
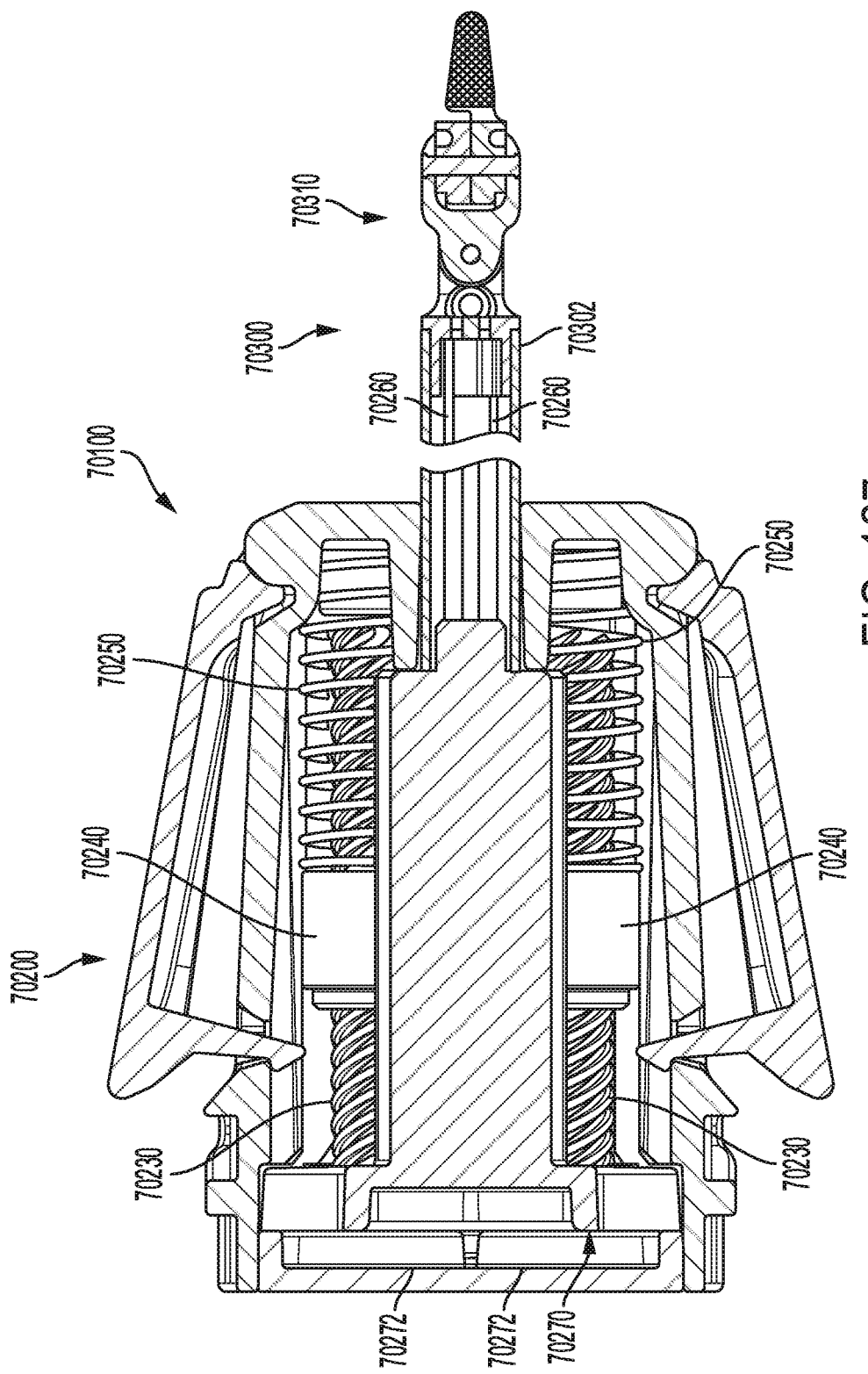
FIG. 127 is a cross-sectional view of the instrument drive connector of the surgical instrument of FIGS. 121-126, taken along line 127-127 of FIG. 122.

Each drive member 70260 (e.g., cables, chains, belts, rods, etc. and/or combinations thereof) includes a proximal end portion 70262 secured to a respective drive nut 70240. Each drive member 70260 extends from a respective drive nut 70240, through a respective groove 70278 of drive assembly frame 70270, and out bore 70211 of housing assembly 70210, and is configured to mechanically engage a portion of end effector 70310 (FIG. 125).

Biasing element 70250 is pre-tensioned to push a respective drive nut 70240 in a proximal direction, thereby applying tension to the respective drive member 70260 and preventing drive member 70260 from going slack. Drive screw 70230, around which biasing element 70250 is disposed, is thus back-drivable allowing for manual operation when instrument drive unit 70050 is not connected to instrument drive connector 70200. Accordingly, when the instrument drive unit 70050 is not connected the instrument drive connector 70200, a clinician may manually rotate input drive coupler(s) 70238 of instrument drive connector 70200 to control the surgical instrument 70100. For example, when surgical instrument 70100 is being retracted from, for example, an access port, and if wrist assembly 70320 and/or jaw assembly 70330 are in a configuration that would not pass through the orifice formed by the access port, the back-drivability of the drive screws 70230 allows wrist assembly 70320 and/or jaw assembly 70330 to be moved and/or straighten for easy removal of surgical instrument 70100 from a patient. As another example, the back-drivability allows for easy manipulation during cleaning of surgical instrument 70100 between uses.

Each drive assembly 70220 is oriented within housing assembly 70210 such that the drive members 70260 are centrally located within housing assembly 70210, and extends through an elongated shaft 70302 of surgical instrument 70100 and into engagement with end effector 70310, for example. It is envisioned that surgical instrument 70100 may include projections or the like to help guide or route drive members 70260 between drive assembly 70220 and end effector 70310.

With reference again to FIGS. 121 and 122, instrument drive connector 70200 is configured to transfer rotational movement supplied by instrument control unit 70050 (see e.g., FIG. 118) into longitudinal movement of drive members 70260 (see e.g., FIG. 124) to effect various functions of end effector 70310.

Figure 131:
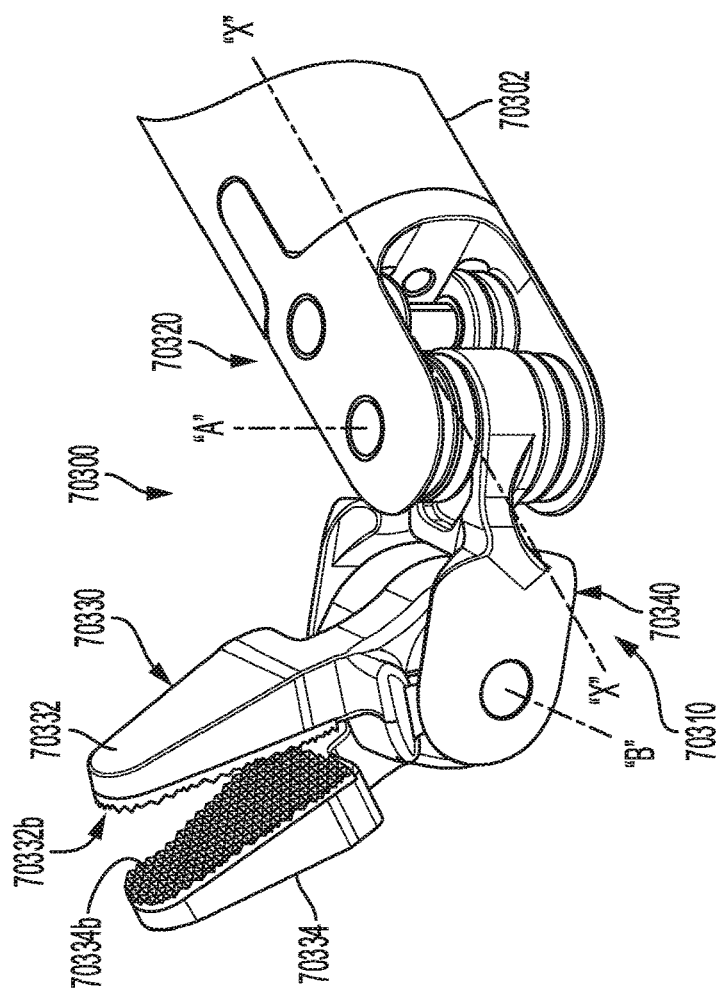
FIG. 131 is a perspective view of an end effector of the surgical instrument of FIGS. 121, 122, 129, and 130 with drive members removed therefrom.

Referring now to FIGS. 129-131, in conjunction with FIGS. 121 and 122, surgical instrument 70100 includes an endoscopic portion 70300 including an elongated shaft 70302 extending along longitudinal axis "X." Elongated shaft 70302 includes a proximal portion 70304 operably connected to or integrally formed with instrument drive connector 70200 and a distal portion 70306 having an end effector 70310. End effector 70310 is a wristed surgical device including a mounting member or wrist assembly 70320, a jaw assembly 70330, and a clevis 70340 connecting the wrist assembly 70320 with the jaw assembly 70330. Wrist assembly 70320 and clevis 70340 are connected to jaw assembly 70330 which moves (e.g., pivots, articulates, rotates, opens, and/or closes) about/relative to longitudinal axis "X" and/or about/relative to pivot axes, such as axis "A" and "B," upon movement of drive member(s) 70260.

Wrist assembly 70320 has a mount body 70322 that extends distally to a pair of spaced-apart arms including a first arm 70324a and a second arm 70324b. The pair of spaced-apart arms 70324a and 70324b defines a first pin channel 70326a and a second pin channel 326b that extend transversely through each of first and second arms 70324a and 70324b. Wrist assembly 70320 supports a first set of idler pulleys 70328a and a second set of idler pulleys 70328b that are aligned with first and second pin channels 70326a and 70326b, respectively, such that the first set of idler pulleys 70328a is located proximal of second set of idler pulleys 70328b. First and second sets of idler pulleys 70328a and 70328b are secured to wrist assembly 70320 via first and second pulley pins 70321a and 70321b, respectively. Second pulley pin 70328b and second set of idler pulleys 70326b define a pivot axis "A" about which first and second jaw members 70332 and 70334 pitch relative to longitudinal axis "X."

Jaw assembly 70330 includes a first jaw member 70332 and a second jaw member 70334 that are pivotably coupled together. First jaw member 70332 includes a grasping portion 70332a that extends distally from a first jaw pulley 70336a. Second jaw member 70334 includes a grasping portion 70334a that extends distally from as second jaw pulley 70336b. First and second jaw pulleys 70336a and 70336b may be integrally formed with grasping portions 70332a, 70334a, respectively, of first and second jaw members 70332 and 70334. Grasping portions 70332a and 70334a include respective tissue-engaging surfaces 70332b, 70334b configured to engage tissue. First and second jaw pulleys 70336a and 70336b define respective first and second drive member channels 70336c and 70336d configured to receive drive members 70260.

Clevis 70340 includes a base portion 70342 having a pair of spaced-apart fingers 70344a and 70344b that extend distally from base portion 70342. The pair of spaced-apart fingers 70344a and 70344b define a pin passage 70346 that extends transversely therethrough. Base portion 70342 is pivotally mounted to second set of idler pulleys 70326b by pivot pin 70321b to enable jaw assembly 70330 to pitch/articulate relative to a longitudinal axis "X" of end effector 70310. Jaw pulleys 70336a and 70336b of jaw assembly 70300 are coupled together and mounted between the pair of fingers 70344a and 70344b of clevis 70340 by pivot pin 70348 to enable jaw assembly 70330 to yaw about pivot axis "B" and/or to open/close jaw assembly 70330 about pivot axis "B."

As shown in FIGS. 129 and 130, each drive member 70260 includes a distal drive member portion 70260a (in the form of a cable or the like) that is routed/wrapped around the set of idler pulleys 70328a and 70238b and jaw pulleys 70336a and 70336b. Each drive member 70260 further includes a proximal drive member portion 70260b (in the form of a rod) that is individually secured to a respective drive nut 70240 (see e.g., FIG. 124) of drive assembly 70220 so that proximal drive member portion 70260b moves in response to movement of respective drive nut 70240, as described above. A plurality of ferrules 70338 (only one being shown) are coupled to the distal drive member portion 70260a of drive member 70260 to secure distal drive member portion 70260a to first jaw member 70332 or second jaw member 70334 of jaw assembly 70330.

In an exemplary method of use, when motor(s) "M1-M4" of instrument drive unit 70050 are activated in coordination with one another to rotate (clockwise or counterclockwise) input drive coupler(s) 70238 of instrument drive connector 70200, rotation of input drive coupler(s) 70238 results in a corresponding rotation of respective drive screw(s) 70230. Rotation of drive screw(s) 70230 causes longitudinal translation (distal or proximal) of respective drive nut(s) 70240, with the direction of longitudinal translation of each drive nut 70240 being determined by the direction of rotation of its respective output drive coupler 70238, and thus drive screw 70230. Translation of drive nut(s) 70240 results in a corresponding translation of respective drive member(s) 70260 which are engaged with drive nut(s) 70240.

Figure 132:
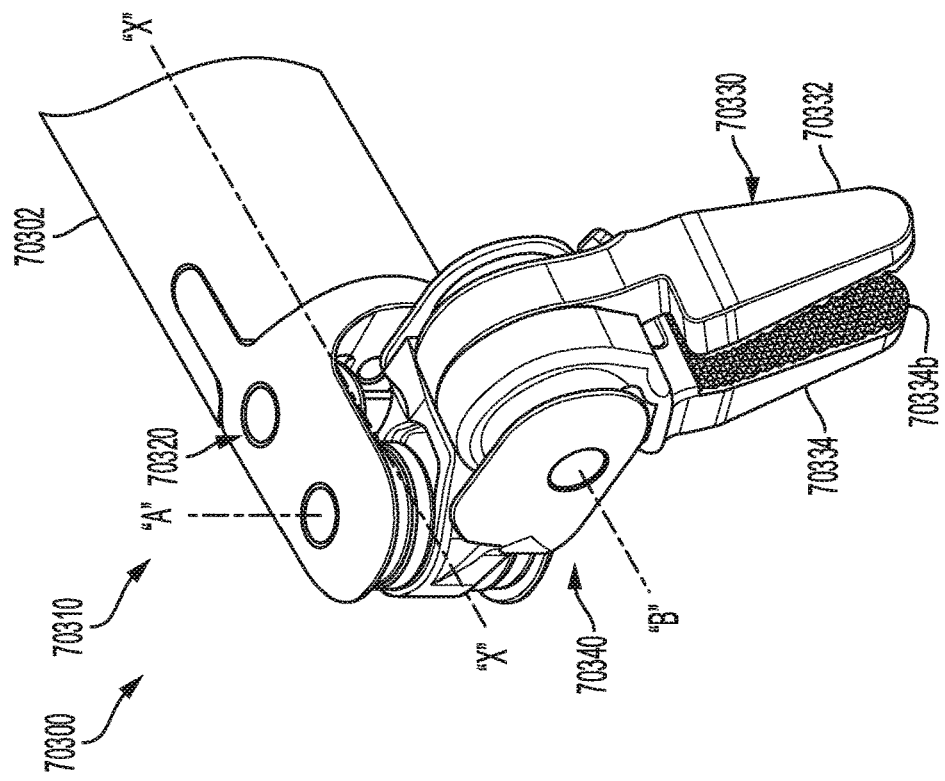
FIG. 132 is a perspective view of the end effector of the surgical instrument of FIGS. 121, 122, and 129-131 with drive members removed therefrom.

Accordingly, one or more of proximal drive member portions 70260b of drive members 70260 can be moved independently of and/or simultaneously with one or more of the other proximal drive member portions 70260b of drive member 70260 in the same and/or in opposite directions to effectuate pitching, yawing, grasping/dissecting, opening/closing, and/or any combination of these motions of end effector 70310, as shown for example in FIGS. 131 and 132. In some embodiments, drive assemblies 70220 utilize differential tension of drive members 70260 to effect operation and/or movement of end effector 70310 of surgical instrument 70100.

While certain embodiments have been described, other embodiments are possible.

Figure 133:
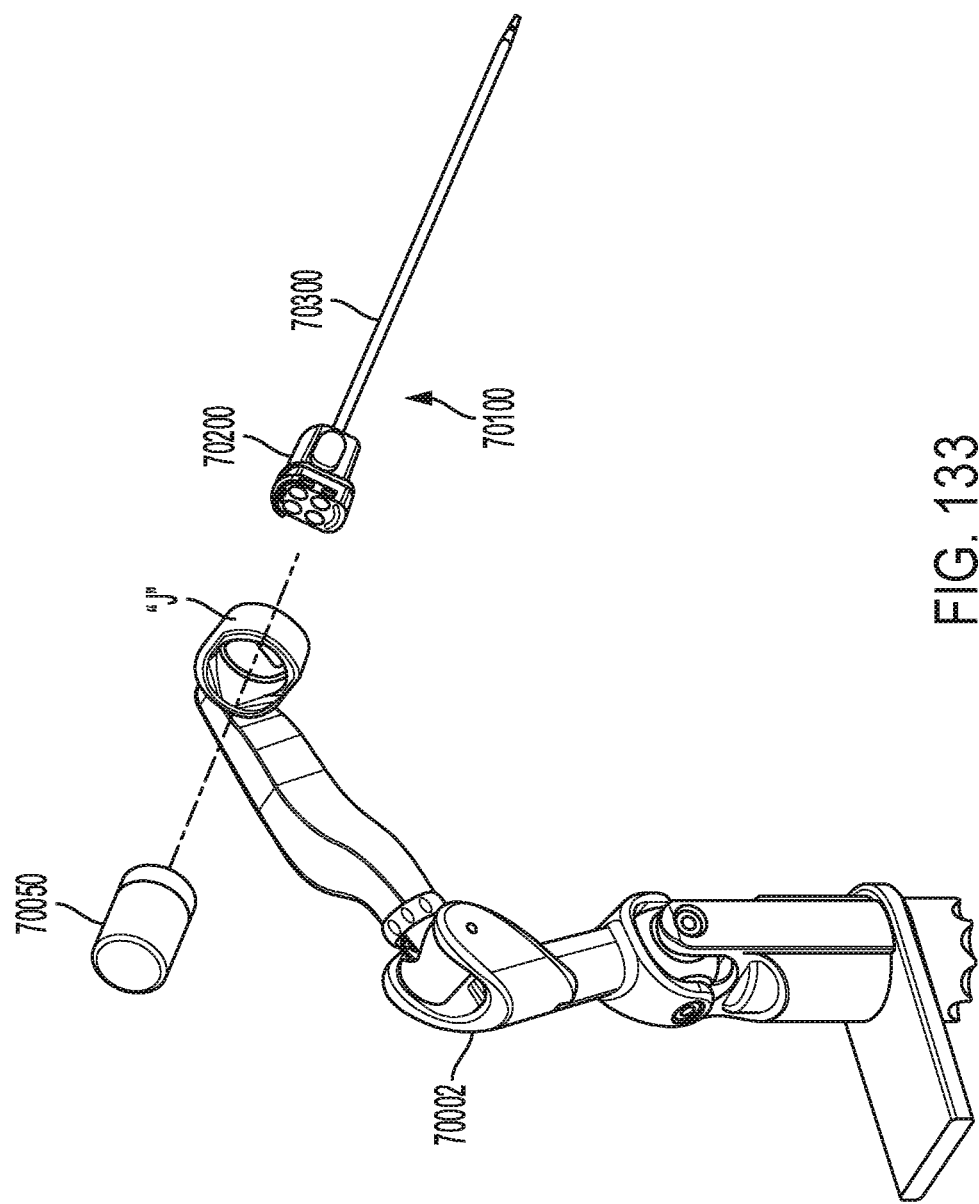
FIG. 133 is a perspective view of a robotic arm of a robotic surgical system including a surgical assembly with parts separated in accordance with the present disclosure.

For example, while instrument drive units have been described as being movably connected to a track of a robotic arm, other configurations are additionally or alternatively possible. For example, as shown in FIG. 133, instrument drive unit 70050 may be directly coupled to a joint "J" disposed at a distal end of robotic arm 70002. Instrument drive connector 70200 of surgical instrument 70100 may be connected/disconnected to instrument drive unit 70050, as described above.

Figures 134, 135:
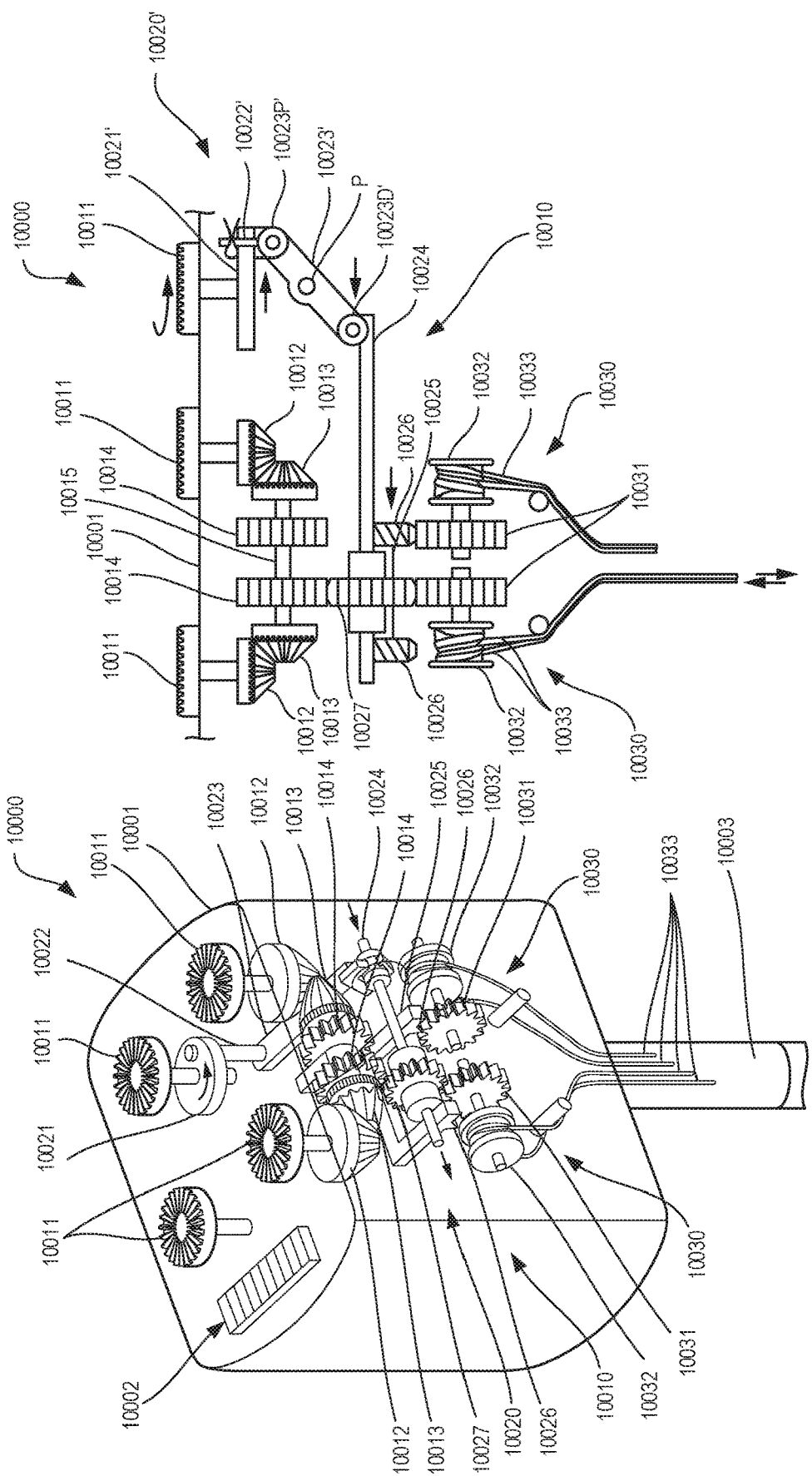
FIG. 134 is a perspective view of a surgical instrument assembly comprising a surgical drive system including a shifter assembly to operably couple multiple drive inputs of the surgical instrument assembly to drive a single output of the surgical instrument assembly.
FIG. 135 is a partial cross-sectional view of the surgical instrument assembly of FIG. 134 comprising a variation of the shifter assembly of FIG. 134.
Figure 138:
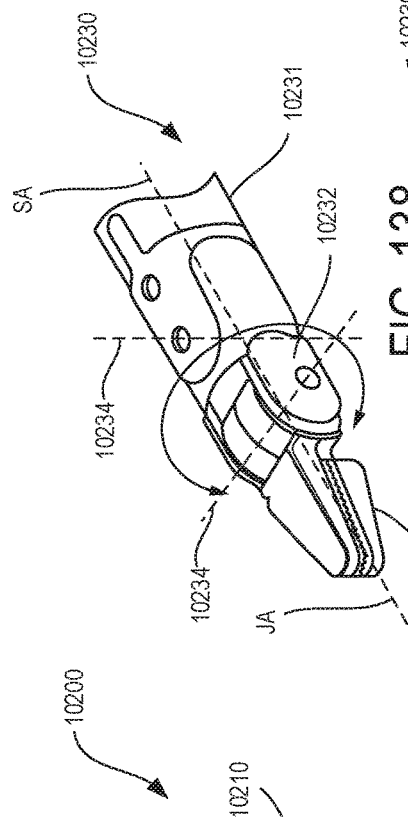
FIG. 138 is partial perspective view of an end effector of the robotic surgical tool of FIG. 137 illustrated in a first configuration.
Figure 139:
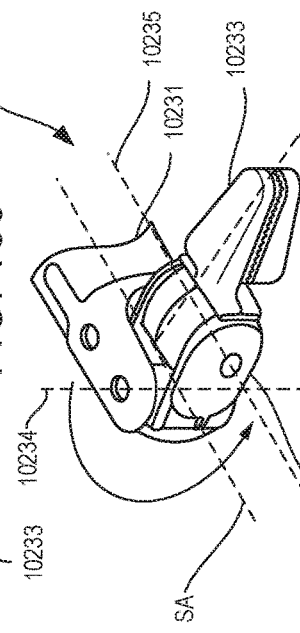
FIG. 139 is partial perspective view of the end effector of FIG. 138 illustrated in a second configuration.
Figure 140:
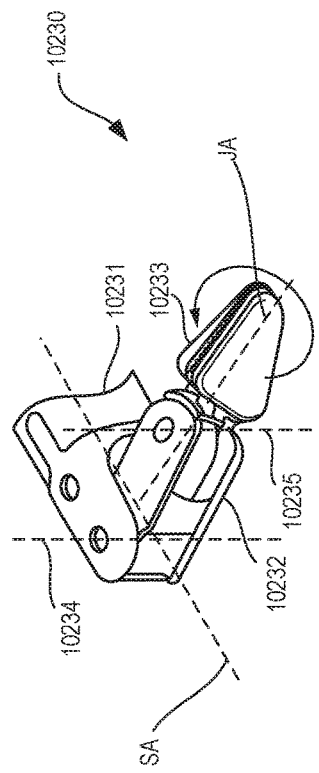
FIG. 140 is partial perspective view of the end effector of FIG. 138 illustrated in a third configuration.
Figure 137:
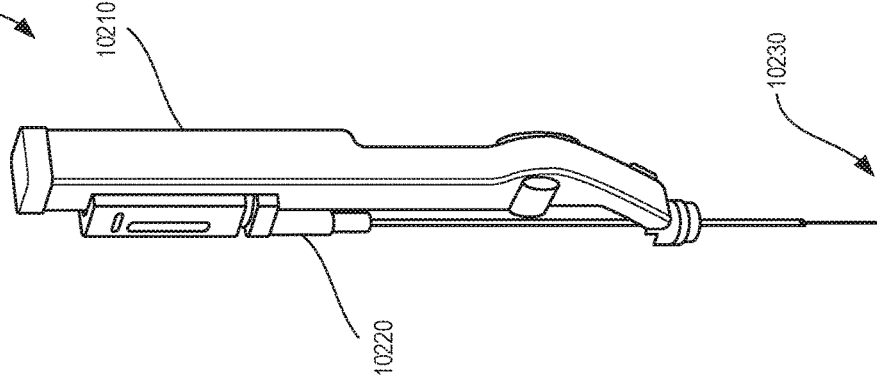
FIG. 137 is a perspective view of a portion of a surgical robot and a robotic surgical tool attached thereto.

FIGS. 134 and 135 depict a surgical instrument assembly 10000 configured for use with a surgical drive interface and a surgical end effector. Such surgical drive interfaces include, for example, a surgical robot including a robotic arm, for example, where the surgical instrument assembly 10000 would be used in a modular robotic tool attachment. Other surgical drive interfaces include a powered and/or non-powered surgical handle assembly. Any suitable drive interface is contemplated. The surgical instrument assembly 10000 comprises a housing 10001 and a shaft 10003 extending distally from the housing 10001. The housing 10001 is configured to house a surgical drive system therein and the shaft 10003 extends distally from the housing to, for example, a surgical end effector to transmit drive members 10033 to the end effector. The housing 10001 further comprises electrical contacts 10002 which can be used for any suitable application such as, for example, transmitting identification information corresponding to the surgical instrument assembly 10000 to the surgical drive interface to which the assembly 10000 is attached. In at least one instance, the electric contacts are configured to transmit identification information corresponding to the end effector to be driven by the surgical instrument assembly 10000 to the surgical drive interface.

The surgical instrument assembly 10000 is configured to be attached to a robotic surgical arm, for example, via the housing 10001 to couple the output drive members of the surgical drive interface to the surgical instrument assembly 10000. The surgical instrument assembly 10000 comprises input drive members 10011 configured to transmit actuation motions received by the output drive members of the surgical drive interface to an end effector, for example, extending distally from a distal end of the shaft 10003. The input drive members 10011 may each comprise a rotary drive gear comprising teeth configured to engage corresponding driving teeth of the output drive members of the surgical drive interface to which the surgical instrument assembly 10000 is attached.

The input drive members 10011 can be configured to actuate any suitable function of the end effector being controlled by the surgical instrument assembly 10000. For example, in a surgical stapling application, clamping and unclamping of jaws, firing the staples from the end effector, end effector rotation about an end effector axis, and/or end effector articulation relative to the shaft 10003 are all examples of functions that may exist in a surgical stapling application where the surgical instrument assembly 10000 can comprise corresponding input drive members 10011 and drive trains to drive such functions. Such functions may be driven by any suitable type of drive train. In one embodiment, any of the functions may be driven by a linearly actuatable gear drive train including, for example, a rack and pinion. In addition to or in lieu to a linearly actuatable gear drive train, any of the functions may be driven by cable pulley systems. For example, a pulley system may be used to articulate in an end effector by pulling a cable relative to a rotation axis located in the end effector. In such an embodiment, the cable can be pulled on one side of the rotation axis to articulate the end effector in a first direction and on another side of the rotation axis to articulate the end effector in a second direction which is opposite the first direction. Such a drive train can be considered antagonistic. Examples of various cable-driven systems can be found in International Application Publication No. WO2017/151996, entitled INVERSE KINEMATIC CONTROL SYSTEMS FOR ROBOTIC SURGICAL SYSTEM and U.S. Patent Application Publication No. US2018/0200894, entitled WRIST AND JAW ASSEMBLIES FOR ROBOTIC SURGICAL SYSTEMS, the entire disclosures of each of which are herein incorporated by reference in their entireties.

The surgical instrument assembly 10000 further comprises a shifter assembly 10020 configured to couple two of the input drive members 10011 to drive a single output of the surgical instrument assembly 10000 and, thus, a single function of the end effector. Such an arrangement may be advantageous where additional torque is desired when actuating a single function of the end effector. In at least one instance, such an arrangement can alleviate some of the load required to drive a single function of the end effector on one input drive member 10011 and corresponding motor, for example, and split the load of the end effector function to two of the input drive members 10011 and corresponding motors, for example. Two of the input drive members 10011 are configured to drive bevel gears 10012. The bevel gears 10012 are meshed with bevel gears 10013. The bevel gears 10013 are attached to a drive shaft 10015. The drive shaft 10015 comprises spur gears 10014 attached thereto which are configured to be rotated upon rotation of the two input drive members 10011 coupled to the bevel gears 10012. The shifter assembly 10020 is configured to direct rotary motions from the two input drive members 10011 to a single output of the surgical instrument assembly 10000.

The shifter assembly 10020 comprises a drive disc 10021 coupled to one of the input drive members 10011, a pin 10022 journably attached to a non-center location of the drive disc 10021, and a shifter link 10023 fixedly attached to the pin 10022 such that rotation of the drive disc 10021 by the input drive member 10011 causes the shifter link 10023 to move linearly within the housing 10001. The shifter link 10023 is coupled to a shaft 10024 such that linear motion of the shifter link 10023 can be transmitted to the shaft 10024. The shifter assembly 10020 further comprises a bracket member 10025 journably attached to the shaft 10024 such that the shaft can rotate relative to the bracket member 10025 but the shaft 10024 can move the bracket member 10025 linearly as the shaft is moved linearly by the shifter link 10023. The shifter assembly further comprises a drive gear 10027 fixedly attached to the shaft 10024 such that both rotational and linear motion of the shaft 10024 is transmitted to the drive gear 10027.

The shifter assembly 10020 is actuatable to move the drive gear 10027 between a first position where the drive gear 10027 is coupled with an output gear 10031 of a drive system 10030 and a second position where the drive gear 10027 is coupled with another output gear 10031 of another drive system 10030. To move the drive gear 10027 between the first position and the second position, the input drive member 10011 coupled to the drive disc 10021 can be actuated by a corresponding drive output of the drive interface and/or manually CW and CCW to linearly actuate the shaft 10024. In at least one instance, the input drive member 10011 coupled to the drive disc 10021 can be configured to rotate in only one direct to move the drive gear 10027 between the first position and the second position.

The bracket member 10025 further comprises locking teeth 10026 extending toward the output gears 10031 such that each locking tooth 10026 locks the drive system 10030 that is not coupled to the input drive gears 10011 with the drive gear 10027. Such a locking mechanism may prevent inadvertent movement of the cable, in this instance, of the drive system 10030 that is not coupled to the drive gear 10027. In at least one instance where the drive systems 10030 are utilized for antagonistic articulation drive systems, bumping the end effector will not back drive movement of the output gear 10031 owing to the locking tooth 10026 thus preventing inadvertent articulation, for example. The drive systems 10030 each comprise a drive spool 10032 configured to be rotated as the output gears 10031 are rotated. Each spool 10032 is further configured to actuate a cable 10033 by pulling the cable 10033 in one direction and providing slack in the other direction in order to antagonistically actuate the cable 10033. As such, two input drive members 10011 and, thus, two motors in the surgical drive interface, for example, are configured to drive a single drive spool 10032. While two input drive members 10011 are operably coupled to one of the drive spools 10032, the other drive spool 10032 is locked owing to the engagement of a locking tooth 10026 with the corresponding output gear 10031.

FIG. 135 depicts a variation of the shifting assembly 10020 referenced as the shifting assembly 10020'. The shifting assembly 10020' is configured to be used with the surgical instrument assembly 10000. The shifting assembly 10020' comprises a drive disc 10021' configured to be driven by an input drive member 10011. The shifting assembly 10020' further comprises a shifter link 10023' mounted within the housing 10001 and configured to rotate about a central pin "P". The shifter link 10023' comprises a proximal end 10023P' coupled to the drive disc 10021' by way of a pin 10022' and a distal end 10023D' coupled to the shaft 10024. Rotation of the drive disc 10021' by the input drive member 10011 causes the shifter link 10023' to be rotated about the central pin "P" to move the shaft 10024 linearly within the housing 10001.

In at least one instance, the gears 10014 are coupled each other by way of a clutch mechanism such that the clutch may be selectively engaged and disengaged depending on the number of input drive gears 10011 desired to drive the end effector function. Such an arrangement can increase flexibility of the surgical instrument assembly 10000 where multi-drive train coupling is not desired. In at least one instance, such a system would permit a single input drive member 10011 to drive one output drive system 10033 while still locking the other output drive system 10030.

In at least one instance, the shifter assembly 10020 can be configured such that the location of the locking teeth thereon can permit the locking of both output drive systems 10030. Such a configured would provide an option of completely locking articulation in both directions while decoupling all input drive systems from the output drive systems 10030.

In at least one instance, such a shifter assembly such as the ones described above allow the input drive members and, thus, motors, for example, of the surgical drive interface, to be retasked to a function that may not be their intended function. For example, in a normal operating state, one of the input drive members 10011 may be responsible for driving clamping and unclamping of jaws while the other of the input drive members 10011 may be responsible for deploying staples out of a staple cartridge. In such an instance, the shifter assembly can retask the normal operating state of the input drive member 10011 that normally clamps and unclamps jaws to deploying staples. Similarly, the shifter assembly can retask the normal operating state of the input drive member 10011 that normally deploys staples out of a staple cartridge to clamp and unclamp jaws. Such a configuration may reduce the number of input drive members required, for example.

In at least one instance, the input drive member 10011 normally responsible for driving articulation of the end effector (which may, in at least one instance, require less force to perform than other functions) may be retasked to aid another input drive member 10011 in driving a higher load function such as clamping and unclamping of jaws and/or deploying staples, for example. In at least one instance, the shifter assembly may be used to shift a drive train between different gears to provide flexibility in speed when actuating a certain function, for example. In such an instance, shifting to a slower speed can provide finer control of the function being actuated. In at least one instance, the gears permitted to be shifted between can correspond to outputting different torques to optimize the actuation of a certain end effector function. In at least one instance, where shifting between multiple gears, a locking system may be utilized to lock the gears before shifting between them. In at least one instance, a synchronizer may be used to allow the gears to be shifted instantly and/or on the fly.

The shifter assembly 10020 may be actuated manually by way of an external lever, for example. In at least one instance, the shifter assembly 10020 could be automatically controlled by a control circuit based on feedback sensed by the control circuit. In at least one instance, shifting of the shifter assembly 10020 is automated. For example, a clinician may switch between articulation and clamping functions of the surgical instrument assembly and the control circuit will automatically shift the shifting assembly 10020 between the two functions. Such functions may include articulation in one plane and articulation in a second plane, where the first plane and second plane are transverse to each other.

FIGS. 136A-136D depict a surgical drive system 10100 comprising a cable-driven system 10110, an actuation member 10130, and a bracket 10120 configured to hold said actuation member relative to said cable-driven system 10110. The cable-driven system 10110 comprises a first drive 10111, a second drive 10112, a pulley 10113, and a cable 10114 attached to the first drive 10111 and the second drive 10112. The cable 10114 is supported by the pulley 10113 such that the cable 10114 may be driven in a clockwise direction CW around the pulley 10113 and a counterclockwise direction CCW around the pulley 10113. The first drive 10111 and second drive 10112 may be actuated by any suitable drive interface.

The bracket 10120 comprises a mounting portion 10122 fixedly attached to the cable 10114 and a pawl 10121 configured to engage the actuation member 10130 in a ratchet-like manner. The actuation member 10130 comprises a proximal end 10131 comprising a linear rack portion 10132 configured to be engaged by the pawl 10121 and a distal end 10133. The actuation member 10130 may comprise, for example, a firing member including a cutting blade for use in a surgical stapling application. When the cable 10114 is actuated, the bracket 10120 is moved longitudinally to actuate the actuation member 10130 between a proximal-most position (FIG. 136A) and a distal-most position (FIG. 136B). The pawl 10121 remains engaged with the rack portion 10132 of the actuation member 10130 to transfer motion of the bracket 10120 to the actuation member 10130.

The surgical drive system 10100 is configured to eliminate cable slack induced during use of the surgical drive system 10100. Such slack may be induced over a period of time causing the cable 10114 to stretch. While pulling the cable 10114 past the yield strength of the cable 10114 may not be desired, such a scenario may still occur. In such a scenario, it may be advantageous to eliminate the slack induced by the permanent elongation of the cable 10114. The surgical drive system 10100 is configured to eliminate such slack.

FIG. 136A illustrates the surgical drive system 10100 in a pre-fired position where the cable 10114 is taught. Cable tension may be important to reduce error in driving the actuation member 10130. To advance the actuation member 10130 distally through an actuation stroke 10101, the first drive 10111 is rotated clockwise a first distance $d_{A1}$ and the second drive 10112 is rotated clockwise a first distance $d_{B1}$—such rotation of the first drive 10111 and the second drive 10112 causes the actuation member 10130 to advance to its distal most position as illustrated in FIG. 136B. As discussed above, the cable 10114 may stretch during such an actuation of the actuation member 10130 owing to unpredictable actuation forces, for example. In such an instance, the actual distance traveled by the first drive 10111 (the actual distance $d_{A2}$) may be greater than the actual distance traveled by the second drive 10112 (the actual distance $d_{B2}$). At this point, the cable 10114 may be considered uncalibrated, and calibration of the cable 10114 to eliminate the possible issues with a stretched cable may be desired.

To retract the actuation member 10130, the first drive 10111 and the second drive 10112 are rotated in a counter clockwise direction. For illustrative purposes, FIG. 136C represents the actuation member 10130 in its proximal-most position as if the first drive 10111 and the second drive 10112 were rotated counterclockwise the same distance (distance $d_{A3}$ is equal to the distance $d_{B3}$). As can be seen in FIG. 136C, the cable is not taught and cable slack 10103 is induced.

Referring now to FIG. 136D, to eliminate the cable slack 10103, the second drive 10112 is configured to continue to rotate in the counterclockwise direction at least an amount equal to the length of slack of the cable slack 10103 induced in the cable 10114. To ensure that the cable slack 10103 is eliminated, a bottom out feature 10102 is provided to hold the actuation member 10130 relative to the cable 10114 and the bracket 10120 when the actuation member 10130 is in its proximal-most position such that the second drive 10112 can continue to rotate in the counterclockwise direction to tighten the cable-driven system 10110 by ratcheting the pawl 10121 against the rack portion 10132. In at least one instance, the surgical drive system 10100 is configured to stop tightening the cable 10114 upon a predetermined number of ratchet clicks, for example. In at least one instance, loads on the drives 10111, 10112 can be monitored and, when a load corresponding to a ratcheting action is detected, the drives 10111, 10112 can be stopped.

In at least one instance, the drives 10111, 10112 can be configured to be cooperatively run such that cable slack is assessed continuously throughout operation of the drives 10111, 10112. This calibration process can be configured to run automatically before and/or after every actuation stroke. While a linearly-driven actuation member is illustrated, the surgical drive system 10100 may be used with any suitable actuation member utilizing a cable-driven system. In at least one instance, cable tension is continuously monitored by directly measuring cable tension on the cable itself. In such an instance, the drives 10111, 10112 can be configured to automatically adjust rotational distances based on the monitored cable tension. In at least one instance, the slack induced by the cable is logged over a period of time and adjustments are made to the drives 10111, 10112 to prolong the life of the cable 10114. For example, the drives 10111, 10112 may reduce available distal actuation force for a cable nearing an end-of-life cycle to prevent premature failure. In at least once instance, a user may be notified when a cable is near the end-of-life cycle. In at least one instance, a control circuit is configured to automatically disable an instrument when a cable exceeds a threshold of slack-elimination adjustments.

In at least one instance, a torque limiter may be used in each drive 10111, 10112. In such an instance, the drives 10111, 10112 can be configured to actuate an actuation member distally to its end-of-stroke and then 'click' a predetermined and/or desired number of times before actuation is complete. Similarly, the drives 10111, 10112 may retract an actuation member proximally to its beginning-of-stroke and then 'click a predetermined and/or desired number of times before retraction is complete. In at least one instance, only one of the drives 10111, 10112 activates its torque limiter. For example, the first drive 10111 may activate its torque limiter upon distal actuation of the actuation member and the second drive 10112 may activate its torque limiter upon proximal retraction of the actuation member. In at least one instance, actuation member travel is monitored and adjustments are made to the drives 10111, 10112 based on the detected location of the actuation member.

Such a surgical drive system 10100 may be advantageous because cables may elongate over time due to regular use and/or overuse, for example. In at least one instance, the calibration process is configured to run after every stroke regardless of whether or not the cable incurred slack and/or stretching, for example.

FIGS. 137-140 depict a surgical instrument assembly 10200 comprising a robotic arm 10210 and a surgical tool 10220 attached to and configured to be controlled by the robotic arm 10210. The surgical tool 10220 may be any type of surgical tool 10220. The surgical tool 10220 comprises an end effector 10230 comprising a first shaft 10231 extending distally from an attachment interface of the surgical tool 10220, a second shaft 10232 rotatably coupled to the first shaft 10231, and a head portion 10233 comprising grasping jaws. The first shaft 10231 is rotatable relative to the shaft axis SA. The second shaft 10232 is rotatable relative to the first shaft 10231 and articulatable relative to the first shaft 10231 about axis 10234. The head portion 10233 is rotatably coupled to the second shaft 10232 for selective rotation relative to the second shaft 10232. The head portion 10233 is rotatable relative to a jaw axis JA. In at least one instance, the head portion 10233 is articulatable about axis 10235. Such a surgical instrument assembly 10200 may be similar in many respects to endoscopic portion 70300 described herein.

The rotation and articulation functions of the end effector 10230 can be controlled by cable-driven systems including antagonistic drive trains, for example. In at least one instance, one or more of the rotation and articulation functions are controlled using flexible drive shafts. In such an instance, the flexible drive shafts may be concentric. In at least one instance, a variety of gears and/or drive screws can be used to control one or more of the rotation and articulation functions. At any rate, any suitable drive train and/or combination of different types of drive trains to control the end effector rotation and articulation functions can be used to transfer motion from the robotic arm 10210 to the surgical tool 10220 and, thus, the end effector 10230.

The rotation and articulation functions of the end effector 10230 can be synchronized by a control circuit to increase usability of the end effector 10230. For example, multiple rotation and articulation functions and/or any combination of the functions can be synchronized by a control circuit to simplify drive trains in the end effector 10230. In such an instance, while in the configuration illustrated in FIG. 139, the first shaft 10231 and the second shaft 10232 may be rotated cooperatively and simultaneously to rotate the head portion 10233 about the jaw axis JA without the need for an additional, independent drive train extending to the head portion 10233 and components needed for operation of the additional, independent drive train to rotate the head portion 10233. Such synchronization of multiple functions can appear to a user as a single head-rotation function, for example.

In at least one instance, head-rotation can be achieved by releasing an actuation member connected to the head portion 10233. The release of this actuation member would permit the head portion 10233 to rotate freely. In at least one instance, release of the actuation member connected to the head portion 10233 releases actuation pressure applied to the head portion 10233. In at least one instance, a drive train extending to the head portion 10233 is configured to be locked into place to hold the jaws clamped, for example, while the head portion 10233 is rotated. In at least one instance, multiple drive trains can be synchronized in a fashion where a difference in actuation of the drive trains causes a function of the jaws such as, for example, clamping and unclamping, to be actuated during the synchronized actuation. In other words, a first drive train may be actuated a first amount and a second drive train may be actuated a second amount which is different than the first amount. The difference in actuation can be translated to actuation of the desired jaw function to be actuated. Such a scenario may permit opening and closing of the jaws, for example, while the head portion 10233 is rotated.

In at least one instance, a surgical tool such as the surgical tool 10220, for example, can comprise three independent drives configured to rotate different portions of the an end effector relative to longitudinal axes defined by each portion of the end effector. In such an instance, the actuation of these drives can be synchronized and monitored by using an encoder, for example, to detect the rotational motion applied to each drive. In at least one instance, each drive comprises its own motor. In such an instance, multiple encoders can be used to determine the rotational distance of each motor during actuation of each drive. Tracking the rotational distance of each motor can be interpreted by a control circuit to determine the actual position and/or configuration of the end effector. All positions may be compared against a home position for each motor. For example, the end effector may comprise a home position from which the data measured by the encoders are compared to determine the actual position of the end effector relative to the home position of the end effector.

Encoders can be used in the drive trains of a surgical tool 10220 to track the position of each member in the end effector capable of performing rotation and/or articulation. Utilizing encoders can also permit a control circuit to return each member of the end effector 10230 to a home position upon detaching the surgical tool 10220 from the robotic arm 10210. In at least one instance, such encoders can also allow a control circuit to find the home position of and reset each member of the end effector 10230 to a home configuration by using encoders and cycling through actuation cycles corresponding to each member.

In at least one embodiment, three concentric drive shafts are contemplated. The concentric drive shafts are coupled at a proximal end of the surgical tool 10220 such as, for example, in the attachment drive interface, with a gear which is aligned with input drive discs which receive rotary motion from the surgical robot drive. The distal ends of the concentric drive shafts are configured to terminate in gearing features integrated in the end effector. Such gearing features may include, for example, a worm gear. Such a worm gear configuration can be coupled to one of the articulation functions of a member of the end effector. In at least one instance, such drive systems may be difficult to back drive reducing the possibility of inadvertent movement of the end effector during an operation, for example. In such an instance, synchronized rotation of multiple end effector members would be the only way to articulate an end effector, for example. Actuators may also be configured to pass through articulation joints and may comprise torsionally-woven flexible drive shafts. Such woven flexible drive shafts may comprise a braided configuration, for example. In at least one instance, the drive shafts can be hollow and also bendable while conducting the rotation of an end effector member.

In at least one embodiment, a surgical drive system may employ an end-of-stroke ratchet tightening system to remove slop during an operation. A worm drives and/or cam disk actuator may integrate a friction tightening locking nut. The nut is configured to be held with a ratchet style restraint permitting an actuation member to run to the end of its stroke. Once at the end of its stroke, the actuation member may run into a stop member. At such point the actuation member is configured to push against the stop and apply a pre-defined torque to the ratchet tightening system. The tightening operation may increase the bind in the drive member creating a dampening force to any additional actuation force applied to the actuation member. This may allow for a mock antagonistic-like restraint as the system is able to compensate for frictional loss within the drive train itself. The frictional loss compensation may be re-calibrated to tighter to a greater degree as the system wears over time by reapplying the torque to the end of stroke condition as discussed above and further tightening the system.

FIGS. 141-144 depict a surgical instrument assembly 11000 comprising a seal 11030 configured to prevent the contamination of the surgical instrument assembly 11000. The surgical instrument assembly 11000 comprises an attachment interface 11010 and a shaft assembly 11040 of a robotic surgical tool attachment, for example, configured to be coupled with the attachment interface 11010. The attachment interface 11010 may comprise a robotic surgical arm, for example, configured to be attached to various surgical tools to drive the surgical tools in a surgical operating environment. The attachment interface 11010 comprises a receiving portion 11020 comprising a shaft 11021. The shaft 11021 comprises an inner cavity 11023 defined therein and a cleanout port 11022 defined in a distal end of the shaft 11021. The seal 11030 is positioned within the inner cavity 11023 such that the seal 11030 fills or, at least substantially fills, the volume of the inner cavity 11023 so as to adequately seal the receiving portion 11020 and, thus, the attachment interface 11010.

It may be advantageous to prevent contaminants and/or debris from getting into the inner cavity 11023 and passing into the attachment interface 11010. The passage of contaminants and/or debris through the receiving portion 11020 into the attachment interface 11010 may cause components to fail such as, for example, gear trains configured to actuate drive shafts of the surgical tool 11040 configured to be coupled with corresponding output drive shafts of the surgical robot comprising the attachment interface 11010 to bind, or lock, up and render the gear trains inoperable. The seal 11030 is configured to remain in the receiving portion 11020 of the attachment interface 11010 before insertion of the surgical tool 11040 into the attachment interface 11010, during operation of the surgical tool 11040 by the surgical robot comprising the attachment interface 11010, and after the surgical tool 11040 is removed from the attachment interface 11010. Embodiments are contemplated where a new seal is inserted each time a surgical tool is inserted into the attachment interface 11010.

The seal 11030 comprises a slit 11031 cut in the seal 11030. In at least one instance, the slit 11031 is central to the seal 11030. The slit 11031 may comprise a cavity and/or channel, for example. Material may be removed when the slit 11031 is cut and the material of the seal 11030 may be cut only during creation of the slit 11031. In at least one instance, the slit 11031 is precut. In at least one instance, a perforation of the slit 11031 is shipped with a new seal and the insertion of the surgical tool 11040 forms the slit 11031 upon insertion of the shaft 11041 through the seal 11030 to attach the surgical tool 11040 to the attachment interface 11010. The slit 11031 may comprise any suitable shape and/or configuration.

Referring to FIG. 142, the slit 11031 comprises a proximal end 11032 positioned at a proximal end of the seal 11030 and a distal, or receiving, end 11033 position at a distal end of the seal 11030. The distal end 11033 of the slit 11031 comprises a slit width $W_D$ and the proximal end 11032 of the slit comprises a slit width $W_P$. The slit width $W_D$ is larger than the slit width $W_P$. The slit 11031 is also formed in the seal 11030 with a spiral shape. As the shaft 11041 is inserted into the attachment interface 11010 the shaft 11041 engages the slit 11031 and passes through the seal 11030. The seal 11030 compresses against the shaft 11041 and the walls of the inner cavity 11023 of the shaft 11021 as the shaft 11041 is inserted into the receiving portion 11020 of the attachment interface 11010. The seal 11030 comprises a tapered opening 11034 (FIG. 143) configured to guide the shaft 11041 into the slit 11031 during installation of the surgical tool 11040 into the attachment interface 11010.

When the shaft 11040 is fully inserted into the attachment interface 11010, the seal 11030 compresses around the portion of the shaft 11041 in contact with the shaft 11040. Specifically, the seal 11030 applies a varying pressure profile to the shaft 11040. This varying pressure profile in connection with the spiral shape of the slit 11031 can help prevent contaminants from passing through the seal 11030 by requiring the contaminants to travel in a spiral direction which is not the direction of travel of the shaft 11041 as well as pass through an increasingly tighter seal along the length of required travel. For example, referring to FIG. 144, F1>F2>F3>F4>F5. Other force profiles are contemplated. In at least one instance, a force profile making it more difficult for contaminants to pass through the seal 11030 with the shaft 11041 as the surgical tool 11040 is installed are contemplated. The spiral shape of the slit 11031 may force debris to migrate diametrically away from the shaft 11041 if the shaft 11041 is rotated within the shaft 11021. Rotation of the shaft 11021 in this instance may push debris further away from the shaft 11041 in the outer portions of the spiral slit 11031.

Removing the shaft 11041 from the attachment interface 11010 will cause the proximal end 11032 of the slit 11031 to tightly seal behind a proximal end of the shaft 11041. As the shaft 11041 is removed, the spiral slit 11031 will continue to seal and possibly encourage debris and/or contaminants to move distally toward to the distal end 11033 of the slit 11031 owing to the gradual re-sealing of the slit 11031. The slit 11031 may also remove contaminants on the surface of the shaft 11041 as the shaft 11041 is inserted into the receiving portion 11020. In at least one instance, the seal 11031 comprises an elastic material. For example, the seal 11031 may comprise an elastic foam. FIG. 143 illustrates the seal 11030 with multiple different sizes of slits 11031', 11031", 11031'".

In at least one instance, a seal such as the seal 11031 comprises a fillable bladder. Such a fillable bladder can be accessible via a port in the attachment interface. In at least one instance, the fillable bladder may already be integrated with the robot, surgical arm, and source of fluid such that the bladder can be filled on demand and with as much fluid as desired depending on the desired degree of seal. Filling of the bladder may be manual. In at least one instance, filling and emptying of the bladder can be automated such that, as the shaft is removed, a control circuit can detect such removal and cause the bladder to be filled in response to the removal of the surgical tool. The amount of fluid injected into the bladder may correspond to the size of the shaft being inserted/removed from the attachment interface. For example, a larger diameter shaft may require less fluid and less expanded volume of the bladder to provide an adequate seal. Such a seal may be able to accommodate many different shapes and sizes of the shafts being inserted into the attachment interface.

Figure 145:
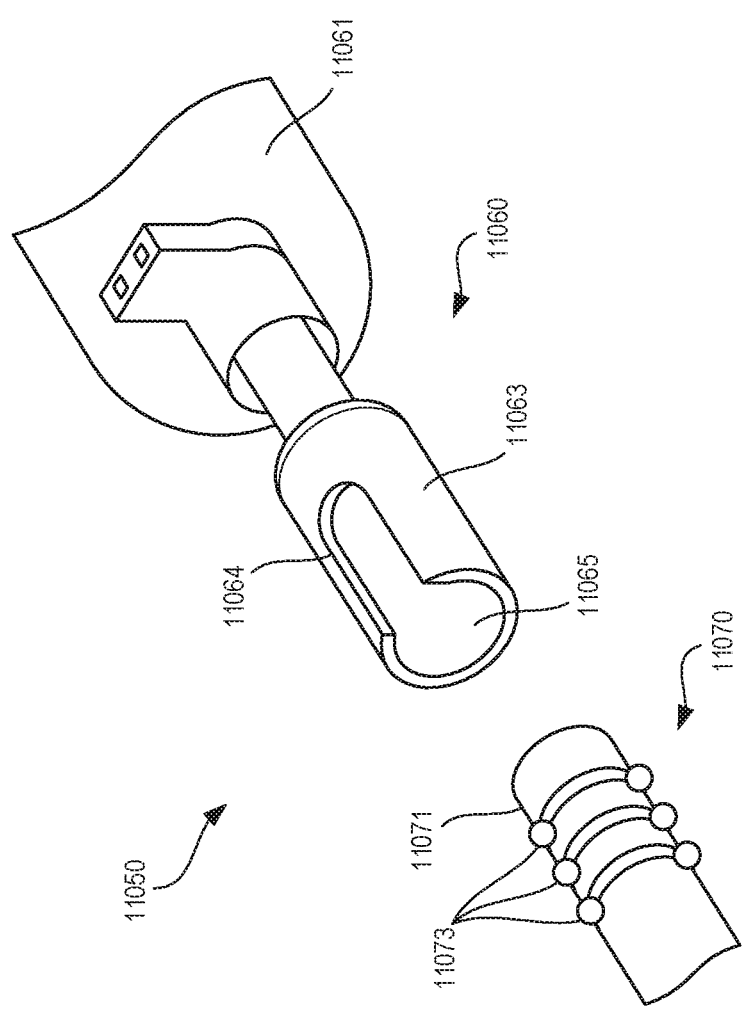
FIG. 145 is a perspective view of an attachment interface and a surgical tool configured to be attached to the attachment interface, wherein the surgical tool comprises a seal.

FIG. 145 depicts a surgical instrument assembly 11050 comprising an attachment interface 11060 and a surgical tool 11070 configured to be operably attached to the attachment interface 11060. The attachment interface comprises a housing 11061 and a receiving shaft 11063 extending distally from the housing 11061 configured to receive a shaft 11071 of the surgical tool 11070. The receiving shaft 11063 further comprises an inner cavity 11065 and an access opening 11064 defined therein. The shaft 11071 is configured to be inserted into the shaft 11063 to operably attach the surgical tool 11070 to the attachment interface 11060. The surgical tool 11070 comprises a seal comprising sealing rings 11073 positioned around a proximal end of the shaft 11071. The sealing rings 11073 may be configured to seat within annual slots defined in the shaft 11071. In at least one instance, the sealing rings 11073 are over molded directly onto the shaft 11071. In at least one instance, the sealing rings 11073 are configured to pass the length of access opening 11064 entirely. In such an instance, washing out the inner cavity 11065 may be possible while the surgical tool 11070 is operably attached to the attachment interface 11010.

In at least one instance, the seals discussed herein can be cleaned with a brush, for example. The seals may be part of the surgical tool attachment and/or the attachment interface to which the surgical tool is attached. The seals may also be entirely separate components. The seals may be replaced in between operations. In at least one instance, the seals are reused during an operation on a single patient but are disposed of between different patients. In at least one instance, the seal comprises constrictive properties to maintain a tight seal along the length of the seal. The seal may also comprise a central circular opening and a slit extending radially outward from the central circular opening. Such a configuration may allow for easier insertion of a shaft of a surgical tool through the seal while still providing the benefits of the slit, as discussed above.

Figure 147:
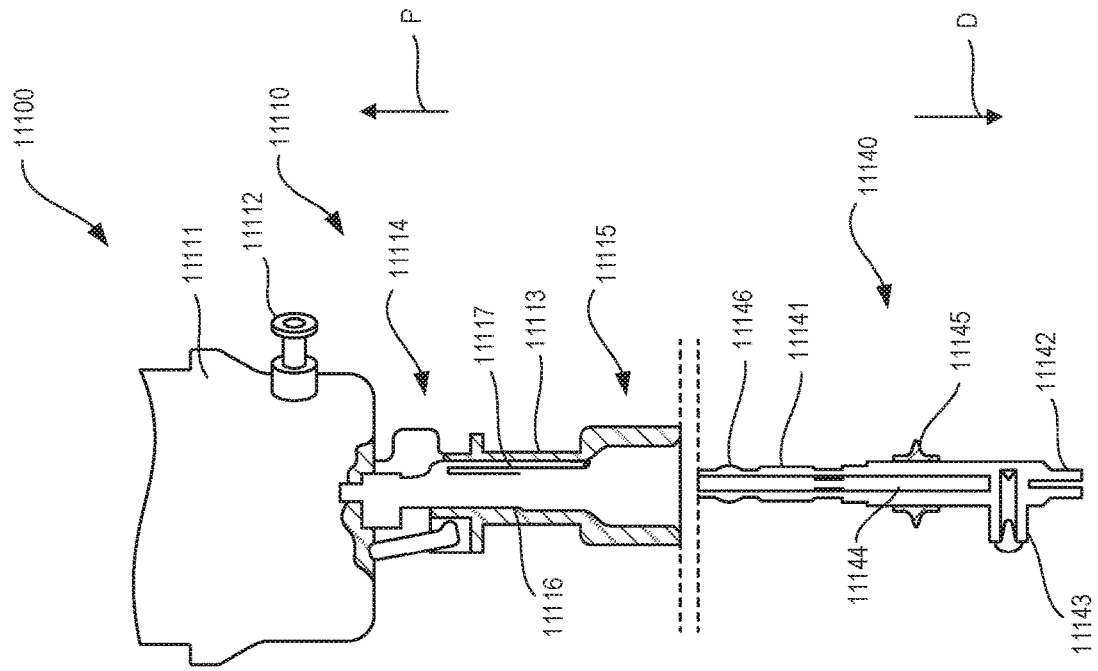
FIG. 147 is a partial cross-sectional view of the attachment interface and shaft of FIG. 146, wherein the shaft is not attached to the attachment interface.
Figure 146:
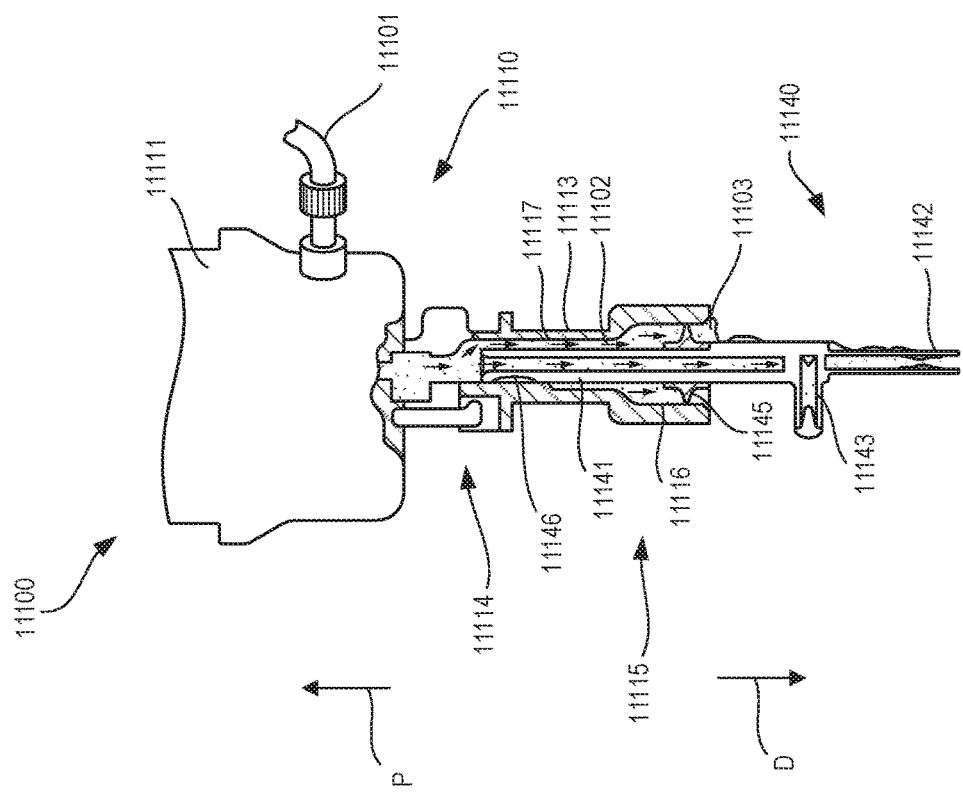
FIG. 146 is a partial cross-sectional view of an attachment interface and a shaft configured to be attached to the attachment interface illustrated in an attached configuration.

FIGS. 146 and 147 depict a surgical instrument assembly 11100 comprising a tool actuation interface 11110 and a surgical tool 11140 configured to be attached to and detached from the actuation interface 11110. The actuation interface 11110 comprises a fluidic drive system configured to transmit fluid 11102 from a surgical robot and/or surgical robotic arm, for example, to the surgical tool 11140 attached to the actuation interface 11110. The fluidic drive system may comprise pneumatic actuator, for example, configured to force air into the surgical tool 11140 to actuate one or more functions of the surgical tool 11140.

The actuation interface 11110 comprises a fluidic source line 11101 attached to a fluidic port 11112 of the actuation interface 11110. The actuation interface 11110 is configured to direct fluid 11102 to the surgical tool 11140 when the surgical tool 11140 is attached to the actuation interface 11110 to actuation one or more functions of the surgical tool 11140. The actuation interface 11110 further comprises a body portion 11111 and an attachment portion 11113 extending distally from the body portion 11111. The attachment portion 11113 comprises a proximal end 11114, a distal end 11115, and an inner fluidic passage 11116 defined in the attachment portion 11113 configured to receive a proximal end 11141 of the surgical tool 11140 therein such that the surgical tool 11140 may be operably coupled to the actuation interface 11110.

The surgical tool 11140 further comprises a proximal attachment portion 11146 configured to be operably coupled with a corresponding attachment portion of the actuation interface 11110, a distal end 11142, and an inner fluidic passage 11144 defined in the surgical tool 11140 and configured to receive drive fluid 11102 from the actuation interface 11110. The surgical tool 11140 further comprises a cleanout port 11143.

The surgical tool 11140 is configured to be inserted into the inner fluidic passage 11116 to couple the surgical tool 11140 to the actuation interface 11110. During insertion of the surgical tool 11140 into the actuation interface 11110, the actuation interface 11110 may be continuously driving fluid such as drive fluid 11102, for example, distally out of the inner fluidic passage 11116 to force any contaminants that may be inside the inner fluidic passage 11116 and to prevent any further contaminants 11103 from getting inside of the inner fluidic passage 11116 during the attachment of the actuation interface 11110 and the surgical tool 11140. The surgical instrument assembly 11100 can comprise features to direct the flow of this fluid 11102 and, thus, debris if present, away from the surgical tool 11140.

The surgical tool 11140 further comprises a seal 11145 configured to prevent external debris and/or fluid 11102, for example, from entering into the inner fluidic passage 11116 once the seal 11145 engages the distal end 11115 of the attachment portion 11113 as the surgical tool 11140 is inserted into the inner fluidic passage 11116. In at least one instance where the surgical tool 11140 comprises a closed fluidic circuit, once the seal 11145 engages the distal end 11115 of the attachment portion 11113, a control circuit may detect an increase in pressure in the fluidic drive system thereby indicating that the surgical tool 11140 is at least partially attached. In at least one instance where the surgical tool 11140 comprises an open fluidic circuit, once the seal 11145 engages the distal end 11115 of the attachment portion 11113, a control circuit may detect a difference in pressure in the fluidic drive system thereby indicating that the surgical tool 11140 is at least partially attached. In at least one instance, the fluidic drive system may be configured to reduce the drive pressure of the drive fluid 11102 at such a detected pressure difference. In at least once instance where the fluidic circuit of the surgical tool 11140 is open, the insufflation pressure in the distal end 11142 of the surgical tool 11140 is less than the fluidic drive pressure provided by the actuation interface 11110. In such an instance, the actuation interface 11110 can maintain distal flow of fluid 11102 through the surgical tool 11140 so as to prevent contaminants from entering through the distal end 11142 of the surgical tool 11140.

The actuation interface 11110 further comprises one or more secondary fluidic channels 11117 (FIG. 147) defined in the inner fluidic passage 11116 and configured to extend alongside the surgical tool 11140 when the surgical tool 11140 is attached to the actuation interface 11110. The secondary fluidic channels 11117 are configured to direct drive fluid 11102 distally past a proximal end of the surgical tool 11140 during and/or after attachment of the surgical tool 11140 to the actuation interface or, fluidic surgical drive assembly, 11110. In at least one instance, the secondary fluidic channels 11117 comprise an exhaust feature configured to direct drive fluid 11102 and possibly contaminants out of the attachment portion 11113 of the actuation interface 11110. In at least one instance, contaminants may be directed into the secondary fluidic channels 11117 during attachment of the surgical tool 11140 and the actuation interface 11110. The secondary fluidic channels 11117 may trap contaminants that were on the proximal end 11141 of the surgical tool 11140. In such an instance, a portion of the proximal end 11141 of the surgical 11140 may seal a distal end of the secondary fluidic channels 11117 such that, when the surgical tool 11140 is removed, any contaminants and drive fluid 11102 trapped in the secondary fluidic channels 11117 may be blown out of the inner fluidic passage once the seal is removed from the distal end of the secondary fluidic channels 11117.

In at least one instance, the seal 11145 is disposable. In at least one instance, the seal 11145 is required to apply fluid flow to the surgical tool 11140 to actuate one or more functions of the surgical tool 11140. In at least one instance, the seal 11145 is configured to seal the secondary fluidic channels 11117 when the surgical tool 11140 is attached to the actuation interface 11110. In at least one instance, a collector or trap can be used to redirect contaminants away from the surgical tool 11140. When the surgical tool 11140 is removed from the actuation interface 11110, a control circuit may automatically initiate a cleanout drive fluid cycle where fluid is actuated through the inner fluidic passage 11116 to clear the inner fluidic passage 11116 of any debris and/or contaminants. In at least one instance, the secondary fluidic channels can be part of the surgical tool 11140. In at least one instance, both the surgical tool 11140 and the actuation interface 11110 comprise secondary fluidic channels. In such an instance, the secondary fluidic channels may be configured to be fluidically coupled with each other upon attachment of the surgical tool 11140 and the actuation interface 11110.

In at least one embodiment a shaft of a surgical tool comprises a holding feature configured to hold the shaft relative to the attachment interface to which the surgical tool is attached. The holding feature may comprise a detent and/or constriction element, for example. To remove the shaft from the attachment interface, the shaft must be pulled away from the attachment interface with sufficient force to disassemble the surgical tool from the attachment interface. At such point the attachment interface and/or the surgical tool can be cleaned, for example, and/or another surgical tool can be attached to the attachment interface. The surgical tool can be reinserted into the attachment interface such that a snapping mechanism can re-engage the holding feature to affirm to a user that the surgical tool is attached to the actuation interface. In at least one instance, where an adapter is used between the shaft and the attachment interface, the holding feature can engage the adapter and properly align the shaft of the surgical tool and the adapter such that the shaft and corresponding driving features of the adapter can be aligned with corresponding driving features of the attachment interface once the adapter is coupled to the attachment interface.

Examples of various shafts, adapters, surgical tools, actuation interfaces, surgical instrument attachments, and surgical instrument assemblies can be found in International Application Publication No. WO2017/116793, entitled ROBOTIC SURGICAL SYSTEMS AND INSTRUMENT DRIVE ASSEMBLIES, the entire disclosure of which is incorporated by reference herein in its entirety.

Figure 148:
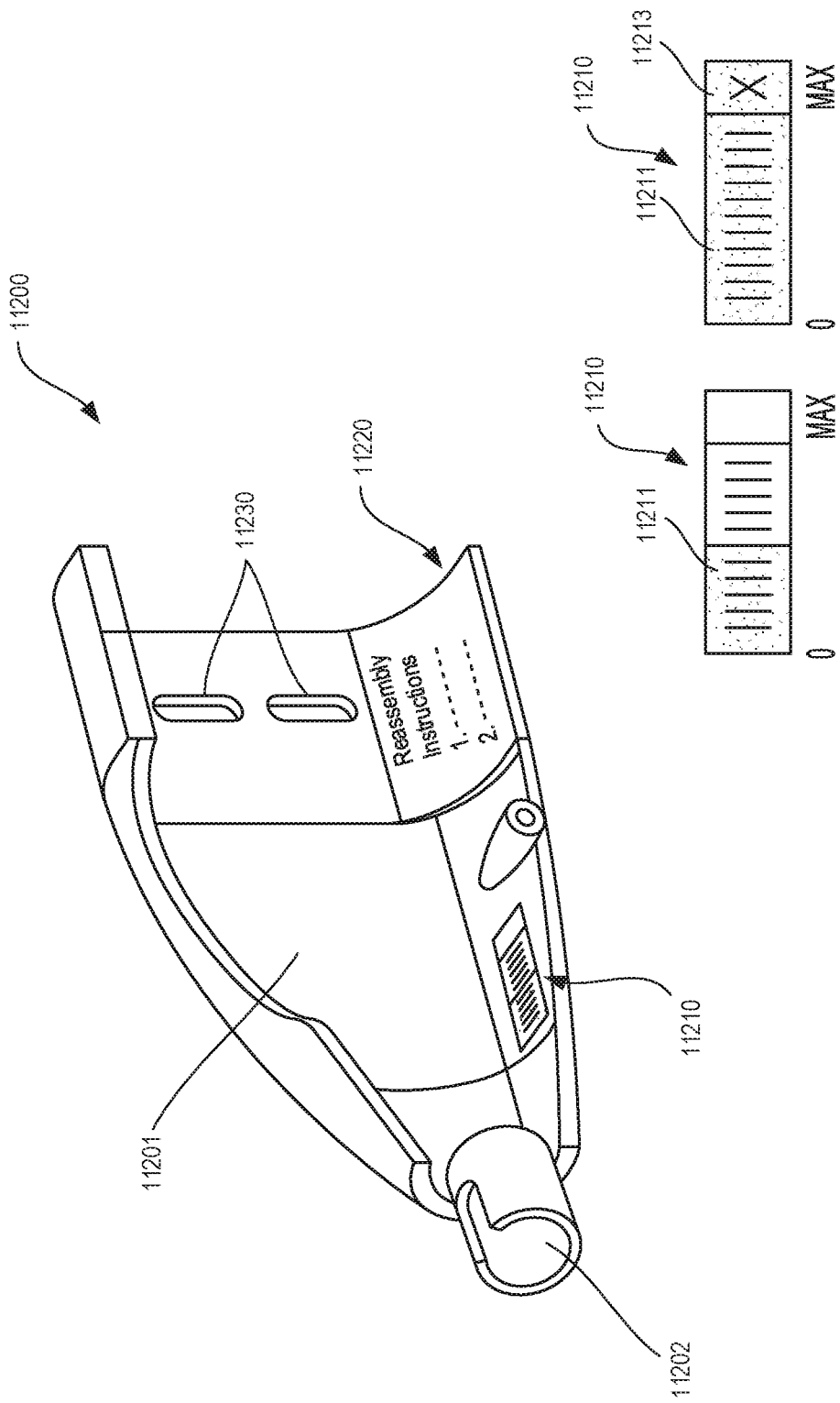
FIG. 148 is a perspective view of a portion of a modular surgical component comprising cleanout ports and a chemical exposure indicator.

FIG. 148 depicts a portion 11201 of a housing 11200 of an attachment interface, or adapter, for use with a surgical instrument assembly. The housing 11200 may be configured to house drive components and/or a shaft of a surgical tool. Surgical tools are configured to be received in a receiving shaft portion 11202 of the housing 11200. The housing 11200 comprises access ports 11230 configured to be used when cleaning the components housed within the housing 11200 and/or surgical tool positioned within the housing 11200. Cleaning tools may direct cleaning solution, for example, into the access ports 11230 to clean the internals of the housing 11200. In at least one instance, cleaning tools are configured to be inserted through the access ports for more of a direct cleaning action. In at least one instance, one port 11230 is an input solution port and another port 11230 is an output solution port. Directional flow of cleaning solution through the housing 11200 may aid in preventing buildup of contaminants, for example, in the housing 11200.

The housing 11200 comprises visual indicia 11210 comprising a chemical indicator 11211 configured to indicate to a user and/or a control circuit, for example, the amount of exposure of cleaning solution, for example, that the housing 11200 has experienced. For example, the more times that cleaning solution is used in the housing 11200, the chemical indicator 11211 level will increase on the visual indicia 11210. The visual indicia 11210 comprises a level indicator, for example, configured to illustrate when the housing 11200 has a reached a predetermined threshold, or max level, 11213 of exposure to cleaning solution.

The housing 11200 further comprises assembly instructions 11220 printed and/or molded onto the inside of the housing, or shroud, 11200. In at least one instance, the housing 11200 is configured to be dissembled during a cleaning process. Such instructions 11220 may aid in the reassembly of the housing 11200 after the cleaning process is complete.

In at least one instance, internal seals in the housing 11200 are removed before a cleaning process is initiated. Removal of seals may permit a solution to be flushed completely through the components housed within the housing 11200. In at least one instance, the access ports 11230 may also be used for inserting lubrication into the housing 11200 to lubricate the components of the housing 11200. In at least one instance, a separate port is used for lubrication only while one or more other ports are used for cleaning solution only. In at least one instance, the application of lubrication may be performed by a specific tool that will only fit in the lubrication port and the application of cleaning solution may be performed by a specific tool that will only fit in the one or more cleaning ports. In at least one instance, seals are configured to be inserted into the receiving portion 11202 of the housing 11200 as well as the access ports 11230 of the housing before using the housing 11200 in a robotic surgical application. In at least one instance, sealing the receiving portion 11202 may be done prior to inserting lubrication into the housing 11200 so as to prevent the lubrication fluid from contaminating a surgical tool configured to be received by the receiving portion 11202.

In at least one instance, cleaning and/or re-assembly instructions may be printed directly on a surgical tool, for example.

In at least one instance, a time-based chemical exposure counter can be used as a chemical indicator indicating to a user and/or surgical robot, for example, how much more time the housing 11200 can be exposed to cleaning solution safely, for example. In at least one instance, a number-of-times-based chemical-exposure counter can be used as a chemical indicator indicating to a user and/or surgical robot, for example, how many more times the housing 11200 may be exposed to cleaning solution safely, for example. The same indicator could be detected by the attachment interface, surgical robot, and/or robotic arm, and a microprocessor could be used to lockout the adapter, or housing, 11200 after an exposure counter has exceeded a predetermined threshold.

In at least one embodiment, seals are provided between all interchangeable components. For example, seals may be provided between a shaft of the surgical tool and the adapter to which the surgical tool is configured to be attached and between the adapter and a robotic arm to which the adapter is configured to be attached. In at least one instance, end effectors are modular and are configured to contain seals to prevent exposure of the internals of the end effector and/or the shaft from which the end effector extends to contaminants during attachment and detachment of other components.

In at least one instance, modular components comprise electrical contacts. In such embodiments, compressible elements such as foam seals, for example, between the interchangeable components may be configured to wipe clean electrical contacts upon attachment and/or reattachment of the modular components to other modular components. This may prolong the life of such electrical contacts and, thus, the modular component thereby increasing the reliability of the modular component. Wiping the electrical contacts clean with the seals eliminates a possible additional step requiring the cleaning of the electrical contacts such that a clinician need not worry about cleaning the electrical contacts to ensure adequate signal transmission between modular components. Such seals may be configured to completely seal electric contact interfaces from external fluid and debris while the modular components are attached. In at least one instance, the compressible elements are radially disposed around the modular shaft components for modular attachment applications that require a twisting motion to connect such modular shaft components such as, for example, a bayonet-style connection.

Figure 150:
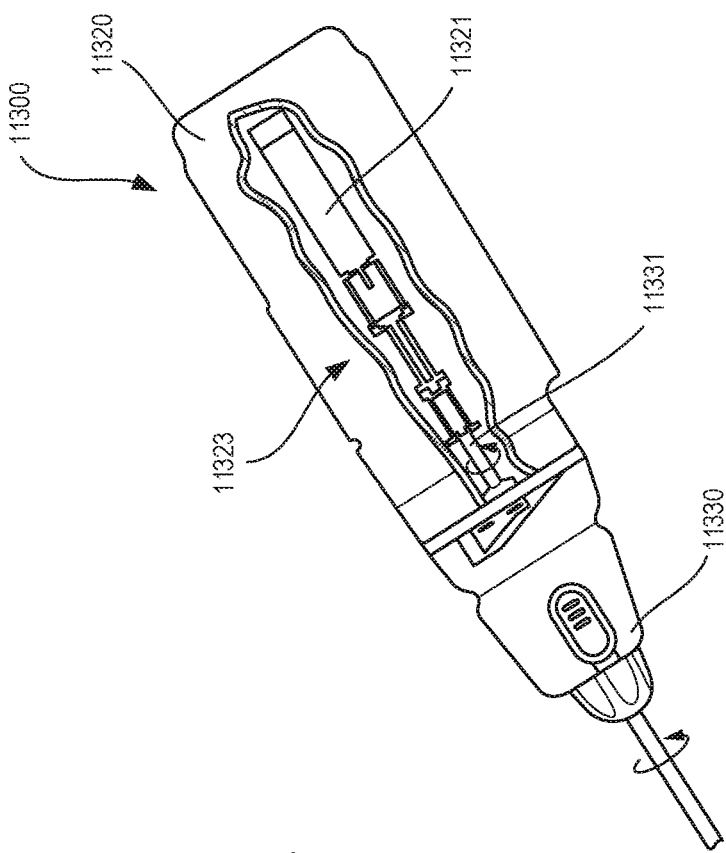
FIG. 150 is a plan view of the surgical tool of FIG. 149 and a second housing, wherein the surgical tool is attached to the second housing and the drive shaft of the surgical tool is operably coupled to a driving component of the second housing.
Figure 149:
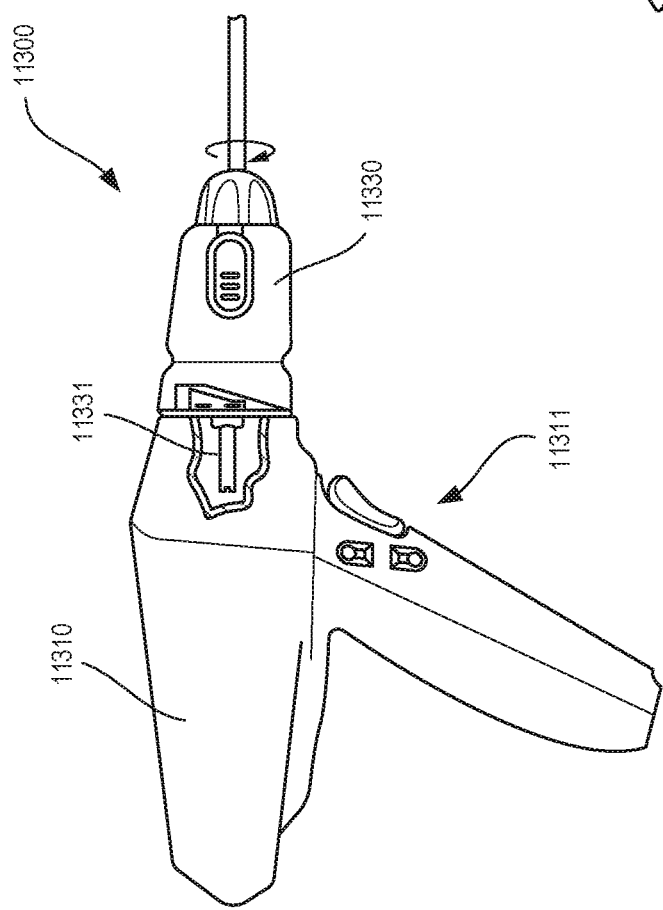
FIG. 149 is a perspective view of a surgical tool and a first housing, wherein the surgical tool is attached to the housing but a drive shaft of the surgical tool is not attached to a driving component of the housing.

FIGS. 149 and 150 depict a surgical instrument assembly 11300 comprising a first drive interface 11310 comprising a grip portion 11311, a second drive interface 11320, and a modular surgical tool 11330 configured to be operably attached to and detached from both the first drive interface 11310 and the second drive interface 11320. The drive interfaces 11310, 11320 may comprise different forms. For example, the drive interfaces 11310, 11320 may comprise hand-held handles and/or robotic arms. Any suitable drive interface is contemplated. The first drive interface 11310 does not include a drive train for coupling with a drive shaft 11331 of the modular surgical tool 11330. As such, when the modular surgical tool 11330 is attached to the first drive interface 11310, the drive shaft 11311 is able to spin freely relative to the first drive interface 11310 so that the function performed by the drive shaft 11331, such as rotation of the modular surgical tool about a tool axis, can be performed manually.

The second drive interface 11320, unlike the first drive interface 11310, includes a drive train 11323 for coupling with the drive shaft 11331 of the modular surgical tool 11330. The drive train 11323 comprises a motor 11321; however, manually actuated systems are contemplated. As such, when the modular surgical tool 11330 is attached to the second drive interface 11320, the drive shaft 11331 is operably coupled to the drive train 11323 such that that second drive interface can control actuation of the function to be performed by the drive shaft 11331, such as rotation of the modular surgical tool about a tool axis, for example.

FIGS. 151 and 152 depict an ultrasonic surgical instrument assembly 11400 comprising a removable transducer module 11450 configured to be operably attached to and detached from various ultrasonic drive interfaces 11410, 11460. Various ultrasonic instruments and systems are disclosed in International Application Publication No. WO2017/151873, entitled ULTRASONIC INSTRUMENTS FOR ROBOTIC SURGICAL SYSTEMS, which is hereby incorporated herein by reference in its entirety. The drive interface 11410 comprises a handle 11411 comprising controls 11413 and one or more triggers 11412. The drive interface 11410 further comprises a detachment lever configured to permit detachment of the removable transducer module 11450 from a cavity 11415 of the handle 11411. The drive interface 11410 further comprises a drive member 11420 configured to be operably coupled to the transducer module 11450 when the transducer module 11450 is attached to the drive interface 11410. The drive interface 11460 comprises a cavity 11461 configured to receive the transducer module 11450 therein. In at least one instance, the drive interface 11460 comprises a modular tool assembly. When the transducer module 11450 is attached to the drive interface 1160, the transducer module 11450 is configured to be operably coupled to a drive member 11463 of the drive interface 11460. The drive interface 11460 may be tethered to an ultrasonic energy source via the cable 11470. The transducer module 11450 comprises a housing 11453, contact rings 11451, and a mounting portion 11455.

The systems, assemblies, devices, embodiments, and components described herein are configured to be used with the various systems, assemblies, devices, embodiments, and components disclosed in International Application Publication No. WO2017/151873, entitled ULTRASONIC INSTRUMENTS FOR ROBOTIC SURGICAL SYSTEMS; International Application Publication No. WO2017/053363, entitled ROBOTIC SURGICAL ASSEMBLIES AND INSTRUMENT DRIVE CONNECTORS THEREOF; U.S. Patent Application Publication No. US2017/0231653, entitled ROBOTICALLY CONTROLLING MECHANICAL ADVANTAGE GRIPPING; International Application Publication No. WO2017/151996, entitled INVERSE KINEMATIC CONTROL SYSTEMS FOR ROBOTIC SURGICAL SYSTEM; International Application Publication No. WO2016/209769, entitled ROBOTIC SURGICAL ASSEMBLIES; U.S. Patent Application Publication No. US2018/0200894, entitled WRIST AND JAW ASSEMBLIES FOR ROBOTIC SURGICAL SYSTEMS; International Application Publication No. WO2017/116793, entitled ROBOTIC SURGICAL SYSTEMS AND INSTRUMENT DRIVE ASSEMBLIES; and U.S. Pat. No. 8,054,184, entitled IDENTIFICATION OF SURGICAL INSTRUMENT ATTACHED TO SURGICAL ROBOT the entire disclosures of each of which are herein incorporated by reference.

Robotic Surgical System with Safety and Cooperative Sensing Control

In various aspects, the present disclosure provides robotic surgical systems incorporating safety and cooperative sensing/control algorithms. The algorithms control robotic tool driver motors based on sensing parameters within the motor and/or motor control circuit in addition to external forces exerted on the motor and/or motor control circuit. In one aspect, a robotic controlled surgical end-effector actuation motor may be controlled based on a parameter of a sensed externally applied force to the end-effector. In one aspect, the externally applied force can be sensed by the robotic arm relative to the end-effector. In another aspect, externally derived control forces can be sensed from within the surgical end-effector by resolving ground response forces compared to internally generated forces. In yet another aspect, the externally derived control forces can be measured as reaction forces within the robotic arm itself. These and other variations of algorithms for controlling robotic surgical tool driver motors based on sensing parameters within the motor and/or the motor control circuit in addition to forces exerted external to the motor and/or the motor control circuit are described hereinbelow and may be implemented on the robotic platform described with reference to FIGS. 1-22 hereinabove.

FIG. 153 is a graphical illustration 6000 of an algorithm implemented in a robotic surgical system for controlling robotic surgical tools based on motor current (I) and externally sensed parameters according to at least one aspect of the present disclosure. In the illustrated aspects, the robotic surgical tool is an end-effector coupled to an articulatable arm. The end-effector includes a clamp to grasp tissue. In various aspects, the externally sensed parameters include robotic tool arm force $F_{arm}$, robotic tool clamp arm torque $T_{arm}$, or robotic tool clamp force $F_{clamp}$, among other parameters. The graphical illustration 6000 includes three separate graphs 6002, 6004, 6006. A first graph 6002 depicts robotic arm force $F_{arm}$, or robotic clamp arm torque $T_{arm}$, as a function of time t, a second graph 6004 depicts motor current (I) as a function of time t, and a third graph 6006 depicts robotic tool clamp arm force $F_{clamp}$ as a function of time t.

FIG. 154 illustrates a distal portion of a motor driven powered robotic surgical tool 6010 grasping tissue 6012 under low lateral tension according to at least one aspect of the present disclosure. The state of the robotic surgical tool 6010 grasping tissue 6012 under low lateral tension is represented in solid lines in the three graphs 6002, 6004, 6006 depicted in FIG. 153. The robotic surgical tool 6010 includes an arm 6024, an end-effector 6016, and an articulatable joint 6014 therebetween. The end-effector 6016 includes two jaws 6018, 6020 for clamping tissue 6012 therebetween and applying a clamping force $F_{clampA}$ to the tissue 6012 under the control of a motor and/or motor control circuit resulting in low macro tension. The direction of the lateral force $F_{tissueA}$ applied to the tissue 6012 is indicated by arrow 6022. A downward force $F_{armA}$ applied to the arm 6024 in the direction indicated by arrow 6023 causes a torque $T_{jawA}$ to be applied to the end-effector 6016 and the jaws 6018, 6020.

FIG. 155 illustrates a distal portion of the motor driven powered robotic surgical tool 6010 grasping tissue 6026 under high downward tension according to at least one aspect of the present disclosure. The state of the robotic surgical tool 6010 grasping tissue 6026 under high downward tension is represented in dashed line in the three graphs 6002, 6004, 6006 depicted in FIG. 153. The clamping force $F_{clampB}$ is applied to the tissue 6026 by a motor controlled by a motor control circuit. The clamping force $F_{clampB}$ results in high macro tension. The direction of the downward force $F_{tissueB}$ applied to the tissue 6026 is indicated by arrow 6028. The downward force $F_{armB}$ applied to the arm 6024 of the robotic surgical tool 6010 causes a torque $T_{jawB}$ to be applied to the end-effector 6016 and the jaws 6018, 6020 in the direction indicated by arrow 6029.

The forces $F_{tissueA}$, $F_{clampA}$ may be sensed by one or more than one strain gauge sensor located within the jaws 6018, 6020 of the end-effector 6016. The arm force $F_{armA}$ may be sensed by a strain gauge sensor located either on the articulation joint 6014 or the arm 6024. The torque $T_{jawA}$ may be sensed by a torque sensor located at the articulation joint 6014. Likewise, the forces $F_{tissueB}$, $F_{clampB}$ may be sensed by one or more than one strain gauge sensor located within the jaws 6018, 6020 of the end-effector 6016 and the force $F_{armB}$ may be sensed by a strain gauge sensor located either on the articulation joint 6014 or the arm 6024. The torque $T_{jawB}$ may be sensed by a torque sensor located at the articulation joint 6014. The outputs of the force and torque sensors may be accomplished by one or more than one of the circuits illustrated in FIGS. 9, 10, 12, and 16-22. Various techniques for implementing sensors into the jaws 6018, 6020 of an end-effector 6016 are described with respect to FIGS. 210-230 and associated description in the specification in commonly owned US Patent Publication No. 2017/0202591A1 filed Dec. 16, 2016, which is herein incorporated by reference in its entirety.

The three graphs 6002, 6004, 6006 depicted in FIG. 153 will now be described in combination with the motor driven powered robotic surgical tool 6010 depicted in FIGS. 154-155. The first graph 6002 depicted in FIG. 153 depicts arm forces 6003, 6005 ($F_{arm}$), or arm torque $T_{arm}$, applied to the arm 6024 as a function of time t, according to at least one aspect of the present disclosure. The first arm force 6003 ($F_{arm}$) shown in solid line is the force applied to the arm 6024 when the powered robotic surgical tool 6010 grasps tissue 6012 under low lateral tension, as depicted in FIG. 154. The first arm force 6003 ($F_{arm}$) remains constant over the time period shown. The second arm force 6005 ($F_{arm}$) shown in dashed line is the force applied to the arm 6024 when the powered robotic surgical tool 6010 grasps tissue 6026 under high downward tension, as depicted in FIG. 155. The second arm force 6005 ($F_{arm}$) also remains constant over the time period shown. As shown, the low lateral tension arm force 6003 ($F_{arm}$) applied to the arm 6024 is lower than the high downward tension arm force 6005 ($F_{arm}$) applied to the arm 6024.

The second graph 6004 depicted in FIG. 155 depicts currents 6007, 6009 (I) drawn by the motor as a function of time (t) according to at least one aspect of the present disclosure. The two motor currents 6007, 6009 (I) represent the current (I) drawn by the motor of the robotic surgical tool 6010 for the two different states depicted in FIGS. 154-155, respectively. The first motor current 6007 (I) shown in solid line is the motor current drawn by the motor when the robotic surgical tool 6010 grasps tissue 6012 under low lateral tension, as depicted in FIG. 154, and second motor current 6009 (I) shown in dashed line is the current drawn by the motor when the robotic surgical tool 6010 grasps tissue 6026 under high downward tension, as depicted in FIG. 155. As shown, both motor currents 6007, 6009 (I) ramp up from zero over an initial period and then level off to a constant during the time period shown. The first current 6007 (I) is lower over the time period shown than the second motor current 6009.

The third graph 6006 depicted in FIG. 153 depicts two clamp forces $F_{clamp}$ applied to the jaws 6018, 6020 of the end-effector 6016 as a function of time (t) according to at least one aspect of the present disclosure. The first clamp force 6011 ($F_{clamp}$) shown in solid line is the force applied to the tissue 6012 under low lateral tension. The second clamp force 6013 ($F_{clamp}$) shown in dashed line is the force applied to the tissue 6026 under high downward tension. For comparison purposes, the first and second clamp forces 6011, 6013 ($F_{clamp}$) are substantially equal over the time period shown.

With reference now to FIGS. 153-155, the first clamp force 6011 ($F_{clampA}$) and the second clamp force 6013 ($F_{clampB}$) (or the different pressures applied to the tissue 6012, 6026) are based on the rotational orientation of the jaws 6018, 6020 relative to the end-effector 6016 torque $T_{jawA}$, $T_{jawB}$ and therefore the first and second clamp forces 6011 ($F_{clampA}$), 6013 ($F_{clampB}$) sensed by the powered robotic surgical tool 6010 exerted on the tissue 6012, 6026. In one aspect, the first and second clamp forces 6011 ($F_{clampA}$), 6013 ($F_{clampB}$) sensed by the powered device 6010 may be compared and then compensating for the motor torques created by the actuation of the drive motors based on the comparison. The motor control circuit could then be impacted based on a combination of the first and second motor currents 6007, 6009 (I) sensed by the motor control circuit, the torque created by the motor to its ground, and the tissue forces 6011 ($F_{clampA}$), 6013 ($F_{clampB}$) exerted on the robotic surgical system.

Without limitation, the robotic surgical tool 6010 may be a motor driven surgical stapler, an ultrasonic device, an electrosurgical device, or a combination device that incorporates one or more features of the stapler, ultrasonic, and electrosurgical devices in a single combination device. In one example, the robotic surgical tool 6010 is a motor driven stapler comprising a linear actuator that includes a longitudinally reciprocatable firing bar to open and close the jaws 6018, 6020, drive staples through tissue 6012, 6026, and drive a knife through the stapled portion of the tissue 6012, 6026 clamped between the jaws 6018, 6020. In a linear actuator, the linear firing rate of the actuator is controlled by a motor and thus the firing rate of the actuator can be controlled by controlling the speed of the motor. The firing rate of the actuator can be reduced when thick tissue 6012, 6026 is sensed between the jaws 6018, 6020 of the end-effector 6016 and the firing rate can be further limited as the macro tissue tension is sensed through the comparison of the differences in torques sensed by the robotic surgical tool 6010 caused by the advancement motor. A slower firing rate under higher macro tissue tensions states improves staple formation by allowing more time for the tissue to stabilize by creeping before stapling and cutting the tissue 6012, 6026 as the pressure wave moves longitudinally proximal to the distal end during firing.

In another example, the energy required to produce a suitable actuation force to clamp the jaws 6018, 6020 on the tissue 6012, 6026 can be limited based on the initial contact with the tissue 6012, 6026 and the rate of tissue compression. The energy may be further reduced based on externally applied macro tension exerted on the knife by the tissue 6012, 6026 due to the support forces sensed by lifting the tissue 6012, 6026 while clamping. By way of comparison, the differences in the torques sensed by the stapler instrument and the torques generated by the actuation motors.

Figures 156, 157:
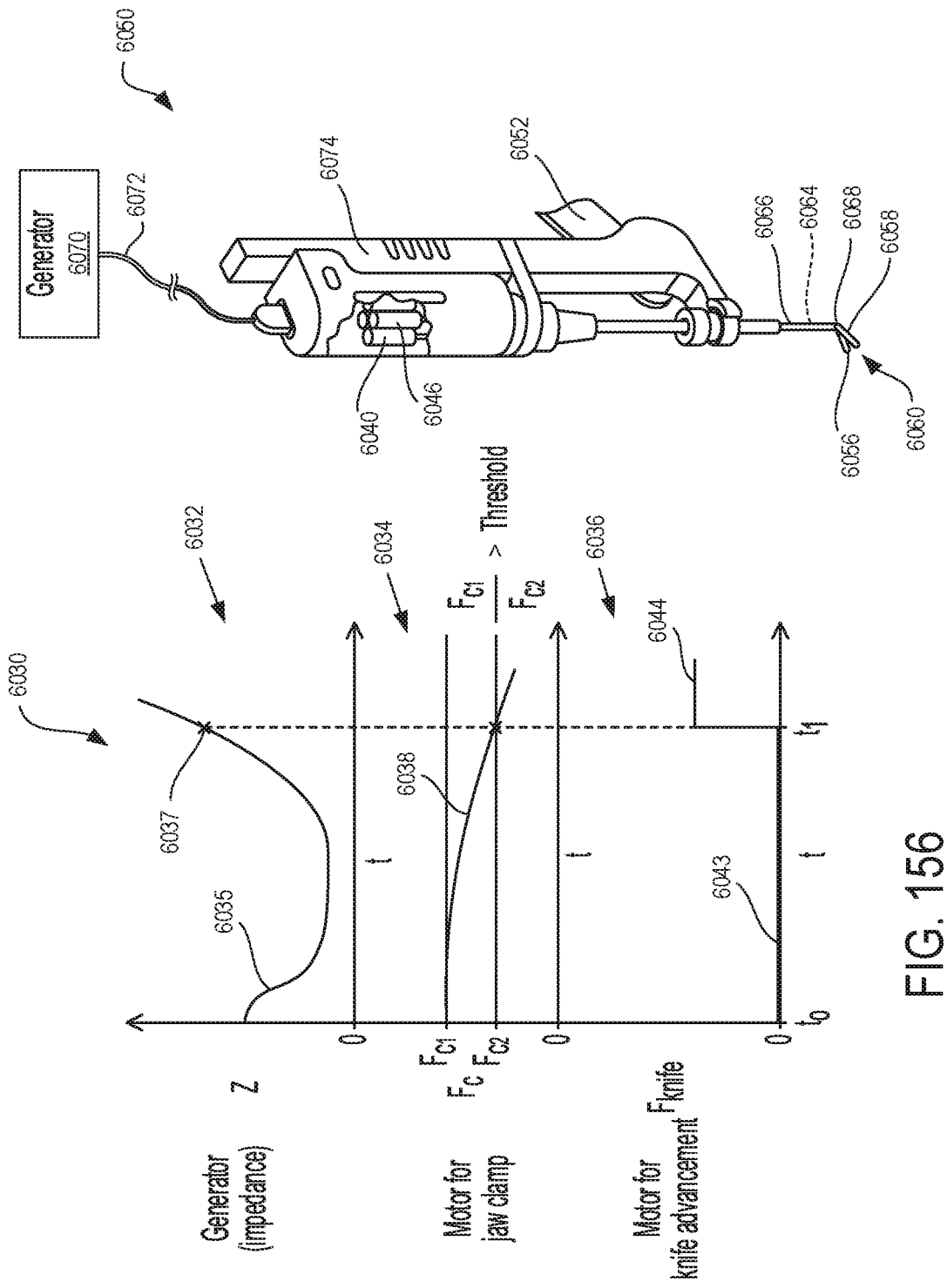
FIG. 156 is a graphical illustration of an algorithm implemented in a robotic surgical system for monitoring a parameter of a control circuit of one motor within a motor pack to influence the control of an adjacent motor control circuit within the motor pack according to at least one aspect of the present disclosure.
FIG. 157 illustrates the motor driven powered robotic surgical tool positioned on a linear slide attached to a robotic arm according to at least one aspect of the present disclosure.

The following section describes a robotic surgical system for monitoring a motor control circuit and adjusting the rate, current, or torque of an adjacent motor control circuit. FIG. 156 is a graphical illustration 6030 of an algorithm implemented in a robotic surgical system for monitoring a parameter of a control circuit of one motor within a motor pack to influence the control of an adjacent motor control circuit within the motor pack according to at least one aspect of the present disclosure. The graphical illustration 6030 includes three separate graphs 6032, 6034, 6036. A first graph 6032 depicts impedance 6035 (Z) of a generator 6070 (FIG. 157) as a function of time (t), a second graph 6036 depicts jaw clamp force 6038 ($F_c$) applied by a clamp jaw motor 6040 (FIG. 157) as a function of time (t), and the third graph 6036 depicts knife advancement force 6044 ($F_{knife}$) applied by a knife motor 6046 as a function of time (t).

FIG. 157 illustrates the motor driven powered robotic surgical tool 6050 positioned on a linear slide 6074 attached to a robotic arm 6052 according to at least one aspect of the present disclosure. The motor driven powered robotic surgical tool 6050 includes a clamp jaw motor 6040 to open and close the jaws 6056, 6058 of the end-effector 6060. The motor driven powered robotic surgical tool 6050 also includes a knife motor 6046 to advance and retract a knife 6064. The end-effector 6060 includes electrodes for delivering RF energy to the tissue clamped between the jaws 6056, 6058 and a knife 6064 for cutting tissue once it has been suitably sealed with RF energy. The motor driven powered robotic surgical tool 6050 also includes an arm 6066 and an articulatable joint 6068. Power is delivered to the motor driven powered robotic surgical tool 6050 from a generator 6070 coupled to the motor driven powered robotic surgical tool 6050 through a cable 6072. Electrical power to operate the motors 6040, 6046 also may be coupled through the cable 6072.

With reference now to both FIGS. 156-157, the first graph 6032 shown in FIG. 156 depicts generator 6070 impedance 6035 (Z) as a function of time (t) from to over a predetermined period. The impedance 6035 (Z) is initially a nonzero value that decreases as pressure is applied to the tissue by clamping the jaws 6056, 6058 on the tissue while applying RF energy, supplied by the generator 6070, through the electrodes in the jaws 6056, 6058. As the RF energy and clamping pressure reduce the liquid content of the tissue, the impedance 6034 (Z) decreases and flattens out for a period of time until the tissue starts to sufficiently heat up and dehydrate causing the impedance 6035 (Z) to increase. At time $t_1$, the impedance 6035 (Z) reaches a predetermined maximum value 6037, which can be used to trigger a number of functions. One function, for example, is cutting off the energy supplied by the generator 6070 to stop heating the tissue before cutting it. The impedance 6035 (Z) curve resembles a bathtub and may be referred to as a "bathtub curve."

With reference still to both FIGS. 156-157, the second graph 6034 shown in FIG. 156 depicts jaw clamp force 6038 ($F_c$) applied by the clamp jaw motor 6040 as a function of time (t). At time $t_0$, the clamp jaw force 6038 ($F_c$) is initially a first value $F_{c1}$ above zero. Over the time period $t_1$, as the tissue is heated, the clamp jaw force 6038 ($F_c$) decreases nonlinearly to a second value $F_{c2}$, below the first value $F_{c1}$, at time $t_1$. This coincides with the maximum impedance (Z) value 6037 in the first graph 6032. The ratio of $F_{c1}$ to $F_{c2}$ can be selected to be greater than a predetermined threshold as follows:

$$\frac{F_{c1}}{F_{c2}} > \text{Threshold}$$

such that as the impedance 6035 (Z) varies from $t_0$ to $t_1$, the clamp jaw force 6038 ($F_c$) drops nonlinearly from $F_{c1}$ to $F_{c2}$, at which point the energy from the generator 6070 is cut off and the knife motor 6046 is actuated as shown in the third graph 6042.

With reference still to both FIGS. 156-157, the third graph 6044 shown in FIG. 156 depicts knife advancement force 6044 ($F_{knife}$) applied by the knife motor 6046 as a function of time (t). Between $t_0$ and $t_1$, prior to the impedance 6035 (Z) reaching the predetermined maximum value 6037, the knife motor 6046 is off and thus the knife advancement force 6043 ($F_{knife}$) is zero. When the impedance 6035 (Z) reaches the predetermined maximum value 6037 and the ratio $$\frac{F_{c1}}{F_{c2}}$$

is greater than the predetermined Threshold, the RF energy supplied by the generator 6070 is cut off and the knife motor 6046 is actuated to advance the knife 6064 to cut tissue located between the jaws 6056, 6058 of the end-effector 6060.

With reference still to both FIGS. 156-157, the motor driven powered surgical robotic tool 6050 may be configured to limit the gripping force generated by the jaw clamp motor 6040 based on the actuation force, rate, or acceleration of the articulation motor being commanded to operate in parallel to the jaw clamp motor 6040. Furthermore, monitoring the clamping force required to maintain a fixed tissue compression can be used in addition to other electrical methods to inform knife motions (e.g., initiation time, speed, etc.).

FIGS. 158-159 illustrate a robotic surgical system and method for sensing forces applied by a robotic surgical tool rotation motor assembly or linear slide and controlling jaw-to-jaw forces based on externally applied torsion along with gripping force generated by the robotic surgical tool actuation motor according to at least one aspect of the present disclosure. As depicted in FIGS. 158-159, first and second forces or reactions are sensed to accurately measure cumulative applied forces. FIG. 28 illustrates a first robotic arm 6080 in a first position A according to at least one aspect of the present disclosure. The robotic arm 6080 includes a rotation portion 6082 rotatably mounted to a base 6084, an articulation portion 6086, and a linear slide portion 6088. A motor driven surgical robotic tool 6090 is attached to a linear slide 6091. The motor driven surgical robotic tool 6090 device may be any one of the motor driven devices disclosed herein, including for example, the motor driven surgical robotic tools 6010, 6050 depicted in FIGS. 154, 155 and 157, without limitation. The motor driven surgical robotic tool 6090 includes a motor pack 6092, a shaft 6094, and an end-effector 6096 that includes a first and second jaw 6098, 6099. The base 6084 of the robotic arm 6080 includes a force plate 6093 to measure the reactionary vector load torque TA and the load force Fi required to lift tissue grasped within the jaws 6098, 6099 of the end-effector 6096. The jaws 6098, 6099 are positioned at a distance $x_1$, $y_1$, $z_1$ from the base 6084 of the robotic arm 6080.

FIG. 159 illustrates a second robotic arm 6100 in a second position B according to at least one aspect of the present disclosure. The robotic arm 6100 includes a rotation portion 6102 rotatably mounted to a base 6104, an articulation portion 6106, and a linear slide portion 6108. A motor driven surgical robotic tool 6110 is attached to the linear slide 6108. The motor driven surgical robotic tool 6110 may be any one of the motor driven devices disclosed herein, including for example, the motor driven surgical robotic tools 6010, 6050 depicted in FIGS. 154, 155, and 157, without limitation. The motor driven surgical robotic tool 6110 includes a motor pack 6112, a shaft 6114, and an end-effector 6116 that includes a first and second jaw 6118, 6119. The base 6104 of the robotic arm 6100 includes a force plate 6122 to measure the reactionary vector load torque $T_B$ and load force $F_2$ required to lift tissue grasped within the jaws 6118, 6119 of the end-effector 6116. The jaws 6118, 6119 are positioned at a distance $x_2$, $y_2$, $z_2$ from the robot base 6104 of the robotic arm 6100.

Figure 160:
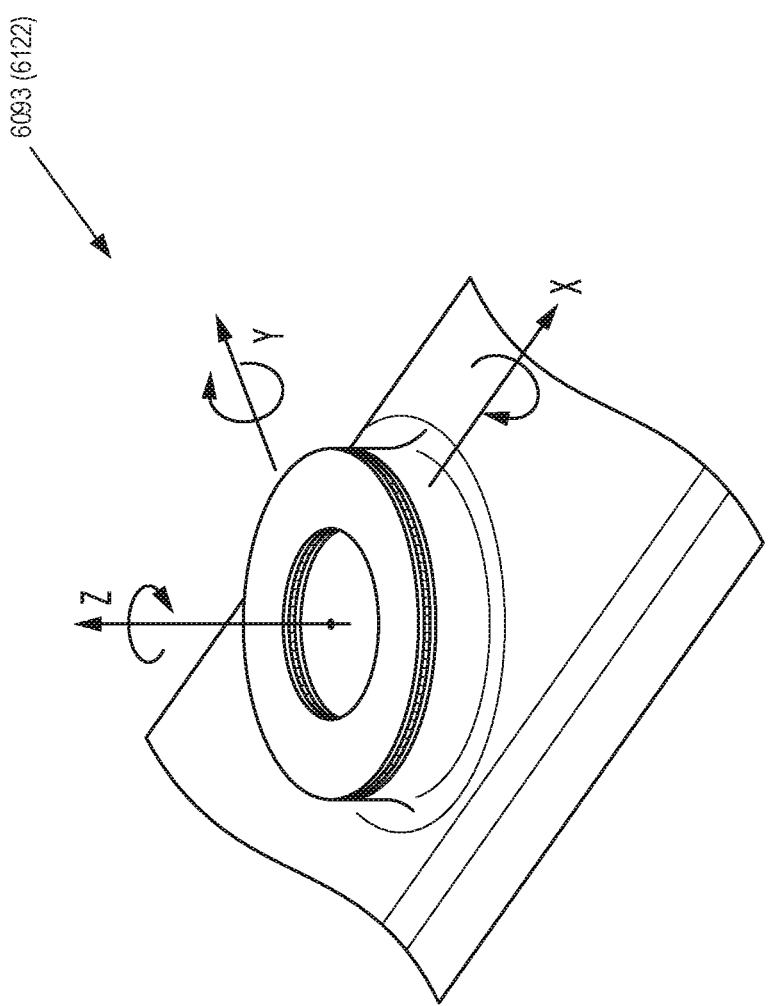
FIG. 160 illustrates one aspect of the force plate located at the base of the robotic arm or operating room (OR) table to measure reactionary vector loads in x, y, z axis according to at least one aspect of the present disclosure.

FIG. 160 illustrates one aspect of the force plate 6093, 6122 located at the base of the robotic arm 6080, 6100 or operating room (OR) table to measure reactionary vector loads in x, y, z axis according to at least one aspect of the present disclosure. With reference to FIGS. 158-160, integrating or attaching a sensing array to the patient or table enables direct measurement of the forces the body is resisting with respect to a common reference location. This enables the robotic arm 6080, 6100 to determine not only the force applied by the motor driven robotic surgical tools 6090, 6110, but to affect that measure by the resistance load entered by the body. This also enables the determination of overall macro tissue tension induced by the manipulation of an actuator such as the forces $F_1$ of the jaws 6098, 6099 and $F_2$ of the jaws 6118, 6119. A comparison of the reactionary vector loads of the robot base 6084, 6104 versus x, y, z motor loads of the robotic arms 6080, 6100 is described below with reference to FIG. 161.

Figure 161:
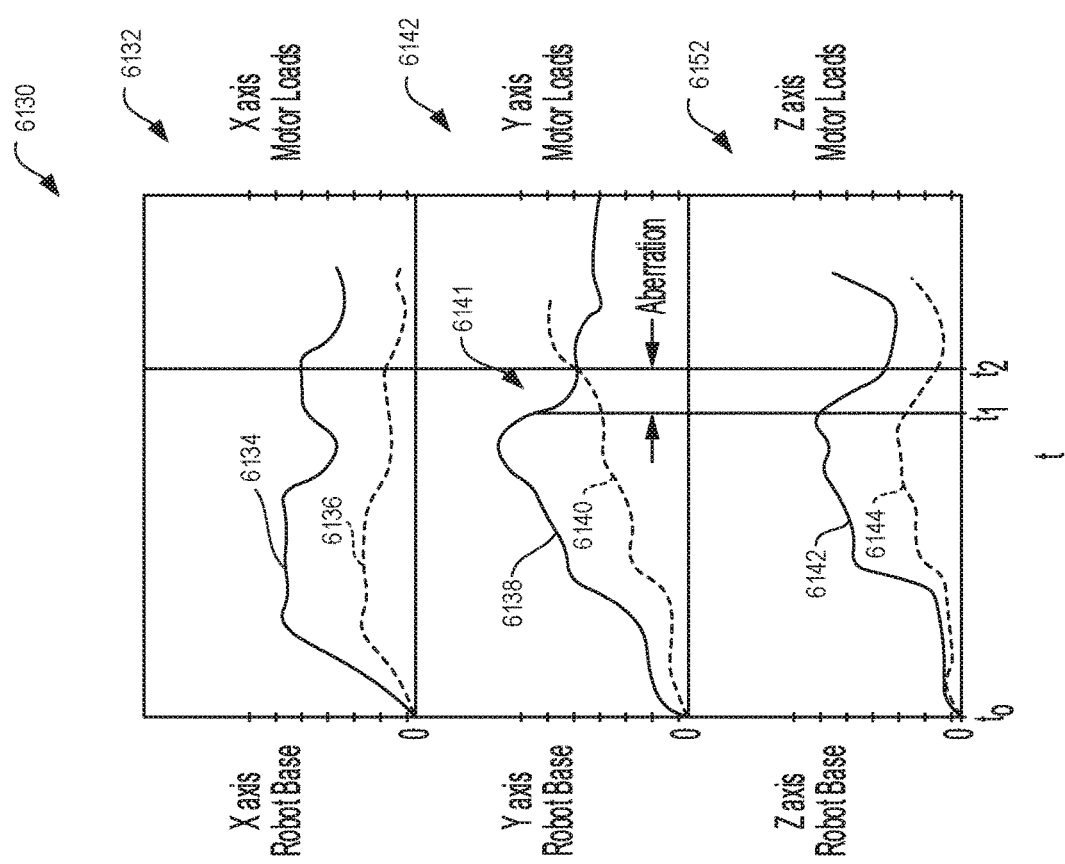
FIG. 161 is a graphical illustration of an algorithm implemented in a robotic surgical system for comparing reactionary vector loads of the robot base versus x, y, z axis motor loads of the robotic arms according to at least one aspect of the present disclosure.

FIG. 161 is a graphical illustration 6130 of an algorithm implemented in a robotic surgical system for comparing reactionary vector loads of the robot base 6084, 6104 versus x, y, z axis motor loads of the robotic arms 6080, 6100 according to at least one aspect of the present disclosure. With reference now to FIGS. 158-161, the first graph 6132 depicted in FIG. 161 illustrates a comparison of the reactionary vector load 6134 along the $x_{axis}$ of the robot base 6084 and the robot motor load 6136 along the $x_{axis}$ of the robot motor 6092 according to at least one aspect of the present disclosure. The second graph 6142 depicted in FIG. 161 illustrates the comparison of the reactionary vector load 6138 along the $y_{axis}$ of the robot base 6084 and the robotic motor load 6140 along the $y_{axis}$ of the robot motor 6092 according to at least one aspect of the present disclosure. The third graph 6152 depicted in FIG. 161 illustrates the comparison of the reactionary vector load 6142 along the $z_{axis}$ of the robot base 6084 and the motor load 6144 along the $z_{axis}$ of the robot motor 6092 according to at least one aspect of the present disclosure. As shown in the first graph 6132, the vector load 6134 and the motor load 6136 along the)(axis of the robot base 6084 and the robot motor 6092 generally track each. Similarly, as shown in the third graph 6152, the vector load 6142 and the motor load 6144 along the $z_{axis}$ of the robot base 6154 and the robot motor 6156 also generally track each other. However, as shown in the second graph 6142, there is an aberration 6141 between the reactionary vector load 6138 and the motor load 6140 along the $y_{axis}$ of the robot base 6144 and the robot motor 6146 between time $t_1$ and $t_2$. An encoder warning is issued when an aberration 6141 is sensed by the central control circuit 15002 (FIG. 22).

An alternative to the secondary measure of force with respect to a common reference may include an optical measurement of tissue strain and the utilization of a predefined imaginary modulus based on the physiologic and anatomic tissue parameters. In this regard, a table of tissue properties can be utilized to create an effective modulus for the tissue based on the optically sensed tissue being manipulated. The strain can be used with the locally applied robotic surgical tools forces to determine the overall macro tissue tension being induced.

The process flow diagrams 6160, 6180, 6190 described hereinbelow with reference to FIGS. 162-163 will be described with reference to FIGS. 153-155 and the robotic platform described with reference to FIGS. 1-22. In particular, FIG. 17 illustrates a schematic diagram of a robotic surgical instrument 700 configured to operate a surgical robotic surgical tool described herein according to one aspect of this disclosure. Further, FIG. 22 illustrates a schematic of a robotic surgical system 15000 that includes a central control circuit 15002, a surgeon's console 15012, a robot 15022 that includes one or more robotic arms 15024, and a primary display 15040 operably coupled to the central control circuit 15002. The central control circuit 15002 comprise a processor 15004 coupled to a memory 15006. It will be appreciated that the central control circuit 15002 may be implemented as a control circuit as defined herein.

Figure 162:
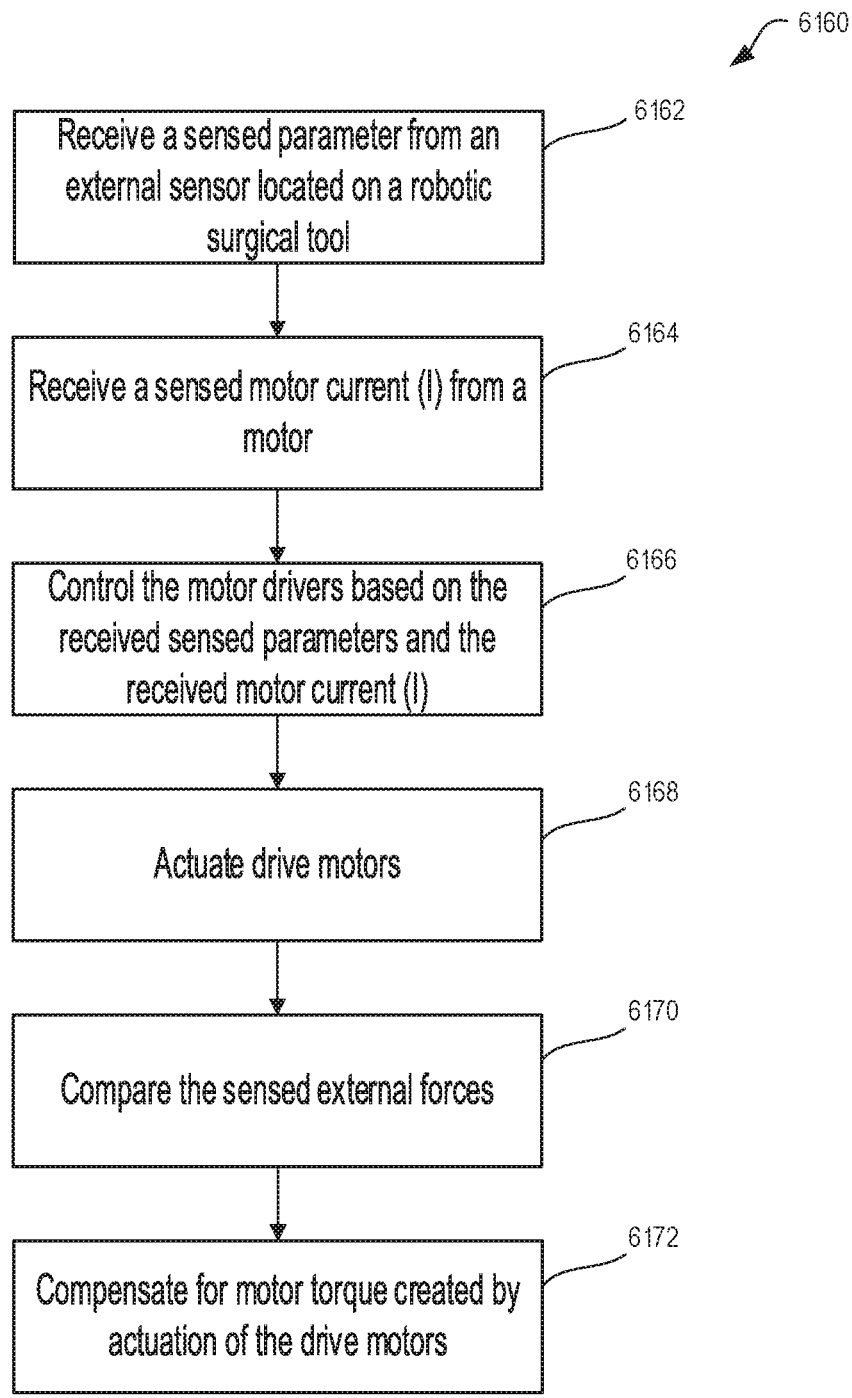
FIG. 162 is a logic flow diagram of a process depicting a control program or a logic configuration for controlling a robotic end-effector actuation motor based on a parameter of a sensed externally applied force to the end-effector according to at least one aspect of the present disclosure.

FIG. 162 is a logic flow diagram 6160 of a process depicting a control program or a logic configuration for controlling a robotic end-effector actuation motor based on a parameter of a sensed externally applied force to the end-effector according to at least one aspect of the present disclosure. The process depicted by the flow diagram 6160 may be represented as a series of machine executable instructions stored in the memory 15006 and executed by the processor 15004 of the central control circuit 15002 of the robotic surgical system 15000 depicted in FIG. 22. With further reference to FIGS. 22, 153-155 and 162, in accordance with the process depicted by the flow diagram 6610, the central control circuit 15002 is configured to receive 6162 a sensed parameter from an external sensor located on a robotic surgical tool 15030 such as the powered surgical robotic tool 6010 depicted in FIGS. 154-155 and graphically depicted in FIG. 153. The external sensor is configured to sense externally applied forces relative to the end-effector 6016. The central control circuit 15002 is configured to receive 6164 a sensed motor current (I) from a motor 15026. The central control circuit 15002 is further configured to control 6166 the motor drivers 15028 based on the received sensed parameter and the received motor current (I). In one aspect, external sensors may include a strain gauge to sense external forces applied to the end-effector 6016 such as lateral or downward tissue force $F_{tissue}$, arm force $F_{arm}$, or clamp force $F_{clamp}$; torque sensors to sense the torque applied to the end-effector 6016 such as $T_{jaw}$. In one aspect, the control 6166 includes adjustment of end-effector 6016 clamp arm pressure P based on the rotational orientation of the jaws 6018, 6020 relative to the torque T and therefore the forces sensed on the robotic surgical tool or motor driven powered device 6010 exerted by the tissue 6012, 6026, for example. The central control circuit 15002 is further configured to actuate 6168 the drive motors 15026, compare 6170 the sensed external forces, and compensate 6172 for motor torque created by actuation of the drive motors 15026.

Still with reference to FIGS. 22 and 162, the central control circuit 15002 is further configured to control the rate of the linear advancement motor 15026 when thick tissue is sensed being fired and further limit the rate of the linear advancement motor 15026 when macro tissue tension is sensed through the comparison of the differences in torques sensed by the powered surgical robotic surgical tool 6010 and caused by the advancement motor 15026. The central control circuit 15002 is further configured to limit energy clamp arm actuation force based on initial contact with tissue and the rate of tissue compression. The central control circuit 15002 is further configured to further reduce energy clamp arm actuation force based on an externally applied macro tension sensed on the blade by the tissue and the central control circuit 15002 is further configured to compare the differences in the torques sensed by the powered surgical robotic surgical tool 6010 and the torques generated by the advancement motors 15026.

Figure 163:
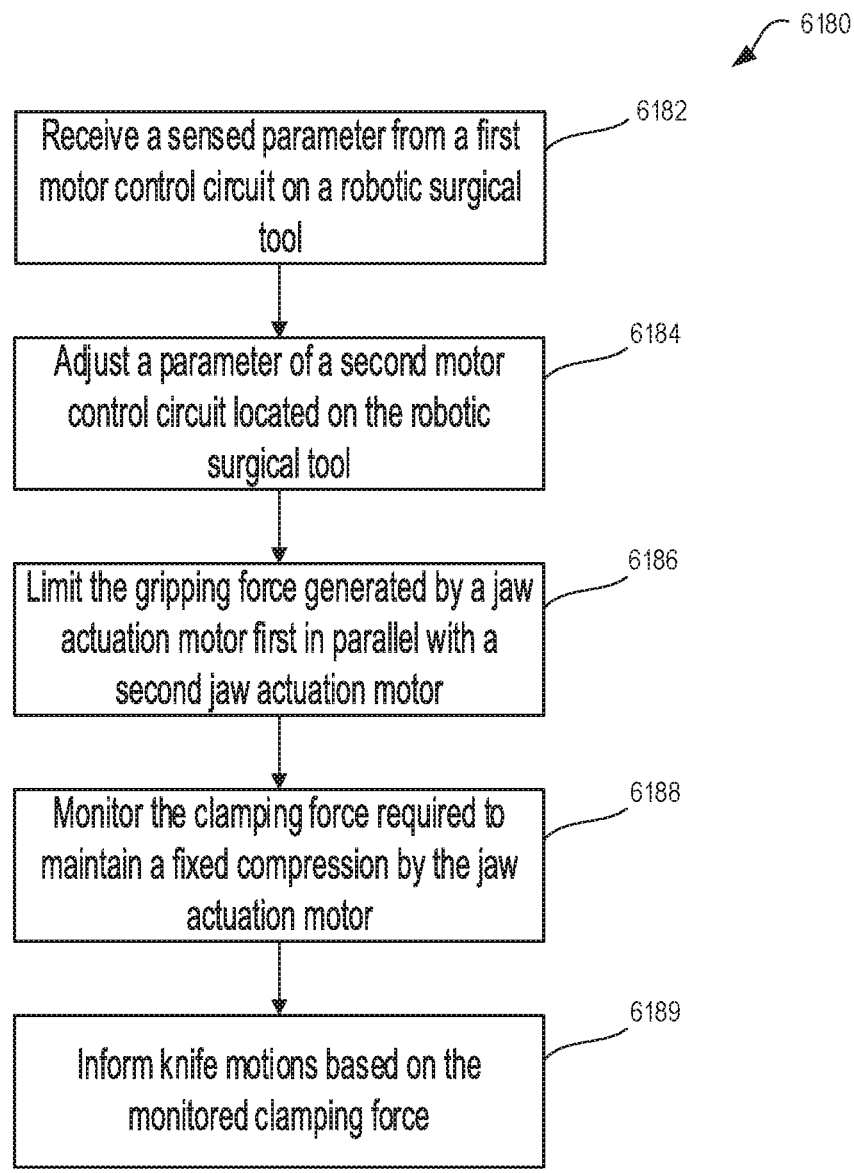
FIG. 163 is a logic flow diagram of a process depicting a control program or a logic configuration for monitoring one motor pack control circuit to adjust the rate, current, or torque of an adjacent motor control circuit according to at least one aspect of the present disclosure.

FIG. 163 is a logic flow diagram 6180 of a process depicting a control program or a logic configuration for monitoring one motor pack control circuit to adjust the rate, current, or torque of an adjacent motor control circuit according to at least one aspect of the present disclosure. The process depicted by the flow diagram 6180 may be represented as a series of machine executable instructions stored in the memory 15006 and executed by the processor 15004 of the central control circuit 15002 of the robotic surgical system 15000 depicted in FIG. 22. With further reference to FIGS. 22, 155-156, 33, in accordance with the process depicted by the flow diagram 6680, the central control circuit 15002 is configured to receive 6182 a sensed parameter from a first motor 15026 ($m_1$) control circuit located on a robotic surgical tool 15030 such as the motor driven powered surgical robotic surgical tool 6050 depicted in FIG. 156 and graphically depicted in FIG. 155 to adjust 6184 a parameter of a second motor 15026 ($m_2$) control circuit located on the robotic surgical tool 15030. The first and second motors 15026 ($m_1$, $m_2$) may be located within the same motor pack of the robotic surgical tool 15030. The adjustment parameter of the second motor 15026 ($m_2$) may be the motor rate, motor current, or motor torque, for example. In one aspect, the central control circuit 15002 is further configured to limit 6186 the gripping force generated by a jaw actuation motor 15026 ($m_2$), e.g., gripping motor, based on the actuation force, rate, or acceleration of an articulation motor 15026 ($m_1$) being commanded to operate in parallel to the jaw actuation motor 15026 ($m_2$). In another aspect, the central control circuit 15002 is further configured to monitor 6188 the clamping force required to maintain a fixed compression by the jaw actuation motor 15026 ($m_2$) and inform 6189 knife motions (e.g., initiation time, speed, etc.) based on the monitored clamping force.

Figure 164:
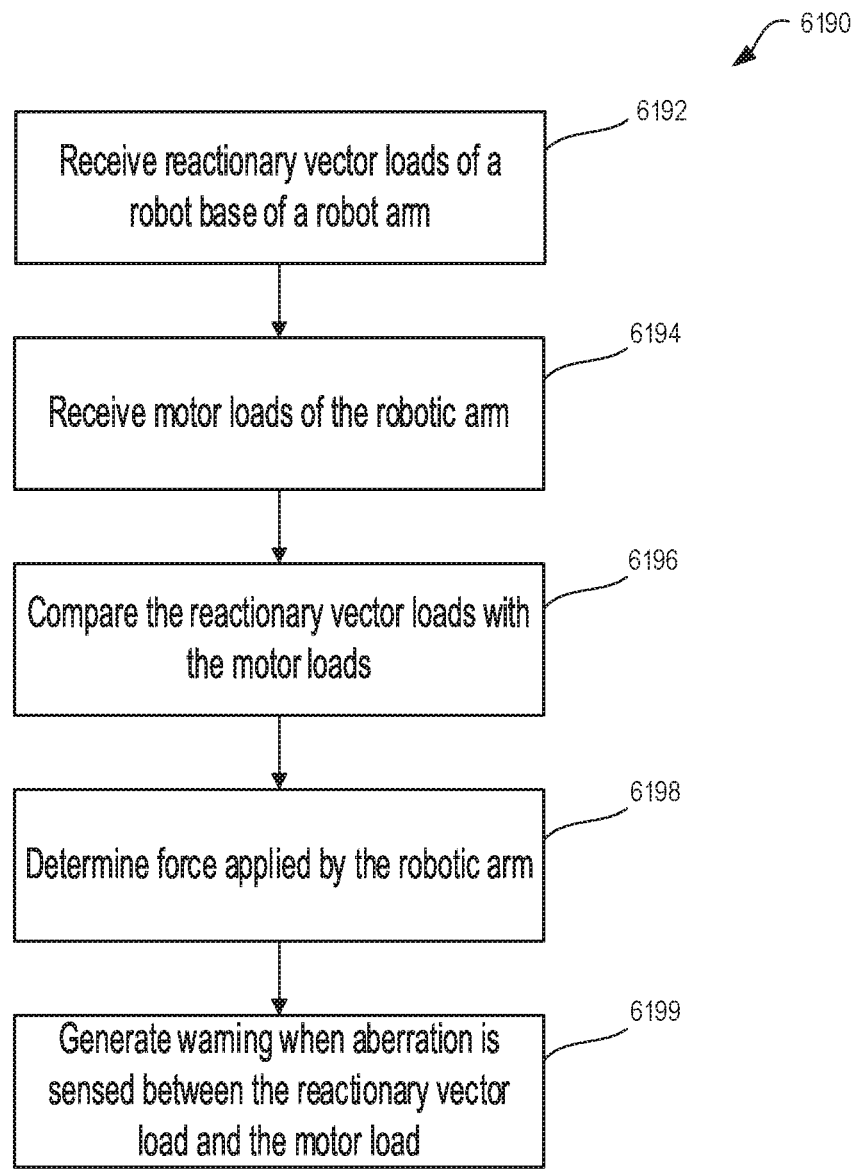
FIG. 164 is a logic flow diagram of a process depicting a control program or a logic configuration for sensing the forces applied by the robotic surgical tool rotation motor or linear slide and the control of jaw to jaw control forces based on that externally applied torsion along with the gripping force generated by the robotic surgical tool actuation motor.

FIG. 164 is a logic flow diagram 6190 of a process depicting a control program or a logic configuration for sensing the forces applied by the robotic surgical tool rotation motor or linear slide and the control of jaw to jaw control forces based on that externally applied torsion along with the gripping force generated by the robotic surgical tool actuation motor. The process depicted by the flow diagram 6190 may be represented as a series of machine executable instructions stored in the memory 15006 and executed by the processor 15004 of the central control circuit 15002 of the robotic surgical system 15000 depicted in FIG. 22. With reference now to FIGS. 22, 158-161, and 164 the central control circuit 15002 is configured to receive 6192 reactionary vector loads of the robot base 6084, 6104 and receive 6194 motor loads of the robotic arms 6080, 6100 as depicted in FIGS. 158-160 and graphically depicted in FIG. 161. The central control circuit 15002 is further configured to compare 6196 the reactionary vector loads of the robot base 6084, 6104 and the motor loads of the robotic arms 6080, 6100 to determine 6198 the force applied by the robotic arms 6080, 6100. The central control circuit 15002 is further configured to generate 6199 a warning when an aberration is sensed between the reactionary vector load of the robot base 6084, 6104 and the motor load of the robotic arm 6080, 6100.

Robotic Surgical System for Controlling Close Operation of End-Effectors

In various aspects, the present disclosure provides robotic surgical systems for modifying control algorithms of robotic surgical tool drivers of a robotic arm based on its relation to another robotic arm employing distance, orientation or location of the one robotic arm position with respect to the distance, orientation or location of the other robotic arm position. In one aspect, the present disclosure provides robotic surgical systems and methods for balancing the operational kinematics of one robotic surgical tool with respect to another robotic surgical tool for operation by employing a parameter of the arm-to-arm relationship as a means to effect robotic tool driver function. In another aspect, the present disclosure provides robotic surgical systems and methods for adjusting the antagonistic relationship of one robotic arm with respect to another robotic arm based on the vertical orientation of the one robotic arm with respect to the other robotic arm. In another aspect, the present disclosure provides robotic surgical systems and methods for adjusting the torque limits or motor current limits of one robotic arm based on the orientation of another robotic arm that is adjacent to the one robotic arm and positioned at an angle with respect to the one robotic arm.

In various aspects, the present disclosure provides robotic surgical systems and methods of verifying jaw position or velocity based on a redundant calculation of a resulting movement from the application of motor control parameters. In one aspect, the verification may be implemented through redundant sensing arrays located within a robotic arm or robotic surgical tool. In another aspect, the verification may be implement by visual tracking and comparative analysis.

In various aspects, the present disclosure provides robotic surgical systems and methods of controlling at least one operational parameter of the robotic surgical tool driver for controlling a circular stapler robotic surgical tool based on another parameter measured within the robotic surgical tool driver for controlling the circular stapler. In one aspect, the operational parameter may be motor current, retraction dependent on the position, magnitude, and forces of the anvil shaft, its drivers, or cutting member.

In one aspect, the present disclosure provides a robotic surgical system and method with arm-to-arm correlation to provide close operation control of an end-effector. In another aspect, adjustment algorithms for one arm may be employed to compensate for arm position relative to a base position of another arm. In another aspect, kinematic control adjustment parameters may be employed to compensate for arm-to-arm variances. For example, a 3D camera can be employed to generate relative positions of the end-effectors (establishing coordinate systems for each robotic surgical tool and then positioning the robotic surgical tool relative to its perceived position). These positions can be employed to back-calculate a perceived position relative to the universal home. Differences in measurements from the arms and from the camera can be used to inform the motion algorithms for each robotic surgical tool. In another aspect, the comparative calculation of the end-effectors relative positions as determined on a 3D camera monitor may be employed to verify the robotic arm joint angles and arm attachment position.

In one aspect, the present disclosure provides robotic surgical systems and methods that include redundant communication connections or sensing means to verify the kinematics of the function of robotic surgical tools. In this regard, safety algorithms are employed to verify expected positioning and orientation. Various aspects of vision systems for tracking instruments and verifying robotic control motions of robotic surgical tools are illustrated in FIGS. 165-169.

Figure 165:
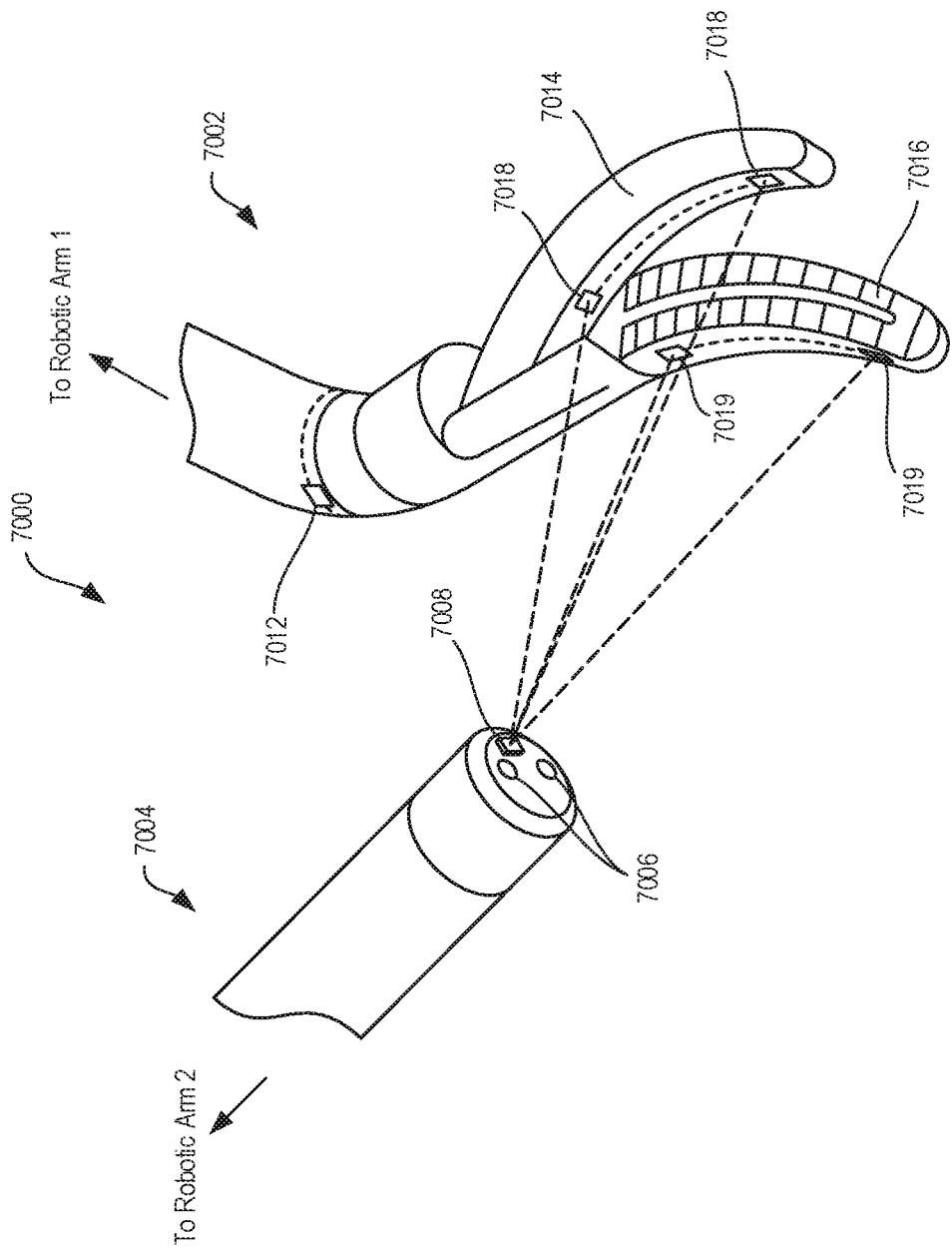
FIG. 165 illustrates a robotic surgical system and method for confirming end-effector kinematics with vision system tracking according to at least one aspect of the present disclosure.

FIG. 165 illustrates a robotic surgical system 7000 and method for confirming end-effector 7002 kinematics with vision system 7004 tracking according to at least one aspect of the present disclosure. The system 7000 includes end-effectors 7002 with reflectors or reflective markers 7012, 7018, 7019 to verify robotic control motions. The end-effector 7002 is coupled to a first robotic arm. The system 7000 also includes a vision system 7004 that includes an optical scope 7006 with at least one fluctuating wavelength emitter 7008. The vision system 7004 is coupled to a second robotic arm. The end-effector 7002 includes reflective markers 7012, 7108, 7019 on a surface that can be scanned by the vision system 7004. The reflective markers 7012, 7018, 7019 may be formed on the surface of the end-effector 7002 or may be applied to the surface of the end-effector 7002. In one aspect, a shaft 7010 of the end-effector 7002 includes a global reflective marker 7012 disposed thereon and the upper jaw 7014 of the end-effector 7002 includes local reflective markers 7018 disposed thereon and the lower jaw 7016 of the end-effector 7002 includes local reflective markers 7019 disposed thereon. The reflective markers 7012, 7018, 7019 are coated with a polymer to allow for the reflectivity of a predefined wavelength. The end-effectors 7002 instrumented with the global and local reflective markers 7012, 7018, 7019 define the position of the end-effector 7002 based on the position and orientation of the global and local reflective markers 7012, 7018, 7019. The global and local reflective markers 7012, 7018, 7019 may be coated or encapsulated with a polymer material that allows for reflectivity of a pre-defined wavelength of light more that other wavelengths. In one aspect, the wavelength may be selected to be inside or outside the visual spectrum. Alternatively, if a wavelength is selected within the visual spectrum, a display algorithm may be employed to remove or eliminated the spotlight reflected from the global and local reflective markers 7012, 7018, 7019 from an image before it is displayed to the user. In one aspect, the reflective markers 7012, 7018, 7019 may be formed or printed directly on the surfaces of the end-effectors 7002 or may be applied in the form of sticker to the surfaces of the end-effectors 7002 or other portions of a robotic arm.

In one aspect, the optical scope 7006 using the fluctuating wavelength emitter 7008 could employ a portion of the rate response to look only for reflective markers 7012, 7018, 7019 within the field of view of the optical scope 7006. The reflective marker 7012, 7018, 7019 within the field of view of the optical scope 7006 may be used to verify the expected distances, orientation, and motions of the end-effector 7002 as it is used during the surgery, completely without the user awareness.

Figure 166:
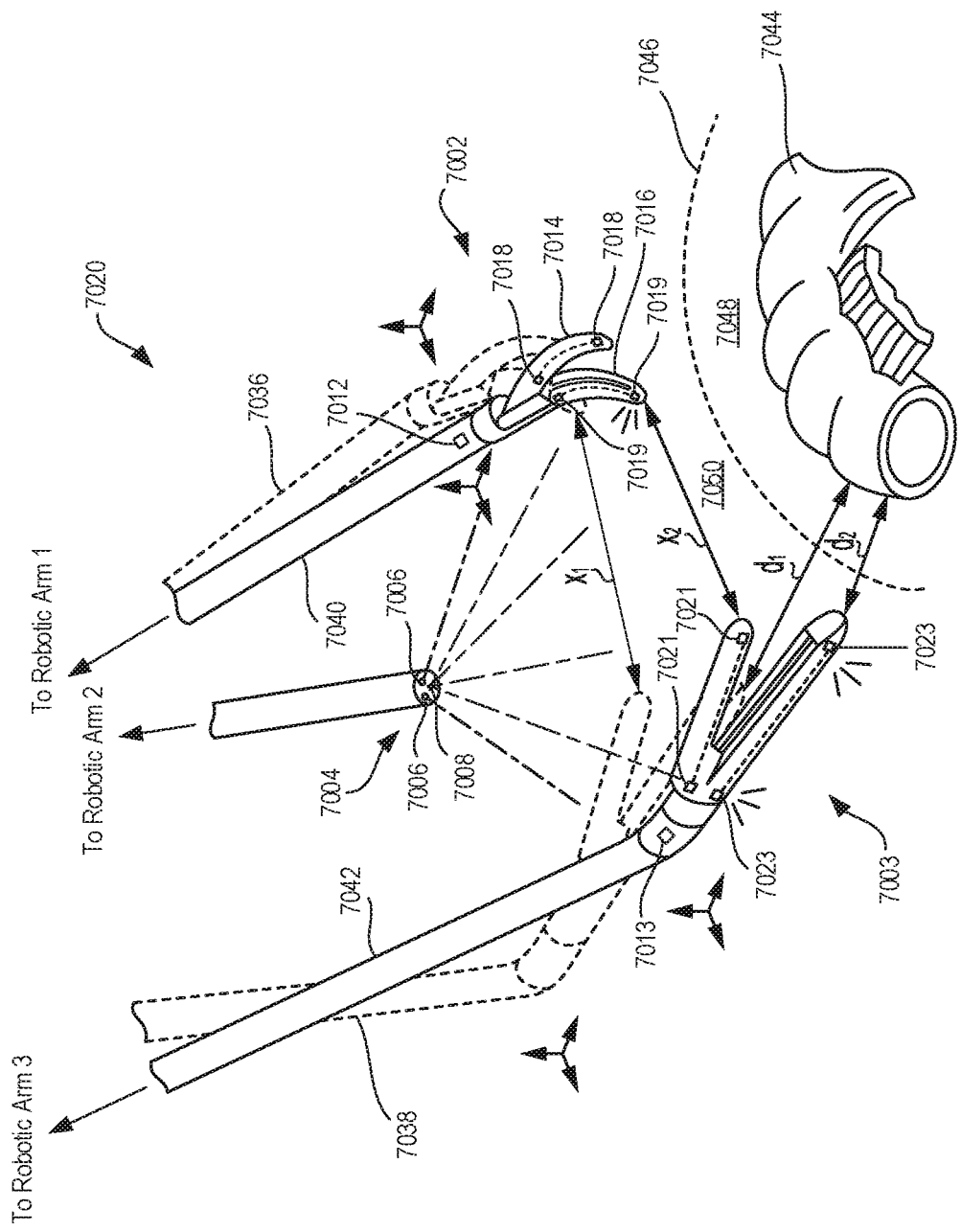
FIG. 166 illustrates a robotic surgical system and method for confirming end-effector kinematics with vision system tracking according to at least one aspect of the present disclosure.

FIG. 166 illustrates a robotic surgical system 7020 and method for confirming end-effector 7002, 7003 kinematics with vision system 7004 tracking according to at least one aspect of the present disclosure. The system 7020 includes two end-effectors 7002, 7003 that include global reflectors or reflective markers 7012, 7013 and local reflectors or reflective markers 7018, 7019, 7021, 7023, respectively, to verify robotic control motions. The two end-effectors 7002, 7003 are coupled to a first and third robotic arm. The system 7020 also includes a vision system 7004 that includes an optical scope 7006 with at least one fluctuating wavelength emitter 7008 that reflects light off the reflective markers 7012, 7013, 7018, 7019, 7021, 7023. The vision system 7004 is coupled to a second robotic arm. Each end-effector 7002, 7003 is characterized by a robot sensed position 7036, 7038 shown in dashed line and a visually verified position 7040, 7042 shown in solid line. Accordingly, a distance $x_1$ is determined between the robot sensed position 7036 of the first end-effector 7002 and the visually verified position 7042 of the second end-effector 7003 based on light reflected by the local reflective markers 7019. Likewise, a distance $x_2$ is determined between the visually verified position 7040 of the first end-effector 7002 based on light reflected by the local reflective markers 7012 and the robot sensed position 7038 of the second end-effector 7003. Distance $d_1$ to a critical structure 7044 is determined between the robot sensed position 7038 of the second end-effector 7003 and distance $d_2$ to the critical structure 7044 is determined between the visually verified position 7042 of the second end-effector 7003 to the critical structure 7044. The determination of the distance between the first end-effector 7002 and the critical structure 7044 can be determined in a similar manner. The critical structure 7044 is located within a boundary 7046 that is considered to be a high risk zone 7048. A low risk zone 7050 is located outside the boundary 7046.

In one aspect, the fluctuating wavelength emitters 7008 imaging source may include a regular white light source. In this case, the reflective marker 7012, 7018 identifiers may be reflective and of a pre-defined color (i.e., white or green). In this case, the creation of the image for display to the user would include eliminating the bright reflection while still enabling the vision system 7004 to track and correlate the robotic arm and end-effector 7002 motions and to minimize the distraction of the user by the reflection.

Figure 167:
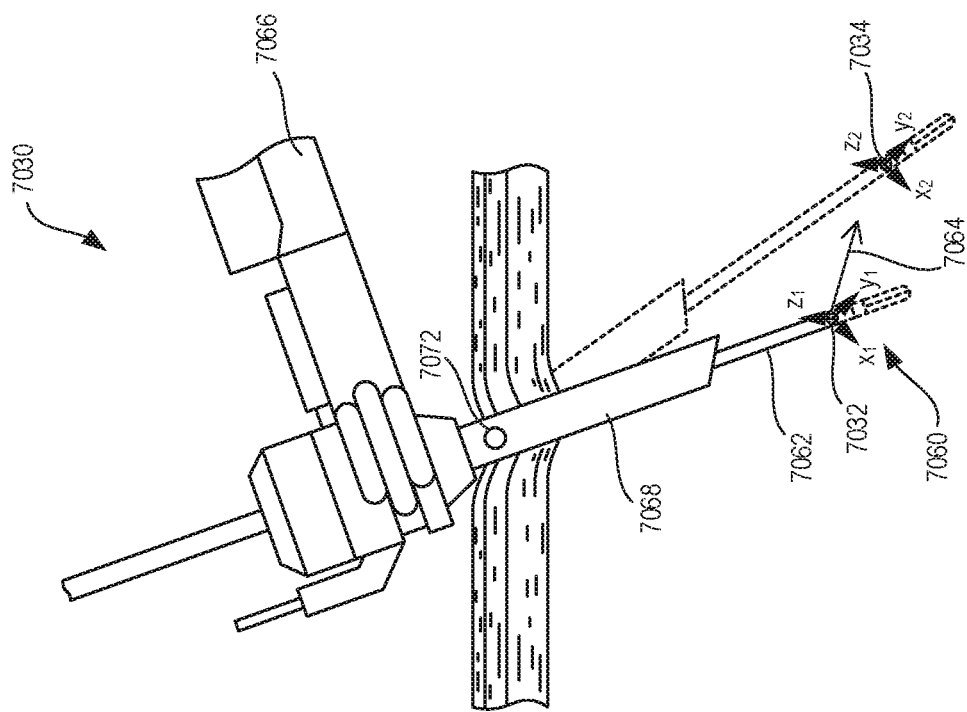
FIG. 167 illustrates a robotic surgical system and method for detecting a location of the distal end of a fixed shaft and a straight-line travel path to an intended position according to at least one aspect of the present disclosure.

FIG. 167 illustrates a robotic surgical system 7030 and method for detecting a location 7032 of the distal end 7060 of a fixed shaft 7062 and a straight-line travel path 7064 to an intended position 7034 according to at least one aspect of the present disclosure. Here, a robotic arm 7066 is attached to a trocar 7068, which is shown inserted through the wall 7070 of a body cavity. The trocar 7068 can rotate about a remote center of motion 7072 (RCM). The distal end 7060 of the fixed shaft 7062 is initially positioned at a first location 7032 referenced by coordinates $x_1$, $y_1$, $z_1$ and the straight-line travel path 7064 of the distal end 7060 of the fixed shaft 7062 is positioned at a second location 7034 referenced by coordinates $x_2$, $y_2$, $z_2$ after the trocar 7068 is rotated by the robotic arm 7066 about the RCM 7072 by a predetermined angular rotation.

Figure 168:
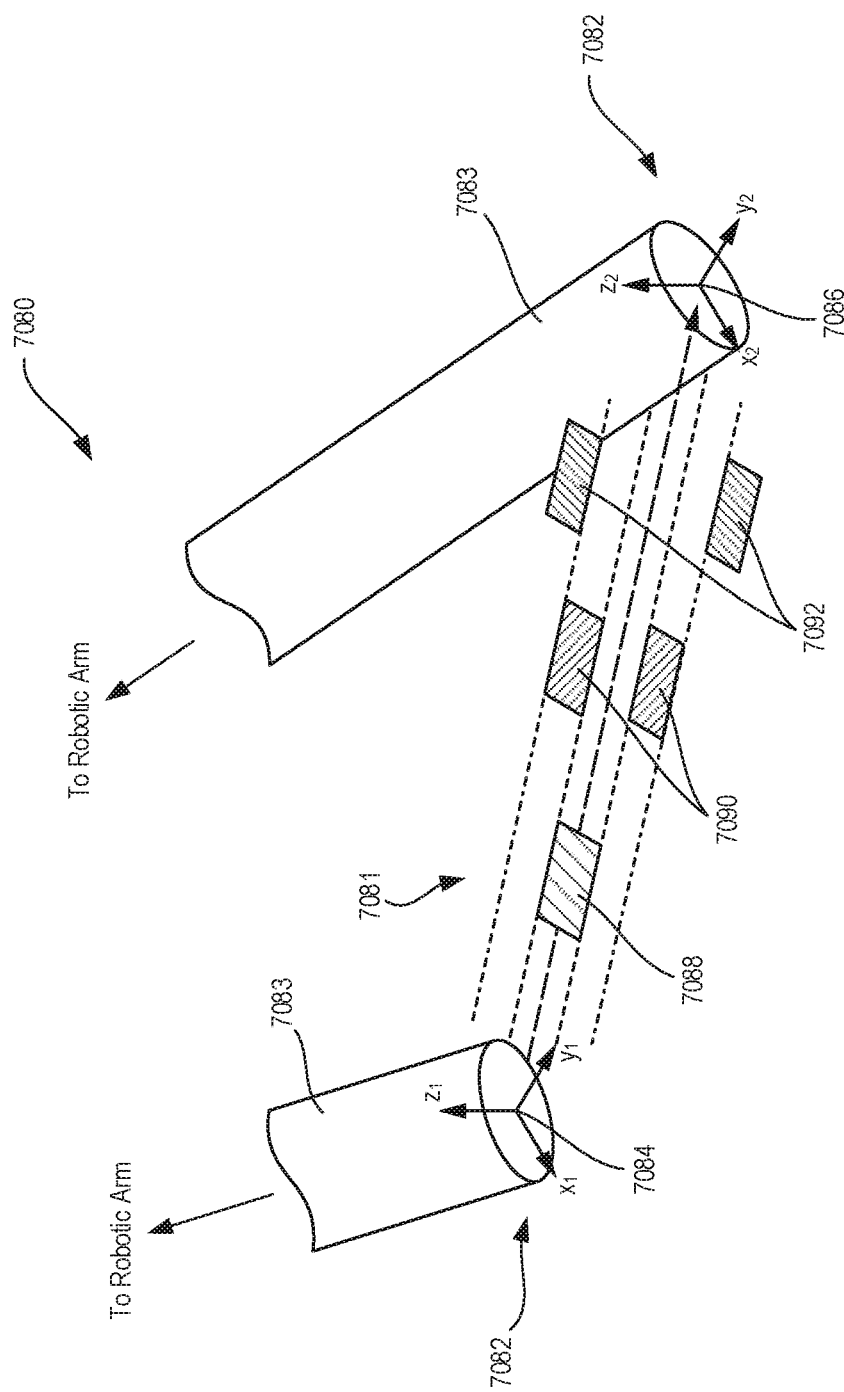
FIG. 168 illustrates tracking system for a robotic surgical system defining a plurality of travel paths of the distal end of an end-effector based on velocity as the distal end of the end-effector travels form a first location to a second location according to at least one aspect of the present disclosure.

FIG. 168 illustrates tracking system 7080 for a robotic surgical system defining a plurality of travel paths 7081 of the distal end 7082 of an end-effector 7083 based on velocity as the distal end 7082 of the end-effector 7083 travels form a first location 7084 to a second location 7086 according to at least one aspect of the present disclosure. The end-effector is coupled to a robotic arm. The first location 7084 of the distal end 7082 of the end-effector 7083 is referenced by coordinates $x_1$, $y_1$, $z_1$ and the second location 7086 of the distal end 7082 of the end-effector 7083 is referenced by coordinates $x_2$, $y_2$, $z_2$. The distal end 7082 of the end-effector 7083 can travel from the first location 7084 to the second location 7086 at full velocity along an optimal travel path 7088, however, the distal end 7082 of the end-effector 7083 can travel from the first location 7084 to the second location 7086 along an acceptable travel path 7090 if it slows down from full velocity. If the distal end 7082 of the end-effector 7083 is detected along an unacceptable travel path 7092, the distal end 7082 of the end-effector 7083 is stopped.

Figure 169:
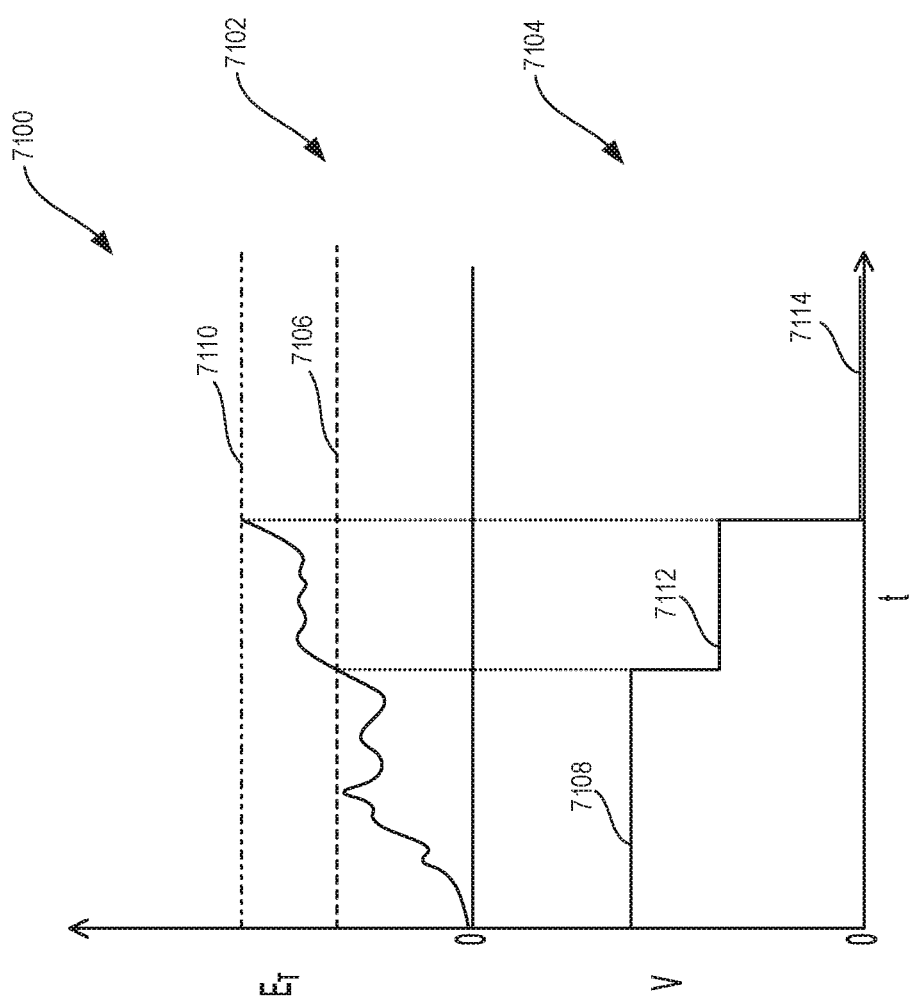
FIG. 169 is a graphical illustration of an algorithm for detecting an error in the tracking system depicted in FIG. 168 and corresponding changes in velocity of the distal end of the end-effector according to at least one aspect of the present disclosure.

FIG. 169 is a graphical illustration 7100 of an algorithm for detecting an error in the tracking system 7080 depicted in FIG. 168 and corresponding changes in velocity of the distal end 7082 of the end-effector 7083 according to at least one aspect of the present disclosure. The first graph 7102 depicts detected error $E_t$ as a function of time and the second graph 7104 is the velocity V of the distal end 7082 of the end-effector 7083 as a function of time. The detected error $E_t$ is given by:

$$E_t = \sqrt{x_2 + y_2 + z_2}$$

The detected error $E_t$, the degree of deviation from what is expected, in the tracking system 7080 could result in varied and escalating responses to correct the correlation or prohibit collateral damage. As shown in the first graph 7102, when the detected error $E_t$ is below a first error threshold 7106 the distal end 7082 of the end-effector 7083 is within the range of the optimal travel path 7088 and can move at full velocity 7108 as shown in the second graph 7104. When the detected error $E_t$ is between a first error threshold 7106 and a second error threshold 7110 the distal end 7082 of the end-effector 7083 is within the range of an acceptable travel path 7090 and can move at a slower velocity 7112 than full velocity 7108 as shown in the second graph 7104. When the detected error $E_t$ exceeds the second error threshold 7110 the distal end 7081 of the end-effector 7082 is in the unacceptable travel path 7092 and it is stopped 7114 as shown in the second graph 7104.

With reference now to FIGS. 165-169, correlation of end-effector 7002, 7003, 7083 action may be determined by verifying the motion the robot is indicating the end-effector 7002, 7003, 7083 to move through to the detected motion of the local reflective markers 7012, 7013, 7018, 7019, 7021, 7023 motion reflections on the end-effector 7002, 7003, 7083. If the motions do not correlate directly, the robot may be incremented through a series of countermeasures including, for example, consecutive execution of countermeasure steps or escalating the response to circumvent the countermeasure steps based on the situational awareness of the system to procedural, surgeon, or device risks. Countermeasures may include, for example, slowing the actuation of advancement of the at-risk portion of the system; identification of the issue to the user; handing off primary control measurements from the primary means to the secondary visually measured means; or shutdown and re-calibration of the sub-system; among others.

A probability assessment may be employed by the robotic surgical system to determine the level of risk in process of operating with the variance detected. This risk probability may take into account aspects such as the magnitude of the variance, whether it is increasing or decreasing, proximity to critical anatomic structures or steps, risk of this particular sub-system resulting in a jammed or can not remove situation, among others.

The robotic surgical system may be configured to record these variances, track them over time, and supply the resulting information to a robot control tower and to an analytic cloud or remote system. Documentation and tracking of the variances may enable the update of the system control algorithms that could compensate, or update the response of the future system to similar issues. Detected variances also may be employed to re-calibrate certain elements of the control system on-the-fly to allow it to update minor detected correlation issues.

In various aspects, with reference back to FIG. 22, the present disclosure provides a robotic surgical system 15000 that includes a central control circuit 15002 configured to compare multiple sensing array outputs to allow the robotic surgical system 15000 to determine which component of the robotic surgical system 15000 is operating outside of an expected manner. In one aspect, the central control circuit 15002 is configured to compare primary motor 15026 (m1)

control sensors with secondary sensors to verify motion of the primary motor 15026 (m1), for example.

With reference still to FIG. 22, in one aspect, a primary controller, such as the central control circuit 15002, of virtual calculated positions is compared by the central control circuit 15002 against a secondary controller located on robotic surgical tool sensors to determine if an algorithm in the primary controller is operating outside of its normal operational range. The secondary control arrays may include the detection of loads or torques in the return or support structure of the robot or end-effector. The analysis may include comparing antagonistic support of one motor 15026 ($m_1$) based on the activation of certain functions of another motor 15026 ($m_2$). It may be indicated by local end-of-stroke switches or other discrete electronic indicators.

With reference still to FIG. 22, an array of piezoelectric crystals can be placed on known locations (e.g., end of robotic surgical tool, specific locations on an OR table, trocar, patch on patient, etc.) of the robotic surgical system 15000 to enable calculation of distance of objects from one another. This would create a local coordinate system that could either be fixed to a global coordinate system (e.g., the robot; X-Y-Z) or to a master arm/robotic surgical tool. In one aspect, with at least two piezoelectric crystals located on the same non-deformable object at a known separation distance and at least one on the distal tip, a calibration constant can be determined to account for changes in local impedance due to contamination. In one aspect, with at least two piezoelectric crystals on the same non-deformable object at a known separation distance, a vector can be established to determine the location of an end-effector without discrete end-effector crystals or sensors.

With reference still to FIG. 22, in one aspect, the robotic surgical system 15000 according to the present disclosure may include a completely autonomous safety measure system may be configured to run in parallel to the control array. If the autonomous system detects, through its autonomous sensors, a variance beyond a pre-defined amount, the autonomous system may limit or shut down the affected system until the variance is resolved. The safety system may include its own sensors or it could employ raw data from shared sensors to the primary control system that provides a secondary pathway for the shared sensors to transmit the relevant information.

Figure 170:
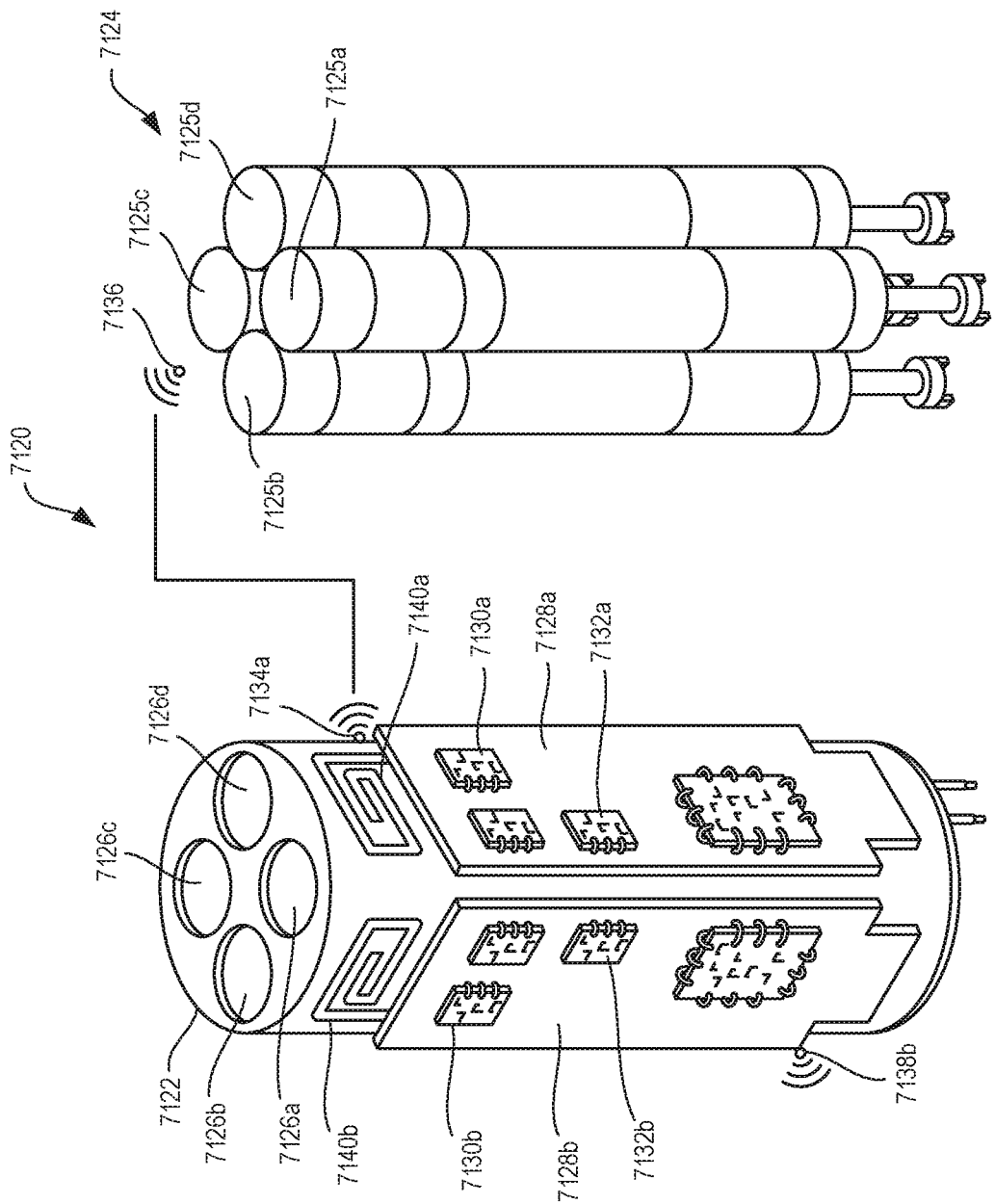
FIG. 170 illustrates a system for verifying the output of a local control circuit and transmitting a control signal according to at least one aspect of the present disclosure.

With reference still to FIG. 22, in various aspects, the robotic surgical system 15000 includes local safety co-processing or processors for each interchangeable system as described with reference to FIGS. 170-174. Turning now to FIG. 170, there is illustrated a system 7120 for verifying the output of a local control circuit and transmitting a control signal according to at least one aspect of the present disclosure. The system 7120 includes a sterile housing 7122 and a motor pack 7124 that includes a plurality of motors 7125a-7125d. In the illustrated aspect, the sterile housing 7122 includes apertures 7126a-7126d to receive the plurality of motors 7125a-7125d. The sterile housing 7122 also includes a semi-autonomous motor control circuit 7128a-7128d (only 7128a and 7128b are shown), one for each of the motors 7125a-7125d. Each of the control circuits 7128a-7128d includes, for each motor 7125a-7125d, a primary control and feedback communication circuit 7130a-7130d (only 7130a and 7130b are shown) and a secondary independent verification communication circuit 7132a-7132d (only 7132a and 7132b are shown). The primary control and feedback communication circuits 7130a-7130d and the secondary independent verification communication circuits 7132a-7132d communicate with the motors 7125a-7125d via corresponding antennas 7140a-7140d (only 7140a and 7140b are shown. The primary control and feedback communication circuit 7130a transmits a wireless communication control signal 7134a to the motor pack 7124 and receives a wireless communication feedback signal 7136 from the motor pack 7124 via the antenna 7140a. The secondary independent verification communication circuit 7132b transmits a secondary wireless control validation signal 7138b via the antenna 7140b.

Still with reference to FIG. 170, a local current and voltage may be provided by a set of sensors located within each local control circuit as well as access to rotary encoder information and other sensors. Sensors include, for example, torque sensor, strain gages, accelerators, hall sensors, which outputs are all independently supplied to a secondary processor to verify the induced motions. The sensor outputs are correlated with the motions the requested primary control and feedback communication circuits 7130a-7130d believes to be correct.

Figure 171:
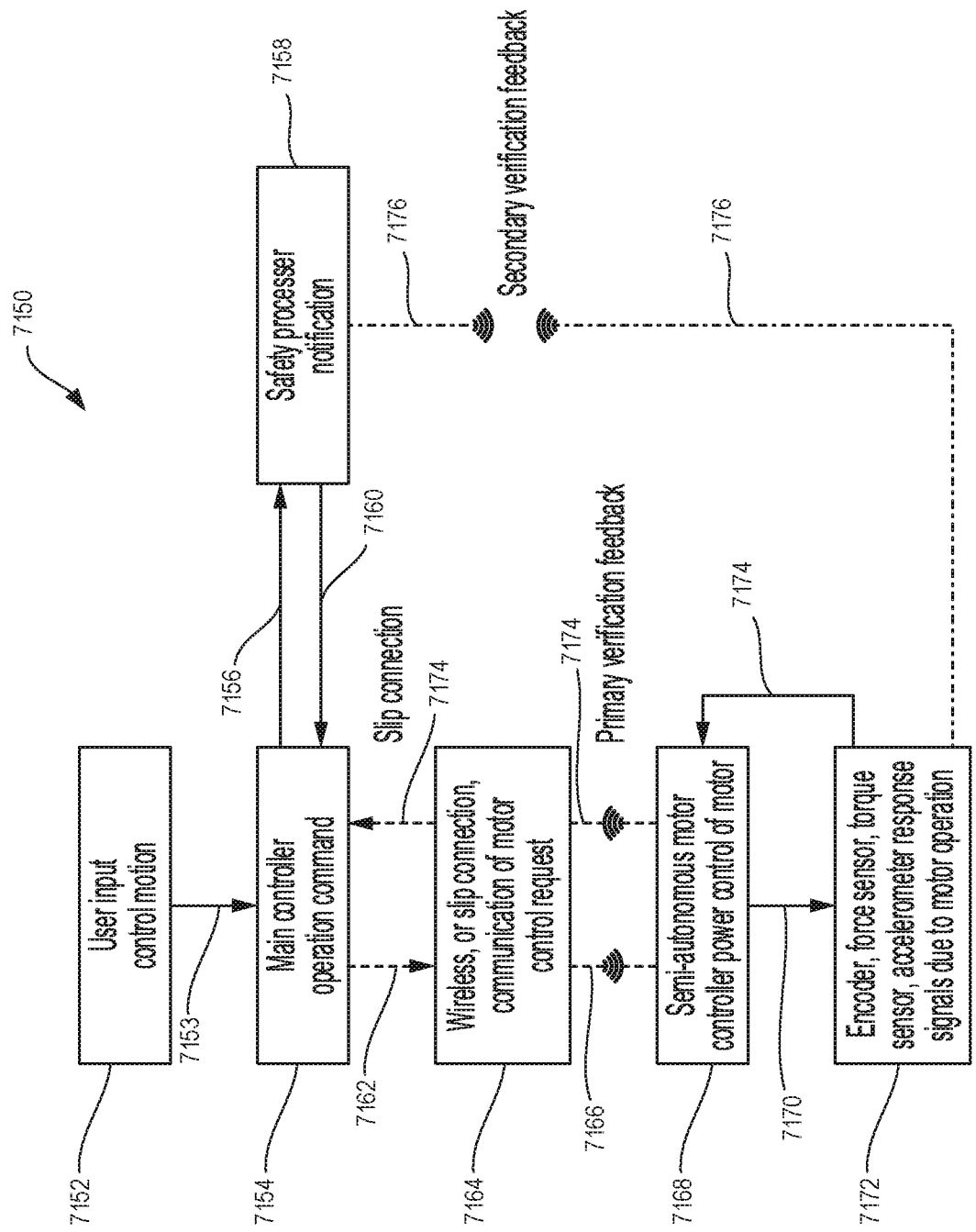
FIG. 171 is a flow diagram of a process depicting a control program or a logic configuration of a wireless primary and secondary verification feedback system according to at least one aspect of the present disclosure.

FIG. 171 is a flow diagram 7150 of a process depicting a control program or a logic configuration of a wireless primary and secondary verification feedback system according to at least one aspect of the present disclosure. The process depicted by the flow diagram 7150 may be represented as a series of machine executable instructions stored in the memory 15006 and executed by the processor 15004 of the central control circuit 15002 of the robotic surgical system 15000 depicted in FIG. 22. With reference now to FIGS. 22 and 171, the user inputs 7152 a control motion into the robotic surgical system 15000 as depicted in FIG. 22. The main controller 7154 or central control circuit 15002 is configured to receive 7153 the user input signal and to send a notification 7156 to a safety processor 7158. The main controller 7154 is configured to receive 7160 a notification from the safety processor 7158 and to issue 7162 an operation command to the motor 15026 via a slip connection, or alternatively, a wireless connection. The main controller 7154 is configured to issue 7164 a request 7166 for motor control to a semi-autonomous motor controller 7168 via a wireless, or slip connection. The semi-autonomous motor controller 7168 is configured to receive the request 7166 and to send a control signal 7170 to one or more than one sensor 7172 to control the power of the motor. The one or more than one sensor 7172 is configured to generate 7174 a response to the motor operation. The one or more than one sensor 7172 may include, for example, an encoder, force sensor, torque sensor, accelerometer, among others. The response 7174 is provided as a primary verification feedback signal to the semi-autonomous motor controller 7168 and to the safety processor 7158 as a secondary verification feedback signal 7176 via a wireless connection, or alternatively a wired connection. The safety processor 7158 provides the notification 7160 to the main controller 7154 based on the secondary verification feedback signal 7176.

Figure 172:
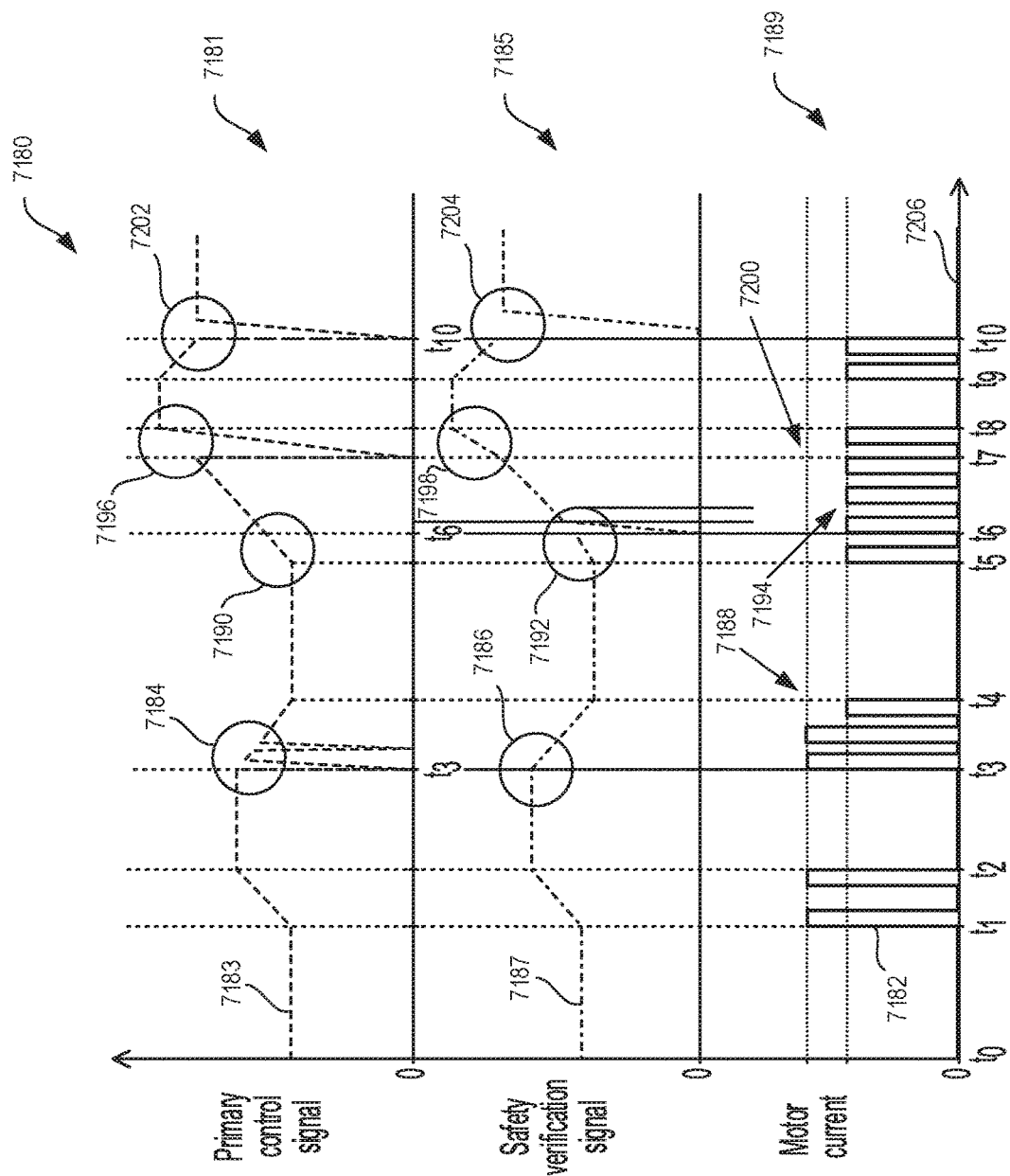
FIG. 172 is a graphical illustration of an algorithm for comparing motor control signals, safety verification signals, and motor current according to at least aspect of the present disclosure.

FIG. 172 is a graphical illustration 7180 of an algorithm for comparing motor control signals, safety verification signals, and motor current according to at least aspect of the present disclosure. A first graph 7181 depicts a primary motor control signal 7183 versus time. A second graph 7185 depicts a safety verification signal 7187 versus time. A third graph 7189 depicts motor current signal 7182 versus time. If there is a discrepancy between the measured signals and the control signals, a warning flag is supplied to the primary control system. If the discrepancy lasts longer than a pre-defined time or its magnitude exceeds a predefined threshold the controller's link to the motor is interrupted and the motor is shut down. Four separate conditions are now described below with reference to first, second, and third graphs 7181, 7185, 7189.

In a first condition, at time $t_3$ there is a loss of the primary control signal 7183 as shown in section 7184 of the primary control signal 7183, for example, where the primary control signal 7183 or feedback signal exhibits intermittent behavior. At time $t_3$, however, there is no loss of the safety verification signal 7187 as shown in section 7186 of the safety verification signal 7187. Accordingly, the motor command is not interrupted and the motor continues to operate as shown in section 7188 of the motor current signal 7182.

In a second condition, at time $t_6$ there is no loss of the primary control signal 7183 as shown in section 7190 of the primary control signal 7183. At time $t_6$, however, there is a temporary loss of the safety verification signal 7187 for a period $t<x_{ms}$ threshold as shown in section 7192 of the safety verification signal 7187. Accordingly, the motor command is not interrupted and the motor continues to operate as shown in section 7194 of the motor current signal 7182.

In a third condition, at time $t_7$ there is a loss of the primary control signal 7183 as shown in section 7196 of the primary control signal 7183. At time $t_7$, however, there is no loss of the safety verification signal 7187 as shown in section 7198 of the safety verification signal 7187. Accordingly, the motor command is not interrupted and the motor continues to operate as shown in section 7200 of the motor current signal 7182.

In a fourth condition, at time $t_{10}$ there is a loss of the primary control signal 7183 as shown in section 7202 of the primary control signal 7183 and at time $t_7$, there also is a loss of the safety verification signal 7187 as shown in section 7204 of the safety verification signal 7187. Accordingly, the motor command is interrupted and the motor is stopped as shown in section 7206 of the motor current signal 7182.

Figure 173:
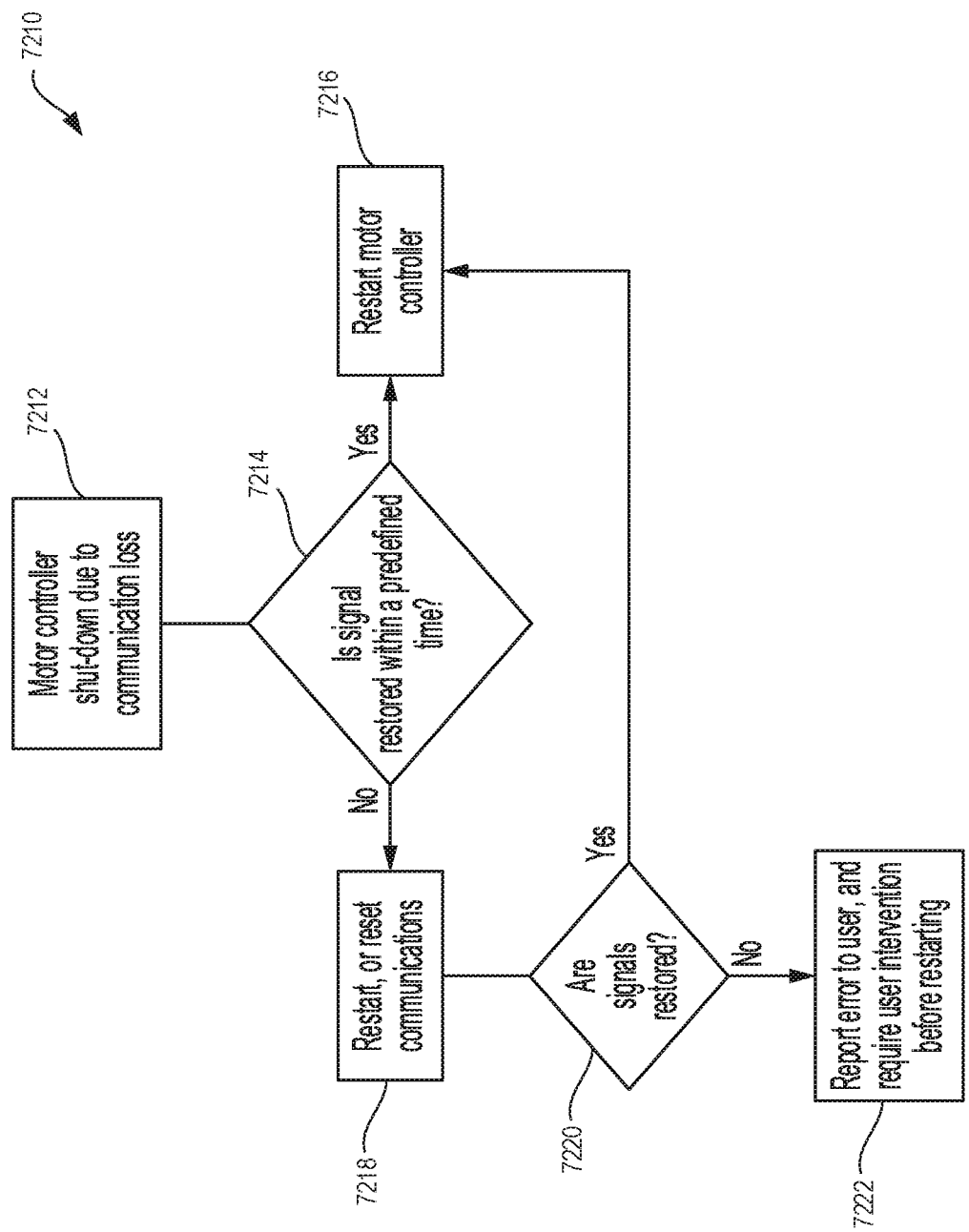
FIG. 173 is a flow diagram of a process depicting a control program or a logic configuration of a motor controller restart process due to motor controller shutdown due to communication loss according to at least one aspect of the present disclosure.

FIG. 173 is a flow diagram 7210 of a process depicting a control program or a logic configuration of a motor controller restart process due to motor controller shutdown due to communication loss according to at least one aspect of the present disclosure. The process depicted by the flow diagram 7210 may be represented as a series of machine executable instructions stored in the memory 15006 and executed by the processor 15004 of the central control circuit 15002 of the robotic surgical system 15000 depicted in FIG. 22. With reference now to FIGS. 22 and 173, in accordance with the process depicted by the flow diagram 7210, the central control circuit 15002 is configured to detect 7212 that the motor controller shut-down due to a loss of communication signal. The central control circuit 15002 is configured to determine 7214 whether the communication signal is restored within a predefined time. When the communication signal is restored within a predefined time, the central control circuit 15002 is configured to continue along the YES branch and to restart 7216 the motor controller. When the communication signal is not restored within a predefined time, the central control circuit 15002 is configured to continue along the NO branch and to restart 7218 or to reset the communication signal. The central control circuit 15002 then is configured to determine 7220 whether the communication signals are restored. When the communication signals are restored, the central control circuit 15002 is configured to continue along the YES branch and restarts 7216 the motor controller. When the communication signals are not restored, the central control circuit 15002 is configured to continue along the NO branch and to report 7222 an error to the user and requires user intervention before restarting the motor controller.

Figure 174:
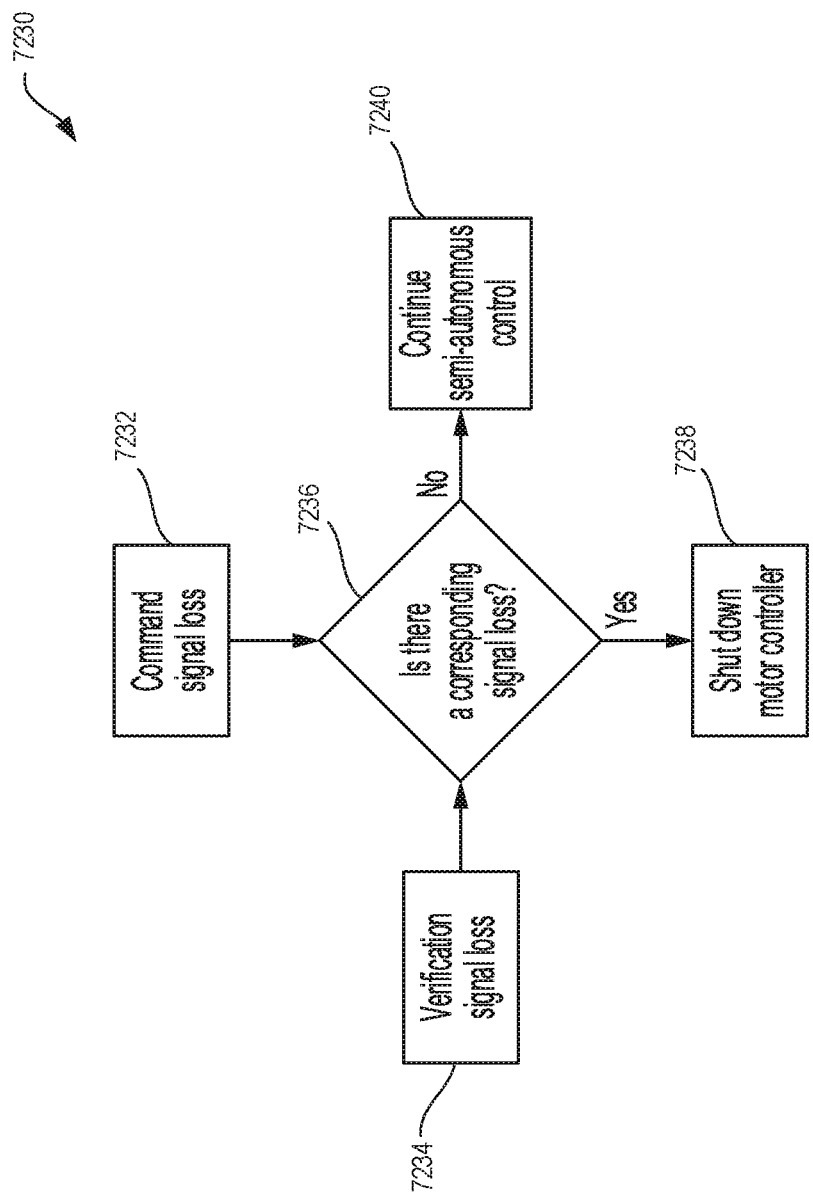
FIG. 174 is a flow diagram of a process depicting a control program or a logic configuration for controlling a motor controller due to command or verification signal loss according to at least one aspect of the present disclosure.

FIG. 174 is a flow diagram 7230 of a process depicting a control program or a logic configuration for controlling a motor controller due to command or verification signal loss according to at least one aspect of the present disclosure. The process depicted by the flow diagram 7230 may be represented as a series of machine executable instructions stored in the memory 15006 and executed by the central control circuit 15002 of the robotic surgical system 15000 depicted in FIG. 22. With reference now to FIGS. 22 and 174, in accordance with the process depicted by the flow diagram 7230, the central control circuit 15002 is configured to detect 7232 either a command signal loss or to detect 7234 a verification signal loss. When a loss of command signal is detected 7232 or loss of verification signal is detected 7234, the central control circuit 15002 is configured to determine 7236 if there is a corresponding signal loss. When there is a corresponding signal loss, the central control circuit 15002 is configured to continue along the YES branch and to shut down 7238 the motor controller. When there is no corresponding signal loss the central control circuit 15002 is configured to continue along the NO branch and to continue 7240 semi-autonomous control of the motor controller.

In accordance with various aspects of the processes depicted by the flow diagrams 7210, 7230, each sub-controller may include an individual safely processor or process overseeing the function of the systems as the system intended. This becomes much more important when the robot has removable and replaceable motor packs which have built in controllers.

In various aspects, the present disclosure provides a robotic surgical system and method that utilizes secondary confirmation of a controlled motor and robotic surgical tool motions to detect and compensate for differences in the system and aging of the system. In one aspect, the present disclosure provides a robotic surgical system and method for on-the-fly secondary source monitoring of mechanical outputs and adjustment of the control signals to compensate for detected differences. In one aspect, the same secondary measurements or motions, work, and output of sub-systems for confirmation of valid control functions of a safety processor may be employed through a secondary process to synchronize the primary control signal with the measured secondary measured signal. This would allow the sub-system to compensate for aging electronics and motors while providing the intended final output. The technique may be employed to compensate for the kinematic differences in mechanical sub-systems and tolerance differences and slop in systems. If the secondary measure is compared to the intended control signal and then the error terms are used to adjust the primary control signal to bring the comparison down below a predefined limit, it would allow the control signal to be adjusted individually for each sub-system and each motor pack.

Figure 175:
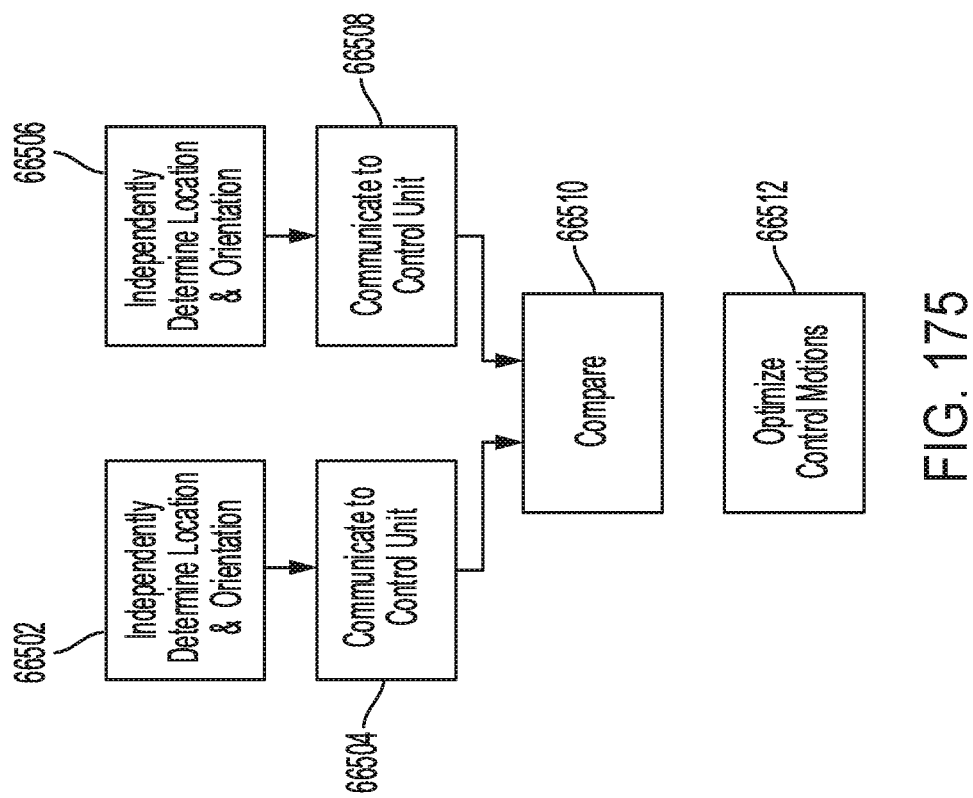
FIG. 175 is a flowchart depicting a robotic surgical system utilizing a plurality of independent sensing systems according to at least one aspect of the present disclosure.

FIG. 175 is a flowchart depicting a robotic surgical system utilizing a plurality of independent sensing systems according to at least one aspect of the present disclosure. Referring now to FIG. 175, a flow chart for a robotic surgical system is depicted. The flow chart can be utilized by a robotic surgical system, for example. In various instances, two independent sensing systems can be configured to detect the location and/or orientation of a surgical component, such as a portion of a robotic arm and/or a surgical robotic surgical tool. The first sensing system, or primary sensing system, can rely on the torque and/or load sensors on the motors and/or motor drivers of the robotic arm. The second sensing system, or secondary sensing system, can rely on magnetic and/or time-of-flight sensors on the robotic arm and/or surgical robotic surgical tool. The first and second sensing systems are configured to operate independently and in parallel. For example, at step 66502, the first sensing system determines the location and orientation of a robotic component and, at step 66504, communicates the detected location and orientation to a control unit. Concurrently, at step 66506, the second sensing system determines the location and orientation of the robotic component and, at step 66508, communicates the detected location and orientation to the control unit.

The independently-ascertained locations and orientations of the robotic component are communicated to a central control circuit at step 66510, such as to a robotic control unit and/or a surgical hub. Upon comparing the locations and/or orientations, the control motions for the robotic component can be optimized at step 66512. For example, discrepancies between the independently-determined positions can be used to improve the accuracy and precision of control motions. In certain instances, the control unit can calibrate the control motions based on the feedback from the secondary sensing system. The data from the primary and secondary sensing systems can be aggregated by a hub and/or data stored in a cloud to further optimize the control motions of the robotic surgical system. Reference may be made to U.S. patent application Ser. No. 15/940,711, the entire contents of which are incorporated herein by reference, for additional detailed discussion.

In various aspects, the present disclosure provides a robotic surgical system with a hierarchical control scheme to relate motions of independent arm or instrument operation. In one aspect, the one of the control arms may be defined as the master axes arm under which the other arms are verified against. Various techniques for detecting a primary control arm and verifying secondary robotic arms are described with reference to FIGS. 175-176.

Figure 176:
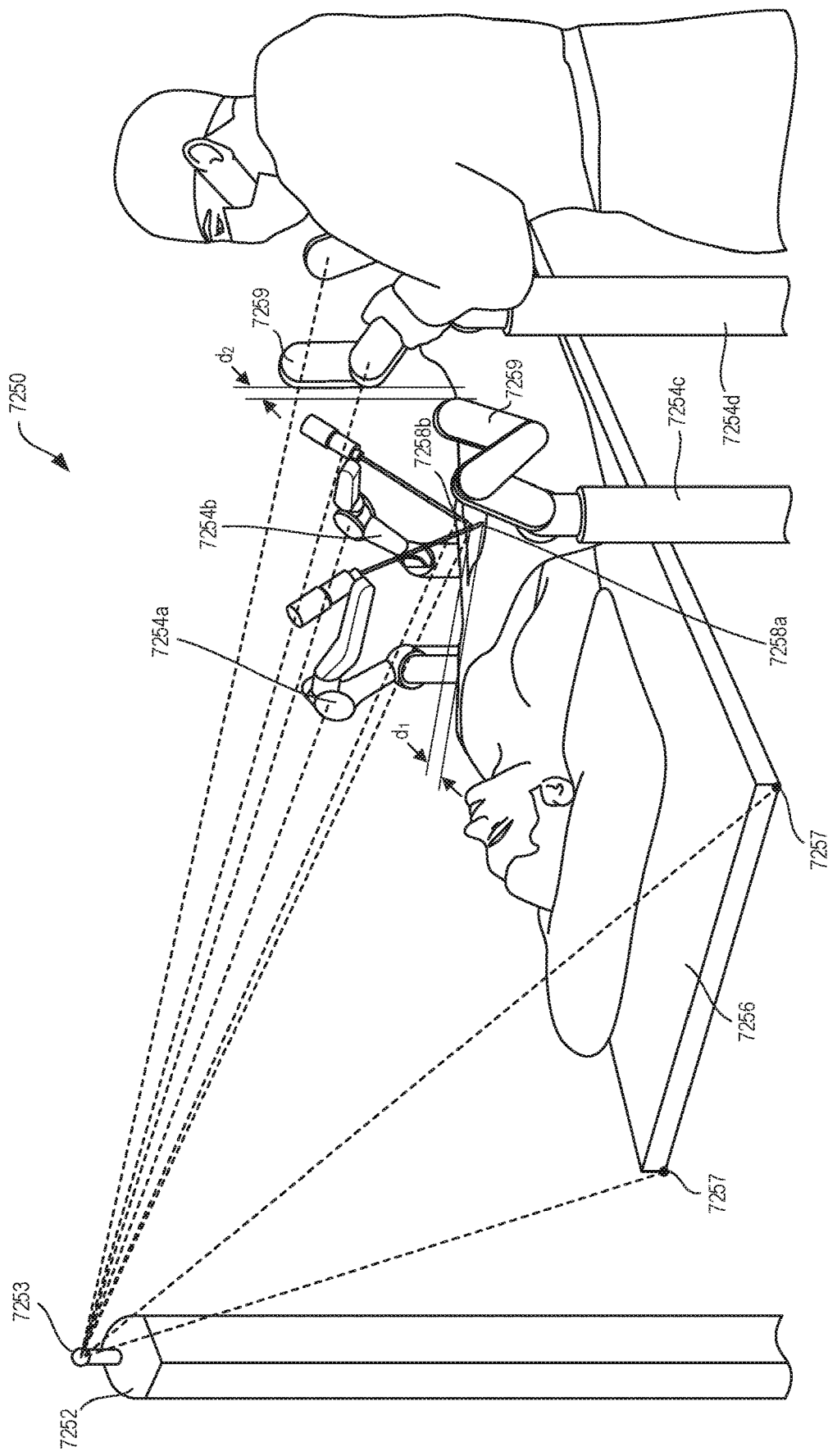
FIG. 176 is a robotic surgical system for controlling a primary robotic arm and detecting and verifying secondary robotic arms according to at least one aspect of the present disclosure.

FIG. 176 is a robotic surgical system 7250 for controlling a primary robotic arm and detecting and verifying secondary robotic arms according to at least one aspect of the present disclosure. The robotic surgical system 7250 includes a master coordinate tower 7252 with sensors 7253 to determine the position of the master coordinate tower 7252 relative to the location of other robotic arms 7254*a*-7254*d* to conform the position, motion, and orientation of the other robotic arms 7254*a*-7254*d*. The master coordinate tower 7252 determines the footprint of the OR table 7256, the position and orientation of other robotic arms 7254*a*-7254*d*, the position and orientation of robotic end-effectors 7258*a*, 7258*b* shown as distance $d_1$, and the position and orientation of adjacent robotic components 7259 shown as dz. In one aspect, a primary sensor 7257 may be positioned on the OR table 7256.

Figure 177:
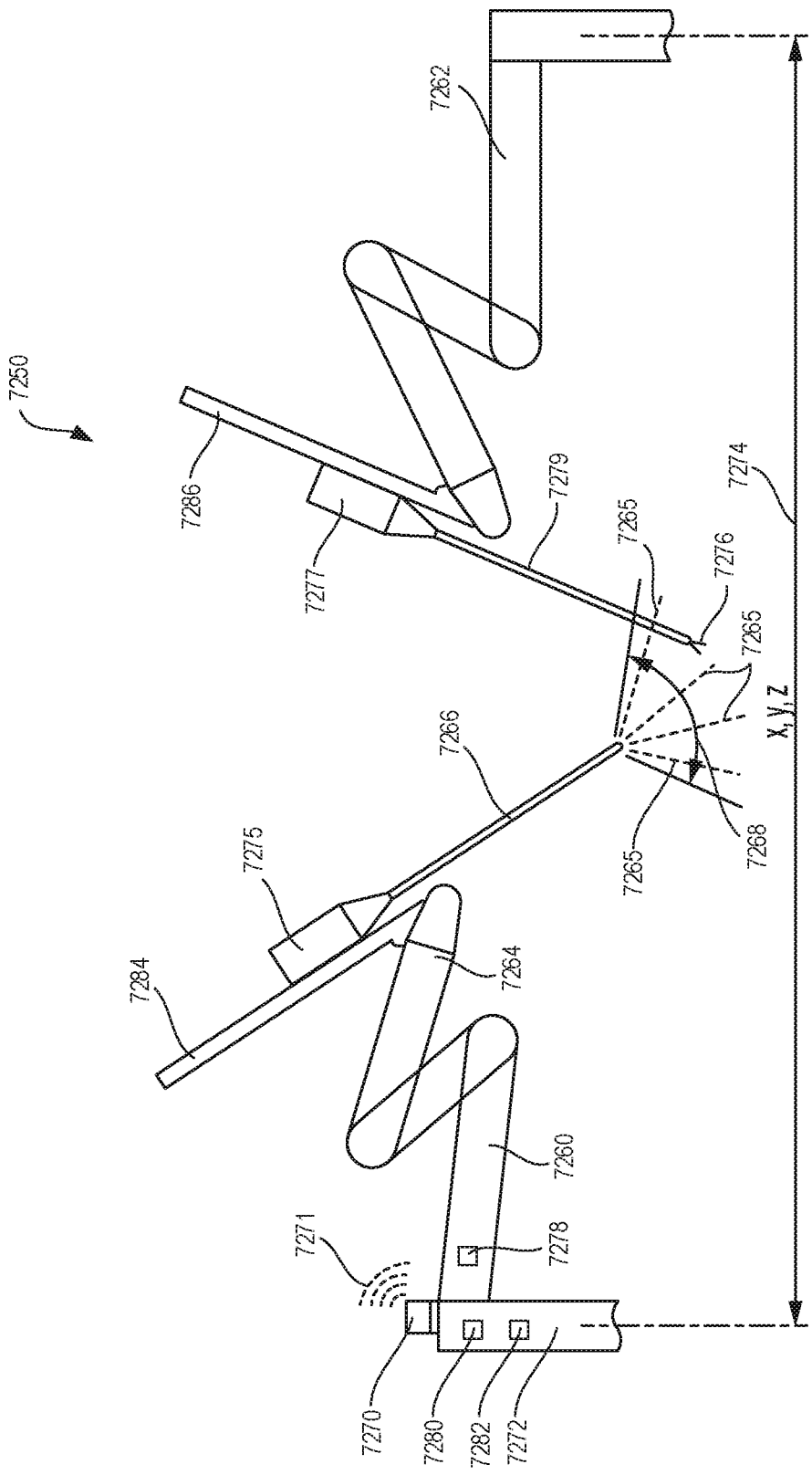
FIG. 177 is a detailed view of the system depicted in FIG. 176 according to at least one aspect of the present disclosure

FIG. 177 is a detailed view of the system 7250 depicted in FIG. 176 according to at least one aspect of the present disclosure. As depicted in FIG. 177, an endoscope control robotic arm 7260 is selected as a master coordinate robotic arm to determine the position and orientation of a secondary robotic arm 7262. The endoscope control robotic arm 7260 includes an endoscope arm 7264 to hold and guide a robotic surgical tool 7275 mounted on a linear slide 7284 equipped with an endoscope 7266. The endoscope 7266 is configured to generate a stereoscopic cos array 7265 in the optical scope field of view 7268. The endoscope control robotic arm 7260 also includes a magnetic field generator 7270 mounted on a fixed component 7272 of the endoscope control robotic arm 7260 to generate a magnetic field 7271. The endoscope control robotic arm 7260 determines the gross orientation 7274 in the x, y, z coordinate system of the secondary robotic arm 7262 relative to the endoscope control robotic arm 7260. The secondary robotic arm 7262 includes a robotic surgical tool 7277 mounted on a linear slide 7286 equipped with a motorized surgical stapler 7279 that includes an end-effector 7276.

With reference now to FIGS. 176-177, in one aspect, the system 7250 may be implemented optically by using the endoscope control arm 7260 as the master control robotic arm. The system 7250 may include both the stereoscopic cos arrays 7265 for visualization as well as secondary sensors 7270, 7278 to determine proximity of adjacent robotic structures, such as the secondary robotic arm 7262. Ultrasonic sensors may be positioned around the perimeter of the stereoscopic cos array 7265 generated by the endoscope 7266 to prevent cross-talk and allow the endoscope 7266 to simultaneously actively ping for distance, size, and orientation of adjacent robotic components 7259, such as the secondary robotic arm 7262. In one aspect, the system 7250 may include the integration of impedance sensors with magnetic field generators 7270 to generate a magnetic field 7271. In one aspect, the system 7250 may include RFID 7278, both active and/or passive RFID sensors, located on the master coordinate robotic arm 7260, such as, for example, the endoscope control arm 7260.

In one aspect, the system 7250 may include a passive method that includes an endoscope arm 7264 configured to generate an RF wake-up signal to be received by the communication array of the adjacent robotic end-effector 7276 or robotic arms 7262 and configured to respond with a measured signal strength and directional aspect to allow the endoscope arm 7264 to calculate the location of an adjacent device, such as the end-effector 7276 located on the secondary robotic arm 7262.

In another aspect, as an alternative to the passive method, the system 7250 may include an active method where a magnetic field generator 7270 is used to generate a magnetic field 7271 to create power within an adjacent RF transmitter 7280 and allow it to transmit a signal back to the master endoscope control arm 7260 device, such as the endoscope 7265. The master device, e.g., the endoscope 7265, would then calculate the signal strength of the returned signal and read its identifier in order to determine what device was responding and where it was located. In the active method, the endoscope control arm 7260 could have both an RF transmitter 7280 for RF signals and a receiver 7282 to receive the bounced back signal. This would allow it to determine the size, location, and orientation of adjacent structures.

Figure 178:
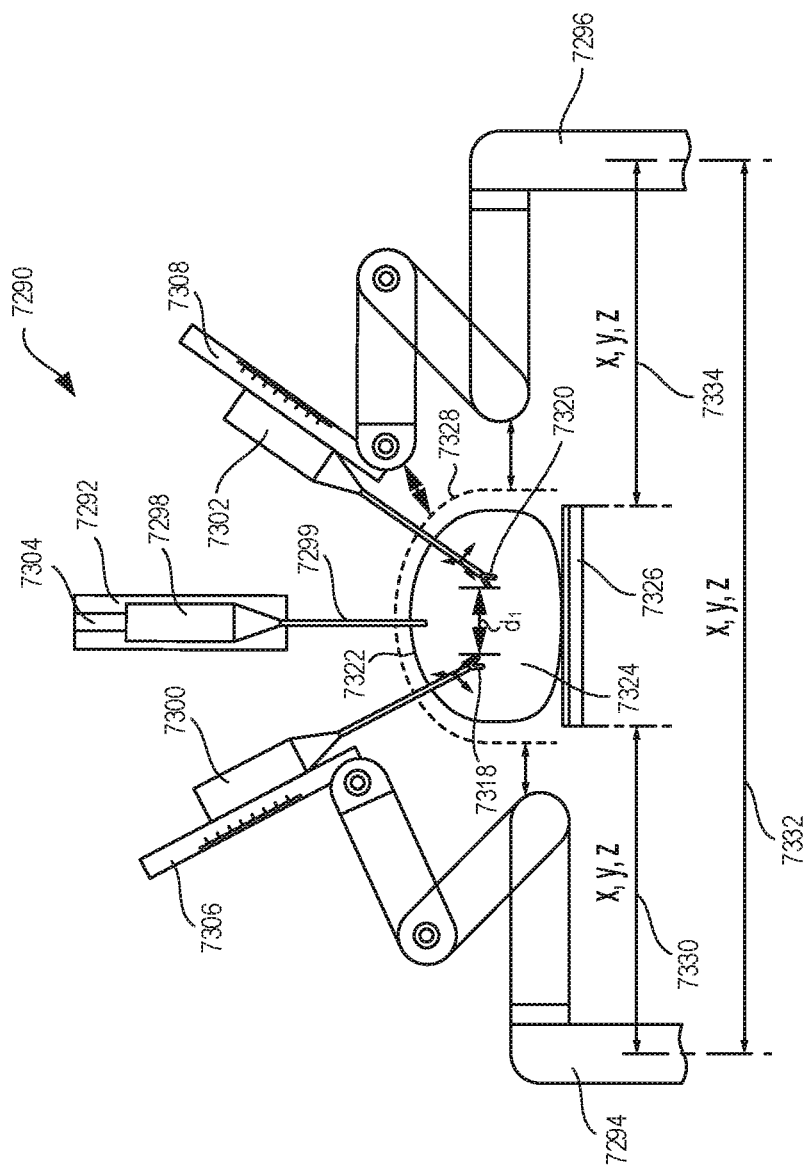
FIG. 178 illustrates a positioning and orientation system for a robotic surgical system that includes an end-effector to end-effector positioning and orientation according to at least one aspect of the present disclosure.
Figure 179:
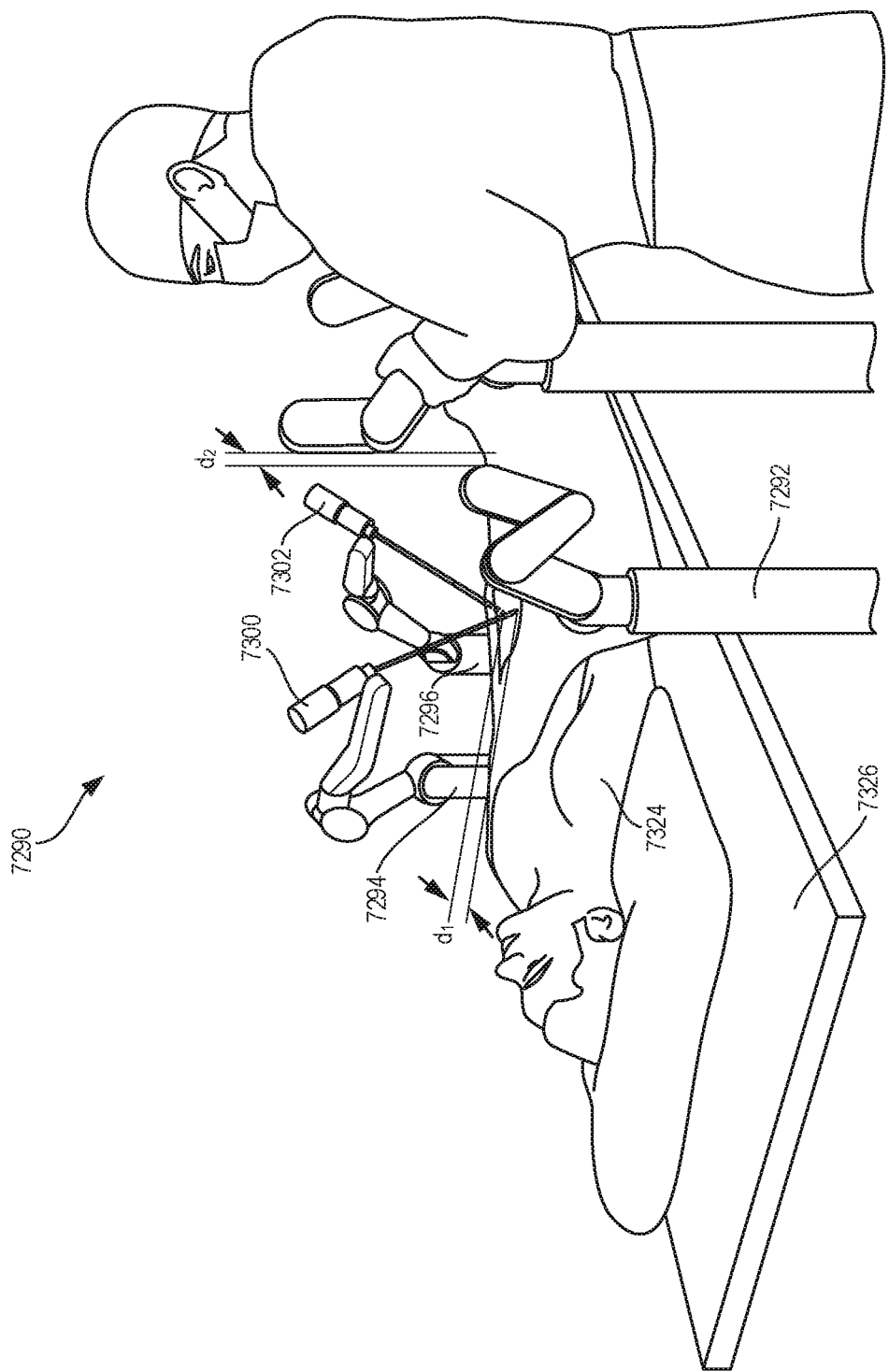
FIG. 179 is a perspective view of the end-effector to end-effector positioning and orientation system depicted in FIG. 178 according to at least one aspect of the present disclosure.
Figure 180:
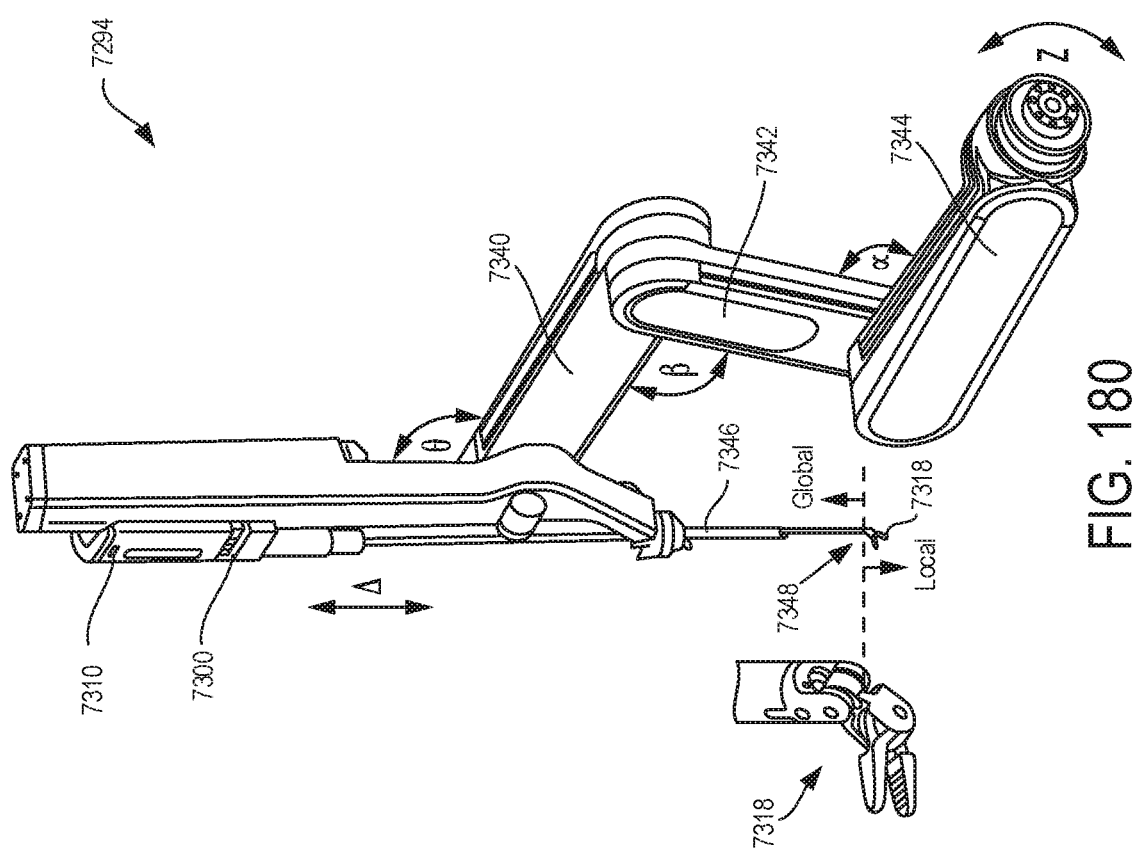
FIG. 180 illustrates one of the second robotic arm depicted in FIGS. 178 and 179, with global and local control of positioning and orientation according to at least one aspect of the present disclosure.

In various aspects, the present disclosure further provides a robotic surgical system and method for controlling and operating the control arms attached to the end-effectors end-effector to end-effector positioning and orientation as a control means for operating the control arms attached to the end-effectors. FIGS. 178-180 illustrate end-effector to end-effector communication and sensing to control robotic arm motions according to various aspects of the present disclosure.

FIG. 178 illustrates a positioning and orientation system 7290 for a robotic surgical system that includes an end-effector 7318 to end-effector 7320 positioning and orientation according to at least one aspect of the present disclosure. In the illustrated example, the positioning and orientation system 7290 includes a first robotic arm 7292, a second robotic arm 7294, and a third robotic arm 7296. It will be appreciated that the positioning and orientation system 7290 may include at least two robotic arms and more than three robotic arms, without limitation. The robotic arms 7292, 7294, 7296 includes linear robotic surgical tools 7298, 7300, 7302 mounted to linear slides 7304, 7306, 7308. The first robotic arm 7292 includes a vision system, such as for example, a visual endoscope 7299. The distal end of the endoscope 7299 includes optics for transmitting and receiving light in various wavelengths, including, for example, the cos array as previously discussed with respect to FIGS. 165, 166, 177. The second and third robotic arms 7294, 7296 each include robotic controlled robotic surgical tools 7300, 7302 that include end-effectors 7318, 7320 for surgical stapling and cutting, ultrasonic sealing and cutting, electrosurgical sealing and cutting, or a combination of stapling and cutting, ultrasonic sealing and cutting and electrosurgical sealing and cutting. The linear robotic surgical tools 7298, 7300, 7302 of each of the robotic arms 7292, 7294, 7296 is controlled by a driver 15028 which is controlled by the central control circuit 15002 as described with reference to FIG. 22 to advance and retract the robotic surgical tools 7298, 7302, 7304. The robotic arms 7292, 7294, 7296 are shown positioned within a body wall 7322 of a patient 7324 lying on an OR table 7326. A spatial envelope 7328, or guard band, is provided between the robotic arms 7292, 7294, 7296 and the body wall 7322 of the patient 7324. The robotic arms 7292, 7294, 7296 are configured to determine gross positioning and orientation 7330, 7332, 7334 in x, y, z coordinate space of each robotic arm 7292, 7294, 7296 and the OR table 7326.

The endoscope 7299 of the vision system is configured to determine positioning and orientation of the end-effectors 7318, 7320, including the distance $d_1$ between the end-effectors 7318, 7320. Certain portions of the second robotic arm 7294 are controlled with respect to the other first and third robotic arms 7292, 7296. Similarly, certain portions of the third robotic arm 7296 are controlled with respect to the first and second robotic arms 7292, 7294.

FIG. 179 is a perspective view of the end-effector to end-effector positioning and orientation system 7290 depicted in FIG. 178 according to at least one aspect of the present disclosure. The perspective view shows the intracorporeal distances $d_1$ between the end-effectors 7318, 7320. The perspective view also shows the extracorporeal distances $d_2$ between any of the robotic arms 7292, 7294, 7336.

FIG. 180 illustrates one of the second robotic arm 7294 depicted in FIGS. 178 and 49, with global and local control of positioning and orientation according to at least one aspect of the present disclosure. The robotic arm 7294 depicted in FIG. 180 is representative of the first robotic arm 7292 equipped with a visual endoscope 7299 as part of the vision system, for example, and also is representative of the third robotic arm 7296. The robotic arm 7294 includes a linear robotic surgical tool 7300 driven and actuated by a linear robotic surgical tool driver 7310 that includes a motor pack and controls local movements. The robotic surgical tool 7300 includes and end-effector 7318. The robotic arm 7294 includes first, second, and third pivotable arms 7340, 7342, 7344 that pivot to define angles θ, β, α as shown. The entire robotic arm 7294 rotates about axis defined by Z. The linear robotic surgical tool driver 7310 advances and retracts the shaft 7346 of the robotic surgical tool 7300 over Δ. The robotic arm 7294 controls global movements Z, θ, β, α. The linear robotic surgical tool driver 7310 controls local movement Δ, where the distal end 7348 of the shaft 7346 of the fixed robotic surgical tool 7300 is the dividing line 7348 between global control and local control.

With reference now to FIGS. 178-180, certain portions of the robotic control arm 7292, 7294, 7296 motions could be controlled based on the displacement of the end-effectors 7318, 7320 with respect to each other. Rather than actuating the linear robotic surgical tool driver 7310 a predefined distance Δ based on the user input, the relative closing of distance $d_1$ between any two end-effectors 7318, 7320 may be used by the central control circuit 15002 (FIG. 22).

With reference still to FIGS. 178-180, the illustrated end-effector 7318 to end-end-effector 7320 positioning and orientation system 7290 may include a vision system endoscope 7299 to determine the distances $d_1$, $d_2$ (FIG. 179), velocities, and orientations of the end-effectors 7318, 7320 directly. The endoscope 7299 is configured to follow the user input motions and to adjust the motions of the robotic control arm 7292 motions as necessary and to move the end-effectors 7318, 7320 in relation to a local coordinate system.

As depicted in FIG. 178, the 3D spatial envelope 7328 is provided for the positioning and orientation system 7290 to reduce collisions between the robotic arms 7292, 7294, 7296 and the body wall 7322 of the patient 7324. With a common coordinate system defined, the approved spatial envelope 7328 can be defined for each robotic arm 7292, 7294, 7296. Each robotic arm 7292, 7294, 7296 is given a 3D spatial envelope 7328 in which it is allowed to operate. Any need to exit this spatial envelope 7328 is requested from either another robotic arm 7292, 7294, 7296, the "master" control system central control circuit 15002 (FIG. 22), or all participants in the communication system (FIGS. 1-22). If the approving authority(s) agree, a new, adjusted envelope may be assigned to all robotic arms 7292, 7294, 7296. Accordingly, every single movement does not have to be negotiated by the control system for the positioning and orientation system 7290, only large-scale movements. This minimizes computational requirements and simplifies collision.

In various aspects, the present disclosure provides a robotic surgical system and method configured to adjust tissue tension based on robot shaft or robot arm measured macro shaft/end-effector torques. The robotic surgical system and method also provides an automation technique for operating an energy robotic surgical tool. The robotic surgical system and method also provides adjustment of control boundaries and warnings based on the determined temperature of the energy device end-effector.

Figure 181:
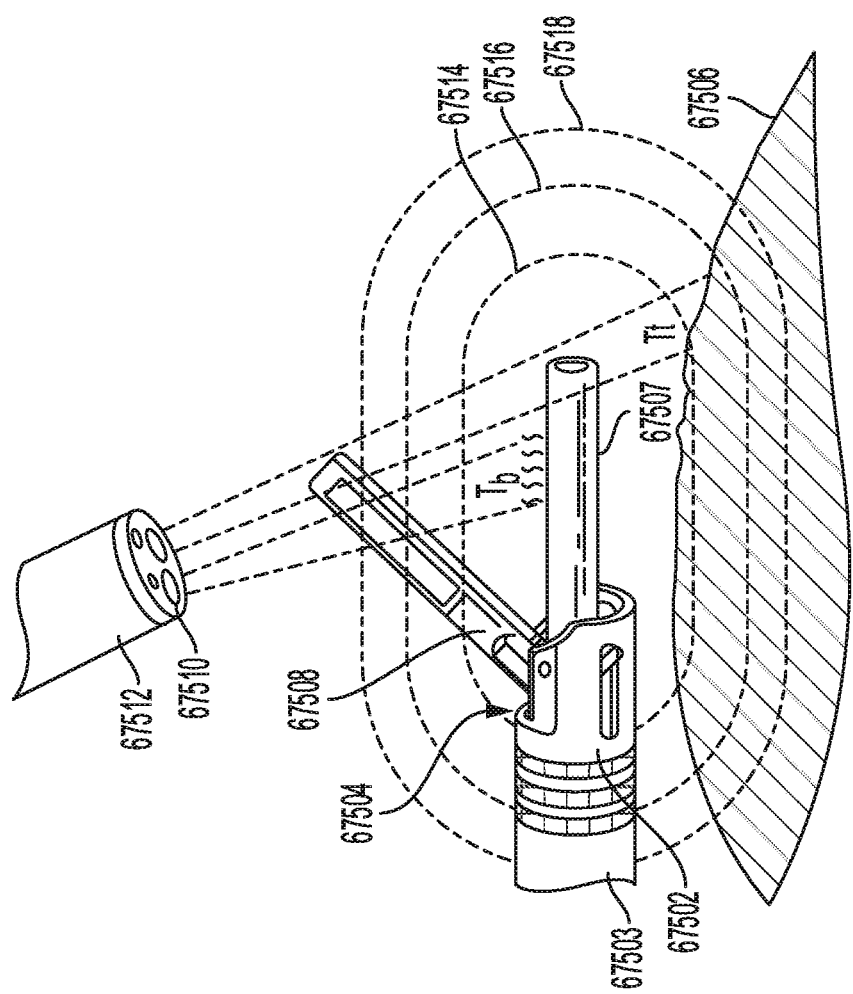
FIG. 181 illustrates an electromechanical robotic surgical tool with a shaft having a distal end and an end-effector mounted to the shaft in the vicinity of patient tissue according to at least one aspect of the present disclosure.

In one aspect, the robotic surgical system and method provide hyper-spectral imaging measurement of blade/end-effector temperature. FIG. 181 illustrates an electromechanical robotic surgical tool with a shaft 67503 having a distal end 67502 and an end-effector 67504 mounted to the shaft 67503 in the vicinity of patient tissue 67506 according to at least one aspect of the present disclosure. The end-effector 67504 includes jaws 67507, 67508, with jaw 67507 being in the form of an ultrasonic blade. The shaft 67503 and the end-effector 67506 are part of a robotic surgical system and can be mounted on an electromechanical arm. The robotic surgical system can include an endoscope, such as binocular scope 67512, having at least one visual sensor 67510. The illustrated visual sensor 67510 is disposed at a distal end of a binocular scope 67512. The illustrated visual sensor 67510 is an infrared sensor, but the visual sensor can be a CCD, a CMOS, or the like. The visual sensor 67510 can be configured to detect the temperature $T_b$ of at least part of the end-effector 67504, for example of the ultrasonic blade 67507 of the end-effector 67504, and/or the temperature $T_t$ of the tissue 67506 of the patient that is adjacent the end-effector 67504.

In one aspect, a controller can be configured to compare the temperature $T_b$ of the ultrasonic blade and the temperature $T_t$ of the tissue of the patient and determine distance thresholds 67514, 67516 and 67518 for different temperatures of the end-effector 67504. The distance thresholds 67514, 67516 and 67518 can represent a variety of safe and/or non-harmful distances for the tissue 67506 and/or the end-effector 67504, such as the closest distance from the end-effector 67504 of the patient that the heated end-effector 67504 can be positioned without causing damage to the tissue 67506. For example, distance threshold 67514 can represent the closest position an end-effector 67504 having a temperature $T_1$ can be positioned with respect to the tissue 67506 of the patient; distance threshold 67516 can represent the closest position an end-effector 67504 having a temperature $T_2$ can be positioned with respect to the tissue 67506 of the patient; and distance threshold 67518 can represent the closest position an end-effector 67504 having a temperature $T_3$ can be positioned with respect to the tissue 67506 of the patient.

Temperature $T_1$ is less than temperature $T_2$ which is less than temperature $T_3$. The temperatures $T_1$, $T_2$, $T_3$ can represent the temperature $T_b$ of the ultrasonic blade 67507 directly or can represent the compared temperatures between the temperature $T_b$ of the ultrasonic blade and the temperature $T_t$ of the tissue. An infrared sensor, such as the Melexis MLX90621, can be integrated into the binocular scope 67512 and/or the end-effector 67504, and can act to compare the end-effector temperature with an adjacent tissue temperature for an accurate indication of temperature. This process can occur before and/or during and/or after use of the end-effector to affect tissue. Force thresholds based on force limits can also be used in addition to or instead of distance thresholds.

Figure 182:
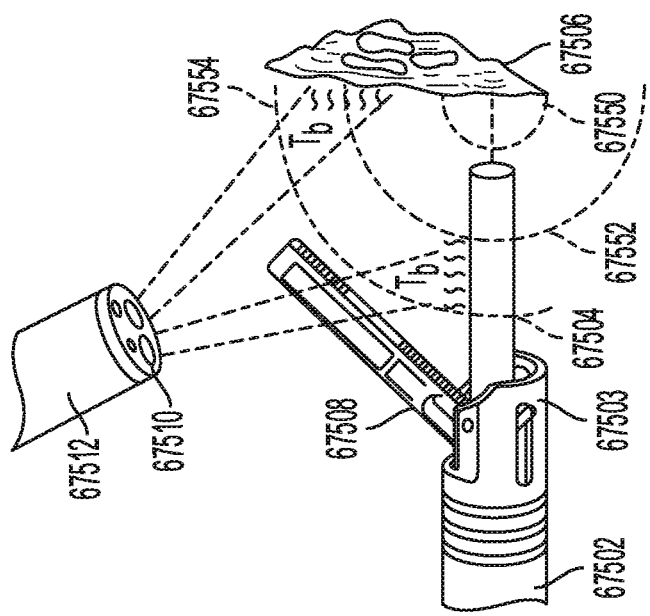
FIG. 182 illustrates the end-effector in the vicinity of tissue according to at least one aspect of the present disclosure.

While FIG. 181 illustrates measuring threshold distances from the end-effector 67504, distances can also be measured from surrounding tissue. For example, FIG. 182 illustrates the end-effector 67504 in the vicinity of tissue 67506 according to at least one aspect of the present disclosure. However, threshold distances 67550, 67552, and 67554 are measured relative to tissue 67506 instead of the end-effector 67504, as is depicted in FIG. 181. A safe threshold distance of the end-effector 67504 from tissue 67506 can thus vary depending on the temperature of the end-effector 67504.

Figure 183:
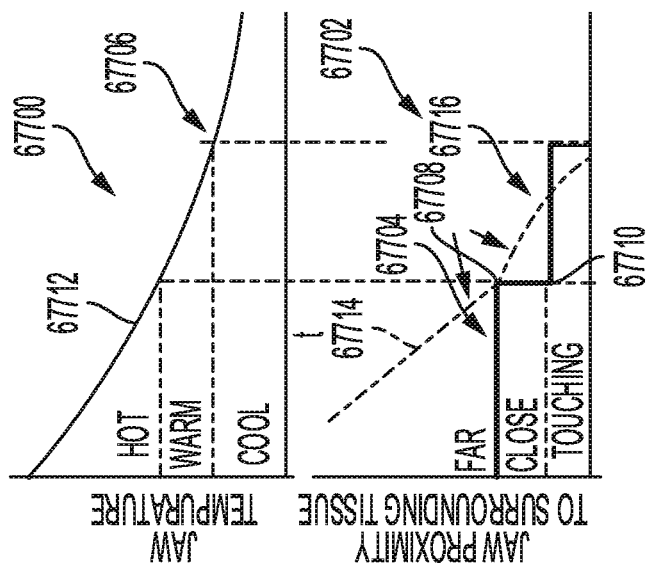
FIG. 183 is a graphical illustration of jaw temperature and jaw proximity to surrounding tissue as a function of time according to at least one aspect of the present disclosure.

As illustrated FIG. 182, the controller can be configured to facilitate movement of the end-effector 67504 toward the tissue 67506 of the patient at varying distances from the tissue based on temperature. When the temperature of the end-effector 67504 is at a highest point (illustrated on the far left of graph 67700 of FIG. 182), the heated end-effector 67504 is disposed at a location farthest from tissue 67506 of the patient (illustrated on the far left of graph 67702 of FIG. 183). Thus graph 67702 illustrates the $T_2$ distance threshold 67704. The $T_2$ distance threshold 67704 is the closest distance that the heated end-effector 67504 having a temperature $T_2$ can get to the tissue 67506 of the patient without causing damage. As the temperature of the end-effector 67504 reduces over time, the end-effector 67504 can get closer to tissue 67506 without damaging the tissue 67506. At 67706 the end-effector 67504 is at a low enough temperature to be able to touch the tissue 67506 without causing damage to the tissue 67506 (illustrated on the far right of graphs 67700, 67702).

With reference to graph 67702, at time 67708 the robotic surgical system can be configured to stop the advance of the end-effector 67504 toward the tissue 67506 until the temperature of the end-effector 67504 has decreased further. For example, line 67710, illustrated in the graph 67702, represents the closest proximity of the end-effector 67504 with respect to the tissue 67506 of the patient when the temperature of the end-effector 67504 is below a temperature 67712.

When the temperature of the end-effector 67504 has a temperature $T_1$, the robotic surgical system can be configured to stop the movement of the end-effector 67504 toward the tissue 67506 of the patient at the distance 67514. The distance 67514 is represented by the line 67710 in graph 67702 of FIG. 183. At 67716, the robotic surgical system can be configured to halt the movement of the end-effector 67504 toward the tissue 67506. Dashed line 67714 of graph 67702 is an exemplary illustration of the velocity of end-effector 67504. As the end-effector 67504 approaches tissue 67506, the velocity of end-effector 67504 can be configured to be reduced to ensure the controller and the overall robotic system can stop the end-effector 67504 at selected distance thresholds. In some variations, an alert can be provided to the operator of the robotic surgical system that the heated end-effector 67504 has reached a threshold distance. Reference may be made to U.S. patent application Ser. No. 15/238,001, now U.S. Patent Application Publication No. 2018/0049792, the entire contents of which are incorporated herein by reference, for additional detailed discussion.

In one aspect, the present disclosure provides a robotic surgical system and method for measuring blade temperature using natural frequency shifting. In one aspect, an internal shaft temperature sensor is employed to sense heat flux from the end-effector.

Figure 184:
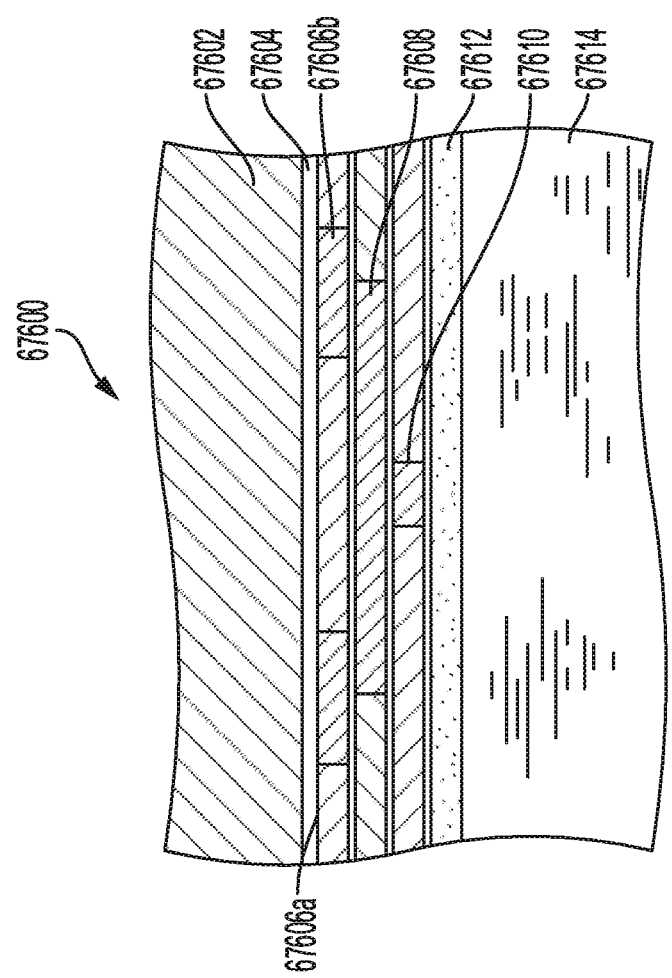
FIG. 184 is a cross-sectional view of one aspect of a flexible circuit 67600 comprising RF electrodes and data sensors embedded therein according to at least one aspect of the present disclosure.
Figure 185:
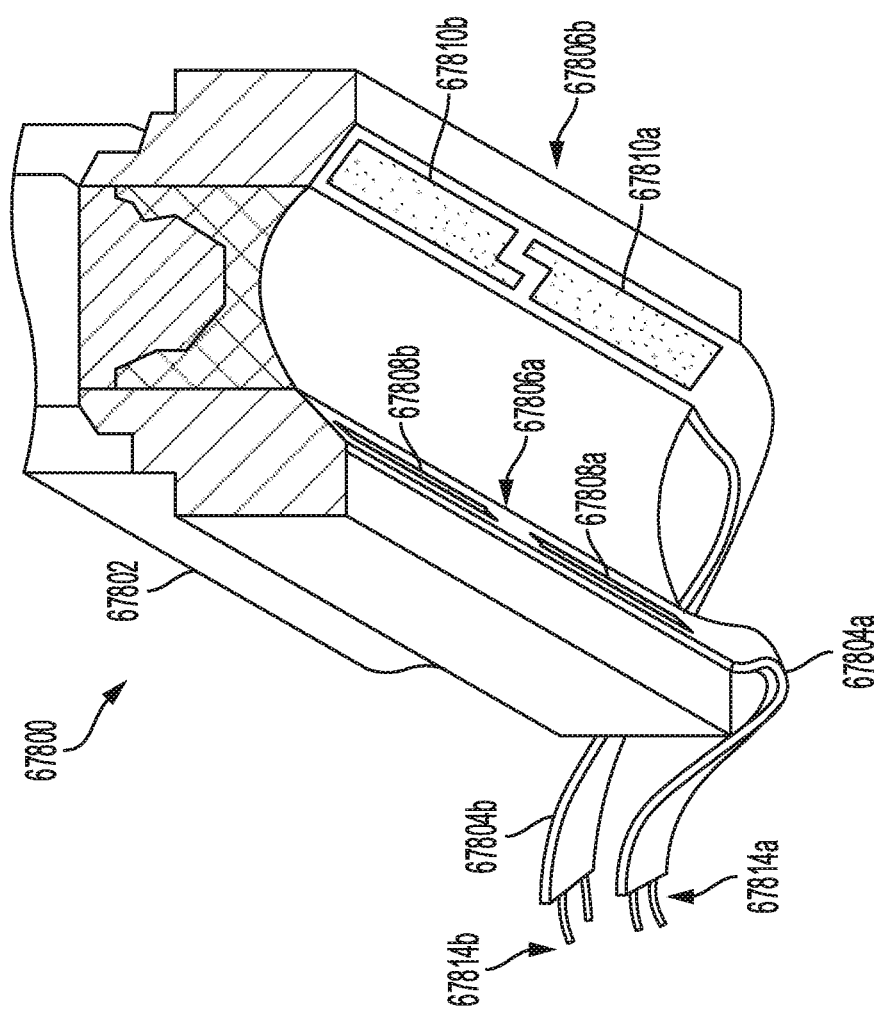
FIG. 185 illustrates an end-effector with a jaw member, flexible circuits, and segmented electrodes provided on each flexible circuit according to at least one aspect of the present disclosure.

In one aspect, the present disclosure provides a robotic surgical system and method that includes an integrated flexible circuit for with a thermal sensor to measure the component temperature of mechanisms and components of a robotic surgical tool. FIG. 184 is a cross-sectional view of one aspect of a flexible circuit 67600 comprising RF electrodes and data sensors embedded therein according to at least one aspect of the present disclosure. The flexible circuit 67600 can be mounted to the right or left portion of an RF clamp arm 67602, which is made of electrically conductive material such as metal. Below the RF clamp arm 67602, down (vertical) force/pressure sensors 67606a, 67606b are embedded below a laminate layer 67604. A transverse force/pressure sensor 67608 is located below the down (vertical) force/pressure sensor 67606a, 67606b layer and a temperature sensor 67610 is located below the transverse force/pressure sensor 67608. An electrode 67612 is electrically coupled to the generator and configured to apply RF energy to the tissue 67614 located below the Turning now to FIG. 185, an end-effector 67800 comprises a jaw member 67802, flexible circuits 67804a, 67804b, and segmented electrodes 67806a, 67806b provided on each flexible circuit 67804a, 67804b. Each segmented electrode 67806a, 67806b comprises several segments. As shown, a first segmented electrode 67806a comprises first and second segment electrode segments 67808a, 67808b and a second segmented electrode 67806b comprises first and second segment electrode segments 67810a, 67810b. The jaw member 67802 is made of metal and conducts heat to maintain the jaw member 67802 cool. Each of the flexible circuits 67804a, 67804b comprises electrically conductive elements 67814a, 67814b made of metal or other electrical conductor materials and are electrically insulated from the metal jaw member 67802 by an electrically insulative laminate. The conductive elements 67814a, 67814b are coupled to electrical circuits located either in a shaft assembly, handle assembly, transducer assembly, or battery assembly.

Figure 186:
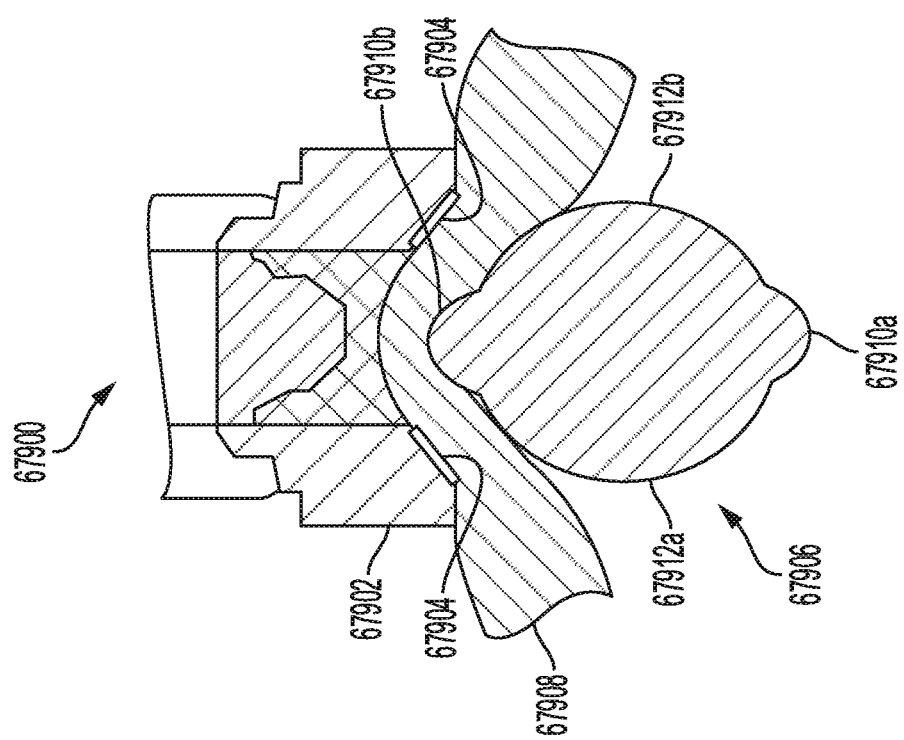
FIG. 186 is a cross sectional view of an end-effector comprising a rotatable jaw member, a flexible circuit, and an ultrasonic blade positioned in a vertical orientation relative to the jaw member with tissue located between the jaw member and the ultrasonic blade according to at least one aspect of the present disclosure.

FIG. 186 is a cross sectional view of an end-effector 67900 comprising a rotatable jaw member 67902, a flexible circuit 67904, and an ultrasonic blade 67906 positioned in a vertical orientation relative to the jaw member with tissue 67908 located between the jaw member 67902 and the ultrasonic blade 67906. The ultrasonic blade 67906 comprises side lobe sections 67910a, 67910b to enhance tissue dissection and uniform sections 67912a, 67912b to enhance tissue sealing. In the vertical orientation depicted in FIG. 186, the ultrasonic blade 67908 is configured for tissue dissection.

The flexible circuit 67904 includes electrodes configured to deliver high-frequency (e.g., RF) current to the tissue 67908 grasped between the jaw member 67902 and the ultrasonic blade 67906. In one aspect, the electrodes may be segmented electrodes as described herein in connection with FIG. 185. The flexible circuit 67904 is coupled to a high-frequency (e.g., RF) current drive circuit. In the illustrated example, the flexible circuit electrodes 67904 are coupled to the positive pole of the high-frequency (e.g., RF) current energy source and the ultrasonic blade 67906 is coupled to the negative (e.g., return) pole of the high-frequency (e.g., RF) current energy source. It will be appreciated that in some configurations, the positive and negative poles may be reversed such that the flexible circuit 67904 electrodes are coupled to the negative pole and the ultrasonic blade 67906 is coupled to the positive pole. The ultrasonic blade 67906 is acoustically coupled to an ultrasonic transducer. In operation, the high-frequency (e.g., RF) current is employed to seal the tissue 67908 and the ultrasonic blade 67906 is used to dissect tissue using ultrasonic vibrations. Reference may be made to U.S. patent application Ser. No. 15/382,238, now U.S. Patent Application Publication No. 2017/0202591, the entire contents of which are incorporated herein by reference, for additional detailed discussion.

In one aspect, the present disclosure provides a robotic surgical system and method for automatic adjustment of robotic drive shafts to control cut techniques. FIGS. 187A and 187B illustrate an embodiment of an end-effector 68400 of a robotic surgical system in accordance with the described techniques. As depicted in FIG. 187A, the end-effector 68400 includes a lower jaw or ultrasonic blade 68410, and an upper jaw or clamp member 68420 that are configured to clamp tissue therebetween. In this example, the end-effector 68400 is shown in operation, when tissue 68430 is clamped between the blade and clamp member 68410, 68420. In the illustrated example, the tissue 68430 is in the form of a blood vessel. A person skilled in the art will appreciate, however, that the tissue can be any other type of tissue.

In operation, as depicted in FIG. 187A, when the clamp member 68420 is brought in proximity to the blade 68410 and the tissue 68430 is clamped therebetween, ultrasound energy is applied to the tissue 68430. FIG. 187A illustrates by way of example the end-effector 68400 engaged with the tissue 68430 when cauterization of the tissue 68430 is complete. The described techniques can be used to coagulate and cauterize tissue, and these processes are used interchangeably. Treating tissue with ultrasound energy involves destroying tissue by cauterization, which leads to coagulation of the tissue—denaturing protein in the tissue and tissue desiccation. To create an effective seal across the tissue 68430, the tissue cauterized and coagulated in a controlled manner. Thus, creation of the tissue involves a precise control over a number of parameters during cauterization, such as a power level, pressure exerted on tissues by the jaws of an end-effector, lift velocity of an ultrasound blade, and other parameters.

As mentioned above, FIG. 187A illustrates the end-effector 68400 when cauterization of the tissue 68430 is completed. As depicted in FIG. 187A, the blade and the clamp member 68410, 68420 are shown in contact with the tissue 68430. When the robotic surgical system determines that the cauterization of the tissue 68430 is complete, the surgical system causes the end-effector 68400 to be lifted, such that the blade 68410 performs a (final) cut through the tissue. FIG. 187B illustrates that the end-effector 68400 (and thus the blade 68410) is lifted, as schematically shown by arrows one of which is labeled as 68414a, and the tissue 68430 is cut, such that a portion of the tissue 68432 is disassociated from the end-effector 68400 (another portion of the cut tissue 68430 is not labeled).

Figure 188:
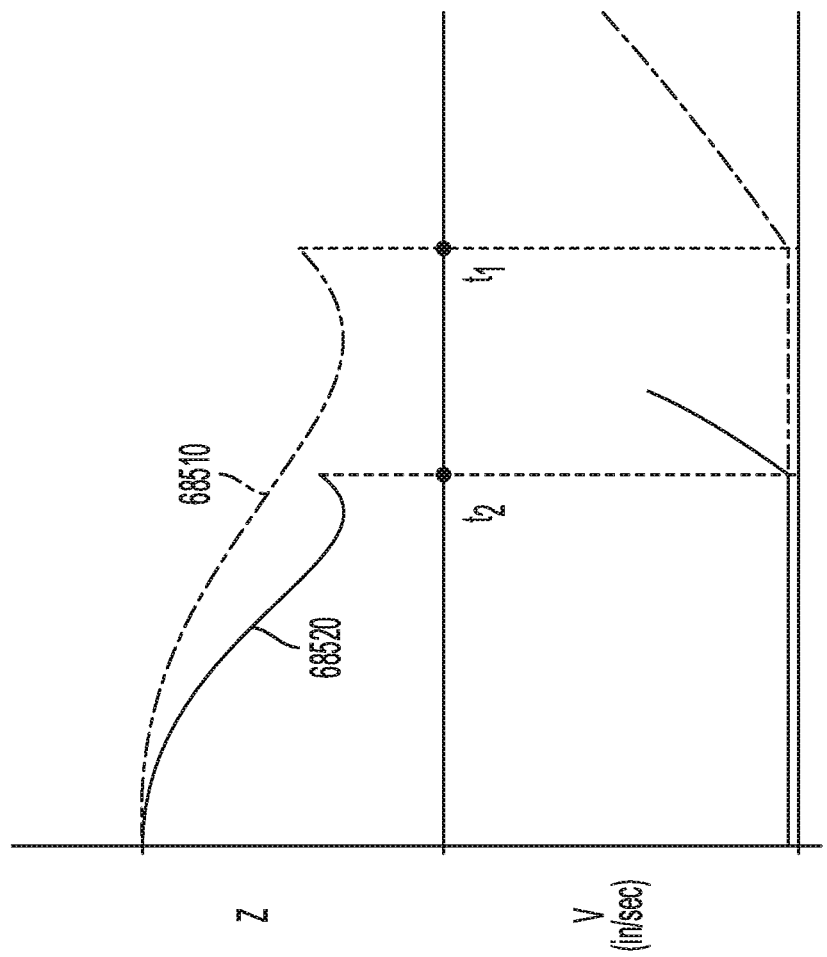
FIG. 188 illustrates two examples of graphs of trajectory curves representing impedance values and corresponding curves representing lift velocities of end-effectors blades for different types of tissues according to at least one aspect of the present disclosure.

FIG. 188 illustrates two examples of graphs of trajectory curves representing impedance values and corresponding curves representing lift velocities of end-effectors blades for different types of tissues. The impedance curves represent tissue impedance values measured when the end-effector, such as the end-effector 68400 in FIGS. 187A and 187B, is used to apply ultrasonic energy to tissue when the end-effector is in contact with the tissue. The lift velocity curves (which can be, in some cases, linear) represent respective velocities with which the end-effector can be automatically lifted once cauterization of tissue having certain characteristics is determined to be complete.

FIG. 188 shows an impedance curve 68510 for one type of tissue, such as a larger (thicker) vessel or other type of tissue. FIG. 188 also shows an impedance curve 68520 for another type of tissue, such as a smaller (thinner) vessel or other type of tissue. The curves 68510, 68520 can be constructed using tissue impedance values (z) as a function of time (t). As shown, both curves 68510, 68520 have a shape resembling a bathtub. In particular, regardless of their specific shapes and length, the curves 68510, 68520 follow a period of a decrease of the initial (relatively high) tissue impedance, which can be followed by a plateau, and then by an increase in electrical impedance of the tissue. The curves 68510, 68520 terminate at first and second time points t1, t2 at which certain threshold impedance values are reached. These indicate a completion of the tissue cauterization process upon which the surgical system can cause a lift of the end-effector. It should be appreciated that the time points t1, t2 are referred to herein as "first" and "second" for description purposes only, and not to indicate any order. Reference may be made to U.S. patent application Ser. No. 15/237,691, now U.S. Patent Application Publication No. 2018/0049798, the entire contents of which are incorporated herein by reference, for additional detailed discussion.

Figure 189:
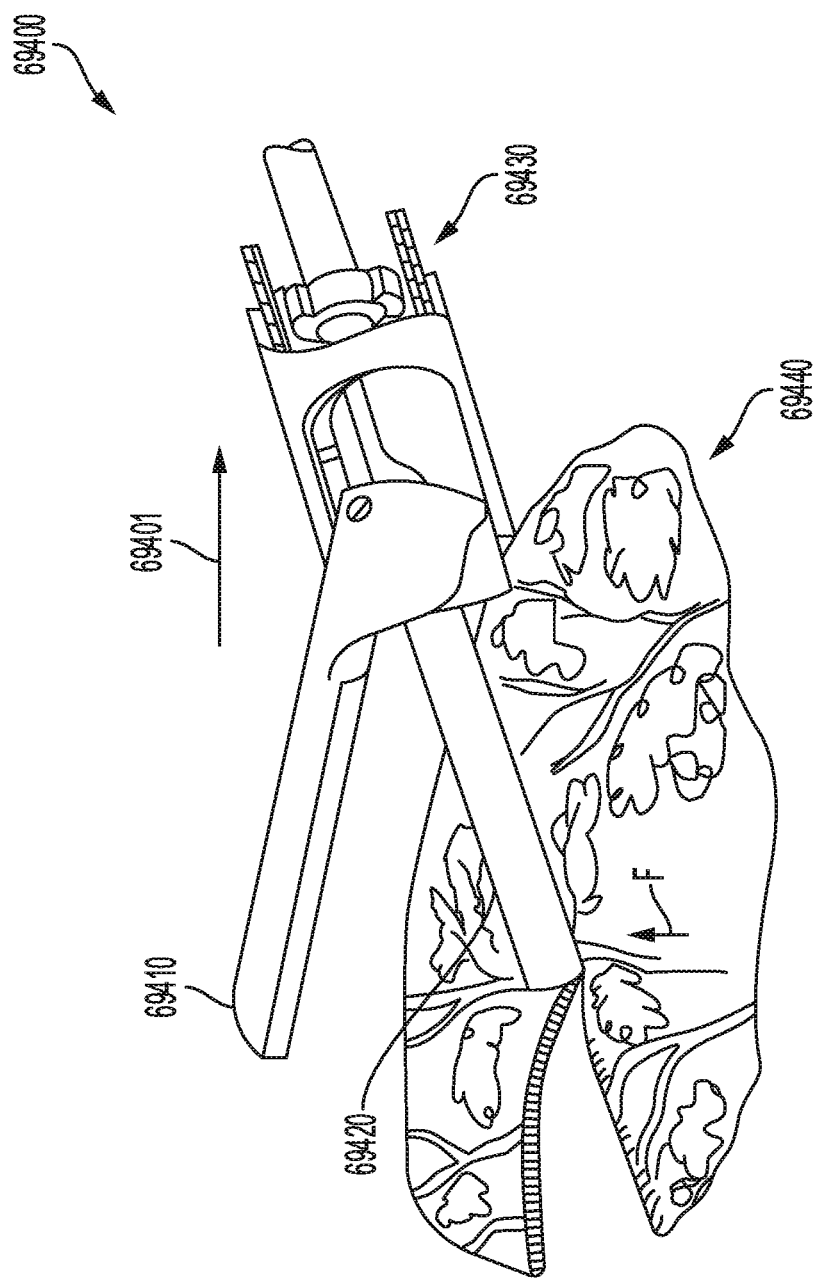
FIG. 189 illustrates an end-effector of a robotic surgical system according to at least one aspect of the present disclosure.

In various aspects, the present disclosure provides a robotic surgical system that includes energy control based on the sensed advancement rate and pressure of drawing an ultrasonic jaw over a tissue structure. FIG. 189 illustrates an end-effector 69400 of a robotic surgical system according to at least one aspect of the present disclosure. The end-effector 69400 is configured to cut and seal tissue by applying one or more forms of energy (e.g., ultrasonic and/or RF) thereto. The end-effector 69400 includes an upper jaw or a clamp member 69410 and a lower jaw or blade 69420 that are configured to clamp tissue therebetween or contact tissue in other ways. The end-effector can also be moved over tissue with an outer surface of the blade 69420 positioned in contact with the tissue. The end-effector can be advanced, dragged, or otherwise moved along the tissue to create a cut therethrough or other feature. The end-effector also includes a strain gauge 69430.

In some embodiments, the end-effector 69400 can be adapted to sense one or more parameters including, for example, a force F exerted against the end-effector 69400. FIG. 188 illustrates by way of example a position of the end-effector 69400 when it is moved (e.g., dragged) along a tissue 69440 in a direction of an arrow 69401. In this example, as shown, the end-effector 69400 is moved in the direction 69401 as the tissue 69440 is being cut such that the cut is created. The strain gauge 69430 can be configured to measure the force F exerted against the end-effector 69400 (e.g., the blade 69420) by the tissue 69440. Specifically, the strain gauge 69430 is subjected to a bend load that corresponds to the force F exerted against the end-effector 69400 (e.g., the blade 69420). In the illustrated example, the tissue 69440 is in the form of mesentery tissue. However, it should be appreciated that the tissue 69440 can be any other type of tissue without departing from the scope of the present disclosure. Reference may be made to U.S. patent application Ser. No. 15/237,700, now U.S. Patent Application Publication No. 2018/0049817, the entire contents of which are incorporated herein by reference, for additional detailed discussion.

FIG. 190 illustrates the sensor assembly 69000 coupled adjacent to an embodiment of an end-effector 69050 that includes a cutting robotic surgical tool 69060 (e.g., tissue boring robotic surgical tool) according to at least one aspect of the present disclosure. As depicted in FIG. 190, the sensor assembly 69000 is coupled to a part of a shaft 69040 with the end-effector 69050 at a distal end of the shaft 69040. Forces applied to a distal end of the cutting robotic surgical tool 69060 are sensed in the shaft 69040 by the sensor assembly 69000. The shaft 69040 and end-effector 69050 can be part of a robotic surgical tool assembly coupled to a robotic arm of a robotic surgical system, with the sensor assembly 69000 in communication with the control system. As such, the control system can control the movement of the robotic arm and thus the cutting robotic surgical tool 69060 to perform a cutting or boring of tissue using the cutting robotic surgical tool 69060. As depicted in FIG. 190, the cutting robotic surgical tool 69060 (which can be an ultrasonic wave guide) has an elongated cylindrical body that is configured to bore into tissue, such as by jackhammering a distal end of the elongated cylindrical body against and through tissue to puncture or cut through the tissue. Although the cutting robotic surgical tool 69060 is depicted in FIG. 190 as having an elongated cylindrical body, the cutting robotic surgical tool 69060 can have any number of various shapes and features for cutting, puncturing, or making an incision in tissue without departing from the scope of this disclosure.

FIGS. 191A-191C illustrate an example of the cutting robotic surgical tool 69060 boring through tissue 69100. As depicted in FIG. 191A, the distal end of the cutting robotic surgical tool 69060 is not in contact with the tissue 69100 and therefore a force is not applied against the distal end of the cutting robotic surgical tool 69060 by the tissue 69100. The control system can detect the absence of the applied force to commence or increase the advancement of the robotic arm in the direction of the tissue 69100 to assist with cutting into the tissue 69100. As depicted in FIG. 191B, the distal end of the cutting robotic surgical tool 69060 is in contact with the tissue 69100 and a force is applied against the distal end of the cutting robotic surgical tool 69060 by the tissue 69100. A variety of forces can be applied to the distal end of the cutting robotic surgical tool 69060 as the cutting robotic surgical tool 69060 advances through the tissue, which can be monitored by the control system for determining appropriate velocities of movement of the robotic arm (e.g., jackhammering velocity, velocity of advancement of cutting robotic surgical tool, etc.). Control of the robotic arm by the control system can be based on such determined appropriate velocities to assist with effectively cutting the tissue 69100. As depicted in FIG. 191C, the distal end of the cutting robotic surgical tool 69060 is extending through the tissue 69100 and is no longer in contact with the tissue 69100. As such, a force is not applied against the distal end of the cutting robotic surgical tool 69060 by the tissue 69100. The control system can detect the absence of the applied force to decrease, including stop, the advancement or movement of the robotic arm, which can prevent unwanted cutting or boring of adjacent tissue. As such, the control system can determine appropriate velocities and directions of movement based on current and past sensed forces and velocities.

Figure 192:
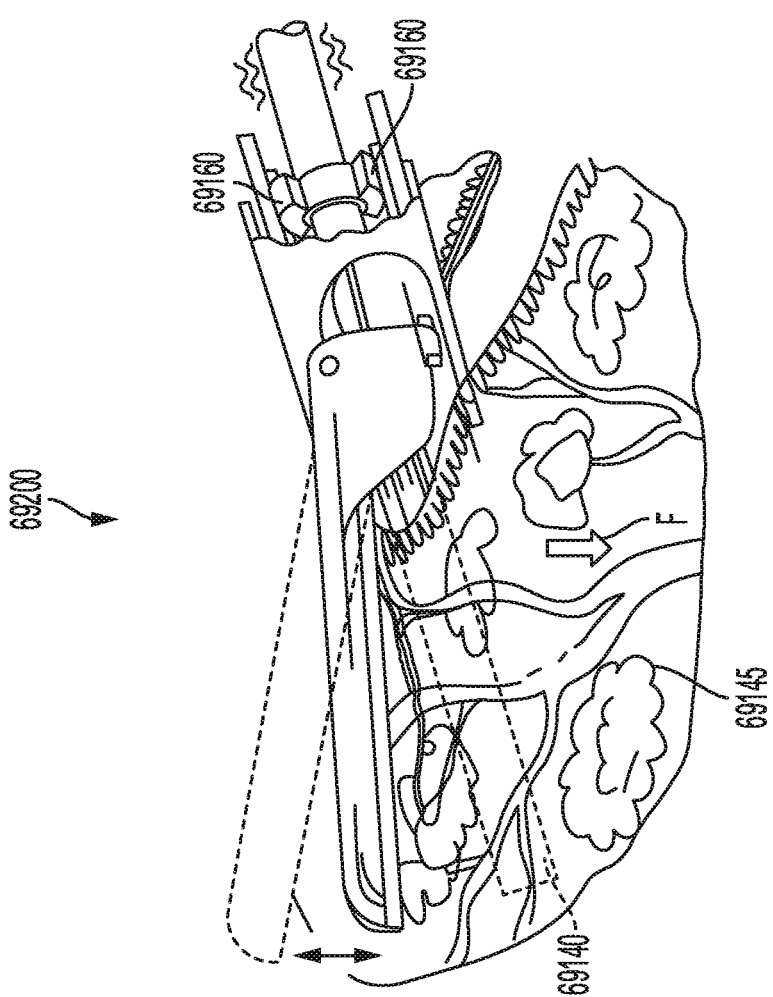
FIG. 192 illustrates an end-effector being lifted or angled to cause the force applied by tissue to increase against an ultrasonic blade thereby assisting with cutting the tissue as the end-effector is advanced in a direction that cuts the tissue according to at least one aspect of the present disclosure.

FIG. 192 illustrates an end-effector being lifted or angled to cause the force applied by the tissue to increase against the ultrasonic blade 69140 thereby assisting with cutting the tissue 69145 as the end-effector 69200 is advanced in a direction that cuts the tissue 69145 according to at least one aspect of the present disclosure. Such lifting or angling can be caused by the control system collecting data from the sensors 69160 and determining that the tissue 69145 does not have a tension that is within the desired or optimal tension range. As such, the control system can either adjust the velocity of movement of the robotic arm (including stop movement) in the advancing direction (e.g., to cut tissue) or adjust the orientation of the end-effector 69200 relative to the tissue (e.g., angle, lift, and/or lower the end-effector 69200). For example, if the control system determines that the tension is too low, the control system can either reduce the velocity of movement of the robotic arm in the advancing direction or move the end-effector 69200 such that it is either lifted or angled to create more tension in the tissue 69145. Based on the determined tissue tension, the control system can determine and control an appropriate energy density that is delivered to or received from the ultrasonic blade 69140. For example, if tissue tension is determined to be below a threshold, the velocity of advancement of the robotic arm may be increased. In contrast, stopping or slowing advancement of the robotic arm may further reduce tension. As such, if the tissue tension is above the threshold, the velocity of the robotic arm can be reduced to prevent damage to the tissue. Furthermore, compression applied to the tissue (e.g., via jaw closure) can be increased when the tissue tension is above a threshold and/or additional power can be applied to the tissue to speed up cutting and thereby assist with decreasing tissue tension.

Figure 193:
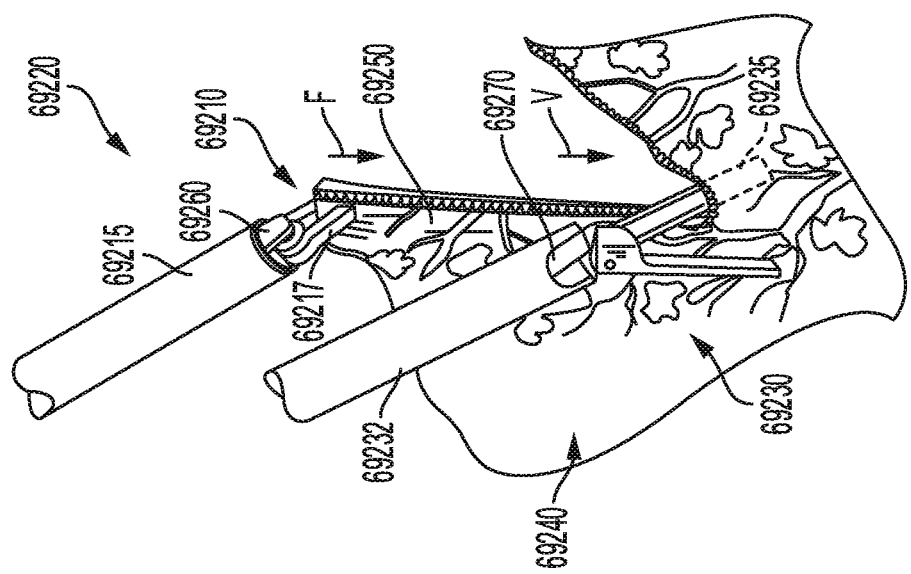
FIG. 193 illustrates a first end-effector of a first robotic surgical tool assembly coupled to a first robotic arm and a second end-effector of a second robotic surgical tool assembly coupled to a second robotic arm according to at least one aspect of the present disclosure.
Figure 200:
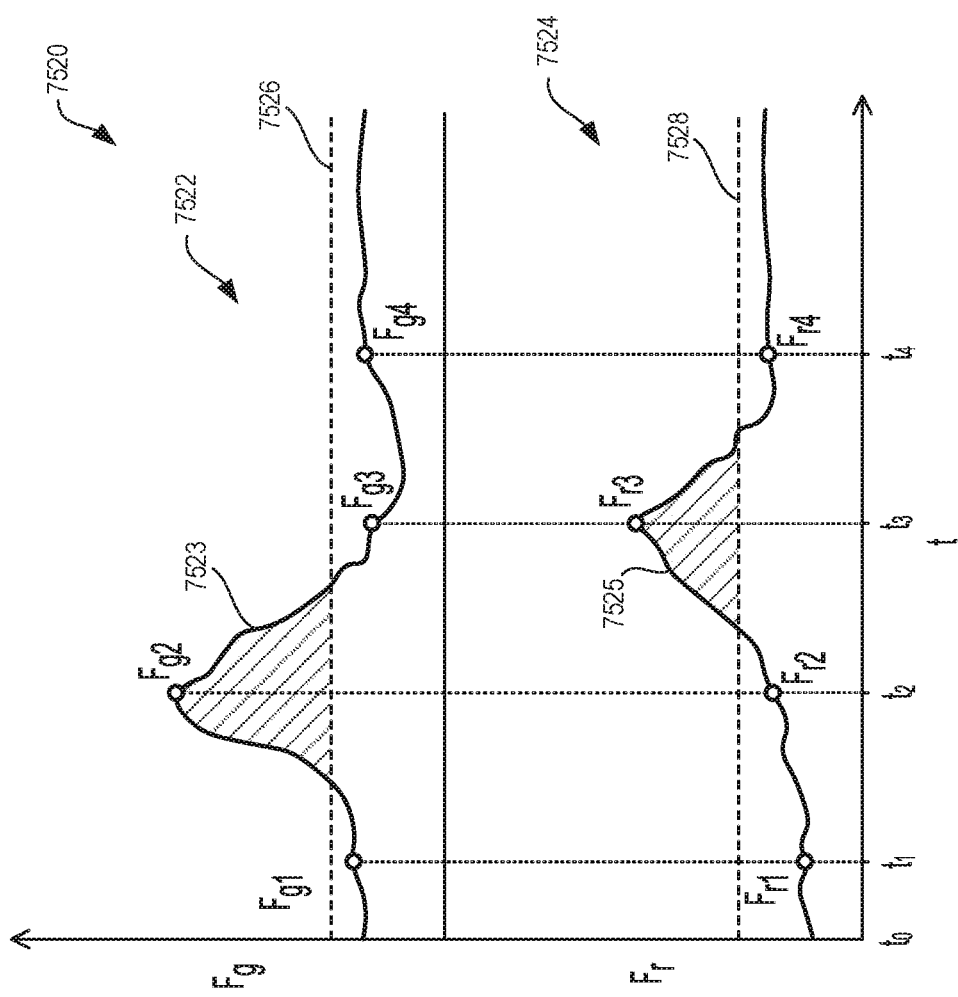
FIG. 200 is a graphical illustration of control of robotic arms of both internal colon grasper device and a shaft of a circular stapler to achieve acceptable tissue tension according to at least aspect of the present disclosure.

FIG. 193 illustrates an embodiment of a first end-effector 69210 of a first robotic surgical tool assembly 69220 coupled to a first robotic arm and a second end-effector 69230 of a second robotic surgical tool assembly 69240 coupled to a second robotic arm according to at least one aspect of the present disclosure. The first end-effector 69210 is coupled to a distal end of a first shaft 69215 of the first robotic surgical tool assembly 69220 and includes a pair of jaws 69217 that are movable between and open and closed configurations. In the closed or partially closed configuration, the pair of jaws 69217 secure a part of tissue 69250 therebetween, as depicted in FIG. 193 The pair of jaws 69217 is in communication with a first sensor 69260 that is configured to measure a tension in the tissue 69250 that is partially captured between the pair of jaws 69217. The first sensor 69260 is in communication with a control system of the robotic surgical system and the control system can detect and monitor the measurements collected by the first sensor 69260. Based on such measurements, the control system can determine and control one or more of a variety of movement parameters associated with either the first or second robotic arm to effectively and efficiently cut the tissue 69250. The first sensor can include one or more of a variety of sensors, such as a strain gauge, and can be positioned in any number of locations along the first end-effector 69210 or first robotic surgical tool assembly 69220 for measuring tension in the tissue 69250. For example, any of the tissue tension measuring features and mechanisms discussed above (such as with respects to FIG. 192) can be implemented in this embodiment for measuring tension in the tissue 69250.

As depicted in FIG. 193, the second end-effector 69230 is positioned at a distal end of a second shaft 69232 of a second robotic surgical tool assembly 69240. The second end-effector 69230 includes a cutting robotic surgical tool or blade 69235 that can be advanced into the tissue 69250 for cutting the tissue. The cutting robotic surgical tool 69235 can include any number of features for assisting with cutting tissue, including any of the features discussed above for cutting tissue, such as the blade 69140 depicted in FIG. 192. The cutting robotic surgical tool 69235 is in communication with a second sensor 69270 that is configured to measure an amount of force applied on the cutting robotic surgical tool 69235. The second sensor 69270 is in communication with the control system, which can detect and monitor the applied forces measured by the second sensor 69270. Based on such measured forces, the control system can determine one or more of a variety of movement parameters associated with either the first or second robotic arm to effectively and efficiently cut the tissue 69250. The second sensor 69270 can include one or more of a variety of sensors, such as a strain gauge, and can be positioned in any number of locations along the second end-effector 69230 or second robotic surgical tool assembly 69240 for measuring the applied forces along the cutting robotic surgical tool 69235. For example, any of the force measuring features and mechanisms discussed above (such as with respects to FIGS. 191A-191C and 192) can be implemented in this embodiment for measuring a force applied against the cutting robotic surgical tool 69235. Reference may be made to U.S. patent application Ser. No. 15/237,753, now U.S. Patent Application Publication No. 2018/0049822, the entire contents of which are incorporated herein by reference, for additional detailed discussion.

In various aspects, FIGS. 194-198 illustrate circular stapler control to allow functional operation by the surgeon while also controlling internal devices according to various aspects of the present disclosure. FIG. 194 illustrates a patient 7400 lying on an OR table 7402 with a robot controlled circular stapler 7404 inserted in the rectal stump 7406 of the patient 7400 according to at least one aspect of the present disclosure. The circular stapler 7404 is controlled by a robotic arm 7408 and driven by a robotic surgical tool driver 7410. The OR table 7402 includes multiple load cells 7410 to measure torque and loads in the x, y, z coordinate space.

The robotic arm 7408 is controlled to minimize the macro tension of the rectal stump 7406 relative to an inside the abdomen measure of stump position, extension, and orientation. FIG. 195 illustrates a limiting robotic surgical tool 7404 induced tissue loading relative to a hard anatomic reference according to at least one aspect of the present disclosure. In the illustrated example, the robotic surgical tool 7404 is a circular stapler inserted in the rectal stump 7406 to a first depth $D_1$ abutting a pliable anatomical structure 7412. The circular stapler robotic surgical tool 7404 is inserted into the rectal stump 7406 in the direction indicated by arrow 7414. As the circular stapler robotic surgical tool 7404 is inserted into the rectal stump 7406 and contacts the pliable anatomical structure 7412 at the first depth $D_1$, the pliable anatomical structure 7412 is under tension and can be measured as the torque T induced on the robotic surgical tool 7404. When the robotic surgical tool 7404 reaches a maximum depth $D_{Max}$, the pliable anatomical structure 7412 is under a maximum tension corresponding to a maximum torque $T_{zMax}$ induced on the robotic surgical tool 7404. The torques T induced by the robotic surgical tool 7404 on the pliable anatomical structures 7412 could be measured by the reaction loads of the robotic surgical tool 7404 being compared to a relative ground based on the torques T measured on the patient 7400 or table 7402 by the load cells 7410.

Having determined the relative torques between the robotic surgical tool 7404 and the hard anatomic references (in this case the pelvis and the skeletal system) limits could be pre-defined to prevent the robotic surgical tool 7404 or robotic surgical tool driver 7410 from exceeding during the manipulation or insertion of the powered circular stapler robotic surgical tool 7404. As depicted in FIG. 195, when the torque induced on the robotic toll 7404 reaches a maximum torque $T_{zMax}$, the robotic surgical tool 7404 retracts slightly to be in ideal tissue tension.

FIGS. 196 and 197 illustrate the insertion of the robotic surgical tool 7404 into the rectal stump 7406 according to various aspects of the present disclosure. As depicted in FIG. 196, the robotic surgical tool 7404 is shown improperly inserted at an angle to the proper direction of insertion indicated by arrow 7414. This is improper and results in forces $F_1$ and $F_2$ inducing a torque T on the robotic surgical tool 7404 the can be measured. As depicted in FIG. 197, the robotic surgical tool 7404 is shown properly inserted in the direction indicated by arrow 7414. When the robotic surgical tool 7404 is properly inserted, there is minimal torque T induced on the robotic surgical tool 7404.

FIG. 198 is a graphical illustration 7420 of measured torque T on the OR table 7402 and robotic surgical tool 7404 positioning and orientation as a function of time t according to at least one aspect of the present disclosure. The three graphs will now be described in conjunction with FIGS. 194-198. The first graph 7422 depicts measured torque $T_x$ in the x-axis and robotic surgical tool 7404 position and orientation angle relative to the x-axis as a function of time t. As shown, there is little fluctuation in torque $T_x$ curve 7428 and x-axis angle 7430 over time about the 0-torque and 0°-angle reference line 7432. Accordingly, there is no robotic surgical tool 7404 adjustment by the robotic arm 7408 and robotic surgical tool driver 7410.

The second graph 7424 depicts measured torque $T_y$ in the y-axis and robotic surgical tool 7404 position and orientation angle relative to the y-axis as a function of time t. As shown, when the torque $T_y$ reaches a maximum torque $T_{yMax}$ limit 7434, the central control circuit 15002 (FIG. 22) adjusts the angle of the robotic surgical tool 7404 until the torque $T_y$ drops below the maximum torque $T_{yMax}$ limit 7434 and the angle relative to the y-axis drops down to 0°.

The third graph 7426 depicts measured torque $T_z$ in the z-axis and robotic surgical tool 7404 position and orientation angle relative to the z-axis, which corresponds to the depth of the robotic surgical tool 7404 inserted into the rectal stump 7406 (*cm*) as a function of time t. Here, as the depth into the rectal stump 7406, the torque $T_z$ remains within the ideal range as indicated by reference lines 7436 until the torque $T_z$ reaches the upper limit 7438 at which point, the central control circuit 15002 (FIG. 22) controls the robotic arm 7408 and driven by a robotic surgical tool driver 7410 to retract the robotic surgical tool 7404 to reduce tissue tension.

FIGS. 199A-199D is a sequence depicting control of the shaft 7500 of a circular stapler robotic surgical tool 7404 as the location of the shaft 7504 of the anvil 7503 is approximated to the extended shaft 7500 of the circular stapler 7404. FIGS. 199A-199D depict the combined multi-arm control motion thresholds for cooperative interactions of a grasper device 7508 located in the colon 7510 and the extended shaft 7500 of the circular stapler 7404 is located in the rectal stump 7406. Accordingly, as the robotic arms advance the shaft 7500 of the circular stapler 7404 and the anvil shaft 7504, the tissue tension $F_g$ on the colon 7510 and the tissue tension $F_r$ on the rectal stump 7406 are measured and the shaft 7500 of the circular stapler 7404 and the anvil shaft 7504 are adjusted to minimize each of the tissue tensions $F_g$, $F_r$.

With reference now to FIGS. 194-200, FIG. 200 is a graphical illustration 7520 of control of robotic arms of both internal colon grasper device 7508 and the shaft 7500 of the circular stapler 7404 to achieve acceptable tissue tension according to at least aspect of the present disclosure. With reference now also to FIGS. 199A-199D, the first graph 7522 depicts tissue tension 7523 ($F_g$) on the colon 7510 as a function of time t and the second graph 7524 depicts tissue tension 7525 ($F_r$) on the rectal stump 7406. The times $t_1$-$t_4$ correspond to the state of the procedure depicted in FIGS. 199A-199D.

With reference still to FIGS. 194-200, as depicted in FIG. 199A, the grasper device 7508 is holding the anvil shaft 7502 and applies a first tissue tension $F_{g1}$ on the colon 7510 according to at least one aspect of the present disclosure. The extended shaft 7500 of the circular stapler 7404 is located in the rectal stump 7406 and applies a first tissue tension $F_{r1}$ on the rectal stump 7406. As shown in the first and second graphs 7522, 7524 depicted in FIG. 200, at time $t_1$, the tension $F_{g1}$ is below the acceptable tissue tension threshold 7526 on the colon 7510 and the tension $F_{r1}$ is below the acceptable tissue tension threshold 7528 on the rectal stump 7406.

With reference still to FIGS. 194-200, as depicted in FIG. 1998, the grasper device 7508 has extended the anvil shaft 7502 into the shaft 7506 of the circular stapler 7404, which has been further extended into the colon 7510 and the rectal stump 7406 according to at least one aspect of the present disclosure. A second tissue tension $F_{g2}$ is applied on the colon 7510 and a second tissue tension $F_{r2}$ is applied on the rectal stump 7406. In this situation, the second tissue tension $F_{g2}$ applied on the colon 7510 is too high. Accordingly, the central control circuit 15002 (FIG. 22) controls the robotic arm and linear drive to reduce the tissue tension $F_{g2}$ on the colon 7510. As shown in the first and second graphs 7522, 7524 depicted in FIG. 200, at time $t_2$, the tension $F_{g2}$ has increased above the acceptable tissue tension threshold 7526 on the colon 7510 and the tension $F_{r2}$ remains below the acceptable tissue tension threshold 7528 on the rectal stump 7406.

With reference still to FIGS. 194-200, as depicted in FIG. 199C, the grasper device 7508 releases the anvil shaft 7502 and the tissue tension $F_{g3}$ on the colon 7510 is reduced according to at least one aspect of the present disclosure. The tissue tension $F_{r3}$ on the rectal stump 7406, however, is now too high. Accordingly, the central control circuit 15002 (FIG. 22) controls the robotic arm and linear drive to reduce the tissue tension $F_{r3}$ on the rectal stump 7406. As shown in the first and second graphs 7522, 7524 depicted in FIG. 200, at time $t_3$, the tension $F_{g3}$ has decreased below the acceptable tissue tension threshold 7526 on the colon 7510 and the tension $F_{r3}$ has increased above the acceptable tissue tension threshold 7528 on the rectal stump 7406.

With reference still to FIGS. 194-200, as depicted in FIG. 199D, the grasper device 7508 has released the anvil shaft 7502 and the tissue tension $F_{g4}$ on the colon 7510 is within an acceptable range according to at least one aspect of the present disclosure. The tissue tension $F_{r4}$ on the rectal stump 7406 also is within an acceptable range and the procedure can be completed. As shown in the first and second graphs 7522, 7524 depicted in FIG. 200, at time $t_4$, the tension $F_{g4}$ has remains below the acceptable tissue tension threshold 7526 on the colon 7510 and the tension $F_{r3}$ has decreased below the acceptable tissue tension threshold 7528 on the rectal stump 7406. Accordingly, the central control circuit 15002 (FIG. 22) determines that the circular stapler 7404 is read to fire.

With reference still to FIGS. 194-200, as illustrated in FIGS. 199A-199D and 200, the present disclosure provides a robotic surgical system and method for detecting the appropriate robotic surgical tool-to-robotic surgical tool coupling loads, such as tissue tension $F_g$, $F_r$, to determine if the anvil 7503 is properly seated on the circular stapler 7404. The present disclosure also provides a method of controlling the macro tissue tension $F_g$, $F_r$ of both the internal robotic arm controlling the grasper device 7508 grasping the anvil shaft 7502 and the external robotic arm controlling the shaft 7506 of the circular stapler 7404 to prevent positional tissue loads $F_g$, $F_r$ from exceeding predefined thresholds 7526, 7528.

Figure 201:
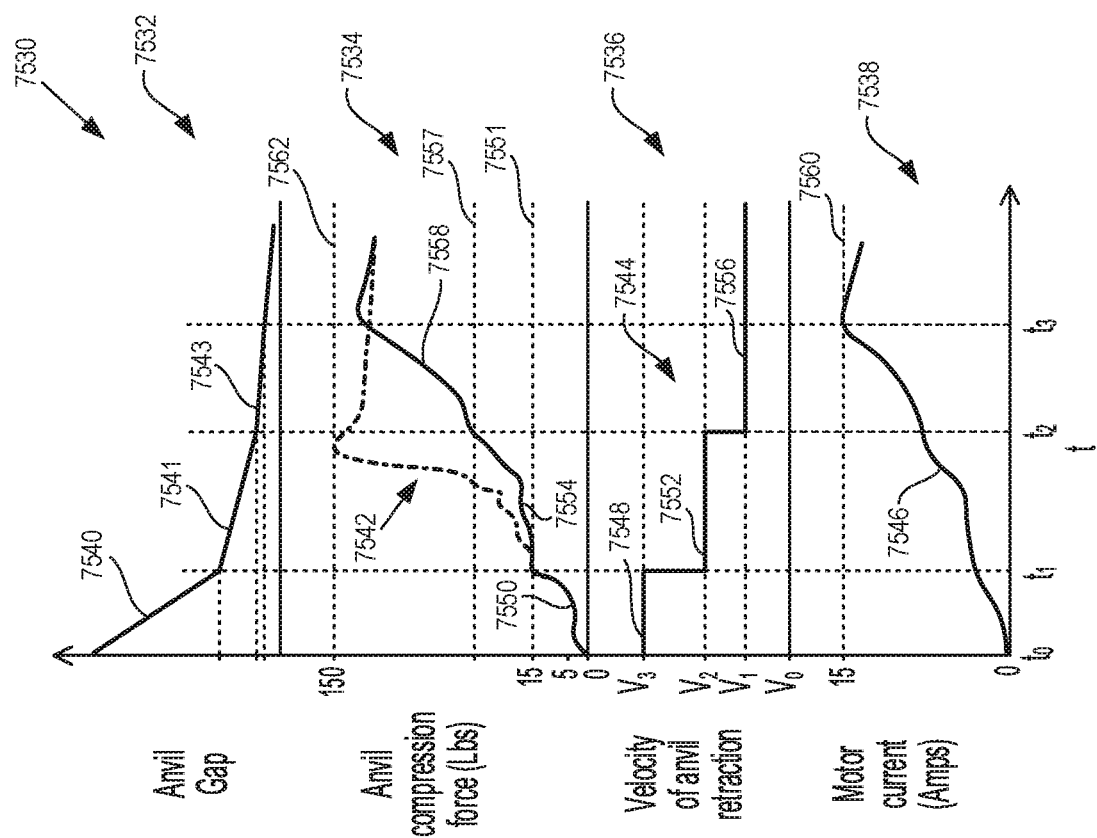
FIG. 201 is a graphical illustration of anvil shaft rate and load control of a robotic circular stapler closing system according to at least one aspect of the present disclosure.

With reference to FIGS. 194-201, in various aspects, the present disclosure provides a robotic surgical system and method for controlling the rate and load at which the anvil 7503 of the circular stapler 7404 is retracted. FIG. 201 is a graphical illustration 7530 of anvil shaft 7502 rate and load control of a robotic circular stapler 7404 closing system according to at least one aspect of the present disclosure. The first graph 7532 depicts anvil 7503 gap 7540 as a function of time (t). The anvil 7503 gap is the greatest as time to. The gap 7540 decreases sharply between $t_0$ and $t_1$ when the velocity 7544 of anvil 7503 retraction is the highest as shown in the third graph 7536. Between time $t_1$ and $t_2$, the gap 7541 decrease at a slower rate as the velocity 7544 of the anvil 7503 retraction is reduced. Between time $t_2$ and $t_3$, the gap 7543 decrease at an even slower rate as the velocity 7544 of anvil 7503 retraction is reduced even further.

With reference still to FIGS. 194-201, the second graph 7534 depicts anvil 7503 compression force 7542 (lbs.) as a function of time t and the fourth graph 7538 depicts motor current 7546 (amps) as a function of time t. The motor current 7546 increases proportionally to the tissue compression force 7542. Detection of the motor control current 7546 or tissue compression 7542 can be used to display initial compressive loading of the tissue and then to monitor the progression of the compression 7542. In one aspect, the present disclosure provides a robotic surgical system with antagonistic control of the anvil 7503 retraction compression 7542 based on the advancement of the staple drivers or cutting blade.

With reference still to FIGS. 194-201, the third graph 7536 depicts velocity 7544 of the anvil 7503 retraction as a function of time t. Limiting the retraction of the robotic circular stapler 7404 trocar rate and force below a predefined first threshold prevents accidental unseating of the anvil 7503 from the trocar. The retraction rate of the anvil 7503 would move at a first approximation rate 7548 when the anvil is first seated to the first tissue compression 7550, and then at a second rate 7552 slower than the first rate 7548 as the tissue compression 7554 progression occurs and the tissue compression exceeds a first threshold 7551, and then at a third rate 7556 slower than the second rate 7552 if the tissue compression 7558 exceeds a predefined threshold 7557 or motor current 7546 exceeds a predefined threshold 7560 and finally stopping if the current or tissue compression exceeds a maximum pre-defined threshold 7562.

In various aspects, the present disclosure provides a robotic surgical system and method for controlling the rate of advancement of staple drivers based on another controlled parameter of a robotic surgical tool such as control rate and thresholds of the stapler drivers based on the anvil clamping system. In one aspect, the central control circuit 15002 (FIG. 22) is configured to limit the rate of advancement of the staple driver based on the macro tissue tension $T_g$, $T_r$ measured by the robotic arm supporting the circular stapler 7404. In one aspect, the central control circuit 15002 (FIG. 22) is configured to limit the advancement rate of the drivers based on the motor current utilized to hold the anvil 7503 in position and resulting from tissue compression.

In various aspects, the present disclosure provides a robotic surgical system and method for controlling the rate or load limit of advancement of the cutting blade based on the reaction load measured through the motor current in the anvil clamping system. FIGS. 202-206 illustrate antagonistic control of the anvil clamping control system and the tissue cutting member control system according to at least one aspect of the present disclosure.

FIG. 202 is a schematic diagram of an anvil clamping control system 7600 of a surgical stapler 7602 grasping tissue 7604 between an anvil 7606 and a staple cartridge 7608 and the force $F_{anvil}$ on the anvil 7606 according to at least one aspect of the present disclosure. A knife 7610 is configured to advance distally to cut the tissue 7604. The diagram 7600 also shows the force $F_{anvil}$ on the anvil 7608 and the force $F_{tissue}$ of the tissue 7604.

FIG. 203 is a schematic diagram of a tissue cutting member control system 7620 of the surgical stapler 7602 depicted in FIG. 202 grasping tissue 7604 between the anvil 7606 and the staple cartridge 7608 and the force $F_{knife}$ on the knife 7610 while cutting the tissue 7604 according to at least one aspect of the present disclosure.

FIG. 204 is a schematic diagram 7630 of an anvil motor 7632 according to at least one aspect of the present disclosure. The anvil motor 7632 is an element of the anvil clamping control system 7600 depicted in FIG. 202. The anvil motor 7632 is configured to open and close the anvil 7606.

FIG. 205 is a schematic diagram 7640 of a knife motor 7642 according to at least one aspect of the present disclosure. The knife motor 7642 is configured to advance and retract the knife 7610 depicted in FIGS. 202-203.

FIG. 206 is a graphical illustration 7650 of an algorithm for antagonistic or cooperative control of the anvil clamping control system 7600 and the tissue cutting member control system 7620 as illustrated in FIGS. 202-205 according to at least one aspect of the present disclosure. The first graph 7652 depicts the anvil force $F_{anvil}$ as a function of time t. A normal anvil force 7660 ($F_{anvil}$) is shown in dashed line and a loaded anvil force 7662 ($F_{anvil}$) in shown in solid line. The second graph 7654 depicts the knife force $F_{knife}$ as a function of time t. A normal knife force 7664 ($F_{knife}$) is shown in dashed line and a loaded knife force 7666 ($F_{knife}$) in shown in solid line. The third graph 7656 depicts anvil motor velocity $V_{anvil}$ motor as a function of time t. A normal anvil motor velocity 7668 ($V_{anvil\ motor}$) is shown in dashed line and a loaded anvil motor velocity 7670 ($V_{anvil\ motor}$) is shown in solid line. The fourth graph 7658 depicts knife motor velocity $V_{knife}$ motor as a function of time t. A normal knife motor velocity 7672 ($V_{knife\ motor}$) is shown in dashed line and a loaded knife motor velocity 7674 ($V_{knife\ motor}$) is shown in solid line. As described herein antagonistic control is when the velocity V of the anvil motor 7632 and the knife motor 7634 are adjusted in an opposite direction and cooperative control is when the velocity V of the anvil motor 7632 and the knife motor 7642 are adjusted the same direction.

With reference now to FIGS. 202-206, at time interval T1 the force 7676 on the anvil 7606 is too high. Accordingly, the loaded anvil motor velocity 7670 ($V_{anvil\ motor}$) is increased 7678 and the loaded knife motor velocity 7674 ($V_{knife\ motor}$) is decreased 7680 by the central control circuit 15002 (FIG. 22) in an antagonistic manner to cooperate with the anvil clamping control system 7600.

With reference still to FIGS. 202-206, at time interval T2 the force 7682 on the knife 7610 is too high. Accordingly, the loaded anvil motor velocity 7670 ($V_{anvil\ motor}$) is increased 7684 and the loaded knife motor velocity 7674 ($V_{knife\ motor}$) also is increased 7686 by the central control circuit 15002 (FIG. 22) in a cooperative manner to cooperate with the tissue cutting member control system 7620.

With reference still to FIGS. 202-206, at time interval T3 the force 7688 on the anvil 7606 is too low. Accordingly, the loaded anvil motor velocity 7670 ($V_{anvil\ motor}$) is decreased 7690 and the loaded knife motor velocity 7674 ($V_{knife\ motor}$) is decreased 7692 by the central control circuit 15002 (FIG. 22) in a cooperative manner to cooperate with the anvil clamping control system 7600.

With reference still to FIGS. 202-206, in various aspects, in several robotic surgical tool configurations (surgical stapler-utters, for example) more than one of the end-effector functions are coupled mechanically to one another during operation. In one aspect, the anvil motor 7632 and the knife motor 7642 systems of a surgical stapler-cutter are often coupled and operate simultaneously to close the anvil 7606 (closing) and advance the knife 7610 while driving staples from the staple cartridge 7608 (firing) during the firing operation. In this case it would be helpful to use one of the anvil motor 7632 and the knife motor 7642 of the two system as a measure of the operation of the other systems or in some circumstances to allow one system to compliment or resist the advance of the other system.

With reference still to FIGS. 202-206, in various aspects, the cooperative or antagonistic operation of two mechanically coupled systems such as the anvil motor 7632 and knife motor 7642 would enable one system to aid in the force distribution of the overall end-effector needs. As described in the FIG. 206, one system could also inhibit the free operation of the other system if the loads induced by the tissue are too low to resist the advancement of one system given an expected advancement and torque rate, improving sensitivity of control and holding.

With reference still to FIGS. 202-206, in various aspects, cooperative or antagonistic operation of two mechanically coupled systems such as the anvil motor 7632 and knife motor 7642 may be implemented with non-symmetric use of a complimentary and/or antagonistic system for advancement and then another variant for retraction. In this way, the mechanically coupled system could limit the speed of advancement in an antagonistic manner and then assure retraction by then reverting to a cooperative retraction manner where the two systems work together to insure proper retraction without system degradation.

In various aspects, with reference back to FIG. 22, the processes described hereinbelow with respect to FIGS. 207-209 may be represented as a series of machine executable instructions stored in the memory 15006 and executed by the processor 15004 of the central control circuit 15002 of the robotic surgical system 15000 depicted in FIG. 22.

Figure 207:
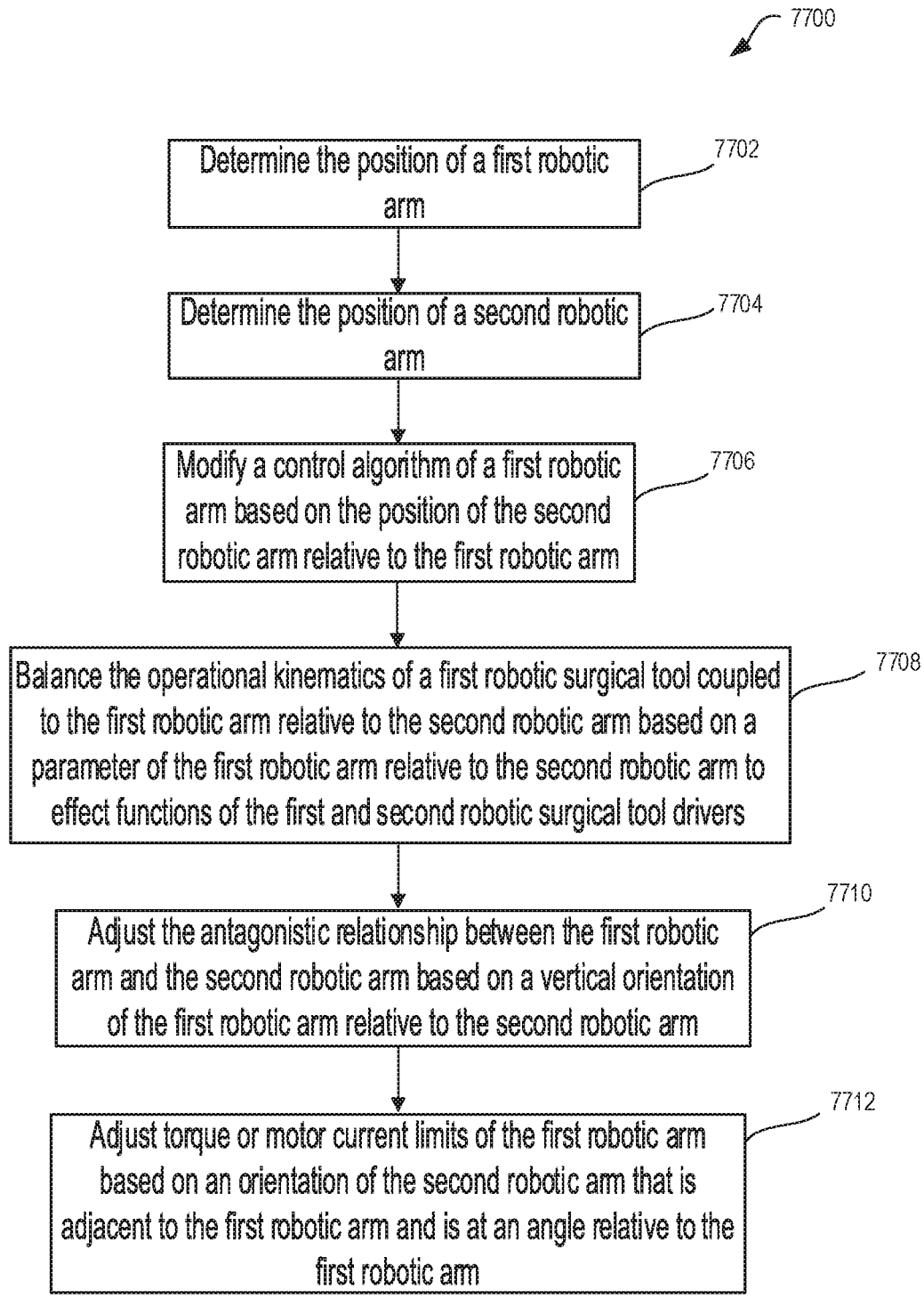
FIG. 207 is a flow diagram of a process depicting a control program or a logic configuration for controlling a first robotic arm relative to a second robotic arm according to at least one aspect of the present disclosure.

FIG. 207 is a flow diagram 7700 of a process depicting a control program or a logic configuration for controlling a first robotic arm relative to a second robotic arm according to at least one aspect of the present disclosure. The first robotic arm includes a first robotic surgical tool and a first robotic surgical tool driver. The second robotic arm includes a second robotic surgical tool and a second robotic surgical tool driver. The process depicted by the flow diagram 7700 may be represented as a series of machine executable instructions stored in the memory 15006 and executed by the central control circuit 15002 of the robotic surgical system 15000 depicted in FIG. 22. With reference now to FIGS. 22 and 207, in one aspect, the process depicted by the flow diagram 7700 may be executed by the central control circuit 15002, where the central control circuit 15002 is configured to determine 7702 the position of a first robotic arm. The central control circuit 15002 is configured to determine 7704 the position of a second robotic arm. The central control circuit 15002 is configured to determine distance, orientation, location of the first robotic arm relative to the second robotic arm. The central control circuit 15002 is configured to modify 7706 a control algorithm for the first robotic arm based on the position of the first robotic arm position relative to the position of the second robotic arm. In one aspect, the central control circuit 15002 modifies 7706 a control algorithm of a first robotic surgical tool driver of the first robotic arm based on the position of the second robotic arm relative to the first robotic arm. In another aspect, the central control circuit 15002 is configured to modify 7706 a control algorithm of a robotic surgical tool driver of the first or second robotic arms based on the relative position of the first and second robotic arms. In another aspect, the central control circuit 15002 is configured to balance 7708 the operational kinematics of a first robotic surgical tool coupled to the first robotic arm relative to the second robotic arm based on a parameter of the first robotic arm relative to the second robotic arm to effect functions of the first or second robotic surgical tool driver. In another aspect, the central control circuit 15502 is configured to adjust 7710 the antagonistic relationship between the first robotic arm and the second robotic arm based on a vertical orientation of the first robotic arm relative to the second robotic arm. In another aspect, the central control circuit 15002 is configured to adjust 7712 the torque limits or motor current limits of the first robotic arm based on an orientation of the second robotic arm that is adjacent to the first robotic arm and is at an angle relative to the first robotic arm.

FIG. 208 is a flow diagram 7800 of a process depicting a control program or a logic configuration for verifying a position or velocity of an end-effector jaw of a first surgical tool coupled to a first robotic arm based on a redundant calculation of a resulting movement of the end-effector from a motor application of control parameters of a second robotic arm coupled to a second surgical tool according to at least one aspect of the present disclosure. The first robotic arm includes a first robotic surgical tool, a first robotic surgical tool driver, and a first sensor to determine a position of the end-effector. The second robotic arm includes a second robotic surgical tool, a second robotic surgical tool driver, and a second sensor to determine the position of the end-effector independently of the first sensor. The process depicted by the flow diagram 7800 may be represented as a series of machine executable instructions stored in the memory 15006 and executed by the central control circuit 15002 of the robotic surgical system 15000 depicted in FIG. 22. With reference now to FIGS. 22 and 208, in one aspect, the process depicted by the flow diagram 7800 may be executed by the central control circuit 15002, where the central control circuit 15002 is configured to determine 7802 the position of the end-effector based on the first sensor. The central control circuit 15002 is configured to determine 7804 the position of the end-effector based on the second sensor. The central control circuit 15002 is configured to verify 7806 the position of the end-effector based on the positions determined by the first and second sensors. In one aspect, the first sensor includes a first sensor array disposed on the first robotic arm and the second sensor includes a second sensor array disposed on the second robotic arm, where the second sensor array is redundant to the first sensor array. The central control circuit 15002 is configured to determine 7808 the position of the end-effector through the first sensor array and to verify 7810 the position of the end-effectors through the second, redundant, sensor array. In one aspect, the first sensor is an internal coordinate tracking system of the first robotic arm and the second sensor is an optical tracking system coupled to the second robotic arm. In this aspect, the central control circuit 15002 is configured to determine the position of the end-effector based on the internal coordinate tracking system of the first robotic arm, determine the position of the end-effector based on the optical tracking system of the second robotic arm, and compare the position of the end-effector determined by the internal coordinate tracking system and the optical tracking system to verify the position of the end-effector. In one aspect, the first sensor is disposed on a master coordinate tower proximal to the first and second robotic arms, where the master coordinate tower is in communication with the central control circuit 15002, which is configured to determine the coordinates of the first and second robotic surgical tools. In one aspect, the first robotic surgical tool includes a first end-effector and the second robotic surgical tool includes a second end effector and the central control circuit 15002 is configured to determine the relative position between the first and second end-effectors. In one aspect, the central control circuit is configured to determine the position between the first and second robotic arms.

FIG. 209 is a flow diagram 7900 of a process depicting a control program or a logic configuration of controlling at least one operational parameter of a robotic surgical tool driver controlling a circular stapler robotic surgical tool based on another parameter measured within the robotic surgical tool driver controlling the circular stapler according to at least one aspect of the present disclosure. The robotic arm includes a circular stapler robotic surgical tool, a robotic surgical tool driver, and a sensor to measure a parameter within the surgical tool driver controlling the circular stapler. The process depicted by the flow diagram 7900 may be represented as a series of machine executable instructions stored in the memory 15006 and executed by the central control circuit 15002 of the robotic surgical system 15000 depicted in FIG. 22. With reference now to FIGS. 22 and 209, in one aspect, the process depicted by the flow diagram 7900 may be executed by the central control circuit 15002, where the central control circuit 15002 is configured to determine 7902 a first operational parameter of the robotic surgical tool and determine a second parameter of the robotic surgical tool based on a measurement. In one aspect, the central control circuit 15002 is configured to measure

7904 a tissue load induced on the tissue by the robotic surgical tool. The central control circuit 15002 is configured to determine 7906 an anatomic reference. The central control circuit 15002 is configured to determine 7908 an operational parameter on the robotic surgical tool based on the measured load induced on the tissue by the robotic surgical tool. The central control circuit 15002 is configured to limit 7910 the load induced on the tissue relative to the anatomic reference. The central control circuit 15002 is configured to control 7912 a rate of retraction of the robotic surgical tool based on the load induced on the tissue relative to the anatomic reference. In one aspect, the central control circuit 15502 is configured to measure the torques induced by the surgical robotic tool on a pliable structure based on a reaction load of the robotic surgical tool compared to a relative ground based on torques measured on either the patient or an operating room table equipped with an array of load sensors. In one aspect, the operational parameter of the surgical robotic tool is the motor current and rate of the retraction of the robotic surgical tool is dependent on a position, magnitude, and force of the anvil shaft, the drivers, or cutting member of the circular stapler.

Robotic Surgical System with Local Sensing of
Functional Parameters Based on Measurements of
Multiple Physical Inputs In various aspects, the present disclosure provides a robotic surgical system and method for monitoring the status of a robotic surgical tool in a redundant manner to verify the operation of the robotic surgical tool through measuring at least two separate sensors monitoring two different physical properties of the robotic surgical tool and robotic arm. In one aspect, one of the physical parameters is used to effect the measure of another physical parameter. In another aspect, at least one of the sensors is located on the robotic surgical tool and the other is located on the other side of a sterile barrier on the control arm. In another aspect, two different physical properties may be motor torque, motor current, strain in the mounting housing of the motor, strain on the sterile barrier mounting feature, reaction load of the arm to table, the reaction load of the patient with respect to the table, load distribution on the table, torque or resulting force within the robotic arm or any of its joints.

In various aspects, the present disclosure provides a robotic surgical system and method with dual modality of power transmission, motor control, and monitoring of a modular motor pack. The power transmission is capable of coupling electrically regardless of the orientation of the motor pack to the stationary wiring module about the primary rotation axis of the motor pack. At least one of the three (power transmission, motor control, data monitoring) includes a wired connection with the remaining couples being wireless. In another aspect, the wired connection includes a management feature within the housing to prevent binding or tangling. In another aspect, the power transmission is wireless power transmission between its fixed wire attachments on either or both sides. The wireless communication or power transmission may be coupled through at least two wire radial wire arrays with a pre-defined alignment between the arrays. The first array being positioned on a portion of the robotic surgical tool driver with the other coupled to the motor pack housed within the sterile barrier housing. In another aspect, the alignment is perpendicular to the axis defined by the tubular body of the sterile barrier clam shell. This configuration will enable more than a full rotation of the motor pack with respect to the robotic surgical tool driver while maintaining the alignment of the arrays. In another aspect, the coupled arrays capable of transmitting power or RF communication between the sterile portion of the robotic surgical tool and the non-sterile portion of the control arm while maintaining a constant signal strength or transmission strength throughout the entire rotation of the motor pack. In another aspect, the attached modular robotic surgical tool assembly capable of receiving high speed data communication and medium wattage power transfer through the sterile barrier.

In various aspects, the present disclosure provides a robotic surgical system and method for sensing a motor parameter or a response parameter to monitor or control the forces applied by a motor to a robotic surgical tool. For example, in one aspect, the central control circuit 15002 (FIG. 22) ma be configured to sense motor torques and/or motor currents to determine loads applied to the motor and infer the loads applied to the robotic surgical tool. The motor forces may be sensed individually to isolate specific force couples, motor torque, and ground response, for example. The measurement of isolated force couples are employed to determine the overall applied forces. Each individual motor attachment location could be instrumented and used to determine the forces exerted on the robotic surgical tool or instrument by that individual motor.

FIG. 210 is a torque transducer having a body connecting a mounting flange and a motor flange according to at least one aspect of the present disclosure. The torque transducer is mounted on a motor. Referring now to FIG. 210, a torque transducer 60600 is disclosed. The torque transducer 60600 includes a mounting flange 60610, a motor flange 60630 and a body 60620 interconnecting the mounting and motor flanges 60610, 60630. The mounting flange 60610 is formed from a ring of radial protrusions 60613 that each define a fastener hole 60614 for receiving a fastener to secure the mounting flange 60610 to a fixed plate. The mounting flange 60610 defines recesses 60616 between each of the radial protrusions 60613. The recesses 60616 may be used to route wiring to the strain gauge 60640 or between an instrument drive unit (IDU) and an adapter. Additionally or alternatively, the recesses 60616 may provide driver access to the fasteners of the motor flange 60630. The mounting flange 60610 may include a locating feature or ring 60612 that extends distally to position or locate the torque transducer 60600 relative to a mounting plate.

The body 60620 is generally cylindrical and formed from a plurality of struts 60628 that extend between the mounting and motor flanges 60610, 60630 to define a channel 60622 through the body 60620. The struts 60628 are configured to deflect or flex in response to torque applied about a transducer axis. The struts include a low stress regions 60624 adjacent each of the mounting and motor flanges 60610, 60630 and a high stress region 60626 between the low stress sections 60626. The body 60620 includes a stress gauge 60640 disposed in the high stress region of at least one of the struts 60628. Reference may be made to U.S. patent application Ser. No. 15/887,391, now U.S. Pat. No. 10,213,266, the entire contents of which are incorporated herein by reference, for additional detailed discussion.

If each motor has an individually isolated measure of axial, transverse, and radially applied forces then the operation of one system (i.e., firing) could be monitored and resolved by using the other motors within the robotic surgical tool, robotic surgical tool driver, and the robotic arm itself. This sum of the forces could be used as a secondary conformation measure of the primary measured motor response load.

If these loads do not confirm each other's motions an induced load could be made on the patient or the OR table. This could be detected by another measure of the resultant forces or the strain within the tissue may be monitored optically.

These overall induced forces as well as the coupled control forces may be used as a secondary safety measure on the control parameters of the operating motor. If the difference becomes more than a predefined threshold the motor control parameters could be limited (slowing, lowering torque, etc.) until the difference diminishes. If the difference continues to elevate the response of the system may be escalated unto and including stopping of reversing the action of the motor.

The individual motor torque may be compared to the motor controller measure of current to create a feedback loop that could verified applied torque. FIG. 211 is a flowchart illustrating a method of controlling an instrument drive unit according to at least one aspect of the present disclosure. With reference to FIG. 211, a method 60200 of verifying torque measurements of a primary sensor or reaction torque transducer 60068 of an instrument drive unit with a sensor 60152 is disclosed. Initially, a controller 60126 receives an instruction signal to rotate a motor. In response to the instruction signal, the controller 60126 sends a control signal to the motor to rotate a drive shaft.

While the motor is rotating, the motor draws current from a motor energy source. This current is measured 60210 by sensor 60152. The sensor 60152 generates 60212 a verification signal indicative of the measured current and transmits 60214 the verification signal to the controller 60126. In addition, while the motor is rotating, a reaction torque transducer measures 60220 torque applied by the motor. The reaction torque transducer generates 60222 a torque signal indicative of the measured torque and transmits 60224 the torque signal to the controller 60126.

The controller 60126 receives 60230 the verification signal and generates an acceptable range of torques which may be applied 60240 by the motor for the given verification signal. The controller 60126 then receives the torque signal from the reaction torque transducer and compares 60250 the torque signal to the acceptable range of torques. If the torque signal is within the acceptable range of torques, the controller 60126 continues 60255 to send a control signal to the motor to rotate the drive shaft. In contrast, if the torque signal is outside of the acceptable range of torques, the controller 60126 stops 60260 rotation of the motor by sending a control signal or ceasing to send a control signal. The controller 60126 then generates 60262 a fault signal indicative of the torque applied by the motor being outside of the acceptable range of torque values. The fault signal may be audible, visual, haptic, or any combination thereof to alert a clinician of the fault. Reference may be made to International Patent Application Serial No. PCT/US2016/037478, now International Patent Application Publication No. WO/2016/205266, the entire contents of which are incorporated herein by reference, for additional detailed discussion.

The torques measured by the sensing system coupled to the motor operation may not only be used to make sure they are within an acceptable range, but they also may be used in place of or in combination with the motor current and a means to change the parameter of the control circuit such as the central control circuit 15002 (FIG. 22). The magnitude of the difference, the amount of time the difference has existed, the increase or decrease of the difference, and the magnitude of either the overall torque or overall motor current may be used to determine the error between the system and its response. This error then may be employed to speed up, slow down, increase the duty cycle, or even limit the control signals to the motor.

This closed loop control of the motor-to-motor controller may be employed in addition to the overall control of the robotic surgical tool and motor to insure more predictable responses, inhibit over-exertion, and improve safe control of the robotic surgical tool. This could potentially predict jams, collisions, etc., as they are occurring and limit the damage done by the system.

In various aspects, the present disclosure provides systems and methods for sensing the resultant forces generated in the support frame of the motor as a proxy for applied motor forces. Sensing torques and moments applied through the motor mounting frame to determine the six degrees of freedom of forces applied by the motor pack. The forces exerted by the robotic surgical tool to both the robotic interface and the patient may be isolated.

FIG. 212 is a front perspective view of an instrument drive unit holder of a robotic surgical assembly with an instrument drive unit and a surgical instrument coupled thereto according to at least one aspect of the present disclosure. FIG. 213A is a side perspective view of a motor pack of the instrument drive unit of FIG. 212 with an integrated circuit in a second configuration and separated from the motor assembly according to at least one aspect of the present disclosure. FIG. 213B is a side perspective view of the motor pack of the instrument drive unit of FIG. 212 with the integrated circuit in a second configuration and separated from the motor assembly according to at least one aspect of the present disclosure.

With reference to FIG. 212, a robotic surgical system includes a surgical assembly, which includes an instrument drive unit holder (hereinafter, "IDU holder") 61102 coupled with or to a robotic arm, an IDU 61100 is couplable to the IDU holder 61102, and the surgical instrument 61010 is couplable to the IDU 61100. IDU holder 61102 of surgical assembly holds IDU 61100 and surgical instrument 61010 and operably couples IDU 61100 to robotic arm. IDU holder 61102 includes an interface panel or carriage 61104 and an outer housing portion 61108 extending perpendicularly from an end of carriage 61104. Carriage 61104 supports or houses a motor "M," which receives controls and power from a control device. Carriage 61104 is slidably mounted onto a rail of robotic arm, and may be moved along rail via a motor driven chain or belt (not shown) or the like. IDU 61100 is non-rotatably couplable to carriage 61104 of IDU holder 61102, and thus slides along rail of robotic arm concomitantly with carriage 61104.

With reference to FIGS. 212, 213A, and 213B, motor pack 61122 of IDU 61100 includes an exemplary motor assembly 61200 and an integrated circuit 61300. It is envisioned that motor pack 61122 may include any number of motors 61150 supported in motor assembly 61200. It is further envisioned that motors 61150 may be arranged in a rectangular formation such that respective drive shafts (not shown) thereof are all parallel to one another and all extending in a common direction. The drive shaft of each motor 61150 may operatively interface with a respective driven shaft of surgical instrument 61010 to independently actuate the driven shafts of surgical instrument 61010.

In the exemplary embodiment illustrated herein, motor pack 61122 includes four motors 61150 supported in motor assembly 61200. Motor assembly 61200 may include a distal mounting flange 61210 disposed at a distal end 61202 thereof, and a proximal mounting structure or frame 61220 disposed at a proximal end 61204 thereof. Proximal mounting structure 61220 includes four struts 61220*a-d* spanning between four posts 61204*a-d*, wherein the proximal mounting structure 61220 defines proximal end 61204 of motor assembly 61200. While four posts 61204*a-d* are shown and described herein, it is contemplated that any number of posts may be provided as needed. Also, while posts 61204*a-d* are arranged and illustrated herein in a rectangular configuration, it should be appreciated that any configuration is contemplated and within the scope of the present disclosure.

With reference to FIG. 213B, another exemplary embodiment of motor assembly 61201 is illustrated which includes distal mounting flange 61210, a proximal mounting cap 61250 and a constrainer 61260. Proximal mounting cap 61250 is configured to sit and nest over integrated circuit 61300, and includes four engagement regions 61252*a-d* configured to correspond with posts 61204*a-d*, respectively. Constrainer 61260 is configured to sit and nest over proximal mounting cap 61250 and integrated circuit 61300, where at least one clip feature 61262 selectively engages at least one wall 61254 of proximal mounting cap 61250. In an embodiment, a screw 61204 passed through a respective screw hole 61266*a-d* of constrainer 61260 and a respective engagement region 61252*a-d*, and threadably engages a respective post 61204*a-d*, thus securing constrainer 61260 and proximal mounting cap 61250 to posts 61204*a-d*.

Integrated circuit 61300 includes a plurality of walls or circuit boards 61320*a-d* and a nexus or hub 61330 (FIG. 213A), where each circuit board 61320*a-d* is coupled, either directly or indirectly, to nexus 61330. Integrated circuit 61300 includes a third circuit board 61320*c* and a fourth circuit board 61320*d* that are coupled on opposing sides of second circuit board 61320*b*. It should be appreciated that circuit boards 61320*a-d* and nexus 61330 of integrated circuit 61300 may be configured in any number of structural combinations, such as, for example, first, second, third, and fourth circuit boards 61320*a-d* being coupled, side-by-side, where one of first, second, third, or fourth circuit board 61320*a-d* is further coupled to one side of the first, second, third, or fourth side 61331*a-d* of nexus 61330. In another exemplary embodiment, first and third circuit boards 61320*a*, 61320*c* may be coupled to first and third sides 61331*a*, 61331*c* of nexus 61330, and second and fourth circuit boards 61320*b*, 61320*d* may be coupled to second and fourth sides 61331*b*, 61331*d* of nexus 61330. Second circuit board 61320*b* has low electrical noise, whereas third and fourth circuit boards 61320*c*, 61320*d* have relatively high electrical noise. Reference may be made to International Patent Application Serial No. PCT/US2017/034394, now International Patent Application Publication No. WO/2017/205576, the entire contents of which are incorporated herein by reference, for additional detailed discussion.

In one aspect, the robotic surgical tool-to-robotic surgical tool driver modular attachment also may have limits on the load threshold that it is allow to sustain before the motors of the robotic arm or robotic surgical tool drivers are limited. The interface between the robotic surgical tool and the robotic surgical tool driver could have non-symmetric maximum restraining loads that correspond to the attachment direction of the coupling and therefore the thresholds before effecting the motor control parameters also may be asymmetric. The forces resisted by the modular joint may be separated into the different degrees-of-freedom (DOF) and each force monitored with respect to pre-defined limits. These limits could be at first optional and then compulsory as the loading increases above a first threshold and then a second threshold. Forces in certain directions may be higher or disregarded based on the DOF and the orientation with respect to the robotic surgical tool and its attachment, or the end-effector force direction.

In various aspects, the present disclosure provides a robotic surgical system and method for limiting the combined functional loading of the patient by determining the torques applied by the motors, their mechanical advantage based on the measured positional and orientation of the robotic surgical tool assembly and the comparison of that against the resultant loading as measured at the robotic surgical tool driver attachment location. If the combined functional loading exceeds a predefined threshold then limit the motors of the motor pack and the arm to stay underneath that threshold.

FIGS. 214-215 illustrate combined functional operating loading to limit robotic surgical tool control motions according to various aspects of the present disclosure. FIG. 214 is a graphical illustration 8000 of limiting combined functional loading on the patient by determining the torques within robotic surgical tool driver and robotic arm/system according to at least one aspect of the present disclosure. The first graph 8002 depicts motor velocity 8004 as a function of time t. The second graph 8006 depicts estimated tissue force 8008 as a function of time. A first curve 8010, shown in solid line, represents the estimated force applied to the on tissue by the robotic surgical tool driver and a second curve 8014, shown in dashed line, represents the estimated force applied to the tissue by the robotic arm system. With reference now to the first and second graphs 8002, 8006, the motor velocity 8004 is adjusted based on the estimated tissue forces 8008. Between $t_0$ and $t_1$, when both of the estimated tissue force curves 8010, 8014 are below a first force threshold 8016 ($F_1$,) the motor velocity 8004 is set to a maximum velocity 8018 ($V_{max}$) by the central control circuit 15002 (FIG. 22). If either one of the estimated tissue force curves 8010, 8014 rises above the first force threshold 8016 ($F_1$), as shown at $t_1$, and remains below a second maximum force threshold 8020 ($F_{max}$), the motor velocity 8004 is set to a lower value 8022 ($V_2$) by the central control circuit 15002 and the control unit 15002 issues a warning signal to take action. If either one of the estimated tissue force curves 8010, 8014 continues to rise towards the second force threshold 8020 ($F_{max}$), as shown between $t_2$ and $t_3$, the motor velocity 8004 is set to an even lower value 8024 ($V_1$) by the central control circuit 15002 and the central control circuit 15002 continues to issue a warning signal to take action. If either one of the estimated tissue force curves 8010, 8014 rises above the second force threshold 8020 ($F_{max}$), as shown at $t_3$, the motor is shut down by setting the motor velocity 8004 to zero 8026 by the central control circuit 15002.

FIG. 215 is a flow diagram 8100 of a system and method of limiting combined functional loading on the patient by determining the torques within robotic surgical tool driver and robotic arm/system according to at least one aspect of the present disclosure. The left side 8101 of the flow diagram 8100 depicts robotic surgical tool driver measurements 8102 and the right side 8103 of the flow diagram 8100 depicts robotic arm/system measurements 8104. Turning to the robotic surgical tool driver measurements 8102, the central control circuit 15002 (FIG. 22) measures 8106 to maintain position. The central control circuit 15002 knows 8108 the geometry and, therefore, the mechanical advantage of the robotic system. The central control circuit 15002 employs the measurement 8106 and the knowledge 8108 to calculate 8110 actual tissue loads. Turning now to the robotic arm/system measurements 8104, the central control circuit 15002 measures 8112 motor torque to maintain position. The central control circuit 15002 knows 8114 the geometry and, therefore, the mechanical advantage of the robotic system. The central control circuit 15002 employs the measurement 8112 and the knowledge 8114 to calculate 8116 actual robot system loads. The central control circuit 15002 then compares 8118 the calculated 8110 actual tissue loads to the calculated 8116 actual robot system loads and determines an estimated force on the tissue. Accordingly, the combined functional loading on the patient is thus limited by determining the torques within the robotic surgical tool driver and the robotic arm/system. The detection system doubles as an active restraining means to reduce overstrain conditions.

In various aspects, the present disclosure provides a robotic surgical system and method for sensing and adjustably restraining a support from further strain. In one aspect, the sensing system also behaves as an active restrainer to reduce overstrain conditions. In its initial operational mode, the sensing system is in an active restraint mode where electrical potential changes as the sensing system is strained. The sensing system may be arranged in an array. However, the array also is capable of receiving a signal and from the signal creating a restraining force to limit further deformation of the sensing array. One example of such sensing system is known as an electroactive polymer (EAP). An EAP changes shape (elongating or contracting) based on an applied electrical potential. This same effect, as manifested in the physical straining of the EAP, causes a measurable electrical parameter change. The sensing system could first be used in passive mode to measure deformation of a motor support frame. Then when a predefined level of strain is reached, an electrical potential is applied to the polymer causing it to either further contract or expand to create a secondary force couple that inhibits any further strain on the sensing system and thus the motor support frame. In a passive restraint mode, a conductive polymer may be utilized such that if resultant forces on the motor support frame exceed a certain limit, the conductive polymer will deform sufficiently to reduce/limit conduction and stop the motor.

In various aspects, the present disclosure provides a robotic surgical system and method for monitoring external parameters associated with the operation of a motor. A flexible circuit or thermocouple may be attached to the exterior of the motor or attached in the center of a group of four motors to monitor the operational temperature of the motor pack. FIGS. 216-217 illustrate how motor control parameters may be adjusted based on the temperature of the motor pack according to various aspects of the present disclosure.

FIG. 216 illustrates a motor pack 8200 according to at least one aspect of the present disclosure. The motor pack 8200 includes a plurality of motors 8202 contained in a motor housing 8204. A flexible circuit 8206 with temperature measurement electronics may be attached to each motor 8202 or may be located inside the motor housing 8204 to measure the heat output by the motors 8202 or the motor pack 8200 as a unit. In one aspect, a thermocouple may be attached to the motors 8202 or located inside the housing 8204 to measure the heat output by the motors 8202 or the motor pack 8200.

FIG. 217 is a graphical illustration 8210 of a temperature control algorithm for monitoring external parameters associated with the operation of a motor according to at least one aspect of the present disclosure. A first graph 8212 depicts motor temperature 8214 as a function of time t as the velocity of the motor 8202 changes over time. A first temperature threshold 8213 ($T_1$) is set to provide a temperature warning and to take precautionary steps. A second temperature threshold 8219 ($T_2$) is set to shut down the motor 8202 if exceeded. A second graph 8216 depicts motor velocity 8218 as a function of time t. With reference to the first and second graphs 8212, 8216, from time $t_0$ to $t_1$, the motor velocity 8218 is set to maximum velocity 8220. This phase of operation may coincide with advancement of a knife prior to contacting tissue and firing staples. During this period, the motor temperature 8214 rises until it crosses 8215 the first temperature threshold 8213 ($T_1$) at time $t_1$. When the motor temperature 8214 crosses the first temperature threshold 8213 ($T_1$), the central control circuit 15002 (FIG. 22) issues a temperature warning to take precautionary steps. Between time $t_1$ and $t_2$ the stapler is fired and the motor velocity 8218 is lowered to "limp mode" velocity 8222 where the motor 8202 is slowed or its functions are limited. During this period, the motor temperature continues to rise until it reaches the second temperature threshold 8219 ($T_2$) at time $t_2$. At time $t_2$, the motor 8202 is temporarily paused and the motor velocity 8218 is set to zero velocity 8224 until the motor temperature 8214 drops below the second threshold 8219 ($T_2$) and begins trending downward until time $t_3$ when the motor velocity 8218 resumes "limp mode" velocity 8226. At time $t_4$, the motor temperature 8214 crosses 8217 the first temperature threshold 8213 ($T_1$) in a downward trend and the motor velocity 8218 is once again set to maximum velocity 8228.

With reference still to FIGS. 216-217, in one aspect, if the motor pack 8200 or the attached control electronics exceeds the first predefined threshold 8213 ($T_1$), the central control circuit 15002 (FIG. 22) of the robotic surgical system 15000 (FIG. 22) may adjust its controls and ventilation in order to limit further heat buildup within the motor pack 8200. If the motor pack 8200 exceeds the second higher temperature threshold 8219 ($T_2$), the central control circuit may begin to limit the motor currents and operational loads of the motor pack 8200 to prevent further heat buildup. Finally if the temperature exceeds a third threshold $T_3$ (not shown) the central control circuit 15002 may completely shut down the motor pack 8200 require that the motor pack 8200 cool below a predetermined temperature before restarting.

In an alternative temperature control algorithm, the central control circuit 15002 (FIG. 22) may pause the motor 8202 between operations or limiting the duty cycle of the motor 8202 instead of lowering the operational loads exerted by the robotic surgical system. The central control circuit 15002 (FIG. 22) monitors the temperature of the motor pack 8200 and provides warnings to the user in advance of the motors 8202 crossing a predetermined temperature threshold $T_1$, $T_2$, $T_3$ . . . $T_n$ to mitigate against a complete shut-down of the motor 8202 during a surgical procedure or a particular step of a surgical procedure. In one aspect, during a surgical procedure or a particular step of a surgical procedure, which could be informed by situational awareness, the user would be informed of actions being taken by the robotic surgical tool (e.g., stapler firing, etc.) based on a risk assessment performed to determine the best route to allow the device to proceed: shut down, go into a limp-mode that slows or limits functions, allow only the current step to be completed, etc.

FIG. 218 is a graphical illustration 8300 of magnetic field strength 8302 (B) of a motor 8202 as a function of time t according to at least one aspect of the present disclosure. FIG. 219 is a graphical illustration 8304 of motor temperature 8306 as a function of time t according to at least one aspect of the present disclosure. FIG. 220 is a graphical illustration 8308 of magnetic field strength (B) as a function motor temperature (T) according to at least one aspect of the present disclosure. The curve 8310 represents ΔB/ΔT the rate of change of magnetic field strength to the change in motor temperature, where T1 is the motor temperature at startup (cold), T2 is the motor temperature with a cooling fan running during calibration/operation, and T3 is the motor temperature without a cooling fan running during calibration/operation. Measuring magnetic field strength (B) and temperature (T) enables the calculation of dB/dT which may be a better indicator of magnet (motor) health vector.

With reference now to FIGS. 22 and 216-220, in one aspect, the central control circuit 15002 (FIG. 22) modulates active cooling (e.g., turns a cooling fan on or off) during motor calibration and detects temperature change as a way to assess the health of the motor magnet. The central control circuit 15002 learns not just the absolute temperature of the motor 8202 but learns the thermal response of the motor 8202. For example, the function of a motor 8202 can be affected by the deterioration of the magnetic field strength (B) of the rotor. Measurement of both magnetic field strength (B) and temperature T can result in guidelines for assessing the health of the motor 8202 based on absolute values or ranges; however, measuring the response of the magnetic field strength (B) as a function of temperature T, the resulting dB/dT, also provides an improved way to assess the health of the magnet even when the magnetic field strength (B) or temperature T are within normal operating ranges by determining or predicting how or if the motor 8202 is trending towards abnormal operating ranges.

With reference still FIGS. 22 and 216-220, in one aspect, electronic circuits located within the motor pack 8200 are configured to monitor an electromagnetic field. If the magnetic field strength (B) exceeds a predefined threshold that could interfere with communication, control, or sensing of a motor operation, the central control circuit 15002 (FIG. 22) may shut down the electrical power to the motor pack 8200. In one aspect, a motor control algorithm may be modified based on an externally applied and monitored magnetic field strength (B). In one aspect, an integrated Hall effect sensor or an inductive sensor may be located within the motor pack 8200 to detect magnetic fields. The controlled activation of the motor 8202 could be based on detecting a predefined magnetic field fingerprint or a functional interaction detected by the Hall effect or inductive sensor and then detecting an external magnetic field and modifying the control algorithm to eliminate the effect of the internal or external magnetic field from the measurement. The resulting magnetic field may be compared against pre-defined thresholds to determine the reaction based on the intensity of the externally applied magnetic fields.

With reference still FIGS. 22 and 216-220, in one aspect, the reactions to the magnetic field measurements may include the central control circuit 15002 (FIG. 22) slowing or stopping the motors 8202. It also may include reliance on secondary non-magnetic measurements of motor operation, or it may result in notation to the user of the issue. In addition to determining if any external magnetic fields are unduly influencing sensing or operation of the motor 8202, additional secondary passive measures also may be monitored and employed by the central control circuit 15002 to control functional aspects of the motor 8202 to prevent interference. In other aspects, the external portion of the motor 8202 may be coupled to a piezoelectric sensor to monitor acoustics of the motor 8202 operation. In other aspects, the external portion of the motor 8202 may be coupled to the piezoelectric sensor to measure vibration of the housing 8204 to monitor motor 8202 operation.

In various aspects, the present disclosure provides a robotic surgical system and method for detecting ground faults in the robotic surgical system 15000 (FIG. 22). If the central control circuit 15002 (FIG. 22) senses a floating ground, leakage current, or other electrical circuit contamination in which the robot, robotic surgical tool, or robotic surgical tool driver, which is now part of the robotic surgical system 15000, the central control circuit 15002 will shut down that robotic arm. Monitoring of the ground condition of the robot, robotic surgical tool, or toll driver may be useful in preventing inadvertent cautery damage. In one aspect, a ground condition may occur from shorting a monopolar instrument onto the ground path of the robotic arm or robotic surgical tool or through capacitive coupling with a monopolar device. Responses to a ground condition may include, for example, preventing the application of RF energy, moving the robotic arms apart to remove interface, preventing further robotic arm or robotic surgical tool motion, or adjusting electrical circuits to eliminate or cause an electrical short circuit.

In one aspect, the robotic surgical system 15000 (FIG. 22) of the present disclosure provides a sensor for detecting both the angle of rotation of the robotic surgical tool with respect to the robotic surgical tool driver and the number of times it has been rotated. Such continuous monitoring of the number of robotic surgical tool rotations may be employed by the central control circuit 15002 to prevent over-exertion of the robotic surgical tool. In one aspect, a resistive element having a multiple loop winding and a contact arm may be configured to move both radially and longitudinally causing the resistance to change as the device is rotated. This resistance continues to drop as the robotic surgical tool is rotated all the way around up to several times. In various aspects, the robotic surgical system 15000 (FIG. 22) of the present disclosure further provides a system and method for calibration loading the robotic surgical tool.

With reference back to FIG. 22, in various aspects, the present disclosure provides a robotic surgical system 15000 and method for rotating the robotic surgical tool 15030. In one aspect, the present disclosure provides an apparatus and method for managing the electrical connections between a rotatable modular robotic surgical tool 15030 and a fixed radial position of the robotic surgical tool driver 15028. Implementation of such robotic surgical tool 15030 rotation capabilities requires the transmission of power and communication signals from the central control circuit 15002 to the robotic surgical tool driver 15028 and the robotic surgical tool 15030.

One example of a hardwired system with coiled length to allow robotic surgical tool rotation is now discussed with respect to FIGS. 221-222. With reference to FIGS. 221-222, a flex spool assembly 62200 includes a first printed circuit board 62212, a second printed circuit board 62214, and a third printed circuit board 62216 according to at least one aspect of the present disclosure. First, second, and third printed circuit boards 62212, 62214, 62216 are rigid circuit boards rather than flex circuits. In some embodiments, first, second, and third printed circuit boards 62212, 62214, 62216 may be flex circuits and/or may be monolithically formed with first flex circuit 62210. First printed circuit board 62212 is connected to a printed circuit board of an instrument drive unit (IDU) holder such that first printed circuit board 62212 is fixed relative to IDU. First printed circuit board 62212 is connected to first end portion 62210*a* of first flex circuit 62210 to transfer power and data to first flex circuit 62210. First printed circuit board 62212 is connected to first end portion 62210*a* of first flex circuit 62210 to transfer power and data to first flex circuit 62210. First printed circuit board 62212 has an electrical connector, for example, a female connector 62212a, configured to be coupled to a corresponding male electrical connector (not explicitly shown) of printed circuit board of IDU holder. In some embodiments, a wire may be used in place of female connector 62212a. It is contemplated that any of the disclosed electrical connectors may be zero insertion force ("ZIF") connectors.

Second and third printed circuit boards 62214, 62216 of flex spool assembly 62200 are each disposed within intermediate portion 62210c of first flex circuit 62210 and are each connected to second end portion 62210b of first flex circuit 62210. Second printed circuit board 62214 is configured to transfer power from first printed circuit board 62212 to a motor assembly of IDU. Second printed circuit board 62214 has an electrical connector, for example, a female connector 62214a, configured to be coupled to first male electrical connector 62128 of integrated circuit 62120. Third printed circuit board 62216 is disposed adjacent second printed circuit board 62214 and is configured to transfer data from first printed circuit board 62212 to various components of IDU and/or a surgical instrument. Third printed circuit board 62216 has an electrical connector, for example, a female connector 62216a, configured to be coupled to second male electrical connector of integrated circuit 62120. Female and male connectors 62214a, 62216a may be pin/position connectors, such as, for example, 40-pin connectors.

With continued reference to FIGS. 221-222, second flex circuit 62220 of flex spool assembly 62200 has a first end portion 62220a connected to a first end portion of first printed circuit board 62212, and a second end portion 62220b disposed adjacent a second end portion of first printed circuit board 62212 to define a U-shaped intermediate portion 62220c that surrounds first flex circuit 62210. First and second ends 62220a, 62220b of second flex circuit 62220 are fixed to a platform 62116 of IDU. Reference may be made to International Patent Application Serial No. PCT/US2017/035607, now International Patent Application Publication No. WO/2017/210516, the entire contents of which are incorporated herein by reference, for additional detailed discussion.

In one aspect, the wire management system may be employed to control the winding of the wire and control of it in the unwound state. In one aspect, a spring biased wrapping system may be employed for wire control of rotating motor units. In one aspect, a spring element may be provided that rewinds the wiring harness as the device is counter rotated back to its hot position. The spring bias on the spindle keeps the tension of the wiring harness as it rolls up to manage the wire. The wire management system could have a spring bias into the coiled state enabling the system to easily re-coil when counter rotated. In another aspect, the housings may include wire control passages that only allow the wire to move from one controlled orientation to another controlled orientation on a second spool without being bunched or tangled in-between. The flex circuit wire may contain structural elements within the flex-wire itself to prevent kinking, twisting, or unintended coiling.

In various aspects, the present disclosure provides an internal receiver cavity to enable the wiring harness to unwind in a controlled manner in order to allow it to fold up rather than twist and bind up. FIGS. 223-224 illustrate an internal receiver 8300 with multiple cavities 8304, 8306 wire control features to maintain orientation and order of the wiring harness 8308 during rotation according to at least one aspect of the present disclosure. The wiring control housing 8302 may include a first cavity 8304 and a second cavity 8306 that are used to store the wiring harness 8308 in its fully retracted state and as the wiring harness 8308 is unrolled, it is contained within the second cavity 8306 to prevent tangling and unintended interactions with itself. The first, internal, receiver cavity 8304 includes a spring biased rotating spool 8312 to allow the wiring harness 8308 to unwind in a controlled manner in order to allow it to fold up rather than twist and bind up.

FIG. 224 illustrates a wiring harness 8308 according to at least one aspect of the present disclosure. The wiring harness 8308 includes a four rotation flex circuit 8310 and as spring biased rotating spool 8312 with electrical contacts 8314. The electrical contacts 8314 connect stationary wiring 8316 to a circuit panel connector 8318, which is used to connect to a circuit panel.

FIGS. 225-228 illustrate a semiautonomous motor controller 8400 local to a motor pack 8402 with a safety circuit according to at least one aspect of the present disclosure. The semiautonomous motor controller 8400 provides infinite rotation power transfer and communication with elements located on a control circuit and semiautonomous continuous motor control local to the motor pack 8402.

FIG. 225 illustrates a semiautonomous motor controller 8400 local to a motor pack 8402 according to at least aspect of the present disclosure. In one aspect, the motor pack 8402 is a modular rotatable motor pack 8402. The semiautonomous motor controller 8400 is located in a sterile field 8406 and communicates wirelessly to a non-sterile field 8408 safety processor 8410 via wireless communication circuits 8412, 8414. A sterile barrier 8405 separates the sterile field 8406 from the non-sterile field 8408. In the illustrated example, a motor housing 8416 of the motor pack 8402 contains up to four motors 8418. A slip ring connector system 8419 includes a plurality of slip ring electrical traces 8420 are disposed on an exterior portion of the motor housing 8416. A plurality of spring loaded plungers 8422 make electrical contact with the corresponding slip ring electrical traces 8420. This configuration provides >360° rotation of the motor housing 8416 within a sterile clam shell housing 8424. Located within the sterile clam shell housing 8424 is a non-rotating contact interface connector 8426 to the robotic surgical tool driver 15028 (FIG. 22) cartridge. In various aspects, the slip ring connector system 8419 provides a rotary interface between the motor pack 8402 and the sterile barrier 8405 through the spring loaded contacts 8422 and electrical wires 8427 coupled to the connector 8426. In one aspect, the slip ring connector system 8419 includes a series of rotatable electrical traces 8420 and spring loaded contacts 8422 that allow for the motor pack 8402 to be rotated while still maintaining electrical contacts.

FIG. 226 is a detailed view of the spring loaded plunger 8422 depicted in FIG. 225 according to at least one aspect of the present disclosure. The spring loaded plunger 8422 included a threaded housing 8428 and an internal spring 8430 to bias an electrical contact 8432 into electrical communication with the slip ring electrical contacts 8421 disposed on the exterior portion of the motor housing 8416. A hook 8434 located at a tip of the electrical contact 8432 prevents the electrical contact 8432 from receding into the threaded housing 8428 and a flange 8435 located at a base of the electrical contact 8432 prevents the electrical contact 8432 from being ejected through the distal end 8436 of the threaded housing 8428. The electrical contacts 8432 connect the slip ring electrical traces 8420 to the connector 8426 through the electrical wires 8427.

FIG. 227 illustrates a wireless power system 8500 for transmission of electrical power between a surgical robot and a motor pack 8504 comprising a plurality of motors 8502 according to at least one aspect of the present disclosure. A magnetic shield 8506 made of suitable materials such as AL—Mn—Fe or Fe—Si—DL, among others, provides magnetic shielding to prevent magnetic field interference outside a sterile housing 8508 of the motor pack 8504. Wireless power transfer coil arrangement includes a power transmitter coil 8510 and a power receiver coil 8512 to transfer electrical power between the surgical robot and the motor pack 8504. A first set of coils includes a power transmitter coil 8510 and power receiver coil 8512 positioned within the robotic surgical tool driver carriage and a second set of coils including a power transmitter coil and a power receiver coil positioned adjacent the first set within the motor pack 8504 when seated in the robotic surgical tool driver 15028 (FIG. 22), and the sterile barrier 8405 (FIG. 225) positioned therebetween. The power transmitter coil 8510 and the receiver coil 8512 may be have a concentric configuration on the same axis about which the motor 8505 is allowed to rotate. This would allow full 360°+ rotation and any number of rotations without forcing the system to be counter-rotated back to a start position. In this configuration the power transmitter and receiver coils 8510, 8512 are mechanically limited to maintain a pre-established alignment. The Qi standard for medium power allows for 5 W-15 W power transfer in an envelope that is smaller than a 2-inch diameter which would allow the power transmitter and receiver coils 8510, 8512 system to be positioned over top of a four motor 8505 motor pack 8504 set without requiring additional space.

FIG. 228 is a diagram 8600 of the wireless power system 8500 for transmission of electrical power between a robot 8502 and a motor pack 8504 depicted in FIG. 227 according to at least one aspect of the present disclosure. With reference now to both FIGS. 227-228, a first wireless power transfer coil 8510 transmits power to a wireless power receiver coil 8512 to supply electrical power to the motor pack 8504. An accelerator 8602 is coupled to the wireless power receiver coil 8512. The power accelerator 8602 is electrically coupled to a boost controller 8604, which is electrically coupled to the wireless power receiver coil 8512 and to motor control circuits 8606. The motor control circuits 8606 are electrically coupled to the motors 8505. Both the motor control circuits 8606 and the motors 8505 are electrically coupled to the wireless power receiver coil 8512.

With reference now to FIGS. 225-228, a rechargeable intermediate accumulator may be provided to improve the pair relationship between the capacity of wireless power transfer and its ability to provide high current draw multi-motor simultaneous operation. The accumulator may be located within the motor pack 8504 to prevent interruption of power, voltage sags, and to handle high current draw operations.

With reference to FIG. 229, a block diagram of an information transfer system according to at least one aspect of the present disclosure. The system 62040 includes a transmit unit 62050 and an intrabody instrument or robotic arm 62060. The transmit unit 62050 may be in operable communication with an energy source 62052 and a storage unit 62054. The robotic arm 62060 may include a receive unit 62062, an energy storage unit 62064, an instrument control electronics unit 62066, a storage unit 62068, and an LED indicating unit 62070. The transmit unit 62050 may communicate with the receive unit 62062 of the robotic arm 62060 via a communications link 62042.

Of course, several different types of connection components or communications links may be used to connect the transmit unit 62050 to the receive unit 62062. As used herein, "connection component" may be intended to refer to a wired or wireless connection between at least two components of system 62040 that provide for the transmission and/or exchange of information and/or power between components. A connection component may operably couple consoles/displays (not shown) and robotic instruments to allow for communication between, for example, power components of robotic instruments and a visual display on, for example, a console. Reference may be made to U.S. patent application Ser. No. 13/024,503, now U.S. Pat. No. 9,107,684, the entire contents of which are incorporated herein by reference, for additional detailed discussion.

FIG. 230 generally depicts system 62100 for providing electrical power to a medical device 62102 according to at least one aspect of the present disclosure. It is contemplated that medical device 62102 could comprise virtually any type of powered medical device, including but not limited to, a cutting/cauterizing robotic surgical tool, an irrigation/aspiration robotic surgical tool, a visualization robotic surgical tool, a recording and/or printing device and the like. Medical device 62102 is provided with electronic circuit 62104 and resonant receiver 62106. Electronic circuit 62104 may comprise any electronic/electrical circuit(s) used to operate medical device 62102. Electronic circuit 62104 is electrically coupled to resonant receiver 62106.

Also depicted in FIG. 230 is power transmitting unit 62108 that includes resonant transmitter 62110. It is contemplated that resonant transmitter 62110 generates a resonant magnetic field 62112 (depicted by the concentric lines) that transmits from power transmitting unit 62108. Resonant receiver 62106 is "tuned" to the same frequency as resonant magnetic field 62112 such that, when resonant receiver 62106 is moved to a location within resonant magnetic field 62112, a strong resonant coupling occurs between resonant receiver 62106 and resonant transmitter 62110. The resonant coupling in one advantageous embodiment, comprises evanescent stationary near-field. While the transmitter/receiver may comprise virtually any type of resonant structure, it is contemplated that in an advantageous embodiment, the electromagnetic resonant system may comprise dielectric disks and capacitively-loaded conducting-wire loops. This arrangement provides the advantages of a strong coupling for relatively large and efficient power transfer as well as relatively weak interaction with other off-resonant environmental objects in the vicinity. Reference may be made to U.S. patent application Ser. No. 12/425,869, now U.S. Pat. No. 9,526,407, the entire contents of which are incorporated herein by reference, for additional detailed discussion.

Referring now to FIG. 231, a surgical instrument 63010 is provided according to at least one aspect of the present disclosure. The surgical instrument 63010 includes a handle 63020, an adaptor 63030, and a disposable loading unit 63040. The adaptor 63030 includes a handle connector 63032 at a proximal end thereof and the handle 63020 defines an adaptor receiver 63026 for receiving the handle connector 63032 to releasably couple the adaptor 63030 to the handle 63020. The disposable loading unit 63040 includes a loading unit connector 63042 at a proximal end thereof and the adaptor 63030 defines a loading unit receiver 63036 adjacent a distal end thereof to releasably couple the disposable loading unit 63040 to the adaptor 63030. The disposable loading unit 63040 includes an end-effector assembly 63140 that includes a first and a second jaw member 63142, 63144, each of which is moveable relative to one another and are configured to act on tissue.

An electrical interface 63050 is disposed within the adaptor receiver 63026 and the handle connector 63032. The electrical interface 63050 is a non-contact electrical interface that transmits energy from the handle 63020 to the adaptor 63030 and transmits data signals from the adaptor 63030 and/or the disposable loading unit 63040 to the handle 63020, between the adaptor receiver 63026 and the handle connector 63032. It is contemplated that control signals are transmitted by the electrical interface 63050 from the handle 63020 to the adaptor 63030. The handle 63020 may include a display 63025 configured to display information from the data signals from the adaptor 63030 and/or the disposable loading unit 63040 to a user of the surgical instrument 63010.

Referring now to FIG. 232, the electrical interface 63050 may include a control circuit 63060 for transmitting the control signals according to at least one aspect of the present disclosure. The control circuit 63060 includes a proximal control coil 63062 and a distal control coil 63064 which form a control transformer 63068 when the handle connector 63032 of the adaptor 63030 is received within the adaptor receiver 63026 of the handle 63020. The proximal control coil 63062 is disposed within a protrusion of the handle 63020 adjacent to but electrically shielded from the proximal coil 63052. The distal control coil 63064 is positioned adjacent to a recess of the adaptor 63030 and to the distal coil 63054 but is electrically shielded from the distal coil 63054. It will be appreciated that the control transformer 63068 is electrically shielded or isolated from the data transformer 63058 such that the data signals do not interfere with the control signals.

The control signals from the processor 63022 of the handle 63020 are transmitted to a control signal processor 63067 thereof. The control signal processor 63067 is substantially similar to the data signal processor 63057 and converts the control signals from the processor 63022 to high frequency control signals for transmission across the control transformer 63068. The high frequency control signals are transmitted from the control signal processor 63067 to the proximal control coil 63062. The proximal control coil 63062 receives energy from the energy source 63024 of the handle 63020. It is also contemplated that the proximal control coil 63062 receives energy from a separate and distinct energy source (not shown). The energy received by the proximal control coil 63062 is inductively transferred across the control transformer 63068 to the distal control coil 63064. Reference may be made to U.S. patent application Ser. No. 14/522,873, now U.S. Pat. No. 10,164,466, the entire contents of which are incorporated herein by reference, for additional detailed discussion.

FIG. 233 schematically illustrates an electrosurgical system (shown generally as 63400) that includes an electric-field capacitive coupler module 63420 coupled between a microwave generator assembly 63486 and a microwave energy delivery device 63410 according to at least one aspect of the present disclosure.

Microwave generator assembly 63486 includes a power generation circuit 63402 that generates and provides DC power from a DC power supply 63404 and a microwave frequency signal from a signal generator 63406. Microwave generator assembly 63486 includes an amplifier unit 63408, and may include a processing unit 63482 communicatively coupled to the amplifier unit 63408 and configured to control the amplifier unit 63408 to amplify the microwave frequency signal generated by the signal generator 63406 to a desired power level. DC power from the DC power supply 63404 and the microwave frequency signal from the signal generator 63406 are supplied to the amplifier unit 63408. Amplifier unit 63408 may include one or more microwave signal amplifiers configured to amplify the microwave frequency signal, e.g., based on one or more signals received from the processing unit 63482, from a first power level to at least one second power level.

The microwave frequency signal outputted from the microwave amplifier unit 63408 is supplied to a first end of the transmission line 63411 connected to the generator connector 63409. In some embodiments, the second end of the transmission line 63411 connects to the delivery device connector 63412 of the microwave energy delivery device 63410. A suitable flexible, semi-rigid or rigid transmission line, e.g., cable assembly 63019, may additionally, or alternatively, be provided to electrically-couple the microwave energy delivery device 63410 to an electric-field capacitive coupler module and/or the generator connector 63409. The microwave frequency signal is passed through the device transmission line 63414 to the antenna 63416 at the distal end of the microwave energy delivery device 63410. Reference may be made to U.S. patent application Ser. No. 14/022,535, now U.S. Pat. No. 9,106,270, the entire contents of which are incorporated herein by reference, for additional detailed discussion.

In various aspects, the present disclosure provides communication on a different return path than electrical power connections. Wired power transfer may be achieved with optical dual direction communication paths for control and sensed data return configured as a hybrid electrical and optical data, power, and control paths.

In one aspect, a high speed alternative to wireless communication may include an optical transfer system between the motor pack and the robotic surgical tool driver. This may be implemented by creating a roughly circular LED laser ring on the rotatable side of the assembly. That would allow a receiver to be a stationary element on the robotic surgical tool driver side that would always have aligned access to a portion of the light ring and therefore capable of receiving high speed high resolution data from the rotary component.

In one aspect, two sets of light rings and receivers may be coupled between the two systems enabling high speed dual direction communication in a non-contact manner. This would allow for the transmission and receiving of data in a sealed manner in-between any modular aspects of the system minimizing the possibility of shorting out or losing the signal due to contaminates or saturation of the joint within a fluid media.

In various aspects, the present disclosure provides a combination of wired and wireless RF communication systems to enable dual data return paths in combination with a single control path. In one aspect, the present disclosure provides a hybrid dual path sensor path may be implemented with a single control path. In another aspect, the present disclosure provides a hybrid direct connection power circuit and a wireless interface for communication and returned sensor data. In this regard, power transmission may be accomplished via a wired or wireless pair coil system as described herein and the communication to and from the modular robotic surgical tool may be accomplished wirelessly.

In one aspect, an antenna receiver of the wireless array may be positioned on an exposed portion of the motor pack at some distance away from the induction coils minimizing the amount interference from the power transmission. The antenna array is position on a portion of the motor pack which is outside of the surgical site, and is flex circuit connected to the sterile barrier and then in turn to the robotic surgical tool module by contacts in thru the sterile barrier The electronic circuits, wire paths and connections are isolated and sealed. The electrical contacts may include a circumferential lip of insulating plastic to insure minimal cross-talk or signal loss even if the system where immersed in conductive fluid. This hybrid arrangement may be configured to provide a closed loop control circuit at all times that is in control of the motor assembly. The dual path return of sensor data would allow the system to verify the integrity of the processed data and allow it to use a safety algorithm to monitor the intended operation and the resulting motions of the drive systems.

In various aspects, the present disclosure provides a robotic surgical tool rotation mechanism. In one aspect, the robotic surgical tool rotation mechanism employs the robotic surgical tool driver linear drive axles to couple raise and lower and rotate.

With reference to FIG. 234, elongate link or slide rail 64040 includes a multidirectional movement mechanism 64100 configured to axially move a surgical instrument along a longitudinal axis of elongate link or slide rail 64040 and to rotate the surgical instrument about its longitudinal axis according to at least one aspect of the present disclosure. Multi-directional movement mechanism 64100 of a robotic arm generally includes a left-handed lead screw 64102, a right-handed lead screw 64104, and a slider 64110 axially movable along lead screws 64102, 64104, but prevented from rotating relative to lead screws 64102, 64104. Left-handed lead screw has a left-handed screw thread, and right-handed lead screw has a right-handed screw thread such that the screw threads for lead screws 64102, 64104 twist in opposite directions. Lead screws 64102, 64104 are disposed in parallel relation to one another within a cavity 64042 defined in elongate link or slide rail 64040. Lead screws 64102, 64104 are rotatable within elongate link or slide rail 64040 while also being axially restrained within elongate link or slide rail 64040.

Lead screws 64102, 64104 each include a respective first end 64102a, 64104a rotatably connected to a first end of elongate link or slide rail 64040, and a respective second end 64102b, 64104b. Second ends 64102b, 64104b of lead screws 64102, 64104 have or are coupled to motors, for example, a first canister motor "M1," and a second canister motor "M2." In some embodiments, gears, universal shafts, flexible shafts, brakes, and/or encoders may be associated with motors "M1," "M2." Motors "M1," "M2" drive a rotation of lead screws 64102, 64104 and are electrically connected to a control device, via cables or a wireless connection, which is configured to independently control the actuation of motors "M1," "M2."

Slider 64110 of multi-directional movement mechanism 64100 is slidably disposed within cavity 64042 of elongate link or slide rail 64040 and operably coupled to lead screws 64102, 64104. Slider 64110 has a generally rectangular shape, but it is contemplated that slider 64110 may assume any suitable shape. Slider 64110 defines a first passageway 64112 therethrough that has left-handed lead screw 64102 extending therethrough, and a second passageway 64114 therethrough that has right-handed lead screw 64104 extending therethrough. Slider 64110 further defines an opening 64116 in a side thereof. Slider 64110 is configured to be coupled to surgical instrument 64200 such that axial movement of slider 64110 relative to and along lead screws 64102, 64104 results in a corresponding axial movement of surgical instrument 64200.

With reference to FIGS. 235A and 235B, to cause a cogwheel 64140, and the attached surgical instrument, to rotate in a clockwise direction as indicated by arrow "C" depicted in FIG. 235B, first and second motors "M1," "M2" of multi-directional movement mechanism 64100 are actuated to rotate both left-handed lead screw 64102 and right-handed lead screw 64104 in a counter-clockwise direction according to at least one aspect of the present disclosure. When left-handed lead screw 64102 is rotated in the counterclockwise direction, first nut 64120 tends to move in the upward or proximal direction indicated by arrow "D" depicted in FIG. 235A, while when right-handed lead screw 64104 is rotated in the counterclockwise direction, second nut 64130 tends to move in the downward or distal direction indicated by arrow "E" depicted in FIG. 235A. Since first and second nuts 64120, 64130 are being driven in opposite longitudinal directions, no movement of slider 64110 results, and first and second nuts 64120, 64130 begin to rotate counter-clockwise integrally with lead screws 64102, 64104 rather than relative to lead screws 64102, 64104. The rotation of first and second nuts 64120, 64130 in the counter-clockwise direction drives a rotation of cogwheel 64140 in the clockwise direction. When the surgical instrument is non-rotatably received within cogwheel 64140, the clockwise rotation of cogwheel 64140 causes surgical instrument 64200 to rotate therewith. Reference may be made to International Patent Application Serial No. PCT/US2017/019241, now International Patent Application Publication No. WO/2017/147353, the entire contents of which are incorporated herein by reference, for additional detailed discussion.

In various aspects, the present disclosure provides supported bearing rotation of a robotic surgical tool about the sterile barrier connection to the robotic surgical tool driver. Turning now to FIG. 236, the robotic surgical assembly 66100 is connectable to an interface panel or carriage 66042 which is slidably mounted onto the rail 66040 according to at least one aspect of the present disclosure. The carriage 66042 supports or houses a motor 66044 that receives controls and power from a control device. The carriage 66042 may be moved along the rail 66040 via a motor driven chain or belt or the like. Alternatively, the carriage 66042 may be moved along the rail 66040 via a threaded rod/nut arrangement. For example, the carriage 66042 may support a threaded nut or collar which receives a threaded rod therethrough. In use, as the threaded rod is rotated, the threaded collar, and in turn, the carriage 66042 are caused to be translated along the rail 66040. A coupling 66046, or the like, is connected to a drive shaft of motor 66044, and may be rotated clockwise or counter clockwise upon an actuation of the motor 66044. While a chain/belt or threaded rod and collar arrangement are described, it is contemplated that any other systems capable of achieving the intended function may be used (e.g., cable drives, pulleys, friction wheels, rack and pinion arrangements, etc.).

The carriage 66042 may rotatably support motor axis gear or pulley 66118 (e.g., a spur gear) and a tension gear or pulley 66120 within a coupling flange. A drive belt 66122 or the like extends around a pulley, a motor axis pulley and the tension pulley 66120. The motor axis pulley is connectable to the coupling 66046 of the motor 66044, and is driven by the motor 66044 upon an actuation thereof. Accordingly, in use, as the motor 66044 is actuated, the motor 66044 drives the coupling 66046, which drives the motor axis pulley, to in turn drive the belt 66122, and in turn, rotate the pulley. Reference may be made to International Patent Application Serial No. PCT/US2017/033899, now International Patent Application Publication No. WO/2017/205308, the entire contents of which are incorporated herein by reference, for additional detailed discussion.

Turning now to FIGS. 237 and 238, surgical instrument holder 65102 of surgical assembly 65100 functions both to actuate a rotation of a body 65114 of instrument drive unit 65110 and to support a housing 65202 of surgical instrument 65200 according to at least one aspect of the present disclosure. Surgical instrument holder 65102 includes a back member or carriage 65104, and an outer member 65106 extending perpendicularly from an end of carriage 65104. In some embodiments, outer member 65106 may extend at various angles relative to carriage 65104 and from various portions of carriage 65104. Carriage 65104 has a first side and a second side 65108b, opposite first side. First side of carriage 65104 is detachably connectable to rail 65040 of a robotic arm. Surgical assembly 65100 is configured such that surgical instrument holder 65102 may slide or translate along rail 65040 of robotic arm. Second side 65108b of carriage 65104 is configured to connect to instrument drive unit 65110. In some embodiments, second side 65108b of carriage 65104 may define a longitudinal track (not shown) configured for slidable receipt of instrument drive unit 65110.

Carriage 65104 of surgical instrument holder 65102 supports or houses a motor, such as, for example, canister motor "M" therein. Motor "M" receives controls and power from a control device to selectively rotate an inner housing or body 65114 of instrument drive unit 65110. Motor "M" has a motor shaft 65109 extending longitudinally through carriage 65104 that is drivingly connected to gear of instrument drive unit 65110. Specifically, motor shaft 65109 includes a gear 65109a for selective connection to gear of instrument drive unit 65110 to effect a rotation of body 65114 of instrument drive unit 65110 about its longitudinal axis "X."

With reference to FIG. 238, instrument drive unit 65110 includes a plate or flange 65116 disposed at proximal end 65114a of body 65114 of instrument drive unit 65110 and which is fixed within outer housing 65112 of instrument drive unit 65110. Plate 65116 has a first portion 65116a and a second portion 65116b extending laterally from first portion 65116a. First portion 65116a of plate 65116 defines an annular cavity 65118 through a thickness thereof. Proximal end 65114a of body 65114 extends through annular cavity 65118 of plate 65116 and is rotatable therein. Second portion 65116b of plate 65116 extends radially beyond a periphery of proximal end 65114a of body 65114 of instrument drive unit 65110.

Instrument drive unit 65110 further includes a driven coupler 65120, a first gear 65130, and a second gear 65140 disposed between driven coupler 65120 and first gear 65130 to transfer rotational motion of driven coupler 65120 to first gear 65130. Each of driven coupler 65120, first gear 65130, and second gear 65140 is rotatably supported on or disposed with plate 65116. In particular, driven coupler 65120 and second gear 65140 are rotatably supported within second portion 65116b of plate 65116, and first gear 65130 is rotatably disposed on first portion 65116a of plate 65116. As such, driven coupler 65120 and second gear 65140 are each laterally offset from longitudinal axis "X" of body 65114, and first gear 65130 is coaxial with longitudinal axis "X" of body 65114. Driven coupler 65120 has a first end 65120a extending proximally from a top surface 65117a of plate 65116, and a second end 65120b extending distally from a bottom surface 65117b of plate 65116. First end 65120a of driven coupler 65120 is in the form of a gear (e.g., a spur gear) having a toothed outer surface 65122 that is in meshing engagement with second gear 65140. Second end 65120b of driven coupler 65120 is in the form of a gear (e.g., a crown gear) having downward projecting teeth configured to be non-rotatably inter-engaged with gear teeth of gear 65109a (FIG. 234) of motor shaft 65109 of surgical instrument holder 65102.

In operation, prior to or during a surgical procedure, instrument drive unit 65110 may be coupled to surgical instrument 65200 and surgical instrument holder 65102. In particular, a proximal end of housing 65202 of surgical instrument 65200 is non-rotatably connected to distal end 65114b of body 65114 of instrument drive unit 65110. Instrument drive unit 65110, with surgical instrument 65200 attached thereto, is positioned relative to surgical instrument holder 65102 to operably couple second end or gear 65120b of driven coupler 65120 of instrument drive unit 65110 with gear 65109a of motor shaft 65109 of surgical instrument holder 65102. With instrument drive unit 65110 operably coupled to surgical instrument holder 65102, motor "M" of surgical instrument holder 65102 may be actuated to ultimately effect rotation of surgical instrument 65200 within outer member 65106 of surgical instrument holder 65102.

As depicted in FIG. 239, an instrument drive unit is provided according to at least one aspect of the present disclosure. Instrument drive unit 65410 includes an outer housing (not shown), a body 65414, a plate 65416, a first gear 65430, and a driven coupler 65420, each being similar to the corresponding components of instrument drive unit 65110 described above. Rather than having a gear-to-gear connection between driven coupler 65420 and first gear 65430, as is the case with instrument drive unit 65110, body 65414 of instrument drive unit 65410 includes a belt or strap 65419 disposed about driven coupler 65420 and first gear 65430 to rotatably interconnect driven coupler 65420 with first gear 65430. Belt 65419 has an outer surface 65419a, and an inner surface 65419b defining a plurality of gear teeth. The gear teeth of belt 65419 are in meshing engagement with a toothed outer surface 65420a of driven coupler 65420 and teeth of first gear 65430 such that rotation of driven coupler 65420 rotates belt 65419, which results in rotation of first gear 65430 to effect rotation of body 65414 about its longitudinal axis. Reference may be made to International Patent Application Serial No. PCT/US2017/034206, now International Patent Application Publication No. WO/2017/205481, the entire contents of which are incorporated herein by reference, for additional detailed discussion.

In various aspects, with reference back to FIG. 22, the processes described hereinbelow with respect to FIG. 240 may be represented as a series of machine executable instructions stored in the memory 15006 and executed by the processor 15004 of the central control circuit 15002 of the robotic surgical system 15000 depicted in FIG. 22.

FIG. 240 is a flow diagram 8700 of a process depicting a control program or a logic configuration for controlling a robotic arm according to at least one aspect of the present disclosure. The robotic arm includes a robotic surgical tool, a robotic surgical tool driver, and at least two sensors disposed on the robotic arm to redundantly monitor a status of the robotic arm and to verify the operation of the surgical robotic tool. The at least two separate sensors monitor two different physical properties of the robotic arm to verify the operation of the robotic surgical tool. With reference now to FIGS. 22 and 240, in one aspect, the process depicted by the flow diagram 8700 may be executed by the central control circuit 15002, where the central control circuit 15002 is configured to measure 8702 a first physical property of the robotic arm based on readings from a first sensor. The central control circuit 15002 is configured to measure 8704 a second physical property of the robotic arm based on readings from a second sensor. The central control circuit 15002 is configured to determine 8706 a status of the robotic arm based on the first and second measurements of the first and second physical properties of the robotic arm. The central control circuit 15002 is configured to determine 8708 the operation of the robotic surgical tool and to verify 8710 the operation of the robotic surgical tool based on the measured first and second physical properties of the robotic arm. In one aspect, the first physical parameter is employed by the central control circuit 15002 to effect measurement of the second physical property. In one aspect, the first sensor is disposed on the robotic surgical tool in a sterile field side of a sterile barrier and the second sensor is located on a portion of the robotic arm located on a non-sterile side of the sterile barrier. In one aspect, the two different physical properties may include motor torque, motor current, strain in the mounting housing of the motor, strain on the sterile barrier mounting feature, reaction load of the robotic arm to the operating table, reaction load of the patient with respect to the operating table, load distribution on the operating table, and/or torque or resulting force within the robotic arm or any of its joints.

Referring primarily to FIGS. 241-243, a surgical visualization system 13500 includes a surgical visualization assembly 13502 coupled to a robotic arm 13200, which is similar in many respects to the robotic arms 13002, 13003 (FIG. 4). The robotic arm 13200 is part of a surgical robotic system 13360 (FIG. 6) that includes a remote command console 13370 (FIG. 6) and a surgical hub 13382 (FIG. 6). Other surgical robotic systems suitable for use with the visualization assembly 13502 include the surgical robotic systems 13000 (FIG. 4), 13400 (FIG. 5). In one example, the surgical visualization assembly 13502 is integrated with the robotic arm 13200. In another example, the surgical visualization assembly 13502 is releasably coupled to the robotic arm 13200. In various examples, the visualization assembly 13502 can be incorporated into a hand-held surgical visualization system for direct user manipulation in a laparoscopic or open surgery, for example.

Referring to FIG. 241, a side view is provided of a robotic arm 13200 including a mounting assembly 13210 for securing surgical tools thereto such as, for example, the visualization assembly 13502. The robotic arm 13200 is made up of three members connected via joints. The mounting assembly 13210 is coupled to a distal end 13220 of the arm 13200 and includes a mounting device 13230 and a longitudinally-extending support 13240. The mounting device 13230 is made up of a housing 13232 which supports a clamping and release assembly 13234 and is configured to selectively secure a variety of surgical tools therein to thereby secure a surgical tool to the robotic arm 13200. Although the mounting device 13230 may be adapted to receive a variety of surgical tools, the mounting device 13230 receives a trocar 13250. The trocar 13250 is releasably secured within the mounting device 13230 through a transition between an open configuration and a closed configuration of the clamping assembly 13234. The trocar 13250 includes a cannula 13252 configured to provide a pathway to a surgical site within the patient and has an access port 13254 for receiving a portion of the visualization assembly 13502.

The longitudinally-extending support 13240 extends substantially perpendicularly relative to the housing 13232 of the mounting device 13230 and supports a vertical rail 13242. The vertical rail 13242 is coupled to the support 13240 and extends along a length of the support 13240. The vertical rail 13242 is configured such that the visualization assembly 13502 may be slidably coupled thereto and aligned with the trocar 13250. In particular, a shaft 262 of the of the imaging device 13503 is substantially aligned with the trocar 13250 so that it can be inserted into or removed from the access port 13254 of the trocar 13250.

In the example illustrated in FIGS. 242 and 243, the surgical visualization assembly 13502 includes an imaging device 13503 and an outer housing 13504 in the form of a tubular member partially encapsulating the imaging device 13503. Specifically, a distal end 13505 of the imaging device 13503, which includes a visualization lens 13506 and a light source 13508, is exposed. In other examples, the distal end 13505 of the imaging device 13503 can be fully encapsulated by the outer housing 13504. The outer housing 13504 may include a transparent lens disposed in front of the distal end 13505 of the imaging device 13503 to protect the visualization lens 13506 and/or the light source 13508 from direct exposure to body fluids. For the purposes of the present disclosure a transparent lens positioned in front of the visualization lens 13506 is considered part of the visualization lens 13506.

Further to the above, the imaging device 13503 is similar in many respects to other imaging devices described in the present disclosure such as, for example, the imaging device 124. Like the imaging device 124, the imaging device 13503 is configured for use in a minimally invasive procedure. In one aspect, the imaging device 13503 employs multi-spectrum monitoring to discriminate topography and underlying structures. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

Referring still to FIGS. 242 and 243, the outer housing 13504 supports components of a lens cleaning system 13510 that includes fluid ports 13512 in the form of nozzles that are disposed at chamfered edges 13514 of a distal portion 13516 of the outer housing 13504 and are directed toward the distal end 13505 of the imaging device 13503. The fluid ports 13512 are connected to one or more fluid tubes 13513, and are configured to clean the distal end 13505 by ejecting fluids at and/or suctioning fluids in near proximity to the distal end 13505 to remove biological material, other debris, moisture/fog, contaminants, and/or any other materials accumulating onto the distal end 13505 against the visualization lens 13506. The fluids utilized by the lens cleaning system 13510 may include various suitable gases such as, for example carbon dioxide and/or liquids such as, for example saline.

FIG. 244 is a logic flow diagram of a process 13520 depicting a control program or a logic configuration for determining whether a visualization lens 13506 of a surgical visualization system 13500 needs cleaning and/or reporting the same. In various instances, the process 13520 includes monitoring 13526 a parameter indicative of lens transparency or lens occlusion. The process 13520 further includes presenting 13528 through a user interface 13522 of the surgical visualization system 13500 a lens transparency level or lens occlusion level based on the monitored parameter.

FIG. 244A is a is a logic flow diagram of a process 13540 depicting a control program or a logic configuration for determining whether a visualization lens 13506 of a surgical visualization system 13500 needs cleaning and triggering the cleaning. In various instances, the process 13540 includes monitoring 13526 a parameter indicative of lens transparency or lens occlusion of the visualization lens 13506. The process 13520 further includes detecting 13542 an excessive deterioration of lens transparency based on the monitored parameter, and automatically activating 13544, or triggering activation, of a lens cleaning system 13510 to remedy the excessive deterioration of the lens transparency.

In various examples, as illustrated in FIG. 245, the surgical visualization system 13500 includes a control circuit 13524 configured to perform the processes 13520, 13540. In the example of FIG. 245, one or both of the processes 13520, 13540 can be embodied as a set of computer-executable instructions stored in a memory 13534 that, when executed by a processor 13533, cause the processor 13533 to perform the processes 13520, 13540. In other examples, the processes 13520, 13540 can be performed by other control circuits such as, for example, the control circuits 500 (FIG. 13), 510 (FIG. 14), 520 (FIG. 15). Further, although the processes 13520, 13540 is described as being executed by a control circuit 13524, this is merely for brevity, and it should be understood that the depicted processes 13520, 13540 can be executed by circuitry that can include a variety of hardware and/or software components and may be located in or associated with various systems integral or connected to a robotic surgical system.

Further to the above, the control circuit 13524 is coupled to a parameter detector 13529 which can be configured to measure values of a parameter indicative of lens transparency or lens occlusion of the visualization lens 13506, in accordance with the processes 13520, 13540. For the purposes of the present disclosure, the terms lens transparency and lens occlusion, although possessing opposite meanings, represent a degree of visibility through the visualization lens 13506. Greater lens transparency correlates to a reduction in lens occlusion.

In addition, the control circuit 13524 is coupled to a user interface 13522. In one example, the user interface 13522 can be at a remote command console 13370 (FIG. 6). In another example, the user interface 13522 can be in the form of an interactive secondary display that is similar in many respects to the interactive secondary displays 13362, 13364 (FIG. 7). Furthermore, the control circuit 13524 is coupled to a lens cleaning system 13510 that may include, for example, fluid pumps for ejecting and/or suctioning fluids at, or near, the distal end 13505 of the imaging device 13503.

In one example, the parameter is time. In other words, the control circuit 13524 is configured to trigger activation of the lens cleaning system 13510 at predetermined time intervals. Additionally, or alternatively, the parameter detector 13529 may include one or more capacitive sensors 13530 disposed at, or near, the distal end 13505 of the imaging device 13503. In one example, the parameter detector 13529 includes a series of capacitive sensors 13530 disposed at, or near, the distal end 13505 around the visualization lens 13506, as illustrated in FIG. 246. The capacitive sensors 13530 detect biological materials and/or other debris accumulation at, or near, the visualization lens 130506. The measured values of the capacitive sensors 13530 represent lens occlusion or transparency levels of the visualization lens 13506. A look-up table or database can be accessed by the control circuit to determine the lens occlusion or transparency levels based on the measured values of the capacitive sensors 13530.

In one example, the memory 13534 of the control circuit 13524 may store an algorithm, an equation, or a look-up table for determining correlations between measurements of one or more of the capacitive sensors 13530 and the lens occlusion or transparency levels of the visualization lens 13506. In addition, a processor 13533 of the control circuit 13524 may employ such algorithm, equation, and/or look-up table to determine the lens occlusion or transparency levels based on the measurements of the capacitive sensors 13530. In certain instances, each of the capacitive sensors 13530 can be assigned to a specific area or portion of the distal end 13505 of the imaging device 13503 to detect biological materials and/or other debris accumulation at, or near, such area or portion. In such instances, different lens occlusion or transparency levels can be ascertained for different areas or portions of the distal end 13505. Alternatively, or additionally, the measurements of some or all of the capacitive sensors 13530 can be aggregated to derive a common lens occlusion or transparency level at the distal end 13505.

Additionally, or alternatively, the parameter detector 13529 may include one or more optical sensors 13532 disposed at, or near, the distal end 13505 of the imaging device 13503. In one example, the parameter detector 13529 includes a series of optical sensors 13532 disposed at, or near, the distal end 13505 around the visualization lens 13506. The optical sensors 13532 detect biological materials and/or other debris accumulation at, or near, the visualization lens 130506 by measuring changes in light diffusion caused by the accumulation. The measured values of the optical sensors 13532 represent lens occlusion or transparency levels of the visualization lens 13506. A look-up table or database can be accessed by the control circuit to determine the lens occlusion or transparency levels based on the measured values of the optical sensors 13532.

In one example, the memory 13534 of the control circuit 13524 may store an algorithm, an equation, or a look-up table for determining correlations between measurements of one or more of the optical sensors 13532 and the lens occlusion or transparency levels of the visualization lens 13506. In addition, a processor 13533 of the control circuit 13524 may employ such algorithm, equation, and/or look-up table to determine the lens occlusion or transparency levels based on the measurements of the optical sensors 13532. In certain instances, each of the optical sensors 13532 can be assigned to a specific area or portion of the distal end 13505 of the imaging device 13503 to detect biological materials and/or other debris accumulation at, or near, such area or portion. In such instances, different lens occlusion or transparency levels can be ascertained for different areas or portions of the distal end 13505. Alternatively, or additionally, the measurements of some or all of the optical sensors 13532 can be aggregated to derive a common lens occlusion or transparency level at the distal end 13505.

In at least one example, a secondary light activator is passed through the face of the visualization lens 13506 and is proportionate to the lens occlusion. In at least one example, an infrared light ("IR") can be passed laterally through a transparent member in front of the visualization lens 13506 and, then, light diffusion in-between imaging passes can be detected. An increase in light diffusion would indicate accumulation of biological materials and/or other debris or contaminants against the visualization lens 13506. The control circuit 13524 can be configured to trigger activation of the lens cleaning system 13510 when the detected light diffusion is greater than or equal to a predetermined threshold that can be stored in the memory 13534, for example.

In various examples, the measurements of the parameter detector 13529 can be compared to a predetermined threshold to assess whether the lens cleaning system 13510 should be activated. In at least one example, as illustrated in FIG. 247, the predetermined threshold is a visibility threshold 13546, and the lens cleaning system 13510 is activated by the control circuit 13524 when the lens occlusion level 13548, as derived from the measurements of the parameter detector 13529, passes 13545 the visibility threshold 13546. Further, the cleaning system 13510 can be automatically deactivated by the control circuit 13524 when the lens occlusion level 13548 falls below the predetermined threshold 13546.

In various examples, the control circuit 13524 may utilize the imaging module 138 (FIG. 3) to determine when to trigger the activation of the cleaning system 13510. The imaging module 138 can be utilized to analyze and/or compare frames captured by the imaging device 13503 looking for either known makers (on instruments) or distinguishable objects within the field of view of the visualization lens 13506 to identify irregular distortions or blurriness beyond accepted predetermined thresholds. Accordingly, the control circuit 13524 can trigger the activation of the cleaning system 13510 based on input from the imaging module 138 indicative of identification of irregular distortions from one or more frames capture by the imaging device 13503 through the visualization lens 13506. If the irregular distortions remain after cleaning is completed, the control circuit 13524 may delay re-triggering of the activation of the lens cleaning system 13510 a predefined amount of time or ignore the irregular distortions in future determinations.

Referring primarily to FIGS. 248-250, in addition to biological material, debris, and/or contaminants, lens fogging is another factor that affects the lens occlusion and transparency levels. Lens fogging occurs when the temperature of a lens becomes lower than its surrounding environment. As illustrated in FIG. 248, a visualization lens 13506 is generally used inside a body cavity 13550 of a patient such as, for example, the abdominal cavity where the temperature is T3. The temperature of the lens outside a patient's body cavity 13550 is room temperature, which is less than the temperature T3. Accordingly, the visualization lens 13506 may fog during, or directly after, introduction into the body cavity 13550.

As illustrated in FIG. 249, lens fogging may also occur after lens cleaning is performed by the lens cleaning system 13510 if the cleaning fluid ejected by the lens cleaning system 13510 is at a temperature T1 below the temperature T3 of the body cavity 13550. The bottom graph of FIG. 249 illustrates how lens visibility 13554 slowly and repeatedly decreases after application 13553 of a cleaning cycle by the lens cleaning system 13510 with a cleaning fluid at the temperature T1 due to repeated fogging of the visualization lens 13506. Lens fogging continues to occur because the cleaning fluid, at temperature T1, maintains a temperature T2 of the visualization lens 13506 below the temperature T3 of the body cavity 13550. Said another way, the cleaning fluid cools the visualization lens 13506 causing lens fogging that, in turn, causes the control circuit 13524 to trigger additional activations of the lens cleaning system 13510. In other instances, lens fogging may occur because the temperature T3 of the body cavity 13550 increases due to external factors. As illustrated in FIG. 248, lens fogging may occur during a surgical procedure due to activation 13555 of an electrosurgical surgical instrument 13552 inside the body cavity 13550, which raises the temperature T3 of the body cavity 13550, as illustrated in FIG. 249.

Referring again to FIG. 245, in various aspects, the parameter detector 13529 may monitor the temperature of the visualization lens 13506, the temperature of the body cavity 13550, and/or the temperature of the cleaning fluid to track lens transparency or lens occlusion levels caused by lens fogging changes from the tracked temperatures. Furthermore, the control circuit 13524 may activate the lens cleaning system 13510 to improve lens transparency levels or reduce lens occlusion levels if it is determined, based on the measurements of the temperature of the visualization lens 13506, the temperature of the body cavity 13550, and/or the temperature of the cleaning fluid, that lens fogging has reached or exceeded a predetermined threshold.

Referring to FIG. 248, in various aspects, a visualization assembly 13502 includes one or more temperature sensors 13556 for measuring the temperature T3 of the body cavity 13550. The temperature sensors 13556 are disposed on a distal portion of the visualization assembly 13502 that is positioned within the body cavity 13550 during a surgical procedure. In other examples, the temperature sensors 13556 can be deployed in any suitable location within the body cavity 13550. The surgical visualization assembly 13502 further includes one or more temperature sensors 13558 form measuring the temperature T2 of the visualization lens 13506. The temperature sensors 13558 are disposed at the distal end 13505 near the visualization lens 13506. The surgical visualization assembly 13502 further includes one or more heating elements 13560 configured to adjust the temperature T1 of the cleaning fluid of the lens cleaning system.

In various aspects, the control circuit 13524 may control the temperature T1 of the cleaning fluid to a desired temperature through the heating elements 13560 in order to avoid, or at least reduce, lens fogging. As illustrated in the top graph of FIG. 250, the temperature T1 of the cleaning fluid is raised above the temperature T3 of the body cavity 13550 by an amount ($\Delta T$) sufficient to maintain the temperature T2 of the visualization lens 13506 above, or at least at, the temperature T3 of the body cavity 13550. The result, as illustrated in bottom graph of FIG. 250, is a reduction in visibility 13554 fluctuation due to lens fogging, as evident from comparing the bottom graphs of FIGS. 249 and 250.

In various aspects, the control circuit 13524 can predict instances of fog occurrences based on the readings of the temperature sensors 13556, 13558, and adjust the temperature T1 of the cleaning fluid, the mount of cleaning fluid applied to the visualization lens 13506, and/or the frequency of cleaning fluid application to the visualization lens 13506 to avoid, or at least reduce, lens fogging. For example, as illustrated in FIGS. 248 and 250, activation of the electrosurgical instrument 13552 may increase the temperature T3 of the body cavity 13550. The control circuit 13524 may receive input from the temperature sensors 13556 indicative of the increase in the temperature T3. In response, the control circuit 13524 may cause the heating elements 13560 to be activated to raise the temperature T2 of the cleaning fluid an amount ($\Delta T'$) and/or cause the lens cleaning system 13510 to increase the amount and/or frequency of application of the heated cleaning fluid to the visualization lens 13506 to maintain the temperature T2 above, or at least at, the increased temperature T3 of the body cavity 13550.

In various aspects, the fluid ports 13512 can be adjusted to control cleaning fluid direction and flow speed. In one example, the control circuit 13524 can be coupled to one or more motors that can move the fluid ports to adjust a flow direction of the cleaning fluid. The fluid ports 13512 may include adjustable openings to control the speed of flow. Additionally, or alternatively, the control circuit 13524 may adjust the flow speed of the cleaning fluid by adjusting power delivered to fluid pumps of the lens cleaning system 13510. The control circuit 13524 can adjust the control cleaning fluid direction and flow speed to effect removal or disposition of biological materials and/or other debris toward a portion of the abdomen which is not in use or toward predefined locations for collection or controlled re-introduction into the body. In various aspects, the control circuit 13524 is configured to adjust the flow speed of the cleaning fluid based on input from the imaging module 138 indicative of the type and/or size of the debris to be removed.

In various instances, automatic control of the activation of the lens cleaning system 13510 is further subject to a predetermined waiting period between consecutive activations. In such instances, the control circuit 13524 is prevented from triggering another lens cleaning system 13510 activation until the predetermined time period has passed.

Referring to FIGS. 251 and 252, a visualization system 13600 includes an insertion port or trocar 13601, which is similar in many respects to the trocar 13250, and an imaging device 13603 insertable into a body cavity through the trocar 13601. The imaging device 13603 is similar in many respects to the imaging device 124 (FIG. 2). In various aspects, the visualization system 13600 is coupled to a robotic arm 13200. The robotic arm 13200 is part of a surgical robotic system 13360 (FIG. 6) that includes a remote command console 13370 (FIG. 6) and a surgical hub 13382 (FIG. 6). Other surgical robotic systems suitable for use with the visualization system 13600 include the surgical robotic systems 13000 (FIG. 4), 13400 (FIG. 5). In one example, the visualization system 13600 is integrated with the robotic arm 13200. In another example, the surgical visualization system 13600 is releasably coupled to the robotic arm 13200. In various examples, the visualization system 13600 can be incorporated into a hand-held surgical visualization system for direct user manipulation in a laparoscopic or open surgery, for example.

The trocar 13601 includes a seal assembly 13610 including an outer housing 13611. A tubular member 1612 extends distally from the outer housing 13611 and cooperates with the seal assembly 13610 to define a longitudinal opening 13613. The imaging device 13603 includes a shaft 13604 that has a distal end 13605 including a visualization lens 13606 and one or more light sources 13607. During a surgical procedure, the trocar 13601 is inserted through a body wall into a body cavity. The shaft 13604 is then inserted through the longitudinal opening of the trocar 13601 to introduce the distal end 13605 into the body cavity. As the surgical procedure progresses, biological material and/or other debris may accumulate on the visualization lens 13606 necessitating removal of imaging device 13603 from the trocar to clean the visualization lens 13606. In a typical trocar, reinsertion of a cleaned imaging device 13603 through the trocar may cause biological material and/or other debris left behind along the longitudinal opening of the trocar during removal of the imaging device 13603 for cleaning to be redeposited onto the visualization lens 13606.

To eliminate, or at least reduce, the redepositing of biological material and/or other debris onto the visualization lens 13606 during reinsertion of the imaging device 13603 through the trocar 13601, the seal assembly 13610 is automatically transitioned from a closed configuration (FIG. 252) to an open configuration (FIG. 251) to accommodate insertion of the imaging device 13603 into the longitudinal opening 13613. The seal assembly 13610 returns to the closed configuration after insertion of shaft 13604 through the seal assembly 13610, as illustrated in FIG. 252.

Referring still to FIGS. 251 and 252, the seal assembly 13610 includes an iris seal 13614 configured to constrict around the shaft 13604 of the imaging device 13603 in the closed configuration. In at least one example, the iris seal 13614 includes leaf members that rotate from a first relative position, substantially open, to a second relative position, substantially closed. Alternatively, the iris seal 13614 may be comprised of one or more elastic, flexible, and/or or shape changing elements that can be expanded, in the closed configuration, and retracted in the open configuration. In at least one example, the expandable elements may include a shape memory element such as, for example, Nitinol. In various aspects, an actuation mechanism for transitioning the iris seal 13614 between the open configuration and the closed configuration may include a motor, one or more sensors, and a control circuit for determining when to transition the iris seal 13614 between the open configuration and the closed configuration based on input signals received from the one or more sensors.

In various aspects, the control circuit is configured to transition the iris seal 13614 between the open configuration and the closed configuration according to the position of the trocar 13601 with respect to the imaging device 13603 and/or with respect to one or more components of the robotic arm 13200, for example. In various instances, the trocar 13601 and the imaging device 13603 are coupled to the robotic arm 13200. In such instances, the robotic arm 13200 causes the imaging device 13603 to be moved toward the trocar 13601 such that the shaft 13604 of the imaging device 13603 is inserted into the longitudinal opening of the trocar 13601. The distance between the distal end 13605 of the imaging device 13603 and the iris seal 13614 can be tracked by the surgical robotic system 13360, for example, by tracking the movement of the imaging device 13603 by the robotic arm 13200 and knowing the starting distance between the distal end 13605 of the imaging device 13603 and the iris seal 13614. As illustrated in FIG. 251, the iris seal 13614 is automatically opened when the distance between the iris seal 13614 and distal end 13605 is less than or equal to a predetermined distance D1. Furthermore, the iris seal 13614 is automatically closed or constricted around the shaft 13604 of the imaging device 13603 when the distal end 13605 has moved through the iris seal 13614 a distance greater than or equal to a predetermined distance D2, for example. This mechanism ensures that the biological material and/or other debris will not be repositioned on the cleaned visualization lens 13606.

In various instances, the above-described mechanism for opening and closing the iris seal 13614 can be similarly adopted with respect to other sealing features of the trocar 13601 such as, for example, an internal duckbill 13615. To prevent, or at least reduce, fluid insufflation loss during the above-described re-insertion process, the seals of a trocar 13601 can be opened and closed sequentially. For example, the iris seal 13614 can be opened then closed or constricted around the shaft 13604 before the distal end 13605 reaches a more distal seal such as, for example, the duckbill 13615. After closing the iris seal 13614, a more distal seal such as, for example, the duckbill 13615 is opened to allow passage of the distal end 13605. The duckbill 13615 is then constricted around the shaft 13604.

Referring to FIGS. 253 and 254, a trocar 13630 includes an integrated lens cleaning system 13631 configured to clean a visualization lens 13606 with fully removing the imaging device 13603 from the trocar 13630. The trocar 13630 includes a seal assembly 13633 that defines a cleaning chamber 13634 for removing biological material and/or other debris from the distal end 13605 of the imaging device 13603. The cleaning chamber 13634 defines an empty space between a proximal seal such as, for example, an iris seal 13636 and a distal seal 13637 such as, for example, a duckbill seal, the empty space being dimensioned to receiving the distal end 13605 of the imaging device 13603. An inlet port 13640 is defined in an outer housing 13641 of the seal assembly 13633. The inlet port 13640 passes flushing fluid from a lens cleaning system 13631 into the empty space of the cleaning chamber 13634. The flushing fluid removes biological material and/or other debris from the distal end 13605 of the imaging device 13603, and exits the cleaning chamber 13634 through the distal seal 13637, for example. Alternatively, the an outlet port can also be defined in the outer housing 13641 for facilitated removal of the flushing fluid and biological material and/or debris from the cleaning chamber 13634 to a collection chamber integrated with, or separate from, the cleaning system 13631.

In various aspects, the position of the imaging device 13603 with respect to a trocar 13630 that is connected to the robotic arm 136120 is controlled and monitored by the robotic surgical system 13360 (FIG. 6). Accordingly, the robotic surgical system 13360 can detect the presence of the distal end 13605 of the imaging device 13603 is in the empty space of the cleaning chamber 13634. Alternatively, or additionally, one or more sensors and/or integrated encoders can be positioned at, or near, the distal end 13605 to detect the presence of the distal end 13605 in the empty space of the cleaning chamber 13634. A control circuit such as, for example, the control circuit 500 can be configured to receive input indicating that the distal end 13605 is in the empty space of the cleaning chamber 13634. In response, the control circuit 500 automatically activates the lens cleaning system 13631 to cause the flushing fluid to remove biological material and/or other debris from the visualization lens 13606, for example. In other aspects, the control circuit 500 may signal a user through a user interface that the imaging device 13603 is ready for cleaning.

In FIG. 255, an invasive portion 50020 comprises a cylindrical section 50022 having a central passageway 50024. An invasive portion retainer 50026 is located on an outer surface 50028 of the invasive portion. The invasive portion retainer functions to retain the invasive portion within the patient during surgery. In the embodiment, the invasive portion retainer comprises threads helically surrounding the outer surface. Other invasive portion retainers will be obvious to those skilled in the art. The invasive portion 50020 further comprises an invasive portion coupler 50030 at its axially outer end 50032. In the embodiment of the device, the invasive portion coupler 50030 comprises a threaded receptacle having an internal diameter D1.

A non-invasive portion 50034 adaptively couples to the invasive portion 50020 at the coupler 50030 by matching threads. The non-invasive portion has a cylindrical main section 50039 of an internal diameter D4, larger than the diameter D2 of the central passageway 50024. The non-invasive portion 50034 tapers to a narrow section 50040, where threads 50042 are located. The narrow section has an internal diameter D3 larger than or equal to the internal diameter D2 of the central passageway and an external threaded diameter which firmly threadably engages into the threads of the internal diameter D1 of coupler 50030. Reference may be made to U.S. patent application Ser. No. 25,024, now U.S. Pat. No. 5,383,860, the entire contents of which are incorporated herein by reference, for additional detailed discussion.

Referring to FIG. 257, cannula assembly 50600 is shown extending through mounting structure 50500. Cannula assembly 50600 includes a cannula or trocar 50610, an attachment member 50620, a barrier 50630, a first seal 50640, and a second seal 50650. Generally, cannula assembly 50600 is configured to provide a passageway for a surgical instrument (e.g., surgical instrument) to be inserted through an incision in a patient's skin and adjacent target tissue. Additionally, the cannula assembly 50600 is configured to minimize or prevent gasses and/or fluids from exiting the patient proximally through cannula assembly 50600, for example.

Cannula 50610 is an elongated, hollow tube that is configured to allow an elongated portion and an end effector of a surgical instrument to pass therethrough and access target tissue within a patient, for example. Cannula 50610 is sized and dimensioned for insertion within a channel 50530 of mounting structure 50500. More particularly, cannula 50610 is configured to be inserted into channel 50530 of mounting structure 50500 in a distal-to-proximal direction (in the general direction of arrow "B" in FIG. 257), and cannula 50610 may be removed from channel 50530 in a proximal-to-distal direction (in the general direction of arrow "C" in FIG. 257). An outer diameter of cannula 50610 and an inner diameter of barrier 50630 (e.g., a distal cylindrical section 50636) within channel 50530 of mounting structure 50500 may be similarly sized to enable a frictional engagement therebetween. Reference may be made to International Application Patent Application Serial No. PCT/US2017/034178, now International Publication No. WO/2017/205467, the entire contents of which are incorporated herein by reference, for additional detailed discussion.

FIG. 258 shows a shaft 50130 of a surgical instrument, such as trocar obturator, inserted through seal assembly 50100 and a duck bill valve or "zero" seal valve 50132 which prevents the escape of insufflation gases in the absence of an instrument in the trocar assembly. As shown in FIG. 258, seal member 50118 provides a seal about the periphery of instrument shaft 50130. Reference may be made to U.S. patent application Ser. No. 11/786,251, now U.S. Patent Application Publication No. 2007/0197972, the entire contents of which are incorporated herein by reference, for additional detailed discussion.

Referring now to FIGS. 259 and 260, a cannula assembly of modular trocar system will now be described. Cannula assembly includes a molded cylindrical base portion 50216 having transversely extending grip portions 50218 formed to extend from an annular flange formed at the proximal end of cylindrical base 50216. A series of slots 50222 are formed along the underside or distal side of grips 50218.

Slots 50222 are particularly advantageous in two respects. First, in assembling cannula assembly, there are three basic principle components: cylindrical base portion 50216 having outwardly directing finger grips 50218, a duck bill valve element 50224 having a flange 50226 which is configured and dimensioned to rest on annular flange 50220 of cylindrical base portion 50216 and a cannula housing cover portion such as proximal housing element 50228 which is configured and dimensioned to rest on duck bill flange 50226 and within the outwardly directed finger grips 50218. It has been found that by coring out the underside of outwardly extending finger grips 50218 with parallel slots 50222, molding sinks which had been previously forming on the proximal side of outwardly extending fingers 50218 of cylindrical base portion 50216 were significantly reduced, thereby providing a much more reliable flat surface, against which duck bill flange 50226 may rest and against which the upper or proximal housing element 50228 may be welded. Reference may be made to U.S. patent application Ser. No.

09/140,076, now U.S. Pat. No. 5,980,493, the entire contents of which are incorporated herein by reference, for additional detailed discussion.

FIG. 261 shows the internal components of the sealing cannula. As shown in FIG. 261, the sealing cannula comprises a cannula cap 51074 having an access orifice 51076 formed thereon positioned on the upper cannula body. The cannula cap 51074 may be attachable to the upper cannula body in a variety of ways, including for example, in snap fit, screw relation, or adhesively joined. An o-ring 51078 and sealing washer 51080 defining a washer orifice are positioned proximal the cannula cap 51074, and act as a sealing conduit between the cannula cap 51074 and the guide member lumen 51086 formed in the guide member 51084. The guide member 51084 is attached to the upper cannula body in screw-like fashion. In alternative embodiments, the guide member 51084 may be attached to the upper cannula body 51066 in slip-fit relation, snap-fit relation, or other manners known in the art. As shown in FIG. 261, the guide member lumen 51086 is tapered. In another embodiment the walls of the guide member 51084 forming the guide member lumen 51086 maybe substantially parallel.

The embodiment further comprises a sealing member 51088 located within the lower cannula body and in communication with the guide member lumen 51086 and the device channel. The sealing member 51088 prevents a backflow of blood or other material from entering the cannula. As shown, the sealing member 51088 comprises a duckbill seal 51090 having at least two sealing leafs 51090a and 51090b forming a sealing receiver 51092. In alternative embodiments, various sealing devices may be incorporated into the sealing cannula, including, for example, sealing irises and flapper valve devices. Reference may be made to U.S. patent application Ser. No. 09/800,390, now U.S. Pat. No. 6,537,290, the entire contents of which are incorporated herein by reference, for additional detailed discussion.

With reference to FIG. 262, an embodiment comprises a suspended, pendent valve module 52040 which can be mounted to an end cap 52013, within a trocar housing, and adapted to receive a wide range of instrument sizes. As illustrated in FIG. 262, the end cap 52013 is typically disposed in a radial plain generally perpendicular to the axis 52015 of the trocar. The module 52040 also has an axis 52047 and is characterized by an elongate tube 52050 having a proximal end 52052 and a distal end 52054. In an embodiment, the proximal end 52052 is coupled to the end cap 52013, while the distal end 52054 carries a septum valve 52056 with an orifice 52057, and a zero valve 52058.

As illustrated in FIG. 263, an instrument 52021 will often be introduced at some angle to the axis 52016 which will cause it to contact the inner surface of the tubular member 52061. This will cause the pendent valve module 52040 to pivot at the flexible coupler 52065, thereby moving the septum valve 52056 and its orifice 52057 toward the distal tip of the instrument 52021. If this tip contacts the frusto-conical edges of the valve 52056, it would do so at a face angle which causes the orifice 52057 to move further toward the instrument 52021. This face angle is advantageously increased due to the pendulating characteristics of the module 52040.

In this case, the highly flexible coupler 52065 of the second tubular member comprises a series of thin, convoluted, folded or corrugated features that allow the pendulous seal module 52040 to move from side-to-side, to bend, to rotate or otherwise to be positioned by the inserted or approaching instrument 52021. An additional embodiment of the highly flexible coupler 52065 may comprise a thin material that stretches and folds to achieve the same goals. An additional embodiment of the highly flexible coupler 52065 may include a support region made of a low durometer material that achieves the same goals. Reference may be made to U.S. patent application Ser. No. 11/423,819, now U.S. Pat. No. 8,613,727, the entire contents of which are incorporated herein by reference, for additional detailed discussion.

Referring now to FIGS. 267 and 268, an assembled trocar 53010 comprises a trocar obturator 53012, a trocar tube 53014, and a valve cartridge 53016. The trocar obturator comprises a head 53012a, an elongate shaft 53012b extending downwardly from the head and terminating in a trocar tip 53012c. The trocar tube includes an upper shell or housing 53018 and a depending tube 53020 through which pass the trocar obturator and surgical instruments (not shown) for endoscopic surgery. The housing has a port 53022 (which may be fitted with a stop clock 53024) used for insufflating and desufflating an abdominal cavity, for example, through the trocar tube. The upper shell is shown cylindrical in shape, however, it can be any suitable shape, box-like for example. The shell has an opening 53026 at its upper end and has an internally threaded flange 53028 or other suitable fastening means to receive and secure the valve cartridge 53016.

The cartridge comprises an upper collar 53030 and a depending cylindrical skirt 53032 for receiving and positioning primary 53034 and secondary seals and the protective insert 53038 for the secondary seal, for attachment to the shell, for defining a sealed axial passage for the trocar as well as instruments passed through the trocar tube, and for admitting peritoneal pressure to the exterior surfaces of the secondary seal. The exterior and interior elements of the cartridge assembly are shown in FIG. 268 and includes cap or collar 53030 and subjacent threaded section 53033 for securing the cartridge to the trocar shell. The remaining skirt portion 53032 of the cartridge is long enough to cover entirely the secondary seal valve while having vents 53035 for the purpose of admitting peritoneal pressure to the exterior surface of the secondary seal. The vents are in the form of slits extending upward from the bottom edge of the skirt best shown in FIG. 268, it being understood that other shaped openings in the skirt may be used for venting. Reference may be made to U.S. patent application Ser. No. 523,108, now U.S. Pat. No. 5,662,615, the entire contents of which are incorporated herein by reference, for additional detailed discussion.

Referring now to FIG. 269, one embodiment of a disclosed trocar assembly, generally designated 54010, may include a sleeve assembly 54012 and an obturator assembly 54014. Optionally, as will be discussed in greater detail below, the trocar assembly 54010 may additionally include an insufflation valve assembly 54016 coupled to the sleeve assembly 54012.

The sleeve assembly 54012 may include a generally cylindrical or tubular cannula 54018, a generally annular housing 54020, a channel seal 54050 received in the housing 54020 and a cap 54056 attached to the housing 54020. The cannula 54018 may be elongated along a longitudinal axis A, and may include an open proximal end 54022 and an open distal end 54024. The open distal end 54024 may included a bevel 54026 that terminates in a pointed tip 54027. A lumen may extend along the axial length of the cannula 54018 between the open proximal end 54022 and the open distal end 54024. The housing 54020 may define an internal volume 54030 and may include an open proximal end 54032 and an open distal end 54034. The open distal end 54034 of the housing 54020 may be connected to the open proximal end 54022 of the cannula 54018 to couple the internal volume 54030 of the housing 54020 with the lumen of the cannula 54018, thereby defining an elongated working channel 54036 that extends axially through the sleeve assembly 54012. Reference may be made to U.S. patent application Ser. No. 12/575,598, now U.S. Pat. No. 8,491,533, the entire contents of which are incorporated herein by reference, for additional detailed discussion.

FIG. 270 shows an adaptor 54300 connected to seal assembly 54400. Threading of adaptor (54300) is connected to threading 54425 of seal assembly 54400. Through this engagement of threading, connections between distal surface 54422 of seal assembly 54400 and proximal end 54310 of adaptor 54300 are sufficient to provide a seal maintaining pneumostasis in an insufflated body cavity of a patient. Also, seal assembly housing is supporting seal assembly 54400, so that if adaptor 54300 is stable, so is seal assembly 54400.

A seal between adaptor 54300 and flange 54240 maintaining pneumostasis can be created using multiple materials, if adaptor 54300 is made entirely out of elastomeric material, interior taper 54330 could be dimensioned for interference with interior wall defining proximal angled opening 54230, exterior taper 54340 could be dimensioned for interference with flange 54240, or both interior taper 54330 and exterior taper 54340 could be dimensioned for interference with interior wall defining proximal angled opening 54230 and flange 54240 respectively. All of these possibilities could create a seal, in effect maintaining pneumostasis in an insufflated body cavity of a patient. Reference may be made to International Application Patent Application Serial No. PCT/US2015/065493, now International Publication No. WO/2016/100181, the entire contents of which are incorporated herein by reference, for additional detailed discussion.

Turning now to FIG. 271, housing 55102 forms a substantially annular member having a partially closed proximal end 55102$a$ and a partially closed distal end 55102$b$. Housing 55102 may instead define an oval, square, rectangular or other suitable profile. Housing 55102 may be constructed of metal, plastic, polymer or other suitable material. Housing 55102 defines a passageway 55101 therethrough for receiving an instrument E (FIG. 272). Proximal end 55102$a$ of housing 55102 defines an opening 55103 configured to receive instrument E therethrough.

Still referring to FIG. 271, distal end 55102$b$ of housing 55102 defines a horizontal slot 55105 for receiving a flange 55115 formed on proximal end 55110$a$ of cannula 55110. As will be discussed in further detail below, distal end 55102$b$ of housing 55102 is configured to floatingly receive flange 55115 therein. A rubber or foam ring 55105$a$ may be included with slot 55105. In the event that housing 55102 is pressurized, foam ring 55105$a$ may form a seal between the connection of housing 55102 and cannula 55110 to prevent leakage of the insufflation gas.

Referring to FIG. 272, when a user applies a lateral force against housing 55102 in a direction indicated by arrow F1, housing 55102 translates horizontally relative to cannula 55110 in the direction force F1. Slot 55105 formed in distal end 55102$b$ of housing 55102 permits this movement of housing 55102 relative to cannula 55110. In this manner, housing 55102 and thus, instrument E inserted therethrough, may be manipulated relative to cannula 55110 without moving cannula 55110. As discussed above, slot 55105 may include a rubber or foam ring 55105$a$ that may compress as housing 55102 is moved about cannula 55110. The release of force F1 against housing 55102 causes ring 55105$a$ to decompress, thereby returning housing 55102 it its initial, concentric position with cannula 55110. In this manner, housing 55102 may be moved any direction in a horizontal plane relative to cannula 55110. By being able to laterally move housing 55102 relative to cannula 55110, a user may more precisely manipulate and have greater control over instrument E inserted therethrough.

During a surgical procedure, a trocar assembly can be introduced into a patient's abdominal wall to provide access to the patient's abdominal cavity. Surgical instruments can be inserted through the trocar assembly and into the abdominal cavity to perform laparoscopic surgical procedures. During a laparoscopic surgical procedure, the abdominal cavity is generally insufflated in order to increase the volume of the working environment. A seal system can be provided in the trocar assembly to inhibit the escape of the insufflation gases therethough. After the surgical procedure, the trocar assembly is typically discarded. It is desirable that a portion of the trocar assembly be reprocessable and reusable for more than one surgical procedure to reduce the costs of performing surgical procedures.

Referring now to FIG. 273, a trocar assembly 13700 is provided that includes a reusable housing 13705. The reusable housing 13705 is made of a material that is able to be sterilized and used for more than one surgical procedure, such as metal. The reusable housing 13705 includes a robot arm holding feature 13710 defined around the outside perimeter of the reusable housing 13705. The robot arm holding feature 13710 is sized and configured to be grasped by an arm of a robotic surgical system. The robot arm holding feature 13710 allows for proper alignment between the arm of the robotic surgical system and the robot arm holding feature of the reusable housing 13705.

The reusable housing 13705 of the trocar assembly includes a distal end 13715 that includes a threaded portion 13720. The threaded portion 13720 is configured to releasably couple the reusable housing 13705 to a disposable cannula 13725 that includes a threaded portion 13730, as is shown in FIG. 273. The disposable cannula 13725 can made of a material that is intended to be disposed of at the conclusion of a surgical procedure, such as plastic. The cannula 13725 is configured to be coupled to the reusable housing 13705 before, or during, a surgical procedure and removed and disposed of after the completion of the surgical procedure. The cannula 13725 facilitates passage of a surgical instrument through the reusable housing 13705 and into a patient.

The reusable housing 13705 further includes a proximal end 13735 defining a proximal opening 13740 into the reusable housing 13705. The proximal opening 13740 is configured to receive an insertable seal system 13750 that includes a first seal 13750$a$ and a second seal 13750$b$.

The second seal 13750$b$ of the insertable seal system 13750 is configured to be inserted into the proximal opening 13740 of the reusable housing 13705 before the first seal 13750$a$. In one example, the second seal 13750$b$ is configured as a "no-instrument seal", such as a duckbill seal, as illustrated in FIG. 273. A no-instrument seal is a seal that is configured to prevent insufflation gases from escaping a patient's abdominal cavity in the absence of a surgical instrument. As is shown in FIG. 273, the distal end 13752 of the second seal 13750$b$ is biased to a closed position when a surgical instrument is not inserted therethrough. While a duckbill seal is illustrated and described, it is also contemplated that a pendulum seal, such as the pendant valve module described in U.S. patent application Ser. No. 11/423, 819, now U.S. Pat. No. 8,613,727, the entire contents of which are incorporated herein by reference, can be utilized.

The duckbill seal 13750b includes a flange 13755 that is configured to seat upon a shoulder 13760 of the reusable housing 13705. The flange 13755 illustrated in FIG. 273 is configured such that, when seated upon the shoulder 13760 of the reusable housing 13705, a clearance gap is formed between the flange and an inside wall 13757 of the reusable housing 13705. In a separate embodiment, the flange 13755 can be configured to extend and make contact with the inside wall 13757 of the reusable housing 13705, leaving no clearance gap therebetween.

The first seal 13750a of the insertable seal system 13750 is configured to be inserted into the proximal opening 13740 of the reusable housing 13705 and positioned on top of the second seal 13750b. The first seal 13750a includes an instrument lip seal 13762, which is configured to prevent insufflation gases from escaping the patient's abdominal cavity in the presence of a surgical instrument. Specifically, when an surgical instrument is inserted through the instrument lip seal 13762, the instrument lip seal 13762 is configured to maintain contact with the surgical instrument and prevent insufflation gases from escaping through the first seal 13750a. The first seal 13750a and the second seal 13750b cooperatively function to provide that, in either the absence or the presence of a surgical instrument, insufflation gases can be sealed in the patient's abdominal cavity.

The first seal 13750a includes an outer sleeve 13765 made of polyisoprene. The first seal 13750a further includes a thin-walled polycarbonate cylinder 13770 configured to be positioned inside of the outer sleeve 13765 to provide structural support to the outer sleeve 13765. The thin-walled cylinder 13770 can have a thickness of approximately 0.02". In one example, the thin-walled cylinder can 13770 can have a thickness in the range of 0.01" and 0.03". In another example, the thin-walled cylinder can 13770 can have a thickness in the range of 0.015" and 0.025".

As described above, the first seal 13750a of insertable seal system 13750 is configured to be inserted into the proximal opening 13740 of reusable housing 13705 and positioned on top of the second seal 13750b. An exterior surface of the first seal 13750a can include an interference lip 13780 extending laterally around the perimeter of the first seal 13750a. The interference lip 13780 is configured to extend from the first seal 13750a and contact the inner wall 13757 of the reusable housing 13705 to create an additional seal to prevent insufflation gases from escaping the patient. The interference lip 13780 can be configured as a continuous member such that the interference lip 13780 makes contact with the inner wall 13757 of the reusable housing 13705 around the entire perimeter of the first seal 13750a. In a separate embodiment, referring briefly to FIG. 274, the interference lip can include a plurality of interference lip members 13782 positioned at discrete points around the perimeter of the first seal 13750a. The interference lip 13780 and interference lip members 13782 can be configured to maintain the position of the first seal 13750a within the reusable housing 13705 and relative to the second seal 13750b.

The bottom surface of the first seal 13750a can also include a ridge member 13790 configured to extend around the bottom surface of the first seal 13750a and contact a top surface of the second seal 13750b. The ridge member 13790 is configured to maintain the first seal 13750a in seating alignment with the second seal 13750b, as well as provide an additional seal to prevent insufflation gases from escaping the patient. Similar to the interference lip 13780 described above, in one embodiment, the ridge member 13790 can be configured to extend continuously around the bottom the bottom surface of the first seal 13750a. In another embodiment, the ridge member can include a plurality of ridge members configured to contact the top surface of the second seal at a discrete number of points.

During a surgical procedure, surgical instruments are susceptible to being covered in bodily fluids and other biological materials, such as blood. In use with the trocar assembly described above, as the surgical instrument is removed from the patient's abdomen, the surgical instrument passes through the second seal (duckbill seal) and then the first seal (instrument lip seal) before being removed from the trocar assembly. While passing through the first seal and the second seal, bodily fluids and other biological materials can scrape against points of contact with the seals and be left behind on the seals. As a result, when the surgical instrument is reintroduced into the trocar assembly, the surgical instrument may contact and be covered in these left behind bodily fluids and other biological materials. This can interfere with laparoscopic imaging devices, such as a camera, where it is important that the lens of the imaging device remain clean so that a clinician can properly visualize the surgical procedure. Biological material will accumulate onto the camera during introduction into the patient's abdominal cavity, thus, obstructing the clinician's view. A need exists to ensure that the seals of a trocar assembly remain clean of bodily fluids and other biological materials when a surgical instrument is removed though the trocar assembly.

Referring now to FIG. 274, an exploded view of a trocar assembly 13800 is shown. The trocar assembly 13800 shown in FIG. 274 is similar in many respects to the trocar assembly shown and described in FIG. 273. The trocar assembly 13800 shown in FIG. 274, however, includes a third 13805 seal for use with an insertable seal system 13750. The third seal 13805 is configured to be positioned in a reusable housing 13705 of the trocar assembly 13800 prior to insertion of the insertable seal system 13750. The third seal 13805 is configured as a scraper seal, which is configured to wipe, wick, and absorb fluids from a surgical instrument as the surgical instrument is being removed from a patient and before the surgical instrument reaches the insertable seal system 13750, functioning to keep the first seal 13750a and the second seal 13750b clean. The third seal is configured to distribute the accumulated biological material away from the center of the third seal 13805 such that the surgical instrument would not contact the accumulated biological material as the surgical instrument passes through the third seal 13805 and into the patient. As an example, distribution of the biological material away from the center of the third seal 13805 allows that an imagining device will remain clean as it is inserted through the third seal 13805 and into a patient, thus allowing for an unobstructed view during a procedure.

Referring still to FIG. 274, the trocar assembly 13800 can include an insufflation port 13810 configured to extend from the reusable housing 13705. The insufflation port 13810 can facilitate passage of insufflation gases into a patient's abdominal cavity to increase the working environment during a surgical procedure. The insufflation port 13810 can further include a lever 13815, which can transition the insufflation port 13810 between an open configuration and a closed configuration. While a lever is illustrated, other means of transitioning the insufflation port between the open configuration and the closed configuration are contemplated, such as with a button or a valve, as an example. In the open configuration, a clinician is able to pass insufflation gases through the insufflation port 13810 and into a patient abdominal cavity. In the closed configuration, the insufflation port 13810 is sealed such that insufflation gases may not escape through the insufflation port 13810. The insufflation port 13810 can further be configured to couple to a luer lock 13817, which can facilitate insufflation gases from an insufflation source into the insufflation port 13810.

Referring now to FIG. 275, a reusable housing 13820 of a trocar assembly 13825 is shown being fixably held by an arm 13830 of a robotic surgical system. The reusable housing 13820 is aligned with the arm 13830 of the robotic surgical system by way of the robot arm holding feature 13835 described above. A cannula 13840 is attached to a distal end of the reusable housing 13820. In one example, the cannula can be attached to the reusable housing 13820 by way of mating threads between the cannula and the reusable housing, described above. While coupling the cannula 13840 and the reusable housing 13820 by way of threads has been described, other ways of coupling the cannula 13840 and the reusable housing 13820 are envisioned, such as by snap-fit, press-fit, or other ways of coupling two members.

A seal assembly 13845 is shown that is positionable in the reusable housing 13820 of the trocar assembly 13825. The seal assembly 13845 can include a first seal 13845a and a second seal 13845b, such as the instrument lip seal and duckbill seal, respectively, as described above. The seal assembly 13845 can also include an insufflation port 13850, which will be described in more detail below. The seal assembly 13845 can further include a gripping feature 13852 configured to assist in positioning the seal assembly 13845 into the reusable housing 13820. In one example, the gripping feature can include two contact members 13853 extending away from the seal assembly 13845 in opposite directions. While two contact members 13853 are shown, more of less than two contact members 13853 can be used.

The seal assembly 13845 further includes a rigid coupling feature 13855 extending from a bottom surface of the seal assembly 13845. In one example, the coupling feature can be made of plastic. The coupling feature 13855 includes a stepped configuration that is configured to mate with a stepped configuration 13857 on an inside surface of the reusable housing 13820. The stepped configuration between the coupling feature 13855 and the stepping configuration 13857 on the inside surface of the reusable housing 13820 provides for a proper alignment between the seal assembly 13845 and the reusable housing 13820. When the seal assembly 13845 is seated within the reusable housing 13820, the reusable housing 13820 floatingly supports the seal assembly 13845. The floating support allows the seal assembly 13845 to adjust relative to the reusable housing 13820 and the cannula 13840 as surgical instruments are inserted and removed from the patient's abdomen. In another embodiment, when the seal assembly 13845 is seated within the reusable housing 13820, the reusable housing 13820 rigidly supports the seal assembly 13845 such that the seal assembly 13845 cannot adjust relative to the reusable housing 13820 and the cannula 13840 as surgical instruments are inserted and removed from the patient's abdomen.

Referring now to FIG. 276, another embodiment of a trocar assembly 13860 is shown. The trocar assembly 13860 is shown including a reusable housing 13865 and a seal assembly 13870. The reusable housing 13865 includes a robot arm holding feature 13875 configured to be grasped by an arm of a robotic surgical system and threads 13880 to threadably engage a disposable cannula (not shown). The seal assembly 13870 includes an elastomer seal housing 13885 configured to house internal components of the seal assembly 13870. The elastomer seal housing 13885 is configured to be flexible, such that, when the elastomer seal housing 13885 experiences outside forces (F1 as an example), the elastomer seal housing 13885 can transition from an unflexed configuration into flexed configuration (illustrated by dotted lines on FIG. 276). Once an outside force is removed, the elastomer seal housing 13885 can return to the unflexed configuration.

The seal assembly 13870 further includes a first seal 13870a and a second seal 13870b. The first seal 13870a, such as an instrument lip seal, is configured to prevent insufflation gases from escaping the patient's abdomen when a surgical instrument is present through the first seal. The second seal 13870b, such as a duckbill seal, is configured to prevent insufflation gases from escaping the patient abdomen when a surgical instrument is not present through the second seal.

The seal assembly 13870 also includes a rigid seal housing 13890 extending from a bottom surface of the elastomer seal housing 13885. The rigid seal housing 13890 includes a threaded portion 13982 that is configured to engage a threaded portion 13983 on an inside surface of the reusable housing 13865 to bring the seal assembly 13870 into threaded engagement with the reusable housing 13865. While coupling the reusable housing 13865 and the seal assembly 13870 by way of threads has been described, other embodiments are envisioned where the reusable housing 13865 and the seal assembly 13870 are coupled by way of snap-fit or press-fit connections, or by another suitable connections.

The seal assembly 13870 further includes an insufflation port 13895 extending from the elastomer seal housing 13885. The insufflation port 13895 is configured to bypass the first seal 13870a and the second seal 13870b of the seal assembly 13870 to provide access into the patient's abdomen. The insufflation port is configurable such that an insufflation stop cock is couplable therewith for use during a surgical procedure. The insufflation stop cock prevents insufflation gases from escaping the patient's abdominal cavity via the insufflation port during the surgical procedure. In a first embodiment, the insufflation port 13895 can be rigid. In a second embodiment, the insufflation port 13985 can be flexible, similar to the elastomer seal housing 13885 such that when the insufflation port 13895 experiences outside forces (F2 and F3 as an example), the elastomer seal housing 13885 can transition from an unflexed configuration into flexed configuration (illustrated by dotted lines on FIG. 276)

As described above, the elastomer seal housing 13885 is movable from an unflexed configured to a flexed configuration when the elastomer seal housing 13885 experiences an outside force. In one example, the robot arm of the robotic surgical system pivots the reusable housing 13865 towards the side of the seal assembly 13870 that includes the insufflation port 13895 and the insufflation port 13895 make contact with an exterior body, such as the patient's abdomen. In an example where the insufflation port 13895 is rigid, the insufflation port 13895 would contact the exterior body and pivot away from the exterior body as a result of the elastomer seal housing 13885 being flexible, reducing trauma on the patient. In an example where the insufflation port 13895 is flexible, the insufflation port 13895 would contact the exterior body and one or both of the insufflation port 13895 and the elastomer seal housing 13885 would flex away from the exterior body. Because of the configuration between the insufflation port 13895 and the elastomer seal housing 13885, the seal on an instrument and the guidance of the instrument into the patient's abdomen would be maintained.

Referring primarily to FIGS. 277-280, a minimally invasive surgical access system 14000 is utilized to perform a thoracic surgery. FIG. 277 illustrates an example surgical access device 14002 of the surgical access system 14000 positioned at the fifth intercostal space 14001 of a patient. The surgical access device 14002 includes three access ports 14006, 14007, 14008 that provide minimally invasive passageways into a thoracic cavity 14003 (FIG. 280) of the patient for a variety of surgical tools. The access ports 14006, 14007, 14008 reside and move within an outer perimeter defined by an atraumatic outer housing 14010 of the surgical access device 14002. The access ports 14006, 14007, 14008 include docking portions 14046, 14047, 14048 for releasably coupling to robotic arms 14026, 14027, 14028, respectively, as illustrated in FIG. 280.

In various examples, a surgical access system may include a surgical access device with more or less than three access ports and more or less than three robotic arms. In one example, a surgical access system may include a surgical access device with four access ports and four robotic arms. In another example, a surgical access system may include a surgical access device with two access ports and two robotic arms. In another example, a surgical access system may include a surgical access device with two access ports and three robotic arms. In another example, a surgical access system may include a surgical access device with three access ports and two robotic arms.

Referring primarily to FIG. 280, robotic arms 14026, 14027, 14028 include surgical mounting devices 14036, 14037, 14038, which include clamping assemblies for releasably coupling to docking portions 14046, 14047, 14048 of the surgical access device 14002. The clamping assemblies of the surgical mounting devices 14036, 14037, 14038 are transitionable between an open configuration and a closed configuration to releasably couple to the docking portions 14046, 14047, 14048, respectively. Additional information about the construction and operation of surgical mounting devices are described in U.S. 2018/0177557, titled MOUNTING DEVICE FOR SURGICAL SYSTEMS AND METHOD OF USE, and filed Jun. 6, 2016, which is hereby incorporated by reference herein in its entirety.

Referring to FIG. 278, to position the surgical access device 14002 at an intercostal space, an incision is made intercostally, or between two ribs of the left chest wall. A surgical retractor 14009 is then used to spread the ribs apart to accommodate the surgical access device 14002. A separate access port 14011 can also be placed intercostally a predetermined distance away from the surgical access device 14002, and can be releasably coupled to a fourth robotic arm 14013. In certain examples, the surgical retractor 14009 is integrated with the surgical access device 14002. In other examples, surgical retractor 14009 is separate from the surgical access device 14002.

In various aspects, as illustrated in FIG. 280, the atraumatic outer housing 14010 comprises a non-radial shape that corresponds to the shape of the ribs. In at least on example, the outer housing 14010 comprises a crescent shape. In at least on example, the outer housing 14010 comprises a general curvature that corresponds to the curvature of the ribs. The access ports 14006, 14007, 14008 are arranged along the curvature of the outer housing 14010. In the example of FIG. 278, the access ports 14006 and 14008 are located near ends 14014, 14015, respectively, of the outer housing 14010, while the access port 14007 is located near its apex 14016. Further, the access port 14007 is larger than the access ports 14006, 14008. It is, however, understood that the size, number, and/or arrangement of the access ports of a surgical access device 14002 can be selected to accommodate various surgical tools. In the example, illustrated in FIG. 280, a surgical stapler 14056 is received through the access port 14006, an imaging device 14057 is received through the access port 14007, and a surgical grasper 14058 is received through the access port 14008. An additional surgical grasper 14051 is received through the access port 14011 for triangulation with the surgical grasper 14058 and/or the surgical stapler 14056, for example.

Referring still to FIG. 280, the outer housing 14010 includes three compartments 14076, 14077, 14078 accommodating the access ports 14006, 14007, 14008, respectively. In various aspects, the access ports 14006, 14007, 14008 are movable within the compartments 14076, 14077, 14078 relative to the outer housing 14010. Further, the robotic arms 14026, 14027, 14028 are configured to cooperate to synchronously move the instruments 14056, 14057, 14058 relative to one another and/or relative to the surgical access device 14002.

In various aspects, the access ports 14006, 14007, 14008 include seal assemblies 14066, 14067, 14068, respectively, that may have one or more seals such as, for example, an iris seal and/or a duckbill seal configured to receive the instruments 14056, 14057, 14058, respectively. In various aspects, the docking portions 14046, 14047, 14048 are located at the seal assemblies 14066, 14067, 14068, and the robotic arms 14026, 14027, 14028 are configured to releasably couple to the docking portions 14046, 14047, 14048 to define remote centers for the instruments 14056, 14057, 14058 at the seal assemblies 14066, 14067, 14068, respectively. Further, the robotic arms 14026, 14027, 14028 are configured to cooperate to synchronously adjust the remote centers of the instruments 14056, 14057, 14058.

The seal assemblies 14066, 14067, 14068 permit the instruments 14056, 14057, 14058 to move within boundaries defined by the compartments 14076, 14077, 14078. Additional movement, however, requires a cooperative effort between the robotic arms 4026, 14027, 14028. Like the robotic arms 13002, 13003 (FIG. 4) the robotic arms 14026, 14027, 14028 may be driven by electric drives that are connected to the control device 13004 (FIG. 4). In various aspects, the control device 13004 automatically coordinates movement of the robotic arms 14026, 14027, 14028 in response to a user input concerning a subset of the robotic arms 14026, 14027, 14028. In other words, a user input for moving one of a plurality of robotic arms coupled to a multi-port surgical access device such as, for example, the surgical access device 14002 causes a control device such as, for example, the control device 13004 to synchronously move the plurality of robotic arms to comply with the user input.

In at least one example, to accommodate a user input to adjust a position of the surgical stapler 14056, the control device 13004 may cause the robotic arms 14026, 14027, 14028 to synchronously move to achieve the desired position of the surgical stapler 14056. The control device 13004 may further cause the imaging device 14057 and/or the surgical grasper 14058 to move relative to their respective seal assemblies 14067, 14068 to maintain their original orientations with respect to one another and/or with respect to a new orientation of the surgical stapler 14056. In various aspects, the control device 13004 may cause the robotic arms 14026, 14027, 14028 to synchronously move to adjust the surgical access device 14002 to a new orientation.

Referring now to FIG. 281, a surgical access device 14100 is similar in many respects to the surgical access device 14002. For example, the surgical access device 14100 is also configured to facilitate access to a body cavity 14101 through a body wall 14103 for the instruments 14056, 14057, 14058. However, the surgical access device 14100 includes only a single access port 14102 configured to accommodate a plurality of instruments such as, for example, the instruments 14056, 14057, 14058. In various aspects, the instruments 14056, 14057, 14058 are passed through a seal assembly 14105 defined in the access port 14102. The seal assembly 14105 includes one or more seals such as, for example, an iris seal and/or a duckbill seal.

The surgical access device 14100 is releasably coupled to a robotic arm 14126, which similar in many respects to the robotic arms 13002, 13003. For example, the robotic arm 14126 may be driven by electric drives that are connected to the control device 13004 (FIG. 4). Also, the robotic arm 14126 includes a mounting device 14109, which can be in the form of a clamp assembly, configured to releasably couple to a docking portion 14111 of the access port 14102.

In various instances, one of the instruments 14056, 14057, 14058 is controlled by the robotic arm 14126, while the other instruments are controlled by separate robotic arms. This arrangement permits the instruments 14056, 14057, 14058 to move relative to one another within a boundary defined by the seal assembly 14105, which permits instrument triangulation. As described in connection with the robotic arms 14026, 14027, 14028, a control device 13004 (FIG. 4) may respond to a user input concerning one of the robotic arms controlling the instruments 14056, 14057, 14058 by synchronously moving two or more of such robotic arms to comply with the user input.

In various instances, the instruments 14056, 14057, 14058 and the surgical access device 14100 are controlled by separate robotic arms. This arrangement permits the robotic arm 14126 to adjust a position and/or orientation of the surgical access device 14100 separately from the robotic arms controlling the instruments 14056, 14057, 14058. As described in connection with the robotic arms 14026, 14027, 14028, a control device 13004 (FIG. 4) may respond to a user input concerning one of the robotic arms controlling the instruments 14056, 14057, 14058 or the robotic arm 140100 by synchronously moving two or more of such robotic arms to comply with the user input.

The reader will appreciate that although FIG. 281 depicts three instruments inserted through the seal assembly 14105, this is not limiting. In certain examples, the seal assembly 14105 may accommodate two, three, four, or more instruments that may be controlled by separate robotic arms. Alternatively, multiple instruments can be controlled by the same robotic arm. For example, a robotic arm, releasably coupled to a surgical access device 14100, can be configured to support and move a plurality of instruments received through the seal assembly 14105 of the surgical access device 14100.

Referring primarily to FIGS. 282-284, surgical access devices such as, for example, a surgical access device 14200 are configured to facilitate insertion of various surgical instruments into a body cavity 14205 of a patient. The surgical access device 14200 includes a housing 14210 and a tubular member 14211 extending distally from the housing 14210. The tubular member 14211 and the housing 14210 define a common passageway 14201. As illustrated in FIG. 282, a shaft 14203 of a surgical instrument 14202 can be inserted through the passageway 14201 to permit an end effector of the surgical instrument 14202 to perform a surgical function in the body cavity 14205.

In many instances, as illustrated in FIG. 282, the shaft 14203 of a surgical instrument 14202 inserted through the surgical access device 14200 has a diameter "SD" that is significantly smaller than an inner diameter "ID" of the inner wall 14212 of the tubular member 14211. The size discrepancy may cause the shaft 14203 to rattle, wobble, or unintentionally change position relative to the surgical access device 14200. This wobbling effect is augmented when the surgical instrument is controlled by a robotic arm that transmits vibrations to the surgical instrument during operation. In situations where the surgical instrument 14202 and/or the surgical access device 14200 are controlled by a robotic arm, these unintended movements may prevent the robotic arm from accurately calculating a present and/or desired position of surgical instrument 14202 and/or the surgical access device 14200.

The surgical access device 14200 includes a translatable member 14204 configured to stabilize a smaller size shaft such as, for example, the shaft 14203 to prevent unintentional movements of the shaft 142023 and/or dampens any vibrations transmitted to the shaft 14203. The translatable member 14204 is movable relative to the housing 14210 between a first position (FIG. 282), which can be a proximal or starting position, and a second position (FIG. 283), which can be a distal or end position, to stabilize the shaft 14203. In the example of FIG. 283, the translatable member 14204 is configured to abut and align the shaft 14203 against an inner wall 14206 of the tubular member 14211 in the second position. As illustrated in FIGS. 282 and 283, the translatable member 14204 is configured to move the shaft 14203 into parallel alignment with the inner wall 14206 such that a longitudinal axis "L" of the shaft 14203 extends in parallel with the inner wall 14206.

In various examples, the translatable member 14204 is integral with the housing 14210. In other examples, the translatable member 14204 can be releasably coupled to the housing 14210. Any suitable fastening mechanism can be employed to releasably and repeatedly couple the translatable member 14204 to the housing 14210.

In various examples, the translatable member 14204 has a partial conical shape, as illustrated in FIG. 284. The translatable member 14204 is configured to be wedged between the shaft 14203 and an inner wall 14216 opposite the inner wall 14206 causing a first wall 14208 of the translatable member 14204 to snuggly abut against the shaft 14203, which causes the shaft 14203 to abut against and be aligned with the inner wall 14206 of the tubular member 14211, as illustrated in FIG. 283. The translatable member 14204 includes a second wall 14212 extending at an acute angle α with the first wall 14208. In the second position, a distal end 14213 of the translatable member 14204 is positioned closer to the inner wall 14206, further away from the inner wall 14216, and deeper into the passageway 14201 than in the first position. The second wall 14212 includes a translation member 14214 with translation features 14217. The translation member 14214 is movably engaged with a translation driver 14215.

In one example, as illustrated in FIGS. 282 and 283, the translatable member 14214 defines a linear gear on the second wall 14212, and the translation driver 14215 defines a rotary driver in movable engagement with the linear gear of the translation member 14214. In such example, rotational motion of the translation driver 14215 causes the translatable member 14204 to move between a number of second or end positions including the second position of FIG. 283. Accordingly, the translatable member 14204 is movably adjustable between a number of second or end positions to accommodate different size shafts of different surgical instruments. The reader will appreciate that other suitable mechanisms for transferring rotary motion to linear motion can be employed to translate the translatable member 14204 between the first position and the second position such as, for example, a slider crank mechanism or a slider crank mechanism with variable sliding length. In other examples, various suitable electro-mechanical mechanisms can be employed to translate the translatable member 14204 between the first position and the second position.

Referring to FIG. 285, a control circuit 14300 includes the controller 14302 that may generally comprise a processor 14308 ("microprocessor") and a storage medium, which may include one or more memory units 14310, operationally coupled to the processor 14308. By executing instruction code stored in the memory 14310, the processor 14308 may control movement of the translatable member 14204 via a motor 14316, for example, in response to an input, which can be received from a user interface 14317 or one or more sensors 14320. In at least one example, the user interface 14317 is integrated with the remote command console 13370 (FIG. 6).

The sensors 14320 can be disposed onto the first wall 14208, and can be configured to detect insertion of a shaft 14203 through the passageway 14201. Further, in various examples, the sensors 14320 can be any suitable motion sensors or any other sensors capable of detecting the insertion of a shaft 14203 through the passageway 14201. Alternatively, the controller 14302 may receive input from the detection of a robotic surgical system to move to the translatable member 14204 between the first position and the second position, based on a determined position of the shaft 14203.

In various examples, the sensors 14320 include pressure sensors configured to assess the pressure exerted by the translatable member 14204 on the shaft 14203. The controller 14302 may adjust the position of the translatable member 14204 to adjust the pressure value within, or in accordance with, a predetermined threshold range.

The controller 14302 may be implemented using integrated and/or discrete hardware elements, software elements, and/or a combination of both. Examples of integrated hardware elements may include processors, microprocessors, controllers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, controllers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 14302 may include a hybrid circuit comprising discrete and integrated circuit elements or components on one or more substrates, for example. In certain instances, the controller 14302 may be a single core or multicore controller LM4F230H5QR.

In various forms, the motor 14316 may be a DC brushed driving motor having a maximum rotation of, approximately, 25,000 RPM, for example. In other arrangements, the motor 14316 may include a brushless motor, a cordless motor, a synchronous motor, a stepper motor, or any other suitable electric motor. A power source 14318 may supply power to the motor 14316, for example.

A motor driver 14305 in operable communication with the controller 14302 can be configured to control a direction of rotation of the motor 14316. In certain instances, the motor driver 14305 may be configured to determine the voltage polarity applied to the motor 14316 by the power source 14318 and, in turn, determine the direction of rotation of the motor 14316 based on input from the controller 14302. For example, the motor 14316 may reverse the direction of its rotation from a clockwise direction to a counterclockwise direction when the voltage polarity applied to the motor 14316 by the power source 14318 is reversed by the motor driver 14305 based on input from the controller 14302. In addition, the motor 14316 is operably coupled to the translation driver 14215 which can be rotated by the motor 14316 to move the translation member 14214 distally, toward the second position, or proximally, toward the first position, depending on the direction in which the motor 14316 rotates, for example.

In various aspects, referring primarily to FIG. 284, the translatable member 14204 includes flexible or resilient features 14220 disposed onto the second wall 14212. The features 14220 are configured to seal the access port defined through the housing 14210, as illustrated in FIG. 283, to maintain insufflation fluid within a suitable range.

As described above, robotic arms produce vibrations that can be transferred to surgical instruments controlled by the robotic arms. Such vibrations may have negative implications on the accuracy of the surgical instruments during a surgical procedure. Further, surgical instruments with shafts comprising significantly smaller diameters than receiving surgical access devices may rattle, wobble, or unintentionally change position relative to the receiving surgical access devices, which can be augmented when the surgical instruments are controlled by robotic arms that transmit vibrations to the surgical instruments during operation. To minimize the effect of vibrations of a robotic arm 14400 on a surgical instrument 14405 being controlled by the robotic arm 14400, and/or reduce wobbling or rattling, during operation, a vibration dampening mechanism 14401 is disclosed. The vibration dampening mechanism 14401 automatically adjusted a mounting assembly 14402 of the robotic arm 14400 to maintain a direct contact between a surgical access device 14403 releasably coupled to the mounting assembly 14402 and the surgical instrument 14405.

Referring primarily to FIGS. 286-288, the robotic arm 14400 is similar in many respects to other robotic arms described herein such as, for example, the robotic arms 13002, 13003 (FIG. 4), 13200 (FIG. 241). Further, the surgical access device 14403 is similar in many respects to other surgical access devices described herein such as, for example, the trocar 13250. The mounting assembly 14402 includes clamp arms 14 configured to hold the surgical access device 14403. Further, the mounting assembly 14402 is configured to slightly adjust the orientation of the surgical access device 14403 to maintain a direct contact between an inner wall 14407 of the surgical access device 14403 and a shaft of 14408 of the surgical instrument 14405 extending through the surgical access device 14403, as illustrated in FIG. 288. The direct contact allows the surgical access device 14403 to act as a vibrations dampener for the surgical instrument 14405.

In the example of FIGS. 287 and 288, the robotic arm 14400 causes the mounting assembly 14402 to be rotated with the surgical access device 14403 an angle α in a clockwise direction to establish and maintain the direct contact between the shaft 14408 and the inner wall 14407. The axis A represents the surgical access device 14403 at a neutral position. The Axis A1 represents the surgical access device 14403 in a first tilted position.

Referring to FIG. 286, the robotic arm 14400 is configured to rotate the tool mount assembly 14402 clockwise and counterclockwise to new positions defined by the axes A1 and A2 from a neutral position defined by the Axis A, for example. The robotic arm 14400 is configured to rotate the tool mount assembly 14402 up and down to new positions defined by the axes B1 and B2 from a neutral position defined by the axis B, for example. Like the robotic arms 13002, 13003 (FIG. 4) the robotic arm 14400 may be driven by electric drives that are connected to the control device 13004 (FIG. 4) for rotation of the tool mount assembly 14402 to establish and maintain a direct contact between the shaft 14408 and the inner wall 14407 of the surgical access device 14403.

In various aspects, the inner wall 14407 can include one or more pressure sensor to detect pressure applied by the inner wall 14407 onto the shaft 14408. The control device 13004 can be configured to receive input indicative of the pressure, and to adjust the position of the surgical access device 14403 in accordance with a predetermined threshold range. In various aspects, achieving or exceeding a predetermined minimum pressure threshold is indicative of the establishment of the direct contact between the shaft 14408 and the inner wall 14407.

Referring to FIGS. 289-291, another vibration dampening mechanism 14501 is disclosed. Unlike the vibration dampening mechanism 14401, the vibration dampening mechanism 14501 does not require manipulating a tool mounting assembly to maintain a direct contact between a surgical instrument and a surgical access device. Instead, the dampening mechanism 14501 equips a surgical instrument such as, for example, an obturator 14504 with dampening features 14505, and a surgical access device 14500 with corresponding stabilizing compartments 14606. In various aspects, a tubular member 14503 of the surgical access device 14500 includes an outer wall that defines stability threads 14524, as illustrated in FIG. 289.

As illustrated in FIG. 291, the dampening features 14505 are received in their respective stabilizing compartments 14506. Vibrations from a robotic arm that are transferred to the obturator 14504 are absorbed and/or transferred by the dampening features 14505 to the surgical access device 14500. Further, the dampening features 14505 cooperate with the stabilizing compartments 14506 to maintain the obturator 14504 along a central axis of the surgical access device 14500. In various aspects, the dampening features 14505 include a proximal dampening feature 14505a and a distal dampening feature 14505b that are spaced apart from one another along a length of the obturator 14504. Further, the stabilizing compartments 14506 include a proximal stabilizing compartment 14506a configured to receive the proximal dampening feature 14505a and a distal stabilizing compartment 14506b configured to receive the distal dampening feature 14505b, as illustrated in FIG. 291.

Referring to FIGS. 292-294, a surgical access device 14600 includes non-concentric instrument support features 14605 arranged along a length of the surgical access device 14600. A shaft 14602 of a surgical instrument 14610 extends through the surgical access device 14600. The shaft 14602 has an outer diameter "OD" smaller than an inner diameter "ID" of an inner wall 14620 of the surgical access device 14600. The non-concentric instrument support features 14605 cooperate to bias the shaft 14602 toward and/or maintain the shaft 14602 at a central axis 14608 defined through a common passageway 14612 of the surgical access device 14600.

As illustrated in FIG. 292, the surgical access device 14600 includes a housing 14614 and a tubular member 14616 extending distally from the housing 14614. The common passageway 14612 is defined through the tubular member 14616 and the housing 14614.

In the example illustrated in FIG. 293, the non-concentric instrument support features 14605 include a first instrument support feature 14605a that has a first opening 14606a therethrough, a second instrument support feature 14605b that has a second opening 14606b therethrough, and a third instrument support feature 14606a that has a third opening 14606c therethrough. The first opening 14606a, the second opening 14606b, and the third opening 14606c are all offset with respect to the central axis 14608 in different directions. In other words, each of the non-concentric instrument support features includes a thicker section and a thinner section around its opening.

In various aspects, the non-concentric instrument support features 14605a are made from deformable, flexible, and/or biasing materials. The thick sections are elastically deformed by the shaft 14602 and, as such, exert biasing forces against the shaft 14602 to bias the shaft 14602 toward and/or maintain the shaft 14602 at the central axis 14608. In various aspects, the non-concentric instrument support features 14605 are made, or at least partially made, from any suitable polymeric material. In various aspects, the non-concentric instrument support features 14605 comprise the same or different material compositions.

In various examples, as illustrated in FIG. 294, the first opening 14606a includes a first center 14607a that is offset from the central axis 14608 in a first direction 14609a, and the second opening 14606b includes a second center 14607b that is offset from the central axis 14608 in a second direction 14609b, and the third opening 14606c includes a third center 14607c that is offset from the central axis 14608 in a third direction 14609c. The first direction 14609a, the second direction 14609b, and the third direction 14609c extend away from the central axis 1608. In at least one example, the first direction 14609a, the second direction 14609b, and the third direction 14609c are transverse, or at least substantially transverse, to the central axis 14608. In at least one example, the first direction 14609a, the second direction 14609b, and the third direction 14609c are spaced apart by angles $\alpha$, $\beta$, $\Delta$ that can be 120 degrees, as illustrated in FIG. 294.

In various aspects, one or more of the non-concentric instrument support features 14605 could form part of a seal assembly of the surgical access device 14600 causing a high insertion and extraction load but tightly holding onto the shaft 14602. In various aspects, the tubular member 14616 includes an outer wall that defines stability threads 14622, as illustrated in FIG. 292. Further, a mounting assembly 14624 of a robotic arm can be threadably engaged to the surgical access device 14600.

In various aspects, one or more instrument support features for stabilizing a surgical instrument shaft within a surgical access device are in the form of inflatable members that can be expanded to at least partially fill an empty space between the outer diameter of the shaft and the inner diameter of the surgical access device to stabilize the surgical instrument. Alternatively, the instrument support features may include inflator baffles to be charged once the surgical instrument is inserted through a surgical access device.

In various aspects, an insufflation port can be interconnected with the inflatable members. Insufflation ports typically inject a fluid such as, for example, carbon dioxide into a body cavity such as, for example, the abdominal cavity to inflate the body cavity creating space for a surgical procedure to be performed in the body cavity. In certain examples, insufflation ports can be integrated with the surgical access devices. In various aspects, an insufflation port can automatically inflate the instrument support features of a surgical access device. Fluid from the insufflation port can be transmitted to the inflatable members of a surgical access device to stabilize a surgical instrument extending through the surgical access device. In various aspects, a control circuit can be configured to detect the insertion of a surgical instrument through the surgical access device, and automatically inflate the inflatable members. Further, the control circuit can be configured to detect the removal of the surgical instrument from the surgical access device, and automatically deflate the inflatable members. The control circuit can be coupled to fluid pump, which can be activated to inflate and/or deflate the inflatable members. In certain aspects, can be configured to trigger opening and closing one or more fluid valves to inflate and/or deflate the inflatable members.

Detecting the insertion and/or removal of the surgical instrument can be accomplished by one or more suitable sensors that can be positioned along a length of the surgical access device. The sensors could be light sensors, motion sensors, pressure sensors, or any other suitable sensors. The sensors may transmit sensor signals to the control circuit indicative of the detection of the insertion and/or removal of the surgical instrument. The control circuit main then inflate or deflate the instrument support features based on the sensor signals.

In certain aspects, pressure sensors can be employed to monitor pressure exerted onto the instrument support features by a shaft of the surgical instrument. For example, pressure sensors can be positioned inside the instrument support features to detect a change in fluid pressure caused by a change in instrument side loads exerted against the instrument support features. In response, the control circuit may adjust fluid pressure within the instrument support features to improve surgical instrument stability. In other examples, pressure inside the instrument support features can be calculated based on the amount of fluid delivered to the instrument support features.

In the embodiment illustrated in FIG. 295, port assembly includes nine inflatable members 56180a-56180i associated therewith (Inflatable members 56180b, 56180e and 56180h are not shown in FIG. 295 due to the particular cross-sectional view illustrated.). The inflatable members 56180a-56180i of the illustrated embodiment include a first, proximal row of three inflatable members 56180a-56180c radially disposed about interior surface of the body, a second, middle row of three inflatable members 56180d-56180f radially disposed about interior surface of the body, and a third, distal row of three inflatable members 56180g-56180i radially disposed about interior surface of the body.

A sensor is configured to communicate the orientation and positioning information of the end effector assembly 56020 with control mechanism including a controller. Moreover, the sensor is configured to communicate the difference between the current orientation and positioning of the end effector assembly 56020 with the stored (e.g., initial) orientation and positioning information. The control mechanism is configured to distribute an inflatable medium to the appropriate inflatable member(s) 56180 in order to move the shaft 56012 of the surgical device 56010 to re-orient the end effector assembly 56020, such that the end effector assembly 56020 moves to its stored (e.g., initial) orientation and position. For example, and with particular reference to FIG. 295, to tilt the end effector 56020 with respect to the longitudinal axis "A" in the general direction of arrow "C," inflatable members 56180a and 56180i could be inflated and/or inflatable members 56180c and 56180g could be deflated. Reference may be made to U.S. patent application Ser. No. 15/520,966, now U.S. Pat. No. 10,251,672, the entire contents of which are incorporated herein by reference, for additional detailed discussion.

In one embodiment, referring now to FIGS. 296-298, an access apparatus, i.e., cannula assembly IOU, includes cannula sleeve 57102 having proximal and distal ends 57101, 57103 and cannula housing 57104 mounted to the proximal end 57101 of the sleeve 57102. Cannula sleeve 57102 defines a longitudinal axis "a" extending along the length of sleeve 57102. Sleeve 57102 includes an inner wall 57102' that further defines an internal longitudinal passage 57106 dimensioned to permit passage of a surgical object such as surgical instrumentation. Sleeve 57102 incorporates sleeve flange 57108 monolithically-formed at the proximal end 57101. Sleeve 57102 may be fabricated of stainless steel or another suitable rigid material such as a polymeric material or the like. Sleeve 57102 may be clear or opaque. The diameter of sleeve 57102 may vary, but, typically ranges from 5 to 15 mm. Sleeve flange 57108 has a seal support integrally formed with or attached to the sleeve flange 57108. Sleeve flange 57108 further includes at least one circumferential recess or slot 57110 within its outer surface. Circumferential slot 57110 mates or cooperates with corresponding structure of cannula housing 57104 to secure cannula sleeve 57102 and cannula housing 57104.

Elongated seal 57204 is coaxially arranged within cannula sleeve 57102 to define an outer passageway 57224 between the elongated seal 57204 and the internal surface of cannula sleeve 57102. The outer passageway 57224 communicates with channel 57138 and port. Elongated seal 57204 further defines a gap 57226 or portion adjacent cannula tip 57216 devoid of the elastomer. The gap 57226 permits the passage of insufflation gases between outer passageway 57224 and internal passageway 57222 of elongated seal 57204. Insufflation gases are introduced from port, through channel 57138 through outer passageway 57224, out gap 57226 into the body cavity, to expand the body cavity. Alternatively or additionally, gap 57226 permits the insufflation gases to pass from outer passageway 57224 to internal passageway 57222, as well as from internal passageway 57222 into outer passageway 57224, to substantially equalize the pressure within the two locations to allow the seal to adjust to instruments of different sizes. The gap 57226 may be provided during the molding process or, alternatively, may be the result of a removal step where the elastomer is removed subsequent to molding to define the gap 57226. The gap 57226 may be created by perforating or forming a slit in the outer elastomeric material 57214. It is further envisioned that cannula sleeve 57102 may include an opening in its outer wall in communication with the outer passageway 57224 to permit passage of gases to the abdominal cavity. Reference may be made to U.S. patent application Ser. No. 12/780,494, now U.S. Pat. No. 8,070,731, the entire contents of which are incorporated herein by reference, for additional detailed discussion.

Referring now to FIGS. 299 and 300, an instrument seal 58114 will be discussed. Instrument seal 58114 is mounted within sleeve 58102 and may be a generally annular or disk-shaped element having inner seal portions defining an internal passage 58116 for reception and passage of a surgical instrument in substantial sealed relation. Internal passage 58116 may be an aperture, slit or the like adapted to permit a surgical instrument to pass through instrument seal 58114. Instrument seal 58114 may be mounted within sleeve 58102 by any conventional means envisioned by one skilled in the art including, e.g., with the use of adhesives, cements or mechanical mounting means. Instrument seal 58114 may comprise any suitable elastomeric material. In one embodiment, instrument seal 58114 comprises an elastomeric material, a fabric material, and/or combinations of these materials. The fabric material may comprise braided, woven, knitted, non-woven materials. In yet a further alternative, instrument seal 58114 is a fabric seal and is arranged so as to have a constricted area. The fabric is constructed of a material that forms a constriction or closure. The seal may also be molded with a resilient material so as to have a constriction. Instrument seal 58114 they comprise a gel or foam material. Other arrangements for instrument seal 58114 are also envisioned.

Instrument seal 58114 is disposed at the rotational center "k" of the cannula assembly 58100. The rotational center "k" may be at the axial midpoint (the midpoint of the axial length "I") of cannula sleeve 58102, or, at the axial midpoint of the combined length "y" of the cannula sleeve 58102 and cannula housing 58104. The disposition of instrument seal 58114 at the rotational center "k" of cannula sleeve 58102 or the combined cannula sleeve 58102 and cannula housing 58104 will enable an inserted surgical instrument "in" to be manipulated through a range of motions as depicted by the directional arrows "b" in FIG. 300 (including angular movement and/or rotational movement) while minimizing distortion of the instrument seal 58114. Specifically, the surgical instrument "m" will angulate about the rotational center "k" thereby minimizing the distortion of at least the inner surface portions of instrument seal 58114 which is positioned adjacent to or exactly at the location of the rotational center "k". This will thereby preserve the integrity of the seal formed by instrument seal 58114 about the surgical instrument "m" and substantially minimize the passage of insufflation gases through the instrument seal 58114. In addition, the disposition of instrument seal 58114 within cannula sleeve 58102 may eliminate the need for cannula housing 58104 or, in the alternative, substantially reduce the height requirement of the cannula housing 58104 in that the instrument seal 58114 does not need to be incorporated within the cannula housing 58104. Reference may be made to U.S. patent application Ser. No. 13/445,023, now U.S. Patent Application Publication No. 2012/0238827, the entire contents of which are incorporated herein by reference, for additional detailed discussion.

FIG. 301 is a side view of an example radial biasing device 59702 that may be used with a trocar assembly, according to one or more embodiments of the present disclosure. The radial biasing device 59702 may be coupled to or otherwise arranged at or near the distal end 59106*b* of the cannula 59104 at an interface 59704 between an annular body and the cannula 59104. The radial biasing device 59702 may include an annular body 59706 that also constitutes a compliant stabilizing member 59708. In the illustrated embodiment, the annular body 59706 and compliant stabilizing member 59708 are in the form of a tube or hose that extends distally from the distal end 59106*b* of the cannula 59104. Moreover, the annular body 59706 and compliant stabilizing member 59708 may be bent or curved such that a centerline B of the radial biasing device 59702 diverges from the centerline A of the cannula 59104 as the annular body 59706 extends distally from the distal end 59106*b* of the cannula 59104.

FIGS. 302 and 303 are cross-sectional side views of the radial biasing device 59702 depicting example operation, according to one or more embodiments. All or a portion of the radial biasing device 59702 may be made of a pliable or elastic material to enable the radial biasing device 59702 to transition between a generally relaxed position, as shown in FIG. 302, and an extended position, as shown in FIG. 303. Reference may be made to U.S. patent application Ser. No. 15/720,612, now U.S. Patent Application Publication No. 2019/0099201, the entire contents of which are incorporated herein by reference, for additional detailed discussion.

Referring now to FIG. 304, the use and function of a system will be discussed. The peritoneal cavity is first insufflated with a suitable biocompatible gas such as, e.g., $CO_2$ gas, such that the cavity wall is raised and lifted away from the internal organs and tissue housed therein, providing greater access thereto, as is known in the art. The insufflation may be performed with an insufflation needle or similar device. Following insufflation, obturator assembly 59900 is positioned within cannula assembly 59800, specifically, first through a seal assembly (not shown), if any, and then through cannula housing 59802 and cannula member 59804, respectively. Thereafter, obturator 59902 is advanced such that contact is made between penetrating end 59908 of obturator 59902 and skin site "S" of tissue "T". A force is then applied to the proximal end of obturator assembly 59900 such that penetrating end 59908 may puncture tissue "T". Following penetration, obturator assembly 59900 is removed from cannula assembly 59800. Thereafter, a variety of surgical instrumentation may be inserted through cannula member 59804 of cannula assembly 59800 to carry out the remainder of the surgical procedure. Upon insertion, a substantially fluid-tight seal will be created between restrictor hinge 59814 and the surface of the instrument. Additionally, restrictor hinge 59814 may maintain the desired orientation of the instrument and may align its axis with that of cannula member 59804. Reference may be made to U.S. patent application Ser. No. 12/468,271, now U.S. Pat. No. 8,197,446, the entire contents of which are incorporated herein by reference, for additional detailed discussion.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of using a surgical modular robotic assembly including an interchangeable motor pack, a hand-held surgical instrument, and a robotic surgical instrument, the method comprising:
   releasably attaching an interface portion of the interchangeable motor pack to the hand-held surgical instrument;
   causing the interchangeable motor pack to drive a first surgical tool of the hand-held surgical instrument;
   stopping the interchangeable motor pack from driving the first surgical tool;
   disconnecting the interface portion from the hand-held surgical instrument; and
   releasably attaching the interface portion of the interchangeable motor pack to the robotic surgical instrument.

2. The method of claim 1, further comprising causing the interchangeable motor pack to drive a second surgical tool.

3. The method of claim 2, further comprising establishing a first connection between the robotic surgical instrument and a first surgical hub.

4. The method of claim 3, further comprising establishing a second connection between the robotic surgical instrument and a second surgical hub.

5. The method of claim 3, further comprising transmitting, by a first processor, a data communication through the first connection.

6. The method of claim 5, further comprising verifying, by a second processor, integrity of the data communication.

7. The method of claim 6, further comprising:
   computing, by the second processor, a security code from the data communication; and
   comparing, by the second processor, the computed security code to a security code received with the data communication.

8. The method of claim 7, further comprising stopping, by the second processor, the interchangeable motor pack from driving the first surgical tool if the computed security code does not match the received security code.

9. The method of claim 5, wherein the data communication is indicative of a position of an end effector of the robotic surgical instrument.

10. The method of claim 5, wherein the data communication is indicative of a motion of an end effector of the robotic surgical instrument.

11. A method of using a surgical modular robotic assembly including an interchangeable motor pack, a hand-held surgical instrument, and a robotic surgical instrument, the method comprising:
    causing the interchangeable motor pack to drive a first surgical tool of the hand-held surgical instrument;
    stopping the interchangeable motor pack from driving the first surgical tool;
    disconnecting the interchangeable motor pack from the hand-held surgical instrument; and
    releasably attaching the interchangeable motor pack to the robotic surgical instrument.

12. The method of claim 11, further comprising causing the interchangeable motor pack to drive a second surgical tool.

13. The method of claim 12, further comprising establishing a first connection between the robotic surgical instrument and a first surgical hub.

14. The method of claim 13, further comprising establishing a second connection between the robotic surgical instrument and a second surgical hub.

15. The method of claim 13, further comprising transmitting, by a first processor, a data communication through the first connection.

16. The method of claim 15, further comprising verifying, by a second processor, integrity of the data communication.

17. The method of claim 16, further comprising:
    computing, by the second processor, a security code from the data communication; and
    comparing, by the second processor, the computed security code to a security code received with the data communication.

18. The method of claim 17, further comprising stopping, by the second processor, the interchangeable motor pack from driving the first surgical tool if the computed security code does not match the received security code.

* * * * *